US007572886B2

(12) United States Patent
Girard et al.

(10) Patent No.: US 7,572,886 B2
(45) Date of Patent: Aug. 11, 2009

(54) DEATH ASSOCIATED PROTEINS, AND THAP1 AND PAR4 PATHWAYS IN APOPTOSIS CONTROL

(75) Inventors: Jean-Philippe Girard, Rebigue (FR); Francois Amalric, Toulouse (FR); Myriam Roussigne, La Bastide sur L'Hers (FR); Thomas Clouaire, Toulouse (FR)

(73) Assignee: Centre National de la Recherche Scientifique, Paris (FR)

( * ) Notice: Subject to any disclaimer, the term of this patent is extended or adjusted under 35 U.S.C. 154(b) by 374 days.

(21) Appl. No.: 10/317,832

(22) Filed: Dec. 10, 2002

(65) Prior Publication Data

US 2003/0186337 A1 Oct. 2, 2003

Related U.S. Application Data

(60) Provisional application No. 60/341,997, filed on Dec. 18, 2001.

(51) Int. Cl.
C07K 14/00 (2006.01)
A01N 37/18 (2006.01)

(52) U.S. Cl. ............................. 530/350; 530/351; 514/2

(58) Field of Classification Search ........................ None
See application file for complete search history.

(56) References Cited

U.S. PATENT DOCUMENTS

| | | | |
|---|---|---|---|
| 4,522,811 A | 6/1985 | Eppstein et al. | |
| 4,656,127 A | 4/1987 | Mundy | |
| 4,683,195 A | 7/1987 | Mullis et al. | |
| 4,683,202 A | 7/1987 | Mullis | |
| 4,736,866 A | 4/1988 | Leder et al. | |
| 4,816,567 A | 3/1989 | Cabilly et al. | |
| 4,870,009 A | 9/1989 | Evans et al. | |
| 4,873,191 A | 10/1989 | Wagner et al. | |
| 5,073,627 A | 12/1991 | Curtis et al. | |
| 5,096,815 A | 3/1992 | Ladner et al. | |
| 5,116,947 A | 5/1992 | Pinori et al. | |
| 5,116,964 A | 5/1992 | Capon et al. | |
| 5,143,854 A | 9/1992 | Pirrung et al. | |
| 5,198,346 A | 3/1993 | Ladner et al. | |
| 5,219,089 A | 6/1993 | Kiolbasa et al. | |
| 5,223,409 A | 6/1993 | Ladner et al. | |
| 5,225,539 A | 7/1993 | Winter | |
| 5,270,181 A | 12/1993 | McCoy et al. | |
| 5,283,317 A | 2/1994 | Saifer et al. | |
| 5,292,646 A | 3/1994 | McCoy et al. | |
| 5,424,186 A | 6/1995 | Fodor et al. | |
| 5,428,130 A | 6/1995 | Capon et al. | |
| 5,434,131 A | 7/1995 | Linsley et al. | |
| 5,457,035 A | 10/1995 | Baum et al. | |
| 5,512,457 A * | 4/1996 | Lyman et al. | ............... 435/69.5 |
| 5,783,667 A | 7/1998 | Wang | |
| 5,843,778 A * | 12/1998 | Rosengard et al. | ........... 435/325 |
| 5,897,999 A | 4/1999 | Vogelstein et al. | |
| 6,191,269 B1 | 2/2001 | Pollock et al. | |
| 6,221,615 B1 | 4/2001 | Chittenden et al. | |
| 6,242,569 B1 | 6/2001 | Shu et al. | |
| 2002/0082206 A1 | 6/2002 | Leach et al. | |

FOREIGN PATENT DOCUMENTS

| | | |
|---|---|---|
| EP | 0 125 023 A1 | 11/1984 |
| EP | 0 173 494 A2 | 3/1986 |
| EP | 0 184 187 A2 | 6/1986 |
| EP | 0 273 085 A1 | 7/1988 |
| EP | 0 171 496 A2 | 2/1996 |
| EP | 0 412 883 B1 | 11/1996 |
| EP | 0 707 592 B1 | 9/1997 |
| EP | 1074617 A2 | 7/2001 |
| EP | 0 785 280 B1 | 4/2003 |
| WO | WO 86/01533 | 3/1986 |
| WO | WO 87/02671 | 5/1987 |
| WO | WO 88/06630 | 9/1988 |
| WO | WO 90/02809 | 3/1990 |
| WO | WO 90/15070 | 12/1990 |
| WO | WO 91/17271 | 11/1991 |
| WO | WO 92/01047 | 1/1992 |
| WO | WO 92/09690 | 6/1992 |
| WO | WO 92/10092 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |

(Continued)

OTHER PUBLICATIONS

Mathews and Van Holde, Biochemistry, 1996, pp. 165-171.*
W. Burgess, AShaheen, et al., Activities of Heparin-binding (Acidic Fibroblast) Growth Factor-1 from Its Receptor-binding Activities by Site-directed Mutagenesis of a Single Lysine Residue.The Journal of Cell Biology. Vo. 111, 1990, 2129-2138.*
Mesh Word, NCBI.*
Skolnick et al., TIB Tech vol. 18, p. 34-39., Jan. 2000.*
Database Geneseq 'Online! Jun. 26, 2001 "Human Protein Sequence SEQ ID No: 11440." XP002309319.
Database accession No. AAM79266. Human proteins SEQ ID 1928. (2001).

(Continued)

*Primary Examiner*—Larry R. Helms
*Assistant Examiner*—Lei Yao
(74) *Attorney, Agent, or Firm*—Knobbe Martens Olson & Bear

(57) ABSTRACT

The invention relates to genes and proteins of the THAP (THanatos (death)-Associated Protein) family comprising a THAP domain, and their use in diagnostics, treatment of disease, and in the identification of molecules for the treatment of disease. The invention also relates to the Par4 protein and SLC chemokine pathways, including the interaction of Par4 and SLC with THAP family proteins, and the recruitment and localization of Par4 to PML nuclear bodies.

8 Claims, 21 Drawing Sheets

FOREIGN PATENT DOCUMENTS

| | | | |
|---|---|---|---|
| WO | WO 93/10151 | | 5/1993 |
| WO | WO 94/02502 | | 2/1994 |
| WO | WO 94/10300 | | 5/1994 |
| WO | WO 94/10308 | | 5/1994 |
| WO | WO 99/31236 | | 6/1999 |
| WO | WO 00/06728 | | 2/2000 |
| WO | WO 00/28047 | | 5/2000 |
| WO | WO 00/58473 | | 5/2000 |
| WO | WO 00/58473 | | 10/2000 |
| WO | WO 01/12659 | | 2/2001 |
| WO | WO 01/57190 | | 8/2001 |
| WO | WO01157190 | * | 8/2001 |
| WO | WO 03/051917 | | 6/2003 |
| WO | WO 2004/055050 | | 7/2004 |

OTHER PUBLICATIONS

International Search Report from co-pending PCT/IB2004/002467 dated Oct. 21, 2004.

Roussigne, Trends in Biochemical Sciences, vol. 28, No. 2, Feb. 2003, Elsevier Publication, Cambridge, EN. *The THAP domain: a novel protein motif with similarity to the DNA-binding domain of P element transposase.*

Roussigne, Oncogene, vol. 22, No. 16, Apr. 24, 2003. *THAP1 is a nuclear proapoptotic factor that links prostate-apoptosis-response-4 (Par-4) to PML nuclear bodies.*

Written Opinion from co-pending PCT/IB2004/002467 dated Oct. 21, 2004.

Abravaya, et al. 1995. Detection of point mutations with a modified ligase chain reaction (Gap-LCR). *Nucleic Acids Research*, 23(4):675-682.

Adams, et al. 1998. The Bcl-2 protein family: Arbiters of cell survival. *Science*, 281:1322-1326.

Alcalay, et al. 1998. The promyelocytic leukemia gene product (PML) forms stable complexes with the retinoblastoma protein. *Molecular and Cellular Biology*, 18(2):1084-1093.

Alt, et al. 2002. Functional expression of the lymphoid chemokines CCL19 (ELC) and CCL 21 (SLC) at the blood-brain barrier suggests their involvement in G-protein-dependent lymphocyte recruitment into the central nervous system during experimental autoimmune encephalomyelitis. *Eur. J. Immunol.*, 32:2133-2144.

Altschul, et al. 1990. Basic local alignment search tool. *J. Mol. Biol.*, 215:403-410.

Altschul, et al. 1997. Gapped BLAST and PSI-BLAST: A new generation of protein database search programs. *Nucleic Acids Research*, 25(17):3389-3402.

Amann, et al. 1988. Tightly regulated *tac* promoter vectors useful for the expression of unfused and fused proteins in *Escherichia coli*. *Gene*, 69:301-315.

Amersham Biosciences. Scintillation Proximity Assay Manual. pp. 1-81.

Ammann, et al. 1997. Transgenic mice expressing soluble tumor necrosis factor-receptor are protected against bone loss caused by estrongen deficiency. *J. Clin. Invest.*, 99(7):1699-1703.

Arcone, et al. 1988. Identification of sequences responsible for acute-phase induction of human C-reactive protein. *Nucleic Acids Research*, 16(8):3195-3207.

Ashkenazi, et al. 1991. Protection against endotoxic shock by a tumor necrosis factor receptor immunoadhesin. *Proc. Natl. Acad. Sci. USA*, 88:10535-10539.

Ausubel, et al. (Eds.). 1998. Current Protocols in Molecular Biology, vol. 1, Unit 6.3.1-6.3.6. John Wiley & Sons, Inc.

Baichwal, et al. 1986. "Vectors for gene transfer derived from animal DNA viruses: Transient and stable expression of transferred genes." In Kucherlapati, R. (Ed.). Gene Transfer, pp. 117-147. New York: Plenum Press.

Baldari, et al. 1987. A novel leader peptide which allows efficient secretion of a fragment of human interleukin 1β in *Saccharomyces cerevisiae*. *The EMBO Journal*, 6(1):229-234.

Balint, et al. 1993. Antibody engineering by parsimonious mutagenesis. *Gene*, 137:109-118.

Barbas, et al. 1991. Assembly of combinatorial antibody libraries on phage surfaces: The gene III site. *Proc. Natl. Acad. Sci. USA*, 88:7978-7982.

Barbas, et al. 1992. Semisynthetic combinatorial antibody libraries: A chemical solution to the diversity problem. *Proc. Natl. Acad. Sci. USA*, 89:4457-4461.

Barradas, et al. 1999. The downregulation of the pro-apoptotic protein Par-4 is critical for Ras-induced survival and tumor progression. *The EMBO Journal*, 18(22):6362-6369.

Bartel, et al. 1993. Elimination of false positives that arise in using the two-hybrid system. *BioTechniques*, 14(6):920-924.

Bartlett, et al. 1996. Efficient expression of protein coding genes from the murine U1 small nuclear RNA promoters. *Proc. Natl. Acad. Sci. USA*, 93:8852-8857.

Beaucage, et al. 1981. Deoxynucleoside phosphoramidites—A new class of key intermediates for deoxypolynucleotide synthesis. *Tetrahedron Letters*, 22(20):1859-1862.

Beidler, et al. 1988. Cloning and high level expression of a chimeric antibody with specificity for human carcinoembryonic antigen. *The Journal of Immunology*, 141(11):4053-4060.

Benvenisty, et al. 1986. Direct introduction of genes into rats and expression of the genes. *Proc. Natl. Acad. Sci. USA*, 83:9551-9555.

Berra, et al. 1997. Positioning atypical protein kinase C isoforms in the UV-induced apoptotic signaling cascade. *Molecular and Cellular Biology*, 17(8):4346-4354.

Besset, et al. 2000. Nuclear localization of PAPS synthetase 1: A sulfate activation pathway in the nucleus of eukaryotic cells. *The FASEB Journal*, 14:345-354.

Better, et al. 1988. *Escherichia coli* secretion of an active chimeric antibody fragment. *Science*, 240:1041-1043.

Blackwell, et al. 1990. Differences and similarities in DNA-binding preferences of MyoD and E2A protein complexes revealed by binding site selection. *Science*, 250:1104-1110.

Bloch, et al. 1999. Structural and functional heterogeneity of nuclear bodies. *Molecular and Cellular Biology*, 19(6):4423-4430.

Boghaert, et al. 1997. Immunohistochemical analysis of the proapoptotic protein Par-4 in normal rat tissues. *Cell Growth & Differentiation*, 8:881-890.

Bouvet, P. 2001. "Determination of nucleic acid recognition sequences by SELEX." In Moss, T. (Ed.). Methods in Molecular Biology, vol. 148, 2nd ed., pp. 603-610.

Brown, et al. 1979. Chemical synthesis and cloning of a tyrosine tRNA gene. *Methods in Enzymology*, 68:109-151.

Brown, et al. 1980. Protein antigens of normal and malignant human cells identified by immunoprecipitation with monoclonal antibodies. *The Journal of Biological Chemistry*, 255(11):4980-4983.

Brown, et al. 1981. Structural characterization of human melanoma-associated antigen p97 with monoclonal antibodies. *The Journal of Immunology*, 127(2):539-546.

Brown, et al. 1992. The promoter for the procyclic acidic repetitive protein (PARP) genes of *Trypanosoma brucei* shares features with RNA polymerase I promoters. *Molecular and Cellular Biology*, 12(6):2644-2652.

Buiting, et al. 1994. Detection of aberrant DNA methylation in unique Prader-Willi syndrome patients and its diagnostic implications. *Human Molecular Genetics*, 3(6):893-895.

Burge, et al. 1997. Prediction of complete gene structures in human genomic DNA. *J. Mol. Biol.*, 268:78-94.

Byrn, et al. 1990. Biological properties of a CD4 immunoadhesin. *Nature*, 344:667-670.

Campbell, et al. 1998. Chemokines and the arrest of lymphocytes rolling under flow conditions. *Science*, 279:381-384.

Campbell, et al. 1998. 6-C-kine (SLC), a lymphocyte adhesion-triggering chemokine expressed by high endothelium, is an agonist for the MIP-3β receptor CCR7. *The Journal of Cell Biology*, 141(4):1053-1059.

Capon, et al. 1989. Designing CD4 immunoadhesins for AIDS therapy. *Nature*, 337:525-531.

Carell, et al. 1994. A novel procedure for the synthesis of libraries containing small organic molecules. *Angew. Chem. Int. Ed: Engl.*, 33(20):2059-2061.

Carell, et al. 1994. A solution-phase screening procedure for the isolation of active compounds from a library of molecules. *Angew. Chem. Int. Ed. Engl.*, 33(20):2061-2064.

Chang, et al. 1991. Hepatitis B virus integration in Hepatitis B virus-related hepatocellular carcinoma in childhood. *Hepatology*, 13(2):316-320.

Chatterjee, et al. 1995. Strategies for efficient gene transfer into hematopoietic cells. *Annals New York Academy of Sciences*, 79-90.

Chen, et al. 1987. High-efficiency transformation of mammalian cells by plasmid DNA. *Molecular and Cellular Biology*, 7(8):2745-2752.

Chen, et al. 1997. Fluorescence energy transfer detection as a homogeneous DNA diagnostic method. *Proc. Natl. Acad. Sci. USA*, 94:10756-10761.

Chen, et al. 1997. Template-directed dye-terminator incorporation (TDI) assay: A homogeneous DNA diagnostic method based on fluorescence resonance energy transfer. *Nucleic Acids Research*, 25(2):347-353.

Chen, et al. 2002. Ectopic expression of the murine chemokines CCL21a and CCL21b induces the formation of lymph node-like structures in pancreas, but not skin, of transgenic mice. *The Journal of Immunology*, 168:1001-1008.

Cho, et al. 1993. An unnatural biopolymer. *Science*, 261:1303-1305.

Clackson, et al. 1991. Making antibody fragments using phage display libraries. *Nature*, 352:624-628.

Cohen, et al. 1984. Glucocorticoid activation of a calcium-dependent endonuclease in thymocyte nuclei leads to cell death. *The Journal of Immunology*, 132(1):38-42.

Cole, et al. 1985. The EBV-hybridoma technique and its application to human lung cancer. *Monoclonal Antibodies and Cancer Therapy*, pp. 77-96.

Cormack, et al. 1996. FACS-optimized mutants of the green fluorescent protein (GFP). Database accession No. U55762.

Coupar, et al. 1988. A general method for the construction of recombinant vaccinia viruses expressing multiple foreign genes. *Gene*, 68:1-10.

Cull, et al. 1992. Screening for receptor ligands using large libraries of peptides linked to the C terminus of the lac repressor. *Proc. Natl. Acad. Sci. USA*, 89:1865-1869.

Cunningham, et al. 1989. High-resolution epitope mapping of hGH-receptor interactions by alanine-scanning mutagenesis. *Science*, 244:1081-1085.

Cwirla, et al. 1990. Peptides on phage: A vast library of peptides for identifying ligands. *Proc. Natl. Acad. Sci. USA*, 87:6378-6382.

Dandliker, et al. 1981. Equilibrium and kinetic inhibition assays based upon fluorescence polarization. *Methods in Enzymology*, 74:3-29.

Dani, et al. 1989. Cloning and regulation of a mRNA specifically expressed in the preadipose state. *The Journal of Biological Chemistry*, 264(17):10119-10125.

Dann, et al. 1986. Human renin: A new class of inhibitors. *Biochemical and Biophysical Research Communications*, 34(1):71-77.

Degterev, et al. 2001. Identification of small-molecule inhibitors of interaction between the BH3 domain and Bcl-$\chi_L$. *Nature Cell Biology*, 3:173-182.

Devlin, et al. 1990. Random peptide libraries: A source of specific protein binding molecules. *Science*, 249:404-406.

DeWitt, et al. 1993. "Diversomers": An approach to nonpeptide, nonoligomeric chemical diversity. *Proc. Natl. Acad. Sci. USA*, 90:6909-6913.

Dieu, et al. 1998. Selective recruitment of immature and mature dendritic cells by distinct chemokines expressed in different anatomic sites. *J. Exp. Med.*, 188(2):373-386.

Dimmeler, et al. 2000. Endothelial cell apoptosis in angiogenesis and vessel regression. *Circulation Research*, 434-439.

Dubensky, et al. 1984. Direct transfection of viral and plasmid DNA into the liver or spleen of mice. *Proc. Natl. Acad. Sci. USA*, 81:7529-7533.

Engvall, E. 1980. Enzyme Immunoassay ELISA and EMIT. *Meth. Enzymol.*, 70:419-439.

Erb, et al. 1994. Recursive deconvolution of combinatorial chemical libraries. *Proc. Natl. Acad. Sci. USA*, 91:11422-11426.

Ewenson, et al. 1985. "Synthesis, characterization and biological activity of keto methylene pseudopeptide analogs related to the C-terminal hexapeptide of substance P." In Deber, et al. (Eds.). Peptides: Structure and Function, Proceedings of the Ninth American Peptide Symposium, pp. 639-643.

Ewenson, et al. 1986. Ketomethylene pseudopeptide analogues of substance P: Synthesis and biological activity. *Journal of Medicinal Chemistry*, 29:295-299.

Fan, et al. 2000. Cutting Edge: Ectopic expression of the chemokine TCA4/SLC is sufficient to trigger lymphoid neogenesis. *The Journal of Immunology*, 164:3955-3959.

Fechheimer, et al. 1987. Transfection of mammalian cells with plasmid DNA by scrape loading and sonication loading. *Proc. Natl. Acad. Sci. USA*, 84:8463-8467.

Felici, et al. 1991. Selection of antibody ligands from a large library of oligopeptides expressed on a multivalent exposition vector. *J. Mol. Biol.*, 222:301-310.

Felsenstein, J. 1989. PHYLIP—Phylogeny Inference Package (Version 3.2). *Cladistics* 5: 164-166.

Ferkol, et al. 1993. Regulation of the phosphoenolpyruvate carboxykinase/human factor IX gene introduced into the livers of adult rats by receptor-mediated gene transfer. *The FASEB Journal*, 7:1081-1091.

Ferrari, et al. 1996. Second-strand synthesis is a rate-limiting step for efficient transduction by recombinant adeno-associated virus vectors. *Journal of Virology*, 70(5):3227-3234.

Fisher, et al. 1996. Transduction with recombinant adeno-associated virus for gene therapy is limited by leading-strand synthesis. *Journal of Virology*, 70(1):520-532.

Flotte, et al. 1993. Stable in vivo expression of the cystic fibrosis transmembrane conductance regulator with an adeno-associated virus vector. *Proc. Natl. Acad. Sci. USA*, 90:10613-10617.

Fodor, et al. 1993. Multiplexed biochemical assays with biological chips. *Nature*, 364:555-556.

Fogal, et al. 2000. Regulation of p53 activity in nuclear bodies by a specific PML isoform. *The EMBO Journal*, 19(22):6185-6195.

Folkman, J. 1995. Angiogenesis in cancer, vascular, rheumatoid and other disease. *Nature Medicine*, 1(1):27-31.

Folkman, J. 1995. Clinical applications of research on angiogenesis. *The New England Journal of Medicine*, 333(26):1757-1763.

Förster, et al. 1999. CCR7 coordinates the primary immune response by establishing functional microenvironments in secondary lymphoid organs. *Cell*, 99:23-33.

Fraley, et al. 1979. Entrapment of a bacterial plasmid in phospholipid vesicles: Potential for gene transfer. *Proc. Natl. Acad. Sci. USA*, 76(7):3348-3352.

Freidinger, et al. 1988. "Design and comparison of nonpeptide and peptide CCK antagonists." In G. R. Marshall (Ed.). Peptides: Chemistry and Biology: Proceedings of the Tenth American Peptide Symposium, pp. 97-100.

Friedmann, T. 1989. Progress toward human gene therapy. *Science*, 244:1275-1281.

Fuchs, et al. 1991. Targeting recombinant antibodies to the surface of *Escherichia coli*: Fusion to a peptidoglycan associated lipoprotein. *BioTechnology*, 9:1370-1372.

Galfre, et al. 1977. Antibodies to major histocompatibility antigens produced by hybrid cell lines. *Nature*, 266:550-552.

Gallop, et al. 1994. Applications of combinatorial technologies to drug discovery. 1. Background and peptide combinatorial libraries. *Journal of Medicinal Chemistry*, 37(9):1233-1251.

Garrard, et al. 1991. F$_{AB}$ assembly and enrichment in a monovalent phage display system. *BioTechnology*, 9:1373-1377.

Garvey, et al. 1988. "Synthesis of conformationally constrained CCK-4 analogs containing a substituted gamma lactam ring." In G. R. Marshall (Ed.). Peptides: Chemistry and Biology: Proceedings of the Tenth American Peptide Symposium, pp. 123-125.

Gefter, et al. 1977. A simple method for polyethylene glycol-promoted hybridization of mouse myeloma cells. *Somatic Cell Genetics*, 3(2):231-236.

GenBank Accession No. U55762, dated Nov. 11, 2003.

GenBank Accession No. U63809, dated Nov. 11, 2003.

Ghosh, et al. 1991. Targeting of Liposomes to Hepatocytes. *Liver Diseases*. Marcel Dekker, Inc. New York. pp. 87-103.

Girard, et al. 1995. Cloning from purified high endothelial venule cells of Hevin, a close relative of the antiadhesive extracellular matrix protein SPARC. *Immunity*, 2:113-123.

Girard, et al. 1995. High endothelial venules (HEVs): Specialized endothelium for lymphocyte migration. *Immunology Today*, 16(9):449-457.

Girard, et al. 1998. Sulfation in high endothelial venules: Cloning and expression of human PAPS synthetase. *The FASEB Journal*, 12:603-612.

Girard, et al. 1999. Heterogeneity of endothelial cells: The specialized phenotype of human high endothelial venules characterized by suppression subtractive hybridization. *American Journal of Pathology*, 155(6):2043-2055.

Girard, et al. 1999. Molecular cloning and functional analysis of SUT-1, a sulfate transporter from human high endothelial venules. *PNAS*, 96(22):12772-12777.

Goeddel, et al. 1990. Systems for heterologous gene expression. *Methods in Enzymology*, 185:3-7.

Goodman, et al. 1994. Recombinant adeno-associated virus-mediated gene transfer into hematopoietic progenitor cells. *Blood*, 84(5):1492-1500.

Gopal, T. V. 1985. Gene transfer method for transient gene expression, stable transformation, and cotransformation of suspension cell cultures. *Molecular and Cellular Biology*, 5(5):1188-1190.

Gordon, et al. 1985. Design of peptide derived amino alcohols as transition-state analog inhibitors of angiotensin converting enzyme. *Biochemical and Biophysical Research Communications*, 126(1):419-426.

Gossen, et al. 1992. Tight control of gene expression in mammalian cells by tetracycline-responsive promoters. *Proc. Natl. Acad. Sci. USA*, 89:5547-5551.

Gossen, et al. 1995. Transcriptional activation by tetracyclines in mammalian cells. *Science*, 268:1766-1769.

Gottesman, S. 1990. Minimizing proteolysis in *Escherichia coli*: Genetic solutions. *Methods in Enzymology*, 185:119-129.

Goward, et al. 1993. Molecular evolution of bacterial cell-surface proteins. *TIBS*, 18:136-140.

Graham, et al. 1973. A new technique for the assay of infectivity of human adenovirus 5 DNA. *Virology*, 52:456-467.

Gram, et al. 1992. In vitro selection and affinity maturation of antibodies from a naive combinatorial immunoglobulin library. *Proc. Natl. Acad. Sci. USA*, 89:3576-3580.

Grant, et al. 2002. Hepatic expression of secondary lymphoid chemokine (CCL21) promotes the development of portal-associated lymphoid tissue in chronic inflammatory liver disease. *American Journal of Pathology*, 160(4):1445-1455.

Griffiths, et al. 1993. Human anti-self antibodies with high specificity from phage display libraries. *The EMBO Journal*, 12(2):725-734.

Grodberg, et al. 1993. Alanine scanning mutagenesis of human erythropoietin identifies four amino acids which are critical for biological activity. *Eur. J. Biochem.*, 218:597-601.

Grompe, et al. 1989. Scanning detection of mutations in human ornithine transcarbamoylase by chemical mismatch cleavage. *Proc. Natl. Acad. Sci. USA*, 85:5888-5892.

Grompe, M. 1993. The rapid detection of unknown mutations in nucleic acids. *Nature Genetics*, 5:111-117.

Gunn, et al. 1998. A chemokine expressed in lymphoid high endothelial venules promotes the adhesion and chemotaxis of naive T lymphocytes. *Proc. Natl. Acad. Sci. USA*, 95:258-263.

Guo, et al. 1998. Par-4 is a mediator of neuronal degeneration associated with the pathogenesis of Alzheimer disease. *Nature Medicine*, 4(8):957-962.

Gustin, et al. 1993. Characterization of the role of individual protein binding motifs within the Hepatitis B virus enhancer I on X promoter activity using linker scanning mutagenesis. *Virology*, 193:653-660.

Harland, et al. 1985. Translation of mRNA injected into *Xenopus* oocytes is specifically inhibited by antisense RNA. *The Journal of Cell Biology*, 101:1094-1099.

Harlow, et al. (Eds.). 1988. Antibodies: A Laboratory Manual. Chapters 5-6, pp. 53-243.

Hawkins, et al. 1992. Selection of phage antibodies by binding affinity mimicking affinity maturation. *J. Mol. Biol.*, 226:889-896.

Hay, et al. 1984. Replication of adenovirus mini-chromosomes. *J. Mol. Biol.*, 175:493-510.

Hay, et al. 1992. Bacteriophage cloning and *Escherichia coli* expression of a human IgM Fab. *Hum. Antibod. Hybridomas*, 3:81-85.

Hearing, et al. 1983. Functional analysis of the nucleotide sequence surrounding the cap site for adenovirus type 5 region E1A messenger RNAs. *J. Mol. Biol.*, 167:809-822.

Hearing, et al. 1987. Identification of a repeated sequence element required for efficient encapsidation of the adenovirus type 5 chromosome. *Journal of Virology*, 61(8):2555-2558.

Hedrick, et al. 1997. Identification and characterization of a novel β chemokine containing six conserved cysteines. *The Journal of Immunology*, 159:1589-1593.

Hjelmström, et al. 2000. Lymphoid tissue homing chemokines are expressed in chronic inflammation. *American Journal of Pathology*, 156(4):1133-1138.

Hogan, et al. 1986. Manipulating the mouse Embryo: A laboratory manual, pp. 151-203. Cold Spring Harbor, NY: Cold Spring Harbor Laboratory.

Hoogenboom, et al. 1991. Multi-subunit proteins on the surface of filamentous phase: Methodologies for displaying antibody (Fab) heavy and light chains. *Nucleic Acids Research*, 19(15):4133-4137.

Horowitz, et al. 1989. Point mutational inactivation of the retinoblastoma antioncogene. *Science*, 243:937-940.

Houghten, et al. 1992. The use of synthetic peptide combinatorial libraries for the identification of bioactive peptides. *BioTechniques*, 13(3):412-421.

Hromas, et al. 1997. Isolation and characterization of Exodus-2, a novel C-C chemokine with a unique 37-amino acid carboxyl-terminal extension. *The Journal of Immunology*, 159:2554-2558.

Hsu, et al. 1995. The TNF receptor 1-associated protein TRADD signals cell death and NF-κB activation. *Cell*, 81:495-504.

Hsu, et al. 1996. TNF-dependent recruitment of the protein kinase RIP to the TNF receptor-1 signaling complex. *Immunity*, 4:387-396.

Hsu, et al. 1996. TRADD-TRAF2 and TRADD-FADD interactions define two distinct TNF receptor 1 signal transduction pathways. *Cell*, 84:299-308.

Huffman, et al. 1988. "Reverse turn mimics." In G. R. Marshall (Ed.). Peptides: Chemistry and Biology: Proceedings of the Tenth American Peptide Symposium, pp. 105-108.

Hunt, et al. 1986. Adipocyte P2 gene: Developmental expression and homology of 5'-flanking sequences among fat cell-specific genes. *Proc. Natl. Acad. Sci. USA*, 83:3786-3790.

Hunter, T. 1993. Braking the cycle. *Cell*, 75:839-841.

Huse, et al. 1989. Generation of a large combinatorial library of the immunoglobulin repertoire in phage lambda. *Science*, 246:1275-1281.

Ike, et al. 1983. Solid phase synthesis of polynucleotides. VIII. Synthesis of mixed oligodeoxyribonucleotides by the phosphotriester solid phase method. *Nucleic Acids Research*, 11(2):477-488.

Ishov, et al. 1999. PML is critical for ND10 formation and recruits the PML-interacting protein Daxx to this nuclear structure when modified by SUMO-1. *The Journal of Cell Biology*, 147:221-233.

Itakura, et al. 1977. Expression in *Escherichia coli* of a chemically synthesized gene for the hormone somatostatin. *Science*, 198:1056-1063.

Itakura, et al. 1981. "Chemical synthesis and application of oligonucleotides of mixed sequence." In Walton, A. G. (Ed.). Recombinant DNA, Proceedings of the Third Cleveland Symposium on Macromolecules, pp. 273-289.

Itakura, et al. 1984. Synthesis and use of synthetic oligonucleotides. *Ann. Rev. Biochem.*, 53:323-356.

Iwabuchi, et al. 1993. Use of the two-hybrid system to identify the domain of p53 involved in oligomerization. *Oncogene*, 8:1693-1696.

Jacobson, et al. 1997. Programmed cell death in animal development. *Cell*, 88:347-354.

Jareborg, et al. 1999. Comparative analysis of noncoding regions of 77 orthologous mouse and human gene pairs. *Genome Research*, 9:815-824.

Jentsch, et al. 2000. Ubiquitin and its kin: How close are the family ties? *Trends in Cell Biology*, 10:335-342.

Johnstone, et al. 1996. A novel repressor, par-4, modulates transcription and growth suppression functions of the Wilms' tumor suppressor WT1. *Molecular and Cellular Biology*, 16(12):6945-6956.

Joki, et al. 1995. Activation of the radiosensitive EGR-1 promoter induces expression of the Herpes Simplex Virus thymidine kinase gene and sensitivity of human glioma cells to ganciclovir. *Human Gene Therapy*, 6:1507-1513.

Jones, et al. 1986. Replacing the complementarity-determining regions in a human antibody with those from a mouse. *Nature*, 321:522-525.

Kageyama, et al. 1987. Differing utilization of homologous transcription initiation sites of rat K and T kininogen genes under inflammation condition. *The Journal of Biological Chemistry*, 262(5):2345-2351.

Kaneda, et al. 1989. Increased expression of DNA cointroduced with nuclear protein in adult rat liver. *Science*, 243:375-378.

Kaplitt, et al. 1994. Long-term gene expression and phenotypic correction using adeno-associated virus vectors in the mammalian brain. *Nature Genetics*, 8:148-154.

Karlin, et al. 1990. Methods for assessing the statistical significance of molecular sequence features by using general scoring schemes. *Proc. Natl. Acad. Sci. USA*, 87:2264-2268.

Karlin, et al. 1993. Applications and statistics for multiple high-scoring segments in molecular sequences. *Proc. Natl. Acad. Sci. USA*, 90:5873-5877.

Karniski, et al. 1998. Immunolocalization of sat-1 sulfate/oxalate/bicarbonate anion exchanger in the rat kidney. *Am. J. Physiol.*, 275:F79-F87.

Kato, et al. 1991. Expression of Hepatitis B virus surface antigen in adult rat liver: Co-introduction of DNA and nuclear protein by a simplified liposome method. *The Journal of Biological Chemistry*, 266(6):3361-3364.

Kaufman, et al. 1987. Translational efficiency of polycistronic mRNAs and their utilization to express heterologous genes in mammalian cells. *The EMBO Journal*, 6(1):187-193.

Kessler, et al. 1996. Gene delivery to skeletal muscle results in sustained expression and systemic delivery of a therapeutic protein. *Proc. Natl. Acad. Sci. USA*, 93:14082-14087.

Klein, et al. 1987. High-velocity microprojectiles for delivering nucleic acids into living cells. *Nature*, 327:70-73.

Ko, et al. 1993. DNA-binding specificities of the GATA transcription factor family. *Molecular and Cellular Biology*, 13(7):4011-4022.

Koeberl, et al. 1997. Persistent expression of human clotting factor IX from mouse liver after intravenous injection of adeno-associated virus vectors. *Proc. Natl. Acad. Sci. USA*, 94:1426-1431.

Köhler, et al. 1975. Continuous cultures of fused cells secreting antibody of predefined specificity. *Nature*, 256:495-497.

Korhonen, et al. 1995. Endothelial-specific gene expression directed by the *tie* gene promoter in vivo. *Blood*, 86(5):1828-1835.

Kozbor, et al. 1983. The production of monoclonal antibodies from human lymphocytes. *Immunology Today*, 4(3):72-79.

Kroeger, et al. 1994. Selection of new HSF1 and HSF2 DNA-binding sites reveals differences in trimer cooperativity. *Molecular and Cellular Biology*, 14(11):7592-7603.

Kumar, et al. 1994. Induction of apoptosis by the mouse *Nedd2* gene, which encodes a protein similar to the product of the *Caenorhabditis elegans* cell death gene *ced-3* and the mammalian IL-1β-converting enzyme. *Genes & Development*, 8:1613-1626.

Kurjan, et al. 1982. Structure of a yeast pheromone gene (*MFα*): A putative α-factor precursor contains four tandem copies of mature α-factor. *Cell*, 30:933-943.

Kyprianou, et al. 1988. Activation of programmed cell death in the rat ventral prostate after castration. *Endocrinology*, 122(2):552-562.

Lallemand-Breitenbach, et al. 2001. Role of promyelocytic leukemia (PML) sumolation in nuclear body formation, 11S proteasome recruitment, and $As_2O_3$-induced PML or PML/retinoic acid receptor α degradation. *J. Exp. Med.*, 193(12):1361-1371.

Lam, K. 1997. Application of combinatorial library methods in cancer research and drug discovery. *Anti-Cancer Drug Design*, 12:145-167.

Lam, et al. 1991. A new type of synthetic peptide library for identifying ligand-binding activity. *Nature*, 354:82-84.

LaMorte, et al. 1998. Localization of nascent RNA and CREB binding protein with the PML-containing nuclear body. *Proc. Natl. Acad. Sci. USA*, 95:4991-4996.

Landegren, et al. 1988. A ligase-mediated gene detection technique. *Science*, 241:1077-1080.

Landegren, et al. 1998. Reading bits of genetic information: Methods for single-nucleotide polymorphism analysis. *Genome Research*, 8:769-776.

Landschulz, et al. 1988. The leucine zipper: A hypothetical structure common to a new class of DNA binding proteins. *Science*, 240:1759-1764.

Lauvau, et al. 2001. CD8 T cell detection of bacterial infection: Sniffing for formyl peptides derived from *Mycobacterium tuberculosis*. *J. Exp. Med.*, 193(10):F35-F39.

Lee, et al. 1998. DNA binding by the KP repressor protein inhibits P-element transposase activity in vitro. *The EMBO Journal*, 17(14):4166-4174.

Lerner, E. A. 1981. How to make a hybridoma. *The Yale Journal of Biology and Medicine*, 54:387-402.

Leung, D. W., et al., 1989. A Method for Random Mutagenesis of a Defined DNA Segment Using a Modified Polymerase Chain Reaction, *Technique-A Journal of Methods in Cell and Molecular Biology*, 1:11-15.

Levrero, et al. 1991. Defective and nondefective adenovirus vectors for expressing foreign genes in vitro and in vivo. *Gene*, 101:195-202.

Li, et al. 2000. Sequestration and inhibition of Daxx-mediated transcriptional repression by PML. *Molecular and Cellular Biology*, 20(5):1784-1796.

Linsley, et al. 1991. Binding of a B cell activation antigen B7 to CD28 costimulates T cell proliferation and interleukin 2 mRNA accumulation. *J. Exp. Med.* 173:721-730.

Linsley, et al. 1991. CTLA-4 is a second receptor for the B cell activation antigen B7. *J. Exp. Med.*, 174:561-569.

Liu, et al. 1987. Chimeric mouse-human IgG1 antibody that can mediate lysis of cancer cells. *Proc. Natl. Acad. Sci. USA*, 84:3439-3443.

Liu, et al. 1987. Production of a mouse-human chimeric monoclonal antibody to CD20 with potent Fc-dependent biologic activity. *The Journal of Immunology*, 139(10):3521-3526.

Lowman, et al. 1991. Selecting high-affinity binding proteins by monovalent phage display. *Biochemistry*, 30:10832-10838.

Luckow, et al. 1989. High level expression of nonfused foreign genes with *Autographa californica* nuclear polyhedrosis virus expression vectors. *Virology*, 170:31-39.

Luther, et al. 2002. Differing activities of homeostatic chemokines CCL19, CCL21, and CXCL12 in lymphocyte and dendritic cell recruitment and lymphoid neogenesis. *The Journal of Immunology*, 169:424-433.

Madura, et al. 1993. N-recognin/Ubc2 interactions in the N-end rule pathway. *The Journal of Biological Chemistry*, 268(16):12046-12054.

Mahajan, et al. 1998. Bcl-2 and Bax interactions in mitochondria probed with green fluorescent protein and fluorescence resonance energy transfer. *Nature Biotechnology*, 16:547-552.

Manival, et al. 2001. RNA-binding strategies common to cold-shock domain- and RNA recognition motif-containing proteins. *Nucleic Acids Research*, 29(11):2223-2233.

Mann, et al. 1983. Construction of a retrovirus packaging mutant and its use to produce helper-free defective retrovirus. *Cell*, 33:153-159.

Marks, et al. 1992. Molecular evolution of proteins on filamentous phage. *The Journal of Biological Chemistry*, 267(23):16007-16010.

Martin, et al. 1988. Inhibitors of protein synthesis and RNA synthesis prevent neuronal death caused by nerve growth factor deprivation. *The Journal of Cell Biology*, 106:829-844.

Mattson, et al. 1999. An emerging pivotal player in neuronal apoptosis and neurodegenerative disorders. *Journal of Molecular Neuroscience*, 13:17-30.

Mattson, et al. 2000. Apoptotic and antiapoptotic mechanisms in stroke. *Cell Tissue Res.*, 301:173-187.

Mattson, et al. 2001. Neurodegenerative disorders and ischemic brain diseases. *Apoptosis*, 6(1/2):69-81.

Maul, et al. 2000. Review: Properties and assembly mechanisms of ND10, PML bodies, or PODs. *Journal of Structural Biology*, 129:278-287.

McCafferty, et al. 1990. Phage antibodies: Filamentous phage displaying antibody variable domains. *Nature*, 348:552-554.

McConnell, et al. 1992. The cytosensor microphysiometer: Biological applications of silicon technology. *Science*, 257:1906-1912.

McCown, et al. 1996. Differential and persistent expression patterns of CNS gene transfer by an adeno-associated virus (AAV) vector. *Brain Research*, 713:99-107.

McKnight, et al. 1982. Transcriptional control signals of a eukaryotic protein-coding gene. *Science*, 217:316-324.

McMahan, et al. 1991. A novel IL-1 receptor, cloned from B cells by mammalian expression, is expressed in many cell types. *The EMBO Journal*, 10(10):2821-2832.

Melchoir, F. 2000. SUMO—non-classical ubiquitin. *Annu. Rev. Cell Dev. Biol.*, 16:591-626.

Merika, et al. 1993. DNA-binding specificity of GATA family transcription factors. *Molecular and Cellular Biology*, 13(7):3999-4010.

Miller, J. H. 1992. A short course in bacterial genetics, p. 73. Cold Spring Harbor, NY: CSH Laboratory Press.

Miura, et al. 1993. Induction of apoptosis in fibroblasts by IL-1β-converting enzyme, a mammalian homolog of the *C. elegans* cell death gene *ced-3*. *Cell*, 75:653-660.

Mizukami, et al. 1996. Adeno-associated virus type 2 binds to a 150-kilodalton cell membrane glycoprotein. *Virology*, 217:124-130.

Mizushima, et al. 1990. pEF-BOS, a powerful mammalian expression vector. *Nucleic Acids Research*, 18(17):5322.

Moreland, et al. 1997. Treatment of rheumatoid arthritis with a recombinant human tumor necrosis factor receptor (p75)-Fc fusion protein. *The New England Journal of Medicine*, 337(3):141-147.

Morrison, S. L. 1985. Transfectomas provide novel chimeric antibodies. *Science*, 229:1202-1207.

Müller, et al. 1998. Conjugation with the ubiquitin-related modifier SUMO-1 regulates the partitioning of PML within the nucleus. *The EMBO Journal*, 17(1):61-70.

Myers, et al. 1986. Fine structure genetic analysis of a β-globin promoter. *Science*, 232:613-618.

Nagai, et al. 1985. Synthesis of a bicyclic dipeptide with the shape of a β-turn central part. *Tetrahedron Letters*, 26(5):647-650.

Nagashima, et al. 1993. Alanine-scanning mutagenesis of the epidermal growth factor-like domains of human thrombomodulin identifies critical residues for its cofactor activity. *The Journal of Biological Chemistry*, 268(4):2888-2892.

Nagira, et al. 1997. Molecular cloning of a novel human CC chemokine secondary lymphoid-tissue chemokine that is a potent chemoattractant for lymphocytes and mapped to chromosome 9p13. *The Journal of Biological Chemistry*, 272(31):19518-19524.

Nakano, et al. 1998. A novel mutant gene involved in T-lymphocyte-specific homing into peripheral lymphoid organs on mouse chromosome 4. *Blood*, 91(8):2886-2895.

Nakazawa, et al. 1994. UV and skin cancer: Specific p53 gene mutation in normal skin as a biologically relevant exposure measurement. *Proc. Natl. Acad. Sci.* USA, 91:360-364.

Narang, et al. 1979. Improved phosphotriester method for the synthesis of gene fragments. *Methods in Enzymology*, 68:90-98.

Nicolas, et al. 1988. "Retroviral Vectors." In Vectors: A Survey of Molecular Cloning Vectors and Their Uses. Rodriguez, et al. (Eds.). Chap. 25, pp. 493-513. Boston: Butterworths.

Nicolau, et al. 1982. Liposome-mediated DNA transfer in eukaryotic cells: Dependence of the transfer efficiency upon the type of liposomes used and the host cell cycle stage. *Biochimica et Biophysica Acta*, 721:185-190.

Nicolau, et al. 1987. Liposomes as carriers for in Vivo gene transfer and expression. *Methods in Enzymology*, 149:157-176.

Nishimura, et al. 1987. Recombinant human-mouse chimeric monoclonal antibody specific for common acute lymphocytic leukemia antigen. *Cancer Research*, 47:999-1005.

Oi, et al. 1986. Chimeric antibodies. *BioTechniques*, 4(3):214-221.

Okamoto, et al. 1994. Cyclin G is a transcriptional target of the p53 tumor suppressor protein. *The EMBO Journal*, 13(19):4816-4822.

Oliviero, et al. 1987. The human haptoglobin gene: Transcriptional regulation during development and acute phase induction. *The EMBO Journal*, 6(7):1905-1912.

Olszewski, et al. 1999. SeqFold—fully automated fold recognition and modeling software—evaluation and application. *Theor. Chem. Acc.*, 101:57-61.

Orita, et al. 1989. Detection of polymorphisms of human DNA by gel electrophoresis as single-strand conformation polymorphisms. *Proc. Natl. Acad. Sci.* USA, 86:2766-2770.

Page, et al. 1999. Interaction partners of Dlk/ZIP kinase: Co-expression of Dlk/ZIP kinase and Par-4 results in cytoplasmic retention and apoptosis. *Oncogene*, 18:7265-7273.

Page, et al. 2002. Anatomic localization of immature and mature dendritic cells in an ectopic lymphoid organ: Correlation with selective chemokine expression in rheumatoid synovium. *The Journal of Immunology*, 168:5333-5341.

Pape, et al. 1989. Transcriptional Regulation of acetyl coenzyme A carboxylase gene expression in tumor necrosis factor in 30A-5 preadipocytes. *Molecular and Cellular Biology*, 9(3):974-982.

Paskind, et al. 1975. Dependence of Moloney murine leukemia virus production on cell growth. *Virology*, 67:242-248.

Pastinen, et al. 1997. Minisequencing: A specific tool for DNA analysis and diagnostics on oligonucleotide arrays. *Genome Research*, 7:606-614.

Perales, et al. 1994. Gene transfer in vivo: Sustained expression and regulatoin of genes introduced into the liver by receptor-targeted uptake. *Proc. Natl. Acad. Sci.* USA, 91:4086-4090.

Ping, et al. 1996. Altered β-adrenergic receptor signaling in heart failure, in vivo gene transfer via adeno and adeno-associated virus. *Microcirculation*, 3(2):225-228.

Poli, et al. 1989. Interleukin 6 induces a liver-specific nuclear protein that binds to the promoter of acute-phase genes. *Proc. Natl. Acad. Sci.* USA, 86:8202-8206.

Pollock, et al. 1990. A sensitive method for the determination of protein-DNA binding specificities. *Nucleic Acids Research*, 18(21):6197-6204.

Potter, et al. 1984. Enhancer-dependent expression of human κ immunoglobulin genes introduced into mouse pre-B lymphocytes by electroporation. *Proc. Natl. Acad. Sci.* USA, 81:7161-7165.

Prowse, et al. 1988. Hepatocyte-stimulating factor, $\beta_{-2}$ Interferon, and Interleukin-1 enhance expression of the rat $\alpha_1$-acid glycoprotein gene via a distal upstream regulatory region. *Molecular and Cellular Biology*, 8(1):42-51.

Quignon, et al. 1998. PML induces a novel caspase-independent death process. *Nature Genetics*, 20:259-265.

Rädler, et al. 1997. Structure of DNA-cationic liposome complexes: DNA intercalation in multilamellar membranes in distinct interhelical packing regimes. *Science*, 275:810-814.

Ridgway, A. A. G. 1988. "Mammalian Expression Vectors." In Vectors: A Survey of Molecular Cloning Vectors and Their Uses. Rodriguez, et al. (Eds.). Chap. 24, pp. 467-492. Boston: Butterworths.

Rippe, et al. 1990. DNA-mediated gene transfer into adult rat hepatocytes in primary culture. *Molecular and Cellular Biology*, 10(2):689-695.

Roberts, et al. 1992. Directed evolution of a protein: Selection of potent neutrophil elastase inhibitors displayed on M13 fusion phage. *Proc. Natl. Acad. Sci.* USA, 89:2429-2433.

Ron, et al. 1991. Angiotensinogen gene-inducible enhancer-binding protein 1, a member of a new family of large nuclear proteins that recognize nuclear factor κB-binding sites through a zinc finger motif. *Molecular and Cellular Biology*, 11(5):2887-2895.

Rossi, et al. 1997. Identification through bioinformatics of two new macrophage proinflammatory human chemokines MIP-3α and MIP-3β[1,2]. *The Journal of Immunology*, 158:1033-1036.

Roux, et al. 1989. A versatile and potentially general approach to the targeting of specific cell types by retroviruses: Application to the infection of human cells by means of major histocompatibility complex class I and class II antigens by mouse ecotropic murine leukemia virus-derived viruses. *Proc. Natl. Acad. Sci.* USA, 86:9079-9083.

Ruf, et al. 1994. Mutational mapping of functional residues in tissue factor: Identification of factor VII recognition determinants in both structural modules of the predicted cytokine receptor homology domain. *Biochemistry*, 33:1565-1672.

Ruggero, et al. 2000. The puzzling multiple lives of PML and its role in the genesis of cancer. *BioEssays*, 22:827-835.

Sallusto, et al. 1998. Rapid and coordinated switch in chemokine receptor expression during dendritic cell maturation. *Eur. J. Immunol.*, 28:2760-2769.

Sallusto, et al. 1999. Two subsets of memory T lymphocytes with distinct homing potentials and effector functions. *Nature*, 401:708-712.

Sambrook, et al. (Eds.). 1989. Molecular Cloning: A Laboratory Manual. Chaps. 16-17, pp. 16.1-17.44. Cold Spring Harbor, NY: Cold Spring Habor Laboratory.

Samulski, et al. 1987. A recombinant plasmid from which an infectious adeno-associated virus genome can be excised in vitro and its use to study viral replication. *Journal of Virology*, 61(10):3096-3101.

Sato, et al. 1986. Synthesis and antibiotic activity of a gramicidin S analogue containing bicyclic β-turn dipeptides. *J. Chem. Soc. Perkin Trans. I*, 1231-1234.

Schultz, et al. 1987. Expression and secretion in yeast of a 400-kDa envelope glycoprotein derived from Epstein-Barr virus. *Gene*, 54:113-123.

Scott, et al. 1990. Searching for peptide ligands with an epitope library. *Science*, 249:386-390.

Seed, B. 1987. An LFA-3 cDNA encodes a phospholipid-linked membrane protein homologous to its receptor CD2. *Nature*, 329:840-842.

Shaw, et al. 1988. Mouse/human chimeric antibodies to a tumor-associated antigen: Biologic activity of the four human IgG subclasses. *Journal of the National Cancer Institute*, 80(19):1553-1559.

Sheffield, et al. 1991. Identification of novel rhodopsin mutations associated with retinitis pigmentosa by GC-clamped denaturing gradient gel electrophoresis. *Am. J. Hum. Genet.*, 49:699-706.

Shu, et al. 1995. A transient associatoin of γ-tubulin at the midbody is required for the completion of cytokinesis during the mammalian cell division. *Journal of Cell Science*, 108:2955-2962.

Sjölander, et al. 1991. Integrated fluid handling system for biomolecular interaction analysis. *Analytical Chemistry*, 63(20):2338-2345.

Smith, et al. 1983. Production of human beta interferon in insect cells infected with a baculovirus expression vector. *Molecular and Cellular Biology*, 3(12):2156-2165.

Smith, et al. 1988. Single-step purification of polypeptides expressed in *Escherichia coli* as fusions with glutathione S-transferase. *Gene*, 67:31-40.

Spiegelman, et al. 1989. Adrenal glucocorticoids regulate adipsin gene expression in genetically obese mice. *The Journal of Biological Chemistry*, 264(3):1811-1815.

Sternsdorf, et al. 1997. Cellular localization, expression, and structure of the nuclear dot protein 52. *The Journal of Cell Biology*, 138(2):435-448.

Sternsdorf, et al. 1999. The nuclear dot protein Sp100, characterization of domains necessary for dimerization, subcellular localization, and modification by small ubiquitin-like modifiers. *The Journal of Biological Chemistry*, 274(18):12555-12566.

Studier, et al. 1990. Use of T7 RNA polymerase to direct expression of cloned genes. *Methods in Enzymology*, 185:60-89.

Sun, et al. 1987. Chimeric antibody with human constant regions and mouse variable regions directed against carcinoma-associated antigen 17-1A. *Proc. Natl. Acad. Sci. USA*, 84:214-218.

Szabo, et al. 1995. Surface plasmon resonance and its use in biomolecular interaction analysis (BIA). *Current Opinion in Structural Biology*, 5:699-705.

Takemura, et al. 2001. Lymphoid neogenesis in rheumatoid synovitis. *The Journal of Immunology*, 167:1072-1080.

Tan, et al. 1990. DNA binding-induced conformational change to the yeast transcriptional activator PRTF. *Cell*, 62:367-377.

Tartaglia, et al. 1993. A novel domain within the 55 kd TNF receptor signals cell death. *Cell*, 74:845-853.

Temin, H. M. 1986. "Retrovirus vectors for gene transfer: Efficient integration into and expression of exogenous DNA in vertebrate cell genomes." In Kucherlapati, R. (Ed.). Gene Transfer, pp. 149-187. New York: Plenum Press.

Terris, et al. 1995. PML nuclear bodies are general targets for inflammation and cell proliferation. *Cancer Research*, 55:1590-1597.

Tibbetts, C. 1977. Viral DNA sequences from incomplete particles of human adenovirus type 7. *Cell*, 12:243-249.

Tur-Kaspa, et al. 1986. Use of electroporation to introduce biologically active foreign genes into primary rat hepatocytes. *Molecular and Cellular Biology*, 6(2):716-718.

Vaitukaitis, et al. 1971. A method for producing specific antisera with small doses of immunogen. *J. Clin. Endocr. Metab.*, 33:988-991.

van der Poll, et al. 1997. Effect of a recombinant dimeric tumor necrosis factor receptor on inflammatory responses to intravenous endotoxin in normal humans. *Blood*, 89(10):3727-3734.

Vaux, et al. 1994. An evolutionary perspective on apoptosis. *Cell*, 76:777-779.

Verhoeyen, et al. 1988. Reshaping human antibodies: Grafting an antilysozyme activity. *Science*, 239(4847):1534(3).

Wada, et al. 1992. Codon usage tabulated from the GenBank genetic sequence data. *Nucleic Acids Research*, 20:2111-2118.

Wagner, et al. 1990. Transferrin-polycation conjugates as carriers for DNA uptake into cells. *Proc. Natl. Acad. Sci. USA*, 87:3410-3414.

Wagner, et al. 1993. Antisense gene inhibition by oligonucleotides containing C-5 propyne pyrimidines. *Science*, 260:1510-1513.

Walther, et al. 1996. Cell type specific and inducible promoters for vectors in gene therapy as an approach for cell targeting. *J. Mol. Med.*, 74:379-392.

Wang, et al. 1994. *Ich-1*, an *Ice/ced-3*-related gene, encodes both positive and negative regulators of programmed cell death. *Cell*, 78:739-750.

Wang, et al. 1994. Single amino acid insertions probe the α subunit of the *Escherichia coli* $F_1F_0$-ATP synthase. *The Journal of Biological Chemistry*, 269(4):3095-3099.

Wang, et al. 1998. Pml is essential for multiple apoptotic pathways. *Nature Genetics*, 20:266-272.

Wang, et al. 1998. Role of PML in cell growth and the retinoic acid pathway. *Science*, 279:1547-1551.

Watt, et al. 1986. Human prostate-specific antigen: Structural and functional similarity with serine proteases. *Proc. Natl. Acad. Sci. USA*, 83:3166-3170.

White, et al. 1992. Detecting single base substitutions as heteroduplex polymorphisms. *Genomics*, 12:301-306.

Wiegmann, et al. 1994. Functional dichotomy of neutral and acidic sphingomyelinases in tumor necrosis factor signaling. *Cell*, 78:1005-1015.

Wilson, et al. 1990. A 58-base-pair region of the human C3 gene confers synergistic inducibility by Interleukin-1 and Interleukin-6. *Molecular and Cellular Biology*, 10(12):6181-6191.

Wong, et al. 1980. Appearance of β-lactamase activity in animal cells upon liposome-mediated gene transfer. *Gene*, 10:87-94.

Wood, et al. 1985. The synthesis and in vivo assembly of functional antibodies in yeast. *Nature*, 314:446-449.

Wu, et al. 1987. Receptor-mediated in vitro gene transformation by a soluble DNA carrier system. *The Journal of Biological Chemistry*, 262(10):4429-4432.

Wu, et al. 1988. Evidence for targeted gene delivery to Hep G2 hepatoma cells in vitro. *Biochemistry*, 27:887-892.

Wu, et al. 1993. Liver-directed gene delivery. *Advanced Drug Delivery Reviews*, 12:159-167.

Xiao, et al. 1996. Efficient long-term gene transfer into muscle tissue of immunocompetent mice by adeno-associated virus vector. *Journal of Virology*, 70(11):8098-8108.

Yang, et al. 1990. In vivo and in vitro gene transfer to mammalian somatic cells by particle bombardment. *Proc. Natl. Acad. Sci. USA*, 87:9568-9572.

Yeh, et al. 1982. A cell-surface antigen which is present in the ganglioside fraction and shared by human melanomas. *Cancer*, 29:269-275.

Yeh, et al. 2000. Ubiquitin-like proteins: New wines in new bottles. *Gene*, 248:1-14.

Yelton, et al. 1980. "Plasmacytomas and hybridomas: Development and applications." In Kennett, et al. (Eds.). Monoclonal Antibodies: Hybridomas: A New Dimension in Biological Analyses, Chap. 1, pp. 3-17. New York: Plenum Press.

Yoneyama, et al. 2001. Regulation by chemokines of circulating dendritic cell precursors, and the formation of portal tract-associated lymphoid tissue, in a granulomatous liver disease. *J. Exp. Med.*, 193(1):35-49.

Yoshida, et al. 1997. Molecular cloning of a novel human CC chemokine EBI1-ligand chemokine that is a specific functional ligand for EBI1, CCR7. *The Journal of Biological Chemistry*, 272(21):13803-13809.

Yoshida, et al. 1998. Secondary lymphoid-tissue chemokine is a functional ligand for the CC chemokine receptor CCR7. *The Journal of Biological Chemistry*, 273(12):7118-7122.

Zabel, et al. 1991. DNA binding of purified transcription factor NF-κB: Affinity, specificity, $Zn^{2+}$ dependence, and differential half-site recognition. *The Journal of Biological Chemistry*, 266(1):252-260.

Zechner, et al. 1988. Recombinant human cachectin/tumor necrosis factor but not Interleukin-1α downregulates lipoprotein lipase gene expression at the transcriptional level in mouse 3T3-L1 adipocytes. *Molecular and Cellular Biology*, 8(6):2394-2401.

Zervos, et al. 1993. Mxi1, a protein that specifically interacts with Max to bind Myc-Max recognition sites. *Cell*, 72:223-232.

Zhong, et al. 1999. A role for PML and the nuclear body in genomic stability. *Oncogene*, 18:7941-7947.

Zhong, et al. 2000. Promyelocytic leukemia protein (PML) and Daxx participate in a novel nuclear pathway for apoptosis. *J. Exp. Med.*, 191(4):631-639.

Zhong, et al. 2000. Role of SUMO-1—modified PML in nuclear body formation. *Blood*, 95(9):2748-2753.

Zhong, et al. 2000. The transcriptional role of PML and the nuclear body. *Nature Cell Biology*, 2:E85-E90.

Zuckerman, et al. 1994. Discovery of nanomolar ligands for 7-transmembrane G-protein-coupled receptors from a diverse N-(Substituted)glycine peptoid library. *Journal of Medicinal Chemistry*, 37(17):2678-2685.

Zurawski, et al. 1980. "Continuously proliferating human cell lines synthesizing antibody of predetermined specificity." In Kennett, et al. (Eds.). Monoclonal Antibodies: Hybridomas: A New Dimension in Biological Analyses, Chap. 2, pp. 19-33. New York: Plenum Press.

Diaz-Meco, et al. 1996. The product of *par-4*, a gene induced during apoptosis, interacts selectively with the atypical isoforms of protein kinase C. *Cell*, 86:777-786.

Isogai, et al. 2000. Hypothetical protein FLJ10477. SWALL database accession No. Q9NVV9 (XP002235128).

Sells, et al. 1997. Expression and function of the leucine zipper protein Par-4 in apoptosis. *Molecular and Cellular Biology*, 17(7):3823-3832. (XP002235127).

International Search Report from co-pending PCT/EP02/14027 dated Jul. 7, 2003.

* cited by examiner

FIGURE 1

A
```
hTHAP1    1  MVQSCSAYGCKNRYDKDKPVSFHKFPLTRPSLCKEWEAAVRRKNFKPTKYSSICSEHFTP
mTHAP1    1  MVQSCSAYGCKNRYDKDKPVSFHKFPLTRPSLCKQWEAAVKRKNFKPTKYSSICSEHFTP
             * * * * * * * * * * * * * * * * * * * * * * * * * * * * * * hTHAP1   61  DCFKRECNNKLLKENAVPTIFLCTEPHDKKEDLLEPQEQLPPPLPPPVSQVDAAIGLLM
mTHAP1   61  DCFKRECNNKLLKENAVPTIFLYIEPHEKKEDL-ESQEQLPSPS--PPASQVDAAIGLLM
             * * * * * * * * * * * * *   * * * *   * * * *     * * * * * * hTHAP1  121  PPLQTPVNLSVFCDHNYTVEDTMHQRKRIHQLEQQVEKLRKKLKTAQQRCRRQERQLEKL
mTHAP1  118  PPLQTPDNLSVFCDHNYTVEDTMHQRKRILQLEQQVEKLRKKLKTAQQRCRRQERQLEKL
             * * * * *   * * * * * * * * * * * *  * * * * * * * * * * * * hTHAP1  181  KEVVHFQKEKDDVSERGYVILPNDYFEIVEVPA
mTHAP1  178  KEVVHFQREKDDASERGYVILPNDYFEIVEVPA
             * * * * * *   * * *   * * * * * *
```

B
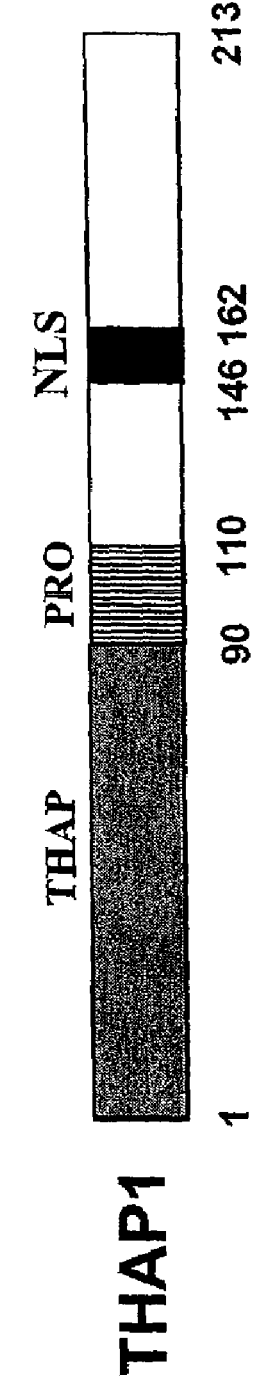

```
mZIP    -VLEDVAAAEQGLREL--QRGRRQCRERVCALRAAAEQREARCRDG
mTHAP-1 -QLEQQVEKLRKKLKTAQQRCRRQERQLEKLKEVHFQREKDDASE
hTHAP-1 -QLEQQVEKLRKKLKTAQQRCRRQERQLEKLKEVHFQKEKDDVSE
```

Consensus Par4 binding site: LE ($X_{12-14}$) QRXRRQXR ($X_{11}$) QXE

B

|  | Two-hybrid bait Par4 wt or Par4DD | Par4DD binding in vitro | in vivo |
|---|---|---|---|
| THAP1 wt | + | + | + |
| THAP1 Δ(QRCRR) | - | - | - |
| THAP1 RR/AA | - | - | - |

```
hTHAP1        1 MVQSCSAYGCKNRYDKDVSFHKFPLTRPSLCKEWEAAVRRKNFKPTKYSICSEHFTP
dmTransposase 1 -MKYC-KICCK-AVTGVKLIHVPKCAIKR----KLWEQSIG---CSLGENSQICDTHEND
consensus     1 mv   Cs y CKn        K   v   K    l Rpslck WE  v rkn      S  IC   HF hTHAP1        61 DCRK------RECNNKLDKENAVPTIFLCTEPHDK
dmTransposase 51 SQKAAPAKGQTFKRFLNADAVPEKVIEPEPEKI
consensus     61        fKaapakg   k L  AVPt   l    EP
```

B

```
hTHAP1   1 MVQS-CSAYGCKNRYD---TKYSSCSEHFTPDCKKECN---NKLKENAVPTILCTEPHDK-
hTHAP3   1 METS-RARGCVNRYSS--KQHTVICSEPHRPCEGSAFGN---RENEHNAVPTILAFQDPTQ-
hTHAP5   1 MPLY-ICCKKRGRNNKD-SKYQF-ICSIHFTPDSLDIRWG---ISLKQTAVPTIFS-LPEDN-
hTHAP8   1 MPIY-RAPNCSNTAGRLGADNKF-SCHOHLCSIHFTPSCIQWRWG---VPFLEPPAVPSIIISRGPPAK-
hTHAP4   1 MVIC-RAVNFSNDQGK-GEK-TKYSFCSEHIKRKDSEKRLED---QHELKPTAVPSIRH--LTEK-
hTHAP2   1 MFTN-AAGPATTYN----GKHTFLCSKHPEASCDLIGQ---TR-RLKMDAVPTIFDFCTHIKSM-
hTHAP0   1 MNF-RAPNCFTRS-----DKTPDQLNKHIYRHETSMICRTSP---YRTVEDNAIPTIFDLTS---
hTHAP7   1 MPPH-SAAGGCTRDTRE-TNBGASHPIARICPPARCOKAENCR-RLDPS-GQGLMD
hTHAP9   1 VMPEH-SAAGGCTRDTVL-SEA---SEYYFCRHFEEDCELVGIS---GYRLKEGAVPTIESFS---
hTHAP6   1 VMGC-SAIGGASHCLPN-SEKGVEM-TDENLR---PGA----LCR-HEKKTDEDRSAPN----IKLRGVPSIEDSPYHLQ-
hTHAP11  1 MGFTCCVPGFLNSH----TTGHRICSVHQGG-------KYTVRVPTIIPLRGVNERKV
hTHAP10  1 MFAR-TWAHGCNTTK---GG------NDSRVICSDHPAPAC DVSSVI--QKNLRAFSQRRUNAGAVPTIH---
dmTransposase 1 -MKY-KFC-QKAVTG---ENSCTDTHINDSQKAAPAKGQTFKRFLNADAVESKVIEPEPEKI--
consensus 1 mpk  C  a  C  nr       P    ics HF         f                       K IK  aVpti t
```

| | | |
|---|---|---|
| GGGCAT | ACTAC | TGGCAA |
| GGGCAA | ACTGT | GGGCAT |
| GGGCAT | ACTAC | TGGCAA |
| GGGCAA | ACTAC | TGGCAA |
| GGGCCA | GTTCG | TTGCAA |
| GGGCAT | GTAC | TGGCAA |
| GGGCAA | CTGT | GGGCAA |
| GGGCAA | CACTAC | TGGCAA |
| GGGCAA | AGTAC | TGGCAA |

1) DR-5 Consensus Motif
*GGGCAA*nnnnn*TGGCAA*
(DR-4, DR-6)

B

| | | |
|---|---|---|
| TTGCCA | GTACTAAGTGT | GGGCAA |
| CTGCCA | GTACATAGTGT | GGGCAA |
| TTGCCA | GTACTAAGTGT | GGGCAA |
| CTGCCA | GTAGATAGTGT | GGGCAA |
| TTGCCA | GTAGTTAGGTGT | GGGCGA |
| TTGCCA | GTAGTTAGTGT | GGGCAA |
| TTGCCA | GTACCTACTAA | GGGCAA |
| TTGCCA | GTAGTTAGTGT | GGGCAG |
| CTGCCA | GTAGTAAGTGT | GGGCAG |

2) ER-11 Consensus Motif
TT*GCCA*nnnnnnnnn*GGGCAA*
(ER-12)

SEQUENCE LISTING

<160> NUMBER OF SEQ ID NOS: 263

<210> SEQ ID NO 1
<211> LENGTH: 74
<212> TYPE: PRT
<213> ORGANISM: Artificial Sequence

```
<220> FEATURE:
<223> OTHER INFORMATION: THAP domain consensus
<220> FEATURE:
<221> NAME/KEY: UNSURE
<222> LOCATION: 2-5, 7-21, 23-31, 33-49, 51-52, 55-73
<223> OTHER INFORMATION: Xaa = any of the twenty amino acids

<400> SEQUENCE: 1

Cys Xaa Xaa Xaa Cys Xaa Xaa Xaa Xaa Xaa Xaa Xaa Xaa Xaa
 1               5                   10                  15

Xaa Xaa Xaa Xaa Xaa Pro Xaa Xaa Xaa Xaa Xaa Xaa Xaa Xaa Trp
            20                  25                  30

Xaa Xaa Xaa Xaa Xaa Xaa Xaa Xaa Xaa Xaa Xaa Xaa Xaa Xaa Xaa
        35                  40                  45

Xaa Cys Xaa Xaa His Phe Xaa Xaa Xaa Xaa Xaa Xaa Xaa Xaa Xaa
    50                  55                  60

Xaa Xaa Xaa Xaa Xaa Xaa Xaa Xaa Xaa Pro
65                  70

<210> SEQ ID NO 2
<211> LENGTH: 81
<212> TYPE: PRT
<213> ORGANISM: Artificial Sequence
<220> FEATURE:
<223> OTHER INFORMATION: THAP domain consensus
<220> FEATURE:
<221> NAME/KEY: UNSURE
<222> LOCATION: 3-4, 6-9, 11-21, 24, 27-35, 37-41, 43-53, 56, 59-62,
      64-71, 74-75, 80
<223> OTHER INFORMATION: Xaa = any of the twenty amino acids

<400> SEQUENCE: 2

Met Pro Xaa Xaa Cys Xaa Xaa Xaa Xaa Cys Xaa Xaa Xaa Xaa Xaa
 1               5                   10                  15

Xaa Xaa Xaa Xaa Xaa Xaa Phe His Xaa Phe Pro Xaa Xaa Xaa Xaa Xaa
            20                  25                  30

Xaa Xaa Xaa Trp Xaa Xaa Xaa Xaa Xaa Arg Xaa Xaa Xaa Xaa Xaa
        35                  40                  45

Xaa Xaa Xaa Xaa Xaa Cys Ser Xaa His Phe Xaa Xaa Xaa Xaa Phe Xaa
    50                  55                  60

Xaa Xaa Xaa Xaa Xaa Xaa Xaa Leu Lys Xaa Xaa Ala Val Pro Thr Xaa
65                  70                  75                  80

Phe

<210> SEQ ID NO 3
<211> LENGTH: 213
<212> TYPE: PRT
<213> ORGANISM: Homo sapiens

<400> SEQUENCE: 3

Met Val Gln Ser Cys Ser Ala Tyr Gly Cys Lys Asn Arg Tyr Asp Lys
 1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80
```

```
Phe Leu Cys Thr Glu Pro His Asp Lys Lys Glu Asp Leu Leu Glu Pro
                85                  90                  95

Gln Glu Gln Leu Pro Pro Pro Leu Pro Pro Val Ser Gln Val
            100                 105                 110

Asp Ala Ala Ile Gly Leu Leu Met Pro Pro Leu Gln Thr Pro Val Asn
        115                 120                 125

Leu Ser Val Phe Cys Asp His Asn Tyr Thr Val Glu Asp Thr Met His
    130                 135                 140

Gln Arg Lys Arg Ile His Gln Leu Glu Gln Gln Val Glu Lys Leu Arg
145                 150                 155                 160

Lys Lys Leu Lys Thr Ala Gln Gln Arg Cys Arg Arg Gln Glu Arg Gln
                165                 170                 175

Leu Glu Lys Leu Lys Glu Val Val His Phe Gln Lys Gly Lys Asp Asp
            180                 185                 190

Val Ser Glu Arg Gly Tyr Val Ile Leu Pro Asn Asp Tyr Phe Glu Ile
        195                 200                 205

Val Glu Val Pro Ala
    210

<210> SEQ ID NO 4
<211> LENGTH: 228
<212> TYPE: PRT
<213> ORGANISM: Homo sapiens

<400> SEQUENCE: 4

Met Pro Thr Asn Cys Ala Ala Gly Cys Ala Thr Thr Tyr Asn Lys
 1               5                  10                  15

His Ile Asn Ile Ser Phe His Arg Phe Pro Leu Asp Pro Lys Arg Arg
             20                  25                  30

Lys Glu Trp Val Arg Leu Val Arg Arg Lys Asn Phe Val Pro Gly Lys
            35                  40                  45

His Thr Phe Leu Cys Ser Lys His Phe Glu Ala Ser Cys Phe Asp Leu
        50                  55                  60

Thr Gly Gln Thr Arg Arg Leu Lys Met Asp Ala Val Pro Thr Ile Phe
65                  70                  75                  80

Asp Phe Cys Thr His Ile Lys Ser Met Lys Leu Lys Ser Arg Asn Leu
                85                  90                  95

Leu Lys Lys Asn Asn Ser Cys Ser Pro Ala Gly Pro Ser Asn Leu Lys
                100                 105                 110

Ser Asn Ile Ser Ser Gln Gln Val Leu Leu Glu His Ser Tyr Ala Phe
        115                 120                 125

Arg Asn Pro Met Glu Ala Lys Lys Arg Ile Ile Lys Leu Glu Lys Glu
    130                 135                 140

Ile Ala Ser Leu Arg Arg Lys Met Lys Thr Cys Leu Gln Lys Glu Arg
145                 150                 155                 160

Arg Ala Thr Arg Arg Trp Ile Lys Ala Thr Cys Leu Val Lys Asn Leu
                165                 170                 175

Glu Ala Asn Ser Val Leu Pro Lys Gly Thr Ser Glu His Met Leu Pro
            180                 185                 190

Thr Ala Leu Ser Ser Leu Pro Leu Glu Asp Phe Lys Ile Leu Glu Gln
        195                 200                 205

Asp Gln Gln Asp Lys Thr Leu Leu Ser Leu Asn Leu Lys Gln Thr Lys
    210                 215                 220

Ser Thr Phe Ile
225
```

```
<210> SEQ ID NO 5
<211> LENGTH: 239
<212> TYPE: PRT
<213> ORGANISM: Homo sapiens

<400> SEQUENCE: 5

Met Pro Lys Ser Cys Ala Ala Arg Gln Cys Cys Asn Arg Tyr Ser Ser
 1               5                  10                  15

Arg Arg Lys Gln Leu Thr Phe His Arg Phe Pro Phe Ser Arg Pro Glu
            20                  25                  30

Leu Leu Lys Glu Trp Val Leu Asn Ile Gly Arg Gly Asn Phe Lys Pro
        35                  40                  45

Lys Gln His Thr Val Ile Cys Ser Glu His Phe Arg Pro Glu Cys Phe
 50                  55                  60

Ser Ala Phe Gly Asn Arg Lys Asn Leu Lys His Asn Ala Val Pro Thr
65                  70                  75                  80

Val Phe Ala Phe Gln Asp Pro Thr Gln Gln Val Arg Glu Asn Thr Asp
                85                  90                  95

Pro Ala Ser Glu Arg Gly Asn Ala Ser Ser Ser Gln Lys Glu Lys Val
            100                 105                 110

Leu Pro Glu Ala Gly Ala Gly Glu Asp Ser Pro Gly Arg Asn Met Asp
        115                 120                 125

Thr Ala Leu Glu Glu Leu Gln Leu Pro Pro Asn Ala Glu Gly His Val
130                 135                 140

Lys Gln Val Ser Pro Arg Arg Pro Gln Ala Thr Glu Ala Val Gly Arg
145                 150                 155                 160

Pro Thr Gly Pro Ala Gly Leu Arg Arg Thr Pro Asn Lys Gln Pro Ser
                165                 170                 175

Asp His Ser Tyr Ala Leu Leu Asp Leu Asp Ser Leu Lys Lys Lys Leu
            180                 185                 190

Phe Leu Thr Leu Lys Glu Asn Glu Lys Leu Arg Lys Arg Leu Gln Ala
        195                 200                 205

Gln Arg Leu Val Met Arg Arg Met Ser Ser Arg Leu Arg Ala Cys Lys
210                 215                 220

Gly His Gln Gly Leu Gln Ala Arg Leu Gly Pro Glu Gln Gln Ser
225                 230                 235

<210> SEQ ID NO 6
<211> LENGTH: 577
<212> TYPE: PRT
<213> ORGANISM: Homo sapiens

<400> SEQUENCE: 6

Met Val Ile Cys Cys Ala Ala Val Asn Cys Ser Asn Arg Gln Gly Lys
 1               5                  10                  15

Gly Glu Lys Arg Ala Val Ser Phe His Arg Phe Pro Leu Lys Asp Ser
            20                  25                  30

Lys Arg Leu Ile Gln Trp Leu Lys Ala Val Gln Arg Asp Asn Trp Thr
        35                  40                  45

Pro Thr Lys Tyr Ser Phe Leu Cys Ser Glu His Phe Thr Lys Asp Ser
 50                  55                  60

Phe Ser Lys Arg Leu Glu Asp Gln His Arg Leu Leu Lys Pro Thr Ala
65                  70                  75                  80

Val Pro Ser Ile Phe His Leu Thr Glu Lys Lys Arg Gly Ala Gly Gly
                85                  90                  95
```

-continued

```
His Gly Arg Thr Arg Arg Lys Asp Ala Ser Lys Ala Thr Gly Gly Val
            100                 105                 110
Arg Gly His Ser Ser Ala Ala Thr Gly Arg Gly Ala Ala Gly Trp Ser
            115                 120                 125
Pro Ser Ser Gly Asn Pro Met Ala Lys Pro Glu Ser Arg Arg Leu
            130                 135                 140
Lys Gln Ala Ala Leu Gln Gly Glu Ala Thr Pro Arg Ala Ala Gln Glu
145                 150                 155                 160
Ala Ala Ser Gln Glu Gln Ala Gln Ala Leu Glu Arg Thr Pro Gly
                    165                 170                 175
Asp Gly Leu Ala Thr Met Val Ala Gly Ser Gln Gly Lys Ala Glu Ala
                180                 185                 190
Ser Ala Thr Asp Ala Gly Asp Glu Ser Ala Thr Ser Ser Ile Glu Gly
                195                 200                 205
Gly Val Thr Asp Lys Ser Gly Ile Ser Met Asp Asp Phe Thr Pro Pro
            210                 215                 220
Gly Ser Gly Ala Cys Lys Phe Ile Gly Ser Leu His Ser Tyr Ser Phe
225                 230                 235                 240
Ser Ser Lys His Thr Arg Glu Arg Pro Ser Val Pro Arg Glu Pro Ile
                245                 250                 255
Asp Arg Lys Arg Leu Lys Lys Asp Val Glu Pro Ser Cys Ser Gly Ser
            260                 265                 270
Ser Leu Gly Pro Asp Lys Gly Leu Ala Gln Ser Pro Ser Ser Ser
            275                 280                 285
Leu Thr Ala Thr Pro Gln Lys Pro Ser Gln Ser Pro Ser Ala Pro Pro
            290                 295                 300
Ala Asp Val Thr Pro Lys Pro Ala Thr Glu Ala Val Gln Ser Glu His
305                 310                 315                 320
Ser Asp Ala Ser Pro Met Ser Ile Asn Glu Val Ile Leu Ser Ala Ser
                325                 330                 335
Gly Ala Cys Lys Leu Ile Asp Ser Leu His Ser Tyr Cys Phe Ser Ser
                340                 345                 350
Arg Gln Asn Lys Ser Gln Val Cys Cys Leu Arg Glu Gln Val Glu Lys
            355                 360                 365
Lys Asn Gly Glu Leu Lys Ser Leu Arg Gln Arg Val Ser Arg Ser Asp
370                 375                 380
Ser Gln Val Arg Lys Leu Gln Glu Lys Leu Asp Glu Leu Arg Arg Val
385                 390                 395                 400
Ser Val Pro Tyr Pro Ser Ser Leu Leu Ser Pro Ser Arg Glu Pro Pro
                405                 410                 415
Lys Met Asn Pro Val Val Glu Pro Leu Ser Trp Met Leu Gly Thr Trp
            420                 425                 430
Leu Ser Asp Pro Pro Gly Ala Gly Thr Tyr Pro Thr Leu Gln Pro Phe
            435                 440                 445
Gln Tyr Leu Glu Glu Val His Ile Ser His Val Gly Gln Pro Met Leu
450                 455                 460
Asn Phe Ser Phe Asn Ser Phe His Pro Asp Thr Arg Lys Pro Met His
465                 470                 475                 480
Arg Glu Cys Gly Phe Ile Arg Leu Lys Pro Asp Thr Asn Lys Val Ala
                485                 490                 495
Phe Val Ser Ala Gln Asn Thr Gly Val Val Glu Val Glu Glu Gly Glu
                500                 505                 510
```

```
Val Asn Gly Gln Glu Leu Cys Ile Ala Ser His Ser Ile Ala Arg Ile
        515                 520                 525

Ser Phe Ala Lys Glu Pro His Val Glu Gln Ile Thr Arg Lys Phe Arg
    530                 535                 540

Leu Asn Ser Glu Gly Lys Leu Glu Gln Thr Val Ser Met Ala Thr Thr
545                 550                 555                 560

Thr Gln Pro Met Thr Gln His Leu His Val Thr Tyr Lys Lys Val Thr
                565                 570                 575

Pro

<210> SEQ ID NO 7
<211> LENGTH: 395
<212> TYPE: PRT
<213> ORGANISM: Homo sapiens

<400> SEQUENCE: 7

Met Pro Arg Tyr Cys Ala Ala Ile Cys Cys Lys Asn Arg Arg Gly Arg
1               5                   10                  15

Asn Asn Lys Asp Arg Lys Leu Ser Phe Tyr Pro Phe Pro Leu His Asp
                20                  25                  30

Lys Glu Arg Leu Glu Lys Trp Leu Lys Asn Met Lys Arg Asp Ser Trp
            35                  40                  45

Val Pro Ser Lys Tyr Gln Phe Leu Cys Ser Asp His Phe Thr Pro Asp
50                  55                  60

Ser Leu Asp Ile Arg Trp Gly Ile Arg Tyr Leu Lys Gln Thr Ala Val
65                  70                  75                  80

Pro Thr Ile Phe Ser Leu Pro Glu Asp Asn Gln Gly Lys Asp Pro Ser
                85                  90                  95

Lys Lys Lys Ser Gln Lys Lys Asn Leu Glu Asp Glu Lys Glu Val Cys
                100                 105                 110

Pro Lys Ala Lys Ser Glu Glu Ser Phe Val Leu Asn Glu Thr Lys Lys
            115                 120                 125

Asn Ile Val Asn Thr Asp Val Pro His Gln His Pro Glu Leu Leu His
130                 135                 140

Ser Ser Ser Leu Val Lys Pro Pro Ala Pro Lys Thr Gly Ser Ile Gln
145                 150                 155                 160

Asn Asn Met Leu Thr Leu Asn Leu Val Lys Gln His Thr Gly Lys Pro
                165                 170                 175

Glu Ser Thr Leu Glu Thr Ser Val Asn Gln Asp Thr Gly Arg Gly Gly
            180                 185                 190

Phe His Thr Cys Phe Glu Asn Leu Asn Ser Thr Thr Ile Thr Leu Thr
        195                 200                 205

Thr Ser Asn Ser Glu Ser Ile His Gln Ser Leu Glu Thr Gln Glu Val
    210                 215                 220

Leu Glu Val Thr Thr Ser His Leu Ala Asn Pro Asn Phe Thr Ser Asn
225                 230                 235                 240

Ser Met Glu Ile Lys Ser Ala Gln Glu Asn Pro Phe Leu Phe Ser Thr
                245                 250                 255

Ile Asn Gln Thr Val Glu Glu Leu Asn Thr Asn Lys Glu Ser Val Ile
            260                 265                 270

Ala Ile Phe Val Pro Ala Glu Asn Ser Lys Pro Ser Val Asn Ser Phe
        275                 280                 285

Ile Ser Ala Gln Lys Glu Thr Thr Glu Met Glu Asp Thr Asp Ile Glu
    290                 295                 300
```

```
Asp Ser Leu Tyr Lys Asp Val Asp Tyr Gly Thr Glu Val Leu Gln Ile
305                 310                 315                 320

Glu His Ser Tyr Cys Arg Gln Asp Ile Asn Lys Glu His Leu Trp Gln
            325                 330                 335

Lys Val Ser Lys Leu His Ser Lys Ile Thr Leu Leu Glu Leu Lys Glu
        340                 345                 350

Gln Gln Thr Leu Gly Arg Leu Lys Ser Leu Glu Ala Leu Ile Arg Gln
    355                 360                 365

Leu Lys Gln Glu Asn Trp Leu Ser Glu Glu Asn Val Lys Ile Ile Glu
370                 375                 380

Asn His Phe Thr Thr Tyr Glu Val Thr Met Ile
385                 390                 395

<210> SEQ ID NO 8
<211> LENGTH: 222
<212> TYPE: PRT
<213> ORGANISM: Homo sapiens

<400> SEQUENCE: 8

Met Val Lys Cys Cys Ser Ala Ile Gly Cys Ala Ser Arg Cys Leu Pro
1               5                   10                  15

Asn Ser Lys Leu Lys Gly Leu Thr Phe His Val Phe Pro Thr Asp Glu
            20                  25                  30

Asn Ile Lys Arg Lys Trp Val Leu Ala Met Lys Arg Leu Asp Val Asn
        35                  40                  45

Ala Ala Gly Ile Trp Glu Pro Lys Lys Gly Asp Val Leu Cys Ser Arg
    50                  55                  60

His Phe Lys Lys Thr Asp Phe Asp Arg Ser Ala Pro Asn Ile Lys Leu
65                  70                  75                  80

Lys Pro Gly Val Ile Pro Ser Ile Phe Asp Ser Pro Tyr His Leu Gln
                85                  90                  95

Gly Lys Arg Glu Lys Leu His Cys Arg Lys Asn Phe Thr Leu Lys Thr
            100                 105                 110

Val Pro Ala Thr Asn Tyr Asn His His Leu Val Gly Ala Ser Ser Cys
        115                 120                 125

Ile Glu Glu Phe Gln Ser Gln Phe Ile Phe Glu His Ser Tyr Ser Val
    130                 135                 140

Met Asp Ser Pro Lys Lys Leu Lys His Lys Leu Asp His Val Ile Gly
145                 150                 155                 160

Glu Leu Glu Asp Thr Lys Glu Ser Leu Arg Asn Val Leu Asp Arg Glu
                165                 170                 175

Lys Arg Phe Gln Lys Ser Leu Arg Lys Thr Ile Arg Glu Leu Lys Asp
            180                 185                 190

Glu Cys Leu Ile Ser Gln Glu Thr Ala Asn Arg Leu Asp Thr Phe Cys
        195                 200                 205

Trp Asp Cys Cys Gln Glu Ser Ile Glu Gln Asp Tyr Ile Ser
    210                 215                 220

<210> SEQ ID NO 9
<211> LENGTH: 309
<212> TYPE: PRT
<213> ORGANISM: Homo sapiens
```

```
<400> SEQUENCE: 9

Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
            20                  25                  30

Asn Pro Arg Arg Gly Leu Trp Leu Ala Asn Cys Gln Arg Leu Asp Pro
        35                  40                  45

Ser Gly Gln Gly Leu Trp Asp Pro Ala Ser Glu Tyr Ile Tyr Phe Cys
    50                  55                  60

Ser Lys His Phe Glu Glu Asp Cys Phe Glu Leu Val Gly Ile Ser Gly
65                  70                  75                  80

Tyr His Arg Leu Lys Glu Gly Ala Val Pro Thr Ile Phe Glu Ser Phe
                85                  90                  95

Ser Lys Leu Arg Arg Thr Thr Lys Thr Lys Gly His Ser Tyr Pro Pro
            100                 105                 110

Gly Pro Pro Glu Val Ser Arg Leu Arg Arg Cys Arg Lys Arg Cys Ser
        115                 120                 125

Glu Gly Arg Gly Pro Thr Thr Pro Phe Ser Pro Pro Pro Ala Asp
    130                 135                 140

Val Thr Cys Phe Pro Val Glu Ala Ser Ala Pro Ala Thr Leu Pro
145                 150                 155                 160

Ala Ser Pro Ala Gly Arg Leu Glu Pro Gly Leu Ser Ser Pro Phe Ser
                165                 170                 175

Asp Leu Leu Gly Pro Leu Gly Ala Gln Ala Asp Glu Ala Gly Cys Ser
            180                 185                 190

Ala Gln Pro Ser Pro Glu Arg Gln Pro Ser Pro Leu Glu Pro Arg Pro
        195                 200                 205

Val Ser Pro Ser Ala Tyr Met Leu Arg Leu Pro Pro Pro Ala Gly Ala
    210                 215                 220

Tyr Ile Gln Asn Glu His Ser Tyr Gln Val Gly Ser Ala Leu Leu Trp
225                 230                 235                 240

Lys Arg Arg Ala Glu Ala Ala Leu Asp Ala Leu Asp Lys Ala Gln Arg
                245                 250                 255

Gln Leu Gln Ala Cys Lys Arg Arg Glu Gln Arg Leu Arg Leu Arg Leu
            260                 265                 270

Thr Lys Leu Gln Gln Glu Arg Ala Arg Glu Lys Arg Ala Gln Ala Asp
        275                 280                 285

Ala Arg Gln Thr Leu Lys Glu His Val Gln Asp Phe Ala Met Gln Leu
    290                 295                 300

Ser Ser Ser Met Ala
305

<210> SEQ ID NO 10
<211> LENGTH: 274
<212> TYPE: PRT
<213> ORGANISM: Homo sapiens

<400> SEQUENCE: 10

Met Pro Lys Tyr Cys Arg Ala Pro Asn Cys Ser Asn Thr Ala Gly Arg
1               5                   10                  15

Leu Gly Ala Asp Asn Arg Pro Val Ser Phe Tyr Lys Phe Pro Leu Lys
            20                  25                  30

Asp Gly Pro Arg Leu Gln Ala Trp Leu Gln His Met Gly Cys Glu His
        35                  40                  45
```

-continued

```
Trp Val Pro Ser Cys His Gln His Leu Cys Ser Glu His Phe Thr Pro
 50                  55                  60

Ser Cys Phe Gln Trp Arg Trp Gly Val Arg Tyr Leu Arg Pro Asp Ala
 65                  70                  75                  80

Val Pro Ser Ile Phe Ser Arg Gly Pro Ala Lys Ser Gln Arg Arg
                 85                  90                  95

Thr Arg Ser Thr Gln Lys Pro Val Ser Pro Pro Pro Leu Gln Lys
                100                 105                 110

Asn Thr Pro Leu Pro Gln Ser Pro Ala Ile Pro Val Ser Gly Pro Val
                115                 120                 125

Arg Leu Val Val Leu Gly Pro Thr Ser Gly Ser Pro Lys Thr Val Ala
130                 135                 140

Thr Met Leu Leu Thr Pro Leu Ala Pro Ala Pro Thr Pro Glu Arg Ser
145                 150                 155                 160

Gln Pro Glu Val Pro Ala Gln Ala Gln Thr Gly Leu Gly Pro Val
                165                 170                 175

Leu Gly Ala Leu Gln Arg Arg Val Arg Arg Leu Gln Arg Cys Gln Glu
                180                 185                 190

Arg His Gln Ala Gln Leu Gln Ala Leu Glu Arg Leu Ala Gln Leu
                195                 200                 205

His Gly Glu Ser Leu Leu Ala Arg Ala Arg Gly Leu Gln Arg Leu
                210                 215                 220

Thr Thr Ala Gln Thr Leu Gly Pro Glu Glu Ser Gln Thr Phe Thr Ile
225                 230                 235                 240

Ile Cys Gly Gly Pro Asp Ile Ala Met Val Leu Ala Gln Asp Pro Ala
                245                 250                 255

Pro Ala Thr Val Asp Ala Lys Pro Glu Leu Leu Asp Thr Arg Ile Pro
                260                 265                 270

Ser Ala

<210> SEQ ID NO 11
<211> LENGTH: 903
<212> TYPE: PRT
<213> ORGANISM: Homo sapiens

<400> SEQUENCE: 11

Met Thr Arg Ser Cys Ser Ala Val Gly Cys Ser Thr Arg Asp Thr Val
 1                5                  10                  15

Leu Ser Arg Glu Arg Gly Leu Ser Phe His Gln Phe Pro Thr Asp Thr
                 20                  25                  30

Ile Gln Arg Ser Lys Trp Ile Arg Ala Val Asn Arg Val Asp Pro Arg
                 35                  40                  45

Ser Lys Lys Ile Trp Ile Pro Gly Pro Gly Ala Ile Leu Cys Ser Lys
 50                  55                  60

His Phe Gln Glu Ser Asp Phe Glu Ser Tyr Gly Ile Arg Arg Lys Leu
 65                  70                  75                  80

Lys Lys Gly Ala Val Pro Ser Val Ser Leu Tyr Lys Ile Pro Gln Gly
                 85                  90                  95

Val His Leu Lys Gly Lys Ala Arg Gln Lys Ile Leu Lys Gln Pro Leu
                100                 105                 110

Pro Asp Asn Ser Gln Glu Val Ala Thr Glu Asp His Asn Tyr Ser Leu
                115                 120                 125

Lys Thr Pro Leu Thr Ile Gly Ala Glu Lys Leu Ala Glu Val Gln Gln
                130                 135                 140
```

-continued

```
Met Leu Gln Val Ser Lys Lys Arg Leu Ile Ser Val Lys Asn Tyr Arg
145                 150                 155                 160

Met Ile Lys Lys Arg Lys Gly Leu Arg Leu Ile Asp Ala Leu Val Glu
                165                 170                 175

Glu Lys Leu Leu Ser Glu Glu Thr Glu Cys Leu Leu Arg Ala Gln Phe
            180                 185                 190

Ser Asp Phe Lys Trp Glu Leu Tyr Asn Trp Arg Glu Thr Asp Glu Tyr
            195                 200                 205

Ser Ala Glu Met Lys Gln Phe Ala Cys Thr Leu Tyr Leu Cys Ser Ser
        210                 215                 220

Lys Val Tyr Asp Tyr Val Arg Lys Ile Leu Lys Leu Pro His Ser Ser
225                 230                 235                 240

Ile Leu Arg Thr Trp Leu Ser Lys Cys Gln Pro Ser Pro Gly Phe Asn
                245                 250                 255

Ser Asn Ile Phe Ser Phe Leu Gln Arg Arg Val Glu Asn Gly Asp Gln
            260                 265                 270

Leu Tyr Gln Tyr Cys Ser Leu Leu Ile Lys Ser Ile Pro Leu Lys Gln
        275                 280                 285

Gln Leu Gln Trp Asp Pro Ser Ser His Ser Leu Gln Gly Phe Met Asp
290                 295                 300

Phe Gly Leu Gly Lys Leu Asp Ala Asp Glu Thr Pro Leu Ala Ser Glu
305                 310                 315                 320

Thr Val Leu Leu Met Ala Val Gly Ile Phe Gly His Trp Arg Thr Pro
                325                 330                 335

Leu Gly Tyr Phe Phe Val Asn Arg Ala Ser Gly Tyr Leu Gln Ala Gln
            340                 345                 350

Leu Leu Arg Leu Thr Ile Gly Lys Leu Ser Asp Ile Gly Ile Thr Val
        355                 360                 365

Leu Ala Val Thr Ser Asp Ala Thr Ala His Ser Val Gln Met Ala Lys
    370                 375                 380

Ala Leu Gly Ile His Ile Asp Gly Asp Asp Met Lys Cys Thr Phe Gln
385                 390                 395                 400

His Pro Ser Ser Ser Gln Gln Ile Ala Tyr Phe Phe Asp Ser Cys
                405                 410                 415

His Leu Leu Arg Leu Ile Arg Asn Ala Phe Gln Asn Phe Gln Ser Ile
            420                 425                 430

Gln Phe Ile Asn Gly Ile Ala His Trp Gln His Leu Val Glu Leu Val
        435                 440                 445

Ala Leu Glu Glu Gln Glu Leu Ser Asn Met Glu Arg Ile Pro Ser Thr
450                 455                 460

Leu Ala Asn Leu Lys Asn His Val Leu Lys Val Asn Ser Ala Thr Gln
465                 470                 475                 480

Leu Phe Ser Glu Ser Val Ala Ser Ala Leu Glu Tyr Leu Leu Ser Leu
                485                 490                 495

Asp Leu Pro Pro Phe Gln Asn Cys Ile Gly Thr Ile His Phe Leu Arg
            500                 505                 510

Leu Ile Asn Asn Leu Phe Asp Ile Phe Asn Ser Arg Asn Cys Tyr Gly
        515                 520                 525

Lys Gly Leu Lys Gly Pro Leu Leu Pro Glu Thr Tyr Ser Lys Ile Asn
    530                 535                 540

His Val Leu Ile Glu Ala Lys Thr Ile Phe Val Thr Leu Ser Asp Thr
545                 550                 555                 560
```

```
Ser Asn Asn Gln Ile Ile Lys Gly Lys Gln Lys Leu Gly Phe Leu Gly
            565                 570                 575

Phe Leu Leu Asn Ala Glu Ser Leu Lys Trp Leu Tyr Gln Asn Tyr Val
            580                 585                 590

Phe Pro Lys Val Met Pro Phe Pro Tyr Leu Leu Thr Tyr Lys Phe Ser
            595                 600                 605

His Asp His Leu Glu Leu Phe Leu Lys Met Leu Arg Gln Val Leu Val
610                 615                 620

Thr Ser Ser Ser Pro Thr Cys Met Ala Phe Gln Lys Ala Tyr Tyr Asn
625                 630                 635                 640

Leu Glu Thr Arg Tyr Lys Phe Gln Asp Glu Val Phe Leu Ser Lys Val
            645                 650                 655

Ser Ile Phe Asp Ile Ser Ile Ala Arg Arg Lys Asp Leu Ala Leu Trp
            660                 665                 670

Thr Val Gln Arg Gln Tyr Gly Val Ser Val Thr Lys Thr Val Phe His
            675                 680                 685

Glu Glu Gly Ile Cys Gln Asp Trp Ser His Cys Ser Leu Ser Glu Ala
            690                 695                 700

Leu Leu Asp Leu Ser Asp His Arg Arg Asn Leu Ile Cys Tyr Ala Gly
705                 710                 715                 720

Tyr Val Ala Asn Lys Leu Ser Ala Leu Leu Thr Cys Glu Asp Cys Ile
            725                 730                 735

Thr Ala Leu Tyr Ala Ser Asp Leu Lys Ala Ser Lys Ile Gly Ser Leu
            740                 745                 750

Leu Phe Val Lys Lys Asn Gly Leu His Phe Pro Ser Glu Ser Leu
            755                 760                 765

Cys Arg Val Ile Asn Ile Cys Glu Arg Val Val Arg Thr His Ser Arg
            770                 775                 780

Met Ala Ile Phe Glu Leu Val Ser Lys Gln Arg Glu Leu Tyr Leu Gln
785                 790                 795                 800

Gln Lys Ile Leu Cys Glu Leu Ser Gly His Ile Asp Leu Phe Val Asp
            805                 810                 815

Val Asn Lys His Leu Phe Asp Gly Glu Val Cys Ala Ile Asn His Phe
            820                 825                 830

Val Lys Leu Leu Lys Asp Ile Ile Ile Cys Phe Leu Asn Ile Arg Ala
            835                 840                 845

Lys Asn Val Ala Gln Asn Pro Leu Lys His His Ser Glu Arg Thr Asp
850                 855                 860

Met Lys Thr Leu Ser Arg Lys His Trp Ser Pro Val Gln Asp Tyr Lys
865                 870                 875                 880

Cys Ser Ser Phe Ala Asn Thr Ser Lys Phe Arg His Leu Leu Ser
            885                 890                 895

Asn Asp Gly Tyr Pro Phe Lys
            900

<210> SEQ ID NO 12
<211> LENGTH: 257
<212> TYPE: PRT
<213> ORGANISM: Homo sapiens

<400> SEQUENCE: 12

Met Pro Ala Arg Cys Val Ala Ala His Cys Gly Asn Thr Thr Lys Ser
1               5                   10                  15

Gly Lys Ser Leu Phe Arg Phe Pro Lys Asp Arg Ala Val Arg Leu Leu
            20                  25                  30
```

```
Trp Asp Arg Phe Val Arg Gly Cys Arg Ala Asp Trp Tyr Gly Gly Asn
     35                  40                  45

Asp Arg Ser Val Ile Cys Ser Asp His Phe Ala Pro Ala Cys Phe Asp
 50                  55                  60

Val Ser Ser Val Ile Gln Lys Asn Leu Arg Phe Ser Gln Arg Leu Arg
 65                  70                  75                  80

Leu Val Ala Gly Ala Val Pro Thr Leu His Arg Val Pro Ala Pro Ala
                 85                  90                  95

Pro Lys Arg Gly Glu Glu Gly Asp Gln Ala Gly Arg Leu Asp Thr Arg
                100                 105                 110

Gly Glu Leu Gln Ala Ala Arg His Ser Glu Ala Ala Pro Gly Pro Val
             115                 120                 125

Ser Cys Thr Arg Pro Arg Ala Gly Lys Gln Ala Ala Ser Gln Ile
         130                 135                 140

Thr Cys Glu Asn Glu Leu Val Gln Thr Gln Pro His Ala Asp Asn Pro
145                 150                 155                 160

Ser Asn Thr Val Thr Ser Val Pro Thr His Cys Glu Gly Pro Val
                 165                 170                 175

His Lys Ser Thr Gln Ile Ser Leu Lys Arg Pro Arg His Arg Ser Val
             180                 185                 190

Gly Ile Gln Ala Lys Val Lys Ala Phe Gly Lys Arg Leu Cys Asn Ala
         195                 200                 205

Thr Thr Gln Thr Glu Glu Leu Trp Ser Arg Thr Ser Ser Leu Phe Asp
210                 215                 220

Ile Tyr Ser Ser Asp Ser Glu Thr Asp Thr Asp Trp Asp Ile Lys Ser
225                 230                 235                 240

Glu Gln Ser Asp Leu Ser Tyr Met Ala Val Gln Val Lys Glu Glu Thr
                245                 250                 255

Cys

<210> SEQ ID NO 13
<211> LENGTH: 314
<212> TYPE: PRT
<213> ORGANISM: Homo sapiens

<400> SEQUENCE: 13

Met Pro Gly Phe Thr Cys Cys Val Pro Gly Cys Tyr Asn Asn Ser His
 1               5                  10                  15

Arg Asp Lys Ala Leu His Phe Tyr Thr Phe Pro Lys Asp Ala Glu Leu
                 20                  25                  30

Arg Arg Leu Trp Leu Lys Asn Val Ser Arg Ala Gly Val Ser Gly Cys
             35                  40                  45

Phe Ser Thr Phe Gln Pro Thr Thr Gly His Arg Leu Cys Ser Val His
         50                  55                  60

Phe Gln Gly Gly Arg Lys Thr Tyr Thr Val Arg Val Pro Thr Ile Phe
 65                  70                  75                  80

Pro Leu Arg Gly Val Asn Glu Arg Lys Val Ala Arg Arg Pro Ala Gly
                 85                  90                  95

Ala Ala Ala Ala Arg Arg Arg Gln Gln Gln Gln Gln Gln Gln Gln Gln
                100                 105                 110

Gln Gln Gln Gln Gln Gln Gln Gln Gln Gln Gln Gln Gln Gln Gln Gln
             115                 120                 125

Gln Gln Gln Gln Ser Ser Pro Ser Ala Ser Thr Ala Gln Thr Ala Gln
         130                 135                 140
```

-continued

Leu Gln Pro Asn Leu Val Ser Ala Ser Ala Val Leu Leu Thr Leu
145                 150                 155                 160

Gln Ala Thr Val Asp Ser Ser Gln Ala Pro Gly Ser Val Gln Pro Ala
        165                 170                 175

Pro Ile Thr Pro Thr Gly Glu Asp Val Lys Pro Ile Asp Leu Thr Val
            180                 185                 190

Gln Val Glu Phe Ala Ala Glu Gly Ala Ala Ala Ala Ala Ala
        195                 200                 205

Ser Glu Leu Gln Ala Ala Thr Ala Gly Leu Glu Ala Ala Glu Cys Pro
    210                 215                 220

Met Gly Pro Gln Leu Val Val Gly Glu Glu Gly Phe Pro Asp Thr
225                 230                 235                 240

Gly Ser Asp His Ser Tyr Ser Leu Ser Ser Gly Thr Thr Glu Glu Glu
                245                 250                 255

Leu Leu Arg Lys Leu Asn Glu Gln Arg Asp Ile Leu Ala Leu Met Glu
                260                 265                 270

Val Lys Met Lys Glu Met Lys Gly Ser Ile Arg His Leu Arg Leu Thr
            275                 280                 285

Glu Ala Lys Leu Arg Glu Glu Leu Arg Glu Lys Asp Arg Leu Leu Ala
    290                 295                 300

Met Ala Val Ile Arg Lys Lys His Gly Met
305                 310

<210> SEQ ID NO 14
<211> LENGTH: 761
<212> TYPE: PRT
<213> ORGANISM: Homo sapiens

<400> SEQUENCE: 14

Met Pro Asn Phe Cys Ala Ala Pro Asn Cys Thr Arg Lys Ser Thr Gln
1               5                   10                  15

Ser Asp Leu Ala Phe Phe Arg Phe Pro Arg Asp Pro Ala Arg Cys Gln
            20                  25                  30

Lys Trp Val Glu Asn Cys Arg Arg Ala Asp Leu Glu Asp Lys Thr Pro
        35                  40                  45

Asp Gln Leu Asn Lys His Tyr Arg Leu Cys Ala Lys His Phe Glu Thr
    50                  55                  60

Ser Met Ile Cys Arg Thr Ser Pro Tyr Arg Thr Val Leu Arg Asp Asn
65                  70                  75                  80

Ala Ile Pro Thr Ile Phe Asp Leu Thr Ser His Leu Asn Asn Pro His
                85                  90                  95

Ser Arg His Arg Lys Arg Ile Lys Glu Leu Ser Glu Asp Glu Ile Arg
                100                 105                 110

Thr Leu Lys Gln Lys Lys Ile Asp Glu Thr Ser Glu Gln Glu Gln Lys
            115                 120                 125

His Lys Glu Thr Asn Asn Ser Asn Ala Gln Asn Pro Ser Glu Glu Glu
    130                 135                 140

Gly Glu Gly Gln Asp Glu Asp Ile Leu Pro Leu Thr Leu Glu Glu Lys
145                 150                 155                 160

Glu Asn Lys Glu Tyr Leu Lys Ser Leu Phe Glu Ile Leu Ile Leu Met
                165                 170                 175

Gly Lys Gln Asn Ile Pro Leu Asp Gly His Glu Ala Asp Glu Ile Pro
                180                 185                 190

Glu Gly Leu Phe Thr Pro Asp Asn Phe Gln Ala Leu Leu Glu Cys Arg
            195                 200                 205

-continued

```
Ile Asn Ser Gly Glu Glu Val Leu Arg Lys Arg Phe Glu Thr Thr Ala
210                 215                 220
Val Asn Thr Leu Phe Cys Ser Lys Thr Gln Gln Arg Gln Met Leu Glu
225                 230                 235                 240
Ile Cys Glu Ser Cys Ile Arg Glu Glu Thr Leu Arg Glu Val Arg Asp
                245                 250                 255
Ser His Phe Phe Ser Ile Ile Thr Asp Asp Val Val Asp Ile Ala Gly
            260                 265                 270
Glu Glu His Leu Pro Val Leu Arg Phe Val Asp Glu Ser His Asn
        275                 280                 285
Leu Arg Glu Glu Phe Ile Gly Phe Leu Pro Tyr Glu Ala Asp Ala Glu
290                 295                 300
Ile Leu Ala Val Lys Phe His Thr Met Ile Thr Glu Lys Trp Gly Leu
305                 310                 315                 320
Asn Met Glu Tyr Cys Arg Gly Gln Ala Tyr Ile Val Ser Ser Gly Phe
                325                 330                 335
Ser Ser Lys Met Lys Val Val Ala Ser Arg Leu Leu Glu Lys Tyr Pro
                340                 345                 350
Gln Ala Ile Tyr Thr Leu Cys Ser Ser Cys Ala Leu Asn Met Trp Leu
            355                 360                 365
Ala Lys Ser Val Pro Val Met Gly Val Ser Val Ala Leu Gly Thr Ile
370                 375                 380
Glu Glu Val Cys Ser Phe Phe His Arg Ser Pro Gln Leu Leu Leu Glu
385                 390                 395                 400
Leu Asp Asn Val Ile Ser Val Leu Phe Gln Asn Ser Lys Glu Arg Gly
                405                 410                 415
Lys Glu Leu Lys Glu Ile Cys His Ser Gln Trp Thr Gly Arg His Asp
                420                 425                 430
Ala Phe Glu Ile Leu Val Glu Leu Leu Gln Ala Leu Val Leu Cys Leu
            435                 440                 445
Asp Gly Ile Asn Ser Asp Thr Asn Ile Arg Trp Asn Asn Tyr Ile Ala
            450                 455                 460
Gly Arg Ala Phe Val Leu Cys Ser Ala Val Ser Asp Phe Asp Phe Ile
465                 470                 475                 480
Val Thr Ile Val Val Leu Lys Asn Val Leu Ser Phe Thr Arg Ala Phe
                485                 490                 495
Gly Lys Asn Leu Gln Gly Gln Thr Ser Asp Val Phe Phe Ala Ala Gly
            500                 505                 510
Ser Leu Thr Ala Val Leu His Ser Leu Asn Glu Val Met Glu Asn Ile
            515                 520                 525
Glu Val Tyr His Glu Phe Trp Phe Glu Glu Ala Thr Asn Leu Ala Thr
530                 535                 540
Lys Leu Asp Ile Gln Met Lys Leu Pro Gly Lys Phe Arg Arg Ala His
545                 550                 555                 560
Gln Gly Asn Leu Glu Ser Gln Leu Thr Ser Glu Ser Tyr Tyr Lys Glu
                565                 570                 575
Thr Leu Ser Val Pro Thr Val Glu His Ile Ile Gln Glu Leu Lys Asp
            580                 585                 590
Ile Phe Ser Glu Gln His Leu Lys Ala Leu Lys Cys Leu Ser Leu Val
            595                 600                 605
Pro Ser Val Met Gly Gln Leu Lys Phe Asn Thr Ser Glu Glu His His
610                 615                 620
```

```
Ala Asp Met Tyr Arg Ser Asp Leu Pro Asn Pro Asp Thr Leu Ser Ala
625                 630                 635                 640

Glu Leu His Cys Trp Arg Ile Lys Trp Lys His Arg Gly Lys Asp Ile
            645                 650                 655

Glu Leu Pro Ser Thr Ile Tyr Glu Ala Leu His Leu Pro Asp Ile Lys
            660                 665                 670

Phe Phe Pro Asn Val Tyr Ala Leu Leu Lys Val Leu Cys Ile Leu Pro
            675                 680                 685

Val Met Lys Val Glu Asn Glu Arg Tyr Glu Asn Gly Arg Lys Arg Leu
            690                 695                 700

Lys Ala Tyr Leu Arg Asn Thr Leu Thr Asp Gln Arg Ser Ser Asn Leu
705                 710                 715                 720

Ala Leu Leu Asn Ile Asn Phe Asp Ile Lys His Asp Leu Asp Leu Met
            725                 730                 735

Val Asp Thr Tyr Ile Lys Leu Tyr Thr Ser Lys Ser Glu Leu Pro Thr
            740                 745                 750

Asp Asn Ser Glu Thr Val Glu Asn Thr
            755                 760

<210> SEQ ID NO 15
<211> LENGTH: 38
<212> TYPE: PRT
<213> ORGANISM: Artificial Sequence
<220> FEATURE:
<223> OTHER INFORMATION: Consensus sequence for PAR4 binding domain of
      THAP
<220> FEATURE:
<221> NAME/KEY: UNSURE
<222> LOCATION: (1)...(38)
<223> OTHER INFORMATION: Xaa = Any Amino Acid

<400> SEQUENCE: 15

Leu Glu Xaa Xaa Xaa Xaa Xaa Xaa Xaa Xaa Xaa Xaa Xaa Xaa
1               5                   10                  15

Gln Arg Xaa Arg Arg Gln Xaa Arg Xaa Xaa Xaa Xaa Xaa Xaa Xaa Xaa
            20                  25                  30

Xaa Xaa Xaa Gln Xaa Glu
            35

<210> SEQ ID NO 16
<211> LENGTH: 73
<212> TYPE: PRT
<213> ORGANISM: Sus scrofa

<400> SEQUENCE: 16

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Lys Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
        50                  55                  60

Arg Glu Cys Asn Asn Lys Leu Leu Lys
65                  70

<210> SEQ ID NO 17
<211> LENGTH: 99
<212> TYPE: PRT
<213> ORGANISM: Sus scrofa
```

<400> SEQUENCE: 17

```
Met Val Lys Cys Cys Ser Ala Ile Gly Cys Ala Ser Arg Cys Leu Pro
1               5                   10                  15

Asn Ser Lys Leu Lys Gly Leu Thr Phe His Val Phe Pro Thr Asp Glu
            20                  25                  30

Lys Val Lys Arg Lys Trp Val Leu Ala Met Lys Arg Leu Asp Val Asn
        35                  40                  45

Ala Ala Gly Met Trp Glu Pro Lys Lys Gly Asp Val Leu Cys Ser Arg
    50                  55                  60

His Phe Lys Lys Thr Asp Phe Asp Arg Thr Thr Pro Asn Ile Lys Leu
65                  70                  75                  80

Lys Pro Gly Val Ile Pro Ser Ile Phe Asp Ser Pro Ser His Leu Thr
                85                  90                  95

Gly Glu Glu
```

<210> SEQ ID NO 18
<211> LENGTH: 103
<212> TYPE: PRT
<213> ORGANISM: Sus scrofa

<400> SEQUENCE: 18

```
Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
            20                  25                  30

Asn Pro Arg Arg Gly Leu Trp Leu Ala Asn Cys Gln Arg Leu Asp Pro
        35                  40                  45

Ser Gly Gln Gly Leu Trp Asp Pro Ala Ser Glu Tyr Ile Tyr Phe Cys
    50                  55                  60

Ser Lys His Phe Glu Glu Asn Cys Phe Glu Leu Val Gly Ile Ser Gly
65                  70                  75                  80

Tyr His Arg Leu Lys Glu Gly Ala Val Pro Thr Ile Phe Glu Ser Phe
                85                  90                  95

Ser Lys Leu Arg Arg Thr Ala
            100
```

<210> SEQ ID NO 19
<211> LENGTH: 99
<212> TYPE: PRT
<213> ORGANISM: Sus scrofa

<400> SEQUENCE: 19

```
Met Thr Arg Ser Cys Ser Ala Val Gly Cys Ser Thr Arg Asp Thr Val
1               5                   10                  15

Leu Ser Arg Glu Arg Gly Leu Ser Phe His Gln Phe Pro Thr Asp Thr
            20                  25                  30

Ile Gln Arg Ser Gln Trp Ile Arg Ala Val Asn Arg Met Asp Pro Arg
        35                  40                  45

Ser Lys Lys Ile Trp Ile Pro Gly Pro Gly Ala Met Leu Cys Ser Lys
    50                  55                  60

His Phe Gln Glu Ser Asp Phe Glu Ser Tyr Gly Ile Arg Arg Lys Leu
65                  70                  75                  80

Lys Lys Gly Ala Val Pro Ser Val Ser Leu Tyr Lys Val Leu Gln Gly
                85                  90                  95

Ala His Leu
```

```
<210> SEQ ID NO 20
<211> LENGTH: 92
<212> TYPE: PRT
<213> ORGANISM: Bos taurus

<400> SEQUENCE: 20

Met Pro Lys Ser Cys Ala Ala Arg Gln Cys Cys Asn Arg Tyr Ser Asn
1               5                   10                  15

Arg Arg Lys Gln Leu Thr Phe His Arg Phe Pro Phe Ser Arg Pro Glu
            20                  25                  30

Leu Leu Lys Glu Trp Val Leu Asn Ile Gly Arg Gly Asp Phe Glu Pro
        35                  40                  45

Lys Gln His Thr Val Ile Cys Ser Glu His Phe Arg Pro Glu Cys Phe
50                  55                  60

Ser Ala Phe Gly Asn Arg Lys Asn Leu Lys His Asn Ala Val Pro Thr
65                  70                  75                  80

Val Phe Ala Phe Gln Gly Pro Pro Gln Leu Val Arg
                85                  90

<210> SEQ ID NO 21
<211> LENGTH: 75
<212> TYPE: PRT
<213> ORGANISM: Bos taurus

<400> SEQUENCE: 21

Arg Leu Pro Lys Lys Asp Asn Pro Arg Arg Gly Leu Trp Leu Ala Asn
1               5                   10                  15

Cys Gln Arg Leu Asp Pro Ser Gly Gln Gly Leu Trp Asp Pro Ala Ser
            20                  25                  30

Glu Tyr Ile Tyr Phe Cys Ser Lys His Phe Glu Asn Cys Phe Glu
        35                  40                  45

Leu Val Gly Ile Ser Gly Tyr His Arg Leu Lys Glu Gly Ala Val Pro
50                  55                  60

Thr Ile Phe Glu Ser Phe Ser Lys Leu Arg Arg
65                  70                  75

<210> SEQ ID NO 22
<211> LENGTH: 91
<212> TYPE: PRT
<213> ORGANISM: Mus musculus

<400> SEQUENCE: 22

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Gln Trp Glu Ala Ala Val Lys Arg Lys Asn Phe Lys Pro Thr
        35                  40                  45

Lys Tyr Ser Ser Ile Cys Ser Glu His Phe Thr Pro Asp Cys Phe Lys
50                  55                  60

Arg Glu Cys Asn Asn Lys Leu Leu Lys Glu Asn Ala Val Pro Thr Ile
65                  70                  75                  80

Phe Leu Tyr Ile Glu Pro His Glu Lys Lys Glu
                85                  90

<210> SEQ ID NO 23
<211> LENGTH: 90
<212> TYPE: PRT
<213> ORGANISM: Mus musculus
```

```
<400> SEQUENCE: 23

Met Pro Thr Asn Cys Ala Ala Gly Cys Ala Ala Thr Tyr Asn Lys
1               5                   10                  15

His Ile Asn Ile Ser Phe His Arg Phe Pro Leu Asp Pro Lys Arg Arg
            20                  25                  30

Lys Glu Trp Val Arg Leu Val Arg Arg Lys Asn Phe Val Pro Gly Lys
        35                  40                  45

His Thr Phe Leu Cys Ser Lys His Phe Glu Ala Ser Cys Phe Asp Leu
    50                  55                  60

Thr Gly Gln Thr Arg Arg Leu Lys Met Asp Ala Val Pro Thr Ile Phe
65                  70                  75                  80

Asp Phe Cys Thr His Ile Lys Ser Leu Lys
                85                  90

<210> SEQ ID NO 24
<211> LENGTH: 92
<212> TYPE: PRT
<213> ORGANISM: Mus musculus

<400> SEQUENCE: 24

Met Pro Lys Ser Cys Ala Ala Arg Gln Cys Cys Asn Arg Tyr Ser Ser
1               5                   10                  15

Arg Arg Lys Gln Leu Thr Phe His Arg Phe Pro Phe Ser Arg Pro Glu
            20                  25                  30

Leu Leu Arg Glu Trp Val Leu Asn Ile Gly Arg Ala Asp Phe Lys Pro
        35                  40                  45

Lys Gln His Thr Val Ile Cys Ser Glu His Phe Arg Pro Glu Cys Phe
    50                  55                  60

Ser Ala Phe Gly Asn Arg Lys Asn Leu Lys His Asn Ala Val Pro Thr
65                  70                  75                  80

Val Phe Ala Phe Gln Asn Pro Thr Glu Val Cys Pro
                85                  90

<210> SEQ ID NO 25
<211> LENGTH: 95
<212> TYPE: PRT
<213> ORGANISM: Mus musculus

<400> SEQUENCE: 25

Met Val Ile Cys Cys Ala Ala Val Asn Cys Ser Asn Arg Gln Gly Lys
1               5                   10                  15

Gly Glu Lys Arg Ala Val Ser Phe His Arg Phe Pro Leu Lys Asp Ser
            20                  25                  30

Lys Arg Leu Ile Gln Trp Leu Lys Ala Val Gln Arg Asp Asn Trp Thr
        35                  40                  45

Pro Thr Lys Tyr Ser Phe Leu Cys Ser Glu His Phe Thr Lys Asp Ser
    50                  55                  60

Phe Ser Lys Arg Leu Glu Asp Gln His Arg Leu Leu Lys Pro Thr Ala
65                  70                  75                  80

Val Pro Ser Ile Phe His Leu Ser Glu Lys Lys Arg Gly Ala Gly
                85                  90                  95

<210> SEQ ID NO 26
<211> LENGTH: 52
<212> TYPE: PRT
<213> ORGANISM: Mus musculus
```

-continued

```
<400> SEQUENCE: 26

Ile Leu Gln Ala Phe Gly Ser Leu Lys Lys Gly Asp Val Leu Cys Ser
1               5                   10                  15

Arg His Phe Lys Lys Thr Asp Phe Asp Arg Ser Thr Leu Asn Thr Lys
            20                  25                  30

Leu Lys Ala Gly Ala Ile Pro Ser Ile Phe Glu Cys Pro Tyr His Leu
        35                  40                  45

Gln Glu Lys Arg
    50

<210> SEQ ID NO 27
<211> LENGTH: 103
<212> TYPE: PRT
<213> ORGANISM: Mus musculus

<400> SEQUENCE: 27

Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
            20                  25                  30

Asn Pro Arg Arg Gly Leu Trp Leu Ala Asn Cys Gln Arg Leu Asp Pro
        35                  40                  45

Ser Gly Gln Gly Leu Trp Asp Pro Thr Ser Glu Tyr Ile Tyr Phe Cys
    50                  55                  60

Ser Lys His Phe Glu Glu Asn Cys Phe Glu Leu Val Gly Ile Ser Gly
65                  70                  75                  80

Tyr His Arg Leu Lys Glu Gly Ala Val Pro Thr Ile Phe Glu Ser Phe
                85                  90                  95

Ser Lys Leu Arg Arg Thr Ala
            100

<210> SEQ ID NO 28
<211> LENGTH: 90
<212> TYPE: PRT
<213> ORGANISM: Mus musculus

<400> SEQUENCE: 28

Met Pro Gly Phe Thr Cys Cys Val Pro Gly Cys Tyr Asn Asn Ser His
1               5                   10                  15

Arg Asp Lys Ala Leu His Phe Tyr Thr Phe Pro Lys Asp Ala Glu Leu
            20                  25                  30

Arg Arg Leu Trp Leu Lys Asn Val Ser Arg Ala Gly Val Ser Gly Cys
        35                  40                  45

Phe Ser Thr Phe Gln Pro Thr Thr Gly His Arg Leu Cys Ser Val His
    50                  55                  60

Phe Gln Gly Gly Arg Lys Thr Tyr Thr Val Arg Val Pro Thr Ile Phe
65                  70                  75                  80

Pro Leu Arg Gly Val Asn Glu Arg Lys Val
                85                  90

<210> SEQ ID NO 29
<211> LENGTH: 96
<212> TYPE: PRT
<213> ORGANISM: Mus musculus
```

-continued

```
<400> SEQUENCE: 29

Met Pro Asn Phe Cys Ala Ala Pro Asn Cys Thr Arg Lys Ser Thr Gln
1               5                   10                  15

Ser Asp Leu Ala Phe Phe Arg Phe Pro Arg Asp Pro Ala Arg Cys Gln
            20                  25                  30

Lys Trp Val Glu Asn Cys Arg Arg Ala Asp Leu Glu Asp Lys Thr Pro
        35                  40                  45

Asp Gln Leu Asn Lys His Tyr Arg Leu Cys Ala Lys His Phe Glu Thr
    50                  55                  60

Ser Met Ile Cys Arg Thr Ser Pro Tyr Arg Thr Val Leu Arg Asp Asn
65                  70                  75                  80

Ala Ile Pro Thr Ile Phe Asp Leu Thr Ser His Leu Asn Asn Pro His
                85                  90                  95

<210> SEQ ID NO 30
<211> LENGTH: 24
<212> TYPE: PRT
<213> ORGANISM: Rattus norvegicus

<400> SEQUENCE: 30

Met Pro Thr Asn Cys Ala Ala Ala Gly Cys Ala Ala Thr Tyr Asn Lys
1               5                   10                  15

His Ile Asn Ile Ser Phe His Arg
            20

<210> SEQ ID NO 31
<211> LENGTH: 85
<212> TYPE: PRT
<213> ORGANISM: Rattus norvegicus

<400> SEQUENCE: 31

Arg Gln Cys Cys Asn Arg Tyr Ser Ser Arg Arg Lys Gln Leu Thr Phe
1               5                   10                  15

His Arg Phe Pro Phe Ser Arg Pro Glu Leu Leu Arg Glu Trp Val Leu
            20                  25                  30

Asn Ile Gly Arg Ala Asp Phe Lys Pro Lys Gln His Thr Val Ile Cys
        35                  40                  45

Ser Glu His Phe Arg Pro Glu Cys Phe Ser Ala Phe Gly Asn Arg Lys
    50                  55                  60

Asn Leu Lys His Asn Ala Val Pro Thr Val Phe Ala Phe Gln Asn Pro
65                  70                  75                  80

Ala Gln Val Cys Pro
                85

<210> SEQ ID NO 32
<211> LENGTH: 70
<212> TYPE: PRT
<213> ORGANISM: Rattus norvegicus

<400> SEQUENCE: 32

Arg Phe Pro Leu Lys Asp Ser Lys Arg Leu Ile Gln Trp Leu Lys Ala
1               5                   10                  15

Val Gln Arg Asp Asn Trp Thr Pro Thr Lys Tyr Ser Phe Leu Cys Ser
            20                  25                  30

Glu His Phe Thr Lys Asp Ser Phe Ser Lys Arg Leu Glu Asp Gln His
        35                  40                  45
```

```
Arg Leu Leu Lys Pro Thr Ala Val Pro Ser Ile Phe His Leu Ser Glu
 50                  55                  60

Lys Lys Arg Gly Ala Gly
 65                  70
```

<210> SEQ ID NO 33
<211> LENGTH: 55
<212> TYPE: PRT
<213> ORGANISM: Rattus norvegicus

<400> SEQUENCE: 33

```
Met Val Lys Cys Cys Ser Ala Ile Gly Cys Ala Ser Arg Cys Leu Pro
 1               5                  10                  15

Asn Ser Lys Leu Lys Gly Leu Thr Phe His Val Phe Pro Thr Asp Glu
                 20                  25                  30

Asn Ile Lys Arg Lys Trp Val Leu Ala Met Lys Arg Leu Asp Val Asn
                 35                  40                  45

Thr Ala Gly Ile Trp Glu Pro
 50                  55
```

<210> SEQ ID NO 34
<211> LENGTH: 103
<212> TYPE: PRT
<213> ORGANISM: Rattus norvegicus

<400> SEQUENCE: 34

```
Met Pro Arg His Cys Ser Ala Ala Gly Cys Cys Thr Arg Asp Thr Arg
 1               5                  10                  15

Glu Thr Arg Asn Arg Gly Ile Ser Phe His Arg Leu Pro Lys Lys Asp
                 20                  25                  30

Asn Pro Arg Arg Gly Leu Trp Leu Ala Asn Cys Gln Arg Leu Asp Pro
                 35                  40                  45

Ser Gly Gln Gly Leu Trp Asp Pro Thr Ser Glu Tyr Ile Tyr Phe Cys
 50                  55                  60

Ser Lys His Phe Glu Glu Asn Cys Phe Glu Leu Val Gly Ile Ser Gly
 65                  70                  75                  80

Tyr His Arg Leu Lys Glu Gly Ala Val Pro Thr Ile Phe Glu Ser Phe
                 85                  90                  95

Ser Lys Leu Arg Arg Thr Ala
                100
```

<210> SEQ ID NO 35
<211> LENGTH: 90
<212> TYPE: PRT
<213> ORGANISM: Rattus norvegicus

<400> SEQUENCE: 35

```
Met Pro Gly Phe Thr Cys Cys Val Pro Gly Cys Tyr Asn Asn Ser His
 1               5                  10                  15

Arg Asp Lys Ala Leu His Phe Tyr Thr Phe Pro Lys Asp Ala Glu Leu
                 20                  25                  30

Arg Arg Leu Trp Leu Lys Asn Val Ser Arg Ala Gly Val Ser Gly Cys
                 35                  40                  45

Phe Ser Thr Phe Gln Pro Thr Thr Gly His Arg Leu Cys Ser Val His
 50                  55                  60
```

```
Phe Gln Gly Gly Arg Lys Thr Tyr Thr Val Arg Val Pro Thr Ile Phe
 65                  70                  75                  80

Pro Leu Arg Gly Val Asn Glu Arg Lys Val
                 85                  90
```

<210> SEQ ID NO 36
<211> LENGTH: 96
<212> TYPE: PRT
<213> ORGANISM: Rattus norvegicus

<400> SEQUENCE: 36

```
Met Pro Asn Phe Cys Ala Ala Pro Asn Cys Thr Arg Lys Ser Thr Gln
  1               5                  10                  15

Ser Asp Leu Ala Phe Phe Arg Phe Pro Arg Asp Pro Ala Arg Cys Gln
                 20                  25                  30

Lys Trp Val Glu Asn Cys Arg Arg Ala Asp Leu Glu Asp Lys Thr Pro
                 35                  40                  45

Asp Gln Leu Asn Lys His Tyr Arg Leu Cys Ala Lys His Phe Glu Thr
 50                  55                  60

Ser Met Ile Cys Arg Thr Ser Pro Tyr Arg Thr Val Leu Arg Asp Asn
 65                  70                  75                  80

Ala Ile Pro Thr Ile Phe Asp Leu Thr Ser His Leu Asn Asn Pro His
                 85                  90                  95
```

<210> SEQ ID NO 37
<211> LENGTH: 94
<212> TYPE: PRT
<213> ORGANISM: Gallus gallus

<400> SEQUENCE: 37

```
Met Val Ile Cys Cys Ala Ala Asn Cys Ser Asn Arg Gln Gly Lys
  1               5                  10                  15

Ala Leu Arg Gly Ala Val Ser Phe His Arg Phe Pro Lys Asp Ser
                 20                  25                  30

Lys Arg Leu Ile Gln Trp Leu Lys Ala Val Gln Arg Asp Asn Trp Thr
                 35                  40                  45

Pro Thr Lys Tyr Ser Phe Leu Cys Ser Glu His Phe Thr Lys Asp Ser
 50                  55                  60

Phe Ser Arg Arg Leu Glu Asp Gln His Arg Leu Leu Lys Pro Thr Ala
 65                  70                  75                  80

Val Pro Thr Ile Phe Gln Leu Ala Glu Lys Lys Arg Asp Asn
                 85                  90
```

<210> SEQ ID NO 38
<211> LENGTH: 94
<212> TYPE: PRT
<213> ORGANISM: Gallus gallus

<400> SEQUENCE: 38

```
Met Pro Arg Tyr Cys Ala Ala Ser Tyr Cys Lys Asn Arg Gly Gly Gln
  1               5                  10                  15

Ser Ala Arg Asp Gln Arg Lys Leu Ser Phe Tyr Pro Phe Pro Leu His
                 20                  25                  30

Asp Lys Glu Arg Leu Glu Lys Trp Leu Arg Asn Met Lys Arg Asp Ala
                 35                  40                  45

Trp Thr Pro Ser Lys His Gln Leu Leu Cys Ser Asp His Phe Thr Pro
 50                  55                  60
```

```
Asp Ser Leu Asp Val Arg Trp Gly Ile Arg Tyr Leu Lys His Thr Ala
 65                  70                  75                  80

Val Pro Thr Ile Phe Ser Ser Pro Asp Asp Glu Glu Lys Gly
                 85                  90

<210> SEQ ID NO 39
<211> LENGTH: 102
<212> TYPE: PRT
<213> ORGANISM: Gallus gallus

<400> SEQUENCE: 39

Met Pro Arg His Cys Ser Ala Ala Gly Cys Cys Thr Arg Asp Thr Arg
 1               5                  10                  15

Glu Thr Arg Ser Arg Gly Ile Ser Phe His Arg Leu Pro Lys Lys Asp
                20                  25                  30

Asn Pro Arg Arg Ala Leu Trp Leu Glu Asn Ser Arg Arg Arg Asp Ala
            35                  40                  45

Ser Gly Glu Gly Arg Trp Asp Pro Ala Ser Lys Tyr Ile Tyr Phe Cys
 50                  55                  60

Ser Gln His Phe Glu Lys Ser Cys Phe Glu Ile Val Gly Phe Ser Gly
 65                  70                  75                  80

Tyr His Arg Leu Lys Gly Ala Val Pro Thr Val Phe Glu Ser Thr
                85                  90                  95

Ser Pro Arg Pro Pro Arg
                100

<210> SEQ ID NO 40
<211> LENGTH: 27
<212> TYPE: PRT
<213> ORGANISM: Gallus gallus

<400> SEQUENCE: 40

Met Thr Arg Ser Cys Ser Ala Leu Gly Cys Ser Ala Arg Asp Asn Gly
 1               5                  10                  15

Arg Ser Arg Glu Arg Gly Ile Ser Phe His Gln
                20                  25

<210> SEQ ID NO 41
<211> LENGTH: 90
<212> TYPE: PRT
<213> ORGANISM: Xenopus laevi

<400> SEQUENCE: 41

Met Val Gln Ser Cys Ser Ala Tyr Gly Cys Lys Asn Arg Tyr Asp Lys
 1               5                  10                  15

Asp Arg Pro Ile Ser Phe His Lys Phe Pro Leu Lys Arg Pro Leu Leu
                20                  25                  30

Cys Lys Lys Trp Glu Ala Ala Val Arg Arg Ala Asp Phe Lys Pro Thr
            35                  40                  45

Lys Tyr Ser Ser Ile Cys Ser Asp His Phe Thr Ala Asp Cys Phe Lys
 50                  55                  60

Arg Glu Cys Asn Asn Lys Leu Leu Lys Asp Asn Ala Val Pro Thr Val
 65                  70                  75                  80

Phe Ala Leu Ala Glu Ile Lys Lys Lys Met
                85                  90
```

<210> SEQ ID NO 42
<211> LENGTH: 103
<212> TYPE: PRT
<213> ORGANISM: Xenopus laevi

<400> SEQUENCE: 42

Met Pro Arg His Cys Ser Ala Leu Gly Cys Thr Thr Arg Asp Ser Arg
1               5                   10                  15

Gln Thr Arg Asn Asn Asn Ile Ser Phe His Arg Leu Pro Arg Lys Asp
            20                  25                  30

Asp Pro Arg Arg Asn Leu Trp Ile Ala Asn Cys Gln Arg Thr Asp Pro
        35                  40                  45

Ser Gly Lys Gly Leu Trp Asp Pro Ser Ser Asp Tyr Val Tyr Phe Cys
    50                  55                  60

Ser Lys His Phe Glu Lys Ser Cys Phe Glu Val Val Gly Thr Ser Gly
65                  70                  75                  80

Tyr His Arg Leu Lys Glu Asp Ala Val Pro Thr Leu Phe Leu Ser Ser
                85                  90                  95

Ala Lys Leu Arg Arg Ala Ala
            100

<210> SEQ ID NO 43
<211> LENGTH: 90
<212> TYPE: PRT
<213> ORGANISM: Xenopus laevi

<400> SEQUENCE: 43

Met Val Arg Ser Cys Ser Ala Ala Asn Cys Val Asn Arg Gln Thr Ala
1               5                   10                  15

Leu Asn Lys Arg Lys Gly Ile Thr Phe His Arg Phe Pro Lys Glu Gln
            20                  25                  30

Ala Arg Arg Gln Leu Trp Ile Thr Ala Val Thr His Ser His Ala Ala
        35                  40                  45

Val Gly Thr Asp Trp Thr Pro Ser Ile His Ser Ser Leu Cys Ser Gln
    50                  55                  60

His Phe Asn Asn Thr Gln Phe Asp Arg Thr Gly Gln Thr Val Arg Leu
65                  70                  75                  80

Arg Asp Ser Ala Val Pro Thr Val Phe Ser
                85                  90

<210> SEQ ID NO 44
<211> LENGTH: 99
<212> TYPE: PRT
<213> ORGANISM: Xenopus laevi

<400> SEQUENCE: 44

Met Pro Val Ser Cys Ala Ala Ser Gly Cys Lys Ser Arg Tyr Thr Met
1               5                   10                  15

Asp Ala Arg Glu Lys Gly Ile Thr Phe His Arg Phe Pro Arg Ser Asn
            20                  25                  30

Pro Thr Leu Leu Glu Lys Trp Arg Leu Ala Met Arg Arg Ser Thr Arg
        35                  40                  45

Asn Gly Glu Leu Trp Met Pro Ser Arg Tyr Gln Arg Leu Cys Ser Leu
    50                  55                  60

His Phe Lys Gln Cys Cys Phe Asp Thr Thr Gly Gln Thr Lys Arg Leu
65                  70                  75                  80

```
Arg Glu Asp Val Ile Pro Thr Ile Phe Asp Phe Pro Glu Glu Thr His
                85                  90                  95

Val Ile Phe

<210> SEQ ID NO 45
<211> LENGTH: 90
<212> TYPE: PRT
<213> ORGANISM: Xenopus laevi

<400> SEQUENCE: 45

Met Pro Ala Cys Ala Ala Ile Asn Cys Thr Ser Arg Gln Thr Arg Gly
 1               5                  10                  15

Cys Gly Lys Ser Phe His Lys Phe Pro His Gly Arg Pro Glu Val Leu
                20                  25                  30

Lys Lys Trp Val Met Asn Met Arg Asp Lys Phe Lys Pro Ser Ser
            35                  40                  45

Lys Ala Val Leu Cys Ser Asp His Phe Glu Phe Cys Phe Asp Arg
        50                  55                  60

Thr Gly Gln Thr Ile Arg Leu Arg Thr Asp Ala Val Pro Val Phe
65                  70                  75                  80

Thr Phe Pro Gly Lys Met Lys Lys Asp Arg
                85                  90

<210> SEQ ID NO 46
<211> LENGTH: 105
<212> TYPE: PRT
<213> ORGANISM: Xenopus laevi

<400> SEQUENCE: 46

Met Pro His Cys Val Val Ser Asn Cys Val His Phe Asn Tyr Lys Lys
 1               5                  10                  15

Ser Asn Leu His Gly Val Ala Leu His Pro Phe Pro Asn Asp Leu Ser
                20                  25                  30

Arg Ile Lys Leu Trp Leu Gln Gln Ile Gly Leu Thr Thr Asp Glu Ile
            35                  40                  45

Asp Tyr Leu Ala Gln Lys Val Val Glu Gly Lys Arg Lys Lys Thr Asp
        50                  55                  60

Ser His Arg Met Cys Ser Ala His Phe Thr Pro Asn Cys Tyr Ile Val
65                  70                  75                  80

Gln Asp Ala Lys Leu Val Leu Arg Ser Asp Ala Ile Pro Thr Met Phe
                85                  90                  95

Pro Gly Leu Ser Ser Ser Thr Thr Asn
                100                 105

<210> SEQ ID NO 47
<211> LENGTH: 104
<212> TYPE: PRT
<213> ORGANISM: Xenopus laevi

<400> SEQUENCE: 47

Met Pro Lys Cys Ile Val Thr Lys Cys Pro His Lys Thr Gly Gln Lys
 1               5                  10                  15

Glu Leu Tyr Pro Ser Val Ile Leu His Pro Phe Pro Gly Asn Ile Glu
                20                  25                  30

Lys Ile Lys Gln Trp Leu Leu Gln Thr Gly Glu Asp Tyr Gly Asp Tyr
            35                  40                  45

Glu Val Phe Ala Glu Lys Val Leu Glu Ala Lys Lys Thr Asp Ala Tyr
        50                  55                  60
```

-continued

```
Arg Ile Cys Ser Arg His Phe Ala Glu Asp Gln Tyr Val Lys Arg Gly
 65                  70                  75                  80

Pro Arg Lys Leu Leu Ser Lys Asp Ala Val Pro Thr Ile Phe Ser Asn
                 85                  90                  95

Leu His Pro Leu Ile Gln Leu His
            100

<210> SEQ ID NO 48
<211> LENGTH: 102
<212> TYPE: PRT
<213> ORGANISM: Xenopus laevi

<400> SEQUENCE: 48

Met Pro Arg Cys Val Val Lys Asn Cys Pro His Trp Thr Gly Lys Lys
 1               5                  10                  15

Gly Ser Gln Val Ile Leu His Gly Phe Pro Asn Asn Ser Arg Leu Ile
                20                  25                  30

Lys Leu Trp Leu Ser Gln Thr Lys Gln Asp Phe Gly Asp Val Glu Asp
             35                  40                  45

Phe Thr Gln Lys Ile Leu Glu Gly Lys Lys Asn Asp Leu Tyr Arg Leu
 50                  55                  60

Cys Ser Lys His Phe Thr Asn Asp Ser Tyr Glu Ile Arg Gly Thr Lys
 65                  70                  75                  80

Arg Phe Leu Lys Tyr Gly Ala Val Pro Thr Val Phe Glu Asp Thr Pro
                 85                  90                  95

Pro Leu Lys Arg Arg Lys
            100

<210> SEQ ID NO 49
<211> LENGTH: 104
<212> TYPE: PRT
<213> ORGANISM: Xenopus laevi

<400> SEQUENCE: 49

Met Pro Asn Cys Ile Val Lys Asp Cys Arg His Lys Ser Gly Gln Lys
 1               5                  10                  15

Ile Gln Asn Pro Asp Val Val Leu His Pro Phe Pro Asn Asn Ile Asn
                20                  25                  30

Met Ile Lys Asn Trp Leu Leu Gln Thr Gly Gln Asp Phe Gly Asp Ile
             35                  40                  45

Asp Val Leu Ala Asp Lys Ile Leu Lys Gly Lys Lys Thr Ala Asn Phe
 50                  55                  60

Arg Met Cys Ser Cys His Phe Thr Arg Asp Ser Tyr Met Ala Arg Gly
 65                  70                  75                  80

Ser Lys Thr Thr Leu Lys Pro Asn Ala Ile Pro Thr Ile Phe Pro Val
                 85                  90                  95

Ile Leu Pro Thr Thr Val Pro Ser
            100

<210> SEQ ID NO 50
<211> LENGTH: 99
<212> TYPE: PRT
<213> ORGANISM: Xenopus laevi
```

<400> SEQUENCE: 50

Met Pro Lys Cys Phe Val Gln Ser Cys Pro His Tyr Thr Gly Arg Asn
1               5                   10                  15

Gly Lys Pro Asp Asn Val Ile Leu His Thr Phe Pro Arg Cys Lys Lys
            20                  25                  30

Gln Val Gln Val Trp Leu Ser Arg Thr Gly Glu Arg Tyr Glu Asn Met
        35                  40                  45

Ala Glu Phe Val Thr Tyr Ile Thr Gln Arg Cys Ser Asn Phe Arg Met
    50                  55                  60

Cys Ser Glu His Phe Thr Asp Asp Cys Tyr Ile Thr Val Glu Gly Lys
65                  70                  75                  80

Arg Arg Leu Met Glu Asn Ser Ala Pro Thr Ile Phe Lys Thr Thr Phe
                85                  90                  95

Arg Gln Asn

<210> SEQ ID NO 51
<211> LENGTH: 104
<212> TYPE: PRT
<213> ORGANISM: Xenopus laevi

<400> SEQUENCE: 51

Met Thr Lys Cys Ile Val Lys Gly Cys Arg His Thr Thr Gly Gln Lys
1               5                   10                  15

Leu Lys Phe Pro His Ile Val Met His Ala Phe Pro Ser Asn Leu Lys
            20                  25                  30

Met Ile Lys Val Trp Leu Lys Gln Thr Gly Gln Tyr Gly Asn Asn Leu
        35                  40                  45

Glu Glu Met Ala Leu Lys Val Leu Gly Gly Lys Lys Ser Asp Ser Tyr
    50                  55                  60

Arg Leu Cys Ser Ala His Phe Thr Val Asp Ser Tyr Ala Leu Arg Arg
65                  70                  75                  80

Ser Lys Asn Met Leu Lys Lys Asp Ala Phe Pro Thr Leu Phe Gly Gln
                85                  90                  95

Asn Gln Ile Asn Ala Ala Asn Val
            100

<210> SEQ ID NO 52
<211> LENGTH: 84
<212> TYPE: PRT
<213> ORGANISM: Xenopus laevi

<400> SEQUENCE: 52

Met Pro Lys Cys Ile Val Ile His Cys Pro His Ser Cys Ser Lys Lys
1               5                   10                  15

Val Thr Lys Asn Thr Gly Val Val Met His Thr Phe Pro Phe Asn Leu
            20                  25                  30

Asp Arg Ile Lys Asn Trp Leu Leu Ser Ile Asp Gln Asn Phe Gly Asn
        35                  40                  45

Ile Asp Thr Leu Ala Asn Arg Ile Leu Glu Glu Lys Lys Lys His Ser
    50                  55                  60

Asp Leu Tyr Arg Leu Cys Ser Glu His Phe Thr Pro Gln Cys Tyr Ile
65                  70                  75                  80

Ser Thr Gly Glu

<210> SEQ ID NO 53
<211> LENGTH: 104
<212> TYPE: PRT
<213> ORGANISM: Xenopus laevi

<400> SEQUENCE: 53

Met Pro Ser Cys Ile Val Lys Gly Cys Pro His Arg Thr Gly Gln Lys
1               5                   10                  15

Asp Lys Phe Pro Asn Val Thr Leu His Asn Phe Pro Lys Thr Ile Pro
            20                  25                  30

Lys Ile Lys Asn Trp Leu Trp Gln Thr Gly Gln Tyr Gly Glu Asp Ser
        35                  40                  45

Asp Ala Ile Ala Glu Glu Ile Leu Gln Gly Leu Lys Thr Cys Arg His
    50                  55                  60

Arg Met Cys Ser Met His Phe Ser Glu Asn Cys Phe Ile Thr Leu Gly
65                  70                  75                  80

Ser Lys Arg Val Leu Thr Arg Asn Ala Val Pro Thr Ile Phe Lys Pro
                85                  90                  95

Gln Thr Thr Pro Ala Ile Leu Ala
            100

<210> SEQ ID NO 54
<211> LENGTH: 104
<212> TYPE: PRT
<213> ORGANISM: Xenopus laevi

<400> SEQUENCE: 54

Met Pro Lys Cys Ile Leu Asn Gly Cys Pro Tyr Arg Thr Gly Gln Lys
1               5                   10                  15

Leu Lys Phe Pro Asp Ile Val Leu His Pro Phe Pro Lys Ser Met Glu
            20                  25                  30

Met Ile Arg Asn Trp Leu Phe Gln Thr Gly Gln His Ala Glu Asp Val
        35                  40                  45

Glu Ser Leu Ser Gln Arg Ile Tyr Gln Gly Leu Lys Thr Ser Asn Phe
    50                  55                  60

Arg Met Cys Ser Lys His Phe Thr Gln Asp Cys Tyr Met Gln Val Gly
65                  70                  75                  80

Ser Arg Lys Cys Leu Lys Pro Asn Ala Val Pro Thr Val Phe Glu Ser
                85                  90                  95

Tyr Asn Val Pro Val Thr Thr Phe
            100

<210> SEQ ID NO 55
<211> LENGTH: 105
<212> TYPE: PRT
<213> ORGANISM: Xenopus laevi

<400> SEQUENCE: 55

Asn Asn Ala Ser Cys Ile Val Arg Gly Cys His His Ser Thr Ala Arg
1               5                   10                  15

Lys Cys Leu Ser Pro Gly Ile Ala Leu His Gly Phe Pro Asn Asn Leu
            20                  25                  30

Ser Arg Ile Lys Gln Trp Leu Val Asn Ile Gly Gln Asn Val Gly Asp
        35                  40                  45

Ile Asp Asp Phe Ala Gln Lys Val Leu Asp Gly Lys Lys Gln Asn Ser
    50                  55                  60

Tyr Arg Ile Cys Ser Ala His Phe Ser Ser Asp Cys Phe Val Gln Phe
65                  70                  75                  80

```
Gly Tyr Ser Lys Gly Leu Lys Ala Asp Ala Val Pro Thr Ile Phe Ala
                85                  90                  95

Trp Asn Thr Pro Glu Ser Arg Gly Arg
                100                 105

<210> SEQ ID NO 56
<211> LENGTH: 107
<212> TYPE: PRT
<213> ORGANISM: Xenopus laevi

<400> SEQUENCE: 56

Met Pro Ser Cys Ile Val Lys Gly Cys Arg His Lys Ser Gly Gln Lys
1               5                   10                  15

Val Leu Tyr Pro Asp Val Val Leu His Ser Phe Pro Asn Asn Ile His
                20                  25                  30

Met Ile Lys Asn Trp Leu Leu Gln Thr Gly Gln Val Phe Gly Asp Ile
                35                  40                  45

Asp Ala Phe Ala Glu Lys Val Leu Lys Gly Asn Lys Thr Ser Ala Phe
        50                  55                  60

Arg Met Cys Ser Arg His Phe Thr Arg Asp Ser Tyr Met Ala Lys Gly
65                  70                  75                  80

Ser Lys Ile Thr Leu Lys Pro Asn Ala Val Pro Thr Ile Phe Asn Thr
                85                  90                  95

Leu Pro Pro Ala Ala Ala Val Pro Ser Leu Met
                100                 105

<210> SEQ ID NO 57
<211> LENGTH: 91
<212> TYPE: PRT
<213> ORGANISM: Danio rerio

<400> SEQUENCE: 57

Met Val Gln Ser Cys Ser Ala Tyr Gly Cys Asn Asn Arg Tyr Gln Lys
1               5                   10                  15

Asp Arg Ile Ile Ser Phe His Lys Phe Pro Leu Ala Arg Pro Glu Val
                20                  25                  30

Cys Val Gln Trp Val Ser Ala Met Ser Arg Arg Asn Phe Lys Pro Thr
                35                  40                  45

Lys Tyr Ser Asn Ile Cys Ser Gln His Phe Thr Ser Asp Cys Phe Lys
        50                  55                  60

Gln Glu Cys Asn Asn Arg Val Leu Lys Asp Asn Ala Val Pro Ser Leu
65                  70                  75                  80

Phe Thr Leu Gln Thr Gln Asp Pro Phe Ser Ala
                85                  90

<210> SEQ ID NO 58
<211> LENGTH: 103
<212> TYPE: PRT
<213> ORGANISM: Danio rerio

<400> SEQUENCE: 58

Met Pro Arg His Cys Ser Ala Val Gly Cys Lys Ser Arg Asp Thr Lys
1               5                   10                  15

Asp Val Arg Lys Ser Gly Ile Thr Phe His Arg Leu Pro Lys Lys Gly
                20                  25                  30

Asn Pro Arg Arg Thr Thr Trp Ile Leu Asn Ser Arg Arg Lys Gly Pro
                35                  40                  45
```

```
Glu Gly Lys Gly Gln Trp Asp Pro Gln Ser Gly Phe Ile Tyr Phe Cys
    50                  55                  60

Ser Lys His Phe Thr Pro Asp Ser Phe Glu Leu Ser Gly Val Ser Gly
 65                 70                  75                  80

Tyr His Arg Leu Lys Asp Asp Ala Ile Pro Thr Val Phe Glu Ile Glu
                85                  90                  95

Pro His Lys Lys Gly Thr Ala
            100

<210> SEQ ID NO 59
<211> LENGTH: 90
<212> TYPE: PRT
<213> ORGANISM: Danio rerio

<400> SEQUENCE: 59

Met Pro Gly Phe Thr Cys Cys Val Pro Gly Cys Tyr Asn Asn Ser His
 1               5                  10                  15

Arg Asp Arg Asp Leu Arg Phe Tyr Thr Phe Pro Lys Asp Pro Thr Gln
                20                  25                  30

Arg Glu Ile Trp Leu Lys Asn Ile Ser Arg Ala Gly Val Ser Gly Cys
            35                  40                  45

Phe Ser Thr Phe Gln Pro Thr Thr Gly His Arg Val Cys Ser Val His
 50                  55                  60

Phe Pro Gly Gly Arg Lys Thr Tyr Thr Ile Arg Val Pro Thr Leu Phe
 65                  70                  75                  80

Pro Leu Arg Gly Val Asn Glu Arg Ser
                85                  90

<210> SEQ ID NO 60
<211> LENGTH: 96
<212> TYPE: PRT
<213> ORGANISM: Danio rerio

<400> SEQUENCE: 60

Met Pro Asn Phe Cys Ala Ala Leu Asn Cys Ser Arg Asn Ser Thr His
 1               5                  10                  15

Ser Val Leu Ala Phe Phe Arg Phe Pro Arg Asp Pro Glu Arg Cys Lys
                20                  25                  30

Lys Trp Val Glu Asn Cys Ser Arg Ser Asp Leu Lys Asp Lys Thr Pro
            35                  40                  45

Asp His Leu Asn Lys Tyr His Arg Leu Cys Ala Arg His Phe Glu Pro
 50                  55                  60

Asn Leu Ile Thr Lys Thr Ser Pro Phe Arg Thr Val Leu Lys Asp Ser
 65                  70                  75                  80

Ala Val Pro Thr Ile Phe Asp Asn Pro Phe Lys Arg Ser Asn Asn Glu
                85                  90                  95

<210> SEQ ID NO 61
<211> LENGTH: 99
<212> TYPE: PRT
<213> ORGANISM: Danio rerio

<400> SEQUENCE: 61

Met Pro Tyr Lys Cys Val Ala Tyr Gly Cys Gly Lys Ile Ser Gly Gln
 1               5                  10                  15

Asn Val Ser Met Phe Arg Phe Pro Lys Asp Pro Glu Glu Phe Ser Lys
                20                  25                  30
```

```
Trp Gln Arg Gln Val Gln Lys Thr Arg Arg Asn Trp Leu Ala Asn Thr
        35                  40                  45

Tyr Ser His Leu Cys Asn Glu His Phe Thr Lys Asp Cys Phe Glu Pro
 50                  55                  60

Lys Thr Tyr Val Thr Ala Lys Ala Ser Gly Phe Lys Arg Leu Lys Leu
 65                  70                  75                  80

Lys Asp Gly Ala Val Pro Thr Val Phe Ile Arg Arg Cys Arg Lys
                 85                  90                  95

Cys Gly Gly

<210> SEQ ID NO 62
<211> LENGTH: 90
<212> TYPE: PRT
<213> ORGANISM: Danio rerio

<400> SEQUENCE: 62

Met Gly Gly Cys Ser Ala Pro Asn Cys Ser Asn Ser Thr Thr Ile Gly
 1               5                  10                  15

Lys Gln Leu Phe Arg Phe Pro Lys Asp Pro Val Arg Met Arg Lys Trp
                 20                  25                  30

Leu Val Asn Cys Arg Arg Asp Phe Val Pro Thr Pro Cys Ser Arg Leu
        35                  40                  45

Cys Gln Asp His Phe Glu Glu Ser Gln Phe Glu Glu Ile Ala Arg Ser
 50                  55                  60

Pro Ala Gly Gly Arg Lys Leu Lys Pro Asn Ala Ile Pro Thr Leu Phe
 65                  70                  75                  80

Asn Val Pro Asp Pro Pro Ser Pro Val Thr
                 85                  90

<210> SEQ ID NO 63
<211> LENGTH: 105
<212> TYPE: PRT
<213> ORGANISM: Danio rerio

<400> SEQUENCE: 63

Met Val Leu Asn Cys Ala Tyr Pro Gly Cys Leu Asn Leu Phe Lys Lys
 1               5                  10                  15

Glu Arg Leu Arg Ser Asn Ser Ser His Gly Gly Lys Leu Thr Phe
                 20                  25                  30

His Arg Phe Pro Thr Leu Glu Pro Gly Arg Leu Leu Leu Trp Arg Ala
        35                  40                  45

Ala Leu Gly Met Asp Pro Asp Thr Pro Met Arg Ser Leu Arg Val Trp
 50                  55                  60

Arg Ile Cys Ser Glu His Phe Ser Pro Glu Asp Phe Arg Ala Val Asn
 65                  70                  75                  80

Gly Asn Lys Val Leu Leu Lys Ala Ser Ala Val Pro Arg Val Tyr Ser
                 85                  90                  95

Thr Pro Ala Pro Gly Ser Arg Ala Asp
                100                 105

<210> SEQ ID NO 64
<211> LENGTH: 99
<212> TYPE: PRT
<213> ORGANISM: Danio rerio
```

```
<400> SEQUENCE: 64

Met Ala Ser Ser Arg Arg Cys Tyr Cys Ser Val Pro Gly Cys Ser Asn
1               5                   10                  15

Ser Lys Lys Arg His Pro Tyr Leu Ser Phe His Asp Phe Pro Lys Asp
            20                  25                  30

Glu Gly Gln Arg Lys Ser Trp Val Lys Phe Ile Arg Arg Glu Glu Gly
        35                  40                  45

Pro Phe Phe Gln Ile Lys Arg Gly Ser Thr Phe Val Cys Ser Met His
50                  55                  60

Phe Lys Ala Asp Asp Ile Tyr Thr Thr Ile Ser Gly Arg Lys Ile
65                  70                  75                  80

Asn Pro Gly Ala Ala Pro Arg Leu Phe Ser Trp Asn Asn Trp Ser Thr
                85                  90                  95

Asp Lys Val

<210> SEQ ID NO 65
<211> LENGTH: 66
<212> TYPE: PRT
<213> ORGANISM: Danio rerio

<400> SEQUENCE: 65

Phe Pro Lys Glu Asn Val Leu Arg Lys Gln Trp Glu Ile Ala Leu Lys
1               5                   10                  15

Arg Lys Gly Phe Ser Ala Ser Glu Ser Ser Val Leu Cys Ser Glu His
            20                  25                  30

Phe Arg Pro Gln Asp Leu Asp Arg Thr Gly Gln Thr Val Arg Val Arg
        35                  40                  45

Asp Gly Ala Lys Pro Ser Val Phe Ser Phe Pro Ala His Met Gln Lys
50                  55                  60

His Val
65

<210> SEQ ID NO 66
<211> LENGTH: 93
<212> TYPE: PRT
<213> ORGANISM: Danio rerio

<400> SEQUENCE: 66

Ser Ser Glu His Cys Cys Val Pro Leu Cys Gly Ala Ser Ser Arg Phe
1               5                   10                  15

Asn Ser Ala Val Ser Phe His Thr Phe Pro Val Ser Thr Glu Ile Arg
            20                  25                  30

Glu Lys Trp Ile Lys Asn Ile Arg Arg Glu Lys Leu Asn Ile Thr Tyr
        35                  40                  45

His Thr Arg Val Cys Cys Arg His Phe Thr Thr Asp Asp Leu Ile Gln
50                  55                  60

Pro Arg Asn Pro Ile Gly Arg Arg Leu Leu Arg Lys Gly Ala Val Pro
65                  70                  75                  80

Thr Leu Phe Lys Trp Asn Gly Tyr Ser Asp Ala Glu Ala
                85                  90

<210> SEQ ID NO 67
<211> LENGTH: 93
<212> TYPE: PRT
<213> ORGANISM: Danio rerio
```

<400> SEQUENCE: 67

Met Pro Asp Phe Cys Ala Ala Tyr Gly Cys Ser Asn Glu Arg Thr Lys
1               5                   10                  15

Lys Leu Lys Asp Lys Gly Ile Thr Phe His Arg Phe Pro Arg Asp Val
            20                  25                  30

Lys Arg Arg Gln Ala Trp Thr Leu Ala Leu Arg Arg Asp Lys Phe Glu
        35                  40                  45

Pro Lys Pro Arg Ser Leu Leu Cys Ser Cys His Phe Arg Pro Glu Asp
    50                  55                  60

Phe Asp Arg Thr Gly Gln Thr Val Arg Leu Arg Asp Gly Val Ile Pro
65                  70                  75                  80

Ser Ile Phe Asn Phe Ser Asn Pro Leu Ser Lys Leu Ser
                85                  90

<210> SEQ ID NO 68
<211> LENGTH: 97
<212> TYPE: PRT
<213> ORGANISM: Danio rerio

<400> SEQUENCE: 68

Met Pro Val Cys Ser Ala Tyr Lys Cys Lys Lys Arg Ser Asp Arg Glu
1               5                   10                  15

Tyr Lys Glu Ala Tyr Lys Arg Gly Glu Phe Ser Phe His Lys Phe Pro
            20                  25                  30

Leu Glu Asp Gly Leu Arg Val Arg Glu Trp Leu Arg Arg Met Arg Trp
        35                  40                  45

Gln Asn Trp Trp Pro Thr Gly Asn Ser Val Leu Cys Ser Asp His Phe
    50                  55                  60

Glu Lys Asp Cys Phe Glu Gln Val Gly Ser His Lys Arg Leu Arg Lys
65                  70                  75                  80

Ser Ala Val Pro Thr Ile Phe Asn Phe Pro Lys His Leu Gln Trp Lys
                85                  90                  95

Val

<210> SEQ ID NO 69
<211> LENGTH: 90
<212> TYPE: PRT
<213> ORGANISM: Danio rerio

<400> SEQUENCE: 69

Met Val Leu Val Cys Ser Ala Tyr Asn Cys Lys Asn Thr Leu Arg Asn
1               5                   10                  15

Lys Ser Val Ser Phe His Leu Phe Pro Leu Lys Asp Pro Ser Leu Leu
            20                  25                  30

Lys Lys Trp Leu Lys Asn Leu Arg Trp Lys Asp Trp Lys Pro Asn Pro
        35                  40                  45

Asn Ser Lys Ile Cys Ser Ala His Phe Glu Glu Lys Cys Phe Ile Leu
    50                  55                  60

Glu Gly Lys Lys Thr Arg Leu His Thr Trp Ala Val Pro Thr Ile Phe
65                  70                  75                  80

Ser Phe Pro Asn Arg Phe Ser Glu Arg Asn
                85                  90

<210> SEQ ID NO 70
<211> LENGTH: 107
<212> TYPE: PRT
<213> ORGANISM: Danio rerio

```
<400> SEQUENCE: 70

Met Asn Ser Ile Ser Leu Lys Tyr Leu Arg Arg Glu Cys Ala Tyr Ser
1               5                   10                  15

Arg Tyr Cys Cys Val Pro Phe Cys Lys Ile Ser Ser Arg Phe Asn Ser
            20                  25                  30

Val Ile Ser Phe His Lys Leu Pro Leu Asp Arg Ala Thr Arg Lys Met
        35                  40                  45

Trp Leu His Asn Ile Arg Arg Lys Thr Phe Glu Val Ser Pro His Val
    50                  55                  60

Arg Val Cys Ser Arg His Phe Thr Asn Asp Asp Phe Ile Glu Pro Ser
65                  70                  75                  80

Tyr Pro Thr Ala Arg Arg Leu Leu Lys Lys Gly Ala Val Pro Thr Leu
                85                  90                  95

Phe Arg Trp Asn Asn Asp Ser Thr Ser Gly Gln
                100                 105

<210> SEQ ID NO 71
<211> LENGTH: 89
<212> TYPE: PRT
<213> ORGANISM: Danio rerio

<400> SEQUENCE: 71

Leu Arg Leu Arg Gln Ser Ala Ser Ser His Glu Glu Ser Leu Thr Phe
1               5                   10                  15

Tyr Ser Leu Pro Leu Gln Asp Phe Lys Arg Leu Asn Leu Trp Leu Asn
            20                  25                  30

Ala Val Arg Arg Asp Thr Lys Ser Ser Ile Arg Asn Ile Arg Gly Leu
        35                  40                  45

Arg Val Cys Ser Glu His Phe Ala Gln Asp Asp Phe Ser Leu Asn Arg
50                  55                  60

Gly Ser Lys Arg Arg Leu Lys Ser Thr Ala Val Pro Lys Cys Asn Glu
65                  70                  75                  80

Ala Leu Pro Gln Ile Arg Arg Ala Gly
                85

<210> SEQ ID NO 72
<211> LENGTH: 105
<212> TYPE: PRT
<213> ORGANISM: Danio rerio

<400> SEQUENCE: 72

Met Val Ile Thr Cys Ala Cys Pro Gly Cys Asp Asn Arg Tyr Lys Thr
1               5                   10                  15

Leu Arg Leu Arg Ser Asp Ser Lys Phe His Pro Gly Lys Leu Thr Phe
            20                  25                  30

His Lys Phe Pro Thr Ser Asp Pro Glu Arg Leu Lys Leu Trp Leu Leu
        35                  40                  45

Ala Leu Gly Leu Asp Ile Asn Thr Pro Leu Ser Val Leu Glu Thr Arg
    50                  55                  60

Arg Ile Cys Ser Asp His Phe Ser Phe Pro Phe Asp Thr Lys
65                  70                  75                  80

Gly Ser Ile Val Gln Leu Lys Ser Trp Ala Val Pro Met Asn Leu Ser
                85                  90                  95

Glu Gln Phe Val Asp Asp Pro Ser Lys
                100                 105
```

<210> SEQ ID NO 73
<211> LENGTH: 96
<212> TYPE: PRT
<213> ORGANISM: Danio rerio

<400> SEQUENCE: 73

```
Met Pro Asp Cys Cys Ala Ala Asn Cys Lys Gln Ser Thr Asp Gln
 1               5                  10                  15

Ser Ser Val Ser Phe Phe Glu Phe Pro Leu Asp Pro Asp Arg Cys Arg
             20                  25                  30

Gln Trp Val Gly Arg Cys Asn Arg Pro Asp Leu Gln Thr Lys Thr Pro
                 35                  40                  45

Glu Asp Leu His Lys Asn Tyr Lys Val Cys Ser Arg His Phe Glu Thr
 50                  55                  60

Ser Met Ile Cys Gln Gln Ser Ala Val Lys Cys Ile Leu Lys Asp Asp
 65                  70                  75                  80

Ala Val Pro Thr Leu Phe Asn Phe Ser Thr Asn Gln Asp Asn Ala Gln
                 85                  90                  95
```

<210> SEQ ID NO 74
<211> LENGTH: 91
<212> TYPE: PRT
<213> ORGANISM: Danio rerio

<400> SEQUENCE: 74

```
Met Val Lys Cys Thr Val Gln Gly Cys Ile Asn Phe Ser Asp Leu Arg
 1               5                  10                  15

Pro Glu Glu Gln Pro Asn Arg Pro Arg Lys Arg Phe Phe Arg Phe Pro
             20                  25                  30

Lys Asp Lys Val Leu Val Lys Val Trp Leu Ala Ala Leu Arg Asp Thr
                 35                  40                  45

Glu Arg Glu Ile Thr Asp Leu His Arg Ile Cys Glu Asp His Phe Leu
 50                  55                  60

Ser His His Ile Thr Ala Asp Gly Ile Ser Pro Asp Ala Ile Pro Ile
 65                  70                  75                  80

Met Pro Pro Leu Asp Gly Pro Val Gly Asn Trp
                 85                  90
```

<210> SEQ ID NO 75
<211> LENGTH: 84
<212> TYPE: PRT
<213> ORGANISM: Danio rerio

<400> SEQUENCE: 75

```
Met Pro Ile Ser Cys Ser Ala Val Asp Cys Ser Asn Arg Phe Val Lys
 1               5                  10                  15

Gly Ser Glu Ile Arg Phe Tyr Arg Phe Pro Ile Ser Lys Pro Gln Leu
             20                  25                  30

Ala Glu Gln Trp Val Arg Ser Leu Gly Arg Lys Asn Phe Val Pro Thr
                 35                  40                  45

Gln Asn Ser Cys Leu Cys Ser Glu His Phe Gln Pro Asp Cys Phe Arg
 50                  55                  60

Asp Tyr Asn Gly Lys Leu Phe Leu Arg Glu Asp Ala Val Pro Thr Ile
 65                  70                  75                  80

Phe Ser Asn Ser
```

<210> SEQ ID NO 76
<211> LENGTH: 95
<212> TYPE: PRT
<213> ORGANISM: Oryzias latipes

<400> SEQUENCE: 76

Met Pro Asn Phe Cys Ala Ala Pro Asn Cys Thr Arg Lys Ser Thr Gln
1               5                   10                  15

Ser Asp Leu Ala Phe Phe Arg Phe Pro Arg Asp Pro Glu Arg Cys Arg
            20                  25                  30

Ile Trp Val Glu Asn Cys Arg Arg Ala Asp Leu Glu Ala Lys Thr Ala
        35                  40                  45

Asp Gln Leu Asn Lys His Tyr Arg Leu Cys Ala Lys His Phe Asp Pro
    50                  55                  60

Ala Met Val Cys Lys Thr Ser Pro Tyr Arg Thr Val Leu Lys Asp Thr
65                  70                  75                  80

Ala Ile Pro Thr Ile Phe Asp Leu Thr Ser His Leu Lys Asn Pro
                85                  90                  95

<210> SEQ ID NO 77
<211> LENGTH: 90
<212> TYPE: PRT
<213> ORGANISM: Oryzias latipes

<400> SEQUENCE: 77

Met Pro Thr Gly Cys Ala His Ala Asn Cys Arg Asn Val Val Gly Lys
1               5                   10                  15

Phe Arg Gly Val Thr Phe His Lys Phe Pro Arg Asp Pro Glu Lys Leu
            20                  25                  30

Ser Arg Trp Thr Lys Phe Met Lys Arg His Glu Ser Trp Val Pro Lys
        35                  40                  45

Tyr Tyr Asp Arg Val Cys Ser Val His Phe Ser Ser Glu His Phe Asp
    50                  55                  60

Arg Thr Gly Gln Thr Val Arg Leu Arg Asp Asn Ala Glu Pro Ser Leu
65                  70                  75                  80

Pro His Leu Pro Trp Arg Phe Pro Lys Ser
                85                  90

<210> SEQ ID NO 78
<211> LENGTH: 94
<212> TYPE: PRT
<213> ORGANISM: Oryzias latipes

<400> SEQUENCE: 78

Met Gln Asn Arg Cys Ala Val Leu Thr Cys Pro Ser Gly Lys Thr Asp
1               5                   10                  15

Phe Gln Pro Met Phe Arg Phe Pro His Asp Gln Glu Arg Ser Arg Arg
            20                  25                  30

Trp Val Glu Lys Cys Gln Gly Glu Asn Leu Ile Gly Lys Ser Pro Glu
        35                  40                  45

Gln Leu Tyr Arg Tyr Tyr Arg Ile Cys Lys Arg His Phe Glu Thr Ser
    50                  55                  60

Ala Phe Asp Cys Asp Ala Asp Gly Ala Val Leu Lys Lys Asp Ala Val
65                  70                  75                  80

Pro Thr Ile Phe Asp Ala Ser Val Pro Pro Gln Ser Ser Gln
                85                  90

<210> SEQ ID NO 79
<211> LENGTH: 92
<212> TYPE: PRT
<213> ORGANISM: Drosophila melanogaster

<400> SEQUENCE: 79

Met Pro Ala His Cys Ala Val Ile Asn Cys Ser His Lys Tyr Val His
1               5                   10                  15

Ala Gly Ser Ile Ser Phe His Arg Phe Pro Phe Lys Arg Lys Asp Leu
            20                  25                  30

Leu Gln Lys Trp Lys Glu Phe Thr Gln Arg Ser Ala Gln Trp Met Pro
        35                  40                  45

Ser Lys Trp Ser Ala Leu Cys Ser Arg His Phe Gly Asp Glu Asp Phe
50                  55                  60

Asn Cys Ser Asn Asn Arg Lys Thr Leu Lys Lys Asn Ala Val Pro Ser
65                  70                  75                  80

Ile Arg Val Ser Glu Asp Asp Ser Met Ser Gly His
            85                  90

<210> SEQ ID NO 80
<211> LENGTH: 90
<212> TYPE: PRT
<213> ORGANISM: Drosophila melanogaster

<400> SEQUENCE: 80

Met Pro Thr Ile Arg Arg Cys Cys Ile Ile Gly Cys Leu Ser Asn Ser
1               5                   10                  15

Arg Gln His Pro Ser Met Gln Phe Phe Ala Phe Pro Arg Pro Glu Asn
            20                  25                  30

Pro Phe His Lys Leu Trp Lys Glu Ala Cys His Ala Ser Leu Arg Arg
        35                  40                  45

Ile Val Pro Phe Lys Lys Pro Val Val Cys Ala Leu His Phe Asp Pro
50                  55                  60

Ser Val Leu Gly Gly Arg Arg Leu Gln Ser Asn Ala Leu Pro Thr Leu
65                  70                  75                  80

Arg Leu Glu Val Pro Ser Asn Leu Glu Ala
            85                  90

<210> SEQ ID NO 81
<211> LENGTH: 104
<212> TYPE: PRT
<213> ORGANISM: Drosophila melanogaster

<400> SEQUENCE: 81

Met Arg Cys Ala Val Pro Asn Cys Arg Asn Phe Ser Asp Cys Arg Ser
1               5                   10                  15

Lys Arg Asn Ala Ala Gln Gln Arg Leu Gly Phe Phe Arg Phe Pro
            20                  25                  30

Lys Cys Pro Asp Thr Phe Lys Ala Trp Leu Ala Phe Cys Gly Tyr Thr
        35                  40                  45

Glu Glu Ser Leu Lys Leu Lys Asn Pro Cys Ile Cys Ile Glu His Phe
50                  55                  60

Lys Asp Glu Asp Ile Glu Gly Ser Leu Lys Phe Glu Met Gly Leu Ala
65                  70                  75                  80

Lys Lys Arg Thr Leu Arg Pro Gly Ala Val Pro Cys Val Asn Lys Ser
            85                  90                  95

Gln Glu Ser Gly Ser Asp Arg Ala
            100

<210> SEQ ID NO 82
<211> LENGTH: 96
<212> TYPE: PRT
<213> ORGANISM: Drosophila melanogaster

<400> SEQUENCE: 82

Met Gly Gly Thr Lys Cys Cys Phe Arg Asp Cys Pro Val Gly Ser Ser
1               5                   10                  15

Arg Asn Pro Asn Met His Phe Phe Lys Phe Pro Val Lys Asp Pro Lys
            20                  25                  30

Arg Leu Lys Asp Trp Val Arg Asn Cys Ser Asn Pro Asp Val Ser Asn
        35                  40                  45

Ala Pro Pro Ser Lys Leu Ala Ala Lys Thr Val Cys Ala Arg His Phe
    50                  55                  60

Arg Ala Glu Cys Phe Met Asn Tyr Lys Met Asp Arg Leu Ile Pro Met
65                  70                  75                  80

Gln Thr Pro Thr Leu Phe Arg Ile Asn Arg Asp Leu Ala Leu Asp Tyr
                85                  90                  95

<210> SEQ ID NO 83
<211> LENGTH: 96
<212> TYPE: PRT
<213> ORGANISM: Drosophila melanogaster

<400> SEQUENCE: 83

Met Ala Thr Arg Ser Cys Ala Tyr Lys Asp Cys Glu Tyr Tyr Tyr Val
1               5                   10                  15

Gly His Glu Asn Ala Leu Thr Lys Gly Arg Thr Leu Phe Ala Phe Pro
            20                  25                  30

Lys Gln Pro Gln Arg Ala Arg Ile Trp His Glu Asn Gly Gln Val His
        35                  40                  45

Pro Lys Ile Pro His Ser Gln Leu Phe Met Cys Ser Leu His Phe Asp
    50                  55                  60

Arg Lys Phe Ile Ser Ser Ser Lys Asn Arg Thr Leu Leu Val Gly Glu
65                  70                  75                  80

Ala Val Pro Phe Pro Tyr Glu Glu Ser Ser Lys Pro Glu Glu Glu
                85                  90                  95

<210> SEQ ID NO 84
<211> LENGTH: 87
<212> TYPE: PRT
<213> ORGANISM: Drosophila melanogaster

<400> SEQUENCE: 84

Met Lys Tyr Cys Lys Phe Cys Cys Lys Ala Val Thr Gly Val Lys Leu
1               5                   10                  15

Ile His Val Pro Lys Cys Ala Ile Lys Arg Lys Leu Trp Glu Gln Ser
            20                  25                  30

Leu Gly Cys Ser Leu Gly Glu Asn Ser Gln Ile Cys Asp Thr His Phe
        35                  40                  45

Asn Asp Ser Gln Trp Lys Ala Pro Ala Lys Gly Gln Thr Phe Lys
    50                  55                  60

Arg Arg Arg Leu Asn Ala Asp Ala Val Pro Ser Lys Val Ile Glu Pro
65                  70                  75                  80

Glu Pro Glu Lys Ile Lys Glu
                85

<210> SEQ ID NO 85
<211> LENGTH: 92
<212> TYPE: PRT
<213> ORGANISM: Anopheles gambiae

<400> SEQUENCE: 85

Met Pro Ala Ser Cys Val Ile Pro Asp Cys Asp Leu Lys Tyr Thr His
1               5                   10                  15

Gly Asp Asp Val Ser Phe His Lys Phe Pro Leu Lys Ser Pro Glu Leu
            20                  25                  30

Leu Lys Gln Trp Ile Gln Phe Thr Gly Arg Asp Glu Gly Trp His Pro
        35                  40                  45

Thr Lys Trp Ser Ala Leu Cys Ser Arg His Phe Val Ala Ser Asp Phe
    50                  55                  60

Lys Gly Cys Ala Ala Arg Lys Ile Leu Leu Pro Thr Ala Val Pro Ser
65                  70                  75                  80

Val Arg Asn Ala Val Ala Ala Lys Ala Gln Pro Asn
            85                  90

<210> SEQ ID NO 86
<211> LENGTH: 108
<212> TYPE: PRT
<213> ORGANISM: Anopheles gambiae

<400> SEQUENCE: 86

Met Ser Ala Val Arg Ser Cys Ala Leu Cys Gln Asn Arg Ser Asn Ile
1               5                   10                  15

Thr Asp Gln Gln Thr Asp Asp Ala Leu Glu Arg Ile Thr Tyr His Lys
            20                  25                  30

Phe Pro Thr Asn Pro Val Arg Arg Asp Arg Trp Ile Glu Phe Cys Asp
        35                  40                  45

Leu Pro Lys Glu Ser Phe Pro Lys Ser Ala Tyr Lys Phe Leu Cys Ser
    50                  55                  60

Ser His Phe Thr Pro Glu Cys Phe Glu Arg Asp Leu Arg Gly Glu Leu
65                  70                  75                  80

Leu Tyr Gly Thr Lys Arg Met Thr Leu Gln Lys Asp Ala Met Pro Thr
            85                  90                  95

Ile Arg Ser Val Ser Gln Gln Leu Lys Arg Thr Thr
        100                 105

<210> SEQ ID NO 87
<211> LENGTH: 100
<212> TYPE: PRT
<213> ORGANISM: Anopheles gambiae

<400> SEQUENCE: 87

Met Trp Asp Cys Ala Val Ile Gly Cys Pro Asn Ser Arg Phe Asn Ala
1               5                   10                  15

Gln Lys Thr Arg Pro Arg Ile Ser Phe His Val Phe Pro His Pro Val
            20                  25                  30

Arg Glu Ser Asn Arg Phe Arg Arg Trp Leu Ala Leu Ile Asn Asn Pro
        35                  40                  45

Arg Leu Phe Arg Leu Asp Pro Leu Asn Val Phe Lys Ser Val Arg Val
    50                  55                  60

Cys Arg Arg His Phe Gly Pro Asp Cys Phe Asn Gly Val Cys Arg Asn
65                  70                  75                  80

```
Leu Leu Pro Thr Ala Ile Pro Thr Leu Asn Leu Pro Glu Val Arg Pro
            85                  90                  95

Val Ala Leu Val
            100

<210> SEQ ID NO 88
<211> LENGTH: 95
<212> TYPE: PRT
<213> ORGANISM: Anopheles gambiae

<400> SEQUENCE: 88

Met Gly Ile Arg Lys Cys Ile Val Pro Glu Cys Pro Ser Ser Ser Ala
1               5                   10                  15

Arg Pro Glu Asp Arg Gly Val Thr Tyr His Lys Ile Pro Tyr Leu Asp
            20                  25                  30

Glu Met Lys Arg Leu Trp Ile Val Ala Cys His Leu Pro Asp Asp Tyr
        35                  40                  45

Phe Ala Thr Lys Ala Ser Asn Val Cys Ser Arg His Phe Arg Arg Ala
    50                  55                  60

Asp Phe Gln Glu Phe Lys Gly Lys Lys Tyr Val Leu Lys Leu Gly Val
65                  70                  75                  80

Val Pro Thr Val Phe Pro Trp Thr Val Thr Lys Pro Pro Gly Glu
                85                  90                  95

<210> SEQ ID NO 89
<211> LENGTH: 107
<212> TYPE: PRT
<213> ORGANISM: Anopheles gambiae

<400> SEQUENCE: 89

Met Gly Lys Ile Ser Gly Ser His Cys Leu Val Gly Cys Arg Asn
1               5                   10                  15

Arg Gln Leu Leu Asn Gln Ala Asn Ile Arg Ser Tyr Phe Arg Phe Pro
            20                  25                  30

Arg Asp Ala Asp Leu Cys Lys Lys Trp Val Asp Phe Cys Asn Arg Pro
        35                  40                  45

Glu Leu Tyr Lys Lys Tyr Asp Glu Asn Gly Pro Glu Tyr Leu Tyr Lys
    50                  55                  60

Ser Ser Arg Ile Cys Ser Asp His Phe Gln Pro Ala Asp Phe Asn Asn
65                  70                  75                  80

Pro Asn Leu Phe Ser Gln Gly Leu Lys Lys Gly Ser Val Pro Ser Val
                85                  90                  95

Asn Pro Ala Asn Leu Glu Ala Ala Lys Pro His
            100                 105

<210> SEQ ID NO 90
<211> LENGTH: 104
<212> TYPE: PRT
<213> ORGANISM: Anopheles gambiae

<400> SEQUENCE: 90

Met Thr Asn Cys Ser Cys Ala Val Ala Asp Cys Asn Asn Asn Arg Arg
1               5                   10                  15

Asn Val Arg Lys Arg Met Leu Asp Ile Gly Phe His Thr Phe Pro Ser
            20                  25                  30

Asp Pro Val Gln Arg Gln Arg Trp Val Lys Phe Cys Gly Arg Glu Pro
        35                  40                  45
```

```
Ser Trp Gln Pro Lys Ser Cys Asp Ser Met Cys Ser Val His Phe Lys
 50                  55                  60

Asp Thr Asp Tyr Gln Met Ser His Ser Pro Leu Ile Arg Leu Ala Thr
 65                  70                  75                  80

Asn Leu Arg Arg Leu Lys Pro Asp Val Ile Pro Thr Ile Arg Lys Gly
                 85                  90                  95

Arg Ala Ile Pro Val Ala Ala Arg
            100

<210> SEQ ID NO 91
<211> LENGTH: 95
<212> TYPE: PRT
<213> ORGANISM: Anopheles gambiae

<400> SEQUENCE: 91

Met Gly Gly Cys Arg Cys Thr Phe Arg Asp Cys Glu Asn Gly Thr Ala
 1               5                  10                  15

Ser Arg Lys Glu Leu His Tyr Phe Arg Tyr Pro Val Arg Asp Gln Glu
                 20                  25                  30

Arg Leu Ile Glu Trp Ala Lys Asn Ala Asp Arg Leu Glu Phe Val Asp
             35                  40                  45

Leu Pro Val Asp Lys Val Ser Asn Lys Val Val Cys Gln Glu His Phe
 50                  55                  60

Glu Arg Lys Met Phe Met Asn Asp Leu Arg Asp Arg Leu Thr Lys Met
 65                  70                  75                  80

Ala Ile Pro Arg Leu Met Val Met Pro Asp Glu Thr Ile Val Asn
                 85                  90                  95

<210> SEQ ID NO 92
<211> LENGTH: 97
<212> TYPE: PRT
<213> ORGANISM: Anopheles gambiae

<400> SEQUENCE: 92

Met Lys Cys Phe Val Ser Gly Cys Asp Thr Asp Asp Asn Val Val Ser
 1               5                  10                  15

Tyr Thr Ser Val Phe Tyr Val Asn Cys Pro Thr Asp Pro Thr Ile Gln
                 20                  25                  30

Gln Gln Trp Phe Thr Leu Leu Glu Val Thr Asp Pro Asp Ala Met Arg
             35                  40                  45

Ala Leu Val Asp Gly Arg Ser Lys Val Cys Ser Cys His Phe Thr Glu
 50                  55                  60

Asp Cys Phe Gly His His Pro Val Tyr Gly Tyr Arg Tyr Leu Leu Ala
 65                  70                  75                  80

Thr Ala Leu Pro Thr Val Phe Pro Pro Arg Lys Glu Ile Glu Gln Pro
                 85                  90                  95

Lys

<210> SEQ ID NO 93
<211> LENGTH: 92
<212> TYPE: PRT
<213> ORGANISM: Bombyx mori

<400> SEQUENCE: 93

Met Pro Arg Cys Ser Val Ile Val Cys Lys Asn Asn Ser Cys Ile Val
 1               5                  10                  15

Asn Tyr Lys Lys Asp Ser Ile Ser Phe His Thr Tyr Pro Lys Asp Pro
                 20                  25                  30
```

```
Lys Ile Lys Glu Met Trp Ile Asn Ala Thr Gly Arg Gly Pro Ser Trp
        35                  40                  45

Phe Pro Thr Lys Asn His Thr Ile Cys Ser Ser His Phe Glu Pro Lys
    50                  55                  60

Cys Phe Gln Pro Leu Lys Lys Val Arg Arg Leu Phe Glu Trp Ser Val
65                  70                  75                  80

Pro Thr Leu Lys Leu Arg Met Val Leu Met Asn Tyr
                85                  90
```

<210> SEQ ID NO 94
<211> LENGTH: 96
<212> TYPE: PRT
<213> ORGANISM: Bombyx mori

<400> SEQUENCE: 94

```
Met Pro Asp Thr His Arg Thr Cys Glu Val Cys Gly Ile Lys Glu Arg
1               5                   10                  15

His Leu Thr Glu Lys Arg Phe Phe Ala Arg Phe Pro Leu Asp Val Asn
            20                  25                  30

Arg Cys Lys Gln Trp Val Lys Met Val Gly Lys Glu Asp Leu Ala Tyr
        35                  40                  45

Leu Gln Val His Met Leu His Asp Leu Lys His Val Cys Glu Ala His
    50                  55                  60

Phe Ser Arg Arg Asp Phe Thr Lys Ser Lys Lys Arg Leu Lys Lys Arg
65                  70                  75                  80

Ala Val Pro Lys Leu Asn Leu Thr Leu Pro Pro Leu Arg Asp Glu Ile
                85                  90                  95
```

<210> SEQ ID NO 95
<211> LENGTH: 89
<212> TYPE: PRT
<213> ORGANISM: Caenorhabditis elegans

<400> SEQUENCE: 95

```
Met Pro Thr Thr Cys Gly Phe Pro Asn Cys Lys Phe Arg Ser Arg Tyr
1               5                   10                  15

Arg Gly Leu Glu Asp Asn Arg His Phe Tyr Arg Ile Pro Lys Arg Pro
            20                  25                  30

Leu Ile Leu Arg Gln Arg Trp Leu Thr Ala Ile Gly Arg Thr Glu Glu
        35                  40                  45

Thr Val Val Ser Gln Leu Arg Ile Cys Ser Ala His Phe Glu Gly Gly
    50                  55                  60

Glu Lys Lys Glu Gly Asp Ile Pro Val Pro Asp Pro Thr Val Asp Lys
65                  70                  75                  80

Gln Ile Lys Ile Glu Leu Pro Pro Lys
                85
```

<210> SEQ ID NO 96
<211> LENGTH: 100
<212> TYPE: PRT
<213> ORGANISM: Caenorhabditis elegans

<400> SEQUENCE: 96

```
Met Tyr Gly Val Gln Ser Glu Cys Val Leu Cys Ala His Ala Asn Asp
1               5                   10                  15

Cys Thr Ala Met Ile Pro Phe Pro Gly Pro Asp Asp Glu Lys Leu Arg
            20                  25                  30
```

```
Thr Lys Trp Ile Asn Ser Met Cys Arg Glu Pro Trp Ile Tyr Arg Tyr
        35                  40                  45

Leu Ser Thr Arg Leu Glu Lys Pro Gly Arg His Tyr Leu Cys Ala Ser
 50                  55                  60

His Phe Asn Arg Asn Ser Leu Arg Tyr His Ala Gly Leu Gly Leu Trp
 65                  70                  75                  80

Arg Arg Ala Ala Ala Cys Pro Val Leu Ala Cys Thr Thr Asp Glu Glu
                 85                  90                  95

Arg Gln Glu Val
            100

<210> SEQ ID NO 97
<211> LENGTH: 86
<212> TYPE: PRT
<213> ORGANISM: Caenorhabditis elegans

<400> SEQUENCE: 97

Met Glu His Pro Leu Gln Cys Cys Tyr Cys Leu Glu Val Tyr Glu Lys
  1               5                  10                  15

Arg Tyr Met Thr Gln Val Pro Lys Thr Glu Gln Arg Ile Ala Arg Trp
             20                  25                  30

Val Ala Ile Leu Gly Glu Gln Phe Arg Ile Arg Leu Arg Met Lys Pro
         35                  40                  45

Ala Asn Tyr Met Cys Arg Lys His Phe Pro Gln Ala Asp Phe Ser Ser
     50                  55                  60

Arg Gly Arg Leu Leu Lys Thr Ala Val Pro Asn Val Val Ser Gln Glu
 65                  70                  75                  80

Lys Val Leu Ala Phe Lys
             85

<210> SEQ ID NO 98
<211> LENGTH: 97
<212> TYPE: PRT
<213> ORGANISM: Caenorhabditis elegans

<400> SEQUENCE: 98

Asn Leu Thr His Lys Pro Cys Thr Val Cys Asn Arg Val Met Lys Ser
  1               5                  10                  15

Gly Glu Met His Leu Asn Phe Pro Ala Asp Leu Asp Arg Arg Arg Ile
             20                  25                  30

Trp Ala Asn Leu Leu Gly Phe Lys Tyr Lys Asp Ile Leu Arg Ser Lys
         35                  40                  45

Met Gly Pro Val Ser Phe Ser Ile Ala Ala Gly Pro Ile Cys Thr Glu
     50                  55                  60

His Phe Ala Glu Glu Cys Phe Arg Asn His Asn Phe Asn Lys Ser Ala
 65                  70                  75                  80

Ile Glu Ala Phe Gly Val Pro Val Ala Ile Ser Pro Asp Val Lys Thr
                 85                  90                  95

Thr

<210> SEQ ID NO 99
<211> LENGTH: 210
<212> TYPE: PRT
<213> ORGANISM: Mus musculus
```

```
<400> SEQUENCE: 99

Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Gln Trp Glu Ala Val Lys Arg Lys Asn Phe Lys Pro Thr
        35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
65                  70                  75                  80

Phe Leu Tyr Ile Glu Pro His Glu Lys Lys Glu Asp Leu Glu Ser Gln
                85                  90                  95

Glu Gln Leu Pro Ser Pro Ser Pro Ala Ser Gln Val Asp Ala Ala
            100                 105                 110

Ile Gly Leu Leu Met Pro Pro Leu Gln Thr Pro Asp Asn Leu Ser Val
            115                 120                 125

Phe Cys Asp His Asn Tyr Thr Val Glu Asp Thr Met His Gln Arg Lys
    130                 135                 140

Arg Ile Leu Gln Leu Glu Gln Gln Val Glu Lys Leu Arg Lys Lys Leu
145                 150                 155                 160

Lys Thr Ala Gln Gln Arg Cys Arg Arg Gln Glu Arg Gln Leu Glu Lys
                165                 170                 175

Leu Lys Glu Val Val His Phe Gln Arg Glu Lys Asp Asp Ala Ser Glu
            180                 185                 190

Arg Gly Tyr Val Ile Leu Pro Asn Asp Tyr Phe Glu Ile Val Glu Val
        195                 200                 205

Pro Ala
    210

<210> SEQ ID NO 100
<211> LENGTH: 217
<212> TYPE: PRT
<213> ORGANISM: Mus musculus

<400> SEQUENCE: 100

Met Pro Thr Asn Cys Ala Ala Gly Cys Ala Ala Thr Tyr Asn Lys
1               5                   10                  15

His Ile Asn Ile Ser Phe His Arg Phe Pro Leu Asp Pro Lys Arg Arg
            20                  25                  30

Lys Glu Trp Val Arg Leu Val Arg Lys Asn Phe Val Pro Gly Lys
        35                  40                  45

His Thr Phe Leu Cys Ser Lys His Phe Glu Ala Ser Cys Phe Asp Leu
    50                  55                  60

Thr Gly Gln Thr Arg Arg Leu Lys Met Asp Ala Val Pro Thr Ile Phe
65                  70                  75                  80

Asp Phe Cys Thr His Ile Lys Ser Leu Lys Leu Lys Ser Arg Asn Leu
                85                  90                  95

Leu Lys Thr Asn Asn Ser Phe Pro Pro Thr Gly Pro Cys Asn Leu Lys
            100                 105                 110

Leu Asn Gly Ser Gln Gln Val Leu Leu Glu His Ser Tyr Ala Phe Arg
            115                 120                 125

Asn Pro Met Glu Ala Lys Lys Arg Ile Ile Lys Leu Glu Lys Glu Ile
            130                 135                 140
```

```
Ala Ser Leu Arg Lys Lys Met Lys Thr Cys Leu Gln Arg Glu Arg Arg
145                 150                 155                 160

Ala Thr Arg Arg Trp Ile Lys Ala Thr Cys Phe Val Lys Ser Leu Glu
                165                 170                 175

Ala Ser Asn Met Leu Pro Lys Gly Ile Ser Glu Gln Ile Leu Pro Thr
            180                 185                 190

Ala Leu Ser Asn Leu Pro Leu Glu Asp Leu Lys Ser Leu Glu Gln Asp
        195                 200                 205

Gln Gln Asp Lys Thr Val Pro Ile Leu
    210                 215

<210> SEQ ID NO 101
<211> LENGTH: 218
<212> TYPE: PRT
<213> ORGANISM: Mus musculus

<400> SEQUENCE: 101

Met Pro Lys Ser Cys Ala Ala Arg Gln Cys Cys Asn Arg Tyr Ser Ser
1               5                   10                  15

Arg Arg Lys Gln Leu Thr Phe His Arg Phe Pro Phe Ser Arg Pro Glu
            20                  25                  30

Leu Leu Arg Glu Trp Val Leu Asn Ile Gly Arg Ala Asp Phe Lys Pro
        35                  40                  45

Lys Gln His Thr Val Ile Cys Ser Glu His Phe Arg Pro Glu Cys Phe
    50                  55                  60

Ser Ala Phe Gly Asn Arg Lys Asn Leu Lys His Asn Ala Val Pro Thr
65                  70                  75                  80

Val Phe Ala Phe Gln Asn Pro Thr Glu Val Cys Pro Glu Val Gly Ala
                85                  90                  95

Gly Gly Asp Ser Ser Gly Arg Asn Met Asp Thr Thr Leu Glu Glu Leu
            100                 105                 110

Gln Pro Pro Thr Pro Glu Gly Pro Val Gln Val Leu Pro Asp Arg
        115                 120                 125

Glu Ala Met Glu Ala Thr Glu Ala Ala Gly Leu Pro Ala Ser Pro Leu
    130                 135                 140

Gly Leu Lys Arg Pro Leu Pro Gly Gln Pro Ser Asp His Ser Tyr Ala
145                 150                 155                 160

Leu Ser Asp Leu Asp Thr Leu Lys Lys Lys Leu Phe Leu Thr Leu Lys
                165                 170                 175

Glu Asn Lys Arg Leu Arg Lys Arg Leu Lys Ala Gln Arg Leu Leu Leu
            180                 185                 190

Arg Arg Thr Cys Gly Arg Leu Arg Ala Tyr Arg Glu Gly Gln Pro Gly
        195                 200                 205

Pro Arg Ala Arg Arg Pro Ala Gln Gly Ser
    210                 215

<210> SEQ ID NO 102
<211> LENGTH: 205
<212> TYPE: PRT
<213> ORGANISM: Mus musculus

<400> SEQUENCE: 102

Met Val Ile Cys Cys Ala Ala Val Asn Cys Ser Asn Arg Gln Gly Lys
1               5                   10                  15

Gly Glu Lys Arg Ala Val Ser Phe His Arg Phe Pro Leu Lys Asp Ser
            20                  25                  30
```

```
Lys Arg Leu Ile Gln Trp Leu Lys Ala Val Gln Arg Asp Asn Trp Thr
            35                  40                  45

Pro Thr Lys Tyr Ser Phe Leu Cys Ser Glu His Phe Thr Lys Asp Ser
 50                  55                  60

Phe Ser Lys Arg Leu Glu Asp Gln His Arg Leu Leu Lys Pro Thr Ala
 65                  70                  75                  80

Val Pro Ser Ile Phe His Leu Ser Glu Lys Lys Arg Gly Ala Gly Gly
                 85                  90                  95

His Gly His Ala Arg Arg Lys Thr Thr Ala Ala Met Arg Gly His Thr
            100                 105                 110

Ser Ala Glu Thr Gly Lys Gly Thr Ile Gly Ser Ser Leu Ser Ser Ser
            115                 120                 125

Asp Asn Leu Met Ala Lys Pro Glu Ser Arg Lys Leu Lys Arg Ala Ser
130                 135                 140

Leu Gln Asp Asp Ala Ala Pro Lys Val Thr Pro Gly Ala Val Ser Gln
145                 150                 155                 160

Glu Gln Gly Gln Ser Leu Glu Lys Thr Pro Gly Asp Pro Ala Ala
                165                 170                 175

Pro Leu Ala Arg Gly Gln Glu Glu Ala Gln Ala Ser Ala Thr Glu Ala
            180                 185                 190

Asp His Gln Lys Ala Ser Ser Ser Thr Asp Ala Glu Gly
            195                 200                 205

<210> SEQ ID NO 103
<211> LENGTH: 186
<212> TYPE: PRT
<213> ORGANISM: Mus musculus

<400> SEQUENCE: 103

Ile Leu Gln Ala Phe Gly Ser Leu Lys Lys Gly Asp Val Leu Cys Ser
 1                   5                  10                  15

Arg His Phe Lys Lys Thr Asp Phe Asp Arg Ser Thr Leu Asn Thr Lys
                20                  25                  30

Leu Lys Ala Gly Ala Ile Pro Ser Ile Phe Glu Cys Pro Tyr His Leu
            35                  40                  45

Gln Glu Lys Arg Glu Lys Leu His Cys Arg Lys Asn Phe Leu Leu Lys
 50                  55                  60

Thr Leu Pro Ile Thr His His Gly Arg Gln Leu Val Gly Ala Ser Cys
 65                  70                  75                  80

Ile Glu Glu Phe Glu Pro Gln Phe Ile Phe Glu His Ser Tyr Ser Val
                 85                  90                  95

Met Asp Ser Pro Lys Lys Leu Lys His Lys Leu Asp Arg Val Ile Ile
            100                 105                 110

Glu Leu Glu Asn Thr Lys Glu Ser Leu Arg Asn Val Leu Ala Arg Glu
            115                 120                 125

Lys His Phe Gln Lys Ser Leu Arg Lys Thr Ile Met Glu Leu Lys Asp
130                 135                 140

Glu Ser Leu Ile Ser Gln Glu Thr Ala Asn Ser Leu Gly Ala Phe Cys
145                 150                 155                 160

Trp Glu Cys Tyr His Glu Ser Thr Ala Gly Gly Cys Ser Cys Glu Val
                165                 170                 175

Ile Ser Tyr Met Leu His Leu Gln Leu Thr
            180                 185
```

<210> SEQ ID NO 104
<211> LENGTH: 194
<212> TYPE: PRT
<213> ORGANISM: Mus musculus

<400> SEQUENCE: 104

Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
            20                  25                  30

Asn Pro Arg Arg Gly Leu Trp Leu Ala Asn Cys Gln Arg Leu Asp Pro
        35                  40                  45

Ser Gly Gln Gly Leu Trp Asp Pro Thr Ser Glu Tyr Ile Tyr Phe Cys
    50                  55                  60

Ser Lys His Phe Glu Glu Asn Cys Phe Glu Leu Val Gly Ile Ser Gly
65                  70                  75                  80

Tyr His Arg Leu Lys Glu Gly Ala Val Pro Thr Ile Phe Glu Ser Phe
                85                  90                  95

Ser Lys Leu Arg Arg Thr Ala Lys Thr Lys Gly His Gly Tyr Pro Pro
            100                 105                 110

Gly Leu Pro Asp Val Ser Arg Leu Arg Arg Cys Arg Lys Arg Cys Ser
        115                 120                 125

Glu Arg Gln Gly Pro Thr Thr Pro Phe Ser Pro Pro Arg Ala Asp
    130                 135                 140

Ile Ile Cys Phe Pro Val Glu Glu Ala Ser Ala Pro Ala Thr Leu Pro
145                 150                 155                 160

Ala Ser Pro Ala Val Arg Leu Asp Pro Gly Leu Asn Ser Pro Phe Ser
                165                 170                 175

Asp Leu Leu Gly Pro Leu Gly Ala Gln Ala Asp Glu Ala Gly Cys Ser
            180                 185                 190

Thr Gln

<210> SEQ ID NO 105
<211> LENGTH: 305
<212> TYPE: PRT
<213> ORGANISM: Mus musculus

<400> SEQUENCE: 105

Met Pro Gly Phe Thr Cys Cys Val Pro Gly Cys Tyr Asn Asn Ser His
1               5                   10                  15

Arg Asp Lys Ala Leu His Phe Tyr Thr Phe Pro Lys Asp Ala Glu Leu
            20                  25                  30

Arg Arg Leu Trp Leu Lys Asn Val Ser Arg Ala Gly Val Ser Gly Cys
        35                  40                  45

Phe Ser Thr Phe Gln Pro Thr Thr Gly His Arg Leu Cys Ser Val His
    50                  55                  60

Phe Gln Gly Gly Arg Lys Thr Tyr Thr Val Arg Val Pro Thr Ile Phe
65                  70                  75                  80

Pro Leu Arg Gly Val Asn Glu Arg Lys Val Ala Arg Arg Pro Ala Gly
                85                  90                  95

Ala Ala Ala Ala Arg Arg Arg Gln Gln Gln Gln Gln Gln Gln Gln Gln
            100                 105                 110

Gln Gln Gln Gln Gln Leu Gln Gln Gln Gln Pro Ser Pro Ser Ser
        115                 120                 125

Ser Thr Ala Gln Thr Thr Gln Leu Gln Pro Asn Leu Val Ser Ala Ser
    130                 135                 140

```
Ala Ala Val Leu Leu Thr Leu Gln Ala Ala Val Asp Ser Asn Gln Ala
145                 150                 155                 160

Pro Gly Ser Val Val Pro Val Ser Thr Thr Pro Ser Gly Asp Asp Val
                165                 170                 175

Lys Pro Ile Asp Leu Thr Val Gln Val Glu Phe Ala Ala Ala Glu Gly
            180                 185                 190

Ala Ala Ala Ala Ala Ala Ser Glu Leu Glu Ala Ala Thr Ala Gly
        195                 200                 205

Leu Glu Ala Ala Glu Cys Thr Leu Gly Pro Gln Leu Val Val Gly
    210                 215                 220

Glu Glu Gly Phe Pro Asp Thr Gly Ser Asp His Ser Tyr Ser Leu Ser
225                 230                 235                 240

Ser Gly Thr Thr Glu Glu Leu Leu Arg Lys Leu Asn Glu Gln Arg
                245                 250                 255

Asp Ile Leu Ala Leu Met Glu Val Lys Met Lys Glu Met Lys Gly Ser
                260                 265                 270

Ile Arg His Leu Arg Leu Thr Glu Ala Lys Leu Arg Glu Glu Leu Arg
            275                 280                 285

Glu Lys Asp Arg Leu Leu Ala Met Ala Val Ile Arg Lys Lys His Gly
    290                 295                 300

Met
305

<210> SEQ ID NO 106
<211> LENGTH: 305
<212> TYPE: PRT
<213> ORGANISM: Mus musculus

<400> SEQUENCE: 106

Met Pro Gly Phe Thr Cys Cys Val Pro Gly Cys Tyr Asn Asn Ser His
1               5                   10                  15

Arg Asp Lys Ala Leu His Phe Tyr Thr Phe Pro Lys Asp Ala Glu Leu
            20                  25                  30

Arg Arg Leu Trp Leu Lys Asn Val Ser Arg Ala Gly Val Ser Gly Cys
        35                  40                  45

Phe Ser Thr Phe Gln Pro Thr Thr Gly His Arg Leu Cys Ser Val His
    50                  55                  60

Phe Gln Gly Gly Arg Lys Thr Tyr Thr Val Arg Val Pro Thr Ile Phe
65                  70                  75                  80

Pro Leu Arg Gly Val Asn Glu Arg Lys Val Ala Arg Arg Pro Ala Gly
                85                  90                  95

Ala Ala Ala Ala Arg Arg Arg Gln Gln Gln Gln Gln Gln Gln Gln
            100                 105                 110

Gln Gln Gln Gln Gln Leu Gln Gln Gln Gln Pro Ser Pro Ser Ser
        115                 120                 125

Ser Thr Ala Gln Thr Thr Gln Leu Gln Pro Asn Leu Val Ser Ala Ser
    130                 135                 140

Ala Ala Val Leu Leu Thr Leu Gln Ala Ala Val Asp Ser Asn Gln Ala
145                 150                 155                 160

Pro Gly Ser Val Val Pro Val Ser Thr Thr Pro Ser Gly Asp Asp Val
                165                 170                 175

Lys Pro Ile Asp Leu Thr Val Gln Val Glu Phe Ala Ala Ala Glu Gly
            180                 185                 190

Ala Ala Ala Ala Ala Ala Ser Glu Leu Glu Ala Ala Thr Ala Gly
        195                 200                 205
```

```
Leu Glu Ala Ala Glu Cys Thr Leu Gly Pro Gln Leu Val Val Gly
    210                 215                 220

Glu Glu Gly Phe Pro Asp Thr Gly Ser Asp His Ser Tyr Ser Leu Ser
225                 230                 235                 240

Ser Gly Thr Thr Glu Glu Leu Leu Arg Lys Leu Asn Glu Gln Arg
                245                 250                 255

Asp Ile Leu Ala Leu Met Glu Val Lys Met Lys Glu Met Lys Gly Ser
                260                 265                 270

Ile Arg His Leu Arg Leu Thr Glu Ala Lys Leu Arg Glu Glu Leu Arg
                275                 280                 285

Glu Lys Asp Arg Leu Leu Ala Met Ala Val Ile Arg Lys Lys His Gly
290                 295                 300

Met
305

<210> SEQ ID NO 107
<211> LENGTH: 652
<212> TYPE: PRT
<213> ORGANISM: Mus musculus

<400> SEQUENCE: 107

Met Pro Asn Phe Cys Ala Ala Pro Asn Cys Thr Arg Lys Ser Thr Gln
1               5                   10                  15

Ser Asp Leu Ala Phe Phe Arg Phe Pro Arg Asp Pro Ala Arg Cys Gln
                20                  25                  30

Lys Trp Val Glu Asn Cys Arg Arg Ala Asp Leu Glu Asp Lys Thr Pro
            35                  40                  45

Asp Gln Leu Asn Lys His Tyr Arg Leu Cys Ala Lys His Phe Glu Thr
    50                  55                  60

Ser Met Ile Cys Arg Thr Ser Pro Tyr Arg Thr Val Leu Arg Asp Asn
65                  70                  75                  80

Ala Ile Pro Thr Ile Phe Asp Leu Thr Ser His Leu Asn Asn Pro His
                85                  90                  95

Ser Arg His Arg Lys Arg Ile Lys Glu Leu Ser Glu Asp Glu Ile Arg
            100                 105                 110

Thr Leu Lys Gln Lys Lys Ile Glu Glu Thr Ser Glu Gln Glu Gln Glu
        115                 120                 125

Thr Asn Thr Asn Ala Gln Asn Pro Ser Ala Glu Ala Val Asn Gln Gln
    130                 135                 140

Asp Ala Asn Val Leu Pro Leu Thr Leu Glu Glu Lys Glu Asn Lys Glu
145                 150                 155                 160

Tyr Leu Lys Ser Leu Phe Glu Ile Leu Val Leu Met Gly Lys Gln Asn
                165                 170                 175

Ile Pro Leu Asp Gly His Glu Ala Asp Glu Val Pro Glu Gly Leu Phe
                180                 185                 190

Ala Pro Asp Asn Phe Gln Ala Leu Leu Glu Cys Arg Ile Asn Ser Gly
            195                 200                 205

Glu Glu Val Leu Arg Lys Arg Phe Glu Ala Thr Ala Val Asn Thr Leu
    210                 215                 220

Phe Cys Ser Lys Thr Gln Gln Arg His Met Leu Glu Ile Cys Glu Ser
225                 230                 235                 240

Cys Ile Arg Glu Glu Thr Leu Arg Glu Val Arg Asp Ser His Phe Phe
                245                 250                 255

Ser Ile Ile Thr Asp Asp Val Val Asp Ile Ala Gly Glu Glu His Leu
                260                 265                 270
```

```
Pro Val Leu Val Arg Phe Val Asp Asp Ala His Asn Leu Arg Glu Glu
        275                 280                 285

Phe Val Gly Phe Leu Pro Tyr Glu Ala Asp Ala Glu Ile Leu Ala Val
        290                 295                 300

Lys Phe His Thr Thr Ile Thr Glu Lys Trp Gly Leu Asn Met Glu Tyr
305                 310                 315                 320

Cys Arg Gly Gln Ala Tyr Ile Val Ser Ser Gly Phe Ser Ser Lys Met
                325                 330                 335

Lys Val Val Ala Ser Arg Leu Leu Glu Lys Tyr Pro Gln Ala Val Tyr
                340                 345                 350

Thr Leu Cys Ser Ser Cys Ala Leu Asn Ala Trp Leu Ala Lys Ser Val
            355                 360                 365

Pro Val Ile Gly Val Ser Val Ala Leu Gly Thr Ile Glu Glu Val Cys
        370                 375                 380

Ser Phe Phe His Arg Ser Pro Gln Leu Leu Glu Leu Asp Ser Val
385                 390                 395                 400

Ile Ser Val Leu Phe Gln Asn Ser Glu Glu Arg Ala Lys Glu Leu Lys
                405                 410                 415

Glu Ile Cys His Ser Gln Trp Thr Gly Arg His Asp Ala Phe Glu Ile
                420                 425                 430

Leu Val Asp Leu Leu Gln Ala Leu Val Leu Cys Leu Asp Gly Ile Ile
            435                 440                 445

Asn Ser Asp Thr Asn Val Arg Trp Asn Asn Tyr Ile Ala Gly Arg Ala
        450                 455                 460

Phe Val Leu Cys Ser Ala Val Thr Asp Phe Asp Phe Ile Val Thr Ile
465                 470                 475                 480

Val Val Leu Lys Asn Val Leu Ser Phe Thr Arg Ala Phe Gly Lys Asn
                485                 490                 495

Leu Gln Gly Gln Thr Ser Asp Val Phe Phe Ala Ala Ser Ser Leu Thr
                500                 505                 510

Ala Val Leu His Ser Leu Asn Glu Val Met Glu Asn Ile Glu Val Tyr
            515                 520                 525

His Glu Phe Trp Phe Glu Glu Ala Thr Asn Leu Ala Thr Lys Leu Asp
        530                 535                 540

Ile Gln Met Lys Leu Pro Gly Lys Phe Arg Arg Ala Gln Gln Gly Asn
545                 550                 555                 560

Leu Glu Ser Gln Leu Thr Ser Glu Ser Tyr Tyr Lys Asp Thr Leu Ser
                565                 570                 575

Val Pro Thr Val Glu His Ile Ile Gln Glu Leu Lys Asp Ile Phe Ser
            580                 585                 590

Glu Gln His Leu Lys Ala Leu Lys Cys Leu Ser Leu Val Pro Ser Val
        595                 600                 605

Met Gly Gln Leu Lys Phe Asn Thr Ser Glu Glu His His Ala Asp Met
        610                 615                 620

Tyr Arg Ser Asp Leu Pro Asn Pro Asp Thr Leu Ser Ala Glu Leu His
625                 630                 635                 640

Cys Trp Arg Ile Lys Trp Lys His Arg Gly Lys Asp
                645                 650

<210> SEQ ID NO 108
<211> LENGTH: 180
<212> TYPE: PRT
<213> ORGANISM: Rattus norvegicus
```

```
<220> FEATURE:
<221> NAME/KEY: UNSURE
<222> LOCATION: 95
<223> OTHER INFORMATION: RAT THAP
<223> OTHER INFORMATION: Xaa = any of the twenty amino acids

<400> SEQUENCE: 108

Arg Gln Cys Cys Asn Arg Tyr Ser Ser Arg Arg Lys Gln Leu Thr Phe
  1               5                  10                  15

His Arg Phe Pro Phe Ser Arg Pro Glu Leu Leu Arg Glu Trp Val Leu
             20                  25                  30

Asn Ile Gly Arg Ala Asp Phe Lys Pro Lys Gln His Thr Val Ile Cys
         35                  40                  45

Ser Glu His Phe Arg Pro Glu Cys Phe Ser Ala Phe Gly Asn Arg Lys
     50                  55                  60

Asn Leu Lys His Asn Ala Val Pro Thr Val Phe Ala Phe Gln Asn Pro
 65                  70                  75                  80

Ala Gln Val Cys Pro Glu Val Gly Ala Gly Gly Asp Ser Ser Xaa Arg
                 85                  90                  95

Asn Met Asp Ala Thr Leu Glu Glu Leu Gln Ser Pro Asn Thr Glu Gly
                100                 105                 110

Pro Met Gln Gln Val Leu Pro Asp Arg Gln Ala Thr Glu Ala Met Glu
                115                 120                 125

Ala Ala Gly Leu Pro Ala Gly Pro Leu Gly Leu Lys Arg Pro Leu Pro
            130                 135                 140

Gly Gln Pro Ser Asp His Ser Tyr Ala Leu Leu Asp Leu Asp Thr Leu
145                 150                 155                 160

Lys Lys Lys Leu Phe Leu Thr Leu Lys Glu Asn Lys Arg Leu Arg Lys
                165                 170                 175

Arg Leu Lys Ala
            180

<210> SEQ ID NO 109
<211> LENGTH: 82
<212> TYPE: PRT
<213> ORGANISM: Rattus norvegicus

<400> SEQUENCE: 109

Met Val Lys Cys Cys Ser Ala Ile Gly Cys Ala Ser Arg Cys Leu Pro
  1               5                  10                  15

Asn Ser Lys Leu Lys Gly Leu Thr Phe His Val Phe Pro Thr Asp Glu
             20                  25                  30

Asn Ile Lys Arg Lys Trp Val Leu Ala Met Lys Arg Leu Asp Val Asn
         35                  40                  45

Thr Ala Gly Ile Trp Glu Pro Ser Leu Gln Pro Glu Ser Phe Tyr Phe
     50                  55                  60

Ile Phe Met Glu Asn Leu Phe Phe Ile Leu Pro Pro Gln Leu Ser His
 65                  70                  75                  80

Ala Val

<210> SEQ ID NO 110
<211> LENGTH: 309
<212> TYPE: PRT
<213> ORGANISM: Rattus norvegicus
```

<400> SEQUENCE: 110

| | | | | | | | | | | | | | | |
|---|---|---|---|---|---|---|---|---|---|---|---|---|---|---|
|Met|Pro|Arg|His|Cys|Ser|Ala|Ala|Gly|Cys|Cys|Thr|Arg|Asp|Thr|Arg|
|1| | | |5| | | | |10| | | | |15| |

Glu Thr Arg Asn Arg Gly Ile Ser Phe His Arg Leu Pro Lys Lys Asp
        20              25              30

Asn Pro Arg Arg Gly Leu Trp Leu Ala Asn Cys Gln Arg Leu Asp Pro
        35              40              45

Ser Gly Gln Gly Leu Trp Asp Pro Thr Ser Glu Tyr Ile Tyr Phe Cys
50              55              60

Ser Lys His Phe Glu Glu Asn Cys Phe Glu Leu Val Gly Ile Ser Gly
65              70              75              80

Tyr His Arg Leu Lys Glu Gly Ala Val Pro Thr Ile Phe Glu Ser Phe
        85              90              95

Ser Lys Leu Arg Arg Thr Ala Lys Thr Lys Val His Gly Tyr Pro Pro
        100            105            110

Gly Leu Pro Asp Val Ser Arg Leu Arg Arg Cys Arg Lys Arg Cys Ser
        115            120            125

Glu Arg Gln Gly Pro Thr Ile Pro Phe Ser Pro Pro Arg Ala Asp
130              135            140

Ile Ile Arg Phe Pro Val Glu Glu Ala Ser Ala Pro Ala Thr Leu Pro
145              150            155            160

Ala Ser Pro Ala Ala Arg Leu Asp Pro Gly Leu Asn Ser Pro Phe Ser
        165            170            175

Asp Leu Leu Gly Pro Leu Gly Ala Gln Ala Asp Glu Ala Gly Cys Ser
        180            185            190

Ala Gln Pro Ser Pro Glu Gln His Pro Ser Pro Leu Glu Pro Gln His
        195            200            205

Val Ser Pro Ser Thr Tyr Met Leu Arg Leu Pro Pro Pro Ala Gly Ala
        210            215            220

Tyr Ile Gln Asn Glu His Ser Tyr Gln Val Gly Ser Ala Leu Leu Trp
225              230            235            240

Lys Arg Arg Ala Glu Ala Ala Leu Asp Ala Leu Asp Lys Thr Gln Arg
        245            250            255

Gln Leu Gln Ala Cys Lys Arg Arg Glu Gln Arg Leu Arg Leu Arg Leu
        260            265            270

Thr Lys Leu Gln Gln Glu Arg Ala Arg Glu Lys Arg Ala Gln Ala Asp
        275            280            285

Ala Arg Gln Thr Leu Lys Asp His Val Gln Asp Phe Ala Met Gln Leu
        290            295            300

Ser Ser Ser Met Ala
305

<210> SEQ ID NO 111
<211> LENGTH: 142
<212> TYPE: PRT
<213> ORGANISM: Rattus norvegicus

<400> SEQUENCE: 111

Met Pro Asn Phe Cys Ala Ala Pro Asn Cys Thr Arg Lys Ser Thr Gln
1              5              10              15

Ser Asp Leu Ala Phe Phe Arg Phe Pro Arg Asp Pro Ala Arg Cys Gln
        20              25              30

Lys Trp Val Glu Asn Cys Arg Arg Ala Asp Leu Glu Asp Lys Thr Pro
        35              40              45

```
Asp Gln Leu Asn Lys His Tyr Arg Leu Cys Ala Lys His Phe Glu Thr
         50                  55                  60

Ser Met Ile Cys Arg Thr Ser Pro Tyr Arg Thr Val Leu Arg Asp Asn
 65                  70                  75                  80

Ala Ile Pro Thr Ile Phe Asp Leu Thr Ser His Leu Asn Asn Pro His
                 85                  90                  95

Ser Arg His Arg Lys Arg Ile Lys Glu Leu Ser Glu Asp Glu Ile Arg
                100                 105                 110

Thr Leu Lys Gln Lys Lys Ile Glu Glu Thr Ser Glu Gln Glu Gln Gly
            115                 120                 125

Thr Asn Ser Asn Ala Gln Tyr Pro Ser Ala Glu Val Gly Asn
            130                 135                 140

<210> SEQ ID NO 112
<211> LENGTH: 104
<212> TYPE: PRT
<213> ORGANISM: Sus scrofa

<400> SEQUENCE: 112

Met Val Lys Cys Cys Ser Ala Ile Gly Cys Ala Ser Arg Cys Leu Pro
 1               5                  10                  15

Asn Ser Lys Leu Lys Gly Leu Thr Phe His Val Phe Pro Thr Asp Glu
             20                  25                  30

Lys Val Lys Arg Lys Trp Val Leu Ala Met Lys Arg Leu Asp Val Asn
         35                  40                  45

Ala Ala Gly Met Trp Glu Pro Lys Lys Gly Asp Val Leu Cys Ser Arg
     50                  55                  60

His Phe Lys Lys Thr Asp Phe Asp Arg Thr Thr Pro Asn Ile Lys Leu
 65                  70                  75                  80

Lys Pro Gly Val Ile Pro Ser Ile Phe Asp Ser Pro Ser His Leu Thr
                 85                  90                  95

Gly Glu Glu Arg Lys Ala Pro Leu
            100

<210> SEQ ID NO 113
<211> LENGTH: 235
<212> TYPE: PRT
<213> ORGANISM: Sus scrofa
<220> FEATURE:
<221> NAME/KEY: UNSURE
<222> LOCATION: 57, 124, 192
<223> OTHER INFORMATION: Xaa = any of the twenty amino acids

<400> SEQUENCE: 113

Met Pro Arg His Cys Ser Ala Ala Gly Cys Cys Thr Arg Asp Thr Arg
 1               5                  10                  15

Glu Thr Arg Asn Arg Gly Ile Ser Phe His Arg Leu Pro Lys Lys Asp
             20                  25                  30

Asn Pro Arg Arg Gly Leu Trp Leu Ala Asn Cys Gln Arg Leu Asp Pro
         35                  40                  45

Ser Gly Gln Gly Leu Trp Asp Pro Xaa Ser Glu Tyr Ile Tyr Phe Cys
     50                  55                  60

Ser Lys His Phe Glu Glu Asn Cys Phe Glu Leu Val Gly Ile Ser Gly
 65                  70                  75                  80

Tyr His Arg Leu Lys Glu Gly Ala Val Pro Thr Ile Phe Glu Ser Phe
                 85                  90                  95

Ser Lys Leu Arg Arg Thr Ala Lys Thr Lys Gly His Ser Tyr Pro Pro
            100                 105                 110
```

```
Gly Pro Pro Asp Val Ser Arg Leu Arg Arg Cys Xaa Lys Arg Cys Ser
            115                 120                 125

Glu Gly Arg Gly Pro Thr Thr Pro Phe Ser Pro Pro Pro Ala Asp
        130                 135                 140

Val Thr Cys Phe Pro Val Glu Glu Ala Ser Ala Pro Ala Ala Leu Ser
145                 150                 155                 160

Ala Ser Pro Thr Gly Arg Leu Glu Pro Gly Leu Ser Ser Pro Phe Ser
                165                 170                 175

Asp Leu Leu Gly Pro Leu Gly Ala Gln Ala Asp Glu Ala Gly Cys Xaa
                180                 185                 190

Thr Gln Pro Ser Pro Glu Arg Glu Pro Glu Arg Gln Pro Ser Pro Leu
                195                 200                 205

Glu Pro Arg Pro Val Ser Pro Ser Ala Tyr Met Leu Arg Leu Pro Pro
            210                 215                 220

Pro Ala Gly Ala Tyr Ile Gln Asn Glu His Ser
225                 230                 235

<210> SEQ ID NO 114
<211> LENGTH: 149
<212> TYPE: PRT
<213> ORGANISM: Sus scrofa

<400> SEQUENCE: 114

Met Thr Arg Ser Cys Ser Ala Val Gly Cys Ser Thr Arg Asp Thr Val
1               5                   10                  15

Leu Ser Arg Glu Arg Gly Leu Ser Phe His Gln Phe Pro Thr Asp Thr
            20                  25                  30

Ile Gln Arg Ser Gln Trp Ile Arg Ala Val Asn Arg Met Asp Pro Arg
        35                  40                  45

Ser Lys Lys Ile Trp Ile Pro Gly Pro Gly Ala Met Leu Cys Ser Lys
    50                  55                  60

His Phe Gln Glu Ser Asp Phe Glu Ser Tyr Gly Ile Arg Arg Lys Leu
65                  70                  75                  80

Lys Lys Gly Ala Val Pro Ser Val Ser Leu Tyr Lys Val Leu Gln Gly
                85                  90                  95

Ala His Leu Lys Gly Lys Ala Arg Gln Lys Ile Leu Lys Gln Pro Leu
            100                 105                 110

Pro Asp Asn Ser Gln Glu Val Ala Thr Glu Asp His Asn Tyr Ser Leu
        115                 120                 125

Lys Gly Pro Leu Thr Ile Gly Ala Glu Lys Leu Ala Glu Val Gln Gln
    130                 135                 140

Met Leu Gln Val Ser
145

<210> SEQ ID NO 115
<211> LENGTH: 43
<212> TYPE: PRT
<213> ORGANISM: Mus musculus

<400> SEQUENCE: 115

Val Leu Glu Asp Val Ala Ala Glu Gln Gly Leu Arg Glu Leu Gln
1               5                   10                  15

Arg Gly Arg Arg Gln Cys Arg Glu Arg Val Cys Ala Leu Arg Ala Ala
            20                  25                  30

Ala Glu Gln Arg Glu Ala Arg Cys Arg Asp Gly
        35                  40
```

<210> SEQ ID NO 116
<211> LENGTH: 45
<212> TYPE: PRT
<213> ORGANISM: Mus musculus

<400> SEQUENCE: 116

Gln Leu Glu Gln Gln Val Glu Lys Leu Arg Lys Lys Leu Lys Thr Ala
1               5                   10                  15

Gln Gln Arg Cys Arg Arg Gln Glu Arg Gln Leu Glu Lys Leu Lys Glu
            20                  25                  30

Val Val His Phe Gln Arg Glu Lys Asp Asp Ala Ser Glu
        35                  40                  45

<210> SEQ ID NO 117
<211> LENGTH: 45
<212> TYPE: PRT
<213> ORGANISM: Homo sapiens

<400> SEQUENCE: 117

Gln Leu Glu Gln Gln Val Glu Lys Leu Arg Lys Lys Leu Lys Thr Ala
1               5                   10                  15

Gln Gln Arg Cys Arg Arg Gln Glu Arg Gln Leu Glu Lys Leu Lys Glu
            20                  25                  30

Val Val His Phe Gln Lys Glu Lys Asp Asp Val Ser Glu
        35                  40                  45

<210> SEQ ID NO 118
<211> LENGTH: 342
<212> TYPE: PRT
<213> ORGANISM: Homo sapiens

<400> SEQUENCE: 118

Met Ala Thr Gly Gly Tyr Arg Thr Ser Ser Gly Leu Gly Gly Ser Thr
1               5                   10                  15

Thr Asp Phe Leu Glu Glu Trp Lys Ala Lys Arg Glu Lys Met Arg Ala
            20                  25                  30

Lys Gln Asn Pro Pro Gly Pro Ala Pro Pro Gly Gly Ser Ser Asp
            35                  40                  45

Ala Ala Gly Lys Pro Pro Ala Gly Ala Leu Gly Thr Pro Ala Ala Ala
50                  55                  60

Ala Ala Asn Glu Leu Asn Asn Leu Pro Gly Gly Ala Pro Ala Ala
65                  70                  75                  80

Pro Ala Val Pro Gly Pro Gly Gly Val Asn Cys Ala Val Gly Ser Ala
                85                  90                  95

Met Leu Thr Arg Ala Pro Pro Ala Arg Gly Pro Arg Arg Ser Glu Asp
            100                 105                 110

Glu Pro Pro Ala Ala Ser Ala Ser Ala Ala Pro Pro Gln Arg Asp
        115                 120                 125

Glu Glu Glu Pro Asp Gly Val Pro Glu Lys Gly Lys Ser Ser Gly Pro
130                 135                 140

Ser Ala Arg Lys Gly Lys Gly Gln Ile Glu Lys Arg Lys Leu Arg Glu
145                 150                 155                 160

Lys Arg Arg Ser Thr Gly Val Val Asn Ile Pro Ala Ala Glu Cys Leu
                165                 170                 175

Asp Glu Tyr Glu Asp Asp Glu Ala Gly Gln Lys Glu Arg Lys Arg Glu
            180                 185                 190

Asp Ala Ile Thr Gln Gln Asn Thr Ile Gln Asn Glu Ala Val Asn Leu
        195                 200                 205

```
Leu Asp Pro Gly Ser Ser Tyr Leu Leu Gln Glu Pro Pro Arg Thr Val
    210                 215                 220

Ser Gly Arg Tyr Lys Ser Thr Thr Ser Val Ser Glu Glu Asp Val Ser
225                 230                 235                 240

Ser Arg Tyr Ser Arg Thr Asp Arg Ser Gly Phe Pro Arg Tyr Asn Arg
                245                 250                 255

Asp Ala Asn Val Ser Gly Thr Leu Val Ser Ser Ser Thr Leu Glu Lys
            260                 265                 270

Lys Ile Glu Asp Leu Glu Lys Glu Val Val Thr Glu Arg Gln Glu Asn
        275                 280                 285

Leu Arg Leu Val Arg Leu Met Gln Asp Lys Glu Glu Met Ile Gly Lys
    290                 295                 300

Leu Lys Glu Glu Ile Asp Leu Leu Asn Arg Asp Leu Asp Asp Ile Glu
305                 310                 315                 320

Asp Glu Asn Glu Gln Leu Lys Gln Glu Asn Lys Thr Leu Leu Lys Val
                325                 330                 335

Val Gly Gln Leu Thr Arg
            340

<210> SEQ ID NO 119
<211> LENGTH: 134
<212> TYPE: PRT
<213> ORGANISM: Homo sapiens

<400> SEQUENCE: 119

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 120
<211> LENGTH: 766
<212> TYPE: PRT
<213> ORGANISM: Drosophila melanogaster

<400> SEQUENCE: 120

Met Lys Tyr Cys Lys Phe Cys Cys Lys Ala Val Thr Gly Val Lys Leu
1               5                   10                  15

Ile His Val Pro Lys Cys Ala Ile Lys Arg Lys Leu Trp Glu Gln Ser
            20                  25                  30

Leu Gly Cys Ser Leu Gly Glu Asn Ser Gln Ile Cys Asp Thr His Phe
        35                  40                  45
```

-continued

```
Asn Asp Ser Gln Trp Lys Ala Ala Pro Ala Lys Gly Gln Thr Phe Lys
     50                  55                  60
Arg Arg Arg Leu Asn Ala Asp Ala Val Pro Ser Lys Val Ile Glu Pro
 65                  70                  75                  80
Glu Pro Glu Lys Ile Lys Glu Gly Tyr Thr Ser Gly Ser Thr Gln Thr
                 85                  90                  95
Glu Ser Cys Ser Leu Phe Asn Glu Asn Lys Ser Leu Arg Glu Lys Ile
                100                 105                 110
Arg Thr Leu Glu Tyr Glu Met Arg Arg Leu Glu Gln Gln Leu Arg Glu
            115                 120                 125
Ser Gln Gln Leu Glu Glu Ser Leu Arg Lys Ile Phe Thr Asp Thr Gln
130                 135                 140
Ile Arg Ile Leu Lys Asn Gly Gly Gln Arg Ala Thr Phe Asn Ser Asp
145                 150                 155                 160
Asp Ile Ser Thr Ala Ile Cys Leu His Thr Ala Gly Pro Arg Ala Tyr
                165                 170                 175
Asn His Leu Tyr Lys Lys Gly Phe Pro Leu Pro Ser Arg Thr Thr Leu
            180                 185                 190
Tyr Arg Trp Leu Ser Asp Val Asp Ile Lys Arg Gly Cys Leu Asp Val
        195                 200                 205
Val Ile Asp Leu Met Asp Ser Asp Gly Val Asp Ala Asp Lys Leu
210                 215                 220
Cys Val Leu Ala Phe Asp Glu Met Lys Val Ala Ala Phe Glu Tyr
225                 230                 235                 240
Asp Ser Ser Ala Asp Ile Val Tyr Glu Pro Ser Asp Tyr Val Gln Leu
                245                 250                 255
Ala Ile Val Arg Gly Leu Lys Lys Ser Trp Lys Gln Pro Val Phe Phe
            260                 265                 270
Asp Phe Asn Thr Arg Met Asp Pro Asp Thr Leu Asn Asn Ile Leu Arg
        275                 280                 285
Lys Leu His Arg Lys Gly Tyr Leu Val Val Ala Ile Val Ser Asp Leu
290                 295                 300
Gly Thr Gly Asn Gln Lys Leu Trp Thr Glu Leu Gly Ile Ser Glu Ser
305                 310                 315                 320
Lys Thr Trp Phe Ser His Pro Ala Asp Asp His Leu Lys Ile Phe Val
                325                 330                 335
Phe Ser Asp Thr Pro His Leu Ile Lys Leu Val Arg Asn His Tyr Val
            340                 345                 350
Asp Ser Gly Leu Thr Ile Asn Gly Lys Lys Leu Thr Lys Lys Thr Ile
        355                 360                 365
Gln Glu Ala Leu His Leu Cys Asn Lys Ser Asp Leu Ser Ile Leu Phe
370                 375                 380
Lys Ile Asn Glu Asn His Ile Asn Val Arg Ser Leu Ala Lys Gln Lys
385                 390                 395                 400
Val Lys Leu Ala Thr Gln Leu Phe Ser Asn Thr Ala Ser Ser Ile
                405                 410                 415
Arg Arg Cys Tyr Ser Leu Gly Tyr Asp Ile Glu Asn Ala Thr Glu Thr
            420                 425                 430
Ala Asp Phe Phe Lys Leu Met Asn Asp Trp Phe Asp Ile Phe Asn Ser
        435                 440                 445
Lys Leu Ser Thr Ser Asn Cys Ile Glu Cys Ser Gln Pro Tyr Gly Lys
450                 455                 460
```

```
Gln Leu Asp Ile Gln Asn Asp Ile Leu Asn Arg Met Ser Glu Ile Met
465                 470                 475                 480

Arg Thr Gly Ile Leu Asp Lys Pro Lys Arg Leu Pro Phe Gln Lys Gly
                485                 490                 495

Ile Ile Val Asn Asn Ala Ser Leu Asp Gly Leu Tyr Lys Tyr Leu Gln
            500                 505                 510

Glu Asn Phe Ser Met Gln Tyr Ile Leu Thr Ser Arg Leu Asn Gln Asp
            515                 520                 525

Ile Val Glu His Phe Phe Gly Ser Met Arg Ser Arg Gly Gly Gln Phe
            530                 535                 540

Asp His Pro Thr Pro Leu Gln Phe Lys Tyr Arg Leu Arg Lys Tyr Ile
545                 550                 555                 560

Ile Ala Arg Asn Thr Glu Met Leu Arg Asn Ser Gly Asn Ile Glu Glu
                565                 570                 575

Gly Met Thr Asn Leu Lys Glu Cys Val Asn Lys Asn Val Ile Pro Asp
            580                 585                 590

Asn Ser Glu Ser Trp Leu Asn Leu Asp Phe Ser Ser Lys Glu Asn Glu
            595                 600                 605

Asn Lys Ser Lys Asp Asp Glu Pro Val Asp Glu Pro Val Asp Glu
            610                 615                 620

Met Leu Ser Asn Ile Asp Phe Thr Glu Met Asp Glu Leu Thr Glu Asp
625                 630                 635                 640

Ala Met Glu Tyr Ile Ala Gly Tyr Val Ile Lys Lys Leu Arg Ile Ser
                645                 650                 655

Asp Lys Val Lys Glu Asn Leu Thr Phe Thr Tyr Val Asp Glu Val Ser
            660                 665                 670

His Gly Gly Leu Ile Lys Pro Ser Glu Lys Phe Gln Glu Lys Leu Lys
            675                 680                 685

Glu Leu Glu Cys Ile Phe Leu His Tyr Thr Asn Asn Asn Phe Glu
            690                 695                 700

Ile Thr Asn Asn Val Lys Glu Lys Leu Ile Leu Ala Ala Arg Asn Val
705                 710                 715                 720

Asp Val Asp Lys Gln Val Lys Ser Phe Tyr Phe Lys Ile Arg Ile Tyr
                725                 730                 735

Phe Arg Ile Lys Tyr Phe Asn Lys Lys Ile Glu Ile Lys Asn Gln Lys
            740                 745                 750

Gln Lys Leu Ile Gly Asn Ser Lys Leu Leu Lys Ile Lys Leu
            755                 760                 765

<210> SEQ ID NO 121
<211> LENGTH: 103
<212> TYPE: PRT
<213> ORGANISM: Homo sapiens

<400> SEQUENCE: 121

Asp Glu Leu Cys Val Val Cys Gly Asp Lys Ala Thr Gly Tyr His Tyr
1               5                   10                  15

Arg Cys Ile Thr Cys Glu Gly Cys Lys Gly Phe Phe Arg Arg Thr Ile
                20                  25                  30

Gln Lys Asn Leu His Pro Ser Tyr Ser Cys Lys Tyr Glu Gly Lys Cys
            35                  40                  45

Val Ile Asp Lys Val Thr Arg Asn Gln Cys Gln Glu Cys Arg Phe Lys
        50                  55                  60

Lys Cys Ile Tyr Val Gly Met Ala Thr Asp Leu Val Leu Asp Asp Ser
65                  70                  75                  80
```

```
Lys Arg Leu Ala Lys Arg Lys Leu Ile Glu Glu Asn Arg Glu Lys Arg
                85                  90                  95

Arg Arg Glu Glu Leu Glu Lys
            100
```

<210> SEQ ID NO 122
<211> LENGTH: 81
<212> TYPE: PRT
<213> ORGANISM: Homo sapiens

<400> SEQUENCE: 122

```
Met Lys Pro Ala Arg Pro Cys Leu Val Cys Ser Asp Glu Ala Ser Gly
1               5                   10                  15

Cys His Tyr Gly Val Leu Thr Cys Gly Ser Cys Lys Val Phe Phe Lys
            20                  25                  30

Arg Ala Val Glu Gly Gln His Asn Tyr Leu Cys Ala Gly Arg Asn Asp
        35                  40                  45

Cys Ile Ile Asp Lys Ile Arg Arg Lys Asn Cys Pro Ala Cys Arg Tyr
50                  55                  60

Arg Lys Cys Leu Gln Ala Gly Met Asn Leu Glu Ala Arg Lys Thr Lys
65                  70                  75                  80

Lys
```

<210> SEQ ID NO 123
<211> LENGTH: 89
<212> TYPE: PRT
<213> ORGANISM: Homo sapiens

<400> SEQUENCE: 123

```
Met Val Gln Ser Cys Ser Ala Tyr Gly Cys Lys Asn Arg Tyr Asp Lys
1               5                   10                  15

Asp Lys Pro Val Ser Phe His Lys Phe Pro Leu Thr Arg Pro Ser Leu
            20                  25                  30

Cys Lys Glu Trp Glu Ala Ala Val Arg Arg Lys Asn Phe Lys Pro Thr
        35                  40                  45

Lys Tyr Ser Ser Ile Cys Ser Glu His Phe Thr Pro Asp Cys Phe Lys
50                  55                  60

Arg Glu Cys Asn Asn Lys Leu Leu Lys Glu Asn Ala Val Pro Thr Ile
65                  70                  75                  80

Phe Leu Cys Thr Glu Pro His Asp Lys
            85
```

<210> SEQ ID NO 124
<211> LENGTH: 85
<212> TYPE: PRT
<213> ORGANISM: Drosophila melanogaster

<400> SEQUENCE: 124

```
Met Lys Tyr Cys Lys Phe Cys Cys Lys Ala Val Thr Gly Val Lys Leu
1               5                   10                  15

Ile His Val Pro Lys Cys Ala Ile Lys Arg Lys Leu Trp Glu Gln Ser
            20                  25                  30

Leu Gly Cys Ser Leu Gly Glu Asn Ser Gln Ile Cys Asp Thr His Phe
        35                  40                  45

Asn Asp Ser Gln Trp Lys Ala Ala Pro Ala Lys Gly Gln Thr Phe Lys
50                  55                  60
```

```
Arg Arg Arg Leu Asn Ala Asp Ala Val Pro Ser Lys Val Ile Glu Pro
 65                  70                  75                  80

Glu Pro Glu Lys Ile
                85

<210> SEQ ID NO 125
<211> LENGTH: 58
<212> TYPE: PRT
<213> ORGANISM: Artificial Sequence
<220> FEATURE:
<223> OTHER INFORMATION: THAP Domain consensus
<220> FEATURE:
<221> NAME/KEY: UNSURE
<222> LOCATION: 2-3, 7, 9, 13-17, 19, 21-23,  25-26, 28, 35, 38-39, 41,
      45-50, 52, 55-56
<223> OTHER INFORMATION: Xaa = any of the twenty amino acids

<400> SEQUENCE: 125

Met Val Xaa Xaa Cys Ser Xaa Tyr Xaa Cys Lys Asn Xaa Xaa Xaa Xaa
 1               5                   10                  15

Xaa Lys Xaa Val Xaa Xaa Xaa Lys Xaa Xaa Leu Xaa Arg Pro Ser Leu
                20                  25                  30

Cys Lys Xaa Trp Glu Xaa Xaa Val Xaa Arg Lys Asn Xaa Xaa Xaa Xaa
            35                  40                  45

Xaa Xaa Ser Xaa Ile Cys Xaa Xaa His Phe
    50                  55

<210> SEQ ID NO 126
<211> LENGTH: 89
<212> TYPE: PRT
<213> ORGANISM: Homo sapiens

<400> SEQUENCE: 126

Met Val Gln Ser Cys Ser Ala Tyr Gly Cys Lys Asn Arg Tyr Asp Lys
 1               5                   10                  15

Asp Lys Pro Val Ser Phe His Lys Phe Pro Leu Thr Arg Pro Ser Leu
                20                  25                  30

Cys Lys Glu Trp Glu Ala Ala Val Arg Arg Lys Asn Phe Lys Pro Thr
            35                  40                  45

Lys Tyr Ser Ser Ile Cys Ser Glu His Phe Thr Pro Asp Cys Phe Lys
    50                  55                  60

Arg Glu Cys Asn Asn Lys Leu Leu Lys Glu Asn Ala Val Pro Thr Ile
 65                  70                  75                  80

Phe Leu Cys Thr Glu Pro His Asp Lys
                85

<210> SEQ ID NO 127
<211> LENGTH: 89
<212> TYPE: PRT
<213> ORGANISM: Homo sapiens

<400> SEQUENCE: 127

Met Pro Lys Ser Cys Ala Ala Arg Gln Cys Cys Asn Arg Tyr Ser Ser
 1               5                   10                  15

Arg Arg Lys Gln Leu Thr Phe His Arg Phe Pro Phe Ser Arg Pro Glu
                20                  25                  30

Leu Leu Lys Glu Trp Val Leu Asn Ile Gly Arg Gly Asn Phe Lys Pro
            35                  40                  45

Lys Gln His Thr Val Ile Cys Ser Glu His Phe Arg Pro Glu Cys Phe
    50                  55                  60
```

-continued

```
Ser Ala Phe Gly Asn Arg Lys Asn Leu Lys His Asn Ala Val Pro Thr
 65                  70                  75                  80

Val Phe Ala Phe Gln Asp Pro Thr Gln
                 85

<210> SEQ ID NO 128
<211> LENGTH: 90
<212> TYPE: PRT
<213> ORGANISM: Homo sapiens

<400> SEQUENCE: 128

Met Pro Arg Tyr Cys Ala Ala Ile Cys Cys Lys Asn Arg Arg Gly Arg
  1               5                  10                  15

Asn Asn Lys Asp Arg Lys Leu Ser Phe Tyr Pro Phe Pro Leu His Asp
                 20                  25                  30

Lys Glu Arg Leu Glu Lys Trp Leu Lys Asn Met Lys Arg Asp Ser Trp
             35                  40                  45

Val Pro Ser Lys Tyr Gln Phe Leu Cys Ser Asp His Phe Thr Pro Asp
 50                  55                  60

Ser Leu Asp Ile Arg Trp Gly Ile Arg Tyr Leu Lys Gln Thr Ala Val
 65                  70                  75                  80

Pro Thr Ile Phe Ser Leu Pro Glu Asp Asn
                 85                  90

<210> SEQ ID NO 129
<211> LENGTH: 92
<212> TYPE: PRT
<213> ORGANISM: Homo sapiens

<400> SEQUENCE: 129

Met Pro Lys Tyr Cys Arg Ala Pro Asn Cys Ser Asn Thr Ala Gly Arg
  1               5                  10                  15

Leu Gly Ala Asp Asn Arg Pro Val Ser Phe Tyr Lys Phe Pro Leu Lys
                 20                  25                  30

Asp Gly Pro Arg Leu Gln Ala Trp Leu Gln His Met Gly Cys Glu His
             35                  40                  45

Trp Val Pro Ser Cys His Gln His Leu Cys Ser Glu His Phe Thr Pro
 50                  55                  60

Ser Cys Phe Gln Trp Arg Trp Gly Val Arg Tyr Leu Arg Pro Asp Ala
 65                  70                  75                  80

Val Pro Ser Ile Phe Ser Arg Gly Pro Pro Ala Lys
                 85                  90

<210> SEQ ID NO 130
<211> LENGTH: 90
<212> TYPE: PRT
<213> ORGANISM: Homo sapiens

<400> SEQUENCE: 130

Met Val Ile Cys Cys Ala Ala Val Asn Cys Ser Asn Arg Gln Gly Lys
  1               5                  10                  15

Gly Glu Lys Arg Ala Val Ser Phe His Arg Phe Pro Leu Lys Asp Ser
                 20                  25                  30

Lys Arg Leu Ile Gln Trp Leu Lys Ala Val Gln Arg Asp Asn Trp Thr
             35                  40                  45

Pro Thr Lys Tyr Ser Phe Leu Cys Ser Glu His Phe Thr Lys Asp Ser
 50                  55                  60
```

Phe Ser Lys Arg Leu Glu Asp Gln His Arg Leu Leu Lys Pro Thr Ala
65                  70                  75                  80

Val Pro Ser Ile Phe His Leu Thr Glu Lys
                85                  90

<210> SEQ ID NO 131
<211> LENGTH: 89
<212> TYPE: PRT
<213> ORGANISM: Homo sapiens

<400> SEQUENCE: 131

Met Pro Thr Asn Cys Ala Ala Gly Cys Ala Thr Thr Tyr Asn Lys
1               5                   10                  15

His Ile Asn Ile Ser Phe His Arg Phe Pro Leu Asp Pro Lys Arg Arg
                20                  25                  30

Lys Glu Trp Val Arg Leu Val Arg Arg Lys Asn Phe Val Pro Gly Lys
            35                  40                  45

His Thr Phe Leu Cys Ser Lys His Phe Glu Ala Ser Cys Phe Asp Leu
        50                  55                  60

Thr Gly Gln Thr Arg Arg Leu Lys Met Asp Ala Val Pro Thr Ile Phe
65                  70                  75                  80

Asp Phe Cys Thr His Ile Lys Ser Met
                85

<210> SEQ ID NO 132
<211> LENGTH: 90
<212> TYPE: PRT
<213> ORGANISM: Homo sapiens

<400> SEQUENCE: 132

Met Pro Asn Phe Cys Ala Ala Pro Asn Cys Thr Arg Lys Ser Thr Gln
1               5                   10                  15

Ser Asp Leu Ala Phe Phe Arg Phe Pro Arg Asp Pro Ala Arg Cys Gln
                20                  25                  30

Lys Trp Val Glu Asn Cys Arg Arg Ala Asp Leu Glu Asp Lys Thr Pro
            35                  40                  45

Asp Gln Leu Asn Lys His Tyr Arg Leu Cys Ala Lys His Phe Glu Thr
        50                  55                  60

Ser Met Ile Cys Arg Thr Ser Pro Tyr Arg Thr Val Leu Arg Asp Asn
65                  70                  75                  80

Ala Ile Pro Thr Ile Phe Asp Leu Thr Ser
                85                  90

<210> SEQ ID NO 133
<211> LENGTH: 97
<212> TYPE: PRT
<213> ORGANISM: Homo sapiens

<400> SEQUENCE: 133

Met Pro Arg His Cys Ser Ala Ala Gly Cys Cys Thr Arg Asp Thr Arg
1               5                   10                  15

Glu Thr Arg Asn Arg Gly Ile Ser Phe His Arg Leu Pro Lys Lys Asp
                20                  25                  30

Asn Pro Arg Arg Gly Leu Trp Leu Ala Asn Cys Gln Arg Leu Asp Pro
            35                  40                  45

Ser Gly Gln Gly Leu Trp Asp Pro Ala Ser Glu Tyr Ile Tyr Phe Cys
        50                  55                  60

```
Ser Lys His Phe Glu Glu Asp Cys Phe Glu Leu Val Gly Ile Ser Gly
 65                  70                  75                  80

Tyr His Arg Leu Lys Glu Gly Ala Val Pro Thr Ile Phe Glu Ser Phe
                 85                  90                  95

Ser

<210> SEQ ID NO 134
<211> LENGTH: 92
<212> TYPE: PRT
<213> ORGANISM: Homo sapiens

<400> SEQUENCE: 134

Met Thr Arg Ser Cys Ser Ala Val Gly Cys Ser Thr Arg Asp Thr Val
 1               5                  10                  15

Leu Ser Arg Glu Arg Gly Leu Ser Phe His Gln Phe Pro Thr Asp Thr
                20                  25                  30

Ile Gln Arg Ser Lys Trp Ile Arg Ala Val Asn Arg Val Asp Pro Arg
             35                  40                  45

Ser Lys Lys Ile Trp Ile Pro Gly Pro Gly Ala Ile Leu Cys Ser Lys
 50                  55                  60

His Phe Gln Glu Ser Asp Phe Glu Ser Tyr Gly Ile Arg Arg Lys Leu
 65                  70                  75                  80

Lys Lys Gly Ala Val Pro Ser Val Ser Leu Tyr Lys
                85                  90

<210> SEQ ID NO 135
<211> LENGTH: 96
<212> TYPE: PRT
<213> ORGANISM: Homo sappiens

<400> SEQUENCE: 135

Met Val Lys Cys Cys Ser Ala Ile Gly Cys Ala Ser Arg Cys Leu Pro
 1               5                  10                  15

Asn Ser Lys Leu Lys Gly Leu Thr Phe His Val Phe Pro Thr Asp Glu
                20                  25                  30

Asn Ile Lys Arg Lys Trp Val Leu Ala Met Lys Arg Leu Asp Val Asn
             35                  40                  45

Ala Ala Gly Ile Trp Glu Pro Lys Lys Gly Asp Val Leu Cys Ser Arg
 50                  55                  60

His Phe Lys Lys Thr Asp Phe Asp Arg Ser Ala Pro Asn Ile Lys Leu
 65                  70                  75                  80

Lys Pro Gly Val Ile Pro Ser Ile Phe Asp Ser Pro Tyr His Leu Gln
                85                  90                  95

<210> SEQ ID NO 136
<211> LENGTH: 90
<212> TYPE: PRT
<213> ORGANISM: Homo sapiens

<400> SEQUENCE: 136

Met Pro Gly Phe Thr Cys Cys Val Pro Gly Cys Tyr Asn Asn Ser His
 1               5                  10                  15

Arg Asp Lys Ala Leu His Phe Tyr Thr Phe Pro Lys Asp Ala Glu Leu
                20                  25                  30

Arg Arg Leu Trp Leu Lys Asn Val Ser Arg Ala Gly Val Ser Gly Cys
             35                  40                  45

Phe Ser Thr Phe Gln Pro Thr Thr Gly His Arg Leu Cys Ser Val His
 50                  55                  60
```

-continued

Phe Gln Gly Gly Arg Lys Thr Tyr Thr Val Arg Val Pro Thr Ile Phe
65                  70                  75                  80

Pro Leu Arg Gly Val Asn Glu Arg Lys Val
                85                  90

<210> SEQ ID NO 137
<211> LENGTH: 90
<212> TYPE: PRT
<213> ORGANISM: Homo sapiens

<400> SEQUENCE: 137

Met Pro Ala Arg Cys Val Ala Ala His Cys Gly Asn Thr Thr Lys Ser
1               5                   10                  15

Gly Lys Ser Leu Phe Arg Phe Pro Lys Asp Arg Ala Val Arg Leu Leu
            20                  25                  30

Trp Asp Arg Phe Val Arg Gly Cys Arg Ala Asp Trp Tyr Gly Gly Asn
        35                  40                  45

Asp Arg Ser Val Ile Cys Ser Asp His Phe Ala Pro Ala Cys Phe Asp
    50                  55                  60

Val Ser Ser Val Ile Gln Lys Asn Leu Arg Phe Ser Gln Arg Leu Arg
65                  70                  75                  80

Leu Val Ala Gly Ala Val Pro Thr Leu His
                85                  90

<210> SEQ ID NO 138
<211> LENGTH: 85
<212> TYPE: PRT
<213> ORGANISM: Drosophila melanogaster

<400> SEQUENCE: 138

Met Lys Tyr Cys Lys Phe Cys Cys Lys Ala Val Thr Gly Val Lys Leu
1               5                   10                  15

Ile His Val Pro Lys Cys Ala Ile Lys Arg Lys Leu Trp Glu Gln Ser
            20                  25                  30

Leu Gly Cys Ser Leu Gly Glu Asn Ser Gln Ile Cys Asp Thr His Phe
        35                  40                  45

Asn Asp Ser Gln Trp Lys Ala Ala Pro Ala Lys Gly Gln Thr Phe Lys
    50                  55                  60

Arg Arg Arg Leu Asn Ala Asp Ala Val Pro Ser Lys Val Ile Glu Pro
65                  70                  75                  80

Glu Pro Glu Lys Ile
                85

<210> SEQ ID NO 139
<211> LENGTH: 63
<212> TYPE: PRT
<213> ORGANISM: Artificial Sequence
<220> FEATURE:
<223> OTHER INFORMATION: THAP Domain consensus
<220> FEATURE:
<221> NAME/KEY: UNSURE
<222> LOCATION: 4-5, 7, 9-10, 12, 15-20, 22, 24, 32, 35, 38-39, 42-43,
      46-47, 49-51, 53-61, 63
<223> OTHER INFORMATION: Xaa = any of the twenty amino acids

<400> SEQUENCE: 139

Met Pro Lys Xaa Xaa Cys Xaa Ala Xaa Xaa Cys Xaa Asn Arg Xaa Xaa
1               5                   10                  15

Xaa Xaa Xaa Xaa Lys Xaa Lys Xaa Val Ser Phe His Lys Phe Pro Xaa
            20                  25                  30

```
His Asp Xaa His Asp Xaa Xaa Arg Arg Xaa Xaa Trp Val Xaa Xaa Val
        35                  40                  45

Xaa Xaa Xaa Arg Xaa Xaa Xaa Xaa Xaa Xaa Xaa Xaa Trp Xaa
    50                  55                  60
```

<210> SEQ ID NO 140
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 140
gggcatacta ctggcaa 17

<210> SEQ ID NO 141
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 141
gggcaaactg tgggcat 17

<210> SEQ ID NO 142
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 142
gggcatacta ctggcaa 17

<210> SEQ ID NO 143
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 143
gggcaaacta ctggcaa 17

<210> SEQ ID NO 144
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 144
gggccagttc gttgcaa 17

<210> SEQ ID NO 145
<211> LENGTH: 16
<212> TYPE: DNA
<213> ORGANISM: Artificial Sequence
<220> FEATURE:
<223> OTHER INFORMATION: DR-5-related sequence

<400> SEQUENCE: 145
gggcatgtac tggcaa 16

```
<210> SEQ ID NO 146
<211> LENGTH: 16
<212> TYPE: DNA
<213> ORGANISM: Artificial Sequence
<220> FEATURE:
<223> OTHER INFORMATION: DR-5-related sequence

<400> SEQUENCE: 146
gggcaactgt gggcaa                                                      16

<210> SEQ ID NO 147
<211> LENGTH: 18
<212> TYPE: DNA
<213> ORGANISM: Artificial Sequence
<220> FEATURE:
<223> OTHER INFORMATION: DR-5-related sequence

<400> SEQUENCE: 147
gggcaacact actggcaa                                                    18

<210> SEQ ID NO 148
<211> LENGTH: 17
<212> TYPE: DNA
<213> ORGANISM: Artificial Sequence
<220> FEATURE:
<223> OTHER INFORMATION: DR-5-related sequence

<400> SEQUENCE: 148
gggcaaagta ctggcaa                                                     17

<210> SEQ ID NO 149
<211> LENGTH: 17
<212> TYPE: DNA
<213> ORGANISM: Artificial Sequence
<220> FEATURE:
<223> OTHER INFORMATION: DR-5 consensus sequence
<220> FEATURE:
<221> NAME/KEY: unsure
<222> LOCATION: 7-11
<223> OTHER INFORMATION: n = any of the four nucleotides

<400> SEQUENCE: 149
gggcaannnn ntggcaa                                                     17

<210> SEQ ID NO 150
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 150
ttgccagtac taagtgtggg caa                                              23

<210> SEQ ID NO 151
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 151
ctgccagtac atagtgtggg caa                                              23
```

```
<210> SEQ ID NO 152
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 152
ttgccagtac taagtgtggg caa                                               23

<210> SEQ ID NO 153
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 153
ctgccagtag atactgtggg caa                                               23

<210> SEQ ID NO 154
<211> LENGTH: 24
<212> TYPE: DNA
<213> ORGANISM: Artificial Sequence
<220> FEATURE:
<223> OTHER INFORMATION: ER-11-related sequence

<400> SEQUENCE: 154
ttgccagtag ttaggtgtgg gcga                                              24

<210> SEQ ID NO 155
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 155
ttgccagtag ttagtgtggg caa                                               23

<210> SEQ ID NO 156
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 156
ttgccagtac ctactaaggg caa                                               23

<210> SEQ ID NO 157
<211> LENGTH: 23
<212> TYPE: DNA
<213> ORGANISM: Artificial Sequence
<220> FEATURE:
<223> OTHER INFORMATION: ER-11-related sequence

<400> SEQUENCE: 157
ttgccagtag ttagtgtggg cag                                               23

<210> SEQ ID NO 158
<211> LENGTH: 23
<212> TYPE: DNA
<213> ORGANISM: Artificial Sequence
<220> FEATURE:
<223> OTHER INFORMATION: ER-11-related sequence
```

```
<400> SEQUENCE: 158
ctgccagtag taagtgtggg cag                                              23

<210> SEQ ID NO 159
<211> LENGTH: 23
<212> TYPE: DNA
<213> ORGANISM: Artificial Sequence
<220> FEATURE:
<223> OTHER INFORMATION: ER-11 consensus sequence
<220> FEATURE:
<221> NAME/KEY: unsure
<222> LOCATION: 7-17
<223> OTHER INFORMATION: n = any of the four nucleotides

<400> SEQUENCE: 159
ttgccannnn nnnnnnnggg caa                                              23

<210> SEQ ID NO 160
<211> LENGTH: 642
<212> TYPE: DNA
<213> ORGANISM: Homo sapiens

<400> SEQUENCE: 160
atggtgcagt cctgctccgc ctacggctgc aagaaccgct acgacaagga caagcccgtt      60
tctttccaca gtttcctct tactcgaccc agtctttgta aagaatggga ggcagctgtc     120
agaagaaaaa actttaaacc caccaagtat agcagtattt gttcagagca ctttactcca    180
gactgcttta agagagagtg caacaacaag ttactgaaag agaatgctgt gcccacaata    240
tttctttgta ctgagccaca tgacaagaaa gaagatcttc tggagccaca ggaacagctt    300
cccccacctc ctttaccgcc tcctgttttc caggttgatg ctgctattgg attactaatg    360
ccgcctcttc agacccctgt taatctctca gttttctgtg accacaacta tactgtggag    420
gatacaatgc accagcggaa aaggattcat cagctagaac agcaagttga aaaactcaga    480
aagaagctca agaccgcaca gcagcgatgc agaaggcaag aacggcagct tgaaaaatta    540
aaggaggttg ttcacttcca gaaagagaaa gacgacgtat cagaaagagg ttatgtgatt    600
ctaccaaatg actactttga aatagttgaa gtaccagcat aa                       642

<210> SEQ ID NO 161
<211> LENGTH: 687
<212> TYPE: DNA
<213> ORGANISM: Homo sapiens

<400> SEQUENCE: 161
atgccgacca attgcgctgc ggcgggctgt gccactacct acaacaagca cattaacatc      60
agcttccaca ggtttccttt ggatcctaaa agaagaaaag aatgggttcg cctggttagg     120
cgcaaaaatt ttgtgccagg aaaacacact tttctttgtt caaagcactt tgaagcctcc    180
tgttttgacc taacaggaca aactcgacga cttaaaatgg atgctgttcc aaccattttt    240
gattttgtta cccatataaa gtctatgaaa ctcaagtcaa ggaatctttt gaagaaaaac    300
aacagttgtt ctccagctgg accatctaat ttaaaatcaa acattagtag tcagcaagta    360
ctacttgaac acagctatgc ctttaggaat cctatggagg caaaaagag gatcattaaa    420 ctggaaaaag aaatagcaag cttaagaaga aaaatgaaaa cttgcctaca aaaggaacgc    480
agagcaactc gaagatggat caaagccacg tgtttggtaa agaatttaga agcaaatagt    540
gtattaccta aaggtacatc agaacacatg ttaccaactg ccttaagcag tcttcctttg    600
```

-continued

| | |
|---|---|
| gaagatttta agatccttga acaagatcaa caagataaaa cactgctaag tctaaatcta | 660 |
| aaacagacca agagtacctt catttaa | 687 |

<210> SEQ ID NO 162
<211> LENGTH: 720
<212> TYPE: DNA
<213> ORGANISM: Homo sapiens

<400> SEQUENCE: 162

| | |
|---|---|
| atgccgaagt cgtgcgcggc ccggcagtgc tgcaaccgct acagcagccg caggaagcag | 60 |
| ctcaccttcc accggtttcc gttcagccgc ccggagctgc tgaaggaatg ggtgctgaac | 120 |
| atcggccggg gcaacttcaa gcccaagcag cacacggtca tctgctccga gcacttccgg | 180 |
| ccagagtgct tcagcgcctt tggaaaccgc aagaacctaa agcacaatgc cgtgcccacg | 240 |
| gtgttcgcct ttcaggaccc cacacagcag gtgagggaga acacagaccc tgccagtgag | 300 |
| agaggaaatg ccagctcttc tcagaaagaa aaggtcctcc ctgaggcggg ggccggagag | 360 |
| gacagtcctg ggagaaacat ggacactgca cttgaagagc ttcagttgcc cccaaatgcc | 420 |
| gaaggccacg taaacaggt ctcgccacg aggccgcaag caacgagggc tgttggccgg | 480 |
| ccgactggcc ctgcaggcct gagaaggacc cccaacaagc agccatctga tcacagctat | 540 |
| gccctttggg acttagattc cctgaagaaa aaactcttcc tcactctgaa ggaaaatgaa | 600 |
| aagctccgga gcgcttgca ggcccagagg ctggtgatgc gaaggatgtc cagccgcctc | 660 |
| cgtgcttgca aagggcacca gggactccag gccagacttg gccagagca gcagagctga | 720 |

<210> SEQ ID NO 163
<211> LENGTH: 1734
<212> TYPE: DNA
<213> ORGANISM: Homo sapiens

<400> SEQUENCE: 163

| | |
|---|---|
| atggtgatct gctgtgcggc cgtgaactgc tccaaccggc agggaaaggg cgagaagcgc | 60 |
| gccgtctcct tccacaggtt cccccctaaag gactcaaaac gtctaatcca atggttaaaa | 120 |
| gctgttcaga gggataactg gactcccact aagtattcat ttctctgtag tgagcatttc | 180 |
| accaaagaca gcttctccaa gaggctggag gaccagcatc gcctgctgaa gcccacggcc | 240 |
| gtgccatcca tcttccacct gaccgagaag aagaggggg ctggaggcca tggccgcacc | 300 |
| cggagaaaag atgccagcaa ggccacaggg ggtgtgaggg gacactcgag tgccgccacc | 360 |
| ggcagaggag ctgcaggttg gtcaccgtcc tcgagtggaa acccgatggc caagccagag | 420 |
| tcccgcaggt tgaagcaagc tgctctgcaa ggtgaagcca cacccagggc ggcccaggag | 480 |
| gccgccagcc aggagcaggc ccagcaagct ctggaacgga ctccaggaga tggactggcc | 540 |
| accatggtgg caggcagtca gggaaaagca gaagcgtctg ccacagatgc tggcgatgag | 600 |
| agcgccactt cctccatcga aggggcgtg acagataaga gtggcatttc tatggatgac | 660 |
| tttacgcccc caggatctgg ggcgtgcaaa tttatcggct cacttcattc gtacagtttc | 720 |
| tcctctaagc acacccgaga aaggccatct gtccccgag agcccattga ccgcaagagg | 780 |
| ctgaagaaag atgtggaacc aagctgcagt gggagcagcc tgggacccga caagggcctg | 840 |
| gcccagagcc ctcccagctc atcacttacc gcgacaccgc agaagccttc ccagagcccc | 900 |
| tctgcccctc ctgccgacgt caccccaaag ccagccacgg aagccgtgca gagcgagcac | 960 |
| agcgacgcca gcccccatgtc catcaacgag gtcatcctgt cggcgtcagg ggcctgcaag | 1020 |
| ctcatcgact cactgcactc ctactgcttc tcctcccggc agaacaagag ccaggtgtgc | 1080 |

```
tgcctgcggg agcaggtgga gaagaagaac ggcgagctga agagcctgcg gcagagggtc    1140
agccgctccg acagccaggt gcggaagcta caggagaagc tggatgagct gaggagagtg    1200
agcgtcccct atccaagtag cctgctgtcg cccagccgcg agcccccaa  gatgaaccca    1260 gtggtggagc cactgtcctg gatgctgggc acctggctgt cggacccacc tggagccggg    1320
acctacccca cactgcagcc cttccagtac ctggaggagg ttacacatctc ccacgtgggc   1380 cagcccatgc tgaacttctc gttcaactcc ttccacccgg acacgcgcaa gccgatgcac    1440
agagagtgtg gcttcattcg cctcaagccc gacaccaaca aggtggcctt tgtcagcgcc    1500
cagaacacag gcgtggtgga agtggaggag ggcgaggtga acgggcagga gctgtgcatc    1560
gcatcccact ccatcgccag gatctccttc gccaaggagc cccacgtaga gcagatcacc    1620
cggaagttca ggctgaattc tgaaggcaaa cttgagcaga cggtctccat ggcaaccacg    1680
acacagccaa tgactcagca tcttcacgtc acctacaaga aggtgacccc gtaa          1734
```

```
<210> SEQ ID NO 164
<211> LENGTH: 1188
<212> TYPE: DNA
<213> ORGANISM: Homo sapiens

<400> SEQUENCE: 164
atgccccgct attgcgcagc gatttgttgt aagaaccgcc ggggacgaaa caataaagac      60
cggaagctga gttttatcc  atttcctcta catgacaaag aaagactgga aaagtggtta    120
aagaatatga agcgagattc atgggttccc agtaaatacc agtttctatg tagtgaccat    180
tttactcctg actctcttga catcagatgg ggtattcgat atttaaaaca aactgcagtt    240
ccaacaatat tttctttgcc tgaagacaat cagggaaaag acccttctaa aaaaaaatcc    300
cagaagaaaa acttggaaga tgagaaagaa gtatgcccaa aagccaagtc agaagaatca    360
tttgtattaa atgagacaaa gaaaaatata gttaacacag atgtgcccca tcaacatcca    420
gaattacttc attcatcttc cttggtaaag ccaccagctc ccaaaacagg aagtatacaa    480
aataacatgt taactcttaa tctagttaaa caacatactg ggaaaccaga atctaccttg    540
gaaacatcag ttaaccaaga tacaggtaga ggtggttttc acacatgttt tgagaatcta    600
aattctacaa ctattacttt gacaacttca aattcagaaa gtattcatca atctttggaa    660
actcaagaag ttcttgaagt aactaccagt catcttgcta atccaaactt tacaagtaat    720
tccatggaaa taaagtcagc acaggaaaat ccattcttat tcagcacaat taatcaaaca    780
gttgaagaat taaacacaaa taagaatct  gttattgcca ttttttgtacc tgctgaaaat    840 tctaaaccct cagttaattc ttttatatct gcacaaaaag aaaccacgga aatggaagac    900
acagacattg aagactcctt gtataaggat gtagactatg ggcagaagt  ttacaaatc     960 gaacattctt actgcagaca agatataaat aaggaacatc tttggcagaa agtctctaag   1020
ctacattcaa agataactct tctagagtta aaagagcaac aaactctagg tagattgaag   1080
tctttggaag ctcttataag gcagctaaag caggaaaact ggctatctga agaaaacgtc   1140
aagattatag aaaaccattt tacaacatat gaagtcacta tgatatag                1188
```

```
<210> SEQ ID NO 165
<211> LENGTH: 669
<212> TYPE: DNA
<213> ORGANISM: Homo sapiens
```

```
<400> SEQUENCE: 165
atggtgaaat gctgctccgc cattggatgt gcttctcgct gcttgccaaa ttcgaagtta      60
aaaggactga catttcacgt attccccaca gatgaaaaca tcaaaaggaa atgggtatta     120
gcaatgaaaa gacttgatgt gaatgcagcc ggcatttggg agcctaaaaa aggagatgtg     180
ttgtgttcga ggcactttaa gaagacagat tttgacagaa gtgctccaaa tattaaactg     240
aaacctggag tcatacctto tatctttgat totccatatc acctacaggg gaaaagagaa     300
aaacttcatt gtagaaaaaa cttcacccto aaaaccgttc cagccactaa ctacaatcac     360
catcttgttg gtgcttccto atgtattgaa gaattccaat cccagttcat ttttgaacat     420
agctacagtg taatggacag tccaaagaaa cttaagcata aattagatca tgtgatcggc     480
gagctagagg atacaaagga aagtctacgg aatgttttag accgagaaaa acgttttcag     540
aaatcattga ggaagacaat cagggaatta aaggatgaat gtctgatcag ccaagaaaca     600
gcaaatagac tggacacttt ctgttgggac tgttgtcagg agagcataga acaggactat     660
atttcatga                                                             669

<210> SEQ ID NO 166
<211> LENGTH: 930
<212> TYPE: DNA
<213> ORGANISM: Homo sapiens

<400> SEQUENCE: 166
atgccgcgtc actgctccgc cgccggctgc tgcacacggg acacgcgcga gacgcgcaac      60
cgcggcatct ccttccacag acttcccaag aaggacaacc cgaggcgagg cttgtggctg     120
gccaactgcc agcggctgga ccccagcggc cagggcctgt gggacccggc atccgagtac     180
atctacttct gctccaaaca cttttgaggag gactgctttg agctggtggg aatcagtgga     240
tatcacaggc taaaggaggg ggcagtcccc accatatttg agtctttctc caagttgcgc     300
cggacaacca agaccaaagg acacagttac ccacctggcc ccctgaagt cagccggctc     360 agacgatgca ggaagcgctg ctccgagggc cgagggccca caactccatt ttctccacct     420
ccacctgctg atgtcacctg ctttcctgtg gaagaggcct cagcacctgc cactttgccg     480
gcctccccag ctgggaggct ggagcctggc cttagcagcc ccttttcaga cctactgggc     540
cccttgggtg cccaggcaga tgaagcaggc tgcagcgccc agccttcacc agagcggcag     600
ccctcccctc tcgaaccacg gccagtctcc ccctcagcgt atatgctgcg cctgccccca     660
cccgccggag cctacatcca gaatgaacac agctaccagg tgggcagcgc cttactctgg     720
aagcggcgag ccgaggcagc ccttgatgcc cttgacaagg cccagcgcca gctgcaggcc     780
tgcaagcggc gggagcagcg gctgcggttg agactgacca agctgcagca ggagcgggca     840
cgggagaagc gggcacaggc agatgcccgc cagactctga aggagcatgt gcaggacttt     900
gccatgcagc tgagcagcag catggcctga                                     930

<210> SEQ ID NO 167
<211> LENGTH: 825
<212> TYPE: DNA
<213> ORGANISM: Homo sapiens

<400> SEQUENCE: 167
atgcccaagt actgcagggc gccgaactgc tccaacactg cggccgcct gggtgcagac      60 aaccgccctg tgagcttcta caagttccca ctgaaggatg gtccccggct gcaggcctgg     120
ctgcagcaca tgggctgtga gcactgggtg cccagctgcc accagcactt gtgcagcgag     180
```

```
cacttcacac cctcctgctt ccagtggcgc tggggtgtgc gctacctgcg gcctgatgca    240
gtgccctcca tcttctcccg gggaccacct gccaagagtc agcggaggac ccgaagcacc    300
cagaagccag tctcgccgcc gcctccccta cagaagaata caccccctgcc ccagagccct    360 gccatcccag tctctggccc agtgcgccta gtggtgctgg ccccacatc ggggagcccc    420 aagactgtgg ccaccatgct cctgaccccc ctggcccctg cgccaactcc tgagcggtca    480
caacctgaag tccctgccca acaggcccag accgggctgg gccagtgct gggagcactg    540 caacgccggg tgcggaggct gcaacggtgc caggagcggc accaggcgca gctgcaggcc    600
ctggaacggc tggcacagca gctacacggg gagagcctgc tggcacgggc acgccggggt    660
ctgcagcgcc tgacaacagc ccagacccctt ggacctgagg aatcccaaac cttcaccatc    720
atctgtggag ggcctgacat agccatggtc cttgcccagg accctgcacc tgccacagtg    780
gatgccaagc cggagctcct ggacactcgg atccccagtg cataa                     825

<210> SEQ ID NO 168
<211> LENGTH: 3171
<212> TYPE: DNA
<213> ORGANISM: Homo sapiens

<400> SEQUENCE: 168
atgacccgaa gttgctccgc agtgggctgc agcacccgtg acaccgtgct cagccgggag     60
cgcggcctct ccttccacca atttccaact gataccatac agcgctcaaa atggatcagg    120
gctgttaatc gtgtggaccc cagaagcaaa aagatttgga ttccaggacc aggtgctata    180
ctgtgttcca acatttttca agaaagtgac tttgagtcat atggcataag aagaaagctg    240
aaaaaaggag ctgtgccttc tgtttctcta tacaagattc ctcaaggtgt acatcttaaa    300
ggtaaagcaa gacaaaaaat cctaaaacaa cctcttccag acaattctca agaagttgct    360
actgaggacc ataactatag tttaaagaca ccttttgacga taggtgcaga gaaactggct    420
gaggtgcaac aaatgttaca agtgtccaaa aaaagactta tctccgtaaa gaactacagg    480
atgatcaaga gagaaaggg tttacgatta attgatgcac ttgtagaaga gaaactactt    540
tctgaagaaa cagagtgtct gctacgagct caattttcag attttaagtg ggagttatat    600
aattggagag aaacagatga gtactccgca gaaatgaaac aatttgcatg tacactctac    660
ttgtgcagta gcaaagtcta tgattatgta agaaagattc ttaagctgcc tcattcttcc    720
atcctcagaa cgtggttatc caaatgccaa cccagtccag gtttcaacag caacattttt    780
tcttttcttc aacgaagagt agagaatgga gatcagctct atcaatactg ttcattgtta    840 ataaaagta tacctctcaa gcaacagctt cagtgggatc ctagcagtca cagtttgcag    900
gggtttatgg actttggtct tggaaaactt gatgctgatg aaacgccact tgcttcagaa    960
actgttttgt taatggcagt gggtatttt ggccattgga gaacacctct tggttatttt   1020
tttgtaaaca gagcatctgg atatttgcag gctcagctgc ttcgtctgac tattggtaaa   1080
ctgagtgaca taggaatcac agttctggct gttacatctg atgccacagc acatagtgtt   1140
cagatggcaa aagcattggg gatacatatt gatggagacg acatgaaatg tacatttcag   1200
catccttcat cttctagtca acagattgca tacttctttg actcttgcca cttgctaaga   1260
ttaataagaa atgcatttca gaattttcaa agcattcagt ttattaatgg tatagcacat   1320
tggcagcacc tcgtggagtt agtagcactg gaggaacagg aattatcaaa tatggaaaga   1380
ataccaagta cacttgcaaa tttgaaaaat catgtactga agtgaatag tgccaccccaa   1440 ctctttagtg agagtgtagc cagtgcatta gaatatttgt tatccttaga cctgccacct   1500
```

```
tttcaaaact gtattggtac catccatttt ttacgtttaa ttaacaatct gtttgacatc    1560
tttaatagta ggaactgtta tggaaaggga cttaaagggc ctctgttgcc tgaaacttac    1620
agtaaaataa accacgtgtt aattgaagcc aagactattt ttgttacatt atctgacact    1680
agcaataatc aaataattaa aggtaagcaa aaactaggat tcctgggatt tttgctcaat    1740
gctgagagct taaatggct ctaccaaaat tatgttttcc caaaggtcat gccttttcct    1800
tatcttctga cttacaaatt cagtcatgat catctggaat tatttctaaa gatgcttagg    1860
caggtattag taacaagttc tagccctacc tgcatggcat tccagaaagc ttactataat    1920
ttggagacca gatacaaatt tcaagatgaa gttttctaa gcaaagtaag catctttgac     1980
atttcaattg ctcgaaggaa agacttggcg ctttggacag ttcaacgtca gtatggtgtc    2040
agcgttacaa agactgtctt tcacgaagag ggtatttgtc aagactggtc tcattgttca    2100
ctaagtgagg cattactaga cctgtcagat cataggcgaa atctcatctg ttatgctggt    2160
tatgttgcaa acaagttatc agctcttta acttgtgagg actgcatcac tgcactgtat     2220
gcatcggatc tcaaagcctc taaaattggg tcactattat ttgttaaaaa gaagaatggt    2280
ttgcattttc cttcagaaag tctgtgtcgg gtcataaata tttgtgagcg agttgtaaga    2340
acccattcaa gaatggcaat ttttgaacta gtttctaaac aaagggaatt gtatcttcaa    2400
cagaaaatat tatgtgagct ttctgggcat attgatcttt ttgtagatgt gaataagcat    2460
ctctttgatg gagaagtgtg tgccatcaat cactttgtca agttgctaaa ggatataata    2520
atctgtttct taaatatcag agctaaaaat gttgcacaga atcctttaaa acatcattca    2580
gagagaactg atatgaaaac tttatcaagg aaacactggt cacctgtaca ggattataaa    2640
tgttcaagtt ttgctaatac cagtagtaaa ttcaggcatt tgctaagtaa cgatggatat    2700
ccattcaaat gagagaccta aaatatatta acatttaat taagaatact tgatcaacat     2760
tttttgaagt tcaatttacc atatttata aattgcgcat tctgcacagt ggacaagttt    2820
gcaattctga cttattaaaa tttcaaattc tgcatatcac aaaatctcct tatacttttg    2880
gtatggcttg cagcatttat gagttttcca aaatatagaa agcagtaggt cagtaggagc    2940
aaactagcca acaggtactg tctttgaatt tactactgta agactaagca gtgttactgg    3000
acacagtttt aacttgttca atctgcttca aaaacaagaa aaacaacaac tatgagttat    3060
caaaatattg actccatttta tgactagact acatttctga aagatctttg gtttacgatt    3120
cttaagaata ttgacaatac ctataaaact ttgaagataa cttttactta a             3171
```

<210> SEQ ID NO 169
<211> LENGTH: 774
<212> TYPE: DNA
<213> ORGANISM: Homo sapiens

<400> SEQUENCE: 169

```
atgccggccc gttgtgtggc cgcccactgc ggcaacacca ccaagtctgg gaagtcgctg      60
ttccgctttc ccaaggaccg ggccgtgcgg ctgctctggg accgcttcgt gcggggttgc     120
cgcgccgact ggtacggagg caatgaccgc tcggtcatct gctctgacca ctttgcccca     180
gcctgttttg acgtctcttc ggttatccag aagaacctgc gcttctccca gcgcctgagg     240
ctggtggcag cgccgtgcc cacctgcac cgggtgcccg ccccggcacc taagagggga      300
gaggagggag accaagcagg ccgcctggac acgcgaggag agctccaggc agccaggcat    360
tctgaggctg ccccaggtcc agtctcctgt acacgcccccc gagctgggaa gcaggctgca    420
gcttcacaga ttacgtgtga aaatgaactt gtgcaaaccc aaccccatgc tgataatcca    480
```

```
tctaatactg tcacttcagt acctactcac tgtgaagaag gcccagtgca taaaagtaca    540
caaatttctt tgaaaaggcc ccgtcaccgt agtgtgggta ttcaagccaa agtgaaagcg    600
tttggaaaaa gactgtgtaa tgcaactact cagacagagg aattgtggtc tagaacttcc    660
tctctctttg acatttactc cagtgattca gaaacagata cagactggga tatcaagagt    720
gaacagagtg atttgtctta tatggctgta caggtgaaag aagaaacatg ttaa          774
```

<210> SEQ ID NO 170
<211> LENGTH: 945
<212> TYPE: DNA
<213> ORGANISM: Homo sapiens

<400> SEQUENCE: 170

```
atgcctggct ttacgtgctg cgtgccaggc tgctacaaca actcgcaccg ggacaaggcg     60
ctgcacttct acacgtttcc aaaggacgct gagttgcggc gcctctggct caagaacgtg    120
tcgcgtgccg gcgtcagtgg gtgcttctcc accttccagc ccaccacagg ccaccgtctc    180
tgcagcgttc acttccaggg cggccgcaag acctacacgg tacgcgtccc caccatcttc    240
ccgctgcgcg cgtcaatga gcgcaaagta gcgcgcagac ccgctggggc cgcggccgcc    300
cgccgcaggc agcagcagca acagcagcag cagcagcaac agcagcaaca gcagcagcag    360
cagcaacagc agcagcagca gcagcagcag cagcagtcct caccctctgc ctccactgcc    420
cagactgccc agctgcagcc gaacctggta tctgcttccg cggccgtgct tctcacccct    480
caggccactg tagacagcag tcaggctccg ggatccgtac agccggcgcc catcactccc    540
actggagaag acgtgaagcc catcgatctc acagtgcaag tggagtttgc agccgcagag    600
ggcgcagccg ctgcggccgc cgcgtcggag ttacaggctg ctaccgcagg gctggaggct    660
gccgagtgcc ctatgggccc ccagttggtg gtggtagggg aagagggctt ccctgatact    720
ggctccgacc attcgtactc cttgtcgtca ggcaccacgg aggaggagct cctgcgcaag    780
ctgaatgagc agcgggacat cctggctctg atggaagtga agatgaaaga gatgaaaggc    840
agcattcgcc acctgcgtct cactgaggcc aagctgcgcg aagaactgcg tgagaaggat    900
cggctgcttg ccatggctgt catccgcaag aagcacggaa tgtga                   945
```

<210> SEQ ID NO 171
<211> LENGTH: 2286
<212> TYPE: DNA
<213> ORGANISM: Homo sapiens

<400> SEQUENCE: 171

```
atgccgaact tctgcgctgc ccccaactgc acgcggaaga gcacgcagtc cgacttggcc     60
ttcttcaggt tcccgcggga ccctgccaga tgccagaagt gggtggagaa ctgtaggaga    120
gcagacttag aagataaaac acctgatcag ctaaataaac attatcgatt atgtgccaaa    180
cattttgaga cctctatgat ctgtagaact agtcctata ggacagttct tcgagataat    240
gcaataccaa caatatttga tcttaccagt catttgaaca acccacatag tagacacaga    300
aaacgaataa agaactgag tgaagatgaa atcaggacac tgaaacagaa aaaaattgat    360
gaaacttctg agcaggaaca aaaacataaa gaaaccaaca atagcaatgc tcagaacccc    420
agcgaagaag agggtgaagg gcaagatgag gacattttac ctctaacccct tgaagagaag    480 gaaaacaaag aataacctaaa atctctattt gaaatcttga ttctgatggg aaagcaaaac    540
atacctctgg atggacatga ggctgatgaa atcccagaag gtctcttac tccagataac    600 tttcaggcac tgctggagtg tcggataaat tctggtgaag aggttctgag aaagcggttt    660
```

-continued

| | |
|---|---|
| gagacaacag cagttaacac gttgttttgt tcaaaaacac agcagaggca gatgctagag | 720 |
| atctgtgaga gctgtattcg agaagaaact ctcagggaag tgagagactc acacttcttt | 780 |
| tccattatca ctgacgatgt agtggacata gcagggaag agcacctacc tgtgttggtg | 840 |
| aggtttgttg atgaatctca taacctaaga gaggaattta taggcttcct gccttatgaa | 900 |
| gccgatgcag aaattttggc tgtgaaattt cacactatga taactgagaa gtggggatta | 960 |
| aatatggagt attgtcgtgg ccaggcttac attgtctcta gtggattttc ttccaaaatg | 1020 |
| aaagttgttg cttctagact tttagagaaa tatccccaag ctatctacac actctgctct | 1080 |
| tcctgtgcct aaaatatgtg gttggcaaaa tcagtacctg ttatgggagt atctgttgca | 1140 |
| ttaggaacaa ttgaggaagt tgttctttt ttccatcgat caccacaact gcttttagaa | 1200 |
| cttgacaacg taatttctgt tcttttttcag aacagtaaaa aaaggggtaa agaactgaag | 1260 |
| gaaatctgcc attctcagtg gacaggcagg catgatgctt tgaaatttt agtggaactc | 1320 |
| ctgcaagcac ttgtttttatg tttagatggt ataaatagtg acacaaatat tagatggaat | 1380 |
| aactatatag ctggccgagc atttgtactc tgcagtgcag tgtcagattt tgatttcatt | 1440 |
| gttactattg ttgttcttaa aaatgtccta tcttttacaa gagcctttgg gaaaaacctc | 1500 |
| caggggcaaa cctctgatgt cttctttgcg gccggtagct tgactgcagt actgcattca | 1560 |
| ctcaacgaag tgatgaaaaa tattgaagtt tatcatgaat tttggtttga ggaagccaca | 1620 |
| aatttggcaa ccaaacttga tattcaaatg aaactccctg ggaaattccg cagagctcac | 1680 |
| cagggtaact tggaatctca gctaacctct gagagttact ataaagaaac cctaagtgtc | 1740 |
| ccaacagtgg agcacattat tcaggaactt aaagatatat tctcagaaca gcacctcaaa | 1800 |
| gctcttaaat gcttatctct ggtaccctca gtcatgggac aactcaaatt caatacgtcg | 1860 |
| gaggaacacc atgctgacat gtatagaagt gacttaccca atcctgacac gctgtcagct | 1920 |
| gagcttcatt gttggagaat caaatggaaa cacaggggga agatataga gcttccgtcc | 1980 |
| accatctatg aagccctcca cctgcctgac atcaagtttt ttcctaatgt gtatgcattg | 2040 |
| ctgaaggtcc tgtgtattct tcctgtgatg aaggttgaga atgagcggta tgaaaatgga | 2100 |
| cgaaagcgtc ttaaagcata tttgaggaac actttgacag accaaaggtc aagtaacttg | 2160 |
| gctttgctta acataaattt tgatataaaa cacgacctgg atttaatggt ggacacatat | 2220 |
| attaaactct atacaagtaa gtcagagctt cctacagata attccgaaac tgtggaaaat | 2280 |
| acctaa | 2286 |

<210> SEQ ID NO 172
<211> LENGTH: 633
<212> TYPE: DNA
<213> ORGANISM: Mus musculus

<400> SEQUENCE: 172

| | |
|---|---|
| atggtgcagt cctgctccgc ctacggctgc aagaaccgct acgacaagga caagcccgtc | 60 |
| tccttccaca gtttcctct tactcgcccc agcctttgta agcagtggga ggcagctgtt | 120 |
| aaaaggaaaa acttcaagcc caccaagtac agcagcatct gctcggagca cttcaccccg | 180 |
| gactgcttta gagggagtg caacaacaag ctactgaagg agaacgctgt gcccacaata | 240 |
| tttctctata tcgagccaca tgagaagaag gaagacctgg aatcccaaga acagctcccc | 300 |
| tctccttcac ccccgcttc ccaggttgat gctgctattg ggctgctaat gccccctctg | 360 |
| cagacccctg ataacctgtc ggttttctgt gaccacaatt acactgtgga ggatacgatg | 420 |
| caccagagga agaggatcct gcagctggag cagcaggtgg agaaactcag gaagaagctc | 480 |

```
aagacggccc agcagcggtg ccggcggcag gagaggcagc tcgagaagct caaggaagtc    540 gtccacttc agagagagaa ggacgacgcg tccgagaggg gctacgtgat cctaccaaat    600
gactactttg aaattgttga agttccagca tga                                633

<210> SEQ ID NO 173
<211> LENGTH: 654
<212> TYPE: DNA
<213> ORGANISM: Mus musculus

<400> SEQUENCE: 173
atgccgacca attgcgccgc ggcgggctgt gctgctacct acaacaagca cattaacatc     60
agcttccaca ggtttccttt ggatcctaaa agaagaaaag aatgggttcg cctggttagg    120
cgcaaaaatt ttgtgccagg aaaacacact tttctttgct caaagcactt tgaagcctcc    180
tgttttgatc taacaggaca aacccgacga cttaaaatgg atgctgttcc aaccattttt    240 gattttgta cccatataaa gtctctgaaa ctcaagtcaa ggaatcttct gaagacaaac    300
aacagttttc ctccaactgg accatgtaat ttaaagctga acggcagtca gcaagtactg    360
cttgaacaca gttatgcctt taggaaccct atggaggcga aaaaaggat aattaaacta    420 gaaaaggaaa tagcaagctt gagaaaaaaa atgaaaactt gcctgcaaag agaacgcaga    480
gcaactcgaa ggtggatcaa agccacgtgc tttgtgaaga gcttagaagc aagtaacatg    540
ctacctaagg gcatctcaga acagatttta ccaactgcct taagcaatct tcctctggaa    600
gatttaaaaa gtcttgaaca agatcaacaa gataaaacag tacccattct ctaa          654

<210> SEQ ID NO 174
<211> LENGTH: 657
<212> TYPE: DNA
<213> ORGANISM: Mus musculus

<400> SEQUENCE: 174
atgccgaagt cttgcgcggc ccggcaatgc tgcaaccgct acagcagccg caggaagcag     60
ctcaccttcc accggttccc cttcagccgc ccggagctgt tgagggagtg ggtgctcaac    120
atcggccggg ctgacttcaa gcctaagcag cacacagtca tctgctcgga acacttcaga    180
cccgagtgct tcagcgcctt tgggaaccga aagaacctga acacaatgc tgtgcccacg     240 gtgttcgctt ttcagaaccc cacagaggtc tgccctgagg tggggctgg tggggacagc    300 tcagggagga acatggacac cacactggaa gaacttcagc ctccaacccc ggaaggcccc    360
gtgcagcagg tcttaccaga tcgagaagca atggaggcca cggaggccgc tggcctgcct    420
gccagccctc tggggttgaa gaggccccctt ccgggacagc cgtctgatca cagttatgcc    480 cttcggact tggatacccct caaaaaaaaaa ctctttctca cactgaagga aaacaagagg    540
cttcggaagc ggctgaaagc ccagaggctg ctgttgcgga ggacatgtgg ccgcctgaga    600
gcctacagag agggacagcc gggacctcgg gccagacggc cggcacaggg aagctga       657

<210> SEQ ID NO 175
<211> LENGTH: 558
<212> TYPE: DNA
<213> ORGANISM: Mus musculus

<400> SEQUENCE: 175
atactgcaag catttggaag cctaaaaaaa ggagatgtgc tgtgttcaag acacttcaag     60
aagacagact ttgacagaag cactctaaac actaagctga aggcaggagc catcccttct    120
atctttgaat gtccatatca cttacaggag aaaagagaaa aacttcactg tagaaaaaac    180
```

| | |
|---|---|
| ttccttctca aaacccttcc catcacccac catggccgcc agcttgttgg tgcctcctgc | 240 |
| attgaagaat tcgaacccca gttcattttt gaacatagct acagtgttat ggacagccca | 300 |
| aagaagctta agcataagct agaccgtgtg atcatcgagc tggagaatac caaggaaagc | 360 |
| ctacggaatg ttttagcccg agaaaaacac tttcaaaagt cactgaggaa gacaatcatg | 420 |
| gaactaaagg atgaaagtct gatcagccag gaaacagcca atagtctggg tgctttctgt | 480 |
| tgggagtgct atcatgaaag cacagcagga ggctgtagtt gtgaagtcat ttcttatatg | 540 |
| cttcatctgc agttgaca | 558 |

<210> SEQ ID NO 176
<211> LENGTH: 1719
<212> TYPE: DNA
<213> ORGANISM: Homo sapiens

<400> SEQUENCE: 176

| | |
|---|---|
| ctttccgcgc ggcggaagag cgcgcgccag cttcggcaca cttgggagcc ggatcccagc | 60 |
| cctacgcctc gtccctaca agctcctcca agcccgccg gctgctgtgg gagcggcggc | 120 |
| cgtcctctcc tggaggtcgt ctcctggcat cctcggggcc gcaggaagga agaggaggca | 180 |
| gcggccggag ccctggtggg cggcctgagg tgagagcccg accggcccct ttgggaatat | 240 |
| ggcgaccggt ggctaccgga ccagcagcgg cctcggcggc agcaccacag acttcctgga | 300 |
| ggagtggaag gcgaaacgcg agaagatgcg cgccaagcag aaccccccgg gcccggcccc | 360 |
| cccggggagg ggcagcagcg acgccgctgg gaagccccc gcggggctc tgggcacccc | 420 |
| ggcggccgcc gctgccaacg agctcaacaa caacctcccg ggcggcgcgc cggccgcacc | 480 |
| tgccgtcccc ggtcccgggg gcgtgaactg cgcggtcggc tccgccatgc tgacgcgggc | 540 |
| gccccggcc cgcggcccgc ggcggtcgga ggacgagccc ccagccgcct ctgcctcggc | 600 |
| tgcaccgccg cccccagcgtg acgaggagga gccggacggc gtcccagaga agggcaagag | 660 |
| ctcgggcccc agtgccagga aaggcaaggg gcagatcgag aagaggaagc tgcgggagaa | 720 |
| gcggcgctcc accggcgtgg tcaacatccc tgccgcagag tgcttagatg agtacgaaga | 780 |
| tgatgaagca gggcagaaag agcggaaacg agaagatgca attacacaac agaacactat | 840 |
| tcagaatgaa gctgtaaact actagatcc aggcagttcc tatctgctac aggagccacc | 900 |
| tagaacagtt tcaggcagat ataaaagcac aaccagtgtc tctgaagaag atgtctcaag | 960 |
| tagatattct cgaacagata gaagtgggtt ccctagatat aacagggatg caaatgtttc | 1020 |
| aggtactctg gtttcaagta gcacactgga aaagaaaatt gaagatcttg aaaaggaagt | 1080 |
| agtaacagaa agacaagaaa acctaagact tgtgagactg atgcaagata aagaggaaat | 1140 |
| gattggaaaa ctcaaagaag aaattgattt attaaataga acctagatg acatagaaga | 1200 |
| tgaaaatgaa cagctaaagc aggaaaataa aactcttttg aaagttgtgg gtcagctgac | 1260 |
| caggtagagg attcaagact caatgtggaa aaaatatttt aaactactga ttgaatgtta | 1320 |
| atggtcaatg ctagcacaat attcctatgc tgcaatacat taaataact aagcaagtat | 1380 |
| atttatttct agcaaacaga tgtttgtttt caaaatactt cttttcatt attggtttta | 1440 |
| aaaaagcatt atcctttat ctcacaaata agtaatatct ttcagttatt aaatgataga | 1500 |
| taatgccttt tggttttgt gtggtattca actaatacat ggtttaaagt cacagccgtt | 1560 |
| tgaatatatt ttatcttggt agtacatttt ctcccttagg aatatacata gtctttgttt | 1620 |
| acatgagttc caatactttt gggatgttac cctcacatgt ccctatactg atgtgtgcca | 1680 |
| ccttttatgt gttgatgact cactcataag gttttggtc | 1719 |

<210> SEQ ID NO 177
<211> LENGTH: 878
<212> TYPE: DNA
<213> ORGANISM: Homo sapiens

<400> SEQUENCE: 177

```
atcccagccc acgcacagac ccccaacttg cagctgccca cctcaccctc agctctggcc      60
tcttactcac cctctaccac agacatggct cagtcactgg ctctgagcct ccttatcctg     120
gttctggcct ttggcatccc caggacccaa ggcagtgatg agggggctca ggactgttgc     180
ctcaagtaca gccaaaggaa gattcccgcc aaggttgtcc gcagctaccg gaagcaggaa     240
ccaagcttag gctgctccat cccagctatc ctgttcttgc cccgcaagcg ctctcaggca     300
gagctatgtg cagacccaaa ggagctctgg gtgcagcagc tgatgcagca tctggacaag     360
acaccatccc cacagaaacc agcccagggc tgcaggaagg cagggggggc ctccaagact     420
ggcaagaaag gaaagggctc caaaggctgc aagaggactg agcggtcaca gaccccctaaa    480
gggccatagc ccagtgagca gcctggagcc ctggagaccc accagcctc accagcgctt      540
gaagcctgaa cccaagatgc aagaaggagg ctatgctcag gggccctgga gcagccaccc     600
catgctggcc ttgccacact ctttctcctg ctttaaccac cccatctgca ttcccagctc     660
taccctgcat ggctgagctg cccacagcag gccaggtcca gagagaccga ggagggagag     720
tctcccaggg agcatgagag gaggcagcag gactgtcccc ttgaaggaga atcatcagga     780
ccctggacct gatacggctc cccagtacac cccacctctt ccttgtaaat atgatttata     840
cctaactgaa taaaaagctg ttctgtcttc ccacccaa                             878
```

<210> SEQ ID NO 178
<211> LENGTH: 34
<212> TYPE: PRT
<213> ORGANISM: Artificial Sequence
<220> FEATURE:
<223> OTHER INFORMATION: Interferon gamma homology motif of THAP1

<400> SEQUENCE: 178

Asn Tyr Thr Val Glu Asp Thr Met His Gln Arg Lys Arg Ile His Gln
1               5                   10                  15

Leu Glu Gln Gln Val Glu Lys Leu Arg Lys Lys Leu Lys Thr Ala Gln
            20                  25                  30

Gln Arg

<210> SEQ ID NO 179
<211> LENGTH: 20
<212> TYPE: PRT
<213> ORGANISM: Artificial Sequence
<220> FEATURE:
<223> OTHER INFORMATION: Nuclear localization sequence of THAP1

<400> SEQUENCE: 179

Arg Lys Arg Ile His Gln Leu Glu Gln Gln Val Glu Lys Leu Arg Lys
1               5                   10                  15

Lys Leu Lys Thr
            20

<210> SEQ ID NO 180
<211> LENGTH: 38
<212> TYPE: PRT
<213> ORGANISM: Artificial Sequence
<220> FEATURE:
<223> OTHER INFORMATION: Consensus sequence for PAR4 binding domain of
      THAP

```
<220> FEATURE:
<221> NAME/KEY: UNSURE
<222> LOCATION: 3-16, 19, 23, 25-35
<223> OTHER INFORMATION: Xaa = any of the twenty amino acids
<220> FEATURE:
<221> NAME/KEY: VARIANT
<222> LOCATION: 37
<223> OTHER INFORMATION: Xaa = Arg or Lys

<400> SEQUENCE: 180

Leu Glu Xaa Xaa Xaa Xaa Xaa Xaa Xaa Xaa Xaa Xaa Xaa Xaa Xaa
 1               5                  10                  15
Gln Arg Xaa Arg Arg Gln Xaa Arg Xaa Xaa Xaa Xaa Xaa Xaa Xaa
             20                  25                  30
Xaa Xaa Xaa Gln Arg Glu
         35

<210> SEQ ID NO 181
<211> LENGTH: 50
<212> TYPE: DNA
<213> ORGANISM: Artificial Sequence
<220> FEATURE:
<223> OTHER INFORMATION: Primer

<400> SEQUENCE: 181
gaattcggcc attatggcct gcaggatccg gccgcctcgg cccaggatcc           50

<210> SEQ ID NO 182
<211> LENGTH: 111
<212> TYPE: PRT
<213> ORGANISM: Homo sapiens
<220> FEATURE:

<400> SEQUENCE: 182

Ser Asp Gly Gly Ala Gln Asp Cys Cys Leu Lys Tyr Ser Gln Arg Lys
 1               5                  10                  15
Ile Pro Ala Lys Val Val Arg Ser Tyr Arg Lys Gln Glu Pro Ser Leu
             20                  25                  30
Gly Cys Ser Ile Pro Ala Ile Leu Phe Leu Pro Arg Lys Arg Ser Gln
         35                  40                  45
Ala Glu Leu Cys Ala Asp Pro Lys Glu Leu Trp Val Gln Gln Leu Met
     50                  55                  60
Gln His Leu Asp Lys Thr Pro Ser Pro Gln Lys Pro Ala Gln Gly Cys
 65                  70                  75                  80
Arg Lys Asp Arg Gly Ala Ser Lys Thr Gly Lys Lys Gly Lys Gly Ser
                 85                  90                  95
Lys Gly Cys Lys Arg Thr Glu Arg Ser Gln Thr Pro Lys Gly Pro
            100                 105                 110

<210> SEQ ID NO 183
<211> LENGTH: 37
<212> TYPE: DNA
<213> ORGANISM: Artificial Sequence
<220> FEATURE:
<223> OTHER INFORMATION: Primer

<400> SEQUENCE: 183
gcgggatccg tagtgatgga ggggctcagg actgttg                         37

<210> SEQ ID NO 184
<211> LENGTH: 35
<212> TYPE: DNA
<213> ORGANISM: Artificial Sequence
```

```
<220> FEATURE:
<223> OTHER INFORMATION: Primer

<400> SEQUENCE: 184
gcgggatccc tatggccctt tagggtctg tgacc                            35

<210> SEQ ID NO 185
<211> LENGTH: 33
<212> TYPE: DNA
<213> ORGANISM: Artificial Sequence
<220> FEATURE:
<223> OTHER INFORMATION: Primer

<400> SEQUENCE: 185
ccgaattcag gatggtgcag tcctgctccg cct                             33

<210> SEQ ID NO 186
<211> LENGTH: 39
<212> TYPE: DNA
<213> ORGANISM: Artificial Sequence
<220> FEATURE:
<223> OTHER INFORMATION: Primer

<400> SEQUENCE: 186
cgcggatcct gctggtactt caactatttc aaagtagtc                       39

<210> SEQ ID NO 187
<211> LENGTH: 33
<212> TYPE: DNA
<213> ORGANISM: Artificial Sequence
<220> FEATURE:
<223> OTHER INFORMATION: Primer

<400> SEQUENCE: 187
ccgaattcag gatggtgcag tcctgctccg cct                             33

<210> SEQ ID NO 188
<211> LENGTH: 39
<212> TYPE: DNA
<213> ORGANISM: Artificial Sequence
<220> FEATURE:
<223> OTHER INFORMATION: Primer

<400> SEQUENCE: 188
cgcggatcct gctggtactt caactatttc aaagtagtc                       39

<210> SEQ ID NO 189
<211> LENGTH: 33
<212> TYPE: DNA
<213> ORGANISM: Artificial Sequence
<220> FEATURE:
<223> OTHER INFORMATION: Primer

<400> SEQUENCE: 189
gcggaattca tggcgaccgg tggctaccgg acc                             33

<210> SEQ ID NO 190
<211> LENGTH: 35
<212> TYPE: DNA
<213> ORGANISM: Artificial Sequence
<220> FEATURE:
<223> OTHER INFORMATION: Primer

<400> SEQUENCE: 190
gcgggatccc tctacctggt cagctgaccc acaac                           35
```

<210> SEQ ID NO 191
<211> LENGTH: 33
<212> TYPE: DNA
<213> ORGANISM: Artificial Sequence
<220> FEATURE:
<223> OTHER INFORMATION: Primer

<400> SEQUENCE: 191
ccgaattcag gatggtgcag tcctgctccg cct                                    33

<210> SEQ ID NO 192
<211> LENGTH: 39
<212> TYPE: DNA
<213> ORGANISM: Artificial Sequence
<220> FEATURE:
<223> OTHER INFORMATION: Primer

<400> SEQUENCE: 192
cgcggatcct gctggtactt caactatttc aaagtagtc                              39

<210> SEQ ID NO 193
<211> LENGTH: 46
<212> TYPE: DNA
<213> ORGANISM: Artificial Sequence
<220> FEATURE:
<223> OTHER INFORMATION: Primer

<400> SEQUENCE: 193
cgcgaattcg ccatcatggg gttccctaga tataacaggg atgcaa                      46

<210> SEQ ID NO 194
<211> LENGTH: 37
<212> TYPE: DNA
<213> ORGANISM: Artificial Sequence
<220> FEATURE:
<223> OTHER INFORMATION: Primer

<400> SEQUENCE: 194
gccggatccg ggttccctag atataacagg gatgcaa                                37

<210> SEQ ID NO 195
<211> LENGTH: 37
<212> TYPE: DNA
<213> ORGANISM: Artificial Sequence
<220> FEATURE:
<223> OTHER INFORMATION: Primer

<400> SEQUENCE: 195
gcgctctaga gccatcatgg aggagcagaa gctgatc                                37

<210> SEQ ID NO 196
<211> LENGTH: 37
<212> TYPE: DNA
<213> ORGANISM: Artificial Sequence
<220> FEATURE:
<223> OTHER INFORMATION: Primer

<400> SEQUENCE: 196
cttgcggccg cctctacctg gtcagctgac ccacaac                                37

<210> SEQ ID NO 197
<211> LENGTH: 37
<212> TYPE: DNA
<213> ORGANISM: Artificial Sequence
<220> FEATURE:
<223> OTHER INFORMATION: Primer

```
<400> SEQUENCE: 197
gcggaattca aagaagatct tctggagcca caggaac                              37

<210> SEQ ID NO 198
<211> LENGTH: 39
<212> TYPE: DNA
<213> ORGANISM: Artificial Sequence
<220> FEATURE:
<223> OTHER INFORMATION: Primer

<400> SEQUENCE: 198
cgcggatcct gctggtactt caactatttc aaagtagtc                            39

<210> SEQ ID NO 199
<211> LENGTH: 35
<212> TYPE: DNA
<213> ORGANISM: Artificial Sequence
<220> FEATURE:
<223> OTHER INFORMATION: Primer

<400> SEQUENCE: 199
gcggaattca tgccgcctct tcagacccct gttaa                                35

<210> SEQ ID NO 200
<211> LENGTH: 36
<212> TYPE: DNA
<213> ORGANISM: Artificial Sequence
<220> FEATURE:
<223> OTHER INFORMATION: Primer

<400> SEQUENCE: 200
gcggaattca tgcaccagcg gaaaaggatt catcag                               36

<210> SEQ ID NO 201
<211> LENGTH: 33
<212> TYPE: DNA
<213> ORGANISM: Artificial Sequence
<220> FEATURE:
<223> OTHER INFORMATION: Primer

<400> SEQUENCE: 201
ccgaattcag gatggtgcag tcctgctccg cct                                  33

<210> SEQ ID NO 202
<211> LENGTH: 39
<212> TYPE: DNA
<213> ORGANISM: Artificial Sequence
<220> FEATURE:
<223> OTHER INFORMATION: Primer

<400> SEQUENCE: 202
gcgggatccc ttgtcatgtg gctcagtaca aagaaatat                            39

<210> SEQ ID NO 203
<211> LENGTH: 34
<212> TYPE: DNA
<213> ORGANISM: Artificial Sequence
<220> FEATURE:
<223> OTHER INFORMATION: Primer

<400> SEQUENCE: 203
cgggatcctg tgcggtcttg agcttctttc tgag                                 34
```

<210> SEQ ID NO 204
<211> LENGTH: 36
<212> TYPE: DNA
<213> ORGANISM: Artificial Sequence
<220> FEATURE:
<223> OTHER INFORMATION: Primer

<400> SEQUENCE: 204
gcgggatccg tcgtctttct ctttctggaa gtgaac                36

<210> SEQ ID NO 205
<211> LENGTH: 36
<212> TYPE: PRT
<213> ORGANISM: Artificial Sequence
<220> FEATURE:
<223> OTHER INFORMATION: Consensus sequence for PAR4 binding domain of
      THAP
<220> FEATURE:
<221> NAME/KEY: UNSURE
<222> LOCATION: 3-14, 17, 21, 23-33, 35
<223> OTHER INFORMATION: Xaa = any of the twenty amino acids

<400> SEQUENCE: 205

Leu Glu Xaa Xaa Xaa Xaa Xaa Xaa Xaa Xaa Xaa Xaa Xaa Xaa Gln Arg
 1               5                  10                  15

Xaa Arg Arg Gln Xaa Arg Xaa Xaa Xaa Xaa Xaa Xaa Xaa Xaa Xaa Xaa
            20                  25                  30

Xaa Gln Xaa Glu
        35

<210> SEQ ID NO 206
<211> LENGTH: 39
<212> TYPE: DNA
<213> ORGANISM: Artificial Sequence
<220> FEATURE:
<223> OTHER INFORMATION: Primer

<400> SEQUENCE: 206
ccgcacagca gcgatgcgct gctcaagaac ggcagcttg                39

<210> SEQ ID NO 207
<211> LENGTH: 39
<212> TYPE: DNA
<213> ORGANISM: Artificial Sequence
<220> FEATURE:
<223> OTHER INFORMATION: Primer

<400> SEQUENCE: 207
caagctgccg ttcttgagca gcgcatcgct gctgtgcgg                39

<210> SEQ ID NO 208
<211> LENGTH: 32
<212> TYPE: DNA
<213> ORGANISM: Artificial Sequence
<220> FEATURE:
<223> OTHER INFORMATION: Primer

<400> SEQUENCE: 208
gctcaagacc gcacagcaag aacggcagct tg                32

<210> SEQ ID NO 209
<211> LENGTH: 32
<212> TYPE: DNA
<213> ORGANISM: Artificial Sequence
<220> FEATURE:
<223> OTHER INFORMATION: Primer

<400> SEQUENCE: 209
caagctgccg ttcttgctgt gcggtcttga gc                                    32

<210> SEQ ID NO 210
<211> LENGTH: 36
<212> TYPE: DNA
<213> ORGANISM: Artificial Sequence
<220> FEATURE:
<223> OTHER INFORMATION: Primer

<400> SEQUENCE: 210
gcgggatccc taaattagaa aggggtgggg gtagcc                                36

<210> SEQ ID NO 211
<211> LENGTH: 32
<212> TYPE: DNA
<213> ORGANISM: Artificial Sequence
<220> FEATURE:
<223> OTHER INFORMATION: Primer

<400> SEQUENCE: 211
gcggaattca tggagcctgc acccgcccga tc                                    32

<210> SEQ ID NO 212
<211> LENGTH: 37
<212> TYPE: DNA
<213> ORGANISM: Artificial Sequence
<220> FEATURE:
<223> OTHER INFORMATION: Primer

<400> SEQUENCE: 212
gcggaattca agaagatct tctggagcca caggaac                                37

<210> SEQ ID NO 213
<211> LENGTH: 39
<212> TYPE: DNA
<213> ORGANISM: Artificial Sequence
<220> FEATURE:
<223> OTHER INFORMATION: Primer

<400> SEQUENCE: 213
cgcggatcct gctggtactt caactatttc aaagtagtc                             39

<210> SEQ ID NO 214
<211> LENGTH: 33
<212> TYPE: DNA
<213> ORGANISM: Artificial Sequence
<220> FEATURE:
<223> OTHER INFORMATION: Primer

<400> SEQUENCE: 214
cgcggatccg tgcagtcctg ctccgcctac ggc                                   33

<210> SEQ ID NO 215
<211> LENGTH: 39
<212> TYPE: DNA
<213> ORGANISM: Artificial Sequence
<220> FEATURE:
<223> OTHER INFORMATION: Primer

<400> SEQUENCE: 215
ccgaattctt atgctggtac ttcaactatt tcaaagtag                             39

```
<210> SEQ ID NO 216
<211> LENGTH: 33
<212> TYPE: DNA
<213> ORGANISM: Artificial Sequence
<220> FEATURE:
<223> OTHER INFORMATION: Primer

<400> SEQUENCE: 216
gccgaattca tgccgaactt ctgcgctgcc ccc                              33

<210> SEQ ID NO 217
<211> LENGTH: 40
<212> TYPE: DNA
<213> ORGANISM: Artificial Sequence
<220> FEATURE:
<223> OTHER INFORMATION: Primer

<400> SEQUENCE: 217
cgcggatcct taggttattt tccacagttt cggaattatc                       40

<210> SEQ ID NO 218
<211> LENGTH: 39
<212> TYPE: DNA
<213> ORGANISM: Artificial Sequence
<220> FEATURE:
<223> OTHER INFORMATION: Primer

<400> SEQUENCE: 218
gcgctgcagc aagctaaatt taaatgaagg tactcttgg                        39

<210> SEQ ID NO 219
<211> LENGTH: 35
<212> TYPE: DNA
<213> ORGANISM: Artificial Sequence
<220> FEATURE:
<223> OTHER INFORMATION: Primer

<400> SEQUENCE: 219
gcgagatctg ggaaatgccg accaattgcg ctgcg                            35

<210> SEQ ID NO 220
<211> LENGTH: 35
<212> TYPE: DNA
<213> ORGANISM: Artificial Sequence
<220> FEATURE:
<223> OTHER INFORMATION: Primer

<400> SEQUENCE: 220
agaggatcct tagctctgct gctctggccc aagtc                            35

<210> SEQ ID NO 221
<211> LENGTH: 32
<212> TYPE: DNA
<213> ORGANISM: Artificial Sequence
<220> FEATURE:
<223> OTHER INFORMATION: Primer

<400> SEQUENCE: 221
agagaattca tgccgaagtc gtgcgcggcc cg                               32

<210> SEQ ID NO 222
<211> LENGTH: 32
<212> TYPE: DNA
<213> ORGANISM: Artificial Sequence
<220> FEATURE:
<223> OTHER INFORMATION: Primer
```

```
<400> SEQUENCE: 222
gcggaattca tgccgcgtca ctgctccgcc gc                                    32

<210> SEQ ID NO 223
<211> LENGTH: 34
<212> TYPE: DNA
<213> ORGANISM: Artificial Sequence
<220> FEATURE:
<223> OTHER INFORMATION: Primer

<400> SEQUENCE: 223
gcgggatcct caggccatgc tgctgctcag ctgc                                  34

<210> SEQ ID NO 224
<211> LENGTH: 38
<212> TYPE: DNA
<213> ORGANISM: Artificial Sequence
<220> FEATURE:
<223> OTHER INFORMATION: Primer

<400> SEQUENCE: 224
gcgagatctc gatggtgaaa tgctgctccg ccattgga                              38

<210> SEQ ID NO 225
<211> LENGTH: 39
<212> TYPE: DNA
<213> ORGANISM: Artificial Sequence
<220> FEATURE:
<223> OTHER INFORMATION: Primer

<400> SEQUENCE: 225
gcgggatcct catgaaatat agtcctgttc tatgctctc                             39

<210> SEQ ID NO 226
<211> LENGTH: 35
<212> TYPE: DNA
<213> ORGANISM: Artificial Sequence
<220> FEATURE:
<223> OTHER INFORMATION: Primer

<400> SEQUENCE: 226
gcgagatctc gatgcccaag tactgcaggg cgccg                                 35

<210> SEQ ID NO 227
<211> LENGTH: 37
<212> TYPE: DNA
<213> ORGANISM: Artificial Sequence
<220> FEATURE:
<223> OTHER INFORMATION: Primer

<400> SEQUENCE: 227
gcggaattct tatgcactgg ggatccgagt gtccagg                               37

<210> SEQ ID NO 228
<211> LENGTH: 32
<212> TYPE: DNA
<213> ORGANISM: Artificial Sequence
<220> FEATURE:
<223> OTHER INFORMATION: Primer

<400> SEQUENCE: 228
gcggaattca tgccggcccg ttgtgtggcc gc                                    32
```

```
<210> SEQ ID NO 229
<211> LENGTH: 39
<212> TYPE: DNA
<213> ORGANISM: Artificial Sequence
<220> FEATURE:
<223> OTHER INFORMATION: Primer

<400> SEQUENCE: 229
gcgggatcct taacatgttt cttctttcac ctgtacagc                39

<210> SEQ ID NO 230
<211> LENGTH: 36
<212> TYPE: DNA
<213> ORGANISM: Artificial Sequence
<220> FEATURE:
<223> OTHER INFORMATION: Primer

<400> SEQUENCE: 230
gcgagatctc gatgcctggc tttacgtgct gcgtgc                  36

<210> SEQ ID NO 231
<211> LENGTH: 36
<212> TYPE: DNA
<213> ORGANISM: Artificial Sequence
<220> FEATURE:
<223> OTHER INFORMATION: Primer

<400> SEQUENCE: 231
gcggaattct cacattccgt gcttcttgcg gatgac                  36

<210> SEQ ID NO 232
<211> LENGTH: 33
<212> TYPE: DNA
<213> ORGANISM: Artificial Sequence
<220> FEATURE:
<223> OTHER INFORMATION: Primer

<400> SEQUENCE: 232
ccgaattcag gatggtgcag tcctgctccg cct                     33

<210> SEQ ID NO 233
<211> LENGTH: 39
<212> TYPE: DNA
<213> ORGANISM: Artificial Sequence
<220> FEATURE:
<223> OTHER INFORMATION: Primer

<400> SEQUENCE: 233
cgcggatcct gctggtactt caactatttc aaagtagtc               39

<210> SEQ ID NO 234
<211> LENGTH: 37
<212> TYPE: DNA
<213> ORGANISM: Artificial Sequence
<220> FEATURE:
<223> OTHER INFORMATION: Primer

<400> SEQUENCE: 234
gcgctctaga gccatcatgg aggagcagaa gctgatc                 37

<210> SEQ ID NO 235
<211> LENGTH: 41
<212> TYPE: DNA
<213> ORGANISM: Artificial Sequence
<220> FEATURE:
<223> OTHER INFORMATION: Primer
```

<400> SEQUENCE: 235
gcgctctaga ttatgctggt acttcaacta tttcaaagta g                41

<210> SEQ ID NO 236
<211> LENGTH: 33
<212> TYPE: DNA
<213> ORGANISM: Artificial Sequence
<220> FEATURE:
<223> OTHER INFORMATION: Primer

<400> SEQUENCE: 236
cgcggatccg tgcagtcctg ctccgcctac ggc                         33

<210> SEQ ID NO 237
<211> LENGTH: 39
<212> TYPE: DNA
<213> ORGANISM: Artificial Sequence
<220> FEATURE:
<223> OTHER INFORMATION: Primer

<400> SEQUENCE: 237
cgcggatcct gctggtactt caactatttc aaagtagtc                   39

<210> SEQ ID NO 238
<211> LENGTH: 37
<212> TYPE: DNA
<213> ORGANISM: Artificial Sequence
<220> FEATURE:
<223> OTHER INFORMATION: Primer

<400> SEQUENCE: 238
gccggatccg ggttccctag atataacagg gatgcaa                     37

<210> SEQ ID NO 239
<211> LENGTH: 35
<212> TYPE: DNA
<213> ORGANISM: Artificial Sequence
<220> FEATURE:
<223> OTHER INFORMATION: Primer

<400> SEQUENCE: 239
gcgggatccc tctacctggt cagctgaccc acaac                       35

<210> SEQ ID NO 240
<211> LENGTH: 35
<212> TYPE: DNA
<213> ORGANISM: Artificial Sequence
<220> FEATURE:
<223> OTHER INFORMATION: Primer

<400> SEQUENCE: 240
gcgggatcca gtgatggagg ggctcaggac tgttg                       35

<210> SEQ ID NO 241
<211> LENGTH: 35
<212> TYPE: DNA
<213> ORGANISM: Artificial Sequence
<220> FEATURE:
<223> OTHER INFORMATION: Primer

<400> SEQUENCE: 241
gcgggatccc tatggcccctt tagggtctg tgacc                       35

<210> SEQ ID NO 242
<211> LENGTH: 33
<212> TYPE: DNA
<213> ORGANISM: Artificial Sequence
<220> FEATURE:
<223> OTHER INFORMATION: Primer

<400> SEQUENCE: 242
gcgcatatgg tgcagtcctg ctccgcctac ggc                         33

<210> SEQ ID NO 243
<211> LENGTH: 36
<212> TYPE: DNA
<213> ORGANISM: Artificial Sequence
<220> FEATURE:
<223> OTHER INFORMATION: Primer

<400> SEQUENCE: 243
gcgctcgagt ttcttgtcat gtggctcagt acaaag                      36

<210> SEQ ID NO 244
<211> LENGTH: 62
<212> TYPE: DNA
<213> ORGANISM: Artificial Sequence
<220> FEATURE:
<223> OTHER INFORMATION: Oligonucleotide
<220> FEATURE:
<221> NAME/KEY: unsure
<222> LOCATION: 21-45
<223> OTHER INFORMATION: n = any of the four nucleotides

<400> SEQUENCE: 244
tgggcactat ttatatcaac nnnnnnnnnn nnnnnnnnnn nnnnnaatgt cgttggtggc     60
cc                                                                    62

<210> SEQ ID NO 245
<211> LENGTH: 30
<212> TYPE: DNA
<213> ORGANISM: Artificial Sequence
<220> FEATURE:
<223> OTHER INFORMATION: Primer

<400> SEQUENCE: 245
accgcaagct tgggcactat ttatatcaac                             30

<210> SEQ ID NO 246
<211> LENGTH: 24
<212> TYPE: DNA
<213> ORGANISM: Artificial Sequence
<220> FEATURE:
<223> OTHER INFORMATION: Primer

<400> SEQUENCE: 246
ggtctagagg gccaccaacg catt                                   24

<210> SEQ ID NO 247
<211> LENGTH: 2173
<212> TYPE: DNA
<213> ORGANISM: Homo sapiens

<400> SEQUENCE: 247
gacgggcgat ggctgtggtc cttctgctaa tgcaaacaac aaaacgggca cactagtcac     60
ccccgaggga ggccaccatc actgtaactg ttggccaaag ctacaaaaga agcgagggaa    120
tccaaccgag cgcagcgaca ctgagaacag cttcccctgc cttctgcggc ggcagaagtg    180

| | |
|---|---|
| aagtgcctga ggaccggaag gatggtgcag tcctgctccg cctacggctg caagaaccgc | 240 |
| tacgacaagg acaagcccgt ttctttccac aagtttcctc ttactcgacc cagtctttgt | 300 |
| aaagaatggg aggcagctgt cagaagaaaa aactttaaac ccaccaagta tagcagtatt | 360 |
| tgttcagagc actttactcc agactgcttt aagagagagt gcaacaacaa gttactgaaa | 420 |
| gagaatgctg tgcccacaat atttctttgt actgagccac atgacaagaa agaagatctt | 480 |
| ctggagccac aggaacagct tcccccacct cctttaccgc ctcctgtttc ccaggttgat | 540 |
| gctgctattg gattactaat gccgcctctt cagacccctg ttaatctctc agttttctgt | 600 |
| gaccacaact atactgtgga ggatacaatg caccagcgga aaaggattca tcagctagaa | 660 |
| cagcaagttg aaaaactcag aagaagctc aagaccgcac agcagcgatg cagaaggcaa | 720 |
| gaacggcagc ttgaaaaatt aaaggaggtt gttcacttcc agaaagagaa agacgacgta | 780 |
| tcagaaagag gttatgtgat tctaccaaat gactactttg aaatagttga agtaccagca | 840 |
| taaaaaaatg aaatgtgtat tgatttctaa tggggcaata ccacatatcc tcctctagcc | 900 |
| tgtaaaggag tttcatttaa aaaaataaca tttgattact tatataaaaa cagttcagaa | 960 |
| tatttttta aaaaaaattc tatatatact gtaaaattat aaatttttt gtttgtaatt | 1020 |
| tcaggttttt tacattttaa caaaatattt taaaagttat aaactaacct cagacctcta | 1080 |
| atgtaagttg gtttcaagat tggggatttt ggggttttt ttttagtatt tatagaaata | 1140 |
| atgtaaaaat aaaaagtaaa gagaatgaga acagtgtggt aaaagggtga tttcagttta | 1200 |
| aaacttaaaa ttagtactgt tttattgaga gaatttagtt atattttaaa tcagaagtat | 1260 |
| gggtcagatc atgggacata acttcttaga atatatatat acatatgtac atattctcat | 1320 |
| atgtaaagtc acaaggttca tttatctttc tgaatcagtt atcaaagata aattggcaag | 1380 |
| tcagtactta agaaaaaaga tttgattatc atcacagcag aaaaaagtca ttgcatatct | 1440 |
| gatcaataac ttcagattct aagagtggat tttttttttt tacatgggct cctatttttt | 1500 |
| cccctactgt cttgcattat aaaattagaa gtgtattttc agtggaagaa acattttca | 1560 |
| ataaataaag taaggcattg tcatcaatga agtaattaaa actgggacct gatctatgat | 1620 |
| acgctttttt ctttcattac accctagctg aaggacatcc cagttcccca gctgtagtta | 1680 |
| tgtatctgcc ttcaagtctc tgacaaatgt gctgtgttag tagagtttga tttgtatcat | 1740 |
| atgataatct tgcacttgac tgagttggga caaggcttca cataaaaaat tatttcttca | 1800 |
| cttttaacac aagttagaaa ttatatccca tttagttaaa tgcgtgattt atattcagaa | 1860 |
| caacctacta tgtagcgttt attttactga atgtggagat ttaaacactg aggtttctgt | 1920 |
| tcaaactgtg agttctgttc tttgtgagaa attttacata tattggaagt gaaaatatgt | 1980 |
| tctgagtaaa caaatattgc tatgggagtt atcttttttag atttagaata actgttccaa | 2040 |
| tgataattat tacttttata tttcaaagta cactaagatc gttgaagagc aatagaacct | 2100 |
| ttaagacagt attaaaggtg tgaaacaaaa aaaaaaaaa taaaaaaaa aaaaaaaaa | 2160 |
| aaaaaaaaaa aaa | 2173 |

<210> SEQ ID NO 248
<211> LENGTH: 1302
<212> TYPE: DNA
<213> ORGANISM: Homo sapiens

<400> SEQUENCE: 248

| | |
|---|---|
| aattgctctg aggaccgctg ccaaagaaac gcagtagatc cgctccctct tgggggcggg | 60 |
| gagaaagaac gggttgtgtc cgccatgttg gtgaagtcaa gcgaaggcga ctagagctcc | 120 |

-continued

| | |
|---|---|
| aggagggcca gttctgtggg ctctagtcgg ccatattaat aaagagaaag ggaaggctga | 180 |
| ccgtccttcg cctccgcccc cacatacaca ccccttcttc ccactccgct ctcacgacta | 240 |
| agctctcacg attaaggcac gcctgcctcg attgtccagc ctctgccaga agaaagctta | 300 |
| gcagccagcg cctcagtaga gacctaaggg cgctgaatga gtgggaaagg gaaatgccga | 360 |
| ccaattgcgc tgcggcgggc tgtgccacta cctacaacaa gcacattaac atcagcttcc | 420 |
| acaggtttcc tttggatcct aaaagaagaa aagaatgggt tcgcctggtt aggcgcaaaa | 480 |
| attttgtgcc aggaaaacac acttttcttt gttcaaagca ctttgaagcc tcctgttttg | 540 |
| acctaacagg acaaactcga cgacttaaaa tggatgctgt tccaaccatt tttgattttt | 600 |
| gtacccatat aaagtctatg aaactcaagt caaggaatct tttgaagaaa acaacagtt | 660 |
| gttctccagc tggaccatct aatttaaaat caaacattag tagtcagcaa gtactacttg | 720 |
| aacacagcta tgcctttagg aatcctatgg aggcaaaaaa gaggatcatt aaactggaaa | 780 |
| aagaaatagc aagcttaaga agaaaaatga aaacttgcct acaaaaggaa cgcagagcaa | 840 |
| ctcgaagatg gatcaaagcc acgtgtttgg taaagaattt agaagcaaat agtgtattac | 900 |
| ctaaaggtac atcagaacac atgttaccaa ctgccttaag cagtcttcct ttggaagatt | 960 |
| ttaagatcct tgaacaagat caacaagata aaacactgct aagtctaaat ctaaaacaga | 1020 |
| ccaagagtac cttcatttaa atttagcttg cacagagctt gatgcctatc cttcattctt | 1080 |
| ttcagaagta agataatta tggcacttat gccaaaattc attatttaat aaagttttac | 1140 |
| ttgaagtaac attactgaat ttgtgaagac ttgattacaa agaataaaa aacttcatat | 1200 |
| ggaaatttta tttgaaaatg agtggaagtg ccttacatta gaattacgga cttaaaaatt | 1260 |
| ttgctaataa attgtgtatt tgaaaaaaaa aaaaaaaaaa aa | 1302 |

<210> SEQ ID NO 249
<211> LENGTH: 1995
<212> TYPE: DNA
<213> ORGANISM: Homo sapiens

<400> SEQUENCE: 249

| | |
|---|---|
| ccagtgacgt cagaggagtc cagacctatt cacaattcaa agccctaaaa acactgaggg | 60 |
| gttggccgtt ggtttccagt tgtccaagcc tgtgagtggc tatgcgtcct ggttgggtgc | 120 |
| tcaaagcaag gaggtgaaag gcgaccagca ttggcgaatg gggtaagact tgcacaggcc | 180 |
| caaggctagg agttgggggtt tcgggcctga attgggccc ggagcacccc tttacgtggc | 240 |
| gccccgggtc ccgtccgacc ctggggagac gcggtggct gggatggcag gatgagcgcg | 300 |
| ccctggaggc gagccaggcc cgtcaccacc tcccagcggc cccgccctc cccgcaggtc | 360 |
| cctccctct ccgcaggccc cgccgccgcc gccatctttg ttgggggcag ccaggcctgg | 420 |
| ctcgagatgc cgaagtcgtg cgcggcccgg cagtgctgca accgctacag cagccgcagg | 480 |
| aagcagctca ccttccaccg gtttccgttc agccgcccgg agctgctgaa ggaatgggtg | 540 |
| ctgaacatcg gccggggcaa cttcaagccc aagcagcaca cggtcatctg ctccgagcac | 600 |
| ttccggccag agtgcttcag cgcctttgga accgcaagga acctaaagca caatgccgtg | 660 |
| cccacggtgt tcgcctttca ggaccccaca cagcaggtga gggagaacac agaccctgcc | 720 |
| agtgagagag gaaatgccag ctcttctcag aaagaaaagg tcctccctga ggcggggcc | 780 |
| ggagaggaca gtcctgggag aaacatggac actgcacttg aagagcttca gttgccccca | 840 |
| aatgccgaag gccacgtaaa acaggtctcg ccacggaggc cgcaagcaac agaggctgtt | 900 |
| ggccggccga ctggccctgc aggcctgaga aggaccccca acaagcagcc atctgatcac | 960 |

```
agctatgccc ttttggactt agattccctg aagaaaaaac tcttcctcac tctgaaggaa    1020
aatgaaaagc tccggaagcg cttgcaggcc cagaggctgg tgatgcgaag gatgtccagc    1080
cgcctccgtg cttgcaaagg caccaggga ctccaggcca gacttgggcc agagcagcag      1140
agctgagccc acaggctcc ggacgcagag gtggcagtgg caccagggcc ggcagagctt      1200
tggagctctg gctgtggaca tttttgtctg ctgtggacac tgagaaagtt ggccatgagg    1260
cctgcttggc cggggatcga gacagtagcc aagctccccg gcgagagccc caatgccgtc    1320
tgggggacgt ttagaggcgt ggcactagga gtgcacatct gtgagcatga caagcttatc    1380
ctcccatggt aacagaagtc caggctgagg ctgattctgg acgctgccct ttcagcacac    1440
gcagagcaaa gatcgttgga agccccagtg tgggagatgc tcctcaggga ggaagccatg    1500 tgaggggct ggctctgtgg cgggtgagtg gtccctcct ccatcagcct ggacagccgc       1560
tcggggttct aaggagtgac tcctgtcccg gcctggtgtg agtgggcagt gtaataaagt    1620
gtctttctat acgtgtcgc tcccatcatc attttctcta gtgccgtgat tccttctaag      1680
aagactgact tccgtggccg ggcgcagtgg ctcatgcctg taatcccagc actttgagag    1740
gccgaggtgg ggagatcact tgaggtcagg agttcaagac cagcctggcc aacatggtga    1800
aatcccatgt ctactaaaaa agacacaaat tagccaggcg tggtggcaca cctgtagt       1860 cccagctacc tgggaggctg agacaggagg atcagctgaa cccgggaggt ggaggttgca    1920
gtgagccgag atcacaccac tgccctctag tattgtcact gggtgacaga gcgagactca    1980
gtctgaaaaa aaaaa                                                     1995

<210> SEQ ID NO 250
<211> LENGTH: 1999
<212> TYPE: DNA
<213> ORGANISM: Homo sapiens

<400> SEQUENCE: 250
gggctagggc cggggcctgg ctgcgcggct gggccaaggc ccgcgatggt gatctgctgt       60
gcggccgtga actgctccaa ccggcaggga aagggcgaga agcgcgccgt ctccttccac     120
aggttccccc taaaggactc aaaacgtcta atccaatggt taaaagctgt tcagagggat     180
aactggactc ccactaagta ttcatttctc tgtagtgagc atttcaccaa agacagcttc     240
tccaagaggc tggaggacca gcatcgcctg ctgaagccca cggccgtgcc atccatcttc     300
cacctgaccg agaagaagag gggggctgga ggccatggcc gcacccggag aaaagatgcc    360
agcaaggcca caggggtgt gaggggacac tcgagtgccg ccaccggcag aggagctgca      420
ggttggtcac cgtcctcgag tggaaacccg atggccaagc cagagtcccg caggttgaag    480
caagctgctc tgcaaggtga agccacaccc agggcggccc aggaggccgc cagccaggag    540
caggcccagc aagctctgga acggactcca ggagatggac tggccaccat ggtggcaggc    600 agtcaggaa aagcagaagc gtctgccaca gatgctggcg atgagagcgc cacttcctcc      660
atcgaagggg gcgtgacaga taagagtggc atttctatgg atgactttac gccccagga     720 tctggggcgt gcaaatttat cggctcactt cattcgtaca gtttctcctc taagcacacc    780
cgagaaaggc catctgtccc ccgagagccc attgaccgca agaggctgaa gaaagatgtg    840
gaaccaagct gcagtgggag cagcctggga cccgacaagg gcctggccca gagccctccc    900
agctcatcac ttaccgcgac accgcagaag ccttcccaga gcccctctgc ccctcctgcc    960 gacgtcacc caaagccagc cacggaagcc gtgcagagcg agcacagcga cgccagcccc     1020
atgtccatca cgaggtcat cctgtcggcg tcaggggcct gcaagctcat cgactcactg     1080
```

```
cactcctact gcttctcctc ccggcagaac aagagccagg tgtgctgcct gcgggagcag    1140
gtggagaaga agaacggcga gctgaagagc ctgcggcaga gggtcagccg ctccgacagc    1200
caggtgcgga agctacagga gaagctggat gagctgagga gagtgagcgt ccctatcca     1260 agtagcctgc tgtcgcccag ccgcgagccc cccaagatga acccagtggt ggagccactg    1320
tcctggatgc tgggcacctg gctgtcggac ccacctggag ccgggaccta ccccacactg    1380
cagcccttcc agtacctgga ggaggttcac atctcccacg tgggccagcc catgctgaac    1440
ttctcgttca actccttcca cccggacacg cgcaagccga tgcacagaga gtgtggcttc    1500
attcgcctca agcccgacac caacaaggtg gcctttgtca cgcgcccagaa cacaggcgtg    1560 gtggaagtgg aggagggcga ggtgaacggg caggagctgt gcatcgcatc ccactccatc    1620
gccaggatct ccttcgccaa ggagcccacc gtagagcaga tcacccggaa gttcaggctg    1680
aattctgaag gcaaacttga gcagacggtc tccatggcaa ccacgacaca gccaatgact    1740
cagcatcttc acgtcaccta caagaaggtg accccgtaaa cctagagctt ctggagccct    1800
cgggagggcc tggctactgt gcctcaacgg ttcggctcct caacagacag tccctgcggc    1860
aaaagtgggt gtggccgtga gcctctgcag gctcaagagt gttgtccaga tgtttctgta    1920
ctggcataga aaaaccaaat aaaaggcctt tattttatg gctgaggatt ttgaatatta     1980
aaaaaaaaaa aaaaaaaaa                                                  1999

<210> SEQ ID NO 251
<211> LENGTH: 1398
<212> TYPE: DNA
<213> ORGANISM: Homo sapiens

<400> SEQUENCE: 251
ggctgtgcgc cacttccggc ttcaaccccc gaaaaggcgg tgcttaaacc ggaggaggcg      60
gaagtgagtc gacagacgag gcggcttttcc cggcagaatg ctagcgcagg cgcaggggct    120
cgagaggcct ggacctgtgg cgcatcctca gtgaggaggg ccgccctgca tccgtcgccg    180
gccccggtct ccaggggcct cacccgagtc atgccccgct attgcgcagc gatttgttgt    240
aagaaccgcc ggggacgaaa caataaagac cggaagctga gttttttatcc atttcctcta    300 catgacaaag aaagactgga aaagtggtta agaatatga agcgagattc atgggttccc     360
agtaaatacc agtttctatg tagtgaccat tttactcctg actctcttga catcagatgg    420
ggtattcgat atttaaaaca aactgcagtt ccaacaatat tttctttgcc tgaagacaat    480
cagggaaaag accccttctaa aaaaaaatcc cagaagaaaa acttggaaga tgagaaagaa    540
gtatgcccaa aagccaagtc agaagaatca tttgtattaa atgagacaaa gaaaatata     600 gttaacacag atgtgcccca tcaacatcca gaattacttc attcatcttc cttggtaaag    660
ccaccagctc ccaaaacagg aagtatacaa ataacatgt taactcttaa tctagttaaa    720
caacatactg ggaaaccaga atctaccttg gaaacatcag ttaaccaaga tacaggtaga    780
ggtggttttc acacatgttt tgagaatcta aattctacaa ctattacttt gacaacttca    840
aattcagaaa gtattcatca atctttggaa actcaagaag ttcttgaagt aactaccagt    900
catcttgcta atccaaactt tacaagtaat tccatggaaa taaagtcagc acaggaaaat    960
ccattcttat tcagcacaat taatcaaaca gttgaagaat taaacacaaa taagaatct   1020 gttattgcca tttttgtacc tgctgaaaat tctaaaccct cagttaattc ttttatatct    1080
gcacaaaaag aaaccacgga aatggaagac acagacattg aagactcctt gtataaggat    1140
gtagactatg ggacagaagt tttacaaatc gaacattctt actgcagaca agatataaat    1200
```

-continued

```
aaggaacatc tttggcagaa agtctctaag ctacattcaa agataactct tctagagtta    1260
aaagagcaac aaactctagg tagattgaag tctttggaag ctcttataag gcagctaaag    1320
caggaaaact ggctatctga agaaaacgtc aagattatag aaaaccattt tacaacatat    1380
gaagtcacta tgatatag                                                 1398

<210> SEQ ID NO 252
<211> LENGTH: 2291
<212> TYPE: DNA
<213> ORGANISM: Homo sapiens

<400> SEQUENCE: 252
agcgaaggca gacgcagtct ccatcgttga cgttagtcgc agtcttcgct gctaacgttt      60
tgttatgagt tgctaaaatg gtgaaatgct gctccgccat ggatgtgct tctcgctgct      120 tgccaaattc gaagttaaaa ggactgacat ttcacgtatt ccccacagat gaaaacatca     180
aaaggaaatg gtattagca atgaaaagac ttgatgtgaa tgcagccggc atttgggagc     240
ctaaaaaagg agatgtgttg tgttcgaggc actttaagaa gacagatttt gacagaagtg     300
ctccaaatat taaactgaaa cctggagtca taccttctat ctttgattct ccatatcacc     360
tacaggggaa aagagaaaaa cttcattgta gaaaaaactt caccctcaaa accgttccag     420
ccactaacta caatcaccat cttgttggtg cttcctcatg tattgaagaa ttccaatccc     480
agttcatttt tgaacatagc tacagtgtaa tggacagtcc aaagaaactt aagcataaat     540
tagatcatgt gatcggcgag ctagaggata caaaggaaag tctacggaat gttttagacc     600
gagaaaaacg ttttcagaaa tcattgagga agacaatcag ggaattaaag gatgaatgtc     660
tgatcagcca agaaacagca aatagactgg acactttctg ttgggactgt tgtcaggaga     720
gcatagaaca ggactatatt tcatgaaata atttcatgtt acgttccacc taaaattgtc     780
attggtacaa attttttataa aatctcattt accatcacta ataatatcc atcatttaaa     840 gtgctgcttt ggattctctg gagcattatg cattatagtt gttatccaaa gacttttttg     900
aaaatatgca gaaatttgtg gtaattatgt atttgtgtct tgtgacaatt atgttttata     960
gacctacact agtgccaggt cactattgta agatgttaaa atctcaagaa aatttcacag    1020
agctaaagaa atgatgtcaa attagtcaca ttaagctata gtagaaggaa ttggacactt    1080
ctccagatat ttggcttcaa aggagtacct ttacttacat gtgctttatg gtaagtacat    1140
tgaattttac tttaaatgca ttttactaca agcacaatt catttgtaat gcatatccat    1200
cttggattca atccaaggtg ctttagctat cagtagtacc aaaggatctt tttacaaggc    1260
ttcctgtggt attgactctg agaataacac atagtgaaga tctgtgggct tttaaaattg    1320
ttcacagcca atttaagaag acccctcatg aagtctcagt tttcagtaca gtacatcatt    1380
cctcctcact aggagcactt tgatgtaaac cagaatagct ttaaaaagac aaaaaggatc    1440
gtagatctga ttttaaatg gttggttgct ctgacagatc tgaacacttt gcttcatgac    1500
tatttcgtca taaggtata tgtttaaaat ctgaatggca gtactagctc tatactttta    1560
atactgcttt gtattttata tgtaaagtag tattgctgac attttaaaaa atacaaaat    1620 acaaagaaa ccattagaaa ttaataactg tggctcttcc agttgaaata ggaattggag    1680 agaaggatt agaatatttt aattagggga gtagattatt gtccaaggc ttttatttag    1740 agaaacgggt aattaaaaca gcagctttag aatagcttct tactgaatat gcaaaagaat    1800
aattccttgt tatttcctaa ttgatccaag tctcataaat ttagcttttg tcataattcc    1860
ttaccgaaaa caactgaaat tgagagtcat aaatactgtg ggttagaata aaaaccattt    1920
```

| | | |
|---|---|---|
| gccaaagcaa cactctactt agaagcacat gtacatacat ggacctcatt cagaagtcca | 1980 |
| tgttgtagca gttagaattt gagtatcagc catttcattg tagtaacaaa aattgaattg | 2040 |
| cattttgtgc tcagttgttt attgtaattt tattttgtt acattaatat tagttaagat | 2100 |
| atggtcactt gaattttttg tatttaagaa ttttctgttt taatgcatgt tatacttta | 2160 |
| tgtaggattc ccaaccttcc ctctaaatgg gatttaaccc acatctgcga gatcagcgtt | 2220 |
| atgctaagag gaaatcactg aggccatatc tttttacaat ctgaaaaaaa agtagtaaaa | 2280 |
| aggtagttaa a | 2291 |

<210> SEQ ID NO 253
<211> LENGTH: 1242
<212> TYPE: DNA
<213> ORGANISM: Homo sapiens

<400> SEQUENCE: 253

| | |
|---|---|
| cgtgagtgcc gctgacagaa gtcaagagaa tcggctggga cggggttggg gcgacaacgg | 60 |
| gccgggggg acccgacagg ccagagcccc ttggggagga gcggcggctg gaggcgcgag | 120 |
| gctcctccgg atgccggag agccgcttgc gacttaactc ccgcctcttt cccagatgcc | 180 |
| gcgtcactgc tccgccgccg gctgctgcac acgggacacg cgcgagacgc gcaaccgcgg | 240 |
| catctccttc cacagacttc ccaagaagga caacccgagg cgaggcttgt ggctggccaa | 300 |
| ctgccagcgg ctggacccca gcggccaggg cctgtgggac ccggcatccg agtacatcta | 360 |
| cttctgctcc aaacactttg aggaggactg ctttgagctg gtgggaatca gtggatatca | 420 |
| caggctaaag gaggggggcag tccccaccat atttgagtct ttctccaagt tgcgccggac | 480 |
| aaccaagacc aaaggacaca gttacccacc tggccccccct gaagtcagcc ggctcagacg | 540 |
| atgcaggaag cgctgctccg agggccgagg gcccacaact ccatttctc cacctccacc | 600 |
| tgctgatgtc acctgctttc ctgtggaaga ggcctcagca cctgccactt tgccggcctc | 660 |
| cccagctggg aggctggagc ctggccttag cagcccttt tcagacctac tgggccctt | 720 |
| gggtgcccag gcagatgaag caggctgcag cgcccagcct tcaccagagc ggcagcctc | 780 |
| ccctctcgaa ccacggccag tctccccctc agcgtatatg ctgcgcctgc ccccacccgc | 840 |
| cggagcctac atccagaatg aacacagcta ccaggtgggc agcgccttac tctggaagcg | 900 |
| gcgagccgag gcagcccttg atgcccttga caaggcccag cgccagctgc aggcctgcaa | 960 |
| gcggcgggag cagcggctgc ggttgagact gaccaagctg cagcaggagc gggcacggga | 1020 |
| gaagcgggca caggcagatg cccgccagac tctgaaggag catgtgcagg actttgccat | 1080 |
| gcagctgagc agcagcatgg cctgagggc tgctggactg accgaggggc tgcccagcaa | 1140 |
| gactgcagcc tcttcctccc tcagatccca ccagacccac caggtgccat aataaagcgg | 1200 |
| attctagacg gagaaaaaaa aaaaaaaaaa aaaaaaaaaa aa | 1242 |

<210> SEQ ID NO 254
<211> LENGTH: 1383
<212> TYPE: DNA
<213> ORGANISM: Homo sapiens

<400> SEQUENCE: 254

| | |
|---|---|
| agcgggggtc ggggttaggc ggcgctccgc gagaaccaaa gtgcagccgc tgacccggca | 60 |
| aaactcagcg ggggctggat agccatgccc aagtactgca gggcgccgaa ctgctccaac | 120 |
| actgcgggcc gctgggtgc agacaaccgc cctgtgagct tctacaagtt cccactgaag | 180 |
| gatggtcccc ggctgcaggc ctggctgcag cacatgggct gtgagcactg ggtgcccagc | 240 |

-continued

```
tgccaccagc acttgtgcag cgagcacttc acaccctcct gcttccagtg gcgctgggt      300
gtgcgctacc tgcggcctga tgcagtgccc tccatcttct cccggggacc acctgccaag      360
agtcagcgga ggacccgaag cacccagaag ccagtctcgc cgccgcctcc cctacagaag      420
aatacacccc tgcccagag ccctgccatc ccagtctctg gccagtgcg cctagtggtg       480
ctgggcccca catcggggag ccccaagact gtggccacca tgctcctgac ccccctggcc      540
cctgcgccaa ctcctgagcg gtcacaacct gaagtccctg cccaacaggc ccagaccggg      600
ctgggcccag tgctgggagc actgcaacgc cgggtgcgga ggctgcaacg gtgccaggag      660
cggcaccagg cgcagctgca ggccctggaa cggctggcac agcagctaca cggggagagc      720
ctgctggcac gggcacgccg gggtctgcag cgcctgacaa cagcccagac ccttggacct      780
gaggaatccc aaaccttcac catcatctgt ggagggcctg acatagccat ggtccttgcc      840
caggaccctg cacctgccac agtggatgcc aagccggagc tcctggacac tcggatcccc      900
agtgcataag gatcaagaca gacaatgtcg agggacaaaa gatagaagat ggaggaggaa      960
agacattata cgtgggcttg cccagcccca ccgcccacg cctgggtagt agcagtgcct     1020
cccctcaaggg cctgggttct accacccac tcctagggat ctcttgaacc ttaggggtga    1080
cctgggccca agtctctcat cagcccccaa tcccctgggt accaggcttc tgccaccccc    1140
ggctcagatc tttgcaaatc agtacgacag cctcagagca gagcaagggt tgtttgggag    1200
aatcataccct ggttctaagg agtcccacgc ttttttgccaa gcctggtact gagttcatga   1260
taccatggtg gacacagctg agaaaatccc tgccctcatg gtgctcattc tacttgagta    1320
gacgatgaac tagtaaacaa ataaacaaga acactgcaga catgaaaaaa aaaaaaaaaa    1380
aaa                                                                  1383
```

<210> SEQ ID NO 255
<211> LENGTH: 3627
<212> TYPE: DNA
<213> ORGANISM: Homo sapiens

<400> SEQUENCE: 255

```
attcatgctg tcgcgggaac cccgaaggtg gggccccacg taacaagaag atgacccgaa       60
gttgctccgc agtgggctgc agcacccgt acaccgtgct cagccgggag cgcggcctct      120
ccttccacca atttccaact gataccatac agcgctcaaa atggatcagg gctgttaatc      180
gtgtggaccc cagaagcaaa aagatttgga ttccaggacc aggtgctata ctgtgttcca     240
aacattttca agaaagtgac tttgagtcat atggcataag aagaaagctg aaaaaaggag     300
ctgtgccttc tgtttctcta tacaagattc ctcaaggtgt acatcttaaa ggtaaagcaa     360
gacaaaaat cctaaaacaa cctcttccag acaattctca agaagttgct actgaggacc     420
ataactatag tttaaagaca cctttgacga taggtgcaga gaaactggct gaggtgcaac     480
aaatgttaca agtgtccaaa aaagactta tctccgtaaa gaactacagg atgatcaaga    540
agagaagg tttacgatta attgatgcac ttgtagaaga gaaactactt tctgaagaaa       600
cagagtgtct gctacgagct caatttttcag atttttaagtg ggagttatat aattggagag   660
aaacagatga gtactccgca gaaatgaaac aatttgcatg tacactctac ttgtgcagta    720
gcaaagtcta tgattatgta agaaagattc ttaagctgcc tcattcttcc atcctcagaa    780
cgtggttatc caaatgccaa cccagtccag gtttcaacag caacatttttt tcttttcttc    840
aacgaagagt agagaatgga gatcagctct atcaatactg ttcattgtta ataaaaagta    900
tacctctcaa gcaacagctt cagtgggatc ctagcagtca cagtttgcag gggtttatgg    960
```

```
actttggtct tggaaaactt gatgctgatg aaacgccact tgcttcagaa actgttttgt    1020
taatggcagt gggtattttt ggccattgga gaacacctct tggttatttt tttgtaaaca    1080
gagcatctgg atatttgcag gctcagctgc ttcgtctgac tattggtaaa ctgagtgaca    1140
taggaatcac agttctggct gttacatctg atgccacagc acatagtgtt cagatggcaa    1200
aagcattggg gatacatatt gatggagacg acatgaaatg tacatttcag catccttcat    1260
cttctagtca acagattgca tacttctttg actcttgcca cttgctaaga ttaataagaa    1320
atgcatttca gaattttcaa agcattcagt ttattaatgg tatagcacat tggcagcacc    1380
tcgtggagtt agtagcactg gaggaacagg aattatcaaa tatggaaaga ataccaagta    1440
cacttgcaaa tttgaaaaat catgtactga aagtgaatag tgccacccaa ctctttagtg    1500
agagtgtagc cagtgcatta gaatatttgt tatccttaga cctgccacct tttcaaaact    1560
gtattggtac catccatttt ttacgtttaa ttaacaatct gtttgacatc tttaatagta    1620
ggaactgtta tggaaaggga cttaaagggc ctctgttgcc tgaaacttac agtaaaataa    1680
accacgtgtt aattgaagcc aagactattt tgttacatt atctgacact agcaataatc    1740
aaataattaa aggtaagcaa aaactaggat tcctgggatt tttgctcaat gctgagagct    1800
taaaatggct ctaccaaaat tatgttttcc caaaggtcat gccttttcct tatcttctga    1860
cttacaaatt cagtcatgat catctggaat tatttctaaa gatgcttagg caggtattag    1920
taacaagttc tagccctacc tgcatggcat tccagaaagc ttactataat ttggagacca    1980
gatacaaatt tcaagatgaa gttttttctaa gcaaagtaag catctttgac atttcaattg    2040
ctcgaaggaa agacttggcg ctttggacag ttcaacgtca gtatggtgtc agcgttacaa    2100
agactgtctt tcacgaagag ggtatttgtc aagactggtc tcattgttca ctaagtgagg    2160
cattactaga cctgtcagat cataggcgaa atctcatctg ttatgctggt tatgttgcaa    2220
acaagttatc agctctttta acttgtgagg actgcatcac tgcactgtat gcatcggatc    2280
tcaaagcctc taaaattggg tcactattat ttgttaaaaa gaagaatggt ttgcattttc    2340
cttcagaaag tctgtgtcgg gtcataaata tttgtgagcg agttgtaaga acccattcaa    2400
gaatggcaat ttttgaacta gtttctaaac aaagggaatt gtatcttcaa cagaaaatat    2460
tatgtgagct ttctgggcat attgatcttt ttgtagatgt gaataagcat ctctttgatg    2520
gagaagtgtg tgccatcaat cactttgtca agttgctaaa ggatataata atctgttctct    2580
taaatatcag agctaaaaat gttgcacaga atccttttaaa acatcattca gagagaactg    2640
atatgaaaac tttatcaagg aaacactggt cacctgtaca ggattataaa tgttcaagtt    2700
ttgctaatac cagtagtaaa ttcaggcatt tgctaagtaa cgatggatat ccattcaaat    2760
gagagaccta aaatatatta acattttaat taagaatact tgatcaacat tttttgaagt    2820
tcaatttacc atattttata aattgcgcat tctgcacagt ggacaagttt gcaattctga    2880
cttattaaaa tttcaaattc tgcatatcac aaaatctcct tatacttttg gtatggcttg    2940
cagcatttat gagttttcca aaatatagaa agcagtaggt cagtaggagc aaactagcca    3000
acaggtactg tctttgaatt tactactgta agactaagca gtgttactgg acacagtttt    3060
aacttgttca atctgcttca aaaacaagaa aaacaacaac tatgagttat caaaatattg    3120
actccattta tgactagact acatttctga agatctttg gtttacgatt cttaagaata    3180
ttgacaatac ctataaaact ttgaagataa cttttactta aatatgaaaa ttatagtttg    3240
aaaattaggc tcaagcaaat atcaaatact gcaaaaatcc ccttgtccca ggatacccta    3300
aaatagaagt atattttgat gtttgtttat tctacctcaa acagaggctt aagttttgaa    3360
```

```
gtgtaaccag tttatacttc attttataca aaacttattg ctgagaagtc tgaatattgt    3420 gcttttgtt gtttgtaaat agaattgaat ttaaatacac caggataaat cttatttaaa    3480
ggaagcctgt ttgaaaatca ccaactttaa cttattgctt atataaatcc aagctctgta    3540
cctgatcttt atgtaaagca agattcatat gtgtagtatc taatgcccctt tggtgttaca   3600 tttgactaaa atacaaatgt ctgtatt                                       3627
```

<210> SEQ ID NO 256
<211> LENGTH: 771
<212> TYPE: DNA
<213> ORGANISM: Homo sapiens

<400> SEQUENCE: 256

```
atgccggccc gttgtgtggc cgcccactgc ggcaacacca ccaagtctgg gaagtcgctg     60
ttccgctttc ccaaggaccg ggccgtgcgg ctgctctggg accgcttcgt gcggggttgc    120
cgcgccgact ggtacggagg caatgaccgc tcggtcatct gctctgacca ctttgcccca    180
gcctgttttg acgtctcttc ggttatccag aagaacctgc gcttctccca gcgcctgagg    240
ctggtggcag cgccgtgcc cacccctgcac cgggtgcccg ccccggcacc taagagggga    300
gaggagggag accaagcagg ccgcctggac acgcgaggag agctccaggc agccaggcat    360
tctgaggctg ccccaggtcc agtctcctgt acacgccccc gagctgggaa gcaggctgca    420
gcttcacaga ttacgtgtga aaatgaactt gtgcaaaccc aaccccatgc tgataatcca    480
tctaatactg tcacttcagt acctactcac tgtgaagaag gcccagtgca taaaagtaca    540
caaatttctt tgaaaaggcc ccgtcaccgt agtgtgggta ttcaagccaa agtgaaagcg    600
tttgaaaaaa gactgtgtaa tgcaactact cagacagagg aattgtggtc tagaacttcc    660
tctctctttg acatttactc cagtgattca gaaacagata cagactggga tatcaagagt    720
gaacagagtg atttgtctta tatggctgta caggtgaaag aagaaacatg t             771
```

<210> SEQ ID NO 257
<211> LENGTH: 942
<212> TYPE: DNA
<213> ORGANISM: Homo sapiens

<400> SEQUENCE: 257

```
atgcctggct ttacgtgctg cgtgccaggc tgctacaaca actcgcaccg ggacaaggcg     60
ctgcacttct acacgtttcc aaaggacgct gagttgcggc gcctctggct caagaacgtg    120
tcgcgtgccg gcgtcagtgg gtgcttctcc accttccagc ccaccacagg ccaccgtctc    180
tgcagcgttc acttccaggg cggccgcaag acctacacgg tacgcgtccc caccatcttc    240
ccgctgcgcg cgtcaatga gcgcaaagta gcgcgcagac ccgctggggc gcggccgcc     300 cgccgcaggc agcagcagca acagcagcag cagcagcaac agcagcaaca gcagcagcag    360
cagcaacagc agcagcagca gcagcagcag cagcagtcct cacctctgc ctccactgcc     420 cagactgccc agctgcagcc gaacctggta tctgcttccg cggccgtgct tctcacccctt    480 caggccactg tagacagcag tcaggctccg ggatccgtac agccggcgcc catcactccc    540
actggagaag acgtgaagcc catcgatctc acagtgcaag tggagtttgc agccgcagag    600
ggcgcagcct ctgcggccgc cgcgtcgag ttacaggctg ctaccgcagg gctgaggct      660 gccgagtgcc ctatgggccc ccagttggtg gtggtagggg aagagggctt ccctgatact    720
ggctccgacc attcgtactc cttgtcgtca ggcaccacgg aggaggagct cctgcgcaag    780
ctgaatgagc agcgggacat cctggctctg atggaagtga agatgaaaga gatgaaaggc    840
```

| | | |
|---|---|---|
| agcattcgcc acctgcgtct cactgaggcc aagctgcgcg aagaactgcg tgagaaggat | 900 |
| cggctgcttg ccatggctgt catccgcaag aagcacggaa tg | 942 |

<210> SEQ ID NO 258
<211> LENGTH: 2283
<212> TYPE: DNA
<213> ORGANISM: Homo sapiens

<400> SEQUENCE: 258

| | |
|---|---|
| atgccgaact tctgcgctgc ccccaactgc acgcggaaga gcacgcagtc cgacttggcc | 60 |
| ttcttcaggt tcccgcggga ccctgccaga tgccagaagt gggtggagaa ctgtaggaga | 120 |
| gcagacttag aagataaaac acctgatcag ctaaataaac attatcgatt atgtgccaaa | 180 |
| cattttgaga cctctatgat ctgtagaact agtccttata ggacagttct tcgagataat | 240 |
| gcaataccaa caatatttga tcttaccagt catttgaaca acccacatag tagacacaga | 300 |
| aaacgaataa aagaactgag tgaagatgaa atcaggacac tgaaacagaa aaaaattgat | 360 |
| gaaacttctg agcaggaaca aaaacataaa gaaaccaaca atagcaatgc tcagaacccc | 420 |
| agcgaagaag agggtgaagg gcaagatgag gacattttac ctctaacccct tgaagagaag | 480 |
| gaaaacaaag aatacctaaa atctctattt gaaatcttga ttctgatggg aaagcaaaac | 540 |
| atacctctgg atggacatga ggctgatgaa atcccagaag gtctctttac tccagataac | 600 |
| tttcaggcac tgctggagtg tcggataaat tctggtgaag aggttctgag aaagcggttt | 660 |
| gagacaacag cagttaacac gttgttttgt tcaaaaacac agcagaggca gatgctagag | 720 |
| atctgtgaga gctgtattcg agaagaaact ctcagggaag tgagagactc acacttcttt | 780 |
| tccattatca ctgacgatgt agtggacata gcaggggaag agcacctacc tgtgttggtg | 840 |
| aggtttgttg atgaatctca taacctaaga gaggaattta taggcttcct gccttatgaa | 900 |
| gccgatgcag aaattttggc tgtgaaattt cacactatga taactgagaa gtggggatta | 960 |
| aatatggagt attgtcgtgg ccaggcttac attgtctcta gtggattttc ttccaaaatg | 1020 |
| aaagttgttg cttctagact tttagagaaa tatccccaag ctatctacac actctgctct | 1080 |
| tcctgtgcct taaatatgtg gttggcaaaa tcagtacctg ttatgggagt atctgttgca | 1140 |
| ttaggaacaa ttgaggaagt tgttctcttt ttccatcgat caccacaact gcttttagaa | 1200 |
| cttgacaacg taatttctgt tcttttttcag aacagtaaag aaagggggtaa agaactgaag | 1260 |
| gaaatctgcc attctcagtg gacaggcagg catgatgctt tgaaattttt agtggaactc | 1320 |
| ctgcaagcac ttgtttttatg tttagatggt ataaatagta cacaaatat tagatggaat | 1380 |
| aactatatag ctggccgagc atttgtactc tgcagtgcag tgtcagattt tgatttcatt | 1440 |
| gttactattg ttgttcttaa aaatgtccta tcttttacaa gagcctttgg gaaaaacctc | 1500 |
| caggggcaaa cctctgatgt cttctttgcg gccggtagct tgactgcagt actgcattca | 1560 |
| ctcaacgaag tgatggaaaa tattgaagtt tatcatgaat tttggtttga ggaagccaca | 1620 |
| aatttggcaa ccaaacttga tattcaaatg aaactccctg ggaaattccg cagagctcac | 1680 |
| cagggtaact tggaatctca gctaacctct gagagttact ataaagaaac cctaagtgtc | 1740 |
| ccaacagtgg agcacattat tcaggaactt aaagatatat tctcagaaca gcacctcaaa | 1800 |
| gctcttaaat gcttatctct ggtaccctca gtcatgggac aactcaaatt caatacgtcg | 1860 |
| gaggaacacc atgctgacat gtatagaagt gacttaccca atcctgacac gctgtcagct | 1920 |
| gagcttcatt gttggagaat caatggaaaa cacaggggga agatataga gcttccgtcc | 1980 |
| accatctatg aagccctcca cctgcctgac atcaagtttt ttcctaatgt gtatgcattg | 2040 |

```
ctgaaggtcc tgtgtattct tcctgtgatg aaggttgaga atgagcggta tgaaaatgga   2100
cgaaagcgtc ttaaagcata tttgaggaac actttgacag accaaaggtc aagtaacttg   2160
gctttgctta acataaattt tgatataaaa cacgacctgg atttaatggt ggacacatat   2220
attaaactct atacaagtaa gtcagagctt cctacagata attccgaaac tgtggaaaat   2280
acc                                                                 2283
```

<210> SEQ ID NO 259
<211> LENGTH: 986
<212> TYPE: DNA
<213> ORGANISM: Mus musculus

<400> SEQUENCE: 259

```
cttctgctaa agcaaacccc acaacggaca gggtagtcac tcgcccaccc caaccccac    60 cccacggcga ggtgatcgtc cccgtaactg ctgaccgacg ccaccgagag cggcgagcgt   120
tatcaaggcc gagcgcggga ccccgacggc ccccttcgcc tgcctcccgg gccgaaggag   180
agtgtggagg gccagaagga tggtgcagtc ctgctccgcc tacggctgca agaaccgcta   240
cgacaaggac aagcccgtct ccttccacaa gtttcctctt actcgcccca gcctttgtaa   300
gcagtgggag gcagctgtta aaaggaaaaa cttcaagccc accaagtaca gcagcatctg   360
ctcggagcac ttcaccccgg actgctttaa gaggagtgc aacaacaagc tactgaagga    420
gaacgctgtg cccacaatat ttctctatat cgagccacat gagaagaagg aagacctgga   480
atcccaagaa cagctcccct ctccttcacc ccccgcttcc caggttgatg ctgctattgg   540
gctgctaatg cccctctgc agacccctga taacctgtcg gttttctgtg accacaatta     600
cactgtggag gatacgatgc accagaggaa gaggatcctg cagctggagc agcaggtgga   660
gaaactcagg aagaagctca agacggccca gcagcggtgc cggcggcagg agaggcagct   720
cgagaagctc aaggaagtcg tccactttca gagagagaag gacgacgcgt ccgagaggggg   780 ctacgtgatc ctaccaaatg actactttga aattgttgaa gttccagcat gaaaaaatga   840
gatgtgttag tgggacaaga ctatacacct tcttttagcc tacatacagg agttcatttg   900
aaaaaataac acttaattac ttgtattaaa aaacaatat ttttttaaaa taaattagat    960
atatactgta aaaaaaaaaa aaaaaa                                        986
```

<210> SEQ ID NO 260
<211> LENGTH: 1515
<212> TYPE: DNA
<213> ORGANISM: Mus musculus

<400> SEQUENCE: 260

```
gctctgccct ccccgcgctc tgcaccgagc tggcggcgcg gggtcgcctg cctcgtttgt    60
ctagcgtttg acagaagctt gcttagcggg cagcgcctcc gaagtggcgt aaggtggcgc   120
cgaatgaggg gccgggggaa atgccgacca attgcgccgc ggcgggctgt gctgctacct   180
acaacaagca cattaacatc agcttccaca ggtttccttt ggatcctaaa agaagaaaag   240
aatgggttcg cctggttagg cgcaaaaatt ttgtgccagg aaaacacact tttctttgct   300
caaagcactt tgaagcctcc tgttttgatc taacaggaca acccgacga cttaaaatgg    360 atgctgttcc aaccatttt gattttgta cccatataaa gtctctgaaa ctcaagtcaa     420
ggaatcttct gaagacaaac aacagttttc ctccaactgg accatgtaat ttaaagctga   480
acggcagtca gcaagtactg cttgaacaca gttatgcctt taggaaccct atggaggcga   540
aaaaaaggat aattaaacta gaaaggaaa tagcaagctt gagaaaaaaa atgaaaactt    600
```

```
gcctgcaaag agaacgcaga gcaactcgaa ggtggatcaa agccacgtgc tttgtgaaga      660
gcttagaagc aagtaacatg ctacctaagg gcatctcaga acagatttta ccaactgcct      720
taagcaatct tcctctggaa gatttaaaaa gtcttgaaca agatcaacaa gataaaacag      780
tacccattct ctaaatgtaa aatggaagag actctctgca ctcaagtttt cctcacacag      840
aacccagtgc ccagctcctg ccgtccccac ccaccgcact ctgacagtta cactacaatc      900
aagtcctgca gttttacttg aagtagtagt gtcagtgtca ctctctggag actgaggaag      960
tgggaaatcc aatgacaagc ttgacaccga gcagaagtgc cttacatgag ggtcacggac     1020
ttaggaaaca ctgccagcag ggtttctgct cttgtttttt taagctgctg tcaaatagga     1080
atgacaagtg atatgttcat aaaagtaaaa gcattccgca ccaaagctgg gatattacat     1140
tctaaagaac atgtgaagta ggagctaact gcattaaata tgatcttaaa actactaatg     1200
tattttgtat gaattaaatt attgggattg tggttgaaaa ttttatagaa taaaacctct     1260
ggggtacggg gcaaggtttg tttctttgtt ttgttttgtt ttttgtcttt tttagccttt     1320
tgtattttaa ctagtaaaag taaacttatc atggcctttt tttataagaa cattgaattt     1380
aaaagtaggt tgtaaaataa tctgaaatag tattttgaat gtgaaatacc tttgaaactc     1440
caaactaggt aaggccccaa gcacctcaga ctgggaaaac ccagtgagtt atagtcaacg     1500
tctaagaaaa tatac                                                      1515

<210> SEQ ID NO 261
<211> LENGTH: 1120
<212> TYPE: DNA
<213> ORGANISM: Mus musculus

<400> SEQUENCE: 261 gagggcagt gggcccatct ccgagatgcc gaagtcttgc gcggcccggc aatgctgcaa       60
ccgctacagc agccgcagga agcagctcac cttccaccgg ttcccttca gccgcccgga      120 gctgttgagg gagtgggtgc tcaacatcgg ccgggctgac ttcaagccta agcagcacac      180
agtcatctgc tcggaacact tcagacccga gtgcttcagc gcctttggga accgcaagaa      240
cctgaaacac aatgctgtgc ccacggtgtt cgcttttcag aacccacag aggtctgccc      300 tgaggtgggg gctggtgggg acagctcagg gaggaacatg gacaccacac tggaagaact      360
tcagcctcca accccggaag gccccgtgca gcaggtctta ccagatcgag aagcaatgga      420
ggccacggag gccgctggcc tgcctgccag ccctctgggg ttgaagaggc ccttccggg      480 acagccgtct gatcacagtt atgccctttc ggacttggat accctcaaaa aaaaactctt      540
tctcacactg aaggaaaaca agaggcttcg gaagcggctg aaagcccaga ggctgctgtt      600
gcggaggaca tgtggccgcc tgagagccta cagagaggga cagccgggac ctcgggccag      660
acggccggca cagggaagct gagcctgagc aagctctggg atgtggggt ggtggcaaca      720 ccttagcagg aagtggtgtt ctggcctgct atgggcgttt ctacccgctg ctgatgctgc      780
aggtgccttg agagtgggat gggatgctgc gacaggcagt tgtcgggtgg gggcccaagt      840
actgcggagg caccgtccca ggtttcttgg gctgaggctg tcagctgtgg ggaagcagca      900
gtgaccaaat gtgagccgtc acaacccct caagagatgc tcccagaggg agagctggtc      960
attcttacag ccggtggggt ccttactgtc tccccatagg agccattctg atggcaggca     1020
gggcaagggt cccgtcagc ctgtatttct gagtgactct ttttctgcc tggttcgtgt      1080 agatgtggaa taaatctttt gaagtctcca aaaaaaaaaa                           1120
```

```
<210> SEQ ID NO 262
<211> LENGTH: 558
<212> TYPE: DNA
<213> ORGANISM: Mus musculus

<400> SEQUENCE: 262
atactgcaag catttggaag cctaaaaaaa ggagatgtgc tgtgttcaag acacttcaag      60
aagacagact ttgacagaag cactctaaac actaagctga aggcaggagc catcccttct     120
atctttgaat gtccatatca cttacaggag aaaagagaaa aacttcactg tagaaaaaac     180
ttccttctca aaaccttcc catcacccac catggccgcc agcttgttgg tgcctcctgc      240
attgaagaat tcgaacccca gttcattttt gaacatagct acagtgttat ggacagccca    300
aagaagctta agcataagct agaccgtgtg atcatcgagc tggagaatac caaggaaagc    360
ctacggaatg ttttagcccg agaaaaacac tttcaaaagt cactgaggaa gacaatcatg    420
gaactaaagg atgaaagtct gatcagccag gaaacagcca atagtctggg tgctttctgt    480
tgggagtgct atcatgaaag cacagcagga ggctgtagtt gtgaagtcat ttcttatatg    540
cttcatctgc agttgaca                                                  558

<210> SEQ ID NO 263
<211> LENGTH: 37
<212> TYPE: PRT
<213> ORGANISM: Artificial Sequence
<220> FEATURE:
<223> OTHER INFORMATION: Consensus sequence for PAR4 binding domain of
      THAP
<220> FEATURE:
<221> NAME/KEY: UNSURE
<222> LOCATION: 3-15, 18, 22, 24-34, 36
<223> OTHER INFORMATION: Xaa = any of the twenty amino acids

<400> SEQUENCE: 263

Leu Glu Xaa Xaa Xaa Xaa Xaa Xaa Xaa Xaa Xaa Xaa Xaa Xaa Xaa Gln
 1               5                  10                  15

Arg Xaa Arg Arg Gln Xaa Arg Xaa Xaa Xaa Xaa Xaa Xaa Xaa Xaa Xaa
            20                  25                  30

Xaa Xaa Gln Xaa Glu
        35
```

DEATH ASSOCIATED PROTEINS, AND THAP1 AND PAR4 PATHWAYS IN APOPTOSIS CONTROL

RELATED APPLICATIONS

This application claims priority from U.S. Provisional Patent Application Ser. No. 60/341,997, entitled NOVEL DEATH ASSOCIATED PROTEINS, AND THAP1 AND PAR4 PATHWAYS IN APOPTOSIS CONTROL, filed Dec. 18, 2001, the disclosure of which is incorporated herein by reference in its entirety.

FIELD OF THE INVENTION

The present invention relates to genes and proteins of the THAP (THanatos (death)-Associated Protein) family, and uses thereof. In particular, the invention relates to polypeptides comprising a THAP domain, the modulation of THAP-mediated activities and the identification of compounds which modulate these activities.

BACKGROUND

Coordination of cell proliferation and cell death is required for normal development and tissue homeostasis in multicellular organisms. A defect in the normal coordination of these two processes is a fundamental requirement for tumorigenesis.

Progression through the cell cycle is highly regulated, requiring the transit of numerous checkpoints (for review, see Hunter, 1993). The extent of cell death is physiologically controlled by activation of a programmed suicide pathway that results in morphologically recognizable form of death termed apoptosis (Jacobson et al, 1997; Vaux et al., 1994). Both extra-cellular signals, such as tumor necrosis factor, and intracellular signals, like p53, can induce apoptotic cell death. Although many proteins involved in apoptosis or the cell cycle have been identified, the mechanisms by which these two processes are coordinated are not well understood.

It is well established that molecules which modulate apoptosis have the potential to treat a wide range of conditions relating to cell death and cell proliferation. For example, such molecules may be used for inducing cell death for the treatment of cancers, inhibiting cell death for the treatment of neurodegenerative disorders, and inhibiting or inducing cell death for regulating angiogenesis. However, because many biological pathways controlling cell cycle and apoptosis have not yet been fully elucidated, there is a need for the identification of biological targets for the development of therapeutic molecules for the treatment of these disorders.

PML Nuclear Bodies

PML nuclear bodies (PML-NBs), also known as PODs (PML oncogenic domains), ND10 (nuclear domain 10) and Kr bodies, are discrete subnuclear domains that are specifically disrupted in cells from acute promyelocytic leukemia (APL), a distinct subtype of human myeloid leukemia (Maul et al., 2000; Ruggero et al., 2000; Zhong et al., 2000a). Their name derives from their most intensively studied protein component, the promyelocytic leukemia protein (PML), a RING finger IFN-inducible protein encoded by a gene originally cloned as the t(15;17) chromosomal translocation partner of the retinoic acid receptor (RAR) locus in APL. In APL cells, the presence of the leukemogenic fusion protein, PML-RAR, leads to the disruption of PML-NBs and the delocalization of PML and other PML-NB proteins into aberrant nuclear structures (Zhong et al., 2000a). Treatment of both APL cell lines and patients with retinoic acid, which induces the degradation of the PML-RAR oncoprotein, results in relocalization of PML and other NBs components into PML-NBs and complete remission of clinical disease, respectively. The deregulation of the PML-NBs by PML-RAR thus appears to play a critical role in tumorigenesis. The analysis of mice, where the PML gene was disrupted by homologous recombination, has revealed that PML functions as a tumor suppressor in vivo (Wang et al., 1998a), that is essential for multiple apoptotic pathways (Wang et al., 1998b). Pml −/− mice and cells are protected from Fas, TNFα, ceramide and IFN-induced apoptosis as well as from DNA damage-induced apoptosis. However, the molecular mechanisms through which PML modulates the response to pro-apoptotic stimuli are not well understood (Wang et al., 1998b; Quignon et al., 1998). Recent studies indicate that PML can participate in both p53-dependent and p53-independent apoptosis pathways (Guo et al., 2000; Fogal et al., 2000). p53-dependent DNA-damage induced apoptosis, transcriptional activation by p53 and induction of p53 target genes are all impaired in PML −/− primary cells (Guo et al., 2000). PML physically interacts with p53 and acts as a transcriptional co-activator for p53. This co-activatory role of PML is absolutely dependent on its ability to recruit p53 in the PML-NBs (Guo et al., 2000; Fogal et al., 2000). The existence of a cross-talk between PML- and p53-dependent growth suppression pathways implies an important role for PML-NBs and PML-NBs-associated proteins as modulators of p53 functions. In addition to p53, the pro-apoptotic factor Daxx could be another important mediator of PML pro-apoptotic activities (Ishov et al., 1999; Zhong et al., 2000b; Li et al., 2000). Daxx was initially identified by its ability to enhance Fas-induced cell death. Daxx interacts with PML and localizes preferentially in the nucleus where it accumulates in the PML-NBs (Ishov et al., 1999; Zhong et al., 2000b; Li et al., 2000). Inactivation of PML results in delocalization of Daxx from PML-NBs and complete abrogation of Daxx pro-apoptotic activity (Zhong et al., 2000b). Daxx has recently been found to possess strong transcriptional repressor activity (Li et al., 2000). By recruiting Daxx to the PML-NBs, PML may inhibit Daxx-mediated transcriptional repression, thus allowing the expression of certain pro-apoptotic genes.

PML-NBs contain several other proteins in addition to Daxx and p53. These include the autoantigens Sp100 (Sternsdorf et al., 1999) and Sp100-related protein Sp140 (Bloch et al., 1999), the retinoblastoma tumor suppressor pRB (Alcalay et al., 1998), the transcriptional co-activator CBP (LaMorte et al., 1998), the Bloom syndrome DNA helicase BLM (Zhong et al., 1999) and the small ubiquitin-like modifier SUMO-1 (also known as sentrin-1 or PIC1; for recent reviews see Yeh et al., 2000; Melchior, 2000; Jentsch and Pyrowolakis, 2000). Covalent modification of PML by SUMO-1 (sumoylation) appears to play a critical role in PML accumulation into NBs (Muller et al., 1998) and the recruitment of other NBs components to PML-NBs (Ishov et al., 1999; Zhong et al., 2000c).

Prostate Apoptosis Response-4

Prostate apoptosis response-4 (PAR4) is a 38 kDa protein initially identified as the product of a gene specifically upregulated in prostate tumor cells undergoing apoptosis (for reviews see Rangnekar, 1998; Mattson et al., 1999). Consistent with an important role of PAR4 in apoptosis, induction of PAR4 in cultured cells is found exclusively during apoptosis and ectopic expression of PAR4 in N1H-3T3 cells (Diaz-Meco et al., 1996), neurons (Guo et al., 1998), prostate cancer and melanoma cells (Sells et al., 1997) has been shown to sensitize these cells to apoptotic stimuli. In addition, down regulation of PAR4 is critical for ras-induced survival and tumor progression (Barradas et al., 1999) and suppression of PAR4 production by antisense technology prevents apoptosis in several systems (Sells et al., 1997; Guo et al., 1998), including different models of neurodegenerative disorders (Mattson et al., 1999), further emphasizing the critical role of PAR4 in apoptosis. At the carboxy terminus, PAR4 contains both a leucine zipper domain (Par4LZ, amino acids 290-332), and a partially overlapping death domain (Par4DD, amino acids 258-332). Deletion of this carboxy-terminal part abrogates the pro-apoptotic function of PAR4 (Diaz-Meco et al., 1996; Sells et al., 1997; Guo et al., 1998). On the other hand, overexpression of PAR4 leucine zipper/death domain acts in a dominant negative manner to prevent apoptosis induced by full-length PAR4 (Sells et al., 1997; Guo et al., 1998). The PAR4 leucine zipper/death domain mediates PAR4 interaction with other proteins by recognizing two different kinds of motifs: zinc fingers of the Wilms tumor suppressor protein WT1 (Johnstone et al., 1996) and the atypical isoforms of protein kinase C (Diaz-Meco et al., 1996), and an arginine-rich domain from the death-associated-protein (DAP)-like kinase Dlk (Page et al., 1999). Among these interactions, the binding of PAR4 to aPKCs and the resulting inhibition of their enzymatic activity is of particular functional relevance because the aPKCs are known to play a key role in cell survival and their overexpression has been shown to abrogate the ability of PAR4 to induce apoptosis (Diaz-Meco et al., 1996; Berra et al., 1997).

SLC/CCL21

Chemokine SLC/CCL21 (also known as SLC, CKβ-9, 6Ckine, and exodus-2) is a member of the CC (beta)-chemokine subfamily. SLC/CCL21 contains the four conserved cysteines characteristic of beta chemokines plus two additional cysteines in its unusually long carboxyl-terminal domain. Human SLC/CCL21 cDNA encodes a 134 amino acid residue, highly basic, precursor protein with a 23 amino acid residue signal peptide that is cleaved to form the predicted 111 amino acid residues mature protein. Mouse SLC/CCL21 cDNA encodes a 133 amino acid residue protein with 23 residue signal peptide that is cleaved to generate the 110 residue mature protein. Human and mouse SLC/CCL21 is highly conserved, exhibiting 86% amino acid sequence identity. The gene for human SLC/CCL21 has been localized at human chromosome 9p13 rather than chromosome 17, where the genes of many human CC chemokines are clustered. The SLC/CCL21 gene location is within a region of about 100 kb as the gene for MIP-3 beta/ELC/CCL19, another recently identified CC chemokine. SLC/CCL21 was previously known to be highly expressed in lymphoid tissues at the mRNA level, and to be a chemoattractant for T and B lymphocytes (Nagira, et al. (1997) J. Biol. Chem. 272:19518-19524; Hromas, et al. (1997) J. Immunol. 159:2554-2558; Hedrick, et al. (1997) J. Immunol. 159:1589-1593; Gunn, et al. (1998) Proc. Natl. Acad. Sci. 95:258-263). SLC/CCL21 also induces both adhesion of lymphocytes to intercellular adhesion molecule-1 and arrest of rolling cells (Campbell, et al. (1998) Science 279:381-384). All of the above properties are consistent with a role for SLC/CCL21 in regulating trafficking of lymphocytes through lymphoid tissues. Unlike most CC chemokines, SLC/CCL21 is not chemotactic for monocytes. However, it has been reported to inhibit hemopoietic progenitor colony formation in a dose-dependent manner (Hromas et al. (1997) J. Immunol. 159: 2554-58).

Chemokine SLC/CCL21 is a ligand for chemokine receptor CCR7 (Rossi et al. (1997) J. Immunol. 158:1033; Yoshida et al. (1997) J. Biol. Chem. 272:13803; Yoshida et al. (1998) J. Biol. Chem. 273:7118; Campbell et al. (1998) J Cell Biol 141:1053). CCR7 is expressed on T cells and dendritic cells (DC), consistent with the chemotactic action of SLC/CCL21 for both lymphocytes and mature DC. Both memory (CD45RO$^+$) and naïve (CD45RA$^+$) CD4$^+$ and CD8$^+$ T cells express the CCR7 receptor (Sallusto et al. (1999) Nature 401:708). Within the memory T cell population, CCR7 expression discriminates between T cells with effector function that can migrate to inflamed tissues (CCR7$^-$) vs. T cells that require a secondary stimulus prior to displaying effector functions (CCR7$^+$) (Sallusto et al. (1999) Nature 401:708). Unlike mature DC, immature DC do not express CCR7 nor do they respond to the chemotactic action of CCL21 (Sallusto et al. (1998) Eur. J. Immunol. 28:2760; Dieu et al. (1998) J. Exp. Med. 188:373).

A key function of CCR7 and its two ligands SLC/CCL21 and MIP3b/CCL19 is facilitating recruitment and retention of cells to secondary lymphoid organs in order to promote efficient antigen exposure to T cells. CCR7-deficient mice demonstrate poorly developed secondary organs and exhibit an irregular distribution of lymphocytes within lymph nodes, Peyer's patches, and splenic periarteriolar lymphoid sheaths (Forster et al. (1999) Cell 99:23). These animals have severely impaired primary T cell responses largely due to the inability of interdigitating DC to migrate to the lymph nodes (Forster et al. (1999) Cell 99:23). The overall findings to date support the notion that CCR7 and its two ligands, CCL19 and CCL21, are key regulators of T cell responses via their control of T cell/DC interactions. CCR7 is an important regulatory molecule with an instructive role in determining the migration of cells to secondary lymphoid organs (Forster et al. (1999) Cell 99:23; Nakano et al. (1998) Blood 91:2886).

SUMMARY OF THE INVENTION

THAP1 (THanatos-Associated-Protein-1)

In the past few years, the inventors have focused on the molecular characterization of novel genes expressed in the specialized endothelial cells (HEVECs) of post-capillary high endothelial venules (Girard and Springer, 1995a; Girard and Springer, 1995b; Girard et al., 1999). In the present invention, they report the analysis of THAP1 (for THanatos (death)-Associated Protein-1), a protein that localizes to PML-NBs. Two hybrid screening of an HEVEC cDNA library with the THAP1 bait lead to the identification of a unique interacting partner, the pro-apoptotic protein PAR4. PAR4 is also found to accumulate into PML-NBs and targeting of the THAP1/PAR4 complex to PML-NLs is mediated by PML. Similarly to PAR4, THAP1 is a proapoptotic polypeptide. Its pro-apoptotic activity requires a novel protein motif in the amino-terminal part called THAP domain. Together these results define a novel PML-NBs pathway for apoptosis that involves the THAP1/PAR4 pro-apoptotic complex.

The present invention includes genes, proteins and biological pathways involved in apoptosis. In some embodiments, the genes, proteins, and pathways disclosed herein may be used for the development of polypeptide, nucleic acid or small molecule therapeutics.

The present invention provides a novel protein motif, the THAP domain. The present inventors initially identified the THAP domain as a 90 residue protein motif in the amino-terminal part of THAP1 and which is essential for THAP1 pro-apoptotic activity. THAP1 (THanatos (death) Associated Protein-1), as determined by the present inventors, is a proapoptotic polypeptide which forms a complex with the pro-apoptotic protein PAR4 and localizes in discrete subnuclear domains known as PML nuclear bodies. However, the THAP domain also defines a novel family of proteins, the THAP family, and the inventors have also provided at least twelve distinct members in the human genome (THAP-0 to THAP11), all of which contain a THAP domain (typically 80-90 amino acids) in their amino-terminal part. The present invention thus includes nucleic acid molecules, including in particular the complete cDNA sequences, encoding members of the THAP family, portions thereof encoding the THAP domain or polypeptides homologous thereto, as well as to polypeptides encoded by the THAP family genes. The invention thus also includes diagnostic and activity assays, and uses in therapeutics, for THAP family proteins or portions thereof, as well as drug screening assays for identifying compounds capable of inhibiting (or stimulating) pro-apoptotic activity of a THAP family member.

In one example of a THAP family member, THAP1 is determined to be an apoptosis inducing polypeptide expressed in human endothelial cells (HEVECs), providing characterization of the THAP sequences required for apoptosis activity in the THAP1 polypeptide. In further aspects, the invention is also directed to the interaction of THAP1 with the pro-apoptotic protein PAR4 and with PML-NBs, including methods of modulating THAP1/PAR4 interactions for the treatment of disease. The invention also concerns interaction between PAR4 and PML-NBs, diagnostics for detection of said interaction (or localization) and modulation of said interactions for the treatment of disease.

Compounds which modulate interactions between a THAP family member and a THAP-family target molecule, a THAP domain or THAP-domain target molecule, or a PAR4 and a PML-NBs protein may be used in inhibiting (or stimulating) apoptosis of different cell types in various human diseases. For example, such compounds may be used to inhibit or stimulate apoptosis of endothelial cells in angiogenesis-dependent diseases including but not limited to cancer, cardiovascular diseases, inflammatory diseases, and to inhibit apoptosis of neurons in acute and chronic neurodegenerative disorders, including but not limited to Alzheimer's, Parkinson's and Huntington's diseases, amyotrophic lateral sclerosis, HIV encephalitis, stroke, epileptic seizures).

Oligonucleotide probes or primers hybridizing specifically with a THAP1 genomic DNA or cDNA sequence are also part of the present invention, as well as DNA amplification and detection methods using said primers and probes.

Fragments of THAP family members or THAP domains include fragments encoded by nucleic acids comprising at least 12, 15, 18, 20, 25, 30, 35, 40, 50, 60, 70, 80, 90, 100, 150, 200, 500, or 1000 consecutive nucleotides selected from the group consisting of SEQ ID NOs: 160-175, or polypeptides comprising at least 8, 10, 12, 15, 20, 25, 30, 40, 50, 100, 150 or 200 consecutive amino acids selected from the group consisting of SEQ ID NOs: 1-114.

A further aspect of the invention includes recombinant vectors comprising any of the nucleic acid sequences described above, and in particular to recombinant vectors comprising a THAP1 regulatory sequence or a sequence encoding a THAP1 protein, THAP family member, THAP domain, fragments of THAP family members and THAP domains, homologues of THAP family members/THAP domains, as well as to cell hosts and transgenic non human animals comprising said nucleic acid sequences or recombinant vectors.

Another aspect of the invention relates to methods for the screening of substances or molecules that inhibit or increase the expression of the THAP1 gene or genes encoding THAP family members, as well as with methods for the screening of substances or molecules that interact with and/or inhibit or increase the activity of a THAP1 polypeptide or THAP family polypeptide.

In accordance with another aspect, the present invention provides a medicament comprising an effective amount of a THAP family protein, e.g. THAP1, or a SLC/CCL21-binding fragment thereof, together with a pharmaceutically acceptable carrier. The medicaments described herein may be useful for treatment and/or prophylaxis.

As related to another aspect the invention is concerned in particular with the use of a THAP family protein, homologs thereof and fragments thereof, for example THAP1, or a SLC/CCL21-binding fragment thereof as an anti-inflammatory agent. The THAP family protein, for example, THAP1 and fragments thereof will be useful for the treatment of conditions mediated by SLC/CCL21.

In a further aspect, the present invention provides a detection method comprising the steps of providing a SLC/CCL21 chemokine-binding molecule which is a THAP family protein, for example, THAP1, or an SLC/CCL21-binding fragment thereof, contacting the SLC/CCL21-binding THAP1 molecule with a sample, and detecting an interaction of the SLC/CCL21-binding THAP1 molecule with SLC/CCL21 chemokine in the sample.

In one example, the invention may be used to detect the presence of SLC/CCL21 chemokine in a biological sample. The SLC/CCL21-binding THAP1 molecule may be usefully immobilized on a solid support, for example as a THAP1/Fc fusion.

In accordance with another aspect, the present invention provides a method for inhibiting the activity of SLC/CCL21 chemokine in a sample, which method comprises contacting the sample with an effective amount of a SLC/CCL21 chemokine-binding molecule which is a THAP1 protein or a SLC/CCL21-binding fragment thereof.

In further aspects the invention provides a purified THAP1 protein or a SLC/CCL21-binding fragment thereof, or a THAP1/Fc fusion, for use in a method or a medicament as described herein; and a kit comprising such a purified THAP1 protein or fragment.

The invention also envisages the use of fragments of the THAP1 protein, which fragments have SLC/CCL21 chemokine-binding properties. The fragments may be peptides derived from the protein. Use of such peptides can be preferable to the use of an entire protein or a substantial part of a protein, for example because of the reduced immunogenicity of a peptide compared to a protein. Such peptides may be prepared by a variety of techniques including recombinant DNA techniques and synthetic chemical methods.

It will also be evident that the THAP1 proteins for use in the invention may be prepared in a variety of ways, in particular as recombinant proteins in a variety of expression systems. Any standard systems may be used such as baculovirus expression systems or mammalian cell line expression systems.

Other aspects of the invention are described in the following numbered paragraphs:
1. A method of identifying a candidate modulator of apoptosis comprising:
    (a) contacting a THAP-family polypeptide or a biologically active fragment thereof with a test compound, wherein said THAP-family polypeptide comprises at least 30% amino acid identity to an amino acid sequence selected from the group consisting of SEQ ID NOs: 1-114; and (b) determining whether said compound selectively modulates the activity of said polypeptide;

wherein a determination that said test compound selectively modulates the activity of said polypeptide indicates that said compound is a candidate modulator of apoptosis.

2. The method of Paragraph 1, wherein the THAP-family polypeptide comprises the amino acid sequence of SEQ ID NO: 3, or a biologically active fragment thereof.

3. The method of Paragraph 1, wherein the THAP-family polypeptide comprises the amino acid sequence of SEQ ID NO: 4, or a biologically active fragment thereof.

4. The method of Paragraph 1, wherein the THAP-family polypeptide comprises the amino acid sequence of SEQ ID NO: 5, or a biologically active fragment thereof.

5. The method of Paragraph 1, wherein the THAP-family polypeptide comprises the amino acid sequence of SEQ ID NO: 6, or a biologically active fragment thereof.

6. The method of Paragraph 1, wherein the THAP-family polypeptide comprises the amino acid sequence of SEQ ID NO: 7, or a biologically active fragment thereof.

7. The method of Paragraph 1, wherein the THAP-family polypeptide comprises the amino acid sequence of SEQ ID NO: 8, or a biologically active fragment thereof.

8. The method of Paragraph 1, wherein the THAP-family polypeptide comprises the amino acid sequence of SEQ ID NO: 9, or a biologically active fragment thereof.

9. The method of Paragraph 1, wherein the THAP-family polypeptide comprises the amino acid sequence of SEQ ID NO: 10, or a biologically active fragment thereof.

10. The method of Paragraph 1, wherein the THAP-family polypeptide comprises the amino acid sequence of SEQ ID NO: 11, or a biologically active fragment thereof.

11. The method of Paragraph 1, wherein the THAP-family polypeptide comprises the amino acid sequence of SEQ ID NO: 12, or a biologically active fragment thereof.

12. The method of Paragraph 1, wherein the THAP-family polypeptide comprises the amino acid sequence of SEQ ID NO: 13, or a biologically active fragment thereof.

13. The method of Paragraph 1, wherein the THAP-family polypeptide comprises the amino acid sequence of SEQ ID NO: 14, or a biologically active fragment thereof.

14. The method of Paragraph 1, wherein the THAP-family polypeptide comprises the amino acid sequence selected from the group consisting of SEQ ID NOs: 15-114, and biologically active fragments thereof.

15. The method of Paragraph 1, wherein said biologically active fragment of said THAP-family protein has at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.

16. The methods of any one of Paragraphs 2-15 wherein said THAP-family polypeptide has at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.

17. An isolated nucleic acid encoding a polypeptide having apoptotic activity, said polypeptide consisting essentially of an amino acid sequence selected from the group consisting of:

(a) amino acid positions 1-90 of SEQ ID NO: 2, a fragment thereof having apoptotic activity, or a polypeptide having at least 30% amino acid identity thereto;

(b) a polypeptide comprising a THAP-family domain consisting essentially of amino acid positions 1 to 89 of SEQ ID NO: 3, a fragment thereof having apoptotic activity, or a polypeptide having at least 30% amino acid identity thereto;

(c) a polypeptide comprising a THAP-family domain consisting essentially of amino acid positions 1 to 89 of SEQ ID NO: 4, a fragment thereof having apoptotic activity, or a polypeptide having at least 30% amino acid identity thereto;

(d) a polypeptide comprising a THAP-family domain consisting essentially of amino acid positions 1 to 89 of SEQ ID NO: 5, a fragment thereof having apoptotic activity, or a polypeptide having at least 30% amino acid identity thereto;

(e) a polypeptide comprising a THAP-family domain consisting essentially of amino acid positions 1 to 90 of SEQ ID NO: 6, a fragment thereof having apoptotic activity or a polypeptide having at least 30% amino acid identity thereto;

(f) a polypeptide comprising a THAP-family domain consisting essentially of amino acid positions 1 to 90 of SEQ ID NO: 7, a fragment thereof having apoptotic activity, or a polypeptide having at least 30% amino acid identity thereto;

(g) a polypeptide comprising a THAP-family domain consisting essentially of amino acid positions 1 to 90 of SEQ ID NO: 8, a fragment thereof having apoptotic activity; or a polypeptide having at least 30% amino acid identity thereto;

(h) a polypeptide comprising a THAP-family domain consisting essentially of amino acid positions 1 to 90 of SEQ ID NO: 9, a fragment thereof having apoptotic activity, or a polypeptide having at least 30% amino acid identity thereto;

(i) a polypeptide comprising a THAP-family domain consisting essentially of amino acid positions 1 to 92 of SEQ ID NO: 10, a fragment thereof having apoptotic activity or a polypeptide having at least 30% amino acid identity thereto;

(j) a polypeptide comprising a THAP-family domain consisting essentially of amino acid positions 1 to 90 of SEQ ID NO: 11, a fragment thereof having apoptotic activity, or a polypeptide having at least 30% amino acid identity thereto;

(k) a polypeptide comprising a THAP-family domain consisting essentially of amino acid positions 1 to 90 of SEQ ID NO: 12, or a fragment thereof having apoptotic activity, or a polypeptide having at least 30% amino acid identity thereto;

(l) a polypeptide comprising a THAP-family domain consisting essentially of amino acid positions 1 to 90 of SEQ ID NO: 13, a fragment thereof having apoptotic activity, or a polypeptide having at least 30% amino acid identity thereto; and (m) a polypeptide comprising a THAP-family domain consisting essentially of amino acid positions 1 to 90 of SEQ ID NO: 14, a fragment thereof having apoptotic activity, or a polypeptide having at least 30% amino acid identity thereto.

18. An isolated nucleic acid encoding a THAP-family polypeptide having apoptotic activity selected from the group consisting of:

(i) a nucleic acid molecule encoding a polypeptide comprising the amino acid sequence of a sequence selected from the group consisting of SEQ ID NOs: 1-114;
(ii) a nucleic acid molecule comprising the nucleic acid sequence of a sequence selected from the group consisting of SEQ ID NOs: 160-175 and the sequences complementary thereto; and
(iii) a nucleic acid the sequence of which is degenerate as a result of the genetic code to the sequence of a nucleic acid as defined in (i) and (ii).
19. The nucleic acid of Paragraph 18, wherein said nucleic acid comprises a nucleic acid selected from the group consisting of SEQ ID NOs. 5, 7, 8 and 11.
20. The nucleic acid of Paragraph 18, wherein said nucleic acid comprises a nucleic acid selected from the group consisting of SEQ ID NOs. 162, 164, 165 and 168.
21. An isolated nucleic acid encoding a THAP-family polypeptide having apoptotic activity comprising:
(i) the nucleic acid sequence of SEQ ID NOs: 1-2 or the sequence complementary thereto; or
(ii) a nucleic acid molecule encoding a polypeptide comprising the amino acid sequence of SEQ ID NOs 1-2;
22. An isolated nucleic acid, said nucleic acid comprising a nucleotide sequence encoding:
i) a polypeptide comprising an amino acid sequence having at least about 80% identity to a sequence selected from the group consisting of the polypeptides of SEQ ID NOs: 1-114 and the polypeptides encoded by the nucleic acids of SEQ ID NOs: 160-175 or
ii) a fragment of said polypeptide which possesses apoptotic activity.
23. The nucleic acid of Paragraph of Paragraph 23, wherein said nucleic acid encodes a polypeptide comprising an amino acid sequence having at least about 80% identity to a sequence selected from the group consisting of the polypeptides of SEQ ID NOs: 5, 7, 8 and 11 and the polypeptides encoded by the nucleic acids of SEQ ID NOs: 162, 164, 165 and 168 or a fragment of said polypeptide which possesses apoptotic activity.
24. The nucleic acid of Paragraph 23, wherein said polypeptide comprises an amino acid sequence selected from the group consisting of the sequences of SEQ ID NOs: 5, 7, 8 and 11 and the polypeptides encoded by the nucleic acids of SEQ ID NOs: 162, 164, 165 and 168.
25. The nucleic acid of Paragraph 23, wherein polypeptide identity is determined using an algorithm selected from the group consisting of XBLAST with the parameters score=50 and wordlength=3, Gapped BLAST with the default parameters of XBLAST, and BLAST with the default parameters of XBLAST.
26. The nucleic acid of Paragraph 17, wherein said nucleic acid is operably linked to a promoter.
27. An expression cassette comprising the nucleic acid of Paragraph 26.
28. A host cell comprising the expression cassette of Paragraph 27.
29. A method of making a THAP-family polypeptide, said method comprising
providing a population of host cells comprising a recombinant nucleic acid encoding said THAP-family protein of any one of SEQ ID NOs. 1-114; and
culturing said population of host cells under conditions conducive to the expression of said recombinant nucleic acid;
whereby said polypeptide is produced within said population of host cells.

30. The method of Paragraph 29 wherein said providing step comprises providing a population of host cells comprising a recombinant nucleic acid encoding said THAP-family protein of any one of SEQ ID NOs. 5, 7, 8 and 11.
31. The method of Paragraph 29, further comprising purifying said polypeptide from said population of cells.
32. An isolated THAP polypeptide encoded by the nucleic acid of any one of SEQ ID Nos. 160-175.
33. The polypeptide of Paragraph 32, wherein said polypeptide is encoded by a nucleic acid selected from the group consisting of SEQ ID NOs. 5, 7, 8, 11, 162, 164, 165 and 168.
34. The polypeptide of Paragraph 32, wherein said polypeptide has at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.
35. An isolated THAP polypeptide or fragment thereof, said polypeptide comprising at least 12 contiguous amino acids of a sequence selected from the group consisting of SEQ ID NOs: 1-114.
36. The polypeptide of Paragraph 35, wherein said polypeptide comprises at least 12 contiguous amino acids of a sequence selected from the group consisting of SEQ ID NOs. 5, 7, 8, and 11.
37. The polypeptide of Paragraph 35, wherein said polypeptide has at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.
38. An isolated THAP polypeptide or fragment thereof, said polypeptide comprising an amino acid sequence having at least about 80% amino acid sequence identity to a sequence selected from the group consisting of SEQ ID NOs: 1-114 or a fragment thereof, said polypeptide or fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.
39. The polypeptide of Paragraph 38, wherein said THAP polypeptide or fragment thereof comprises an amino acid sequence having at least about 80% amino acid sequence identity to a sequence selected from the group consisting of SEQ ID NOs: 5, 7, 8 and 11 or a fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.
40. The polypeptide of Paragraph 38, wherein said polypeptide is selectively bound by an antibody raised against an antigenic polypeptide, or antigenic fragment thereof, said antigenic polypeptide comprising the polypeptide of any one of SEQ ID NOs: 1-114.

41. The polypeptide of Paragraph 38, wherein said polypeptide is selectively bound by an antibody raised against an antigenic polypeptide, or antigenic fragment thereof, said antigenic polypeptide comprising the polypeptide of any one of SEQ ID NOs: 5, 7, 8 and 11.

42. The polypeptide of Paragraph 38, wherein said polypeptide comprises the polypeptide of SEQ ID NOs: 1-114.

43. The polypeptide of Paragraph 38, wherein said polypeptide comprises a polypeptide selected from the group consisting of SEQ ID NOs. 5, 7, 8 and 11.

44. An antibody that selectively binds to the polypeptide of Paragraph 38.

45. An antibody according to Paragraph 44, wherein said antibody is capable of inhibiting binding of said polypeptide to a THAP-family target polypeptide.

46. An antibody according to Paragraph 44, wherein said antibody is capable of inhibiting apoptosis mediated by said polypeptide.

47. The polytide of Paragraph 38, wherein identity is determined using an algorithm selected from the group consisting of XBLAST with the parameters score=50 and wordlength=3, Gapped BLAST with the default parameters of XBLAST, and BLAST with the default parameters of XBLAST.

48. A method of assessing the biological activity of a THAP-family polypeptide comprising:
(a) providing a THAP-family polypeptide or a fragment thereof; and
(b) assessing the ability of the THAP-family polypeptide to induce apoptosis of a cell.

49. A method of assessing the biological activity of a THAP-family polypeptide comprising:
(a) providing a THAP-family polypeptide or a fragment thereof; and
(b) assessing the DNA binding activity of the THAP-family polypeptide.

50. The method of Paragraphs 48 or 49, wherein step (a) comprises introducing to a cell a recombinant vector comprising a nucleic acid encoding a THAP-family polypeptide.

51. The method of Paragraphs 49 or 50, wherein the THAP-family polypeptide comprises a THAP consensus amino acid sequence depicted in SEQ ID NOs: 1-2, or a fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.

52. The method of Paragraph 49, wherein the THAP-family polypeptide comprises an amino acid sequence selected from the group of sequences consisting of SEQ ID NOs: 1-114 or a fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.

53. The method of Paragraph 49, wherein the THAP-family polypeptide comprises a native THAP-family polypeptide, or a fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis.

54. The method of Paragraph 49, wherein the THAP-family polypeptide comprises a THAP-family polypeptide or a fragment thereof having at least one activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis, wherein said THAP-family polypeptide or fragment thereof comprises at least one amino acid deletion, substitution or insertion.

55. An isolated THAP-family polypeptide comprising an amino acid sequence of SEQ ID NOs: 1-114, wherein said polypeptide comprises at least one amino acid deletion, substitution or insertion with respect to said amino acid sequence of SEQ ID NOs. 1-114.

56. A THAP-family polypeptide comprising an amino acid sequence selected from the group consisting of SEQ ID NOs: 1-114, wherein said polypeptide comprises at least one amino acid deletion, substitution or insertion with respect to said amino acid sequence of one of SEQ ID NOs. 1-114 and displays a reduced ability to induce apoptosis or bind DNA compared to the wild-type polypeptide.

57. A THAP-family polypeptide comprising an amino acid sequence of SEQ ID NOs: 1-114, wherein said polypeptide comprises at least one amino acid deletion, substitution or insertion with respect to said amino acid sequence of one of SEQ ID NOs. 1-114 and displays a increased ability to induce apoptosis or bind DNA compared to the wild-type polypeptide.

58. A method of determining whether a THAP-family polypeptide is expressed within a biological sample, said method comprising the steps of:
(a) contacting a biological sample from a subject with:
a polynucleotide that hybridizes under stringent conditions to a nucleic acid of SEQ ID NOs: 160-175 or
a detectable polypeptide that selectively binds to the polypeptide of SEQ ID NOs: 1-114; and
(b) detecting the presence or absence of hybridization between said polynucleotide and an RNA species within said sample, or the presence or absence of binding of said detectable polypeptide to a polypeptide within said sample;
wherein a detection of said hybridization or of said binding indicates that said THAP-family polypeptide is expressed within said sample.

59. The method of Paragraph 58, wherein said subject suffers from, is suspected of suffering from, or is susceptible to a cell proliferative disorder.

60. The method of Paragraph 59, wherein said cell proliferative disorder is a disorder related to regulation of apoptosis.

61. The method of Paragraph 58, wherein said polynucleotide is a primer, and wherein said hybridization is detected by detecting the presence of an amplification product comprising said primer sequence.

62. The method of Paragraph 58, wherein said detectable polypeptide is an antibody.

63. A method of assessing THAP-family activity in a biological sample, said method comprising the steps of:
(a) contacting a nucleic acid molecule comprising a binding site for a THAP-family polypeptide with:

(i) a biological sample from a subject or (ii) a THAP-family polypeptide isolated from a biological sample from a subject, the polypeptide comprising the amino acid sequences of one of SEQ ID NOs: 1-114; and (b) assessing the binding between said nucleic acid molecule and a THAP-family polypeptide wherein a detection of decreased binding compared to a reference THAP-family nucleic acid binding level indicates that said sample comprises a deficiency in THAP-family activity.

64. A method of determining whether a mammal has an elevated or reduced level of THAP-family expression, said method comprising the steps of:

(a) providing a biological sample from said mammal; and (b) comparing the amount of a THAP-family polypeptide of SEQ ID NOs: 1-114 or of a THAP-family RNA species encoding a polypeptide of SEQ ID NOs: 1-114 within said biological sample with a level detected in or expected from a control sample;

wherein an increased amount of said THAP-family polypeptide or said THAP-family RNA species within said biological sample compared to said level detected in or expected from said control sample indicates that said mammal has an elevated level of THAP-family expression, and wherein a decreased amount of said THAP-family polypeptide or said THAP-family RNA species within said biological sample compared to said level detected in or expected from said control sample indicates that said mammal has a reduced level of THAP-family expression.

65. The method of Paragraph 64, wherein said mammal suffers from, is suspected of suffering from, or is susceptible to a cell proliferative disorder.

66. A method of identifying a candidate inhibitor of a THAP-family polypeptide, a candidate inhibitor of apoptosis, or a candidate compound for the treatment of a cell proliferative disorder, said method comprising:

(a) contacting a THAP-family polypeptide according to SEQ ID NOs: 1-114 or a fragment comprising a contiguous span of at least 6 contiguous amino acids of a polypeptide according to SEQ ID NOs: 1-114 with a test compound; and (b) determining whether said compound selectively binds to said polypeptide;

wherein a determination that said compound selectively binds to said polypeptide indicates that said compound is a candidate inhibitor of a THAP-family polypeptide, a candidate inhibitor of apoptosis, or a candidate compound for the treatment of a cell proliferative disorder.

67. A method of identifying a candidate inhibitor of apoptosis, a candidate compound for the treatment of a cell proliferative disorder, or a candidate inhibitor of a THAP-family polypeptide of SEQ ID NOs: 1-114 or a fragment comprising a contiguous span of at least 6 contiguous amino acids of a polypeptide according to SEQ ID NOs: 1-114, said method comprising:

(a) contacting said THAP-family polypeptide with a test compound; and (b) determining whether said compound selectively inhibits at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis;

wherein a determination that said compound selectively inhibits said at least one biological activity of said polypeptide indicates that said compound is a candidate inhibitor of a THAP-family polypeptide, a candidate inhibitor of apoptosis, or a candidate compound for the treatment of a cell proliferative disorder.

68. A method of identifying a candidate inhibitor of apoptosis, a candidate compound for the treatment of a cell proliferative disorder, or a candidate inhibitor of a THAP-family polypeptide of SEQ ID NOs: 1-114 or a fragment comprising a contiguous span of at least 6 contiguous amino acids of a polypeptide according to SEQ ID NOs: 1-114, said method comprising:

(a) contacting a cell comprising said THAP-family polypeptide with a test compound; and (b) determining whether said compound selectively inhibits at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis;

wherein a determination that said compound selectively inhibits said at least one biological activity of said polypeptide indicates that said compound is a candidate inhibitor of a THAP-family polypeptide, a candidate inhibitor of apoptosis, or a candidate compound for the treatment of a cell proliferative disorder.

69. The method of Paragraphs 67 or 68, wherein step (b) comprises assessing apoptotic activity, and wherein a determination that said compound inhibits apoptosis indicates that said compound is a candidate inhibitor of said THAP-family polypeptide.

70. The method of Paragraph 68 comprising introducing a nucleic acid comprising the nucleotide sequence encoding said THAP-family polypeptide according to any one of Paragraphs 32-43 into said cell.

71. A polynucleotide according to any one of Paragraphs 17-25 attached to a solid support.

72. An array of polynucleotides comprising at least one polynucleotide according to Paragraph 71.

73. An array according to Paragraph 72, wherein said array is addressable.

74. A polynucleotide according to any one of Paragraphs 17 to 25 further comprising a label.

75. A method of identifying a candidate activator of a THAP-family polypeptide, said method comprising:

a) contacting a THAP-family polypeptide according to SEQ ID NOs: 1-114 or a fragment comprising a contiguous span of at least 6 contiguous amino acids of a polypeptide according to SEQ ID NOs: 1-114 with a test compound; and b) determining whether said compound selectively binds to said polypeptide;

wherein a determination that said compound selectively binds to said polypeptide indicates that said compound is a candidate activator of said polypeptide.

76. A method of identifying a candidate activator of a THAP-family polypeptide of SEQ ID NOs: 1-114 or a fragment comprising a contiguous span of at least 6 contiguous amino acids of a polypeptide according to SEQ ID NOs: 1-114, said method comprising:

(a) contacting said polypeptide with a test compound; and (b) determining whether said compound selectively activates at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis;

wherein a determination that said compound selectively activates said at least one biological activity of said polypeptide indicates that said compound is a candidate activator of said polypeptide.

77. A method of identifying a candidate activator of a THAP-family polypeptide of SEQ ID NOs: 1-114 or, a fragment comprising a contiguous span of at least 6 contiguous amino acids of a polypeptide according to SEQ ID NOs: 1-114, said method comprising:
(a) contacting a cell comprising said THAP-family polypeptide with a test compound; and
(b) determining whether said compound selectively activates at least one biological activity selected from the group consisting of interaction with a THAP-family target protein, binding to a nucleic acid sequence, binding to PAR-4, binding to PML, binding to a polypeptide found in PML-NBs, localization to PML-NBs, targeting a THAP-family target protein to PML-NBs, and inducing apoptosis;
wherein a determination that said compound selectively activates said at least one biological activity of said polypeptide indicates that said compound is a candidate activator of said polypeptide.

78. The method of Paragraphs 76 or 77, wherein said determining step comprises assessing apoptotic activity, and wherein a determination that said compound increases apoptosis activity indicates that said compound is a candidate activator of said THAP-family polypeptide.

79. The method of Paragraph 77 wherein step a) comprises introducing a nucleic acid comprising the nucleotide sequence encoding said THAP-family polypeptide according to any one of Paragraphs 17-25 into said cell.

80. A method of identifying a candidate modulator of PAR4 activity, said method comprising:
(a) providing a PAR4 polypeptide or a fragment thereof; and
(b) providing a PML-NB polypeptide, or a polypeptide associated with PML-NBs, or a fragment thereof; and
(c) determining whether a test compound selectively modulates the ability of said PAR4 polypeptide to bind to said PML-NB polypeptide or polypeptide associated with PML-NBs;
wherein a determination that said test compound selectively inhibits the ability of said PAR4 polypeptide to bind to said PML-NB polypeptide or polypeptide associated with PML-NBs indicates that said compound is a candidate modulator of PAR4 activity.

81. A method of identifying a candidate modulator of PAR4 activity, said method comprising:
(a) providing a PAR4 polypeptide or a fragment thereof; and
(b) determining whether a test compound selectively modulates the ability of said PAR4 polypeptide to localise in PML-NBs;
wherein a determination that said test compound selectively inhibits the ability of said PAR4 polypeptide to localise in PML-NBs indicates that said compound is a candidate modulator of PAR4 activity.

82. A method of identifying a candidate inhibitor of THAP-family activity, said method comprising:

(a) providing a THAP-family polypeptide of SEQ ID NOs: 1-114 or, a fragment comprising a contiguous span of at least 6 contiguous amino acids of a polypeptide according to SEQ ID NOs: 1-114; and
(b) providing a THAP-family target polypeptide or a fragment thereof; and
(c) determining whether a test compound selectively inhibits the ability of said THAP-family polypeptide to bind to said THAP-family target polypeptide;
wherein a determination that said test compound selectively inhibits the ability of said THAP-family polypeptide to bind to said THAP-family target polypeptide indicates that said compound is a candidate inhibitor of THAP-family activity.

83. The method of Paragraph 82, comprising providing a cell comprising:
(a) a first expression vector comprising a nucleic acid encoding a THAP-family polypeptide of SEQ ID NOs: 1-114 or, a fragment comprising a contiguous span of at least 6 contiguous amino acids of a polypeptide according to SEQ ID NOs: 1-114; and
(b) a second expression vector comprising a nucleic acid encoding a THAP-family target polypeptide, or a fragment thereof.

84. The method of Paragraph 82, wherein said THAP-family activity is apoptosis activity.

85. The method of Paragraph 82, wherein said THAP-family target protein is PAR-4.

86. The method of Paragraph 82, wherein said THAP-family polypeptide is a THAP-1, THAP-2 or THAP-3 protein and said THAP-family target protein is PAR-4.

87. A method of modulating apoptosis in a cell comprising modulating the activity of a THAP-family protein.

88. The method of Paragraph 87, wherein said THAP-family protein is selected from the group consisting of SEQ ID NOs. 1-114.

89. A method of modulating apoptosis in a cell comprising modulating the recruitment of PAR-4 to a PML nuclear body.

90. The method of Paragraph 89 wherein modulating the activity of a THAP-family protein comprises modulating the interaction of a THAP-family protein and a THAP-family target protein.

91. The method of Paragraph 89 wherein modulating the activity of a THAP-family protein comprises modulating the interaction of a THAP-family protein and a PAR4 protein.

92. The method of Paragraph 91 comprising modulation the interaction between a THAP-1, THAP-2, or THAP-3 protein and a PAR-4 protein.

93. A method of modulating the recruitment of PAR-4 to a PML nuclear body comprising modulating the interaction of said PAR-4 protein and a THAP-family protein.

94. The method of Paragraph 93, wherein said THAP-family protein is selected from the group consisting of SEQ ID NOs. 1-114.

95. A method of modulating angiogenesis in an individual comprising modulating the activity of a THAP-family protein in said individual.

96. The method of Paragraph 95, wherein said THAP-family protein is selected from the group consisting of SEQ ID NOs. 1-114.

97. A method of preventing cell death in an individual comprising inhibiting the activity of a THAP-family protein in said individual.

98. The method of Paragraph 97, wherein said THAP-family protein is selected from the group consisting of SEQ ID NOs. 1-114.
99. The method according to Paragraph 97, wherein the activity of said THAP-family protein is inhibited in the CNS.
100. A method of inducing angiogenesis in an individual comprising inhibiting the activity of a THAP-family protein in said individual.
101. The method of Paragraph 100, wherein said THAP-family protein is selected from the group consisting of SEQ ID NOs. 1-114.
102. A method according to Paragraph 100, wherein the activity of said THAP-family protein is inhibited in endothelial cells.
103. A method of inhibiting angiogenesis or treating cancer in an individual comprising increasing the activity of a THAP-family protein in said individual.
104. The method of Paragraph 103, wherein said THAP-family protein is selected from the group consisting of SEQ ID NOs. 1-114.
105. A method of treating inflammation or an inflammatory disorder in an individual comprising increasing the activity of a THAP-family protein in said individual.
106. The method of Paragraph 105, wherein said THAP-family protein is selected from the group consisting of SEQ ID NOs. 1-114.
107. A method according to Paragraphs 103 or 105, wherein the activity of said THAP-family protein is increased in endothelial cells.
108. A method of treating cancer in an individual comprising increasing the activity of a THAP-family protein in said individual.
109. The method of Paragraph 108, wherein said THAP-family protein is selected from the group consisting of SEQ ID NOs. 1-114.
110. The method of Paragraph 108, wherein increasing the activity of said THAP family protein induces apoptosis, inhibits cell division, inhibits metastatic potential, reduces tumor burden, increases sensitivity to chemotherapy or radiotherapy, kills a cancer cell, inhibits the growth of a cancer cell, kills an endothelial cell, inhibits the growth of an endothelial cell, inhibits angiogenesis, or induces tumor regression.
111. A method according to any one of Paragraphs 87-110, comprising contacting said subject with a recombinant vector encoding a THAP-family protein according to any one of Paragraphs 32-43 operably linked to a promoter that functions in said cell.
112. The method of Paragraph 111, wherein said promoter functions in an endothelial cell.
113. A viral composition comprising a recombinant viral vector encoding a THAP-family protein according to Paragraphs 32-43.
114. The composition of Paragraph 113, wherein said recombinant viral vector is an adenoviral, adeno-associated viral, retroviral, herpes viral, papilloma viral, or hepatitus B viral vector.
115. A method of obtaining a nucleic acid sequence which is recognized by a THAP-family polypeptide comprising contacting a pool of random nucleic acids with said THAP-family polypeptide or a portion thereof and isolating a complex comprising said THAP-family polypeptide and at least one nucleic acid from said pool.
116. The method of Paragraph 115 wherein said pool of nucleic acids are labeled.
117. The method of Paragraph 116 wherein said complex is isolated by performing a gel shift analysis.
118. A method of identifying a nucleic acid sequence which is recognized by a THAP-family polypeptide comprising:
    (a) incubating a THAP-family polypeptide with a pool of labeled random nucleic acids;
    (b) isolating a complex between said THAP-family polypeptide and at least one nucleic acid from said pool;
    (c) performing an amplification reaction to amplify the at least one nucleic acid present in said complex;
    (d) incubating said at least one amplified nucleic acid with said THAP-family polypeptide;
    (e) isolating a complex between said at least one amplified nucleic acid and said THAP-family polypeptide;
    (f) repeating steps (c), (d) and (e) a plurality of times;
    (g) determining the sequence of said nucleic acid in said complex.
119. A method of identifying a compound which inhibits the ability of a THAP-family polypeptide to bind to a nucleic acid comprising: incubating a THAP-family polypeptide or a fragment thereof which recognizes a binding site in a nucleic acid with a nucleic acid containing said binding site in the presence or absence of a test compound and determining whether the level of binding of said THAP-family polypeptide to said nucleic acid in the presence of said test compound is less than the level of binding in the absence of said test compound.
120. A method of identifying a test compound that modulates THAP-mediated activities comprising:
    contacting a THAP-family polypeptide or a biologically active fragment thereof with a test compound, wherein said THAP-family polypeptide comprises an amino acid sequence having at least 30% amino acid identity to an amino acid sequence of SEQ ID NO: 1; and
    determining whether said test compound selectively modulates the activity of said THAP-family polypeptide or biologically active fragment thereof, wherein a determination that said test compound selectively modulates the activity of said polypeptide indicates that said test compound is a candidate modulator of THAP-mediated activities.
121. The method of Paragraph 120, wherein the THAP-family polypeptide comprises the amino acid sequence of SEQ ID NO: 1, or a biologically active fragment thereof.
122. The method of Paragraph 120, wherein the THAP-family polypeptide comprises the amino acid sequence of SEQ ID NO: 2, or a biologically active fragment thereof.
123. The method of Paragraph 120, wherein the THAP-family polypeptide comprises the amino acid sequence of SEQ ID NO: 3, or a biologically active fragment thereof.
124. The method of Paragraph 120, wherein the THAP-family polypeptide comprises the amino acid sequence of SEQ ID NO: 4, or a biologically active fragment thereof.
125. The method of Paragraph 120, wherein the THAP-family polypeptide comprises the amino acid sequence of SEQ ID NO: 5, or a biologically active fragment thereof.

126. The method of Paragraph 120, wherein the THAP-family polypeptide comprises the amino acid sequence of SEQ ID NO: 6, or a biologically active fragment thereof.

127. The method of Paragraph 120, wherein the THAP-family polypeptide comprises the amino acid sequence of SEQ ID NO: 7, or a biologically active fragment thereof.

128. The method of Paragraph 120, wherein the THAP-family polypeptide comprises the amino acid sequence of SEQ ID NO: 8, or a biologically active fragment thereof.

129. The method of Paragraph 120, wherein the THAP-family polypeptide comprises the amino acid sequence of SEQ ID NO: 9, or a biologically active fragment thereof.

130. The method of Paragraph 120, wherein the THAP-family polypeptide comprises the amino acid sequence of SEQ ID NO: 10, or a biologically active fragment thereof.

131. The method of Paragraph 120, wherein the THAP-family polypeptide comprises the amino acid sequence of SEQ ID NO: 11, or a biologically active fragment thereof.

132. The method of Paragraph 120, wherein the THAP-family polypeptide comprises the amino acid sequence of SEQ ID NO: 12, or a biologically active fragment thereof.

133. The method of Paragraph 120, wherein the THAP-family polypeptide comprises the amino acid sequence of SEQ ID NO: 13, or a biologically active fragment thereof.

134. The method of Paragraph 120, wherein the THAP-family polypeptide comprises the amino acid sequence of SEQ ID NO: 14 or a biologically active fragments thereof.

135. The method of Paragraph 120, wherein the THAP-family polypeptide comprises the amino acid sequence selected from the group consisting of SEQ ID NOs: 15-114 or a biologically active fragments thereof.

136. The method of Paragraph 120, wherein said THAP-mediated activity is selected from the group consisting of interaction with a THAP-family target protein, binding to a nucleic acid, binding to PAR-4, binding to SLC, binding to PML, binding to a polypeptide found in PML-NBs, localization to PML-NBs, targeting a THAP-family target protein to PML-NBs, and inducing apoptosis 137. The method of Paragraph 136, wherein said THAP-mediated activity is binding to PAR-4.

138. The method of Paragraph 136, wherein said THAP-mediated activity is binding to SLC.

139. The method of Paragraph 136, wherein said THAP-mediated activity is inducing apoptosis.

140. The method of Paragraph 136, wherein said nucleic acid comprises a nucleotide sequence selected from the group consisting of SEQ ID NOs: 140-159.

141. The method of Paragraph 120, wherein said amino acid identity is determined using an algorithm selected from the group consisting of XBLAST with the parameters, score=50 and wordlength=3, Gapped BLAST with the default parameters of XBLAST, and BLAST with the defaul parameters of XBLAST.

142. An isolated or purified THAP domain polypeptide consisting essentially of an amino acid sequence selected from the group consisting of SEQ ID NOs: 1-2, amino acids 1-89 of SEQ ID NOs: 3-5, amino acids 1-90 of SEQ ID NOs: 6-9, amino acids 1-92 of SEQ ID NO: 10, amino acids 1-90 of SEQ ID NOs: 11-14 and homologs having at least 30% amino acid identity to any aforementioned sequence, wherein said polypeptide binds to a nucleic acid.

143. The isolated or purified THAP domain polypeptide of Paragraph 142 consisting essentially of SEQ ID NO: 1.

144. The isolated or purified THAP domain polypeptide of Paragraph 142, wherein said amino acid identity is determined using an algorithm selected from the group consisting of XBLAST with the parameters, score=50 and wordlength=3, Gapped BLAST with the default parameters of XBLAST, and BLAST with the defaul parameters of XBLAST.

145. The isolated or purified THAP domain polypeptide of Paragraph 142, wherein said nucleic acid comprises a nucleotide sequence selected from the group consisting of SEQ ID NOs: 140-159.

146. An isolated or purified nucleic acid which encodes the THAP domain polypeptide of Paragraph 142 or a complement thereof.

147. An isolated or purified PAR4-binding domain polypeptide consisting essentially of an amino acid sequence selected from the group consisting of amino acids 143-192 of SEQ ID NO: 3, amino acids 132-181 of SEQ ID NO: 4, amino acids 186-234 of SEQ ID NO: 5, SEQ ID NO: 15 and homologs having at least 30% amino acid identity to any aforementioned sequence, wherein said polypeptide binds to PAR4.

148. The isolated or purified PAR4-binding domain of Paragraph 147 consisting essentially of SEQ ID NO: 15.

149. The isolated or purified PAR4-binding domain of Paragraph 147 consisting essentially of amino acids 143-193 of SEQ ID NO: 3.

150. The isolated or purified PAR4-binding domain of Paragraph 147 consisting essentially of amino acids 132-181 of SEQ ID NO: 4.

151. The isolated or purified PAR4-binding domain of Paragraph 147 consisting essentially of amino acids 186-234 of SEQ ID NO: 5.

152. The isolated or purified PAR4-binding domain polypeptide of Paragraph 147, wherein said amino acid identity is determined using an algorithm selected from the group consisting of XBLAST with the parameters, score=50 and wordlength=3, Gapped BLAST with the default parameters of XBLAST, and BLAST with the defaul parameters of XBLAST.

153. An isolated or purified nucleic acid which encodes the PAR4-binding domain polypeptide of Paragraph 147 or a complement thereof.

154. An isolated or purified SLC-binding domain polypeptide consisting essentially of an amino acid sequence selected from the group consisting of amino acids 143-213 of SEQ ID NO: 3 and homologs thereof having at least 30% amino acid identity, wherein said polypeptide binds to SLC.

155. The isolated or purified SLC-binding domain polypeptide of Paragraph 154, wherein said amino acid identity is determined using an algorithm selected from the group consisting of XBLAST with the parameters, score=50 and wordlength=3, Gapped BLAST with the default parameters of XBLAST, and BLAST with the defaul parameters of XBLAST.

156. An isolated or purified nucleic acid which encodes the SLC-binding domain polypeptide of Paragraph 154 or a complement thereof.

157. A fusion protein comprising an Fc region of an immunoglobulin fused to a polypeptide comprising an amino acid sequence selected from the group consisting of amino acids 143-213 of SEQ ID NO: 3 and homologs thereof having at least 30% amino acid identity.

158. An oligomeric THAP protein comprising a plurality of THAP polypeptides, wherein each THAP polypeptide comprises an amino acid sequence selected from the group consisting of amino acid 143-213 of SEQ ID NO: 3 and homologs thereof having at least 30% amino acid identity.

159. A medicament comprising an effective amount of a THAP1 polypeptide or an SLC-binding fragment thereof, together with a pharmaceutically acceptable carrier.

160. An isolated or purified THAP dimerization domain polypeptide consisting essentially of an amino acid sequence selected from the group consisting of amino acids 143 and 192 of SEQ ID NO: 3 and homologs thereof having at least 30% amino acid identity, wherein said polypeptide binds to a THAP-family polypeptide.

161. The isolated or purified THAP dimerization domain polypeptide of Paragraph 160, wherein said amino acid identity is determined using an algorithm selected from the group consisting of XBLAST with the parameters, score=50 and wordlength=3, Gapped BLAST with the default parameters of XBLAST, and BLAST with the defaul parameters of XBLAST.

162. An isolated or purified nucleic acid which encodes the THAP dimerization domain polypeptide of Paragraph 160 or a complement thereof.

163. An expression vector comprising a promoter operably linked to a nucleic acid having a nucleotide sequence selected from the group consisting of SEQ ID NOs: 160-175 and portions thereof comprising at least 18 consecutive nucleotides.

164. The expression vector of Paragraph 163, wherein said promoter is a promoter which is not operably linked to said nucleic acid selected from the group consisting of SEQ ID NOs.: 160-175 in a naturally occurring genome.

165. A host cell comprising the expression vector of Paragraph 163.

166. An expression vector comprising a promoter operably linked to a nucleic acid encoding a polypeptide comprising an amino acid sequence selected from the group consisting of SEQ ID NOs: 1-114 and portions thereof comprising at least 18 consecutive nucleotides.

167. The expression vector of Paragraph 166, wherein said promoter is a promoter which is not operably linked to said nucleic acid selected from the group consisting of SEQ ID NOs.: 160-175 in a naturally occurring genome.

168. A host cell comprising the expression vector of Paragraph 166.

169. A method of identifying a candidate inhibitor of a THAP-family polypeptide, a candidate inhibitor of apoptosis, or a candidate compound for the treatment of a cell proliferative disorder, said method comprising:
    contacting a THAP-family polypeptide comprising an amino acid sequence selected from the group consisting of SEQ ID NOs: 1114 or a fragment comprising a span of at least 6 contiguous amino acids of a polypeptide comprising an amino acid sequence selected from the group consisting of SEQ ID NOs: 1-114 with a test compound; and
    determining whether said compound selectively binds to said polypeptide, wherein a determination that said compound selectively binds to said polypeptide indicates that said compound is a candidate inhibitor of a THAP-family polypeptide, a candidate inhibitor of apoptosis, or a candidate compound for the treatment of a cell proliferative disorder.

170. A method of identifying a candidate inhibitor of apoptosis, a candidate compound for the treatment of a cell proliferative disorder, or a candidate inhibitor of a THAP-family polypeptide of SEQ ID NOs: 1-114 or a fragment comprising a span of at least 6 contiguous amino acids of a polypeptide according to SEQ ID NOs: 1-114, said method comprising:
    contacting said THAP-family polypeptide with a test compound; and
    determining whether said compound selectively inhibits at least one biological activity selected from the group consisting of interaction with a THAP-family target protein, binding to a nucleic acid sequence, binding to PAR-4, binding to SLC, binding to PML, binding to a polypeptide found in PML-NBs, localization to PML-NBs, targeting a THAP-family target protein to PML-NBs, and inducing apoptosis, wherein a determination that said compound selectively inhibits said at least one biological activity of said polypeptide indicates that said compound is a candidate inhibitor of a THAP-family polypeptide, a candidate inhibitor of apoptosis, or a candidate compound for the treatment of a cell proliferative disorder.

171. A method of identifying a candidate inhibitor of apoptosis, a candidate compound for the treatment of a cell proliferative disorder, or a candidate inhibitor of a THAP-family polypeptide of SEQ ID NOs: 1-114 or a fragment comprising a span of at least 6 contiguous amino acids of a polypeptide according to SEQ ID NOs: 1-114, said method comprising:
    contacting a cell comprising said THAP-family polypeptide with a test compound; and
    determining whether said compound selectively inhibits at least one biological activity selected from the group consisting of interaction with a THAP-family target protein, binding to a nucleic acid sequence, binding to PAR-4, binding to SLC, binding to PML, binding to a polypeptide found in PML-NBs, localization to PML-NBs, targeting a THAP-family target protein to PML-NBs, and inducing apoptosis, wherein a determination that said compound selectively inhibits said at least one biological activity of said polypeptide indicates that said compound is a candidate inhibitor of a THAP-family polypeptide, a candidate inhibitor of apoptosis, or a candidate compound for the treatment of a cell proliferative disorder.

172. A method of identifying a candidate modulator of THAP-family activity, said method comprising:
    providing a THAP-family polypeptide of SEQ ID NOs: 1-114 or, a fragment comprising a span of at least 6 contiguous amino acids of a polypeptide according to SEQ ID NOs: 1-114; and
    providing a THAP-family target polypeptide or a fragment thereof; and
    determining whether a test compound selectively modulates the ability of said THAP-family polypeptide to bind to said THAP-family target polypeptide, wherein a determination that said test compound selectively modulates the ability of said THAP-family polypeptide to bind to said THAP-family target polypeptide indicates that said compound is a candidate modulator of THAP-family activity.

173. The method of Paragraph 172, wherein said THAP-family polypeptide is provided by a first expression vector comprising a nucleic acid encoding a THAP-family polypeptide of SEQ ID NOs: 1-114 or, a fragment comprising a contiguous span of at least 6 contiguous amino acids of a polypeptide according to SEQ ID NOs: 1-114, and wherein said THAP-family target polypeptide is provided by a second expression vector comprising a nucleic acid encoding a THAP-family target polypeptide, or a fragment thereof.

174. The method of Paragraph 172, wherein said THAP-family activity is apoptosis activity.

175. The method of Paragraph 172, wherein said THAP-family target protein is PAR-4.

176. The method of Paragraph 172, wherein said THAP-family polypeptide is a THAP-1, THAP-2 or THAP-3 protein and said THAP-family target protein is PAR-4.

177. The method of Paragraph 172, wherein said THAP-family target protein is SLC.

178. A method of modulating apoptosis in a cell comprising modulating the activity of a THAP-family protein.

179. The method of Paragraph 178, wherein said THAP-family protein is selected from the group consisting of SEQ ID NOs: 1-114.

180. The method of Paragraph 178, wherein modulating the activity of a THAP-family protein comprises modulating the interaction of a THAP-family protein and a THAP-family target protein.

181. The method of Paragraph 178, wherein modulating the activity of a THAP-family protein comprises modulating the interaction of a THAP-family protein and a PAR4 protein.

182. A method of identifying a candidate activator of a THAP-family polypeptide, a candidate activator of apoptosis, or a candidate compound for the treatment of a cell proliferative disorder, said method comprising:
  contacting a THAP-family polypeptide comprising an amino acid sequence selected from the group consisting of SEQ ID NOs: 1-98 or a fragment comprising a span of at least 6 contiguous amino acids of a polypeptide comprising an amino acid sequence selected from the group consisting of SEQ ID NOs: 1-98 with a test compound; and
  determining whether said compound selectively binds to said polypeptide, wherein a determination that said compound selectively binds to said polypeptide indicates that said compound is a candidate activator of a THAP-family polypeptide, a candidate activator of apoptosis, or a candidate compound for the treatment of a cell proliferative disorder.

183. A method of identifying a candidate activator of apoptosis, a candidate compound for the treatment of a cell proliferative disorder, or a candidate activator of a THAP-family polypeptide of SEQ ID NOs: 1-98 or a fragment comprising a span of at least 6 contiguous amino acids of a polypeptide according to SEQ ID NOs: 1-98, said method comprising:
  contacting said THAP-family polypeptide with a test compound; and
  determining whether said compound selectively activates at least one biological activity selected from the group consisting of interaction with a THAP-family target protein, binding to a nucleic acid sequence, binding to PAR-4, binding to SLC, binding to PML, binding to a polypeptide found in PML-NBs, localization to PML-NBs, targeting a THAP-family target protein to PML-NBs, and inducing apoptosis, wherein a determination that said compound selectively activates said at least one biological activity of said polypeptide indicates that said compound is a candidate activator of a THAP-family polypeptide, a candidate activator of apoptosis, or a candidate compound for the treatment of a cell proliferative disorder.

184. A method of identifying a candidate activator of apoptosis, a candidate compound for the treatment of a cell proliferative disorder, or a candidate activator of a THAP-family polypeptide of SEQ ID NOs: 1 to 98 or a fragment comprising a span of at least 6 contiguous amino acids of a polypeptide according to SEQ ID NOs: 1-98, said method comprising:
  contacting a cell comprising said THAP-family polypeptide with a test compound; and
  determining whether said compound selectively activates at least one biological activity selected from the group consisting of interaction with a THAP-family target protein, binding to a nucleic acid sequence, binding to PAR-4, binding to SLC, binding to PML, binding to a polypeptide found in PML-NBs, localization to PML-NBs, targeting a THAP-family target protein to PML-NBs, and inducing apoptosis, wherein a determination that said compound selectively activates said at least one biological activity of said polypeptide indicates that said compound is a candidate activator of a THAP-family polypeptide, a candidate activator of apoptosis, or a candidate compound for the treatment of a cell proliferative disorder.

185. A method of ameliorating a condition associated with the activity of SLC in an individual comprising administering a polypeptide comprising the SLC binding domain of a THAP-family protein to said individual.

186. The method of Paragraph 185, wherein said polypeptide comprises a fusion protein comprising an Fc region of an immunoglobulin fused to a polypeptide comprising an amino acid sequence selected from the group consisting of amino acids 143-213 of SEQ ID NO: 3 and homologs thereof having at least 30% amino acid identity.

187. The method of Paragraph 185, wherein said polypeptide comprises an oligomeric THAP protein comprising a plurality of THAP polypeptides, wherein each THAP polypeptide comprises an amino acid sequence selected from the group consisting of amino acid 143-213 of SEQ ID NO: 3 and homologs thereof having at least 30% amino acid identity.

188. A method of modulating angiogenesis in an individual comprising modulating the activity of a THAP-family protein in said individual.

189. The method of Paragraph 188, wherein said THAP-family protein is selected from the group consisting of SEQ ID NOs: 1-114.

190. The method of Paragraph 188, wherein said modulation is inhibition.

191. The method of Paragraph 188, wherein said modulation is induction.

192. A method of reducing cell death in an individual comprising inhibiting the activity of a THAP-family protein in said individual.

193. The method of Paragraph 192, wherein said THAP-family protein is selected from the group consisting of SEQ ID NOs: 1-114.

194. The method according to Paragraph 192, wherein the activity of said THAP-family protein is inhibited in the CNS.

195. A method of reducing inflammation or an inflammatory disorder in an individual comprising modulating the activity of a THAP-family protein in said individual.

196. The method of Paragraph 195, wherein said THAP-family protein is selected from the group consisting of SEQ ID NOs: 1-114.

197. A method of reducing the extent of cancer in an individual comprising modulating the activity of a THAP-family protein in said individual.

198. The method of Paragraph 197, wherein said THAP-family protein is selected from the group consisting of SEQ ID NOs: 1-114.

199. The method of Paragraph 197, wherein increasing the activity of said THAP family protein induces apoptosis, inhibits cell division, inhibits metastatic potential, reduces tumor burden, increases sensitivity to chemotherapy or radiotherapy, kills a cancer cell, inhibits the growth of a cancer cell, kills an endothelial cell, inhibits the growth of an endothelial cell, inhibits angiogenesis, or induces tumor regression.

BRIEF DESCRIPTION OF THE DRAWINGS

FIG. 1A illustrates an amino acid sequence alignment of human THAP1 (hTHAP1) (SEQ ID NO: 3) and mouse THAP1 (mTHAP1) (SEQ ID NO: 99) orthologous polypeptides. Identical amino acid residues are indicated with an asterisk.

FIG. 1B depicts the primary structure of the human THAP1 polypeptide. Positions of the THAP domain, the proline-rich region (PRO) and the bipartite nuclear localization sequence (NLS) are indicated.

FIG. 5A depicts an amino acid sequence alignment of the Par4 binding domain of human THAP1 (SEQ ID NO: 117) and mouse THAP1 (SEQ ID NO: 116) orthologues with that of mouse ZIP kinase (SEQ ID NO: 115), another Par4 binding partner. An arginine-rich consensus Par4 binding site (SEQ ID NO: 15), derived from this alignment, is also indicated.

FIG. 5B shows the primary structure of the THAP1 wild-type polypeptide and two THAP1 mutants (THAP1Δ(QR-CRR) and THAP1 RR/AA). THAP1Δ(QRCRR) is a deletion mutant having a deletion of amino acids at positions 168-172 of THAP1 (SEQ ID NO: 3) whereas THAP RR/AA is a mutant having the two arginines located at amino acid positions 171 and 172 to THAP1 (SEQ ID NO: 3) replaced with alanines. Results obtained, in yeast two-hybrid system with Par4 and Par4DD baits (two hybrid bait), in GST pull down assays with GST-Par4DD (in vitro) and in the in vivo interaction test with myc-Par4DD in primary human endothelial cells (in vivo) are summarized.

FIG. 9A depicts an amino acid sequence alignment of the THAP domain of human THAP1 (hTHAP1, SEQ ID NO: 123) with the DNA binding domain of drosophila melanogaster P-element transposase (dmTransposase, SEQ ID NO: 124). Identical residues are boxed in black and conserved residues in grey. A THAP domain consensus sequence (SEQ ID NO: 125) is also shown.

FIG. 9B depicts an amino acid sequence alignment of the THAP domains of twelve members of the human THAP family (hTHAP1, SEQ ID NO: 126; hTHAP2, SEQ ID NO: 131; hTHAP3, SEQ ID NO: 127; hTHAP4, SEQ ID NO: 130; hTHAP5, SEQ ID NO: 128; hTHAP6, SEQ ID NO: 135; hTHAP7, SEQ ID NO: 133; hTHAP8, SEQ ID NO: 129; hTHAP9, SEQ ID NO: 134; hTHAP10, SEQ ID NO: 137; hTHAP11, SEQ ID NO: 136; hTHAP0, SEQ ID NO: 132) with the DNA binding domain of Drosophila melanogaster P-element transposase (dmTranspoase, SEQ ID NO: 138). Residues conserved among at least seven of the thirteen sequences are boxed. Black boxes indicate identical residues whereas boxes shaded in grey show similar amino acids. Dashed lines represent gaps introduced to align sequences. A THAP domain consensus sequence (SEQ ID NO: 139) is also shown.

FIG. 9C depicts an amino acid sequence alignment of 95 distinct THAP domain sequences, including hTHAP1 through hTHAP11 and hTHAP0 (SEQ ID NOs: 3-14, listed sequentially beginning from the top), with 83 THAP domains from other species (SEQ ID NOs: 1-98, listed sequentially beginning at the sequence denoted sTHAP1 and ending at the sequence denoted ceNP_498747.1), which were identified by searching GenBank genomic and EST databases with the human THAP sequences. Residues conserved among at least 50% of the sequences are boxed. Black boxes indicate identical residues whereas boxes shaded in grey show similar amino acids. Dashed lines represent gaps introduced to align sequences. The species are indicated: *Homo sapiens* (h); *Sus scrofa* (s); *Bos taurus* (b); *Mus musculus* (m); *Rattus norvegicus* (r); *Gallus gallus* (g); *Xenopus laevi* (x); *Danio rerio* (z); *Oryzias latipes* (O); *Drosophila melanogaster* (dm); *Anopheles gambiae* (a); *Bombyx mori* (bm); *Caenorhabditis. elegans* (ce). A consensus sequence (SEQ ID NO: 2) is also shown. Amino acids underlined in the consensus sequence are residues which are conserved in all 95 THAP sequences.

FIG. 18A shows a specific DNA binding site recognized by the THAP domain of human THAP1. The THAP domain recognizes GGGCAA or TGGCAA DNA target sequences preferentially organized as direct repeats with 5 nucleotide spacing (DR-5). The consensus sequence 5'-GGGCAAnnnnnTGGCAA-3' (SEQ ID NO: 149). The DR-5 consensus was generated by examination of 9 nucleic acids bound by THAP1 (SEQ ID NO: 140-148, beginning sequentially from the top).

FIG. 18B shows a second specific DNA binding site recognized by the THAP domain of human THAP1. The THAP domain recognizes everted repeats with II nucleotide spacing (ER-11) having a consensus sequence 5'-TTGCAnnnnnnnnnnnGGGCAA-3' (SEQ ID NO: 159). The ER-11 consensus was generated by examination of 9 nucleic acids bound by THAP1 (SEQ ID NO: 150-158, beginning sequentially from the top).

DETAILED DESCRIPTION OF THE INVENTION

THAP and PAR4 Biological Pathways

Figure 2:
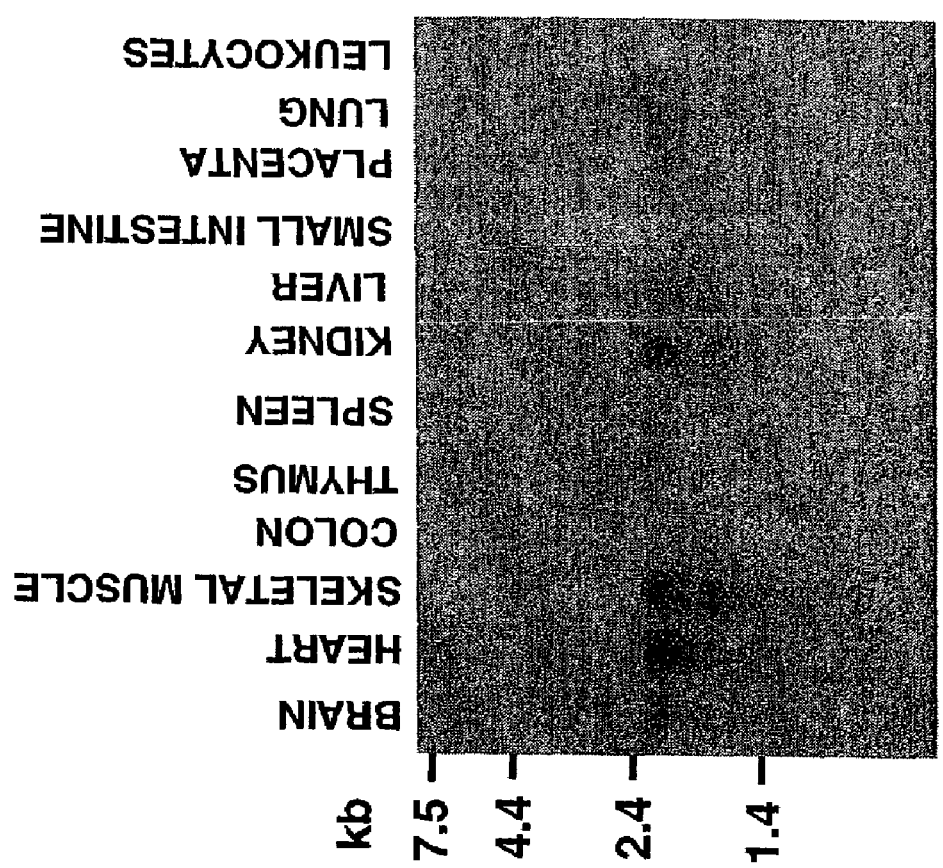
FIG. 2 depicts the results of a Northern Blot analysis of THAP1 mRNA expression in 12 human tissues. Each lane contains 2 μg of poly A$^+$ RNA isolated from the indicated human tissues. The blot was hybridized, under high-stringency conditions, with a $^{32}$P-labeled THAP1 cDNA probe, and exposed at −70° C. for 72 hours.

As mentioned above, the inventors have discovered a novel class of proteins involved in apoptosis. Then, the inventors have also linked a member of this novel class to another (PAR4) apoptosis pathway, and further linked both of these pathways to PML-NBs. Moreover, the inventors have also linked both of these pathways to endothelial cells, providing a range of novel and potentially selective therapeutic treatments. In particular, it has been discovered that THAP1 (THanatos (death)-Associated-Protein-1) localizes to PML-NBs. Furthermore, two hybrid screening of an HEVEC cDNA library with the THAP1 bait lead to the identification of a unique interacting partner, the pro-apoptotic protein PAR4. PAR4 is also found to accumulate into PML-NBs. Targeting of the THAP-1/PAR4 complex to PML-NBs is mediated by PML. Similarly to PAR4, THAP1 has a pro-apoptotic activity. This activity includes a novel motif in the amino-terminal part called THAP domain. Together these results define a novel PML-NBs pathway for apoptosis that involves the THAP1/PAR4 proapoptotic complex.

THAP-Family Members, and Uses Thereof

The present invention includes polynucleotides encoding a family of proapoptotic polypeptides THAP-0 to THAP11, and uses thereof for the modulation of apoptosis-related and other THAP-mediated activities. Included is THAP1, which forms a complex with the pro-apoptotic protein PAR4 and localizes in discrete subnuclear domains known as PML nuclear bodies. Additionally, THAP-family polypeptides can be used to alter or otherwise modulate bioavailability of SLC/CCL21 (SLC).

The present invention also includes a novel protein motif, the THAP domain, which is found in an 89 amino acid domain in the amino-terminal part of THAP1 and which is involved in THAP1 pro-apoptotic activity. The THAP domain defines a novel family of proteins, the THAP-family, with at least twelve distinct members in the human genome (THAP-0 to THAP11), which all contain a THAP domain in their amino-terminal part. The present invention thus pertains to nucleic acid molecules, including genomic and in particular the complete cDNA sequences, encoding members of the THAP-family, as well as with the corresponding translation products, nucleic acids encoding THAP domains, homologues thereof, nucleic acids encoding at least 10, 12, 15, 20, 25, 30, 40, 50, 100, 150 or 200 consecutive amino acids, to the extent that said span is consistent with the particular SEQ ID NO, of a sequence selected from the group consisting of SEQ ID NOs: 160-175.

THAP1 has been identified based on its expression in HEVs, specialized postcapillary venules found in lymphoid tissues and nonlymphoid tissues during chronic inflammatory diseases that support a high level of lymphocyte extravasation from the blood. An important element in the cloning of the THAP1 cDNA from HEVECs was the development of protocols for obtaining HEVECs RNA, since HEVECs are not capable of maintaining their phenotype outside of their native environment for more than a few hours. A protocol was developed where total RNA was obtained from HEVECs freshly purified from human tonsils. Highly purified HEVECs were obtained by a combination of mechanical and enzymatic procedures, immunomagnetic depletion and positive selection. Tonsils were minced finely with scissors on a steel screen, digested with collagenase/dispase enzyme mix and unwanted contaminating cells were then depleted using immunomagnetic depletion. HEVECs were then selected by immunomagnetic positive selection with magnetic beads conjugated to the HEV-specific antibody MECA-79. From these HEVEC that were 98% MECA-79-positive, 1 μg of total RNA was used to generate full length cDNAs for THAP1 cDNA cloning and RT-PCR analysis.

As used herein, the term "nucleic acids" and "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule. Also, used interchangeably herein are terms "nucleic acids", "oligonucleotides", and "polynucleotides".

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated THAP-family nucleic acid molecule can contain less than about 5 kb, 4 kb, 0.3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule of the present invention, e.g., a nucleic acid molecule having the nucleotide sequence of SEQ ID NOs: 160-175, a portion thereof, can be isolated using standard molecular biology techniques and the sequence information provided herein. Using all or a portion of the nucleic acid sequence of SEQ ID NOs: 160-175, as a hybridization probe, THAP-family nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of e.g. SEQ ID NOs: 160-175, can be isolated by the polymerase chain reaction (PCR) using synthetic oligonucleotide primers designed based upon the sequence of SEQ ID NOs: 160-175.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to THAP-family nucleotide sequences can be prepared by standard synthetic techniques, e.g., using an automated DNA synthesizer.

As used herein, the term "hybridizes to" is intended to describe conditions for moderate stringency or high stringency hybridization, preferably where the hybridization and washing conditions permit nucleotide sequences at least 60% homologous to each other to remain hybridized to each other. Preferably, the conditions are such that sequences at least about 70%, more preferably at least about 80%, even more preferably at least about 85%, 90%, 95% or 98% homologous to each other typically remain hybridized to each other. Stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are as follows: the hybridization step is realized at 65° C. in the presence of 6×SSC buffer, 5× Denhardt's solution, 0.5% SDS and 100 µg/ml of salmon sperm DNA. The hybridization step is followed by four washing steps:

two washings during 5 min, preferably at 65° C. in a 2×SSC and 0.1%SDS buffer;

one washing during 30 min, preferably at 65° C. in a 2×SSC and 0.1% SDS buffer, one washing during 10 min, preferably at 65° C. in a 0.1×SSC and 0.1%SDS buffer, these hybridization conditions being suitable for a nucleic acid molecule of about 20 nucleotides in length. It will be appreciated that the hybridization conditions described above are to be adapted according to the length of the desired nucleic acid, following techniques well known to the one skilled in the art, for example be adapted according to the teachings disclosed in Hames B. D. and Higgins S. J. (1985) *Nucleic Acid Hybridization: A Practical Approach.* Hames and Higgins Ed., IRL Press, Oxford; and Current Protocols in Molecular Biolog (supra). Preferably, an isolated nucleic acid molecule of the invention that hybridizes under stringent conditions to a sequence of SEQ ID NOs: 160-175 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90% or 95% of the length of the reference sequence (e.g., when aligning a second sequence to e.g. a THAP-1 amino acid sequence of SEQ ID NO: 3 having 213 amino acid residues, at least 50, preferably at least 100, more preferably at least 200, amino acid residues are aligned or when aligning a second sequence to the THAP-1 cDNA sequence of SEQ ID NO: 160 having 2173 nucleotides or nucleotides 202-835 which encode the amino acids of the THAP1 protein, preferably at least 100, preferably at least 200, more preferably at least 300, even more preferably at least 400, and even more preferably at least 500, 600, at least 700, at least 800, at least 900, at least 1000, at least 1200, at least 1400, at least 1600, at least 1800, or at least 2000 nucleotides are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "identity" is equivalent to amino acid or nucleic acid "homology"). The percent homology between the two sequences is a function of the number of identical positions shared by the sequences (i.e., % homology=number (#) of identical positions/total number (#) of positions 100).

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77, the disclosures of which are incorporated herein by reference in their entireties. Such an algorithm is incorporated into the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to THAP-family nucleic acid molecules of the invention. BLAST protein searches can be performed with the XBLAST program, score=50, wordlength=3 to obtain amino acid sequences homologous to THAP-family protein molecules of the invention. To obtain gapped alignments for comparison purposes, Gapped BLAST can be utilized as described in Altschul et al., (1997) Nucleic Acids Research 25(17):3389-3402. When utilizing BLAST and Gapped BLAST programs, the default parameters of the respective programs (e.g., XBLAST and NBLAST) can be used (see, www.ncbi.nlm.nih.gov, the disclosures of which are incorporated herein by reference in their entireties). Another preferred, non-limiting example of a mathematical algorithm utilized for the comparison of sequences is the algorithm of Myers and Miller, CABIOS (1989), the disclosures of which are incorporated herein by reference in their entireties. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

An "isolated" or "purified" protein or biologically active portion thereof is substantially free of cellular material or other contaminating proteins from the cell or tissue source from which the THAP family or THAP domain polypeptide, or a biologically active fragment or homologue thereof protein is derived, or substantially free from chemical precursors or other chemicals when chemically synthesized. The language "substantially free of cellular material" includes preparations of a protein according to the invention (e.g. THAP family or THAP domain polypeptide, or a biologically active fragment or homologue thereof) in which the protein is separated from cellular components of the cells from which it is isolated or recombinantly produced. In one embodiment, the language "substantially free of cellular material" includes preparations of a protein according to the invention having less than about 30% (by dry weight) of protein other than the THAP-family protein (also referred to herein as a "contaminating protein"), more preferably less than about 20% of protein other than the protein according to the invention, still more preferably less than about 10% of protein other than the protein according to the invention, and most preferably less than about 5% of protein other than the protein according to the invention. When the protein according to the invention or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of THAP family or THAP domain polypeptide, or a biologically active fragment or homologue thereof in which the protein is separated from chemical precursors or other chemicals which are involved in the synthesis of the protein. In one embodiment, the language "substantially free of chemical precursors or other chemicals" includes preparations of a THAP-family protein having less than about 30% (by dry weight) of chemical precursors or non-THAP-family chemicals, more preferably less than about 20% chemical precursors or non-THAP-family or THAP-domain chemicals, still more preferably less than about 10% chemical precursors or non-THAP-family or THAP-domain chemicals, and most preferably less than about 5% chemical precursors or non-THAP-family or THAP-domain chemicals.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

Accordingly, another aspect of the invention pertains to anti-THAP-family or THAP-domain antibodies. The term "antibody" as used herein refers to immunoglobulin molecules and immunologically active portions of immunoglobulin molecules, i.e., molecules that contain an antigen binding site which specifically binds (immunoreacts with) an antigen, such as a THAP family or THAP domain polypeptide, or a biologically active fragment or homologue thereof. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind a THAP family or THAP domain polypeptide, or a biologically active fragment or homologue thereof. The term "monoclonal antibody" or "monoclonal antibody composition", as used herein, refers to a population of antibody molecules that contain only one species of an antigen binding site capable of immunoreacting with a particular epitope of a THAP-family or THAP domain polypeptide. A monoclonal antibody composition thus typically displays a single binding affinity for a particular THAP-family or THAP domain protein with which it immunoreacts.

PAR4

As mentioned above, Prostate apoptosis response-4 (PAR4) is a 38 kDa protein initially identified as the product of a gene specifically upregulated in prostate tumor cells undergoing apoptosis (for reviews see Rangnekar, 1998; Mattson et al., 1999). The PAR4 nucleic acid and amino acid sequences, see Johnstone et al, Mol. Cell. Biol. 16 (12), 6945-6956 (1996); and Genbank accession no. U63809 (SEQ ID NO: 118).

As used interchangeably herein, a "PAR4 activity", "biological activity of a PAR4" or "functional activity of a PAR4", refers to an activity exerted by a PAR4 protein, polypeptide or nucleic acid molecule as determined in vivo, or in vitro, according to standard techniques. In one embodiment, a PAR4 activity is a direct activity, such as an association with a PAR4-target molecule or most preferably apoptosis induction activity, or inhibition of cell proliferation or cell cycle. As used herein, a "target molecule" is a molecule with which a PAR4 protein binds or interacts in nature, such that PAR4-mediated function is achieved. An example of a PAR4 target molecule is a THAP-family protein such as THAP1 or THAP2, or a PML-NBs protein. A PAR4 target molecule can be a PAR4 protein or polypeptide or a non-PAR4 molecule. For example, a PAR4 target molecule can be a non-PAR4 protein molecule. Alternatively, a PAR4 activity is an indirect activity, such as an activity mediated by interaction of the PAR4 protein with a PAR4 target molecule such that the target molecule modulates a downstream cellular activity (e.g., interaction of a PAR4 molecule with a PAR4 target molecule can modulate the activity of that target molecule on an intracellular signaling pathway).

Binding or interaction with a PAR4 target molecule (such as THAP1/PAR4 described herein) or with other targets can be detected for example using a two hybrid-based assay in yeast to find drugs that disrupt interaction of the PAR4 bait with the target (e.g. PAR4) prey, or an in vitro interaction assay with recombinant PAR4 and target proteins (e.g. THAP1 and PAR4).

SLC/CCL21 (SLC)

Biological Roles of SLC

The signals which mediate T-cell infiltration during T-cell auto-immune diseases are poorly understood. SLC/CCL21 (SEQ ID NO: 119) is highly potent and highly specific for attracting T-cell migration. It was initially thought to be expressed only in secondary lymphoid organs, directing naive T-cells to areas of antigen presentation. However, using immunohistology it was found that expression of CCL21 was highly induced in endothelial cells of T-cell auto-immune infiltrative skin diseases (Christopherson et al. (2002) Blood electronic publication prior to printed publication). No other T-cell chemokine was consistently induced in these T cell skin diseases. The receptor for CCL21, CCR7, was also found to be highly expressed on the infiltrating T-cells, the majority of which expressed the memory CD45Ro phenotype. Inflamed venules endothelial cells expressing SLC/CCL21 in T cell infiltrative autoimmune skin diseases may therefore play a key role in the regulation of T-cell migration into these tissues.

There are a number of other autoimmune diseases where induced expression of SLC/CCL21 in endothelial cells may cause abnormal recruitment of T-cells from the circulation to sites of pathologic inflammation. For instance, chemokine SLC/CCL21 appears to be important for aberrant T-cell infiltration in experimental autoimmune encephalomyelitis (EAE), an animal model for multiple sclerosis (Alt et al. (2002) Eur J Immunol 32:2133-44). Migration of autoaggressive T cells across the blood-brain barrier (BBB) is critically involved in the initiation of EAE. The direct involvement of chemokines in this process was suggested by the observation that G-protein-mediated signaling is required to promote adhesion strengthening of encephalitogenic T cells on BBB endothelium in vivo. A search for chemokines present at the BBB, by in situ hybridizations and immunohistochemistry revealed expression of the lymphoid chemokines CCL19/ ELC and CCL21/SLC in venules surrounded by inflammatory cells (Alt et al. (2002) Eur J Immunol 32:2133-44). Their expression was paralleled by the presence of their common receptor CCR7 in inflammatory cells in brain and spinal cord sections of mice afflicted with EAE. Encephalitogenic T cells showed surface expression of CCR7 and specifically chemotaxed towards both CCL19 or CCL21 in a concentration dependent and pertussis toxin-sensitive manner comparable to naive lymphocytes in vitro. Binding assays on frozen sections of EAE brains demonstrated a functional involvement of CCL19 and CCL21 in adhesion strengthening of encephalitogenic T lymphocytes to inflamed venules in the brain (Alt et al. (2002) Eur J Immunol 32:2133-44). Taken together these data suggested that the lymphoid chemokines CCL19 and CCL21 besides regulating lymphocyte homing to secondary lymphoid tissue are involved in T lymphocyte migration into the immunoprivileged central nervous system during immunosurveillance and chronic inflammation.

Other diseases where induced expression of SLC/CCL21 in venular endothelial cells has been observed include rheumatoid arthritis (Page et al. (2002) J Immunol 168:5333-5341) and experimental autoimmune diabetes (Hjelmstrom et al. (2000) Am J Path 156:1133-1138). Therefore, chemokine SLC/CCL21 may be an important pharmacological target in T-cell auto-immune diseases. Inhibitors of SLC/CCL21 may be effective agents at treating these T cell infiltrative diseases by interfering with the abnormal recruitment of T cells, from the circulation to sites of pathologic inflammation, by endothelial cells expressing SLC/CCL21. The reduction in T cell migration into involved tissue would reduce the T-cell inflicted damage seen in those diseases.

Ectopic lymphoid tissue formation is a feature of many chronic inflammatory diseases, including rheumatoid arthritis, inflammatory bowel diseases (Crohn's disease, ulcerative colitis), autoimmune diabetes, chronic inflammatory skin diseases (lichen panus, psoriasis, . . . ), Hashimoto's thyroiditis, Sjogren's syndrome, gastric lymphomas and chronic inflammatory liver disease (Girard and Springer (1995) Immunol today 16:449-457; Takemura et al. (2001) J Immunol 167:1072-1080; Grant et al. (2002) Am J Pathol 2002 160:1445-55; Yoneyama et al. (2001) J Exp Med 193:35-49).

Ectopic expression of SLC/CCL21 has been shown to induce lymphoid neogenesis, both in mice and in human inflammatory diseases. In mice, transgenic expression of SLC/CCL21 in the pancreas (Fan et al. (2000) J Immunol 164:3955-3959; Chen et al. (2002) J Immunol 168:1001-1008; Luther et al. (2002) J Immunol 169:424-433), a non-lymphoid tissue, has been found to be sufficient for the development and organization of ectopic lymphoid tissue through differential recruitment of T and B lymphocytes and induction of high endothelial venules, specialized blood vessels for lymphocyte migration (Girard and Springer (1995) Immunol today 16:449-457). In humans, hepatic expression of SLC/ CCL21 has been shown to promote the development of high endothelial venules and portal-associated lymphoid tissue in chronic inflammatory liver disease (Grant et al. (2002) Am J Pathol 2002 160:1445-55; Yoneyama et al. (2001) J Exp Med 193:35-49). The chronic inflammatory liver disease primary sclerosing cholangitis (PSC) is associated with portal inflammation and the development of neolymphoid tissue in the liver. More than 70% of patients with PSC have a history of inflammatory bowel disease and strong induction of SLC/ CCL21 on CD34(+) vascular endothelium in portal associated lymphoid tissue in PSC has been reported (Grant et al. (2002) Am J Pathol 2002 160:1445-55). In contrast, CCL21 is absent from LYVE-1(+) lymphatic vessel endothelium. Intrahepatic lymphocytes in PSC include a population of CCR7(+) T cells only half of which express CD45RA and which respond to CCL21 in migration assays. The expression of CCL21 in association with mucosal addressin cell adhesion molecule-1 in portal tracts in PSC may promote the recruitment and retention of CCR7(+) mucosal lymphocytes leading to the establishment of chronic portal inflammation and the expanded portal-associated lymphoid tissue. These findings are supported by studies in an animal model of chronic hepatic inflammation, that have shown that anti-SLC/CCL21 antibodies prevent the development of high endothelial venules and portal-associated lymphoid tissue (Yoneyama et al. (2001) J Exp Med 193:35-49).

Induction of chemokine SLC/CCL21 at a site of inflammation could convert the lesion from an acute to a chronic state with corresponding development of ectopic lymphoid tissue. Blocking chemokine SLC/CCL21 activity in chronic inflammatory diseases may therefore have significant therapeutic value.

As used herein, "SLC/CCL21" and "SLC" are synonymous.

THAP-Family Members Comprising a THAP Domain

Based on the elucidation of a biological activity of the THAP1 protein in apoptosis as described herein, the inventors have identified and further characterized a novel protein motif, referred to herein as THAP domain. The THAP domain has been identified by the present inventors in several other polypeptides, as further described herein. Knowledge of the structure and function of the THAP domain allows the performing of screening assays that can be used in the preparation or screening of medicaments capable of modulating interaction with a THAP-family-target molecule, modulating cell cycle and cell proliferation, inducing apoptosis or enhancing or participating in the induction of apoptosis.

As used interchangeably herein, a THAP-family protein or polypeptide, or a THAP-family member refers to any polypeptide having a THAP domain as described herein. As mentioned, the inventors have provided several specific THAP-family members. Thus, as referred to herein, a THAP-family protein or polypeptide, or a THAP-family member, includes but is not limited to a THAP-0, THAP1, THAP-2, THAP-3, THAP-4, THAP-5, THAP-6, THAP-7, THAP-8, THAP-9, THAP10 or a THAP11 polypeptide.

As used interchangeably herein, a "THAP-family activity", "biological activity of a THAP-family member" or "functional activity of a THAP-family member", refers to an activity exerted by a THAP family or THAP domain polypeptide or nucleic acid molecule, or a biologically active fragment or homologue thereof comprising a THAP as determined in vivo, or in vitro, according to standard techniques. In one embodiment, a THAP-family activity is a direct activity, such as an association with a THAP-family-target molecule or most preferably apoptosis induction activity, or inhibition of cell proliferation or cell cycle. As used herein, a "THAP-family target molecule" is a molecule with which a THAP-family protein binds or interacts in nature, such that a THAP family-mediated function is achieved. For example, a THAP family target molecule can be another THAP-family protein or polypeptide which is substantially identical or which shares structural similarity (e.g. forming a dimer or multimer). In another example, a THAP family target molecule can be a non-THAP family comprising protein molecule, or a non-self molecule such as for example a Death Domain receptor. Binding or interaction with a THAP family target molecule (such as THAP1/PAR4 described herein) or with other targets can be detected for example using a two hybrid-based assay in yeast to find drugs that disrupt interaction of the THAP family bait with the target (e.g. PAR4) prey, or an in vitro interaction assay with recombinant THAP family and target proteins (e.g. THAP1 and PAR4). In yet another example, a THAP family target molecule can be a nucleic acid molecule. For instance, a THAP family target molecule can be DNA.

Alternatively, a THAP-family activity may be an indirect activity, such as an activity mediated by interaction of the THAP-family protein with a THAP-family target molecule such that the target molecule modulates a downstream cellular activity (e.g., interaction of a THAP-family molecule with a THAP-family target molecule can modulate the activity of that target molecule on an intracellular signaling pathway).

THAP-family activity is not limited to the induction of apoptotic activity, but may also involve enhancing apoptotic activity. As death domains may mediate protein-protein interactions, including interactions with other death domains, THAP-family activity may involve transducing a cytocidal signal.

Assays to detect apoptosis are well known. In a preferred example, an assay is based on serum-withdrawal induced apoptosis in a 3T3 cell line with tetracycline-regulated expression of a THAP family member comprising a THAP domain. Other non-limiting examples are also described.

In one example, a THAP family or THAP domain polypeptide, or a biologically active fragment or homologue thereof can be the minimum region of a polypeptide that is necessary and sufficient for the generation of cytotoxic death signals. Exemplary assays for apoptosis activity are further provided herein.

In specific embodiments, PAR4 is a preferred THAP1 and/or THAP2 target molecule. In another aspect, a THAP1 target molecule is a PML-NB protein.

In further aspects, THAP-domain or a THAP-family polypeptide comprises a DNA binding domain.

In other aspects, a THAP-family activity is detected by assessing any of the following activities: (1) mediating apoptosis or cell proliferation when expressed in or introduced into a cell, most preferably inducing or enhancing apoptosis, and/or most preferably reducing cell proliferation; (2) mediating apoptosis or cell proliferation of an endothelial cell; (3) mediating apoptosis or cell proliferation of a hyperproliferative cell; (4) mediating apoptosis or cell proliferation of a CNS cell, preferably a neuronal or glial cell; (5) an activity determined in an animal selected from the group consisting of mediating, preferably inhibiting angiogenesis, mediating, preferably inhibiting inflammation, inhibition of metastatic potential of cancerous tissue, reduction of tumor burden, increase in sensitivity to chemotherapy or radiotherapy, killing a cancer cell, inhibition of the growth of a cancer cell, or induction of tumor regression; or (6) interaction with a THAP family target molecule or THAP domain target molecule, preferably interaction with a protein or a nucleic acid. Detecting THAP-family activity may also comprise detecting any suitable therapeutic endpoint discussed herein in the section titled "Methods of Treatment". THAP-family activity may be assessed either in vitro (cell or non-cell based) or in vivo depending on the assay type and format.

A THAP domain has been identified in the N-terminal region of the THAP1 protein, from about amino acid 1 to about amino acid 89 of SEQ ID NO: 3 based on sequence analysis and functional assays. A THAP domain has also been identified in THAP2 to THAP0 of SEQ ID NOs: 4-14. However, it will be appreciated that a functional THAP domain may be only a small portion of the protein, about 10 amino acids to about 15 amino acids, or from about 20 amino acids to about 25 amino acids, or from about 30 amino acids to about 35 amino acids, or from about 40 amino acids to about 45 amino acids, or from about 50 amino acids to about 55 amino acids, or from about 60 amino acids to about 70 amino acids, or from about 80 amino acids to about 90 amino acids, or about 100 amino acids in length. Alternatively, THAP domain or THAP family polypeptide activity, as defined above, may require a larger portion of the native protein than may be defined by protein-protein interaction, DNA binding, cell assays or by sequence alignment. A portion of a THAP domain-containing polypeptide from about 110 amino acids to about 115 amino acids, or from about 120 amino acids to 130 amino acids, or from about 140 amino acids to about 150 amino acids, or from about 160 amino acids to about 170 amino acids, or from about 180 amino acids to about 190 amino acids, or from about 200 amino acids to about 250 amino acids, or from about 300 amino acids to about 350 amino acids, or from about 400 amino acids to about 450 amino acids, or from about 500 amino acids to about 600 amino acids, to the extent that said length is consistent with the SEQ ID No, or the full length protein, for example any full length protein in SEQ ID NOs: 1-114, may be required for function.

As discussed, the invention includes a novel protein domain, including several examples of THAP-family members. The invention thus encompasses a THAP-family member comprising a polypeptide having at least a THAP domain sequence in the protein or corresponding nucleic acid molecule, preferably a THAP domain sequence corresponding to SEQ ID NOs: 1-2. A THAP-family member may comprise an amino acid sequence of at least about 25, 30, 35, 40, 45, 50, 60, 70, 80 to 90 amino acid residues in length, of which at least about 50-80%, preferably at least about 60-70%, more preferably at least about 65%, 75% or 90% of the amino acid residues are identical or similar amino acids-to the THAP consensus domain SEQ ID NOs: 1-2.

Identity or similarity may be determined using any desired algorithm, including the algorithms and parameters for determining homology which are described herein.

Optionally, a THAP-domain-containing THAP-family polypeptide comprises a nuclear localization sequence (NLS). As used herein, the term nuclear localization sequence refers to an amino sequence allowing the THAP-family polypeptide to be localized or transported to the cell nucleus. A nuclear localization sequence generally comprises at least about 10, preferably about 13, preferably about 16, more preferably about 19, and even more preferably about 21, 23, 25, 30, 35 or 40 amino acid residues. Alternatively, a THAP-family polypeptide may comprise a deletion of part or the entire NLS or a substitution or insertion in a NLS sequence, such that the modified THAP-family polypeptide is not localized or transported to the cell nucleus.

Isolated proteins of the present invention, preferably THAP family or THAP domain polypeptides, or a biologically active fragments or homologues thereof, have an amino acid sequence sufficiently homologous to the consensus amino acid sequence of SEQ ID NOs: 1-2. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 30-40% identity, preferably at least about 40-50% identity, more preferably at least about 50-60%, and even more preferably at least about 60-70%, 70-80%, 80%, 90%, 95%, 97%, 98%, 99% or 99.8% identity across the amino acid sequences of the domains and contain at least one and preferably two structural domains or motifs, are defined herein as sufficiently homologous. Furthermore, amino acid or nucleotide sequences which share at least about 30%, preferably at least about 40%, more preferably at least about 60%, 70%, 80%, 90%, 95%, 97%, 98%, 99% or 99.8% identity and share a common functional activity are defined herein as sufficiently homologous.

It be appreciated that the invention encompasses any of the THAP-family polypeptides, as well as fragment thereof, nucleic acids complementary thereto and nucleic acids capable of hybridizing thereto under stringent conditions.

THAP-0 to THAP11

As mentioned, the inventors have identified several THAP-family members, including THAP-0, THAP1, THAP-2, THAP-3, THAP-4, THAP-5, THAP-6, THAP-7, THAP-8, THAP-9, THAP10 and THAP11.

THAP1 Nucleic Acids

The human THAP1 coding sequence, which is approximately 639 nucleotides in length shown in SEQ ID NO: 160, encodes a protein which is approximately 213 amino acid residues in length. One aspect of the invention pertains to purified or isolated nucleic acid molecules that encode THAP1 proteins or biologically active portions thereof as further described herein, as well as nucleic acid fragments thereof. Said nucleic acids may be used for example in therapeutic methods and drug screening assays as further described herein.

The human THAP1 gene is localized at chromosomes 8, 18, 11.

The THAP1 protein comprises a THAP domain at amino acids 1-89, the role of which in apoptosis is further demonstrated herein. The THAP1 protein comprises an interferon gamma homology motif at amino acids 136-169 of human THAP1 (NYTVEDTMHQRKRIHQLEQQVEKL-RKKLKTAQQR) (SEQ ID NO: 178), exhibiting 41% identity in a 34 residue overlap with human interferon gamma (amino acids 98-131). PML-NBs are closely linked to IFN-gamma, and many PML-NB components are induced by IFN-gamma, with IFNgamma responsive elements in the promoters of the corresponding genes. The THAP1 protein also includes a nuclear localization sequence at amino acids 146-165 of human THAP1 (RKRIHQLEQQVEKLRKKLKT) (SEQ ID NO: 179). This sequence is responsible for localization of THAP1 in the nucleus. As demonstrated in the examples provided herein, deletion mutants of THAP1 lacking this sequence are no longer localized in the cell nucleus. The THAP1 protein further comprises a PAR4 binding motif (LE(X)$_{14}$ QRXRRQXR(X)$_{11}$QR/KE) (SEQ ID NO: 180). The core of this motif has been defined experimentally by site directed mutagenesis and by comparison with mouse ZIP/DAP-like kinase (another PAR4 binding partner) it overlaps amino acids 168-175 of human THAP1 but the motif may also include a few residues upstream and downstream.

ESTs corresponding to THAP1 have been identified, and may be specifically included or excluded from the nucleic acids of the invention. The ESTs, as indicated below by accession number, provide evidence for tissue distribution for THAP1 as follows: AL582975 (B cells from Burkitt lymphoma); BG708372 (Hypothalamus); BG563619 (liver); BG497522 (adenocarcinoma); BG616699 (liver); BE932253 (head_neck); AL530396 (neuroblastoma cells).

An object of the invention is a purified, isolated, or recombinant nucleic acid comprising the nucleotide sequence of SEQ ID NO: 160, complementary sequences thereto, and fragments thereof. The invention also pertains to a purified or isolated nucleic acid comprising a polynucleotide having at least 95% nucleotide identity with a polynucleotide of SEQ ID NO: 160, advantageously 99% nucleotide identity, preferably 99.5% nucleotide identity and most preferably 99.8% nucleotide identity with a polynucleotide of SEQ ID NO: 160, or a sequence complementary thereto or a biologically active fragment thereof. Another object of the invention relates to purified, isolated or recombinant nucleic acids comprising a polynucleotide that hybridizes, under the stringent hybridization conditions defined herein, with a polynucleotide of SEQ ID NO: 160, or a sequence complementary thereto or a variant thereof or a biologically active fragment thereof. In further embodiments, nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO: 160, or the complements thereof.

Also encompassed is a purified, isolated, or recombinant nucleic acid polynucleotide encoding a THAP1 polypeptide of the invention, as further described herein.

In another preferred aspect, the invention pertains to purified or isolated nucleic acid molecules that encode a portion or variant of a THAP1 protein, wherein the portion or variant displays a THAP1 activity of the invention. Preferably said portion or variant is a portion or variant of a naturally occurring full-length THAP1 protein. In one example, the invention provides a polynucleotide comprising, consisting essentially of, or consisting of a contiguous span of at least 12, 15, 18, 20, 25, 30, 35, 40, 50, 60, 70, 80, 90, 100, 150, 200, 500, or 1000 nucleotides of SEQ ID NO: 160, wherein said nucleic acid encodes a THAP1 portion or variant having a THAP1 activity described herein. In other embodiments, the invention relates to a polynucleotide encoding a THAP1 portion consisting of 8-20, 20-50, 50-70, 60-100, 100-150, 150-200, 200-205 or 205-212 amino acids of SEQ ID NO: 3, or a variant thereof, wherein said THAP1 portion displays a THAP1 activity described herein.

The sequence of SEQ ID NO: 160 corresponds to the human THAP1 cDNA. This cDNA comprises sequences encoding the human THAP1 protein (i.e., "the coding region", from nucleotides 202 to 840, as well as 5' untranslated sequences (nucleotides 1-201) and 3' untranslated sequences (nucleotides 841 to 2173).

Also encompassed by the THAP1 nucleic acids of the invention are nucleic acid molecules which are complementary to THAP1 nucleic acids described herein. Preferably, a complementary nucleic acid is sufficiently complementary to the nucleotide sequence shown in SEQ ID NO: 160, such that it can hybridize to the nucleotide sequence shown in SEQ ID NO: 160, thereby forming a stable duplex.

Another object of the invention is a purified, isolated, or recombinant nucleic acid encoding a THAP1 polypeptide comprising, consisting essentially of, or consisting of the amino acid sequence of SEQ ID NO: 3, or fragments thereof, wherein the isolated nucleic acid molecule encodes one or more motifs selected from the group consisting of a THAP domain, a THAP1 target binding region, a nuclear localization signal and a interferon gamma homology motif. Preferably said THAP1 target binding region is a PAR4 binding region or a DNA binding region. For example, the purified, isolated or recombinant nucleic acid may comprise a genomic DNA or fragment thereof which encodes the polypeptide of SEQ ID NO: 3 or a fragment thereof or a cDNA consisting of, consisting essentially of, or comprising the sequence of SEQ ID NO: 160 or fragments thereof, wherein the isolated nucleic acid molecule encodes one or more motifs selected from the group consisting of a THAP domain, a THAP1-target binding region, a nuclear localization signal and a interferon gamma homology motif. Any combination of said motifs may also be specified. Preferably said THAP1 target binding region is a PAR4 binding region or a DNA binding region. Particularly preferred nucleic acids of the invention include isolated, purified, or recombinant THAP1 nucleic acids comprising, consisting essentially of, or consisting of a contiguous span of at least 12, 15, 18, 20, 25, 30, 35, 40, 50, 60, 70, 80, 90, 100, 150, 200 or 300 nucleotides of a sequence selected from the group consisting of nucleotide positions ranges consisting of 607 to 708, 637 to 696 and 703 to 747 of SEQ ID NO: 160. In preferred embodiments, a THAP1 nucleic acid encodes a THAP1 polypeptide comprising at least two THAP1 functional domains, such as for example a THAP domain and a PAR4 binding region.

In further preferred embodiments, a THAP1 nucleic acid comprises a nucleotide sequence encoding a THAP domain having the consensus amino acid sequence of the formula of SEQ ID NOs: 1-2. A THAP1 nucleic acid may also encode a THAP domain wherein at least about 95%, 90%, 85%, 50-80%, preferably at least about 60-70%, more preferably at least about 65% of the amino acid residues are identical or similar amino acids-to the THAP domain consensus sequence (SEQ ID NOs: 1-2). The present invention also embodies isolated, purified, and recombinant polynucleotides which encode a polypeptide comprising a contiguous span of at least 6 amino acids, preferably at least 8 or 10 amino acids, more preferably at least 15, 25, 30, 35, 40, 45, 50, 60, 70, 80 or 90 amino acids according to the formula of SEQ ID NO: 1-2.

The nucleotide sequence determined from the cloning of the THAP1 gene allows for the generation of probes and primers designed for use in identifying and/or cloning other THAP1 family members (e.g. sharing the novel functional domains), as well as THAP1 homologues from other species.

A nucleic acid fragment encoding a "biologically active portion of a THAP1 protein" can be prepared by isolating a portion of the nucleotide sequence of SEQ ID NO: 160, which encodes a polypeptide having a THAP1 biological activity (the biological activities of the THAP1 proteins described herein), expressing the encoded portion of the THAP1 protein (e.g., by recombinant expression in vitro or in vivo) and assessing the activity of the encoded portion of the THAP1 protein.

The invention further encompasses nucleic acid molecules that differ from the THAP1 nucleotide sequences of the invention due to degeneracy of the genetic code and encode the same THAP1 proteins and fragment of the invention.

In addition to the THAP1 nucleotide sequences described above, it will be appreciated by those skilled in the art that DNA sequence polymorphisms that lead to changes in the amino acid sequences of the THAP1 proteins may exist within a population (e.g., the human population). Such genetic polymorphism may exist among individuals within a population due to natural allelic variation. Such natural allelic variations can typically result in 1-5% variance in the nucleotide sequence of a THAP1 gene.

Nucleic acid molecules corresponding to natural allelic variants and homologues of the THAP1 nucleic acids of the invention can be isolated based on their homology to the THAP1 nucleic acids disclosed herein using the cDNAs disclosed herein, or a portion thereof, as a hybridization probe according to standard hybridization techniques under stringent hybridization conditions.

Probes based on the THAP1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a THAP1 protein, such as by measuring a level of a THAP1-encoding nucleic acid in a sample of cells from a subject e.g., detecting THAP1 mRNA levels or determining whether a genomic THAP1 gene has been mutated or deleted.

THAP1 Polypeptides

The term "THAP1 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies THAP1 proteins from humans, including isolated or purified THAP1 proteins consisting of, consisting essentially of, or comprising the sequence of SEQ ID NO: 3.

The invention concerns the polypeptide encoded by a nucleotide sequence of SEQ ID NO: 160, a complementary sequence thereof or a fragment thereto.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID NO: 3. In other preferred embodiments the contiguous stretch of amino acids comprises the site of a mutation or functional mutation, including a deletion, addition, swap or truncation of the amino acids in the THAP1 protein sequence. The invention also concerns the polypeptide encoded by the THAP1 nucleotide sequences of the invention, or a complementary sequence thereof or a fragment thereof.

One aspect of the invention pertains to isolated THAP1 proteins, and biologically active portions thereof, as well as polypeptide fragments suitable for use as immunogens to raise anti-THAP1 antibodies. In one embodiment, native THAP1 proteins can be isolated from cells or tissue sources by an appropriate purification scheme using standard protein purification techniques. In another embodiment, THAP1 proteins are produced by recombinant DNA techniques. Alternative to recombinant expression, a THAP1 protein or polypeptide can be synthesized chemically using standard peptide synthesis techniques.

Typically, biologically active portions comprise a domain or motif with at least one activity of the THAP1 protein. The present invention also embodies isolated, purified, and recombinant portions or fragments of one THAP1 polypeptide comprising a contiguous span of at least 6 amino acids, preferably at least 8 to 10 amino acids, more preferably at least 12, 15, 20, 25, 30, 40, 50, 100 or 200 amino acids of SEQ ID NO: 3. Also encompassed are THAP1 polypeptide which comprise between 10 and 20, between 20 and 50, between 30 and 60, between 50 and 100, or between 100 and 200 amino acids of SEQ ID NO: 3. In other preferred embodiments the contiguous stretch of amino acids comprises the site of a mutation or functional mutation, including a deletion, addition, swap or truncation of the amino acids in the THAP1 protein sequence.

A biologically active THAP1 protein may, for example, comprise at least 1, 2, 3, 5, 10, 20 or 30 amino acid changes from the sequence of SEQ ID NO: 3, or may encode a biologically active THAP1 protein comprising at least 1%, 2%, 3%, 5%, 8%, 10% or 15% changes in amino acids from the sequence of SEQ ID NO: 3.

In a preferred embodiment, the THAP1 protein comprises, consists essentially of, or consists of a THAP domain at amino acid positions 1 to 89 shown in SEQ ID NO: 3, or fragments or variants thereof. In other aspects, a THAP1 polypeptide comprises a THAP1-target binding region, a nuclear localization signal and/or a Interferon Gamma Homology Motif. Preferably a THAP1 target binding region is a PAR4 binding region or a DNA binding region. The invention also concerns the polypeptide encoded by the THAP1 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80, 90 or 100 amino acids of an amino acid sequence selected from the group consisting of positions 1 to 90, 136 to 169, 146 to 165 and 168 to 175 of SEQ ID NO: 3. In another aspect, a THAP1 polypeptide may encode a THAP domain wherein at least about 95%, 90%, 85%, 50-80%, preferably at least about 60-70%, more preferably at least about 65% of the amino acid residues are identical or similar amino acids-to the THAP domain consensus sequence (SEQ ID NOs: 1-2). Also encompassed by the present invention are isolated, purified, nucleic acids encoding a THAP1 polypeptide comprising, consisting essentially of, or consisting of a THAP domain at amino acid positions 1 to 90 shown in SEQ ID NO: 3, or fragments or variants thereof.

In other embodiments, the THAP1 protein is substantially homologous to the sequences of SEQ ID NO: 3, and retains the functional activity of the THAP1 protein, yet differs in amino acid sequence due to natural allelic variation or mutagenesis, as described further herein. Accordingly, in another embodiment, the THAP1 protein is a protein which comprises an amino acid sequence shares more than about 60% but less than 100% homology with the amino acid sequence of SEQ ID NO: 3 and retains the functional activity of the THAP1 proteins of SEQ ID NO: 3, respectively. Preferably, the protein is at least about 30%, 40%, 50%, 60%, 70%, 80%, 85%, 90%, 92%, 95%, 97%, 98%, 99% or 99.8% homologous to SEQ ID NO: 3, but is not identical to SEQ ID NO: 3. Preferably the THAP1 is less than identical (e.g. 100% identity) to a naturally occurring THAP1. Percent homology can be determined as further detailed above.

THAP-2 to THAP11 and THAP-0 Nucleic Acids

As mentioned, the invention provides several members of the THAP-family. THAP-2, THAP-3, THAP-4, THAP-5, THAP-6, THAP-7, THAP-8, THAP-9, THAP10, THAP11 and THAP-0 are described herein. The human and mouse nucleotide sequences corresponding to the human cDNA sequences are listed in SEQ ID NOs: 161-171; and the human amino acid sequences are listed respectively in SEQ ID NOs: 4-14. Also encompassed by the invention are orthologs of said THAP-family sequences, including mouse, rat, pig and other orthologs, the amino acid sequences of which are listed in SEQ ID NOs: 16-114 and the cDNA sequences are listed in SEQ ID NOs: 172-175.

THAP-2

The human THAP-2 cDNA, which is approximately 1302 nucleotides in length shown in SEQ ID NO: 161, encodes a protein which is approximately 228 amino acid residues in length, shown in SEQ ID NO: 4. One aspect of the invention pertains to purified or isolated nucleic acid molecules that encode THAP-2 proteins or biologically active portions thereof as further described herein, as well as nucleic acid fragments thereof. Said nucleic acids may be used for example in therapeutic methods and drug screening assays as further described herein. The human THAP-2 gene is localized at chromosomes 12 and 3. The THAP-2 protein comprises a THAP domain at amino acids 1 to 89. Analysis of expressed sequences (accession numbers indicated, which may be specifically included or excluded from the nucleic acids of the invention) in databases suggests that THAP-2 is expressed as follows: BG677995 (squamous cell carcinoma); AV718199 (hypothalamus); BI600215 (hypothalamus); AI208780 (Soares_testis_NHT); BE566995 (carcinoma cell line); AI660418 (thymus pooled)

THAP-3

The human THAP-3 cDNA which is approximately 1995 nucleotides in length shown in SEQ ID NO: 162. The THAP-3 gene encodes a protein which is approximately 239 amino acid residues in length, shown in SEQ ID NO: 5. One aspect of the invention pertains to purified or isolated nucleic acid molecules that encode THAP-3 proteins or biologically active portions thereof as further described herein, as well as nucleic acid fragments thereof. Said nucleic acids may be used for example in therapeutic methods and drug screening assays as further described herein. The human THAP-3 gene is localized at chromosome 1. The THAP-3 protein comprises a THAP domain at amino acids 1 to 89. Analysis of expressed sequences (accession numbers indicated, which may be specifically included or excluded from the nucleic acids of the invention) in databases suggests that THAP-3 is expressed as follows: BG700517 (hippocampus); BI460812 (testis); BG707197 (hypothalamus); AW960428 (–); BG437177 (large cell carcinoma); BE962820 (adenocarcinoma); BE548411 (cervical carcinoma cell line); AL522189 (neuroblastoma cells); BE545497 (cervical carcinoma cell line); BE280538 (choriocarcinoma); BI086954 (cervix); BE744363 (adenocarcinoma cell line); and BI549151 (hippocampus).

THAP-4

The human THAP-4cDNA, shown as a sequence having 1999 nucleotides in length shown in SEQ ID NO: 163, encodes a protein which is approximately 577 amino acid residues in length, shown in SEQ ID NO: 6. One aspect of the invention pertains to purified or isolated nucleic acid molecules that encode THAP-4 proteins or biologically active portions thereof as further described herein, as well as nucleic acid fragments thereof. Said nucleic acids may be used for example in therapeutic methods and drug screening assays as further described herein. The THAP-4 protein comprises a THAP domain at amino acids 1 to 90. Analysis of expressed sequences (accession numbers indicated, which may be specifically included or excluded from the nucleic acids of the invention) in databases suggests that THAP-4 is expressed as follows: AL544881 (placenta); BE384014 (melanotic melanoma); AL517205 (neuroblastoma cells); BG394703 (retinoblastoma); BG472327 (retinoblastoma); BI 196071 (neuroblastoma); BE255202 (retinoblastoma); BI017349 (lung_tumor); BF972153 (leiomyosarcoma cell line);

BG116061 (duodenal adenocarcinoma cell line); AL530558 (neuroblastoma cells); AL520036 (neuroblastoma cells); AL559902 (B cells from Burkitt lymphoma); AL534539 (Fetal brain); BF686560 (leiomyosarcoma cell line); BF345413 (anaplastic oligodendroglioma with 1p/19q loss); BG117228 (adenocarcinoma cell line); BG490646 (large cell carcinoma); and BF769104 (epid_tumor).

THAP-5

The human THAP-5 cDNA, shown as a sequence having 1034 nucleotides in length shown in SEQ ID NO: 164, encodes a protein which is approximately 239 amino acid residues in length, shown in SEQ ID NO: 7. One aspect of the invention pertains to purified or isolated nucleic acid molecules that encode THAP-5 proteins or biologically active portions thereof as further described herein, as well as nucleic acid fragments thereof. Said nucleic acids may be used for example in therapeutic methods and drug screening assays as further described herein. The human THAP-5 gene is localized at chromosome 7. The THAP-5 protein comprises a THAP domain at amino acids 1 to 90. Analysis of expressed sequences (accession numbers indicated, which may be specifically included or excluded from the nucleic acids of the invention) in databases suggests that THAP-5 is expressed as follows: BG575430 (mammary adenocarcinoma cell line); BI545812 (hippocampus); BI560073 (testis); BG530461 (embryonal carcinoma); BF244164 (glioblastoma); BI461364 (testis); AW407519 (germinal center B cells); BF103690 (embryonal carcinoma); and BF939577 (kidney).

THAP-6

The human THAP-6cDNA, shown as a sequence having 2291 nucleotides in length shown in SEQ ID NO: 165, encodes a protein which is approximately 222 amino acid residues in length, shown in SEQ ID NO: 8. One aspect of the invention pertains to purified or isolated nucleic acid molecules that encode THAP-6 proteins or biologically active portions thereof as further described herein, as well as nucleic acid fragments thereof. Said nucleic acids may be used for example in therapeutic methods and drug screening assays as further described herein. The human THAP-6 gene is localized at chromosome 4. The THAP-6 protein comprises a THAP domain at amino acids 1 to 90. Analysis of expressed sequences (accession numbers indicated, which may be specifically included or excluded from the nucleic acids of the invention) in databases suggests that THAP-6 is expressed as follows: AV684783 (hepatocellular carcinoma); AV698391 (hepatocellular carcinoma); BI560555 (testis); AV688768 (hepatocellular carcinoma); AV692405 (hepatocellular carcinoma); and AV696360 (hepatocellular carcinoma).

THAP-7

The human THAP-7 cDNA, shown as a sequence having 1242 nucleotides in length shown in SEQ ID NO: 166, encodes a protein which is approximately 309 amino acid residues in length, shown in SEQ ID NO: 9. One aspect of the invention pertains to purified or isolated nucleic acid molecules that encode THAP-7 proteins or biologically active portions thereof as further described herein, as well as nucleic acid fragments thereof. Said nucleic acids may be used for example in therapeutic methods and drug screening assays as further described herein. The human THAP-7 gene is localized at chromosome 22q11.2. The THAP-7 protein comprises a THAP domain at amino acids 1 to 90. Analysis of expressed sequences (accession numbers indicated, which may be specifically included or excluded from the nucleic acids of the invention) in databases suggests that THAP-7 is expressed as follows: BI193682 (epithelioid carcinoma cell line); BE253146 (retinoblastoma); BE622113 (melanotic melanoma); BE740360 (adenocarcinoma cell line); BE513955 (Burkitt lymphoma); AL049117 (testis); BF952983 (nervous_normal); AW975614 (–); BE273270 (renal cell adenocarcinoma); BE738428 (glioblastoma); BE388215 (endometrium adenocarcinoma cell line); BF762401 (colon_est); and BG329264 (retinoblastoma).

THAP-8

The human THAP-8 cDNA, shown as a sequence having 1383 nucleotides in length shown in SEQ ID NO: 167, encodes a protein which is approximately 274 amino acid residues in length, shown in SEQ ID NO: 10. One aspect of the invention pertains to purified or isolated nucleic acid molecules that encode THAP-8 proteins or biologically active portions thereof as further described herein, as well as nucleic acid fragments thereof. Said nucleic acids may be used for example in therapeutic methods and drug screening assays as further described herein. The human THAP-8 gene is localized at chromosome 19. The THAP-8 protein comprises a THAP domain at amino acids 1 to 92. Analysis of expressed sequences (accession numbers indicated, which may be specifically included or excluded from the nucleic acids of the invention) in databases suggests that THAP-8 is expressed as follows: BG703645 (hippocampus); BF026346 (melanotic melanoma); BE728495 (melanotic melanoma); BG334298 (melanotic melanoma); and BE390697 (endometrium adenocarcinoma cell line).

THAP-9

The human THAP-9 cDNA, shown as a sequence having 693 nucleotides in length shown in SEQ ID NO: 168, encodes a protein which is approximately 231 amino acid residues in length, shown in SEQ ID NO: 11. One aspect of the invention pertains to purified or isolated nucleic acid molecules that encode THAP-9 proteins or biologically active portions thereof as further described herein, as well as nucleic acid fragments thereof. Said nucleic acids may be used for example in therapeutic methods and drug screening assays as further described herein. The THAP-9 protein comprises a THAP domain at amino acids 1 to 92. Analysis of expressed sequences (accession numbers indicated, which may be specifically included or excluded from the nucleic acids of the invention) in databases suggests that THAP-9 is expressed as follows: AA333595 (Embryo 8 weeks).

THAP10

The human THAP10 cDNA, shown as a sequence having 771 nucleotides in length shown in SEQ ID NO: 169, encodes a protein which is approximately 257 amino acid residues in length, shown in SEQ ID NO: 12. One aspect of the invention pertains to purified or isolated nucleic acid molecules that encode THAP10 proteins or biologically active portions thereof as further described herein, as well as nucleic acid fragments thereof. Said nucleic acids may be used for example in therapeutic methods and drug screening assays as further described herein. The human THAP10 gene is localized at chromosome 15. The THAP10 protein comprises a THAP domain at amino acids 1 to 90. Analysis of expressed sequences (accession numbers indicated, which may be specifically included or excluded from the nucleic acids of the invention) in databases suggests that THAP10 is expressed as follows: AL526710 (neuroblastoma cells); AV725499 (Hypothalamus); AW966404 (–); AW296810 (lung); and AL557817 (T cells from T cell leukemia).

THAP11

The human THAP11 cDNA, shown as a sequence having 942 nucleotides in length shown in SEQ ID NO: 170, encodes a protein which is approximately 314 amino acid residues in length, shown in SEQ ID NO: 13. One aspect of the invention pertains to purified or isolated nucleic acid molecules that encode THAP11 proteins or biologically active portions thereof as further described herein, as well as nucleic acid fragments thereof. Said nucleic acids may be used for example in therapeutic methods and drug screening assays as further described herein. The human THAP11 gene is localized at chromosome 16. The THAP11 protein comprises a THAP domain at amino acids 1 to 90. Analysis of expressed sequences (accession numbers indicated, which may be specifically included or excluded from the nucleic acids of the invention) in databases suggests that THAP11 is expressed as follows: AU142300 (retinoblastoma); BI261822 (lymphoma cell line); BG423102 (renal cell adenocarcinoma); and BG423864 (kidney).

THAP-0

The human THAP-0 cDNA, shown as a sequence having 2283 nucleotides in length shown in SEQ ID NO: 171, encodes a protein which is approximately 761 amino acid residues in length, shown in SEQ ID NO: 14. One aspect of the invention pertains to purified or isolated nucleic acid molecules that encode THAP-0 proteins or biologically active portions thereof as further described herein, as well as nucleic acid fragments thereof. Said nucleic acids may be used for example in therapeutic methods and drug screening assays as further described herein. The human THAP-0 gene is localized at chromosome 11. The THAP-0 protein comprises a THAP domain at amino acids 1 to 90. Analysis of expressed sequences (accession numbers indicated, which may be specifically included or excluded from the nucleic acids of the invention) in databases suggests that THAP-0 is expressed as follows: BE713222 (head_neck); BE161184 (head_neck); AL119452 (amygdala); AU129709 (teratocarcinoma); AW965460 (−); AW965460(−); AW958065 (−); and BE886885 (leiomyosarcoma).

An object of the invention is a purified, isolated, or recombinant nucleic acid comprising the nucleotide sequence of SEQ ID NOs: 161-171, 173-175 or complementary sequences thereto, and fragments thereof. The invention also pertains to a purified or isolated nucleic acid comprising a polynucleotide having at least 95% nucleotide identity with a polynucleotide of SEQ ID NOs: 161-171 or 173-175, advantageously 99% nucleotide identity, preferably 99.5% nucleotide identity and most preferably 99.8% nucleotide identity with a polynucleotide of SEQ ID NOs: 161-171, 173-175 or a sequence complementary thereto or a biologically active fragment thereof. Another object of the invention relates to purified, isolated or recombinant nucleic acids comprising a polynucleotide that hybridizes, under the stringent hybridization conditions defined herein, with a polynucleotide of SEQ ID NOs: 161-171, 173-175 or a sequence complementary thereto or a variant thereof or a biologically active fragment thereof. In further embodiments, nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of a sequence selected from the group consisting of SEQ ID NOs: 161-171, 173-175 or the complements thereof.

Also encompassed is a purified, isolated, or recombinant nucleic acid polynucleotide encoding a THAP-2 to THAP11 or THAP-0 polypeptide of the invention, as further described herein.

In another preferred aspect, the invention pertains to purified or isolated nucleic acid molecules that encode a portion or variant of a THAP-2 to THAP11 or THAP-0 protein, wherein the portion or variant displays a THAP-2 to THAP11 or THAP-0 activity of the invention. Preferably said portion or variant is a portion or variant of a naturally occurring full-length THAP-2 to THAP11 or THAP-0 protein. In one example, the invention provides a polynucleotide comprising, consisting essentially of, or consisting of a contiguous span of at least 12, 15, 18, 20, 25, 30, 35, 40, 50, 60, 70, 80, 90, 100, 150, 200, 500, or 1000 nucleotides, to the extent that the length of said span is consistent with the length of the SEQ ID NO, of a sequence selected from the group consisting of SEQ ID NOs: 161-171, 173-175, wherein said nucleic acid encodes a THAP-2 to THAP11 or THAP-0 portion or variant having a THAP-2 to THAP11 or THAP-0 activity described herein. In other embodiment, the invention relates to a polynucleotide encoding a THAP-2 to THAP11 or THAP-0 portion consisting of 8-20, 20-50, 50-70, 60-100, 100-150, 150-200, 200-250 or 250-350 amino acids, to the extent that the length of said portion is consistent with the length of the SEQ ID NO: of a sequence selected from the group consisting of SEQ ID NOs: 4-14, 17-21, 23-40, 42-56, 58-98, 100-114 or a variant thereof, wherein said THAP-2 to THAP11 or THAP-0 portion displays a THAP-2 to THAP11 or THAP-0 activity described herein.

A THAP-2 to THAP11 or THAP-0 variant nucleic acid may, for example, encode a biologically active THAP-2 to THAP11 or THAP-0 protein comprising at least 1, 2, 3, 5, 10, 20 or 30 amino acid changes from the respective sequence selected from the group consisting of SEQ ID NO: 4-14, 17-21, 23-40, 42-56, 58-98 and 100-114 or may encode a biologically active THAP-2 to THAP11 or THAP-0 protein comprising at least 1%, 2%, 3%, 5%, 8%, 10% or 15% changes in amino acids from the respective sequence of SEQ ID NOs: 4-14, 17-21, 23-40, 42-56, 58-98 and 100-114.

The sequences of SEQ ID NOs: 4-14 correspond to the human THAP-2 to THAP11 and THAP-0 DNAs respectively. SEQ ID NOs: 17-21, 23-40, 42-56, 58-98, 100-114 correspond to mouse, rat, pig and other orthologs.

Also encompassed by the THAP-2 to THAP11 and THAP-0 nucleic acids of the invention are nucleic acid molecules which are complementary to THAP-2 to THAP11 or THAP-0 nucleic acids described herein. Preferably, a complementary nucleic acid is sufficiently complementary to the nucleotide respective sequence shown in SEQ ID NOs: 161-171 and 173-175 such that it can hybridize to said nucleotide sequence shown in SEQ ID NOs: 161-171 and 173-175, thereby forming a stable duplex.

Another object of the invention is a purified, isolated, or recombinant nucleic acid encoding a THAP-2 to THAP11 or THAP-0 polypeptide comprising, consisting essentially of, or consisting of an amino acid sequence selected from the group consisting of SEQ ID NOs: 4-14, 17-21, 23-40, 42-56, 58-98, 100-114 or fragments thereof, wherein the isolated nucleic acid molecule encodes a THAP domain or a THAP-2 to THAP11 or THAP-0 target binding region. Preferably said target binding region is a protein binding region, preferably a PAR-4 binding region, or preferably said target binding region is a DNA binding region. For example, the purified, isolated or recombinant nucleic acid may comprise a genomic DNA or fragment thereof which encodes a polypeptide having a sequence selected from the group consisting of SEQ ID NOs: 4-14, 17-21, 23-40, 42-56, 58-98, 100-114 or a fragment thereof. The purified, isolated or recombinant nucleic acid may alternatively comprise a cDNA consisting of, consisting essentially of, or comprising a sequence selected from the group consisting of SEQ ID NOs: 4-14, 17-21, 23-40, 42-56, 58-98, 100-114 or fragments thereof, wherein the isolated nucleic acid molecule encodes a THAP domain or a THAP-2 to THAP11 or THAP-0 target binding region. In preferred embodiments, a THAP-2 to THAP11 or THAP-0 nucleic acid encodes a THAP-2 to THAP11 or THAP-0 polypeptide comprising at least two THAP-2 to THAP11 or THAP-0 functional domains, such as for example a THAP domain and a THAP-2 to THAP11 or THAP-0 target binding region.

Particularly preferred nucleic acids of the invention include isolated, purified, or recombinant THAP-2 to THAP11 or THAP-0 nucleic acids comprising, consisting essentially of, or consisting of a contiguous span of at least 12, 15, 18, 20, 25, 30, 35, 40, 50, 60, 70, 80, 90, 100, 150, 200 or 250 nucleotides of a sequence selected from the group consisting of nucleotide positions coding for the relevant amino acids as given in the SEQ ID NO: 161-171 and 173-175.

In further preferred embodiments, a THAP-2 to THAP11 or THAP-0 nucleic acid comprises a nucleotide sequence encoding a THAP domain having the consensus amino acid sequence of the formula of SEQ ID NOs: 1-2. A THAP-2 to THAP11 or THAP-0 nucleic acid may also encode a THAP domain wherein at least about 95%, 90%, 85%, 50-80%, preferably at least about 60-70%, more preferably at least about 65% of the amino acid residues are identical or similar amino acids-to the THAP consensus domain (SEQ ID NOs: 1-2). The present invention also embodies isolated, purified, and recombinant polynucleotides which encode a polypeptide comprising a contiguous span of at least 6 amino acids, preferably at least 8 or 10 amino acids, more preferably at least 15, 25, 30, 35, 40, 45, 50, 60, 70, 80 or 90 amino acids of SEQ ID NOs: 1-2.

The nucleotide sequence determined from the cloning of the THAP-2 to THAP11 or THAP-0 genes allows for the generation of probes and primers designed for use in identifying and/or cloning other THAP family members, particularly sequences related to THAP-2 to THAP11 or THAP-0 (e.g. sharing the novel functional domains), as well as THAP-2 to THAP11 or THAP-0 homologues from other species.

A nucleic acid fragment encoding a biologically active portion of a THAP-2 to THAP11 or THAP-0 protein can be prepared by isolating a portion of a nucleotide sequence selected from the group consisting of SEQ ID NOs: 161-171 and 173-175, which encodes a polypeptide having a THAP-2 to THAP11 or THAP-0 biological activity (the biological activities of the THAP-family proteins described herein), expressing the encoded portion of the THAP-2 to THAP11 or THAP-0 protein (e.g., by recombinant expression in vitro or in vivo) and assessing the activity of the encoded portion of the THAP-2 to THAP11 or THAP-0 protein.

The invention further encompasses nucleic acid molecules that differ from the THAP-2 to THAP11 or THAP-0 nucleotide sequences of the invention due to degeneracy of the genetic code and encode the same THAP-2 to THAP11 or THAP-0 protein, or fragment thereof, of the invention.

In addition to the THAP-2 to THAP11 or THAP-0 nucleotide sequences described above, it will be appreciated by those skilled in the art that DNA sequence polymorphisms that lead to changes in the amino acid sequences of the respective THAP-2 to THAP11 or THAP-0 protein may exist within a population (e.g., the human population). Such genetic polymorphism may exist among individuals within a population due to natural allelic variation. Such natural allelic variations can typically result in 1-5% variance in the nucleotide sequence of a particular THAP-2 to THAP11 or THAP-0 gene.

Nucleic acid molecules corresponding to natural allelic variants and homologues of the THAP-2 to THAP11 or THAP-0 nucleic acids of the invention can be isolated based on their homology to the THAP-2 to THAP11 or THAP-0 nucleic acids disclosed herein using the cDNAs disclosed herein, or a portion thereof, as a hybridization probe according to standard hybridization techniques under stringent hybridization conditions.

Probes based on the THAP-2 to THAP11 or THAP-0 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a THAP-2 to THAP11 or THAP-0 protein, such as by measuring a level of a THAP-2 to THAP11 or THAP-O-encoding nucleic acid in a sample of cells from a subject e.g., detecting THAP-2 to THAP11 or THAP-0 mRNA levels or determining whether a genomic THAP-2 to THAP11 or THAP-0 gene has been mutated or deleted.

THAP-2 to THAP11 and THAP-0 Polypeptides

The term "THAP-2 to THAP11 or THAP-0 polypeptides" is used herein to embrace all of the proteins and polypeptides of the present invention relating to THAP-2, THAP-3, THAP-4, THAP-5, THAP-6, THAP-7, THAP-8, THAP-9, THAP10, THAP11 and THAP-0. Also forming part of the invention are polypeptides encoded by the polynucleotides of the invention, as well as fusion polypeptides comprising such polypeptides. The invention embodies THAP-2 to THAP11 or THAP-0 proteins from humans, including isolated or purified THAP-2 to THAP11 or THAP-0 proteins consisting of, consisting essentially of, or comprising a sequence selected from the group consisting of SEQ ID NOs: 4-14, 17-21, 23-40, 42-56, 58-98 and 100-114.

The invention concerns the polypeptide encoded by a nucleotide sequence selected from the group consisting of SEQ ID NOs: 161-171, 172-175 and a complementary sequence thereof and a fragment thereof.

The present invention embodies isolated, purified, and recombinant polypeptides comprising a contiguous span of at least 6 amino acids, preferably at least 8 to 10 amino acids, more preferably at least 12, 15, 20, 25, 30, 40, 50, 100, 150, 200, 300 or 500 amino acids, to the extent that said span is consistent with the particular SEQ ID NO:, of a sequence selected from the group consisting of SEQ ID NOs: 4-14, 17-21, 23-40, 42-56, 58-98 and 100-114. In other preferred embodiments the contiguous stretch of amino acids comprises the site of a mutation or functional mutation, including a deletion, addition, swap or truncation of the amino acids in the THAP-2 to THAP11 or THAP-0 protein sequence.

One aspect of the invention pertains to isolated THAP-2 to THAP11 and THAP-0 proteins, and biologically active portions thereof, as well as polypeptide fragments suitable for use as immunogens to raise anti-THAP-2 to THAP11 or THAP-0 antibodies. In one embodiment, native THAP-2 to THAP11 or THAP-0 proteins can be isolated from cells or tissue sources by an appropriate purification scheme using standard protein purification techniques. In another embodiment, THAP-2 to THAP11 or THAP-0 proteins are produced by recombinant DNA techniques. Alternative to recombinant expression, a THAP-2 to THAP11 or THAP-0 protein or polypeptide can be synthesized chemically using standard peptide synthesis techniques.

Biologically active portions of a THAP-2 to THAP11 or THAP-0 protein include peptides comprising amino acid sequences sufficiently homologous to or derived from the amino acid sequence of the THAP-2 to THAP11 or THAP-0 protein, e.g., an amino acid sequence shown in SEQ ID NOs: 4-14, 17-21, 23-40, 42-56, 58-98 or 100-114, which include less amino acids than the respective full length THAP-2 to THAP11 or THAP-0 protein, and exhibit at least one activity of the THAP-2 to THAP11 or THAP-0 protein. The present invention also embodies isolated, purified, and recombinant portions or fragments of a THAP-2 to THAP11 or THAP-0 polypeptide comprising a contiguous span of at least 6 amino acids, preferably at least 8 to 10 amino acids, more preferably at least 12, 15, 20, 25, 30, 40, 50, 100, 150, 200, 300 or 500 amino acids, to the extent that said span is consistent with the particular SEQ ID NO, of a sequence selected from the group consisting of SEQ ID NOs: 4-14, 17-21, 23-40, 42-56, 58-98 and 100-114. Also encompassed are THAP-2 to THAP11 or THAP-0 polypeptides which comprise between 10 and 20, between 20 and 50, between 30 and 60, between 50 and 100, or between 100 and 200 amino acids of a sequence selected from the group consisting of SEQ ID NOs: 4-14, 17-21, 23-40, 42-56, 58-98 and 100-114. In other preferred embodiments the contiguous stretch of amino acids comprises the site of a mutation or functional mutation, including a deletion, addition, swap or truncation of the amino acids in the THAP-2 to THAP11 or THAP-0 protein sequence.

A biologically active THAP-2 to THAP11 or THAP-0 protein may, for example, comprise at least 1, 2, 3, 5, 10, 20 or 30 amino acid changes from the sequence of SEQ ID NOs: 4-14, 17-21, 23-40, 42-56, 58-98 or 100-114, or may encode a biologically active THAP-2 to THAP11 or THAP-0 protein comprising at least 1%, 2%, 3%, 5%, 8%, 10% or 15% changes in amino acids from the sequence of SEQ ID NOs: 4-14, 17-21, 23-40, 42-56, 58-98 or 100-114.

In a preferred embodiment, the THAP-2 protein comprises, consists essentially of, or consists of a THAP-2 THAP domain, preferably having the amino acid sequence of amino acid positions 1 to 89 shown in SEQ ID NO: 4, or fragments or variants thereof. The invention also concerns the polypeptide encoded by the THAP-2 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 89 amino acids of a sequence comprising amino acid positions 1 to 89 of SEQ ID NO: 4. In another aspect, a THAP-2 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-2 polypeptide comprising, consisting essentially of, or consisting of a THAP domain at amino acid positions 1 to 89 shown in SEQ ID NO: 4, or fragments or variants thereof. Preferably, said THAP-2 polypeptide comprises a PAR-4 binding domain and/or a DNA binding domain.

In a preferred embodiment, the THAP-3 protein comprises, consists essentially of, or consists of a THAP-3 THAP domain, preferably having the amino acid sequence of amino acid positions 1 to 89 shown in SEQ ID NO: 5, or fragments or variants thereof. The invention also concerns the polypeptide encoded by the THAP-3 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 89 amino acids of a sequence comprising amino acid positions 1 to 89 of SEQ ID NO: 5. In another aspect, a THAP-3 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-3 polypeptide comprising, consisting essentially of, or consisting of a THAP domain at amino acid positions. 1 to 89 shown in SEQ ID NO: 5, or fragments or variants thereof. Preferably, said THAP-3 polypeptide comprises a PAR-4 binding domain and/or a DNA binding domain.

In a preferred embodiment, the THAP-4 protein comprises, consists essentially of, or consists of a THAP-4 THAP domain, preferably having the amino acid sequence of amino acid positions 1 to 90 shown in SEQ ID NO: 6, or fragments or variants thereof. The invention also concerns the polypeptide encoded by the THAP-4 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 6. In another aspect, a THAP-4 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-4 polypeptide comprising, consisting essentially of, or consisting of a THAP domain at amino acid positions 1 to 90 shown in SEQ ID NO: 6, or fragments or variants thereof.

In a preferred embodiment, the THAP-5 protein comprises, consists essentially of, or consists of a THAP-5 THAP domain, preferably having the amino acid sequence of amino acid positions 1 to 90 shown in SEQ ID NO: 7, or fragments or variants thereof. The invention also concerns the polypeptide encoded by the THAP-5 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 7. In another aspect, a THAP-5 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-5 polypeptide comprising, consisting essentially of, or consisting of a THAP domain at amino acid positions 1 to 90 shown in SEQ ID NO: 7, or fragments or variants thereof.

In a preferred embodiment, the THAP-6 protein comprises, consists essentially of, or consists of a THAP-6 THAP domain, preferably having the amino acid sequence of amino acid positions 1 to 90 shown in SEQ ID NO: 8, or fragments or variants thereof. The invention also concerns the polypeptide encoded by the THAP-6 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 8. In another aspect, a THAP-6 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-6 polypeptide comprising, consisting essentially of, or consisting of a THAP domain at amino acid positions 1 to 90 shown in SEQ ID NO: 8, or fragments or variants thereof.

In a preferred embodiment, the THAP-7 protein comprises, consists essentially of, or consists of a THAP-7 THAP domain, preferably having the amino acid sequence of amino acid positions 1 to 90 shown in SEQ ID NO: 9, or fragments or variants thereof. The invention also concerns the polypeptide encoded by the THAP-7 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 9. In another aspect, a THAP-7 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-7 polypeptide comprising, consisting essentially of, or consisting of a THAP domain at amino acid positions 1 to 90 shown in SEQ ID NO: 9, or fragments or variants thereof.

In a preferred embodiment, the THAP-8 protein comprises, consists essentially of, or consists of a THAP-8 THAP domain, preferably having the amino acid sequence of amino acid positions 1 to 92 shown in SEQ ID NO: 10, or fragments or variants thereof. The invention also concerns the polypeptide encoded by the THAP-8 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 92 of SEQ ID NO: 10. In another aspect, a THAP-8 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-8 polypeptide comprising, consisting essentially of, or consisting of a THAP domain at amino acid positions 1 to 92 shown in SEQ ID NO: 10, or fragments or variants thereof.

In a preferred embodiment, the THAP-9 protein comprises, consists essentially of, or consists of a THAP-9 THAP domain, preferably having the amino acid sequence of amino acid positions 1 to 92 shown in SEQ ID NO: 11, or fragments or variants thereof. The invention also concerns the polypeptide encoded by the THAP-9 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 92 of SEQ ID NO: 11. In another aspect, a THAP-9 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-9 polypeptide comprising, consisting essentially of, or consisting of a THAP domain at amino acid positions 1 to 92 shown in SEQ ID NO: 11, or fragments or variants thereof.

In a preferred embodiment, the THAP10 protein comprises, consists essentially of, or consists of a THAP10 THAP domain, preferably having the amino acid sequence of amino acid positions 1 to 90 shown in SEQ ID NO: 12, or fragments or variants thereof. The invention also concerns the polypeptide encoded by the THAP10 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 12. In another aspect, a THAP10 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP10 polypeptide comprising, consisting essentially of, or consisting of a THAP domain at amino acid positions 1 to 90 shown in SEQ ID NO: 12, or fragments or variants thereof.

In a preferred embodiment, the THAP11 protein comprises, consists essentially of, or consists of a THAP11 THAP domain, preferably having the amino acid sequence of amino acid positions 1 to 90 shown in SEQ ID NO: 13, or fragments or variants thereof. The invention also concerns the polypeptide encoded by the THAP11 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 13. In another aspect, a THAP11 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP11 polypeptide comprising, consisting essentially of, or consisting of a THAP domain at amino acid positions 1 to 90 shown in SEQ ID NO: 13, or fragments or variants thereof.

In a preferred embodiment, the THAP-0 protein comprises, consists essentially of, or consists of a THAP-0 THAP domain, preferably having the amino acid sequence of amino acid positions 1 to 90 shown in SEQ ID NO: 14, or fragments or variants thereof. The invention also concerns the polypeptide encoded by the THAP-0 nucleotide sequences of the invention, or a complementary sequence thereof or a fragment thereof. The present invention thus also embodies isolated, purified, and recombinant polypeptides comprising, consisting essentially of or consisting of a contiguous span of at least 6 amino acids, preferably at least 8 to 10 amino acids, more preferably at least 12, 15, 20, 25, 30, 40, 50, 70, 80 or 90 amino acids of a sequence comprising amino acid positions 1 to 90 of SEQ ID NO: 14. In another aspect, a THAP-0 polypeptide may comprise a THAP domain wherein at least about 95%, 90%, 85%, 50-80%, preferably at least about 60-70%, more preferably at least about 65% of the amino acid residues are identical or similar amino acids-to the THAP domain consensus domain (SEQ ID NOs: 1-2). Also encompassed by the present invention are isolated, purified, nucleic acids encoding a THAP-0 polypeptide comprising, consisting essentially of, or consisting of a THAP domain at amino acid positions 1 to 90 shown in SEQ ID NO: 14, or fragments or variants thereof.

In other embodiments, the THAP-2 to THAP11 or THAP-0 protein is substantially homologous to the sequences of SEQ ID NOs: 4-14, 17-21, 23-40, 42-56, 58-98 or 100-114 and retains the functional activity of the THAP-2 to THAP11 or THAP-0 protein, yet differs in amino acid sequence due to natural allelic variation or mutagenesis, as described further herein. Accordingly, in another embodiment, the THAP-2 to THAP11 or THAP-0 protein is a protein which comprises an amino acid sequence that shares more than about 60% but less than 100% homology with the amino acid sequence of SEQ ID NOs: 4-14, 17-21, 23-40, 42-56, 58-98 or 100-114 and retains the functional activity of the THAP-2 to THAP11 or THAP-0 proteins of SEQ ID NOs: 4-14, 17-21, 23-40, 42-56, 58-98 or 100-114, respectively. Preferably, the protein is at least about 30%, 40%, 50%, 60%, 70%, 80%, 85%, 90%, 92%, 95%, 97%, 98%, 99% or 99.8% homologous to SEQ ID NOs: 4-14, 17-21, 23-40, 42-56, 58-98 or 100-114, but is not identical to SEQ ID NOs: 4-14, 17-21, 23-40, 42-56, 58-98 or 100-114. Preferably the THAP-2 to THAP11 or THAP-0 is less than identical (e.g. 100% identity) to a naturally occurring THAP-2 to THAP11 or THAP-0. Percent homology can be determined as further detailed above.

Assessing Polypeptides, Methods for Obtaining Variant Nucleic Acids and Polypeptides It will be appreciated that by characterizing the function of THAP-family polypeptides, the invention further provides methods of testing the activity of, or obtaining, functional fragments and variants of THAP-family and THAP domain nucleotide sequences involving providing a variant or modified THAP-family or THAP domain nucleic acid and assessing whether a polypeptide encoded thereby displays a THAP-family activity of the invention. Encompassed is thus a method of assessing the function of a THAP-family or THAP domain polypeptide comprising: (a) providing a THAP family or THAP domain polypeptide, or a biologically active fragment or homologue thereof; and (b) testing said THAP family or THAP domain polypeptide, or a biologically active fragment or homologue thereof for a THAP-family activity. Any suitable format may be used, including cell free, cell-based and in vivo formats. For example, said assay may comprise expressing a THAP-family or THAP domain nucleic acid in a host cell, and observing THAP-family activity in said cell. In another example, a THAP family or THAP domain polypeptide, or a biologically active fragment or homologue thereof is introduced to a cell, and a THAP-family activity is observed. THAP-family activity may be any activity as described herein, including (1) mediating apoptosis or cell proliferation when expressed or introduced into a cell, most preferably inducing or enhancing apoptosis, and/or most preferably reducing cell proliferation; (2) mediating apoptosis or cell proliferation of an endothelial cell; (3) mediating apoptosis or cell proliferation of a hyperproliferative cell; (4) mediating apoptosis or cell proliferation of a CNS cell, preferably a neuronal or glial cell; or (5) an activity determined in an animal selected from the group consisting of mediating, preferably inhibiting angiogenesis, mediating, preferably inhibiting inflammation, inhibition of metastatic potential of cancerous tissue, reduction of tumor burden, increase in sensitivity to chemotherapy or radiotherapy, killing a cancer cell, inhibition of the growth of a cancer cell, or induction of tumor regression.

In addition to naturally-occurring allelic variants of the THAP-family or THAP domain sequences that may exist in the population, the skilled artisan will appreciate that changes can be introduced by mutation into the nucleotide sequences of SEQ ID NOs: 160-171, thereby leading to changes in the amino acid sequence of the encoded THAP-family or THAP domain proteins, with or without altering the functional ability of the THAP-family or THAP domain proteins.

Several types of variants are contemplated including 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated THAP-family or THAP domain polypeptide is fused with another compound, such as a compound to increase the half-life of the polypeptide (for example, polyethylene glycol), or 4) one in which the additional amino acids are fused to the mutated THAP-family or THAP domain polypeptide, such as a leader or secretory sequence or a sequence which is employed for purification of the mutated THAP-family or THAP domain polypeptide or a preprotein sequence. Such variants are deemed to be within the scope of those skilled in the art.

For example, nucleotide substitutions leading to amino acid substitutions can be made in the sequences of SEQ ID NOs: 160-175 that do not substantially change the biological activity of the protein. An amino acid residue-can be altered from the wild-type sequence encoding a THAP family or THAP domain polypeptide, or a biologically active fragment or homologue thereof without altering the biological activity In general, amino acid residues that are conserved among the THAP-family of THAP domain-containing proteins of the present invention, are predicted to be less amenable to alteration. Furthermore, additional conserved amino acid residues may be amino acids that are conserved between the THAP-family proteins of the present invention.

In one aspect, the invention pertains to nucleic acid molecules encoding THAP family or THAP domain polypeptides, or biologically active fragments or homologues thereof that contain changes in amino acid residues that are not essential for activity. Such THAP-family proteins differ in amino acid sequence from SEQ ID NOs: 1-114 yet retain biological activity. In one embodiment, the isolated nucleic acid molecule comprises a nucleotide sequence encoding a protein, wherein the protein comprises an amino acid sequence at least about 60% homologous to an amino acid sequence selected from the group consisting of SEQ ID NOs: 1-114. Preferably, the protein encoded by the nucleic acid molecule is at least about 65-70% homologous to an amino acid sequence selected from the group consisting of SEQ ID NOs: 1-114, more preferably sharing at least about 75-80% identity with an amino acid sequence selected from the group consisting of SEQ ID NOs: 1-114, even more preferably sharing at least about 85%, 90%, 92%, 95%, 97%, 98%, 99% or 99.8% identity with an amino acid sequence selected from the group consisting of SEQ ID NOs: 1-114.

In another aspect, the invention pertains to nucleic acid molecules encoding THAP-family proteins that contain changes in amino acid residues that result in increased biological activity, or a modified biological activity. In another aspect, the invention pertains to nucleic acid molecules encoding THAP-family proteins that contain changes in amino acid residues that are essential for a THAP-family activity. Such THAP-family proteins differ in amino acid sequence from SEQ ID NOs: 1-114 and display reduced or essentially lack one or more THAP-family biological activities. The invention also encompasses a THAP family or THAP domain polypeptide, or a biologically active fragment or homologue thereof which may be useful as dominant negative mutant of a THAP family or THAP domain polypeptide.

An isolated nucleic acid molecule encoding a THAP family or THAP domain polypeptide, or a biologically active fragment or homologue thereof homologous to a protein of any one of SEQ ID NOs: 1-114 can be created by introducing one or more nucleotide substitutions, additions or deletions into the nucleotide sequence of SEQ ID NOs: 1-114 such that one or more amino acid substitutions, additions or deletions are introduced into the encoded protein. Mutations can be introduced into any of SEQ ID NOs: 1-114, by standard techniques, such as site-directed mutagenesis and PCR-mediated mutagenesis. For example, conservative amino acid substitutions may be made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a THAP family or THAP domain polypeptide, or a biologically active fragment or homologue thereof may be replaced with another amino acid residue from the same side chain family. Alternatively, in another embodiment, mutations can be introduced randomly along all or part of a THAP-family or THAP domain coding sequence, such as by saturation mutagenesis, and the resultant mutants can be screened for THAP-family biological activity to identify mutants that retain activity. Following mutagenesis of one of SEQ ID NOs: 1-114, the encoded protein can be expressed recombinantly and the activity of the protein can be determined.

In a preferred embodiment, a mutant THAP family or THAP domain polypeptide, or a biologically active fragment or homologue thereof encoded by a THAP family or THAP domain polypeptide, or a biologically active fragment or homologue thereof of THAP domain nucleic acid of the invention can be assayed for a THAP-family activity in any suitable assay, examples of which are provided herein.

The invention also provides THAP-family or THAP domain chimeric or fusion proteins. As used herein, a THAP-family or THAP domain "chimeric protein" or "fusion protein" comprises a THAP-family or THAP domain polypeptide of the invention operatively linked, preferably fused in frame, to a non-THAP-family or non-THAP domain polypeptide. In a preferred embodiment, a THAP-family or THAP domain fusion protein comprises at least one biologically active portion of a THAP-family or THAP domain protein. In another preferred embodiment, a THAP-family fusion protein comprises at least two biologically active portions of a THAP-family protein. For example, in one embodiment, the fusion protein is a GST-THAP-family fusion protein in which the THAP-family sequences are fused to the C-terminus of the GST sequences. Such fusion proteins can facilitate the purification of recombinant THAP-family polypeptides. In another embodiment, the fusion protein is a THAP-family protein containing a heterologous signal sequence at its N-terminus, such as for example to allow for a desired cellular localization in a certain host cell.

The THAP-family or THAP domain fusion proteins of the invention can be incorporated into pharmaceutical compositions and administered to a subject in vivo. Moreover, the THAP-family-fusion or THAP domain proteins of the invention can be used as immunogens to produce anti-THAP-family or anti or THAP domain antibodies in a subject, to purify THAP-family or THAP domain ligands and in screening assays to identify molecules which inhibit the interaction of THAP-family or THAP domain with a THAP-family or THAP domain target molecule.

Furthermore, isolated peptidyl portions of the subject THAP-family or THAP domain proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a THAP-family or THAP domain protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a THAP-family protein activity, such as by microinjection assays or in vitro protein binding assays. In an illustrative embodiment, peptidyl portions of a THAP-family protein, such as a THAP domain or a THAP-family target binding region (e.g. PAR4 in the case of THAP1, THAP-2 and THAP-3), can be tested for THAP-family activity by expression as thioredoxin fusion proteins, each of which contains a discrete fragment of the THAP-family protein (see, for example, U.S. Pat. Nos. 5,270,181 and 5,292,646; and PCT publication WO94/02502, the disclosures of which are incorporated herein by reference).

The present invention also pertains to variants of the THAP-family or THAP domain proteins which function as either THAP-family or THAP domain mimetics or as THAP-family or THAP domain inhibitors. Variants of the THAP-family or THAP domain proteins can be generated by mutagenesis, e.g., discrete point mutation or truncation of a THAP-family or THAP domain protein. An agonist of a THAP-family or THAP domain protein can retain substantially the same, or a subset, of the biological activities of the naturally occurring form of a THAP-family or THAP domain protein. An antagonist of a THAP-family or THAP domain protein can inhibit one or more of the activities of the naturally occurring form of the THAP-family or THAP domain protein by, for example, competitively inhibiting the association of a THAP-family or THAP domain protein with a THAP-family target molecule. Thus, specific biological effects can be elicited by treatment with a variant of limited function. In one embodiment, variants of a THAP-family or THAP domain protein which function as either THAP-family or THAP domain agonists (mimetics) or as THAP-family or THAP domain antagonists can be identified by screening combinatorial libraries of mutants, e.g., truncation mutants, of a THAP-family or THAP domain protein for THAP-family or THAP domain protein agonist or antagonist activity. In one embodiment, a variegated library of THAP-family variants is generated by combinatorial mutagenesis at the nucleic acid level and is encoded by a variegated gene library. A variegated library of THAP-family variants can be produced by, for example, enzymatically ligating a mixture of synthetic oligonucleotides into gene sequences such that a degenerate set of potential THAP-family sequences is expressible as individual polypeptides, or alternatively, as a set of larger fusion proteins (e.g., for phage display) containing the set of THAP-family sequences therein. There are a variety of methods which can be used to produce libraries of potential THAP-family variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential THAP-family sequences.

In addition, libraries of fragments of a THAP-family or THAP domain protein coding sequence can be used to generate a variegated population of THAP-family or THAP domain fragments for screening and subsequent selection of variants of a THAP-family or THAP domain protein. In one embodiment, a library of coding sequence fragments can be generated by treating a double stranded PCR fragment of a THAP-family coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the THAP-family protein.

Modified THAP-family or THAP domain proteins can be used for such purposes as enhancing therapeutic or prophylactic efficacy, or stability (e.g., ex vivo shelf life and resistance to proteolytic degradation in vivo). Such modified peptides, when designed to retain at least one activity of the naturally occurring form of the protein, are considered functional equivalents of the THAP-family or THAP domain protein described in more detail herein. Such modified peptide can be produced, for instance, by amino acid substitution, deletion, or addition.

Whether a change in the amino acid sequence of a peptide results in a functional THAP-family or THAP domain homolog (e.g. functional in the sense that it acts to mimic or antagonize the wild-type form) can be readily determined by assessing the ability of the variant peptide to produce a response in cells in a fashion similar to the wild-type THAP-family or THAP domain protein or competitively inhibit such a response. Peptides in which more than one replacement has taken place can readily be tested in the same manner.

This invention further contemplates a method of generating sets of combinatorial mutants of the presently disclosed THAP-family or THAP domain proteins, as well as truncation and fragmentation mutants, and is especially useful for identifying potential variant sequences which are functional in binding to a THAP-family- or THAP domain-target protein but differ from a wild-type form of the protein by, for example, efficacy, potency and/or intracellular half-life. One purpose for screening such combinatorial libraries is, for example, to isolate novel THAP-family or THAP domain homologs which function as either an agonist or an antagonist of the biological activities of the wild-type protein, or alternatively, possess novel activities all together. For example, mutagenesis can give rise to THAP-family homologs which have intracellular half-lives dramatically different than the corresponding wild-type protein. The altered protein can be rendered either more stable or less stable to proteolytic degradation or other cellular process which result in destruction of, or otherwise inactivation of, a THAP-family protein. Such THAP-family homologs, and the genes which encode them, can be utilized to alter the envelope of expression for a particular recombinant THAP-family protein by modulating the half-life of the recombinant protein. For instance, a short half-life can give rise to more transient biological effects associated with a particular recombinant THAP-family protein and, when part of an inducible expression system, can allow tighter control of recombinant protein levels within a cell. As above, such proteins, and particularly their recombinant nucleic acid constructs, can be used in gene therapy protocols.

In an illustrative embodiment of this method, the amino acid sequences for a population of THAP-family homologs or other related proteins are aligned, preferably to promote the highest homology possible. Such a population of variants can include, for example, THAP-family homologs from one or more species, or THAP-family homologs from the same species but which differ due to mutation. Amino acids which appear at each position of the aligned sequences are selected to create a degenerate set of combinatorial sequences. There are many ways by which the library of potential THAP-family homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential THAP-family sequences. The synthesis of degenerate oligonucleotides is well known in the art (see for example. Narang, S A (1983) Tetrahedron 393; Itakura et al. (1981) Recombinant DNA, Proc 3rd Cleveland Sympos. Macromolecules, ed. A G Walton, Amsterdam: Elsevier pp. 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223, 409, 5,198,346, and 5,096,815). The disclosures of the above references are incorporated herein by reference in their entireties.

Alternatively, other forms of mutagenesis can be utilized to generate a combinatorial library, particularly where no other naturally occurring homologs have yet been sequenced. For example, THAP-family homologs (both agonist and antagonist forms) can be generated and isolated from a library by screening using, for example, alanine scanning mutagenesis and the like (Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244: 1081-1085), by linker scanning mutagenesis (Gustin et al. (1993) Virology 193:653-660; Brown et al. (1992) Mol. Cell Biol. 12:2644 2652; McKnight et al. (1982) Science 232: 316); by saturation mutagenesis (Meyers et al. (1986) Science 232:613); by PCR mutagenesis (Leung et al. (1989) Method Cell Mol Biol 1: 1-19); or by random mutagenesis (Miller et al. (1992) A Short Course in Bacterial Genetics, CSHL Press, Cold Spring Harbor, N.Y.; and Greener et al. (1994) Strategies in Mol Biol 7:32-34, the disclosures of which are incorporated herein by reference in their entireties).

A wide range of techniques are known in the art for screening gene products of combinatorial libraries made by point mutations, as well as for screening cDNA libraries for gene products having a certain property. Such techniques will be generally adaptable for rapid screening of the gene libraries generated by the combinatorial mutagenesis of THAP-family proteins. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Each of the illustrative assays described below are amenable to high through-put analysis as necessary to screen large numbers of degenerate THAP-family or THAP domain sequences created by combinatorial mutagenesis techniques. In one screening assay, the candidate gene products are displayed on the surface of a cell or viral particle, and the ability of particular cells or viral particles to bind a THAP-family target molecule (protein or DNA) via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371, and Goward et al. (1992) TIBS 18:136 140). In a similar fashion, fluorescently labeled THAP-family target can be used to score for potentially functional THAP-family homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffiths et al. (1993) EMBO J. 12:725-734; Clackson et al. (1991) Nature 352:624-628; and Barbas et al. (1992) PNAS 89:4457 4461, the disclosures of which are incorporated herein by reference in their entireties). In an illustrative embodiment, the recombinant phage antibody system (RPAS, Pharmacia Catalog number 27-9400-01) can be easily modified for use in expressing THAP-family combinatorial libraries, and the THAP-family phage library can be panned on immobilized THAP family target molecule (glutathione immobilized THAP-family target-GST fusion proteins or immobilized DNA). Successive rounds of phage amplification and panning can greatly enrich for THAP-family homologs which retain an ability to bind a THAP-family target and which can subsequently be screened further for biological activities in automated assays, in order to distinguish between agonists and antagonists.

The invention also provides for identification and reduction to functional minimal size of the THAP-family domains, particularly a THAP domain of the subject THAP-family to generate mimetics, e.g. peptide or non-peptide agents, which are able to disrupt binding of a polypeptide of the present invention with a THAP-family target molecule (protein or DNA). Thus, such mutagenic techniques as described above are also useful to map the determinants of THAP-family proteins which participate in protein-protein or protein-DNA interactions involved in, for example, binding to a THAP-family or THAP domain target protein or DNA. To illustrate, the critical residues of a THAP-family protein which are involved in molecular recognition of the THAP-family target can be determined and used to generate THAP-family target-13P-derived peptidomimetics that competitively inhibit binding of the THAP-family protein to the THAP-family target. By employing, for example, scanning mutagenesis to map the amino acid residues of a particular THAP-family protein involved in binding a THAP-family target, peptidomimetic compounds can be generated which mimic those residues in binding to a THAP-family target, and which, by inhibiting binding of the THAP-family protein to the THAP-family target molecule, can interfere with the function of a THAP-family protein in transcriptional regulation of one or more genes. For instance, non hydrolyzable peptide analogs of such residues can be generated using retro-inverse peptides (e.g., see U.S. Pat. Nos. 5,116,947 and 5,219,089; and Pallai et al. (1983) Int J Pept Protein Res 21:84-92), benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides.—Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), P-turn dipeptide cores (Nagai et al. (1985) Tetrahedron Left 26:647; and Sato et al. (1986) J Chem Soc Perkin Trans 1: 1231), and P-aminoalcohols (Gordon et al. (1985) Biochem Biophys Res Commun 126:419; and Dann et al. (1986) Biochem Biophys Res Commun 134:71, the disclosures of which are incorporated herein by reference in their entireties).

An isolated THAP-family or THAP domain protein, or a portion or fragment thereof, can be used as an immunogen to generate antibodies that bind THAP-family or THAP domain proteins using standard techniques for polyclonal and monoclonal antibody preparation. A full-length THAP-family protein can be used or, alternatively, the invention provides antigenic peptide fragments of THAP-family or THAP domain proteins for use as immunogens. Any fragment of the THAP-family or THAP domain protein which contains at least one antigenic determinant may be used to generate antibodies. The antigenic peptide of a THAP-family or THAP domain protein comprises at least 8 amino acid residues of an amino acid sequence selected from the group consisting of SEQ ID NOs: 1-114 and encompasses an epitope of a THAP-family or THAP domain protein such that an antibody raised against the peptide forms a specific immune complex with a THAP-family or THAP domain protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of a THAP-family or THAP domain protein that are located on the surface of the protein, e.g., hydrophilic regions.

A THAP-family or THAP domain protein immunogen typically is used to prepare antibodies by immunizing a suitable subject, (e.g., rabbit, goat, mouse or other mammal) with the immunogen. An appropriate immunogenic preparation can contain, for example, recombinantly expressed THAP-family or THAP domain protein or a chemically synthesized THAP-family or THAP domain polypeptide. The preparation can further include an adjuvant, such as Freund's complete or incomplete adjuvant, or similar immunostimulatory agent. Immunization of a suitable subject with an immunogenic THAP-family or THAP domain protein preparation induces a polyclonal anti-THAP-family or THAP domain protein antibody response.

The invention concerns antibody compositions, either polyclonal or monoclonal, capable of selectively binding, or selectively bind to an epitope-containing a polypeptide comprising a contiguous span of at least 6 amino acids, preferably at least 8 to 10 amino acids, more preferably at least 12, 15, 20, 25, 30, 40, 50, 100, or more than 100 amino acids of an amino acid sequence selected from the group consisting of amino acid positions 1 to approximately 90 of SEQ ID NOs: 1-114. The invention also concerns a purified or isolated antibody capable of specifically binding to a mutated THAP-family or THAP domain protein or to a fragment or variant thereof comprising an epitope of the mutated THAP-family or THAP domain protein.

Oligomeric Forms of THAP1

Certain embodiments of the present invention encompass THAP1 polypeptides in the form of oligomers, such as dimers, trimers, or higher oligomers. Oligomers may be formed by disulfide bonds between cysteine residues on different THAP1 polypeptides, for example. In other embodiments, oligomers comprise from two to four THAP1 polypeptides joined by covalent or non-covalent interactions between peptide moieties fused to the THAP1 polypeptides. Such peptide moieties may be peptide linkers (spacers), or peptides that have the property of promoting oligomerization. Leucine zippers and certain polypeptides derived from antibodies are among the peptides that can promote oligomerization of THAP1 polypeptides attached thereto. DNA sequences encoding THAP1 oligomers, or fusion proteins that are components of such oligomers, are provided herein.

In one embodiment of the invention, oligomeric THAP1 may comprise two or more THAP1 polypeptides joined through peptide linkers. Examples include those peptide linkers described in U.S. Pat. No. 5,073,627, the disclosure of which is incorporated herein by reference in its entirety. Fusion proteins comprising multiple THAP1 polypeptides separated by peptide linkers may be produced using conventional recombinant DNA technology.

Another method for preparing THAP1 oligomers involves use of a leucine zipper. Leucine zipper domains are peptides that promote oligomerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. Examples of leucine zipper domains suitable for producing THAP1 oligomers are those described International Publication WO 94/10308, the disclosure of which is incorporated herein by reference in its entirety. Recombinant fusion proteins comprising a THAP1 polypeptide fused to a peptide that dimerizes or trimerizes in solution are expressed in suitable host cells, and the resulting soluble oligomeric THAP1 is recovered from the culture supernatant.

In some embodiments of the invention, a THAP1 dimer is created by fusing THAP1 to an Fc region polypeptide derived from an antibody, in a manner that does not substantially affect the binding of THAP1 to the chemokine SLC/CCL21. Preparation of fusion proteins comprising heterologous polypeptides fused to various portions of antibody-derived polypeptides (including Fc region) has been described, e.g., by Ashkenazi et al. (1991) PNAS 88:10535, Byrn et al. (1990) Nature 344:667, and Hollenbaugh and Aruffo "Construction of Immunoglobulin Fusion Proteins", in Current Protocols in Immunology, Supp. 4, pages 10.19.1-10.19-11, 1992, the disclosures of which are incorporated herein by reference in their entireties. The THAP1/Fc fusion proteins are allowed to assemble much like antibody molecules, whereupon interchain disulfide bonds form between Fc polypeptides, yielding divalent THAP1. Similar fusion proteins of TNF receptors and Fc (see for example Moreland et al. (1997) N. Engl. J. Med. 337(3):141-147; van der Poll et al. (1997) Blood 89(10):3727-3734; and Ammann et al. (1997) J. Clin. Invest. 99(7):1699-1703) have been used successfully for treating rheumatoid arthritis. Soluble derivatives have also been made of cell surface glycoproteins in the immunoglobulin gene superfamily consisting of an extracellular domain of the cell surface glycoprotein fused to an immunoglobulin constant (Fc) region (see e.g., Capon, D. J. et al. (1989) Nature 337: 525-531 and Capon U.S. Pat. Nos. 5,116,964 and 5,428,130 [CD4-IgG1 constructs]; Linsley, P. S. et al. (1991) J. Exp. Med. 173:721-730 [a CD28-IgG1 construct and a B7-1-IgG1 construct]; and Linsley, P. S. et al. (1991) J. Exp. Med. 174: 561-569 and U.S. Pat. No. 5,434,131 [a CTLA4-IgG1], the disclosures of which are incorporated herein by reference in their entirety). Such fusion proteins have proven useful for modulating receptor-ligand interactions.

Some embodiments relate to THAP-immunoglobulin fusion proteins and THAP SLC-binding domain fusions with immunoglobulin molecules or fragments thereof. Such fusions can be produced using standard methods, for example, by creating an expression vector encoding the SLC/CCL21 chemokine-binding protein THAP1 fused to the antibody polypeptide and inserting the vector into a suitable host cell. One suitable Fc polypeptide is the native Fc region polypeptide derived from a human IgG1, which is described in International Publication WO 93/10151, the disclosure of which is incorporated herein by reference in its entirety. Another useful Fc polypeptide is the Fc mutein described in U.S. Pat. No. 5,457,035, the disclosure of which is incorporated herein by reference in its entirety. The amino acid sequence of the mutein is identical to that of the native Fc sequence presented in International Publication WO 93/10151, the disclosure of which is incorporated herein by reference in its entirety, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

SLC-binding fragments of human THAP1, rather than the full protein, can also be employed in methods of the invention. Fragments may be less immunogenic than the corresponding full-length proteins. The ability of a fragment to bind chemokine SLC can be determined using a standard assay. Fragments can be prepared by any of a number of conventional methods. For example, a desired DNA sequence can be synthesized chemically or produced by restriction endonuclease digestion of a full length cloned DNA sequence and isolated by electrophoresis on agarose gels. Linkers containing restriction endonuclease cleavage sites can be employed to insert the desired DNA fragment into an expression vector, or the fragment can be digested at naturally-present cleavage sites. The polymerase chain reaction (PCR) can also be employed to isolate a DNA sequence encoding a desired protein fragment. Oligonucleotides that define the termini of the desired fragment are used as 5' and 3' primers in the PCR procedure. Additionally, known mutagenesis techniques can be used to insert a stop codon at a desired point, e.g., immediately downstream of the codon for the last amino acid of the desired fragment.

In other embodiments, THAP1 or a biologically active fragment thereof, for example, an SLC-binding domain of THAP1 may be substituted for the variable portion of an antibody heavy or light chain. If fusion proteins are made with both heavy and light chains of an antibody, it is possible to form a THAP1 oligomer with at least two, at least three, at least four, at least five, at least six, at least seven, at least eight, at least nine, or more than nine THAP1 polypeptides.

In some embodiments of the present invention, THAP-SLC binding can be provided to decrease the biological availability of SLC or otherwise disrupt the activity of SLC. For example, THAP-family polypeptides, SLC-binding domains of THAP-family polypeptides, THAP oligomers, and SLC-binding domain-THAP1-immunoglobulin fusion proteins of the invention can be used to interact with SLC thereby preventing it from performing its normal biological role. In some embodiments, the entire THAP1 polypeptide (SEQ ID NO: 3) can be used to bind to SLC. In other embodiments, fragments of THAP1, such as the SLC-binding domain of the THAP1 (amino acids 143-213 of SEQ ID NO: 3) can used to bind to SLC. Such fragments can be from at least 8, at least 10, at least 12, at least 15, at least 20, at least 25, at least 30, at least 35, at least 40, at least 45, at least 50, at least 55, at least 60, at least 65, at least 70, at least 80, at least 90, at least 100, at least 110, at least 120, at least 130, at least 140, at least 150, at least 160, at least 170, at least 180, at least 190, at least 200, at least 210 or at least 213 consecutive amino acids of SEQ ID NO: 3. In some embodiments, fragments can be from at least 8, at least 10, at least 12, at least 15, at least 20, at least 25, at least 30, at least 35, at least 40, at least 45, at least 50, at least 55, at least 60, at least 65 or at least 70 consecutive amino acids of (amino acids 143-213 of SEQ ID NO: 3). THAP-family polypeptides that may be capable of binding SLC, for example THAP2-11 and THAP0 or biologically active fragments thereof can also be used to bind to SLC so as to decrease its biological availability or otherwise disrupt the activity of this chemokine.

In some embodiments, a plurality of THAP-family proteins, such as a fusion of two or more THAP1 proteins or fragments thereof which comprise an SLC-binding domain (amino acids 143-213 of SEQ ID NO: 3) can be used to bind SLC. For example, oligomers comprising THAP1 fragments of a size of at least 8, at least 10, at least 12, at least 15, at least 20, at least 25, at least 30, at least 35, at least 40, at least 45, at least 50, at least 55, at least 60, at least 65 or at least 70 consecutive amino acids of SEQ ID NO: 3 (amino acids 143-213) can be generated. Amino acid fragments which make up the THAP oligomer may be of the same or different lengths. In some embodiments, the entire THAP1 protein or biologically active portions thereof may be fused together to form an oligomer capable of binding to SLC. THAP-family polypeptides that may be capable of binding SLC, for example THAP2-11 and THAP0, the THAP-family polypeptides of SEQ ID NOs: 16-114 or biologically active fragments thereof can also be used to create oligomers which bind to SLC so as to decrease its biological availability or otherwise disrupt the activity of this chemokine.

According to another embodiment of the present invention, THAP-family proteins, such as THAP1 or portion of THAP1 which comprise an SLC binding domain (amino acids 143-213 of SEQ ID NO: 3), may be fused to an immunoglobulin or portion thereof. The portion may be an entire immunoglobulin, such as IgG, IgM, IgA or IgE. Additionally, portions of immunoglobulins, such as an Fc domain of the immunoglobulin, can be fused to a THAP-family polypeptide, such as THAP1, fragments thereof or oligomers thereof. Fragments of THAP1 can be, for example, at least 8, at least 10, at least 12, at least 15, at least 20, at least 25, at least 30, at least 35, at least 40, at least 45, at least 50, at least 55, at least 60, at least 65 or at least 70 consecutive amino acids of SEQ ID NO: 3 (amino acids 143-213). In some embodiments, THAP-family polypeptides that may be capable of binding SLC, for example THAP2-11 and THAP0, the THAP-family polypeptides of SEQ ID NOs: 16-114 or biologically active fragments thereof can also be used to form immunoglobulin fusion that bind to SLC so as to decrease its biological availability or otherwise disrupt the activity of this chemokine.

In accordance with another aspect of the invention, THAP-family polypeptides, SLC-binding domains of THAP-family polypeptides, THAP oligomers, and SLC-binding domain-THAP1-immunoglobulin fusion proteins of the invention can be incorporated into pharmaceutical compositions. Such pharmaceutical compositions can be used to decrease the bioavailability and functionality of SLC. For example, THAP-family polypeptides, SLC-binding domains of THAP-family polypeptides, THAP oligomers, and SLC-binding domain-THAP1-immunoglobulin fusion proteins of the present invention can be administered to a subject to inhibit an interaction between SLC and its receptor, such as CCR7, on the surface of cells, to thereby suppress SLC-mediated responses. The inhibition of chemokine SLC may be useful therapeutically for both the treatment of inflammatory or proliferative disorders, as well as modulating (e.g., promoting or inhibiting) cell differentiation, cell proliferation, and/or cell death.

In an additional embodiment of the present invention, the THAP-family polypeptides, SLC-binding domains of THAP-family polypeptides, THAP oligomers, and SLC-binding domain-THAP1-immunoglobulin fusion proteins of the present invention can be used to detect the presence of SLC in a biological sample and in screening assays to identify molecules which inhibit the interaction of THAP1 with SLC. Such screening assays are similar to those described below for PAR4-THAP interactions.

Certain aspects of the present invention related to a method of identifying a test compound that modulates THAP-mediated activites. In some cases the THAP-mediated acitivity is SLC-binding. Test compounds which affect THAP-SLC binding can be identified using a screening method wherein a THAP-family polypeptide or a biologically active fragment thereof is contacted with a test compound. In some embodiments, the THAP-family polypeptide comprises an amino acid sequence having at least 30% amino acid identity to an amino acid sequence of SEQ ID NO: 1 or SEQ ID NO: 2. Whether the test compound modulates the binding of SLC with a THAP-family polypeptide, such as THAP1 (SEQ ID NO: 3), is determined by determining whether the test compound modulates the activity of the THAP-family polypeptide or biologically active fragment thereof. Biologically active framents of a THAP-family polypeptide may be at least 5, at least 8, at least 10, at least 12, at least 15, at least 18, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220 or at least more than 220 amino acids in length. A determination that the test compound modulates the activity of said polypeptide indicates that the test compound is a candidate modulator of THAP-mediated activities.

Although THAP-family polypeptides, SLC-binding domains of THAP-family polypeptides, THAP oligomers, and SLC-binding domain-THAP1-immunoglobulin fusion proteins can be used for the above-mentioned SLC interactions, it will be appreciated that homologs of THAP-family polypeptides, SLC-binding domains of THAP-family polypeptides, THAP oligomers, and SLC-binding domain-THAP1-immunoglobulin fusion proteins can be used in place of THAP-family polypeptides, SLC-binding domains of THAP-family polypeptides, THAP oligomers, and SLC-binding domain-THAP1-immunoglobulin fusion proteins. For example, homologs having at least about 30-40% identity, preferably at least about 40-50% identity, more preferably at least about 50-60%, and even more preferably at least about 60-70%, 70-80%, 80%, 90%, 95%, 97%, 98%, 99% or 99.8% identity across the amino acid sequences of SEQ ID NOs: 1-114 or portions thereof can be used.

Primers and Probes

Primers and probes of the invention can be prepared by any suitable method, including, for example, cloning and restriction of appropriate sequences and direct chemical synthesis by a method such as the phosphodiester method of Narang S A et al (Methods Enzymol 1979;68:90-98), the phosphodiester method of Brown E L et al (Methods Enzymol 1979;68: 109-151), the diethylphosphoramidite method of Beaucage et al (Tetrahedron Lett 1981, 22: 1859-1862) and the solid support method described in EP 0 707 592, the disclosures of which are incorporated herein by reference in their entireties.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. If desired, the probe may be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in (Urdea et al. (Nucleic Acids Research. 11:4937-4957, 1988) or Sanchez-Pescador et al. (J. Clin. Microbiol. 26(10):1934-1938, 1988). In addition, the probes according to the present invention may have structural characteristics such that they allow the signal amplification, such structural characteristics being, for example, branched DNA probes as those described by Urdea et al (Nucleic Acids Symp. Ser. 24:197-200, 1991) or in the European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in a THAP-family gene or mRNA using other techniques.

Any of the nucleic acids, polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes and other configurations known to those of ordinary skill in the art. The nucleic acids, polynucleotides, primers and probes of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Any polynucleotide provided herein may be attached in overlapping areas or at random locations on a solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips, and has been generally described in U.S. Pat. No. 5,143,854; PCT publications WO 90/15070 and 92/10092, the disclosures of which are incorporated herein by reference in their entireties.

Recombinant Expression Vectors and Host Cells

Another aspect of the invention pertains to vectors, preferably expression vectors, containing a nucleic acid encoding a THAP family or THAP domain polypeptide, or a biologically active fragment or homologue thereof.

Vectors may have particular use in the preparation of a recombinant protein of the invention, or for use in gene therapy. Gene therapy presents a means to deliver a THAP family or THAP domain polypeptide, or a biologically active fragment or homologue thereof to a subject in order to regulate apoptosis for treatment of a disorder.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a THAP-family or THAP domain nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990), the disclosure of which is incorporated herein by reference in its entirety. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., THAP-family proteins, mutant forms of THAP-family proteins, fusion proteins, or fragments of any of the preceding proteins, etc.).

The recombinant expression vectors of the invention can be designed for expression of a THAP family or THAP domain polypeptide, or a biologically active fragment or homologue thereof in prokaryotic or eukaryotic cells. For example, THAP-family or THAP domain proteins can be expressed in bacterial cells such as E. coli, insect cells (using baculovirus expression vectors) yeast cells, or mammalian cells. Suitable host cells are discussed further in Goeddel, Gene Expression Technology: Methods in Enzymology 185, Academic Press, San Diego, Calif. (1990), the disclosure of which is incorporated herein by reference in its entirety. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.), the disclosures of which are incorporated herein by reference in their entireties, which fuse glutathione S-transferase (GST), maltose E binding protein, or protein A, respectively, to the target recombinant protein.

Purified fusion proteins can be utilized in THAP-family activity assays, (e.g., direct assays or competitive assays described in detail below), or to generate antibodies specific for THAP-family or THAP domain proteins, for example. In a preferred embodiment, a THAP-family or THAP domain fusion protein expressed in a retroviral expression vector of the present invention can be utilized to infect bone marrow cells which are subsequently transplanted into irradiated recipients. The pathology of the subject recipient is then examined after sufficient time has passed (e.g. six (6) weeks).

Examples of suitable inducible non-fusion *E. coli* expression vectors include pTrc (Amann et al., (1988) Gene 69:301-315) and pET 11d (Studier et al., Gene Expression Technology: Methods in Enzymology 185, Academic Press, San Diego, Calif. (1990) 60-89), the disclosures of which are incorporated herein by reference in their entireties. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn 1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128, the disclosure of which is incorporated herein by reference in its entirety). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118, the disclosure of which is incorporated herein by reference in its entirety). Such alteration of nucleic acid sequences of the invention can be carried out by standard DNA synthesis techniques.

In another embodiment, the THAP-family expression vector is a yeast expression vector. Examples of vectors for expression in yeast *S. cerivisae* include pYepSec 1 (Baldari, et al., (1987) Embo J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.), the disclosures of which are incorporated herein by reference in their entireties.

Alternatively, THAP-family or THAP domain proteins can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170: 31-39), the disclosures of which are incorporated herein by reference in their entireties. In particularly preferred embodiments, THAP-family proteins are expressed according to Karniski et al, Am. J. Physiol. (1998) 275: F79-87, the disclosure of which is incorporated herein by reference in its entirety.

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195), the disclosures of which are incorporated herein by reference in their entireties. When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989, the disclosure of which is incorporated herein by reference in its entirety. In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art, and are further described below.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to THAP-family mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986, the disclosure of which is incorporated herein by reference in its entirety.

Another aspect of the invention pertains to host cells into which a recombinant expression vector of the invention has been introduced. The terms "host cell" and "recombinant host cell" are used interchangeably herein. It is understood that such term refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a THAP-family protein can be expressed in bacterial cells such as *E. coli*, insect cells, yeast or mammalian cells (such as Chinese hamster ovary cells (CHO) or COS cells or human cells). Other suitable host cells are known to those skilled in the art, including mouse 3T3 cells as further described in the Examples.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989, the disclosure of which is incorporated herein by reference in its entirety), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a THAP-family protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a THAP-family protein. Accordingly, the invention further provides methods for producing a THAP-family protein using the host cells of the invention. In one embodiment, the method comprises culturing the host cell of invention (into which a recombinant expression vector encoding a THAP-family protein has been introduced) in a suitable medium such that a THAP-family protein is produced. In another embodiment, the method further comprises isolating a THAP-family protein from the medium or the host cell.

In another embodiment, the invention encompasses a method comprising: providing a cell capable of expressing a THAP family or THAP domain polypeptide, or a biologically active fragment or homologue thereof, culturing said cell in a suitable medium such that a THAP-family or THAP domain protein is produced, and isolating or purifying the THAP-family or THAP domain protein from the medium or cell.

The host cells of the invention can also be used to produce nonhuman transgenic animals, such as for the study of disorders in which THAP family proteins are implicated. For example, in one embodiment, a host cell of the invention is a fertilized oocyte or an embryonic stem cell into which THAP-family- or THAP domain-coding sequences have been introduced. Such host cells can then be used to create non-human transgenic animals in which exogenous THAP-family or THAP domain sequences have been introduced into their genome or homologous recombinant animals in which endogenous THAP-family or THAP domain sequences have been altered. Such animals are useful for studying the function and/or activity of a THAP-family or THAP domain polypeptide or fragment thereof and for identifying and/or evaluating modulators of a THAP-family or THAP domain activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous THAP-family or THAP domain gene has been altered by homologous recombination between the endogenous gene and an exogenous DNA molecule introduced into a cell of the animal, e.g., an embryonic cell of the animal, prior to development of the animal. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986, the disclosures of which are incorporated herein by reference in their entireties).

Gene Therapy Vectors

Preferred vectors for administration to a subject can be constructed according to well known methods. Vectors will comprise regulatory elements (e.g. promotor, enhancer, etc) capable of directing the expression of the nucleic acid in the targeted cell. Thus, where a human cell is targeted, it is preferable to position the nucleic acid coding region adjacent to and under the control of a promoter that is capable of being expressed in a human cell.

In various embodiments, the human cytomegalovirus (CMV) immediate early gene promoter, the SV40 early promoter, the Rous sarcoma virus long terminal repeat, β actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constituitively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristerone A. Another inducible system that would be useful is the Tet-Off or Tet On system (Clontech, Palo Alto, Calif.) originally developed by Gossen and Bujard (Gossen and Bujard, 1992; Gossen et al, 1995). This system also allows high levels of gene expression to be regulated in response to tetracycline or tetracycline derivatives such as doxycycline. In the Tet-On system, gene expression is turned on in the presence of doxycycline, whereas in the Tet-Off system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet Off system, of the VP16 domain from the herpes simplex virus and the wild-type tertracycline repressor.

Thus in the absence of doxycycline, transcription is constituitively on. In the Tet-OnTm system, the tetracycline repressor is not wild-type and in the presence of doxycycline activates transcription. For gene therapy vector production, the Tet Off system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic_cells is desired, retroviral promoters such as the LTRs from MLV or MMTV are often used. Other viral promoters that may be used depending on the desired effect include SV40, RSV LTR, HIV-1 and HfV-2 LTR, adenovirus promoters such as from the EIA, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters as follows may be used to target gene expression in other tissues.

Tissue specific promoters include in (a) pancreas: insulin, elastin, amylase, pdr-I, pdx-I, glucokinase; (b) liver: albumin PEPCK, HBV enhancer, alpha fetoprotein, apolipoprotein C, alpha-I antitrypsin, vitellogenin, NF-AB, Transthyretin; (c) skeletal muscle: myosin H chain, muscle creatine kinase, dystrophin, calpain p94, skeletal alpha-actin, fast troponin 1; (d) skin: keratin K6, keratin KI; (e) lung: CFTR, human cytokeratin IS (K 18), pulmonary surfactant proteins A, B and C, CC-10, Pi; (f) smooth muscle: sm22 alpha, SM-alpha-actin; (g) endothelium: endothelin-I, E-selectin, von Willebrand factor, TIE (Korhonen et al., 1995), KDR/flk-I; (h) melanocytes: tyrosinase; (i) adipose tissue: lipoprotein lipase (Zechner et al., 1988), adipsin (Spiegelman et al., 1989), acetyl-CoA carboxylase (Pape and Kim, 1989), glycerophosphate dehydrogenase (Dani et al., 1989), adipocyte P2 (Hunt et al., 1986); and (j) blood: P-globin.

In certain indications, it may be desirable to activate transcription at specific times after administration of the gene therapy vector. This may be done with such promoters as those that are hormone or cytokine regulatable. For example in gene therapy applications where the indication is in a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1antitypsin, lipoprotein lipase (Zechner et al., 1988), angiotensinogen (Ron et al., 1991), fibrinogen, c-jun (inducible by phorbol esters, TNF alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-I antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2FI, p53 and BRCAI could be used.

Tumor specific promoters such as osteocalcin, hypoxia-responsive element (HRE), NIAGE-4, CEA, alpha-fetoprotein, GRP78/BiP and tyrosinase also may be used to regulate gene expression in tumor cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996), the disclosure of which is incorporated herein by reference.

It is envisioned that any of the above promoters alone or in combination with another may be useful according to the present invention depending on the action desired.

In addition, this list of promoters should not be considered to be exhaustive or limiting, those of skill in the art will know of other promoters that may be used in conjunction with the THAP-family and THAP domain nucleic acids and methods disclosed herein.

Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (list of enhancers, and Table 1). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

Suitable enhancers include: Immunoglobulin Heavy Chain; Immunoglobulin Light Chain; T-Cell Receptor; HLA DQ (x and DQ beta; beta-Interferon; Interleukin-2; Interleukin-2 Receptor; MHC Class II 5; MHC Class II HLA-DRalpha; beta-Actin; Muscle Creatine Kinase; Prealbumin (Transthyretin); Elastase I; Metallothionein; Collagenase; Albumin Gene; alpha-Fetoprotein; -Globin; beta-Globin; e-fos; c-HA-ras; Insulin; Neural Cell Adhesion Molecule (NCAM); alpha al-Antitrypsin; $H_2B$ (TH2B) Histone; Mouse or Type I Collagen; Glucose-Regulated Proteins (GRP94 and GRP78); Rat Growth Hormone; Human Serum Amyloid A (SAA); Troponin I (TN 1); Platelet-Derived Growth Factor; Duchenne Muscular Dystrophy; SV40; Polyoma; Retroviruses; THAPilloma Virus; Hepatitis B Virus; Human Immunodeficiency Virus; Cytomegalovirus; and Gibbon Ape Leukemia Virus.

TABLE 1

| Element | Inducer |
| --- | --- |
| MT 11 Heavy metals MMTV (mouse mammary tumor Glucocorticoids virus) | Phorbol Ester (TPA) |
| B-Interferon | poly(rI)X; poly(rc) |
| Adenovirus 5 E2 | Ela |
| c-jun | Phorbol Ester (TPA), H2O2 |

TABLE 1-continued

| Element | Inducer |
| --- | --- |
| H202 Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| oc-2-Macroglobulin | IL-6 |
| Vimentin Serum NMC Class I Gene H-2kB | Interferon |
| HSP70 | Ela, SV40 Large T Antigen |
| Insulin E Box | Glucose |
| Proliferin | Phorbol Ester-TPA |
| Tumor Necrosis Factor | FMA |
| Thyroid Stimulating Hormone alpha Gene | Thyroid Hormone |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986, the disclosures of which are incorporated herein by reference). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum.

Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

(iii) Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

Antisense Constructs

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, micleic acid sequences of fifteen bases in length may be termed complementary when they have a complementary nucleotide at thirteen or fourteen positions with only single or double mismatches. Naturally, nucleic acid sequences which are "completely complementary" will be nuleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence.

Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines.

Oligonucleotides which contain C-5 propyne analogues of uridine and cytidine have been shown to bind RNA with high affinity and to be potent antisense inhibitors of gene expression (Wagner et al, 1993).

Ribozyme Constructs

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

Methods of Gene Transfer

In order to mediate the effect of transgene expression in a cell, it will be necessary to transfer the therapeutic expression constructs of the present invention into a cell. This section provides a discussion of methods and compositions of viral production and viral gene transfer, as well as non-viral gene transfer methods.

(i) Viral Vector-Mediated Transfer

The THAP-family gene is incorporated into a viral infectious particle to mediate gene transfer to a cell. Additional expression constructs encoding other therapeutic agents as described herein may also be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral or non-viral vectors, as discussed below.

Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis acting elements necessary for viral DNA replication and packaging. The early (E) and late (L) regions of the genome that contain different transcription units are divided by the onset of viral DNA replication.

The E1 region (EIA and EIB) encodes proteins responsible for the regulation of transcription of the viral genome and a few cellular genes. The expression of the E2 region (E2A and E2B) results in the synthesis of the proteins for viral DNA replication.

These proteins are involved in DNA replication, late gene expression, and host cell shut off (Renan, 1990). The products of the late genes (L I, L2, U, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative case.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194 385 bp (0.5-1.1 map units) at the left end of the viral genome (Hearing et al., 1987). This signal mimics the protein recognition site in bacteriophage k DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed.

These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the EIA (194-358 bp) region of the genome grew poorly even in a cell line that complemented the early (EIA) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins.

The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed T, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and T components is constructed (Mann et al., 1983). When a recombinant plasmid containing a human cDNA, together with the retroviral LTR and T sequences is introduced into this cell line (by calcium phosphate precipitation for example), the T sequence allows the RNA transcript of the recombinant plasmid to be packaged into viral particles, which are then secreted into the culture media (Nicolas and Rubenstein, 1988; Temin, 1986; Mann et al., 1983, the disclosures of which are incorporated herein by reference). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP 2 and VP-3.

The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced.

The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus.

The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al, 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site specific integration.

The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chattedee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996; Xiao et al., 1996, the disclosures of which are incorporated herein by reference in their entireties).

AAV-mediated efficient gene transfer and expression in the lung has led to clinical trials for the treatment of cystic fibrosis (Carter and Flotte, 1996; Flotte et al., 1993, the disclosures of which are incorporated herein by reference). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; and Xiao et al., 1996, the disclosures of which are incorporated herein by reference in their entireties.).

Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) and hepatitus B viruses have also been developed and are useful in the present invention. They offer several attractive features for various mammalian cells (Friedmann, 1989; Ridgeway, 1988; Baichwal and Sugden, 1986; Coupar et al., 1988; and Horwich et al., 1990, the disclosures of which are incorporated herein by reference in their entireties.).

With the recent recognition of defective hepatitis B viruses, new insight was gained into the structure-function relationship of different viral sequences. In vitro studies showed that the virus could retain the ability for helper dependent packaging and reverse transcription despite the deletion of up to 80% of its genome (Horwich et al., 1990). This suggested that large portions of the genome could be replaced with foreign genetic material. Chang et al., recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

(ii) Non-Viral Transfer

DNA constructs of the present invention are generally delivered to a cell. In certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur Kaspa et al., 1986; Potter et al., 1984), direct microinjection (Harland and Weintraub, 1985), DNA loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988), the disclosures of which are incorporated herein by reference in their entireties.

Once the construct has been delivered into the cell the nucleic acid encoding the therapeutic gene may be positioned and expressed at different sites. In certain embodiments, the nucleic acid encoding the therapeutic gene may be stably integrated into the genome of the cell. Thi-s integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the P-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989).

In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor mediated endocytosis in almost all eukaryotic cells. Because of the cell type specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990).

Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al, (1987) employed lactosyl-ceramide, a galactose terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al, 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al, (1984) successfully injected polyornavirus DNA in the form of CaP04 precipitates into liver and spleen of adult and newborn mice demonstrating active viral replication and acute infection.

Benvenisty and Neshif (1986) also demonstrated that direct intraperitoneal injection of CaP04 precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al, 1987). Several devices for accelerating small particles have been developed. One such device relies on a high voltage discharge to generate an electrical cur-rent, which in turn provides the motive force (Yang et al, 1990). The microprojectiles used have consisted of biologically inert substances such as tungsten or gold beads.

Antibodies

Polyclonal anti-THAP-family or anti-THAP domain antibodies can be prepared as described above by immunizing a suitable subject with a THAP-family or THAP domain immunogen. The anti-THAP-family or anti-THAP domain antibody titer in the immunized subject can be monitored over time by standard techniques, such as with an enzyme linked immunosorbent assay (ELISA) using immobilized THAP-family or THAP domain protein. If desired, the antibody molecules directed against THAP-family can be isolated from the mammal (e.g., from the blood) and further purified by well known techniques, such as protein A chromatography to obtain the IgG fraction. At an appropriate time after immunization, e.g., when the anti-THAP-family antibody titers are highest, antibody-producing cells can be obtained from the subject and used to prepare monoclonal antibodies by standard techniques, such as those described in the following references, the disclosures of which are incorporated herein by reference in their entireties: the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) PNAS 76:2927-31; and Yeh et al. (1982) Int. J. Cancer 29:269-75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Briefly, an immortal cell line (typically a myeloma) is fused to lymphocytes (typically splenocytes) from a mammal immunized with a THAP-family immunogen as described above, and the culture supernatants of the resulting hybridoma cells are screened to identify a hybridoma producing a monoclonal antibody that binds THAP-family.

Any of the many well known protocols used for fusing lymphocytes and immortalized cell lines can be applied for the purpose of generating an anti-THAP-family or anti-THAP domain monoclonal antibody (see, e.g., G. Galfre et al. (1977) Nature 266:55052; Gefter et al. Somatic Cell Genet., cited supra; Lerner, Yale J. Biol. Med, cited supra; Kenneth, Monoclonal Antibodies, cited supra), the disclosures of which are incorporated herein by reference in their entireties. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a THAP-family or THAP domain protein, e.g., using a standard ELISA assay.

Alternative to preparing monoclonal antibody-secreting hybridomas, a monoclonal anti-THAP-family or anti-THAP domain antibody can be identified and isolated by screening a recombinant combinatorial immunoglobulin library (e.g., an antibody phage display library) with THAP-family or THAP domain protein to thereby isolate immunoglobulin library members that bind THAP-family or THAP domain proteins. Kits for generating and screening phage display libraries are commercially available (e.g., the Pharmacia Recombinant Phage Antibody System, Catalog No. 27-9400-01; and the Stratagene SurfZAP.TM. Phage Display Kit, Catalog No. 240612), the disclosures of which are incorporated herein by reference in their entireties. Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) PNAS 89:3576-3580; Garrad et al. (1991) Bio/Technology 9:1373-1377; Hoogenboom et al. (1991) Nuc. Acid Res. 19:4133-4137; Barbas et al. (1991) PNAS 88:7978-7982; and McCafferty et al. Nature (1990) 348:552-554, the disclosures of which are incorporated herein by reference in their entireties.

Additionally, recombinant anti-THAP-family or anti-THAP domain antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041-1043; Liu et al. (1987) PNAS 84:3439-3443; Liu et al. (1987) J. Immunol. 139:3521-3526; Sun et al. (1987) PNAS 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060, the disclosures of which are incorporated herein by reference in their entireties.

An anti-THAP-family of anti-THAP domain antibody (e.g., monoclonal antibody) can be used to isolate THAP-family or THAP domain protein by standard techniques, such as affinity chromatography or immunoprecipitation. For example, an anti-THAP-family antibody can facilitate the purification of natural THAP-family from cells and of recombinantly produced THAP-family expressed in host cells. Moreover, an anti-THAP-family antibody can be used to detect THAP-family protein (e.g., in a cellular lysate or cell supernatant) in order to evaluate the abundance and pattern of expression of the THAP-family protein. Anti-THAP-family antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Drug Screening Assays

The invention provides a method (also referred to herein as a "screening assay") for identifying modulators, i.e., candidate or test compounds or agents (e.g., preferably small molecules, but also peptides, peptidomimetics or other drugs) which bind to THAP-family or THAP domain proteins, have an inhibitory or activating effect on, for example, THAP-family expression or preferably THAP-family activity, or have an inhibitory or activating effect on, for example, the activity of an THAP-family target molecule. In some embodiments small molecules can be generated using combinatorial chemistry or can be obtained from a natural products library. Assays may be cell based, non-cell-based or in vivo assays. Drug screening assays may be binding assays or more preferentially functional assays, as further described.

In general, any suitable activity of a THAP-family protein can be detected in a drug screening assay, including: (1) mediating apoptosis or cell proliferation when expressed or introduced into a cell, most preferably inducing or enhancing apoptosis, and/or most preferably reducing cell proliferation; (2) mediating apoptosis or cell proliferation of an endothelial cell; (3) mediating apoptosis or cell proliferation of a hyperproliferative cell; (4) mediating apoptosis or cell proliferation of a CNS cell, preferably a neuronal or glial cell; (5) an activity indicative of a biological function in an animal selected from the group consisting of mediating, preferably inhibiting angiogenesis, mediating, preferably inhibiting inflammation, inhibition of metastatic potential of cancerous tissue, reduction of tumor burden, increase in sensitivity to chemotherapy or radiotherapy, killing a cancer cell, inhibition of the growth of a cancer cell, or induction of tumor regression; or (6) interaction with a THAP family target molecule or THAP domain target molecule, preferably interaction with a protein or a nucleic acid.

The invention also provides a method (also referred to herein as a "screening assay") for identifying modulators, i.e., candidate or test compounds or agents (e.g., preferably small molecules, but also peptides, peptidomimetics or other drugs) which bind to THAP1, PAR4 or PML-NB proteins, and have an inhibitory or activating effect on PAR4 or THAP1 recruitment or binding to or association with PML-NBs or interaction, such as binding, of SLC with a THAP-family polypeptide or a cellular response to SLC which is mediated by a THAP-family polypeptide.

In one embodiment, the invention provides assays for screening candidate or test compounds which are target molecules of a THAP family or THAP domain polypeptide, or a biologically active fragment or homologue thereof. In another embodiment, the invention provides assays for screening candidate or test compounds which bind to or modulate the activity of a THAP family or THAP domain polypeptide, or a biologically active fragment or homologue thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is used with peptide libraries, while the other four approaches are applicable to peptide, non-peptide oligomer or small molecule libraries of compounds (Lam, K. S. (1997) Anticancer Drug Des. 12:145, the disclosure of which is incorporated herein by reference in its entirety).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, the disclosures of which are incorporated herein by reference in their entireties.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devin (1990) Science 249:404-406); (Cwirla et al. (1990) Proc. Natl. Acad. Sci. 87:6378-6382); (Felici (1991) J. Mol. Biol. 222:301-310); (Ladner supra.), the disclosures of which are incorporated herein by reference in their entireties.

Determining the ability of the test compound to inhibit or increase THAP-family polypeptide activity can also be accomplished, for example, by coupling the THAP family or THAP domain polypeptide, or a biologically active fragment or homologue thereof with a radioisotope or enzymatic label such that binding of the THAP family or THAP domain polypeptide, or a biologically active fragment or homologue thereof to its cognate target molecule can be determined by detecting the labeled THAP family or THAP domain polypeptide, or a biologically active fragment or homologue thereof in a complex. For example, compounds (e.g., THAP family or THAP domain polypeptide, or a biologically active fragment or homologue thereof) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product. The labeled molecule is placed in contact with its cognate molecule and the extent of complex formation is measured. For example, the extent of complex formation may be measured by immuno precipitating the complex or by performing gel electrophoresis.

It is also within the scope of this invention to determine the ability of a compound (e.g., THAP family or THAP domain polypeptide, or biologically active fragment or homologue thereof) to interact with its cognate target molecule without the labeling of any of the interactants. For example, a microphysiometer can be used to detect the interaction of a compound with its cognate target molecule without the labeling of either the compound or the target molecule. McConnell, H. M. et al. (1992) Science 257:1906-1912, the disclosure of which is incorporated herein by reference in its entirety. A microphysiometer such as a cytosensor is an analytical instrument that measures the rate at which a cell acidifies its environment using a light-addressable potentiometric sensor (LAPS). Changes in this acidification rate can be used as an indicator of the interaction between compound and cognate target molecule.

In a preferred embodiment, the assay comprises contacting a cell which expresses a THAP family or THAP domain polypeptide, or biologically active fragment or homologue thereof, with a THAP-family or THAP domain protein target molecule to form an assay mixture, contacting the assay mixture with a test compound, and determining the ability of the test compound to inhibit or increase the activity of the THAP family or THAP domain polypeptide, or biologically active fragment or homologue thereof, wherein determining the ability of the test compound to inhibit or increase the activity of the THAP family or THAP domain polypeptide, or biologically active fragment or homologue thereof, comprises determining the ability of the test compound to inhibit or increase a biological activity of the THAP-family polypeptide expressing cell.

In another embodiment, the assay comprises contacting a cell which expresses a THAP family or THAP domain polypeptide, or biologically active fragment or homologue thereof, with a test compound, and determining the ability of the test compound to inhibit or increase the activity of the THAP family or THAP domain polypeptide, or biologically active fragment or homologue thereof, wherein determining the ability of the test compound to inhibit or increase the activity of the THAP family or THAP domain polypeptide, or biologically active fragment or homologue thereof, comprises determining the ability of the test compound to inhibit or increase a biological activity of the THAP-family polypeptide expressing cell.

In another preferred embodiment, the assay comprises contacting a cell which is responsive to a THAP family or THAP domain polypeptide, or a biologically active fragment or homologue thereof, with a THAP-family protein or biologically-active portion thereof, to form an assay mixture, contacting the assay mixture with a test compound, and determining the ability of the test compound to modulate the activity of the THAP-family protein or biologically active portion thereof, wherein determining the ability of the test compound to modulate the activity of the THAP-family protein or biologically active portion thereof comprises determining the ability of the test compound to modulate a biological activity of the THAP-family polypeptide-responsive cell (e.g., determining the ability of the test compound to modulate a THAP-family polypeptide activity.

In another embodiment, an assay is a cell-based assay comprising contacting a cell expressing a THAP-family target molecule (i.e. a molecule with which THAP-family polypeptide interacts) with a test compound and determining the ability of the test compound to modulate (e.g. stimulate or inhibit) the activity of the THAP-family target molecule. Determining the ability of the test compound to modulate the activity of a THAP-family target molecule can be accomplished, for example, by determining the ability of the THAP family or THAP domain polypeptide, or a biologically active fragment or homologue thereof to bind to or interact with the THAP-family target molecule.

Determining the ability of the THAP family or THAP domain polypeptide, or a biologically active fragment or homologue thereof to bind to or interact with a THAP-family target molecule can be accomplished by one of the methods described above for determining direct binding. In a preferred embodiment, determining the ability of the THAP family or THAP domain polypeptide, or a biologically active fragment or homologue thereof to bind to or interact with a THAP-family target molecule can be accomplished by determining the activity of the target molecule. For example, the activity of the target molecule can be determined by contacting the target molecule with the THAP family or THAP domain polypeptide, or a biologically active fragment or homologue thereof and measuring induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, signal transduction or protein:protein interactions.

In yet another embodiment, an assay of the present invention is a cell-free assay in which a THAP family or THAP domain polypeptide, or a biologically active fragment or homologue thereof is contacted with a test compound and the ability of the test compound to bind to the THAP family or THAP domain polypeptide, or a biologically active fragment or homologue thereof is determined. Binding of the test compound to the THAP family or THAP domain polypeptide, or a biologically active fragment or homologue thereof can be determined either directly or indirectly as described above. In a preferred embodiment, the assay includes contacting the THAP family or THAP domain polypeptide, or a biologically active fragment or homologue thereof with a known compound which binds THAP-family polypeptide (e.g., a THAP-family target molecule) to form an assay mixture, contacting the assay mixture with a test compound, and determining the ability of the test compound to interact with a THAP family or THAP domain polypeptide, or a biologically active fragment or homologue thereof, wherein determining the ability of the test compound to interact with a THAP-family protein comprises determining the ability of the test compound to preferentially bind to THAP family or THAP domain polypeptide, or a biologically active fragment or homologue thereof as compared to the known compound.

In another embodiment, the assay is a cell-free assay in which a THAP family or THAP domain polypeptide, or a biologically active fragment or homologue thereof is contacted with a test compound and the ability of the test compound to modulate (e.g., stimulate or inhibit) the activity of the THAP family or THAP domain polypeptide, or a biologically active fragment or homologue thereof is determined. Determining the ability of the test compound to modulate the activity of a THAP-family protein can be accomplished, for example, by determining the ability of the THAP family or THAP domain polypeptide, or a biologically active fragment or homologue thereof to bind to a THAP-family target molecule by one of the methods described above for determining direct binding. Determining the ability of the THAP family or THAP domain polypeptide, or a biologically active fragment or homologue thereof to bind to a THAP-family target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705, the disclosures of which are incorporated herein by reference in their entireties. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a THAP family or THAP domain polypeptide, or a biologically active fragment or homologue thereof can be accomplished by determining the ability of the THAP family or THAP domain polypeptide, or a biologically active fragment or homologue thereof to further modulate the activity of a downstream effector (e.g., a growth factor mediated signal transduction pathway component) of a THAP-family target molecule. For example, the activity of the effector molecule on an appropriate target can be determined or the binding of the effector to an appropriate target can be determined as previously described.

In yet another embodiment, the cell-free assay involves contacting a THAP family or THAP domain polypeptide, or a biologically active fragment or homologue thereof with a known compound which binds the THAP-family protein to form an assay mixture, contacting the assay mixture with a test compound, and determining the ability of the test compound to interact with the THAP-family protein, wherein determining the ability of the test compound to interact with the THAP-family protein comprises determining the ability of the THAP family or THAP domain polypeptide, or a biologically active fragment or homologue thereof to preferentially bind to or modulate the activity of a THAP-family target molecule.

The cell-free assays of the present invention are amenable to use of both soluble and/or membrane-bound forms of isolated proteins (e.g. THAP family or THAP domain polypeptide, or a biologically active fragment or homologue thereof or molecules to which THAP-family targets bind). In the case of cell-free assays in which a membrane-bound form an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton.[™. X-100, Triton.™. X-114, Thesit.™.], Isotridecypoly(ethylene glycol ether),,,3-[(3-cholamidopropyl) dimethylamminio]-1-propane sulfonate (CHAPS), 3-[(3- cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either THAP family or THAP domain polypeptide, or a biologically active fragment or homologue thereof or a target molecule thereof to facilitate separation of complexed from uncomplexed forms of one or both of the proteins, as well as to accommodate automation of the assay. Binding of a test compound to a THAP family or THAP domain polypeptide, or a biologically active fragment or homologue thereof, or interaction of a THAP-family protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/THAP-family fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or THAP-family protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of THAP-family polypeptide binding or activity determined using standard techniques.

Other techniques for immobilizing proteins on matrices can also be used in the screening assays of the invention. For example, either a THAP-family protein or a THAP-family target molecule can be immobilized utilizing conjugation of biotin and streptavidin. Biotinylated THAP-family protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a THAP-family protein or target molecule but which do not interfere with binding of the THAP-family protein to its target molecule can be derivatized to the wells of the plate, and unbound target or THAP-family protein trapped in the wells by antibody conjugation. Methods for detecting such complexes, in addition to those described above for the GST-immobilized complexes, include immunodetection of complexes using antibodies reactive with the THAP-family protein or target molecule, as well as enzyme-linked assays which rely on detecting an enzymatic activity associated with the THAP-family protein or target molecule.

In another embodiment, modulators of THAP-family or THAP domain polypeptides expression are identified in a method wherein a cell is contacted with a candidate compound and the expression of THAP-family or THAP domain polypeptides mRNA or protein in the cell is determined. The level of expression of THAP-family polypeptide mRNA or protein in the presence of the candidate compound is compared to the level of expression of THAP-family polypeptide or THAP domain mRNA or protein in the absence of the candidate compound. The candidate compound can then be identified as a modulator of THAP-family polypeptide expression based on this comparison. For example, when expression of THAP-family polypeptide or THAP domain mRNA or protein is greater (statistically significantly greater) in the presence of the candidate compound than in its absence, the candidate compound is identified as a stimulator of THAP-family polypeptide or THAP domain mRNA or protein expression. Alternatively, when expression of THAP-family polypeptide or THAP domain mRNA or protein is less (statistically significantly less) in the presence of the candidate compound than in its absence, the candidate compound is identified as an inhibitor of THAP-family polypeptide or THAP domain mRNA or protein expression. The level of THAP-family polypeptide or THAP domain mRNA or protein expression in the cells can be determined by methods described herein for detecting THAP-family polypeptide or THAP domain mRNA or protein.

In yet another aspect of the invention, the THAP family or THAP domain polypeptide, or a biologically active fragment or homologue thereof can be used as "bait proteins" in a two-hybrid assay or three-hybrid assay using the methods described above for use in THAP-family polypeptide/PAR4 interactions assays, to identify other proteins which bind to or interact with THAP-family polypeptide ("THAP-family-binding proteins" or "THAP-family-bp") and are involved in THAP-family polypeptide activity. Such THAP-family- or THAP domain-binding proteins are also likely to be involved in the propagation of signals by the THAP-family or THAP domain proteins or THAP-family or THAP domain proteins targets as, for example, downstream elements of a THAP-family polypeptide- or THAP domain-mediated signaling pathway. Alternatively, such THAP-family-binding proteins are likely to be THAP-family polypeptides inhibitors.

THAP/DNA Binding Assays

In another embodiment of the invention a method is provided for identifying compounds which interfere with THAP-family DNA binding activity, comprising the steps of: contacting a THAP-family protein or a portion thereof immobilized on a solid support with both a test compound and DNA fragments, or contacting a DNA fragment immobilized on a solid support with both a test compound and a THAP-family protein. The binding between DNA and the THAP-protein or a portion thereof is detected, wherein a decrease in DNA binding when compared to DNA binding in the absence of the test compound indicates that the test compound is an inhibitor of THAP-family DNA binding activity, and an increase in DNA binding when compared to DNA binding in the absence of the test compound indicates that the test compound is an inducer of or restores THAP-family DNA binding activity. As discussed further, DNA fragments may be selected to be specific THAP-family protein target DNA obtained for example as described in Example 28, or may be non-specific THAP-family target DNA. Methods for detecting protein-DNA interactions are well known in the art, including most commonly used electrophoretic mobility shift assays (EMSAs) or by filter binding (Zabel et al, (1991) J. Biol. Chem., 266:252; and Okamoto and Beach, (1994) Embo J. 13: 4816). Other assays are available which are amenable for high throughput detection and quantification of specific and nonspecific DNA binding (Amersham, N.J.; and Gal S. et al, $6^{th}$ Ann. Conf. Soc. Biomol. Screening, 6-9 Sept 2000, Vancouver, B.C.).

In a first aspect, a screening assay involves identifying compounds which interfere with THAP-family DNA binding activity without prior knowledge about specific THAP-family binding sequences. For example, a THAP-family protein is contacted with both a test compound and a library of oligonucleotides or a sample of DNA fragments not selected based on specific DNA sequences. Preferably the THAP-family protein is immobilized on a solid support (such as an array or a column). Unbound DNA is separated from DNA which is bound to the THAP-famliy protein, and the DNA which is bound to THAP-family protein is detected and can be quantitated by any means known in the art. For example, the DNA fragment is labelled with a detectable moiety, such as a radioactive moiety, a colorimetric moiety or a fluorescent moiety. Techniques for so labelling DNA are well known in the art.

The DNA which is bound to the THAP-family protein or a portion thereof is separated from unbound DNA by immunoprecipitation with antibodies which are specific for the THAP-family protein or a portion thereof. Use of two different monoclonal anti-THAP-family antibodies may result in more complete immunoprecipitation than either one alone. The amount of DNA which is in the immunoprecipitate can be quantitated by any means known in the art. THAP-family proteins or portions thereof which bind to the DNA can also be detected by gel shift assays (Tan, Cell, 62:367, 1990), nuclease protection assays, or methylase interference assays.

It is still another object of the invention to provide methods for identifying compounds which restore the ability of mutant THAP-family proteins or portions thereof to bind to DNA sequences. In one embodiment a method of screening agents for use in therapy is provided comprising: measuring the amount of binding of a THAP-family protein or a portion thereof which is encoded by a mutant gene found in cells of a patient to DNA molecules, preferably random oligonucleotides or DNA fragments from a nucleic acid library; measuring the amount of binding of said THAP-family protein or a portion thereof to said nucleic acid molecules in the presence of a test substance; and comparing the amount of binding of the THAP-family protein or a portion thereof in the presence of said test substance to the amount of binding of the THAP-family protein in the absence of said test-substance, a test substance which increases the amount of binding being a candidate for use in therapy.

In another embodiment of the invention, oligonucleotides can be isolated which restore to mutant THAP-family proteins or portions thereof the ability to bind to a consensus binding sequence or conforming sequences. Mutant THAP-family protein or a portion thereof and random oligonucleotides are added to a solid support on which THAP-family-specific DNA fragments are immobilized. Oligonucleotides which bind to the solid support are recovered and analyzed. Those whose binding to the solid support is dependent on the presence of the mutant THAP-family protein are presumptively binding the support by binding to and restoring the conformation of the mutant protein.

If desired, specific binding can be distinguished from non-specific binding by any means known in the art. For example, specific binding interactions are stronger than non-specific binding interactions. Thus the incubation mixture can be subjected to any agent or condition which destabilizes protein/DNA interactions such that the specific binding reaction is the predominant one detected. Alternatively, as taught more specifically below, a non-specific competitor, such as dI-dC, can be added to the incubation mixture. If the DNA containing the specific binding sites is labelled and the competitor is unlabeled, then the specific binding reactions will be the ones predominantly detected upon measuring labelled DNA.

According to another embodiment of the invention, after incubation of THAP-family protein or a portion thereof with specific DNA fragments all components of the cell lysate which do not bind to the DNA fragments are removed. This can be accomplished, among other ways, by employing DNA fragments which are attached to an insoluble polymeric support such as agarose, cellulose and the like. After binding, all non-binding components can be washed away, leaving THAP-family protein or a portion thereof bound to the DNA/solid support. The THAP-family protein or a portion thereof can be quantitated by any means known in the art. It can be determined using an immunological assay, such as an ELISA, RIA or Western blotting.

In another embodiment of the invention a method is provided for identifying compounds which specifically bind to THAP-family-specific-DNA sequences, comprising the steps of: contacting a THAP-family-specific DNA fragment immobilized on a solid support with both a test compound and wild-type THAP-family protein or a portion thereof to bind the wild-type THAP-family protein or a portion thereof to the DNA fragment; determining the amount of wild-type THAP-family protein which is bound to the DNA fragment, inhibition of binding of wild-type THAP-family protein by the test compound with respect to a control lacking the test compound suggesting binding of the test compound to the THAP-family-specific DNA binding sequences.

It is still another object of the invention to provide methods for identifying compounds which restore the ability of mutant THAP-family proteins or portions thereof to bind to specific DNA binding sequences. In one embodiment a method of screening agents for use in therapy is provided comprising: measuring the amount of binding of a THAP-family protein or a portion thereof which is encoded by a mutant gene found in cells of a patient to a DNA molecule which comprises more than one monomer of a specific THAP-family target nucleotide sequence; measuring the amount of binding of said THAP-family protein to said nucleic acid molecule in the presence of a test substance; and comparing the amount of binding of the THAP-family protein in the presence of said test substance to the amount of binding of the THAP-family protein or a portion thereof in the absence of said test substance, a test substance which increases the amount of binding being a candidate for use in therapy.

In another embodiment of the invention a method is provided for screening agents for use in therapy comprising: contacting a transfected cell with a test substance, said transfected cell containing a THAP-family protein or a portion thereof which is encoded by a mutant gene found in cells of a patient and a reporter gene construct comprising a reporter gene which encodes an assayable product and a sequence which conforms to a THAP-family DNA binding site, wherein said sequence is upstream from and adjacent to said reporter gene; and determining whether the amount of expression of said reporter gene is altered by the test substance, a test substance which alters the amount of expression of said reporter gene being a candidate for use in therapy.

In still another embodiment a method of screening agents for use in therapy is provided comprising: adding RNA polymerase ribonucleotides and a THAP-family protein or a portion thereof to a transcription construct, said transcription construct comprising a reporter gene which encodes an assayable product and a sequence which conforms to a THAP-family consensus binding site, said sequence being upstream from and adjacent to said reporter gene, said step of adding being effected in the presence and absence of a test substance; determining whether the amount of transcription of said reporter gene is altered by the presence of said test substance, a test substance which alters the amount of transcription of said reporter gene being a candidate for use in therapy.

According to the present invention compounds which have THAP-family activity are those which specifically complex with a THAP-family-specific DNA binding site. Oligonucleotides and oligonucleotide containing nucleotide analogs are also contemplated among those compounds which are able to complex with a THAP-family-specific DNA binding site.

Further Assays to Modulate THAP-Family Polypeptide Activity In Vivo

It will be appreciated that any suitable assay that allows detection of THAP-family polypeptide or THAP domain activity can be used. Examples of assays for testing protein interaction, nucleic acid binding or modulation of apoptosis in the presence or absence of a test compound are further described herein. Thus, the invention encompasses a method of identifying a candidate THAP-family polypeptide modulator (e.g. activator or inhibitor), said method comprising:

a) providing a cell comprising a THAP family or THAP domain polypeptide, or a biologically active fragment or homolog thereof;

b) contacting said cell with a test compound; and c) determining whether said compound selectively modulates (e.g. activates or inhibits) THAP-family polypeptide activity, preferably pro-apoptotic activity, or THAP family or THAP domain target binding; wherein a determination that said compound selectively modulates (e.g. activates or inhibits) the activity of said polypeptide indicates that said compound is a candidate modulator (e.g. activator or inhibitor respectively) of said polypeptide. Preferably, the THAP family or THAP domain target is a protein or nucleic acid.

Preferably the cell is a cell which has been transfected with an recombinant expression vector encoding a THAP family or THAP domain polypeptide, or a biologically active fragment or homologue thereof.

Several examples of assays for the detection of apoptosis are described herein, in the section titled "Apoptosis assays". Several examples of assays for the detection of THAP family or THAP domain target interactions are described herein, including assays for detection of protein interactions and nucleic acid binding.

In one example of an assay for apoptosis activity, a high throughput screening assay for molecules that abrogate or stimulate THAP-family polypeptide proapoptotic activity is provided based on serum-withdrawal induced apoptosis in a 3T3 cell line with tetracycline-regulated expression of a THAP family or THAP domain polypeptide, or a biologically active fragment or homologue thereof. Apoptotic cells can be detected by TUNEL labeling in 96- or 384-wells microplates. A drug screening assay can be carried out along the lines as described in Example 23. 3T3 cells, which have previously been used to analyze the pro-apoptotic activity of PAR4 (Diaz-Meco et al, 1996; Berra et al., 1997), can be transfected with expression vectors encoding a THAP-family or THAP domain polypeptide allowing the ectopic expression of THAP-family polypeptide. Then, the apoptotic response to serum withdrawal is assayed in the presence of a test compound, allowing the identification of test compounds that either enhance or inhibit the ability of THAP-family or THAP domain polypeptide to induce apoptosis. Transfected cells are deprived of serum and cells with apoptotic nuclei are counted. Apoptotic nuclei can be counted by DAPI staining and in situ TUNEL assays.

Further THAP-Family Polypeptide/THAP-Target Interaction Assays

In exemplary methods THAP/THAP target interaction assays are described in the context of THAP1 and the THAP target Par4. However, it will be appreciated that assays for screening for modulators of other THAP family members or THAP domains and other THAP target molecules may be carried out by substituting these for THAP1 and Par4 in the methods below. For example, in some embodiments, modulators which affect the interaction between a THAP-family polypeptide and SLC are identified.

Figure 3:
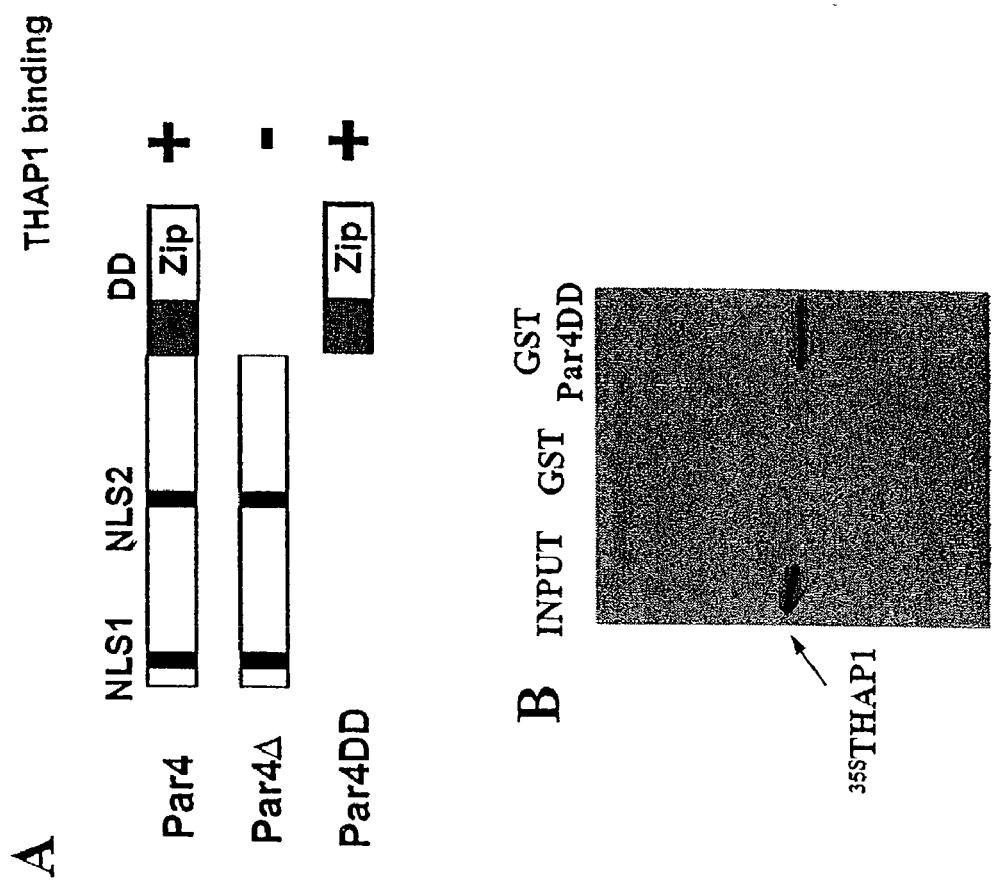
FIG. 3A illustrates the interaction between THAP1 and PAR4 in a yeast two-hybrid system. In particular, THAP1 binds to wild-type Par4 (Par4) and the leucine zipper-containing Par4 death domain (Par4DD) (amino acids 250-342 of PAR4) but not a Par4 deletion mutant lacking the death domain (PAR4Δ) (amino acids 1-276 of PAR4). A (+) indicates binding whereas a (−) indicated lack of binding.
FIG. 3B shows the binding of in vitro translated, $^{35}$S-methionine-labeled THAP1 to a GST-Par4DD polypeptide fusion. Par4DD was expressed as a GST fusion protein then purified on an affinity matrix of glutathione sepharose. GST served as negative control. The input represents 1/10 of the material used in the binding assay.

As demonstrated in Examples 4, 5, 6, and 7 and FIGS. 3, 4 and 5, the inventors have demonstrated using several experimental methods that THAP1 interacts with the pro-apoptotic protein Par4. In particular, it has been shown that THAP1 interacts with Par4 wild type (Par4) and a Par4 death domain (Par4DD) in a yeast two-hybrid system. Yeast cells were cotransformed with BD7-THAP1 and AD7-Par4, AD7, AD7-Par4DD or AD7-Par4) expression vectors. Transformants were selected on media lacking histidine and adenine. Identical results were obtained by cotransformation of AD7-THAP1 with BD7-Par4, BD7, BD7-Par4DD or BD7-Par4).

The inventors have also demonstrated in vitro binding of THAP1 to GST-Par4DD. Par4DD was expressed as a GST fusion protein, purified on glutathione sepharose and employed as an affinity matrix for binding of in vitro translated $^{35}$S-methionine labeled THAP1. GST served as negative control.

Futhermore, the inventors have shown that THAP1 interacts with both Par4DD and SLC in vivo. Myc-Par4DD and GFP-THAP1 expression vectors were cotransfected in primary human endothelial cells. Myc-Par4DD was stained with monoclonal anti-myc antibody. Green fluorescence, GFP-THAP1; red fluorescence, Par4DD.

The invention thus encompasses assays for the identification of molecules that modulate (stimulate or inhibit) THAP-family polypeptide/PAR4 binding. In preferred embodiments, the invention includes assays for the identification of molecules that modulate (stimulate or inhibit) THAP1/PAR4 binding or THAP1/SLC binding.

Four examples of high throughput screening assays include:

1) a two hybrid-based assay in yeast to find drugs that disrupt interaction of the THAP-family bait with the PAR4 or SLC as prey 2) an in vitro interaction assay using recombinant THAP-family polypeptide and PAR4 or SLC proteins 3) a chip-based binding assay using recombinant THAP-family polypeptide and PAR4 or SLC proteins 2) a fluorescence resonance energy transfer (FRET) cell-based assay using THAP-family polypeptide and PAR4 or SLC proteins fused with fluorescent proteins The invention thus encompasses a method of identifying a candidate THAP-family polypeptide/PAR4 or SLC interaction modulator, said method comprising:

a) providing a THAP family or THAP domain polypeptide, or a biologically active fragment or homologue thereof and a PAR4 or SLC polypeptide or fragment thereof;

b) contacting said THAP family or THAP domain polypeptide with a test compound; and c) determining whether said compound selectively modulates (e.g. activates or inhibits) THAP-family/PAR4 or SLC interaction activity.

Also envisioned is a method comprising:

a) providing a cell comprising a THAP family or THAP domain polypeptide, or a biologically active fragment or homologue thereof and a PAR4 or SLC polypeptide or fragment thereof;

b) contacting said cell with a test compound; and c) determining whether said compound selectively modulates (e.g. activates or inhibits) THAP-family/PAR4 or SLC interaction activity.

In general, any suitable assay for the detection of protein-protein interaction may be used.

In one example, a THAP family or THAP domain polypeptide, or a biologically active fragment or homologue thereof can be used as a "bait protein" and a PAR4 or SLC protein can be used as a "prey protein" (or vice-versa) in a two-hybrid assay (see, e.g., U.S. Pat. No. 5,283,317; Zervos et al. (1993) Cell 72:223-232; Madura et al. (1993) J. Biol. Chem. 268: 12046-12054; Bartel et al. (1993) Biotechniques 14:920-924; Iwabuchi et al. (1993) Oncogene 8:1693-1696; and Brent WO94/10300, the disclosures of which are incorporated herein by reference in their entireties). The two-hybrid system is based on the modular nature of most transcription factors, which consist of separable DNA-binding and activation domains. Briefly, the assay utilizes two different DNA constructs. In one construct, the gene that codes for a THAP family or THAP domain polypeptide, or a biologically active fragment or homologue thereof is fused to a gene encoding the DNA binding domain of a known transcription factor (e.g., GAL-4). In the other construct, the gene that codes for a THAP family or THAP domain polypeptide, or a biologically active fragment or homologue thereof ("prey" or "sample") is fused to a gene that codes for the activation domain of the known transcription factor. If the "bait" and the "prey" proteins are able to interact, in vivo, forming a THAP-family polypeptide/PAR4 complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the THAP-family protein. This assay can thus be carried out in the presence or absence of a test compound, whereby modulation of THAP-family polypeptide/PAR4 or SLC interaction can be detected by lower or lack of transcription of the reported gene.

In other examples, in vitro THAP-family polypeptide/PAR4 or SLC interaction assays can be carried out, several examples of which are further described herein. For example, a recombinant THAP family or THAP domain polypeptide, or a biologically active fragment or homologue thereof is contacted with a recombinant PAR4 or SLC protein or biologically active portion thereof, and the ability of the PAR4 or SLC protein to bind to the THAP-family protein is determined. Binding of the PAR4 or SLC protein compound to the THAP-family protein can be determined either directly or indirectly as described herein. In a preferred embodiment, the assay includes contacting the THAP family or THAP domain polypeptide, or a biologically active fragment or homologue thereof with a PAR4 or SLC protein which binds a THAP-family protein (e.g., a THAP-family target molecule) to form an assay mixture, contacting the assay mixture with a test compound, and determining the ability of the test compound to interact with a THAP-family protein, wherein determining the ability of the test compound to interact with a THAP-family protein comprises determining the ability of the test compound to preferentially bind to THAP-family or biologically active portion thereof as compared to the PAR4 or SLC protein. For example, the step of determining the ability of the test compound to interact with a THAP-family protein may comprise determining the ability of the compound to displace Par4 or SLC from a THAP-family protein/Par4 or SLC complex thereby forming a THAP-family protein/compound complex. Alternatively, it will be appreciated that it is also possible to determine the ability of the test compound to interact with a PAR4 or SLC protein, wherein determining the ability of the test compound to interact with a PAR4 or SLC protein comprises determining the ability of the test compound to preferentially bind to PAR4 or SLC or biologically active portion thereof as compared to the THAP-family protein. For example, the step of determining the ability of the test compound to interact with a THAP-family protein may comprise determining the ability of the compound to displace Par4 or SLC from a THAP-family protein/Par4 or SLC complex thereby forming a THAP-family protein/compound complex.

Assays to Modulate THAP-Family Polypeptide and/or Par4 Trafficking in the PML Nuclear Bodies (PML NBs)

As demonstrated in Examples 8 and 9, the inventors have demonstrated using several experimental methods that THAP1 and Par4 localize in PML NBs.

The inventors demonstrated that THAP1 is a novel protein associated with PML-nuclear bodies. Double immunofluorescence staining showed colocalization of THAP1 with PML-NBs proteins, PML and Daxx. Primary human endothelial cells were transfected with GFP-THAP1 expression vector; endogenous PML and Daxx were stained with monoclonal anti-PML and polyclonal anti-Daxx antibodies, respectively.

The inventors also demonstrated that Par4 is a novel component of PML-NBs that colocalizes with THAP1 in vivo by several experiments. In one experiments, double immunofluorescence staining revealed colocalization of Par4 and PML at PML-NBs in primary human endothelial cells or fibroblasts. Endogenous PAR4 and PML were stained with polyclonal anti-PAR4 and monoclonal anti-PML antibodies, respectively. In another experiment, double staining revealed colocalization of Par4 and THAP1 in cells expressing ectopic GFP-THAP1. Primary human endothelial cells or fibroblasts were transfected with GFP-THAP1 expression vector; endogenous Par4 was stained with polyclonal anti-PAR4 antibodies.

The inventors further demonstrated that PML recruits the THAP1/Par4 complex to PML-NBs. Triple immunofluorescence staining showed colocalization of THAP1, Par4 and PML in cells overexpressing PML and absence of colocalization in cells expressing ectopic Sp100. Hela cells were cotransfected with GFP-THAP1 and HA-PML or HA-SP100 expression vectors; HA-PML or HA-SP100 and endogenous Par4 were stained with monoclonal anti-HA and polyclonal anti-Par4 antibodies, respectively.

Assays to Modulate THAP Family Protein Trafficking in the PML Nuclear Bodies

Provided are assays for the identification of drugs that modulate (stimulate or inhibit) THAP-family or THAP domain protein, particularly THAP1, binding to PML-NB proteins or localization to PML-NBs. In general, any suitable assay for the detection of protein-protein interaction may be used. Two examples of high throughput screening assays include 1) a two hybrid-based assay in yeast to find compounds that disrupt interaction of the THAP1 bait with the PML-NB protein prey; and 2) in vitro interaction assays using recombinant THAP1 and PML-NB proteins. Such assays may be conducted as described above with respect to THAP-family/Par4 assays except that the PML-NB protein is used in place of Par4. Binding may be detected, for example, between a THAP-family protein and a PML protein or PML associated protein such as daxx, sp100, sp140, p53, pRB, CBP, BLM or SUMO-1.

Other assays for which standard methods are well known include assays to identify molecules that modulate, generally inhibit, the colocalization of THAP1 with PML-NBs. Detection can be carried out using a suitable label, such as an anti-THAP1 antibody, and an antibody allowing the detection of PML-NB protein.

Assays to Modulate PAR4 Trafficking in the PML Bodies

Provided are assays for the identification of drugs that modulate (stimulate or inhibit) PAR4 binding to PML-NB proteins or localization to PML-NBs. In general, any suitable assay for the detection of protein-protein interaction may be used. Two examples of high throughput screening assays include 1) a two hybrid-based assay in yeast to find compounds that disrupt interaction of the PAR4 bait with the PML-NB protein prey; and 2) in vitro interaction assays using recombinant PAR4 and PML-NB proteins. Such assays may be conducted as described above with respect to THAP-family polypeptide/Par4 assays except that the PML-NB protein is used in place of the THAP-family polypeptide. Binding may be detected, for example, between a Par4 protein and a PML protein or PML associated protein such as daxx, sp100, sp140, p53, pRB, CBP, BLM or SUMO-1.

Other assays for which standard methods are well known include assays to identify molecules that modulate, generally inhibit, the colocalization of PAR4 with PML-NBs. Detection can be carried out using a suitable label, such as an anti-PAR4 antibody, and an antibody allowing the detection of PML-NB protein.

This invention further pertains to novel agents identified by the above-described screening assays and to processes for producing such agents by use of these assays. Accordingly, in one embodiment, the present invention includes a compound or agent obtainable by a method comprising the steps of any one of the aforementioned screening assays (e.g., cell-based assays or cell-free assays). For example, in one embodiment, the invention includes a compound or agent obtainable by a method comprising contacting a cell which expresses a THAP-family target molecule with a test compound and determining the ability of the test compound to bind to, or modulate the activity of, the THAP-family target molecule. In another embodiment, the invention includes a compound or agent obtainable by a method comprising contacting a cell which expresses a THAP-family target molecule with a THAP-family protein or biologically-active portion thereof, to form an assay mixture, contacting the assay mixture with a test compound, and determining the ability of the test compound to interact with, or modulate the activity of, the THAP-family target molecule. In another embodiment, the invention includes a compound or agent obtainable by a method comprising contacting a THAP-family protein or biologically active portion thereof with a test compound and determining the ability of the test compound to bind to, or modulate (e.g., stimulate or inhibit) the activity of, the THAP-family protein or biologically active portion thereof. In yet another embodiment, the present invention includes a compound or agent obtainable by a method comprising contacting a THAP-family protein or biologically active portion thereof with a known compound which binds the THAP-family protein to form an assay mixture, contacting the assay mixture with a test compound, and determining the ability of the test compound to interact with, or modulate the activity of the THAP-family protein.

Accordingly, it is within the scope of this invention to further use an agent identified as described herein in an appropriate animal model. For example, an agent identified as described herein (e.g., a THAP-family or THAP domain modulating agent, an antisense THAP-family or THAP domain nucleic acid molecule, a THAP-family- or THAP domain-specific antibody, or a THAP-family- or THAP domain-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a THAP-family target molecule is contacted with a test compound and the ability of the test compound to bind to, or modulate the activity of, the THAP-family target molecule is determined. In another exemplary embodiment, the present invention includes a method of synthesizing or producing a drug or pharmaceutical composition based on the structure and/or properties of a compound obtainable by a method in which a THAP-family protein or biologically active portion thereof is contacted with a test compound and the ability of the test compound to bind to, or modulate (e.g., stimulate or inhibit) the activity of, the THAP-family protein or biologically active portion thereof is determined.

Apoptosis Assays

It will be appreciated that any suitable apoptosis assay may be used to assess the apoptotic activity of a THAP family or THAP domain polypeptide, or a biologically active fragment or homologue thereof.

Apoptosis can be recognized by a characteristic pattern of morphological, biochemical, and molecular changes. Cells going through apoptosis appear shrunken, and rounded; they also can be observed to become detached from culture dish. The morphological changes involve a characteristic pattern of condensation of chromatin and cytoplasm which can be readily identified by microscopy. When stained with a DNA-binding dye, e.g., H33258, apoptotic cells display classic condensed and punctate nuclei instead of homogeneous and round nuclei.

A hallmark of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pairs. This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the contemplation of the invention.

Abnormal DNA breaks which are characteristic of apoptosis can be detected by any means known in the art. In one preferred embodiment, DNA breaks are labeled with biotinylated dUTP (b-dUTP). As described in U.S. Pat. No. 5,897,999, the disclosure of which is incorporated herein by reference, cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

Assessing THAP-Family, THAP Domain and PAR4 Polypeptides Activity

For assessing the nucleic acids and polypeptides of the invention, the apoptosis indicator which is assessed in the screening method of the invention may be substantially any indicator of the viability of the cell. By way of example, the viability indicator may be selected from the group consisting of cell number, cell refractility, cell fragility, cell size, number of cellular vacuoles, a stain which distinguishes live cells from dead cells, methylene blue staining, bud size, bud location, nuclear morphology, and nuclear staining. Other viability indicators and combinations of the viability indicators described herein are known in the art and may be used in the screening method of the invention.

Cell death status can be evaluated based on DNA integrity. Assays for this determination include assaying DNA on an agarose gel to identify DNA breaking into oligonucleosome ladders and immunohistochemically detecting the nicked ends of DNA by labeling the free DNA end with fluorescein or horseradish peroxidase-conjugated UTP via terminal transferase. Routinely, one can also examine nuclear morphology by propidium iodide (PI) staining. All three assays (DNA ladder, end-labelling, and PI labelling) are gross measurements and good for those cells that are already dead or at the end stage of dying.

In a preferred example, an apoptosis assay is based on serum-withdrawal induced apoptosis in a 3T3 cell line with tetracycline-regulated expression of a THAP family or THAP domain polypeptide, or a biologically active fragment or homologue thereof. Detection of apoptotic cells is accomplished by TUNEL labeling cells in 96- or 384-well microplates. This example is further described in Example 23.

In other aspects, assays may test for the generation of cytotoxic death signals, anti-viral responses (Tartaglia et al., (1993) Cell 74(5):845-531), and/or the activation of acid sphingomyelinase (Wiegmann et al., (1994) Cell 78(6):1005-15) when the THAP-family protein is overexpressed or ectopically expressed in cells. Assaying for modulation of apoptosis can also be carried out in neuronal cells and lymphocytes for example, where factor withdrawal is known to induce cell suicide as demonstrated with neuronal cells requiring nerve growth factor to survive (Martin, D. P. et al, (1988) J. Cell Biol 106, 829-844) and lymphocytes depending on a specific lymphokine to live (Kyprianou, N. and Isaacs, J. T. (1988) Endrocrinology 122:552-562). The above disclosures are incorporated herein by reference.

THAP-Family or THAP Domain Polypeptide-Marker Fusions in Cell Assays

In one method, an expression vector encoding the a THAP family or THAP domain polypeptide, or a biologically active fragment or homologue thereof can be used to evaluate the ability of the polypeptides of the invention to induce apoptosis in cells. If desired, a THAP-family or THAP domain polypeptide may be fused to a detectable marker in order to facilitate identification of those cells expressing the a THAP family or THAP domain polypeptide, or a biologically active fragment or homologue thereof. For example, a variant of the *Aequoria victoria* GFP variant, enhanced green fluorescent protein (EGFP), can be used in fusion protein production (CLONTECH Laboratories, Inc., 1020 East Meadow Circle, Palo Alto, Calif. 94303), further described in U.S. Pat. No. 6,191,269, the disclosure of which is incorporated herein by reference.

The THAP-family- or THAP domain polypeptide cDNA sequence is fused in-frame by insertion of the THAP-family- or THAP domain polypeptide encoding cDNA into the SalI-BamHI site of plasmid pEGFP-N1 (GenBank Accession # U55762). Cells are transiently transfected by the method optimal for the cell being tested (either CaPO$^4$ or Lipofectin). Expression of a THAP-family or THAP domain polypeptide and induction of apoptosis is examined using a fluorescence microscope at 24 hrs and 48 hrs post-transfection. Apoptosis can be evaluated by the TUNEL method (which involves 3' end-labeling of cleaved nuclear and/or morphological criteria DNA) (Cohen et al. (1984) J. Immunol. 132:38-42, the disclosure of which is incorporated herein by reference). Where the screen uses a fusion polypeptide comprising a THAP-family or THAP domain polypeptide and a reporter polypeptide (e.g., EGFP), apoptosis can be evaluated by detection of nuclear localization of the reporter polypeptide in fragmented nuclear bodies or apoptotic bodies. For example, where a THAP-family or THAP domain polypeptide-EGFP fusion polypeptide is used, distribution of THAP-family or THAP domain polypeptide EGFP-associated fluorescence in apoptotic cells would be identical to the distribution of DAPI or Hoechst 33342 dyes, which are conventionally used to detect the nuclear DNA changes associated with apoptosis (Cohen et al., supra). A minimum of approximately 100 cells, which display characteristic EGFP fluorescence, are evaluated by fluorescence microscopy. Apoptosis is scored as nuclear fragmentation, marked apoptotic bodies, and cytoplasmic boiling. The characteristics of nuclear fragmentation are particularly visible when THAP-family or THAP domain polypeptide-EGFP condenses in apoptotic bodies.

The ability of the THAP-family- or THAP domain polypeptides to undergo nuclear localization and to induce apoptosis can be tested by transient expression in 293 human kidney cells. If proved susceptible to THAP-family- or THAP domain-induced apoptosis, 293 cells can serve as a convenient initial screen for those THAP family or THAP domain polypeptides, or biologically active fragments or homologues thereof that will likely also induce apoptosis in other (e.g. endothelial cells or cancer cells). In an exemplary protocol, 293 cells are transfected with plasmid vectors expressing THAP-family- or THAP domain-EGFP fusion protein. Approximately 5*10$^6$ 293 cells in 100 mm dishes were transfected with 10 g of plasmid DNA using the calcium-phosphate method. The plasmids used are comprise CMV enhancer/promoter and THAP-family- or THAP domain-EGFP coding sequence). Apoptosis is evaluated 24 hrs after transfection by TUNEL and DAPI staining. The THAP-family- or THAP domain-EGFP vector transfected cells are evaluated by fluorescence microscopy with observation of typical nuclear aggregation of the EGFP marker as an indication of apoptosis. If apoptotic, the distribution of EGFP signal in cells expressing THAP-family- or THAP domain-EGFP will be identical to the distribution of DAPI or Hoechst 33342 dyes, which are conventionally used to detect the nuclear DNA changes associated with apoptosis (Cohen et al., supra).

The ability of the THAP family or THAP domain polypeptides, or biologically active fragments or homologues thereof to induce apoptosis can also be tested by expression assays in human cancer cells, for example as available from NCI. Vector type (for example plasmid or retroviral or sindbis viral) can be selected based on efficiency in a given cell type. After the period indicated, cells are evaluated for morphological signs of apoptosis, including aggregation of THAP-family- or THAP domain-EGFP into nuclear apoptotic bodies. Cells are counted under a fluorescence microscope and scored as to the presence or absence of apoptotic signs, or cells are scored by fluorescent TUNEL assay and counted in a flow cytometer. Apoptosis is expressed as a percent of cells displaying typical advanced changes of apoptosis.

Cells from the NCI panel of tumor cells include from example:
- colon cancer, expression using a retroviral expression vector, with evaluation of apoptosis at 96 hrs post-infection (cell lines KM12; HT-29; SW-620; COL0205; HCT-5; HCC 2998; HCT-116);
- CNS tumors, expression using a retroviral expression vector, with evaluation of apoptosis at 96 hrs post-infection (cell lines SF-268, astrocytoma; SF-539, glioblastoma; SNB-19, gliblastoma; SNB-75, astrocytoma; and U251, glioblastoma;
- leukemia cells, expression using a retroviral expression vector, with evaluation of apoptosis at 96 hrs post-infection (cell lines CCRF-CEM, acute lymphocytic leukemia (ALL); K562, acute myelogenous leukemia (AML); MOLT-4, ALL; SR, immunoblastoma large cell; and RPMI 8226, Myeloblastoma);
- prostate cancer, expression using a retroviral expression vector, with evaluation of apoptosis at 96 hrs post-infection (PC-3);
- kidney cancer, expression using a retroviral expression vector, with evaluation of apoptosis at 96 hrs post-infection (cell lines 768-0; UO-31; TK10; ACHN);
- skin cancer, expression using a retroviral expression vector, with evaluation of apoptosis at 96 hrs post-infection (Melanoma) (cell lines SKMEL-28; M14; SKMEL-5; MALME-3);
- lung cancer, expression using a retroviral expression vector, with evaluation of apoptosis at 96 hrs post-infection (cell lines HOP-92; NCI-H460; HOP-62; NCI-H522; NCI-H23; A549; NCI-H226; EKVX; NCI-H322);
- breast cancer, expression using a retroviral expression vector, with evaluation of apoptosis at 96 hrs post-infection (cell lines MCF-7; T-47D; MCF-7/ADR; MDAMB43; MDAMB23; MDA-N; BT-549);
- ovary cancer, expression using either a retroviral expression vector and protocol or the Sindbis viral expression vector and protocol, with evaluation of apoptosis at 96 hrs post-infection with retrovirus or at 24 hrs post-infection with Sindbis viral vectors (cell lines OVCAR-8; OVCAR-4; IGROV-1; OVCAR-5; OVCAR3; SK-OV-3).

In a further representative example, the susceptibility of malignant melanoma cells to apoptosis induced by a THAP family or THAP domain polypeptide, or a biologically active fragment or homologue thereof can be tested in several known melanoma cell types: human melanoma WM 266-4 (ATCC CRL-1676); human malignant melanoma A-375 (ATCC CRL-1619); human malignant, melanoma A2058 (ATCC CRL-11147); human malignant melanoma SK-MEL-31 (ATCC HTB-73); human malignant melanoma RPMI-7591 ATCC HTB-66 (metastasis to lymph node). Primary melanoma isolates can also be tested. In addition, human chronic myelogenous leukemia K-562 cells (ATCC CCL-243), and 293 human kidney cells (ATCC CRL-1573) (transformed primary embryonal cell) are tested. Normal human primary dermal fibroblasts and Rat-i fibroblasts serve as controls. All melanoma cell lines are metastatic on the basis of their isolation from metastases or metastatic nodules. A transient expression strategy is used in order to evaluate induction of a THAP-family or THAP domain polypeptide-mediated apoptosis without artifacts associated with prolonged selection. An expression vector encoding the THAP-family or THAP domain polypeptide-EGFP fusion protein described below can be used in order to facilitate identification of those cells expressing the a THAP-family or THAP domain polypeptide. Cells are transiently transfected by the method optimal for the cell being tested (either $CaPO_4$ or Lipofectin). Expression of a THAP-family or THAP domain polypeptide and induction of apoptosis is examined using a fluorescence microscope at 24 hrs and 48 hrs post-transfection. A minimum of approximately 100 cells, which display characteristic EGFP fluorescence, are evaluated by fluorescence microscopy. Apoptosis is scored as nuclear fragmentation, marked apoptotic bodies, and cytoplasmic boiling. The characteristics of nuclear fragmentation are particularly visible when THAP-family or THAP domain polypeptide-EGFP condenses in apoptotic bodies.

In a further example, the susceptibility of endothelial cells to apoptosis induced by a THAP family or THAP domain polypeptide, or a biologically active fragment or homologue thereof can be tested in several known endothelial cell types: HUVEC (human umbilical vein endothelial cells; BioWhittaker-Clonetics, 8830 Biggs Ford Road, Walkersville, Md. 21793-0127, Cat N° CC-2519), HMVEC-L (human microvascular endothelial cells from the lung; BioWhittaker-Clonetics, 8830 Biggs Ford Road, Walkersville, Md. 21793-0127, Cat N° CC-2527), HMVEC-d (human microvascular endothelial cells from the dermis; BioWhittaker-Clonetics, 8830 Biggs Ford Road, Walkersville, Md. 21793-0127, Cat N° CC-2543). These and other endothelial cell types may be useful as models in providing an indication of the ability of THAP-family or THAP domain polypeptides to induce apoptosis in therapeutic strategies for the regulation of angiogenesis. A transient expression strategy is used in order to evaluate induction of a THAP-family or THAP domain polypeptide-mediated apoptosis without artifacts associated with prolonged selection. An expression vector encoding the a THAP-family or THAP domain polypeptide-EGFP fusion protein described below can be used in order to facilitate identification of those cells expressing the a THAP-family or THAP domain polypeptide. Cells are transiently transfected by the method optimal for the cell being tested (either $CaPO_4$ or Lipofectin). Expression of a THAP-family or THAP domain polypeptide and induction of apoptosis is examined using a fluorescence microscope at 24 hrs and 48 hrs post-transfection. A minimum of approximately 100 cells, which display characteristic EGFP fluorescence, are evaluated by fluorescence microscopy. Apoptosis is scored as nuclear fragmentation, marked apoptotic bodies, and cytoplasmic boiling. The characteristics of nuclear fragmentation are particularly visible when THAP-family or THAP domain polypeptide-EGFP condenses in apoptotic bodies.

In another example, a transient transfection assay procedure is similar to that previously described for detecting apoptosis induced by IL-1-beta-converting enzyme (Miura et al., Cell 75: 653-660 (1993); Kumar et al., Genes Dev. 8: 1613-

1626 (1994); Wang et al., Cell 78: 739-750 (1994); and U.S. Pat. No. 6,221,615, the disclosures of which are incorporated herein by reference). One day prior to transfection, cells (for example Rat-1 cells) are plated in 24 well dishes at $3.5*10^4$ cells/well. The following day, the cells are transfected with a marker plasmid encoding beta-galactosidase, in combination with an expression plasmid encoding THAP-family or THAP domain polypeptide, by the Lipofectamine procedure (Gibco/BRL). At 24 hours post transfection, cells are fixed and stained with X-Gal to detect beta-galactosidase expression in cells that received plasmid DNA (Miura et al., supra). The number of blue cells is counted by microscopic examination and scored as either live (flat blue cells) or dead (round blue cells). The cell killing activity of the THAP-family or THAP domain polypeptide in this assay is manifested by a large reduction in the number of blue cells obtained relative to co-transfection of the beta-gal plasmid with a control expression vector (i.e., with no THAP-family or THAP domain polypeptide cDNA insert).

In yet another example, beta-galactosidase co-transfection assays can be used for determination of cell death. The assay is performed as described (Hsu, H. et al, (1995). Cell 81,495-504; Hsu, H. et al, (1996a). Cell 84, 299-308; and Hsu, H. et al, (1996b) Inmunity 4, 387-396 and U.S. Pat. No. 6,242,569, the disclosures of which are incorporated herein by reference). Transfected cells are stained with X-gal as described in Shu, H. B. et al, ((1995) J. Cell Sci. 108, 2955-2962, the disclosure of which is incorporated herein by reference). The number of blue cells from 8 viewing fields of a 35 mm dish is determined by counting. The average number from one representative experiment is shown.

Assays for apoptosis can also be carried out by making use of any suitable biological marker of apoptosis. Several methods are described as follows.

In one aspect, fluorocytometric studies of cell death status can be carried out. Technology used in fluorocytometric studies employs the identification of cells at three different phases of the cell cycle: $G_1$, S. and $G_2$. This is largely performed by DNA quantity staining by propidium iodide labelling. Since the dying cell population contains the same DNA quantity as the living counterparts at any of the three phases of the cell cycle, there is no way to distinguish the two cell populations. One can perform double labelling for a biological marker of apoptosis (e.g. terminin Tp30, U.S. Pat. No. 5,783,667) positivity and propidium iodide (PI) staining together. Measurement of the labelling indices for the biological marker of apoptosis and PI staining can be used in combination to obtain the exact fractions of those cells in $G_1$ that are living and dying. Similar estimations can be made for the S-phase and $G_2$ phase cell populations.

In this assay, the cells are processed for formaldehyde fixation and extraction with 0.05% Triton. Afterwards, the cell specimens are incubated with monoclonal antibody to a marker of apoptosis overnight at room temperature or at 37 C for one hour. This is followed by further incubation with fluoresceinated goat antimouse antibody, and subsequent incubation by propidium iodide staining. The completely processed cell specimens are then evaluated by fluorocytometric measurement on both fluorescence (marker of apoptosis) and rhodamine (PI) labelling intensity on a per cell basis, with the same cell population simultaneously.

In another aspect, it is possible to assess the inhibitory effect on cell growth by therapeutic induction of apoptosis. One routine method to determine whether a particular chemotherapeutic drug can inhibit cancerous cell growth is to examine cell population size either in culture, by measuring the reduction in cell colony size or number, or measuring soft agar colony growth or in vivo tumor formation in nude mice, which procedures require time for development of the colonies or tumor to be large enough to be detectable. Experiments involved in these approaches in general require large-scale planning and multiple repeats of lengthy experimental span (at least three weeks). Often these assays do not take into account the fact that a drug may not be inhibiting cell growth, but rather killing the cells, a more favorable consequence needed for chemotherapeutic treatment of cancer. Thus, assays for the assessment of apoptotis activity can involve using a biological or biochemical marker specific for quiescent, non-cycling or non-proliferating cells. For example, a monoclonal antibody can be used to assess the non-proliferating population of cells in a given tissue which indirectly gives a measure of the proliferating component of a tumor or cell mass. This detection can be combined with a biological or biochemical marker (e.g. antibodies) to detect the dying cell population pool, providing a powerful and rapid assessment of the effectiveness of any given drugs in the containment of cancerous cell growth. Applications can be easily performed at the immunofluorescence microscopic level with cultured cells or tissue sections.

In other aspects, a biological or biochemical marker can be used to assess pharmacological intervention on inhibition of cell death frequency in degenerative diseases. For degenerative diseases such as Alzheimer's or Parkinson's disease, these losses may be due to the premature activation of the cell death program in neurons. In osteoporosis, the cell loss may be due to an improper balance between osteoblast and osteoclast cells, due to the too active programmed cell death process killing more cells than the bone tissue can afford. Other related phenomena may also occur in the wound healing process, tissue transplantation and cell growth in the glomerus during kidney infection, where the balance between living and dying cell populations is an essential issue to the health status of the tissue, and are further described in the section titled "Methods of treatment". A rapid assessment of dying cell populations can be made through the immunohistochemical and biochemical measurements of a biological or biochemical marker of apoptosis in degenerative tissues. In one example, a biological or biochemical marker can be used to assess cell death status in oligodendrocytes associated with Multiple Sclerosis. Positive staining of monoclonal antibody to a marker of apoptosis (such as Tp30, U.S. Pat. No. 5,783, 667, the disclosure of which is incorporated herein by reference) occurs in dying cultured human oligodendrocytes. The programmed cell death event is activated in these oligodendrocytes by total deprivation of serum, or by treatment with tumor necrosis factor (TNF).

In general, a biological or biochemical marker can also be used to assess cell death status in pharmacological studies in animal models. Attempting to control either a reduced cell death rate, in the case of cancer, or an increased cell death rate, in the case of neurodegeneration, has been recently seen as a new mode of disease intervention. Numerous approaches via either intervention with known drugs or gene therapy are in progress, starting from the base of correcting the altered programmed cell death process, with the concept on maintaining a balanced cell mass in any given tissue. For these therapeutic interventions, the bridge between studies in cultured cells and clinical trials is animal studies, i.e. success in intervention with animal models, in either routine laboratory animals or transgenic mice bearing either knock-out or over-expression phenotypes. Thus, a biological or biochemical marker of apoptosis, such as an antibody for an apoptosis-specific protein, is a useful tool for examining apoptotic death status in terms of change in dying cell numbers between normal and experimentally manipulated animals. In this context the invention, as a diagnostic tool for assessing cell death status, could help to determine the efficacy and potency of a drug or a gene therapeutic approach.

As discussed, provided are methods for assessing the activity of THAP-family members and therapeutic treatment acting on THAP-family members or related biological pathways. However, in other aspects, the same methods may be used for assessment of apoptosis in general, when a THAP-family member is used as a biological marker of apoptosis. Thus, the invention also provides diagnostic and assay methods using a THAP-family member as a marker of cell death or apoptotic activity. Further diagnostic assays are also provided herein in the section titled 'Diagnostic and prognostic uses'.

Methods of Treatment

A large body of evidence gathered from experiments carried out with apoptosis modulating strategies suggests that treatments acting on apoptosis-inducing or cell proliferation-reducing proteins may offer new treatment methods for a wide range of disorders. Methods of treatment according to the invention may act in a variety of manners, given the novel function provided for a number of proteins, and the linking of several biological pathways.

Provided herein are treatment methods based on the functionalization of the THAP-family members. THAP family or THAP domain polypeptides, and biologically active fragments and homologues thereof, as described further herein may be useful in modulation of apoptosis or cell proliferation.

The methods of treatment involve acting on a molecule of the invention (that is, a THAP family member polypeptide, THAP-family target, or PAR4 or PAR4 target). Included are methods which involve modulating THAP-family polypeptide activity, THAP-family target activity, or PAR4 or PAR4 target activity. This modulation (increasing or decreasing) of activity can be carried out in a number of suitable ways, several of which have been described in the present application.

For example, methods of treatment may involve modulating a "THAP-family activity", "biological activity of a THAP-family member" or "functional activity of a THAP-family member". Modulating THAP-family activity may involve modulating an association with a THAP-family-target molecule (for example, association of THAP1, THAP2 or THAP3 with Par4 or association of THAP1, THAP2 or THAP3 with a PML-NB protein) or preferably any other activity selected from the group consisting of: (1) mediating apoptosis or cell proliferation when expressed or introduced into a cell, most preferably inducing or enhancing apoptosis, and/or most preferably reducing cell proliferation; (2) mediating apoptosis or cell proliferation of an endothelial cell; (3) mediating apoptosis or cell proliferation of a hyperproliferative cell; (4) mediating apoptosis or cell proliferation of a CNS cell, preferably a neuronal or glial cell; or (5) an activity determined in an animal selected from the group consisting of mediating, preferably inhibiting angiogenesis, mediating, preferably inhibiting inflammation, inhibition of metastatic potential of cancerous tissue, reduction of tumor burden, increase in sensitivity to chemotherapy or radiotherapy, killing a cancer cell, inhibition of the growth of a cancer cell, or induction of tumor regression. Detecting THAP-family activity may also comprise detecting any suitable therapeutic endpoint associated with a disease condition discussed herein.

In another example, methods of treatment may involve modulating a "PAR4 activity", "biological activity of PAR4" or "functional activity of PAR4". Modulating PAR4 activity may involve modulating an association with a PAR4-target molecule (for example THAP1, THAP2, THAP3 or PML-NB protein) or most preferably PAR4 apoptosis inducing or enhancing (e.g. signal transducing) activity, or inhibition of cell proliferation or cell cycle.

Methods of treatment may involve modulating the recruitment, binding or association of proteins to PML-NBs, or otherwise modulating PML-NBs activity. The present invention also provides methods for modulating PAR4 activity, comprising modulating PAR4 interactions with THAP-family proteins, and PAR4 and PML-NBs, as well as modulating THAP-family activity, comprising modulating for example THAP1 interactions with PML-NBs. The invention encompasses inhibiting or increasing the recruitment of THAP1, or PAR4 to PML-NBs. Preventing the binding of either or both of THAP1 or PAR4 to PML-NBs may increase the bioavailability or THAP1 and/or PAR4, thus providing a method of increasing THAP1 and/or PAR4 activity. The invention also encompasses inhibiting or increasing the binding of a THAP-family protein (such as THAP1) or PAR4 to PML-NBs or to another protein associated with PML-NBs, such as a protein selected from the group consisting of daxx, sp100, sp140, p53, pRB, CBP, BLM, SUMO-1. For example, the invention encompasses modulating PAR4 activity by preventing the binding of THAP1 to PAR4, or by preventing the recruitment or binding of PAR4 to PML-NBs.

Therapeutic methods and compositions of the invention may involve (1) modulating apoptosis or cell proliferation, most preferably inducing or enhancing apoptosis, and/or most preferably reducing cell proliferation; (2) modulating apoptosis or cell proliferation of an endothelial cell (3) modulating apoptosis or cell proliferation of a hyperproliferative cell; (4) modulating apoptosis or cell proliferation of a CNS cell, preferably a neuronal or glial cell; (5) inhibition of metastatic potential of cancerous tissue, reduction of tumor burden, increase in sensitivity to chemotherapy or radiotherapy, killing a cancer cell, inhibition of the growth of a cancer cell, or induction tumor regression; or (6) interaction with a THAP family target molecule or THAP domain target molecule, preferably interaction with a protein or a nucleic acid. Methods may also involve improving a symptom of or ameliorating a condition as further described herein.

Antiapoptotic Therapy

Molecules of the invention (e.g. those obtained using the screening methods described herein, dominant negative mutants, antibodies etc.) which inhibit apoptosis are also expected to be useful in the treatment and/or prevention of disease. Diseases in which it is desirable to prevent apoptosis include neurodegenerative diseases such as Alzheimer's disease, Parkinson's disease, amyotrophic lateral sclerosis, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; and etc. The apoptosis inhibitor of the present invention is especially preferably used as an agent for prophylaxis or treatment of a neurodegenerative disease (see also Adams, J. M., Science, 281:1322 (1998).

Included as inhibitors of apoptosis as described herein are generally any molecule which inhibits activity of a THAP family or THAP domain polypeptide, or a biologically active fragment or homologue thereof, a THAP-family target protein or PAR4 (particularly PAR4/PML-NB protein interactions). THAP-family and THAP domain polypeptides inhibitors may include for example antibodies, peptides, dominant negative THAP-family or THAP domain analogs, small molecules, ribozyme or antisense nucleic acids. These inhibitors may be particularly advantageous in the treatment of neurodegenerative disorders. Particularly preferred are inhibitors which affect binding of THAP-family protein to a THAP-family target protein, and inhibitors which affect the DNA binding activity of a THAP-family protein.

In further preferred aspects the invention provides inhibitors of THAP-family activity, including but not limited to molecules which interfere or inhibit interactions of THAP-family proteins with PAR4, for th e treatment of endothelial cell related disorders and neurodegenerative disorders. Support is found in the literature, as PAR4 appears to play a key role in neuronal apoptosis in various neurodegenerative disorders (Guo et al., 1998; Mattson et al., 2000; Mattson et al., 1999; Mattson et al., 2001). THAP1, which is expressed in brain and associates with PAR4 may therefore also play a key role in neuronal apoptosis. Drugs that inhibit THAP-family and/or inhibit THAP-family/PAR4 complex formation may lead to the development of novel preventative and therapeutic strategies for neurodegenerative disorders.

Apoptosis Regulation in Endothelial Cells

The invention also provides methods of regulating angiogenesis in a subject which are expected to be useful in the treatment of cancer, cardiovascular diseases and inflammatory diseases. An inducer of apoptosis of immortalized cells is expected to be useful in suppressing tumorigenesis and/or metastasis in malignant tumors. Examples of malignant tumors include leukemia (for example, myelocytic leukemia, lymphocytic leukemia such as Burkitt lymphoma), digestive tract carcinoma, lung carcinoma, pancreas carcinoma, ovary carcinoma, uterus carcinoma, brain tumor, malignant melanoma, other carcinomas, and sarcomas. The present inventors have isolated both THAP1 and PAR4 cDNAs from human endothelial cells, and both PAR4 and PML are known to be expressed predominantly in blood vessel endothelial cells (Boghaert et al., (1997) Cell Growth Differ 8(8):881-90; Terris B. et al, (1995) Cancer Res. 55(7):1590-7, 1995, the disclosures of which are incorporated herein by reference), suggesting that the PML-NBs-and the newly associated THAP1/PAR4 proapoptotic complex may be a major regulator of endothelial cell apoptosis in vivo and thus constitute an attractive therapeutic target for angiogenesis-dependent diseases. For example, THAP1 and PAR4 pathways may allow selective treatments that regulate (e.g. stimulate or inhibit) angiogenesis.

In a first aspect, the invention provides methods of inhibiting endothelial cell apoptosis, by administering a THAP1 or PAR4 inhibitor, or optionally a THAP1/PAR4 interaction inhibitor or optionally an inhibitor of THAP1 DNA binding activity. As further described herein, the THAP domain is involved in THAP1 pro-apoptotic activity. Deletion of the THAP domain abrogates the proapoptotic activity of THAP1 in mouse 3T3 fibroblasts, as shown in Example 11. Also, as further described herein, deletion of residues 168-172 or replacement of residues 171-172 abrogates THAP1 binding to PAR4 both in vitro and in vivo and results in lack of recruitment of PAR4 by THAP1 to PML-NBs. For PAR4, the leucine zipper domain is required (and is sufficient) for binding to THAP1.

Inhibiting endothelial cell apoptosis may improve angiogenesis and vasculogenesis in patients with ischemia and may also interfere with focal dysregulated vascular remodeling, the key mechanism for atherosclerotic disease progression.

In another aspect, the invention provides methods of inducing endothelial cell apoptosis, by administering for example a biologically active THAP family polypeptide such as THAP1, a THAP domain polypeptide or a PAR4 polypeptide, or a biologically active fragment or homologue thereof, or a THAP1 or PAR4 stimulator. Stimulation of endothelial cell apoptosis may prevent or inhibit angiogenesis and thus limit unwanted neovascularization of tumors or inflamed tissues (see Dimmeler and Zeiher, Circulation Research, 2000, 87:434-439, the disclosure of which is incorporated herein by reference).

Angiogenesis

Angiogenesis is defined in adult organism as the formation of new blood vessels by a process of sprouting from pre-existing vessels. This neovascularization involves activation, migration, and proliferation of endothelial cells and is driven by several stimuli, among those shear stress. Under normal physiological conditions, humans or animals undergo angiogenesis only in very specific restricted situations. For example, angiogenesis is normally observed in wound healing, fetal and embryonal development and formation of the corpus luteum, endometrium and placenta. Molecules of the invention may have endothelial inhibiting or inducing activity, having the capability to inhibit or induce angiogenesis in general.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases. It is thus an object of the present invention to provide methods and compositions for treating diseases and processes that are mediated by angiogenesis including, but not limited to, hemangioma, solid tumors, leukemia, metastasis, telangiectasia psoriasis scleroderma, pyogenic granuloma, Myocardial angiogenesis, plaque neovascularization, cororany collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

(i) Anti-Angiogenic Therapy

In one aspect the invention provides anti-angiogenic therapies as potential treatments for a wide variety of diseases, including cancer, arteriosclerosis, obesity, arthritis, duodenal ulcers, psoriasis, proliferative skin disorders, cardiovascular disorders and abnormal ocular neovascularization caused, for example, by diabetes (Folkman, Nature Medicine 1:27 (1995) and Folkman, Seminars in Medicine of the Beth Israel Hospital, Boston, New England Journal of Medicine, 333: 1757 (1995)). Anti-angiogenic therapies are thought to act by inhibiting the formation of new blood vessels.

The present invention thus provides methods and compositions for treating diseases and processes mediated by undesired and uncontrolled angiogenesis by administering to a human or animal a composition comprising a substantially purified THAP family or THAP domain polypeptide, or a biologically active fragment, homologue or derivative thereof in a dosage sufficient to inhibit angiogenesis, administering a vector capable of expressing a nucleic acid encoding a THAP-family or THAP domain protein, or administering any other inducer of expression or activity of a THAP-family or THAP domain protein. The present invention is particularly useful for treating or for repressing the growth of tumors. Administration of THAP-family or THAP domain nucleic acid, protein or other inducer to a human or animal with prevascularized metastasized tumors will prevent the growth or expansion of those tumors. THAP-family activity may be used in combination with other compositions and procedures for the treatment of diseases. For example, a tumor may be treated conventionally with surgery, radiation or chemotherapy combined with THAP-family or THAP domain protein and then THAP-family or THAP domain protein may be subsequently administered to the patient to extend the dormancy of micrometastases and to stabilize any residual primary tumor.

In a preferred example, a THAP-family polypeptide activity, preferably a THAP1 activity is used for the treatment of arthritis, for example rheumatiod arthritis. Rheumatoid arthritis is characterized by symmetric, polyarticular inflammation of synovial-lined joints, and may involve extraarticular tissues, such as the pericardium, lung, and blood vessels.

(ii) Angiogenic Therapy

In another aspect, the inhibitors of THAP-family protein activity, particularly THAP1 activity, could be used as an anti-apoptotic and thus as an angiogenic therapy. Angiogenic therapies are potential treatments for promoting wound healing and for stimulating the growth of new blood vessels to by-pass occluded ones. Thus, pro-angiogenic therapies could potentially augment or replace by-pass surgeries and balloon angioplasty (PTCA). For example, with respect to neovascularization to bypass occluded blood vessels, a "therapeutically effective amount" is a quantity which results in the formation of new blood vessels which can transport at least some of the blood which normally would pass through the blocked vessel.

The THAP-family protein of the present invention can for example be used to generate antibodies that can be used as inhibitors of apoptosis. The antibodies can be either polyclonal antibodies or monoclonal antibodies. In addition, these antibodies that specifically bind to the THAP-family protein can be used in diagnostic methods and kits that are well known to those of ordinary skill in the art to detect or quantify the THAP-family protein in a body fluid. Results from these tests can be used to diagnose or predict the occurrence or recurrence of a cancer and other angiogenic mediated diseases.

It will be appreciated that other inhibitors of THAP-family and THAP domain proteins can also be used in angiogenic therapies, including for example small molecules, antisense nucleic acids, dominant negative THAP-family and THAP domain proteins or peptides identified using the above methods.

In view of applications in both angiogenic and antiangiogenic therapies, molecules of the invention may have endothelial inhibiting or inducing activity, having the capability to inhibit or induce angiogenesis in general. It will be appreciated that methods of assessing such capability are known in the art, including for example assessing antiangiogenic properties as the ability inhibit the growth of bovine capillary endothelial cells in culture in the presence of fibroblast growth factor.

It is to be understood that the present invention is contemplated to include any derivatives of the THAP family or THAP domain polypeptides, and biologically active fragments and homologues thereof that have endothelial inhibitory or apoptotic activity. The present invention includes full-length THAP-family and THAP domain proteins, derivatives of the THAP-family and THAP domain proteins and biologically-active fragments of the THAP-family and THAP domain proteins. These include proteins with THAP-family protein activity that have amino acid substitutions or have sugars or other molecules attached to amino acid functional groups. The methods also contemplate the use of genes that code for a THAP-family protein and to proteins that are expressed by those genes.

As discussed, several methods are described herein for delivering a modulator to a subject in need of treatment, including for example small molecule modulators, nucleic acids including via gene therapy vectors, and polypeptides including peptide mimetics, active polypeptides, dominant negative polypeptides and antibodies. It will be thus be appreciated that modulators of the invention identified according to the methods in the section titled "Drug Screening Assays" can be further tested in cell or animal models for their ability to ameliorate or prevent a condition involving a THAP-family polypeptide, particularly THAP1, THAP1, THAP2 or THAP3/PAR4 interactions, THAP-family DNA binding or PAR4/PML-NBs interactions. Likewise, nucleic acids, polypeptides and vectors (e.g. viral) can also be assessed in a similar manner.

An "individual" treated by the methods of this invention is a vertebrate, particularly a mammal (including model animals of human disease, farm animals, sport animals, and pets), and typically a human.

"Treatment" refers to clinical intervention in an attempt to alter the natural course of the individual being treated, and may be performed either for prophylaxis or during the course of clinical pathology. Desirable effects include preventing occurrence or recurrence of disease, alleviation of symptoms, diminishment of any direct or indirect pathological consequences of the disease, such as hyperresponsiveness, inflammation, or necrosis, lowering the rate of disease progression, amelioration or palliation of the disease state, and remission or improved prognosis. The "pathology" associated with a disease condition is anything that compromises the well-being, normal physiology, or quality of life of the affected individual.

Treatment is performed by administering an effective amount of a THAP-family polypeptide inhibitor or activator. An "effective amount" is an amount sufficient to effect a beneficial or desired clinical result, and can be administered in one or more doses.

The criteria for assessing response to therapeutic modalities employing the lipid compositions of this invention are dictated by the specific condition, measured according to standard medical procedures appropriate for the condition.

Pharmaceutical Compositions

Compounds capable of inhibiting THAP-family activity, preferably small molecules but also including peptides, THAP-family nucleic acid molecules, THAP-family proteins, and anti-THAP-family antibodies (also referred to herein as "active compounds") of the invention can be incorporated into pharmaceutical compositions suitable for administration. Such compositions typically comprise a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL$\alpha$ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Where the active compound is a protein, peptide or anti-THAP-family antibody, sterile injectable solutions can be prepared by incorporating the active compound (e.g.,) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. For administration by inhalation, the compounds are delivered in the form of an aerosol spray from pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Most preferably, active compound is delivered to a subject by intravenous injection.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the disclosure of which is incorporated herein by reference in its entirety.

It is especially advantageous to formulate oral or preferably parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Diagnostic and Prognostic Uses

The nucleic acid molecules, proteins, protein homologues, and antibodies described herein can be used in one or more of the following methods: diagnostic assays, prognostic assays, monitoring clinical trials, and pharmacogenetics; and in drug screening and methods of treatment (e.g., therapeutic and prophylactic) as further described herein.

The invention provides diagnostic and prognosite assays for detecting THAP-family members, as further described. Also provided are diagnostic and prognostic assays for detecting interactions between THAP-family members and THAP-family target molecules. In a preferred example, a THAP-family member is THAP1, THAP2 or THAP3 and the THAP-family target is PAR4 or a PML-NB protein.

The invention also provides diagnostic and prognosite assays for detecting THAP1 and/or PAR4 localization to or association with PML-NBs, or association with or binding to a PML-NB-associated protein, such as daxx, sp100, sp140, p53, pRB, CBP, BLM or SUMO-1. In a preferred method, the invention provides detecting PAR4 localization to or association with PML-NBs. In a further aspect, the invention provides detecting THAP-family nucleic acid binding activity.

The isolated nucleic acid molecules of the invention can be used, for example, to detect THAP-family polypeptide mRNA (e.g., in a biological sample) or a genetic alteration in a THAP-family gene, and to modulate a THAP-family polypeptide activity, as described further below. The THAP-family proteins can be used to treat disorders characterized by insufficient or excessive production of a THAP-family protein or THAP-family target molecules. In addition, the THAP-family proteins can be used to screen for naturally occurring THAP-family target molecules, to screen for drugs or compounds which modulate, preferably inhibit THAP-family activity, as well as to treat disorders characterized by insufficient or excessive production of THAP-family protein or production of THAP-family protein forms which have decreased or aberrant activity compared to THAP-family wild type protein. Moreover, the anti-THAP-family antibodies of the invention can be used to detect and isolate THAP-family proteins, regulate the bioavailability of THAP-family proteins, and modulate THAP-family activity.

Accordingly one embodiment of the present invention involves a method of use (e.g., a diagnostic assay, prognostic assay, or a prophylactic/therapeutic method of treatment) wherein a molecule of the present invention (e.g., a THAP-family protein, THAP-family nucleic acid, or most preferably a THAP-family inhibitor or activator) is used, for example, to diagnose, prognose and/or treat a disease and/or condition in which any of the aforementioned THAP-family activities is indicated. In another embodiment, the present invention involves a method of use (e.g., a diagnostic assay, prognostic assay, or a prophylactic/therapeutic method of treatment) wherein a molecule of the present invention (e.g., a THAP-family protein, THAP-family nucleic acid, or a THAP-family inhibitor or activator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment) involve administering to a subject, preferably a human subject, a molecule of the present invention (e.g., a THAP-family protein, THAP-family nucleic acid, or a THAP-family inhibitor or activator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a THAP-family protein, THAP-family nucleic acid, or a THAP-family inhibitor or activator).

For example, the invention encompasses a method of determining whether a THAP-family member is expressed within a biological sample comprising: a) contacting said biological sample with: ii) a polynucleotide that hybridizes under stringent conditions to a THAP-family nucleic acid; or iii) a detectable polypeptide (e.g. antibody) that selectively binds to a THAP-family polypeptide; and b) detecting the presence or absence of hybridization between said polynucleotide and an RNA species within said sample, or the presence or absence of binding of said detectable polypeptide to a polypeptide within said sample. A detection of said hybridization or of said binding indicates that said THAP-family member is expressed within said sample. Preferably, the polynucleotide is a primer, and wherein said hybridization is detected by detecting the presence of an amplification product comprising said primer sequence, or the detectable polypeptide is an antibody.

Also envisioned is a method of determining whether a mammal, preferably human, has an elevated or reduced level of expression of a THAP-family member, comprising: a) providing a biological sample from said mammal; and b) comparing the amount of a THAP-family polypeptide or of a THAP-family RNA species encoding a THAP-family polypeptide within said biological sample with a level detected in or expected from a control sample. An increased amount of said THAP-family polypeptide or said THAP-family RNA species within said biological sample compared to said level detected in or expected from said control sample indicates that said mammal has an elevated level of THAP-family expression, and a decreased amount of said THAP-family polypeptide or said THAP-family RNA species within said biological sample compared to said level detected in or expected from said control sample indicates that said mammal has a reduced level of expression of a THAP-family member.

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining THAP-family protein and/or nucleic acid expression as well as THAP-family activity, in the context of a biological sample (e.g., blood, serum, cells, tissue) to thereby determine whether an individual is afflicted with a disease or disorder, or is at risk of developing a disorder, associated with aberrant THAP-family expression or activity. The invention also provides for prognostic (or predictive) assays for determining whether an individual is at risk of developing a disorder associated with a THAP-family protein, nucleic acid expression or activity. For example, mutations in a THAP-family gene can be assayed in a biological sample. Such assays can be used for prognostic or predictive purpose to thereby phophylactically treat an individual prior to the onset of a disorder characterized by or associated with a THAP-family protein, nucleic acid expression or activity.

Accordingly, the methods of the present invention are applicable generally to diseases related to regulation of apoptosis, including but not limited to disorders characterized by unwanted cell proliferation or generally aberrant control of differentiation, for example neoplastic or hyperplastic disorders, as well as disorders related to proliferation or lack thereof of endothelial cells, inflammatory disorders and neurodegenerative disorders.

Diagnostic Assays

An exemplary method for detecting the presence (quantitative or not) or absence of a THAP-family protein or nucleic acid in a biological sample involves obtaining a biological sample from a test subject and contacting the biological sample with a compound or an agent capable of detecting a THAP-family protein or nucleic acid (e.g., mRNA, genomic DNA) that encodes THAP-family protein such that the presence of the THAP-family protein or nucleic acid is detected in the biological sample. A preferred agent for detecting a THAP-family mRNA or genomic DNA is a labeled nucleic acid probe capable of hybridizing to a THAP-family mRNA or genomic DNA. The nucleic acid probe can be, for example, a full-length THAP-family nucleic acid, such as the nucleic acid of SEQ ID NO: 160 such as a nucleic acid of at least 15, 30, 50, 100, 250, 400, 500 or 1000 nucleotides in length and sufficient to specifically hybridize under stringent conditions to a THAP-family mRNA or genomic DNA or a portion of a THAP-family nucleic acid. Other suitable probes for use in the diagnostic assays of the invention are described herein.

In preferred embodiments, the subject method can be characterized by generally comprising detecting, in a tissue sample of the subject (e.g. a human patient), the presence or absence of a genetic lesion characterized by at least one of (i) a mutation of a gene encoding one of the subject THAP-family proteins or (ii) the mis-expression of a THAP-family gene. To illustrate, such genetic lesions can be detected by ascertaining the existence of at least one of (i) a deletion of one or more nucleotides from a THAP-family gene, (ii) an addition of one or more nucleotides to such a THAP-family gene, (iii) a substitution of one or more nucleotides of a THAP-family gene, (iv) a gross chromosomal rearrangement or amplification of a THAP-family gene, (v) a gross alteration in the level of a messenger RNA transcript of a THAP-family gene, (vi) aberrant modification of a THAP-family gene, such as of the methylation pattern of the genomic DNA, (vii) the presence of a non-wild type splicing pattern of a messenger RNA transcript of a THAP-family gene, and (viii) a non-wild type level of a THAP-family-target protein.

A preferred agent for detecting a THAP-family protein is an antibody capable of binding to a THAP-family protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect a THAP-family mRNA, protein, or genomic DNA in a biological sample in vitro as well as in vivo. For example, in vitro techniques for detection of a THAP-family mRNA include Northern hybridizations and in situ hybridizations. In vitro techniques for detection of a THAP-family protein include enzyme linked immunosorbent assays (ELISAs), Western blots, immunoprecipitations and immunofluorescence. In vitro techniques for detection of a THAP-family genomic DNA include Southern hybridizations. Furthermore, in vivo techniques for detection of a THAP-family protein include introducing into a subject a labeled anti-THAP-family antibody. For example, the antibody can be labeled with a radioactive marker whose presence and location in a subject can be detected by standard imaging techniques.

In yet another exemplary embodiment, aberrant methylation patterns of a THAP-family gene can be detected by digesting genomic DNA from a patient sample with one or more restriction endonucleases that are sensitive to methylation and for which recognition sites exist in the THAP-family gene (including in the flanking and intronic sequences). See, for example, Buiting et al. (1994) Human Mol Genet 3:893-895. Digested DNA is separated by gel electrophoresis, and hybridized with probes derived from, for example, genomic or cDNA sequences. The methylation status of the THAP-family gene can be determined by comparison of the restriction pattern generated from the sample DNA with that for a standard of known methylation.

Furthermore, gene constructs such as those described herein can be utilized in diagnostic assays to determine if a cell's growth or differentiation state is no longer dependent on the regulatory function of a THAP-family protein, e.g. in determining the phenotype of a transformed cell. Such knowledge can have both prognostic and therapeutic benefits. To illustrate, a sample of cells from the tissue can be obtained from a patient and dispersed in appropriate cell culture media, a portion of the cells in the sample can be caused to express a recombinant THAP-family protein or a THAP-family target protein, e.g. by transfection with a expression vector described herein, or to increase the expression or activity of an endogenous THAP-family protein or THAP-family target protein, and subsequent growth of the cells assessed. The absence of a change in phenotype of the cells despite expression of the THAP-family or THAP-family target protein may be indicative of a lack of dependence on cell regulatory pathways which includes the THAP-family or THAP-family target protein, e.g. THAP-family- or THAP-family target-mediated transcription. Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art.

In yet another embodiment, a diagnostic assay is provided which detects the ability of a THAP-family gene product, e.g., isolated from a biopsied cell, to bind to other cellular proteins. For instance, it will be desirable to detect THAP-family mutants which, while expressed at appreciable levels in the cell, are defective at binding a THAP-family target protein (having either diminished or enhanced binding affinity). Such mutants may arise, for example, from mutations, e.g., point mutants, which may be impractical to detect by the diagnostic DNA sequencing techniques or by the immunoassays described above. The present invention accordingly further contemplates diagnostic screening assays which generally comprise cloning one or more THAP-family genes from the sample cells, and expressing the cloned genes under conditions which permit detection of an interaction between that recombinant gene product and a target protein, e.g., for example the THAP1 gene and a target PAR4 protein or a PML-NB protein. As will be apparent from the description of the various drug screening assays set forth below, a wide variety of techniques can be used to determine the ability of a THAP-family protein to bind to other cellular components. These techniques can be used to detect mutations in a THAP-family gene which give rise to mutant proteins with a higher or lower binding affinity for a THAP-family target protein relative to the wild-type THAP-family. Conversely, by switching which of the THAP-family target protein and THAP-family protein is the "bait" and which is derived from the patient sample, the subject assay can also be used to detect THAP-family target protein mutants which have a higher or lower binding affinity for a THAP-family protein relative to a wild type form of that THAP-family target protein.

In an exemplary embodiment, a PAR4 or a PMB-NB protein (e.g. wild-type) can be provided as an immobilized protein (a "target"), such as by use of GST fusion proteins and glutathione treated microtitre plates. A THAP1 gene (a "sample" gene) is amplified from cells of a patient sample, e.g., by PCR, ligated into an expression vector, and transformed into an appropriate host cell. The recombinantly produced THAP1 protein is then contacted with the immobilized PAR4 or PMB-NB protein, e.g., as a lysate or a semi-purified preparation, the complex washed, and the amount of PAR4 or PMB-NB protein/THAP1 complex determined and compared to a level of wild-type complex formed in a control. Detection can be by, for instance, an immunoassay using antibodies against the wild-type form of the THAP1 protein, or by virtue of a label provided by cloning the sample THAP1 gene into a vector which provides the protein as a fusion protein including a detectable tag. For example, a myc epitope can be provided as part of a fusion protein with the sample THAP1 gene. Such fusion proteins can, in addition to providing a detectable label, also permit purification of the sample THAP1 protein from the lysate prior to application to the immobilized target. In yet another embodiment of the subject screening assay, the two hybrid assay, described in the appended examples, can be used to detect mutations in either a THAP-family gene or THAP-family target gene which alter complex formation between those two proteins.

Accordingly, the present invention provides a convenient method for detecting mutants of THAP-family genes encoding proteins which are unable to physically interact with a THAP-family target "bait" protein, which method relies on detecting the reconstitution of a transcriptional activator in a THAP-family/THAP-family target-dependent fashion.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject. In another embodiment, the methods further involve obtaining a control biological sample from a control subject, contacting the control sample with a compound or agent capable of detecting a THAP-family protein, mRNA, or genomic DNA, such that the presence of a THAP-family protein, mRNA or genomic DNA is detected in the biological sample, and comparing the presence of a THAP-family protein, mRNA or genomic DNA in the control sample with the presence of a THAP-family protein, mRNA or genomic DNA in the test sample. The invention also encompasses kits for detecting the presence of THAP-family protein, mRNA or genomic DNA in a biological sample. For example, the kit can comprise a labeled compound or agent capable of detecting a THAP-family protein or mRNA or genomic DNA in a biological sample; means for determining the amount of a THAP-family member in the sample; and means for comparing the amount of THAP-family member in the sample with a standard. The compound or agent can be, packaged in a suitable container. The kit can further comprise instructions for using the kit to detect THAP-family protein or nucleic acid.

In certain embodiments, detection involves the use of a probe/primer in a polymerase chain reaction (PCR) (see, e.g., U.S. Pat. Nos. 4,683,195 and 4,683,202, the disclosures of which are incorporated herein by reference in their entireties), such as anchor PCR or RACE PCR, or, alternatively, in a ligation chain reaction (LCR) (see, e.g., Landegren et al. (1988) Science 241:1077-1080; and Nakazawa et al. (1994) PNAS 91:360-364, the disclosures of which are incorporated herein by reference in their entireties), the latter of which can be particularly useful for detecting point mutations in the THAP-family-gene (see Abravaya et al. (1995) Nucleic Acids Res. 23:675-682, the disclosure of which is incorporated herein by reference in its entirety). This method can include the steps of collecting a sample of cells from a patient, isolating nucleic acid (e.g., genomic, mRNA or both) from the cells of the sample, contacting the nucleic acid sample with one or more primers which specifically hybridize to a THAP-family gene under conditions such that hybridization and amplification of the THAP-family-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Genotyping assays for diagnostics generally require the previous amplification of the DNA region carrying the biallelic marker of interest. However, ultrasensitive detection methods which do not require amplification are also available. Methods well-known to those skilled in the art that can be used to detect biallelic polymorphisms include methods such as, conventional dot blot analyzes, single strand conformational polymorphism analysis (SSCP) described by Orita et al., PNAS 86: 2766-2770 (1989), the disclosure of which is incorporated herein by reference in its entirety, denaturing gradient gel electrophoresis (DGGE), heteroduplex analysis, mismatch cleavage detection, and other conventional techniques as described in Sheffield et al. (1991), White et al. (1992), and Grompe et al. (1989 and 1993) (Sheffield, V. C. et al, Proc. Natl. Acad. Sci. U.S.A 49:699-706 (1991); White, M. B. et al., Genomics 12:301-306 (1992); Grompe, M. et al., Proc. Natl. Acad. Sci. U.S.A 86:5855-5892 (1989); and Grompe, M. Nature Genetics 5:111-117 (1993), the disclosures of which are incorporated herein by reference in their entireties). Another method for determining the identity of the nucleotide present at a particular polymorphic site employs a specialized exonuclease-resistant nucleotide derivative as described in U.S. Pat. No. 4,656,127, the disclosure of which is incorporated herein by reference in its entirety. Further methods are described as follows.

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms". Preferably, the amplified DNA is subjected to automated dideoxy terminator sequencing reactions using a dye-primer cycle sequencing protocol. Sequence analysis allows the identification of the base present at the biallelic marker site.

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way. Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883, the disclosure of which is incorporated herein by reference in its entirety. Alternatively capillary electrophoresis can be used in order to process a higher number of assays simultaneously. Different approaches can be used for the labeling and detection of ddNTPs. A homogeneous phase detection method based on fluorescence resonance energy transfer has been described by Chen and Kwok (1997) and, Chen and Kwok (*Nucleic Acids Research* 25:347-353 1997) and Chen et al. (*Proc. Natl. Acad. Sci. USA* 94/20 10756-10761,1997), the disclosures of which are incorporated herein by reference in their entireties). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997, Genome Research, 7:378-388, 1997, the disclosure of which is incorporated herein by reference in its entirety). In another example, Pastinen et al., (Genome Research 7:606-614, 1997), the disclosure of which is incorporated herein by reference in its entirety) describe a method for multiplex detection of single nucleotide polymorphism in which the solid phase minisequencing principle is applied to an oligonucleotide array format. High-density arrays of DNA probes attached to a solid support (DNA chips) are further described below.

Other assays include mismatch detection assays, based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end.

A preferred method of determining the identity of the nucleotide present at an allele involves nucleic acid hybridization. Any hybridization assay may be used including Southern hybridization, Northern hybridization, dot blot hybridization and solid-phase hybridization (see Sambrook et al., Molecular Cloning—A Laboratory Manual, Second Edition, Cold Spring Harbor Press, N.Y., 1989), the disclosure of which is incorporated herein by reference in its entirety). Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Further, standard heterogeneous assay formats are suitable for detecting the hybrids using the labels present on the primers and probes. (see Landegren U. et al., Genome Research, 8:769-776,1998, the disclosure of which is incorporated herein by reference in its entirety).

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Chips of various formats for use in detecting biallelic polymorphisms can be produced on a customized basis by Affymetrix (GeneChip), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280, the disclosure of which is incorporated herein by reference in its entirety, describes a tiling strategy for the detection of single nucleotide polymorphisms. Briefly, arrays may generally be "tiled" for a large number of specific polymorphisms, further described in PCT application No. WO 95/11995, the disclosure of which is incorporated herein by reference in its entirety. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186, the disclosures of which are incorporated herein by reference in their entireties. Solid supports and polynucleotides of the present invention attached to solid supports are further described in "Oligonucleotide Probes And Primers".

Having generally described this invention, a further understanding can be obtained by reference to certain specific examples which are provided herein for purposes of illustration only, and are not intended to be limiting unless otherwise specified.

EXAMPLES

Example 1

Isolation of the THAP1 cDNA in a Two-Hybrid Screen With Chemokine SLC/CCL21

In an effort to define the function of novel HEVEC proteins and the cellular pathways involved, we used different baits to screen a two-hybrid cDNA library generated from microvascular human HEV endothelial cells (HEVEC). HEVEC were purified from human tonsils by immunomagnetic selection with monoclonal antibody MECA-79 as previously described (Girard and Springer (1995) Immunity 2:113-123). The SMART PCR cDNA library Construction Kit (Clontech, Palo Alto, Calif., USA) was first used to generate full-length cDNAs from 1 µg HEVEC total RNA. Oligo-dT-primed HEVEC cDNA were then digested with SfiI and directionally cloned into pGAD424-Sfi, a two-hybrid vector generated by inserting a SfiI linker (5'-GAATTC GGCCATTATGGCCTGCAGGATCC GGCCGCCTCGGCCCAGGATCC-3') (SEQ ID NO: 181) between EcoRI and BamHI cloning sites of pGAD424 (Clontech). The resulting pGAD424-HEVEC cDNA two-hybrid library (mean insert size >1 kb, ~3×10$^6$ independant clones) was amplified in E. coli. To identify potential protein partners of chemokine SLC/6Ckine, screening of the two-hybrid HEVEC cDNA library was performed using as bait a cDNA encoding the mature form of human SLC/CCL21 (amino acids 24-134, GenBank Accession No: NP_002980, SEQ ID NO: 182), amplified by PCR from HEVEC RNA with primers hSLC.5' (5'-GCGGGATCCGTAGTGATGGAGGGGCT-CAGGACTGTTG-3') (SEQ ID NO: 183) and hSLC.3' (5'-GCGGGATCCCTATGGCCCTTTAGGGGTCTGTGACC-3') (SEQ ID NO: 184), digested with BamHI and inserted into the BamHI cloning site of MATCHMAKER two-hybrid system 2 vector pGBT9 (Clontech). Briefly, pGBT9-SLC was cotransformed with the pGAD424-HEVEC cDNA library in yeast strain Y190 (Clontech). 1.5×10$^7$ yeast transformants were screened and positive protein interactions were selected by His auxotrophy. The plates were incubated at 30° C. for 5 days. Plasmid DNA was extracted from positive colonies and used to verify the specificity of the interaction by cotransformation in AH109 with pGBT9-SLC or control baits pGBT9, pGBT9-lamin. Eight independent clones isolated in this two-hybrid screen were characterized. They were found to correspond to a unique human cDNA encoding a novel human protein of 213 amino acids, designated THAP1, that exhibits 93% identity with its mouse orthologue (FIG. 1A). The only noticeable motifs in the THAP1 predicted protein sequence were a short proline-rich domain in the middle part and a consensus nuclear localization sequence (NLS) in the carboxy terminal part (FIG. 1B). Databases searches with the THAP1 sequence failed to reveal any significant similarity to previously characterized proteins with the exception of the first 90 amino acids that may define a novel protein motif associated with apoptosis, hereafter referred to as THAP domain (see FIG. 1B, FIGS. 9A-9C, and FIG. 10).

Example 2

Northern Blot

To determine the tissue distribution of THAP1 mRNA, we performed Northern blot analysis of 12 different adult human tissues (FIG. 2). Multiple Human Tissues Northern Blots (CLONTECH) were hybridized according to manufacturer's instructions. The probe was a PCR product corresponding to the THAP1 ORF, $^{32}$P-labeled with the Prime-a-Gene Labeling System (PROMEGA).A 2.2-kb mRNA band was detected in brain, heart, skeletal muscle, kidney, liver, and placenta. In addition to the major 2.2 kb band, lower molecular weight bands were detected, that are likely to correspond to alternative splicing or polyadenylation of the THAP1 pre-mRNA. The presence of THAP1 mRNAs in many different tissues suggests that THAP1 has a widespread, although not ubiquitous, tissue distribution in the human body.

Example 3

Analysis of the Subcellular THAP1 Localization

To analyze the subcellular localization of the THAP1 protein, the THAP1 cDNA was fused to the coding sequence of GFP (Green Fluorescent Protein). The full-length coding region of THAP1 was amplified by PCR from HEVEC cDNA with primers 2HMR10 (5'-CCGAATTCAGGATGGTG-CAGTCCTGCTCCGCCT-3') (SEQ ID NO: 185) and 2HMR9 (5'-CGCGGATCCTGCTGGTACTTCAAC-TATTTCAAAGTAGTC-3') (SEQ ID NO: 186), digested with EcoRI and BamHI, and cloned in frame downstream of the Enhanced Green Fluorescent Protein (EGFP)ORF in pEGFP.C2 vector (Clontech) to generate pEGFP.C2-THAP1. The GFP/THAP1 expression construct was then transfected into human primary endothelial cells from umbilical vein (HUVEC, PromoCell, Heidelberg, Germany). HUVEC were grown in complete ECGM medium (PromoCell, Heidelberg, Germany), plated on coverslips and transiently transfected in RPMI medium using GeneJammer transfection reagent according to manufacturer instructions (Stratagene, La Jolla, Calif., USA). Analysis by fluorescence microscopy 24 h later revealed that the GFP/THAP1 fusion protein localizes exclusively in the nucleus with both a diffuse distribution and an accumulation into speckles while GFP alone exhibits only a diffuse staining over the entire cell. To investigate the identity of the speckled domains with which GFP/THAP1 associates, we used indirect immunofluorescence microscopy to examine a possible colocalization of the nuclear dots containing GFP/THAP1 with known nuclear domains (replication factories, splicing centers, nuclear bodies).

Cells transfected with GFP-tagged expression constructs were allowed to grow for 24 h to 48 h on coverslips. Cells were washed twice with PBS, fixed for 15 min at room temperature in PBS containing 3.7% formaldehyde, and washed again with PBS prior to neutralization with 50 mM NH$_4$Cl in PBS for 5 min at room temperature. Following one more PBS wash, cells were permeabilized 5 min at room temperature in PBS containing 0.1% Triton-X100, and washed again with PBS. Permeabilized cells were then blocked with PBS-BSA (PBS with 1% bovine serum albumin) for 10' and then incubated 2 hr at room temperature with the following primary antibodies diluted in PBS-BSA: rabbit polyclonal antibodies against human Daxx (1/50, M-112, Santa Cruz Biotechnology) or mouse monoclonal antibodies anti-PML (mouse IgG1, 1/30, mAb PG-M3 from Dako, Glostrup, Denmark). Cells were then washed three times 5 min at room temperature in PBS-BSA, and incubated for 1 hr with Cy3 (red fluorescence)-conjugated goat anti-mouse or anti-rabbit IgG (1/1000, Amersham Pharmacia Biotech) secondary antibodies, diluted in PBS-BSA. After extensive washing in PBS, samples were air dried and mounted in Mowiol. Images were collected on a Leica confocal laser scanning microscope. The GFP (green) and Cy3 (red) fluorescence signals were recorded sequentially for identical image fields to avoid cross-talk between the channels.

This analysis revealed that GFP-THAP1 staining exhibits a complete overlap with the staining pattern obtained with antibodies directed against PML. The colocalization of GFP/THAP1 and PML was observed both in nuclei with few PML-NBs (less than ten) and in nuclei with a large number of PML-NBs. Indirect immunofluorescence staining with antibodies directed against Daxx, another well characterized component of PML-NBs, was performed to confirm the association of GFP/THAP1 with PML-NBs. We found a complete colocalization of GFP/THAP1 and Daxx in PML-NBs. Together, these results reveal that THAP1 is a novel protein associated with PML-NBs.

Example 4

Identification of Proteins Interacting With THAP1 in Human HEVECs: Two-Hybrid Assay THAP1 Forms a Complex With the Pro-Apoptotic Protein PAR4

To identify potential protein partners of THAP1, screening of the two-hybrid HEVEC cDNA library was performed using as a bait the human THAP1 full length cDNA inserted into the MATCHMAKER two-hybrid system 3 vector pGBKT7 (Clontech). Briefly, the full-length coding region of THAP1 was amplified by PCR from HEVEC cDNA with primers 2HMR10 (5'-CCGAATTCAGGATGGTGCAGTC-CTGCTCCGCCT-3') (SEQ ID NO: 187) and 2HMR9 (5'-CGCGGATCCTGCTGGTACTTCAAC-TATTTCAAAGTAGTC-3') (SEQ ID NO: 188), digested with EcoRI and BamHI, and cloned in frame downstream of the Gal4 Binding Domain (Gal4-BD) in pGBKT7 vector to generate pGBKT7-THAP1. pGBKT7-THAP1 was then cotransformed with the pGAD424-HEVEC cDNA library in yeast strain AH109 (Clontech). 1.5×10$^7$ yeast transformants were screened and positive protein interactions were selected by His and Ade double auxotrophy according to manufacturer's instructions (MATCHMAKER two-hybrid system 3, Clontech). The plates were incubated at 30° C. for 5 days. Plasmid DNA was extracted from these positive colonies and used to verify the specificity of the interaction by cotransformation in AH109 with pGBKT7-THAP1 or control baits pGBKT7, pGBKT7-lamin and pGBKT7-hevin. Three clones which specifically interacted with THAP1 were obtained in the screen; sequencing of these clones revealed three identical library plasmids that corresponded to a partial cDNA coding for the last 147 amino acids (positions 193-342) of the human pro-apoptotic protein PAR4 (FIG. 3A). Positive interaction between THAP1 and Par4 was confirmed using full length Par4 bait (pGBKT-Par4) and prey (pGADT7-Par4). Full-length human Par4 was amplified by PCR from human thymus cDNA (Clontech), with primers Par4.8 (5'-GCGGAAT-TCATGGCGACCGGTGGCTACCGGACC-3') (SEQ ID NO: 189) and Par4. 5 (5'-GCGGGATCCCTCTACCTGGT-CAGCTGACCCACAAC-3') (SEQ ID NO: 190), digested with EcoRI and BamHI, and cloned in pGBKT7 and pGADT7 vectors, to generate pGBKT7-Par4 and pGADT7-Par4. Positive interaction between THAP1 and Par4 was confirmed by cotransformation of AH109 with pGBKT7-THAP1 and pGADT7-Par4 or pGBKT7-Par4 and pGADT7-THAP1 and selection of transformants by His and Ade double auxotrophy according to manufacturer's instructions (MATCHMAKER two-hybrid system 3, Clontech). To generate pGADT7-THAP1, the full-length coding region of THAP1 was amplified by PCR from HEVEC cDNA with primers 2HMR10 (5'-CCGAATTCAGGATGGTGCAGTC-CTGCTCCGCCT-3') (SEQ ID NO: 191) and 2HMR9 (5'-CGCGGATCCTGCTGGTACTTCAAC-TATTTCAAAGTAGTC-3') (SEQ ID NO: 192), digested with EcoRI and BamHI, and cloned in frame downstream of the Gal-4 Activation Domain (Gal4-AD) in pGADT7 two-hybrid vector (Clontech).

We then examined whether the leucine zipper/death domain at the C-terminus of Par4, previously shown to be involved in Par4 binding to WT-1 and aPKC, was required for the interaction between THAP1 and Par4. Two Par4 mutants were constructed for that purpose, Par4Δ and Par4DD. Par4Δ lacks the leucine zipper/death domain while Par4DD contains this domain. pGBKT7-Par4Δ (amino acids 1-276) and pGADT7-Par4Δ were constructed by sub-cloning a EcoRI-BglII fragment from pGADT7-Par4 into the EcoRI and BamHI sites of pGBKT7 and pGADT7. Par4DD (amino acids 250-342) was amplified by PCR, using pGBKT7-Par4 as template, with primers Par4.4 (5'-CGCGAATTCGCCAT-CATGGGGTTCCCTAGATATAACAGGGATGCAA-3') (SEQ ID NO: 193) and Par4.5, and cloned into the EcoRI and BamHI sites of pGBKT7 and pGADT7 to obtain pGBKT7-Par4DD and pGADT7-Par4DD. Two-hybrid interaction between THAP1 and Par4 mutants was tested by cotransformation of AH109 with pGBKT7-THAP1 and pGADT7-Par4A or pGADT7-Par4DD and selection of transformants by His and Ade double auxotrophy according to manufacturer's instructions (MATCHMAKER two-hybrid system 3, Clontech). We found that the Par4 leucine zipper/death domain (Par4DD) is not only required but also sufficient for the interaction with THAP1 (FIG. 3A). Similar results were obtained when two-hybrid experiments were performed in the opposite orientation using Par4 or Par4 mutants (Par4A and Par4DD) as baits instead of THAP1 (FIG. 3A).

Example 5

In Vitro THAP1/Par4 Interaction Assay

To confirm the interaction observed in yeast, we performed in vitro GST pull down assays. Par4DD, expressed as a GST-tagged fusion protein and immobilized on glutathione sepharose, was incubated with radiolabeled in vitro translated THAP1. To generate the GST-Par4DD expression vector, Par4DD (amino acids 250-342) was amplified by PCR with primers Par4.10 (5'-GCCGGATCCGGGTTCCCTA-GATATAACAGGGATGCAA-3') (SEQ ID NO: 194) and Par4. 5, and cloned in frame downstream of the Glutathion S-Transferase ORF, into the BamHI site of the pGEX-2T prokaryotic expression vector (Amersham Pharmacia Biotech, Saclay, France). GST-Par4DD(amino acids 250-342) fusion protein encoded by plasmid pGEX-2T-Par4DD and control GST protein encoded by plasmid pGEX-2T, were then expressed in E. Coli DH5α and purified by affinity chromatography with glutathione sepharose according to supplier's instructions (Amersham Pharmacia Biotech). The yield of proteins used in GST pull-down assays was determined by SDS-Polyarylamide Gel Electrophoresis (PAGE) and Coomassie blue staining analysis. In vitro-translated THAP1 was generated with the TNT-coupled reticulocyte lysate system (Promega, Madison, Wis., USA) using pGBKT7-THAP1 vector as template. 25 μl of $^{35}$S-labelled wild-type THAP1 was incubated with immobilized GST-Par4 or GST proteins overnight at 4° C., in the following binding buffer: 10 mM NaPO4 pH 8.0, 140 mM NaCl, 3 mM MgCl$_{12}$, 1 mM dithiothreitol (DTT), 0.05% NP40, and 0.2 mM phenylmethyl sulphonyl fluoride (PMSF), 1 mM Na Vanadate, 50 mM β Glycerophosphate, 25 μg/ml chimotrypsine, 5 μg/ml aprotinin, 10 μg/ml Leupeptin. Beads were then washed 5 times in 1 ml binding buffer. Bound proteins were eluted with 2×Laemmli SDS-PAGE sample buffer, fractionated by 10% SDS-PAGE and visualized by fluorography using Amplify (Amersham Pharmacia Biotech). As expected, GST/Par4DD interacted with THAP1 (FIG. 3B). In contrast, THAP1 failed to interact with GST beads.

Example 6

In Vivo THAP1/Par4 Interaction Assay

To provide further evidence for a physiological interaction between THAP1 and Par4 in vivo interactions between THAP1 and PAR4 were investigated. For that purpose, confocal immunofluorescence microscopy was used to analyze the subcellular localization of epitope-tagged Par4DD in primary human endothelial cells transiently cotransfected with pEF-mycPar4DD eukaryotic expression vector and GFP or GFP-THAP1 expression vectors (pEGFP.C2 and pEGFP.C2-THAP1, respectively). To generate pEF-mycPar4DD, mycPar4DD (amino acids 250-342) was amplified by PCR using pGBKT7-Par4DD as template, with primers myc.BD7 (5'-GCGCTCTAGAGCCATCATGGAGGAGCA-GAAGCTGATC-3') (SEQ ID NO: 195) and Par4.9 (5'-CT-TGCGGCCGCCTCTACCTGGTCAGCTGACCCACAAC-3') (SEQ ID NO: 196), and cloned into the XbaI and NotI sites of the pEF-BOS expression vector (Mizushima and Nagata, Nucleic Acids Research, 18:5322, 1990). Primary human endothelial cells from umbilical vein (HUVEC, PromoCell, Heidelberg, Germany) were grown in complete ECGM medium (PromoCell, Heidelberg, Germany), plated on coverslips and transiently transfected in RPMI medium using GeneJammer transfection reagent according to manufacturer instructions (Stratagene, La Jolla, Calif., USA). Cells cotransfected with pEF-mycPar4DD and GFP-tagged expression constructs were allowed to grow for 24 h to 48 h on coverslips. Cells were washed twice with PBS, fixed for 15 min at room temperature in PBS containing 3.7% formaldehyde, and washed again with PBS prior to neutralization with 50 mM NH$_4$Cl in PBS for 5 min at room temperature. Following one more PBS wash, cells were permeabilized 5 min at room temperature in PBS containing 0.1% Triton-X100, and washed again with PBS. Permeabilized cells were then blocked with PBS-BSA (PBS with 1% bovine serum albumin) for 10' and then incubated 2 hr at room temperature with mouse monoclonal antibody anti-myc epitope (mouse IgG1, 1/200, Clontech) diluted in PBS-BSA. Cells were then washed three times 5 min at room temperature in PBS-BSA, and incubated for 1 hr with Cy3 (red fluorescence)-conjugated goat anti-mouse (1/1000, Amersham Pharmacia Biotech) secondary antibodies, diluted in PBS-BSA. After extensive washing in PBS, samples were air dried and mounted in Mowiol. Images were collected on a Leica confocal laser scanning microscope. The GFP (green) and Cy3 (red) fluorescence signals were recorded sequentially for identical image fields to avoid cross-talk between the channels.

In cells transiently co-transfected with pEF-mycPar4DD and GFP expression vector, ectopically expressed myc-Par4DD was found to accumulate both in the cytoplasm and the nucleus of the majority of the cells. In contrast, transient cotransfection of pEF-mycPar4DD and GFP-THAP1 expression vectors dramatically shifted myc-Par4DD from a diffuse cytosolic and nuclear localization to a preferential association with PML-NBs. The effect of GFP-THAP1 on myc-Par4DD localization was specific since it was not observed with GFP-APS kinase-1 (APSK-1), a nuclear enzyme unrelated to THAP1 and apoptosis [Besset et al., Faseb J, 14:345-354, 2000]. This later result shows that GFP-THAP1 recruits myc-Par4DD at PML-NBs and provides in vivo evidence for a direct interaction of THAP1 with the pro-apoptotic protein Par4.

Example 7

Identification of a Novel Arginine-Rich Par4 Binding Motif

To identify the sequences mediating THAP1 binding to Par4, a series of THAP1 deletion constructs was generated. Both amino-terminal (THAP1-C1, -C2, -C3) and carboxy-terminal (THAP1-N1, -N2, -N3) deletion mutants (FIG. 4A) were amplified by PCR using plasmid pEGFP.C2-THAP1 as a template and the following primers:
2HMR12 (5'-GCGGAATTCAAAGAAGATCTTCTG-GAGCCACAGGAAC-3') (SEQ ID NO: 197)
and 2HMR9 (5'-CGCGGATCCTGCTGGTACTTCAAC-TATTTCAAAGTAGTC-3') (SEQ ID NO: 198) for THAP1-C1 (amino acids 90-213);
PAPM2 (5'-GCGGAATTCATGCCGCCTCTTCAGAC-CCCTGTTAA-3') (SEQ ID NO: 199)
and 2HMR9 for THAP1-C2 (amino acids 120-213);
PAPM3 (5'-GCGGAATTCATGCACCAGCGGAAAAG-GATTCATCAG-3') (SEQ ID NO: 200)
and 2HMR9 for THAP1-C3 (amino acids 143-213);
2HMR10 (5'-CCGAATTCAGGATGGTGCAGTCCT-GCTCCGCCT-3') (SEQ ID NO: 201)
and 2HMR17 (5'-GCGGGATCCCTTGTCATGTGGCT-CAGTACAAAGAAATAT-3') (SEQ ID NO: 202) for THAP1-N1 (amino acids 1-90);
2HMR10 and PAPN2 (5'-CGGGATCCTGTGCGGTCT-TGAGCTTCTTTCTGAG-3') (SEQ ID NO: 203) for THAP1-N2 (amino acids 1-166); and
2HMR10 and PAPN3 (5'-GCGGGATC-CGTCGTCTTTCTCTTTCTGGAAGTGAAC-3') (SEQ ID NO: 204) for THAP1-N3 (amino acids 1-192).

The PCR fragments, thus obtained, were digested with EcoRI and BamHI, and cloned in frame downstream of the Gal4 Binding Domain (Gal4-BD) in pGBKT7 two-hybrid vector (Clontech) to generate pGBKT7-THAP1-C1, -C2, -C3, -N1, -N2 or -N3, or downstream of the Enhanced Green Fluorescent Protein (EGFP)ORF in pEGFP.C2 vector (Clontech) to generate pEGFP.C2-THAP1-C1, -C2, -C3, -N1, -N2 or -N3.

Two-hybrid interaction between THAP1 mutants and Par4DD was tested by cotransformation of AH 109 with pGBKT7-THAP1-C1, -C2, -C3, -N1, -N2 or -N3 and pGADT7-Par4DD and selection of transformants by His and Ade double auxotrophy according to manufacturer's instructions (MATCHMAKER two-hybrid system 3, Clontech). Positive two-hybrid interaction with Par4DD was observed with mutants THAP1-C1, -C2, -C3, -and -N3 but not with mutants THAP1-N1 and -N2, suggesting the Par4 binding site is found between THAP1 residues 143 and 192.

THAP1 mutants were also tested in the in vitro THAP1/Par4 interaction assay. In vitro-translated THAP1 mutants were generated with the TNT-coupled reticulocyte lysate system (Promega, Madison, Wis., USA) using pGBKT7-THAP1-C1, -C2, -C3, -N1, -N2 or -N3 vector as template. 25 µl of each $^{35}$S-labelled THAP1 mutant was incubated with immobilized GST or GST-Par4 protein overnight at 4° C., in the following binding buffer: 10 mM NaPO4 pH 8.0, 140 mM NaCl, 3 mM MgCl2, 1 mM dithiothreitol (DTT), 0.05% NP40, and 0.2 mM phenylmethyl sulphonyl fluoride (PMSF), 1 mM Na Vanadate, 50 mM β Glycerophosphate, 25 µg/ml chimotrypsine, 5 µg/ml aprotinin, 10 µg/ml Leupeptin. Beads were then washed 5 times in 1 ml binding buffer. Bound proteins were eluted with 2×Laemmli SDS-PAGE sample buffer, fractionated by 10% SDS-PAGE and visualized by fluorography using Amplify (Amersham Pharmacia Biotech). As expected, THAP1-C1, -C2, -C3, -and -N3 interacted with GST/Par4DD (FIG. 4B). In contrast, THAP1-N1 and -N2 failed to interact with GST/Par4DD beads.

Finally, Par4 binding activity of THAP1 mutants was also analyzed by the in vivo THAP1/Par4 interaction assay as described in Example 6 using pEF-mycPar4DD and pEGFP.C2-THAP1-C1, -C2, -C3, -N1, -N2 or -N3 expression vectors.

Figure 4A:
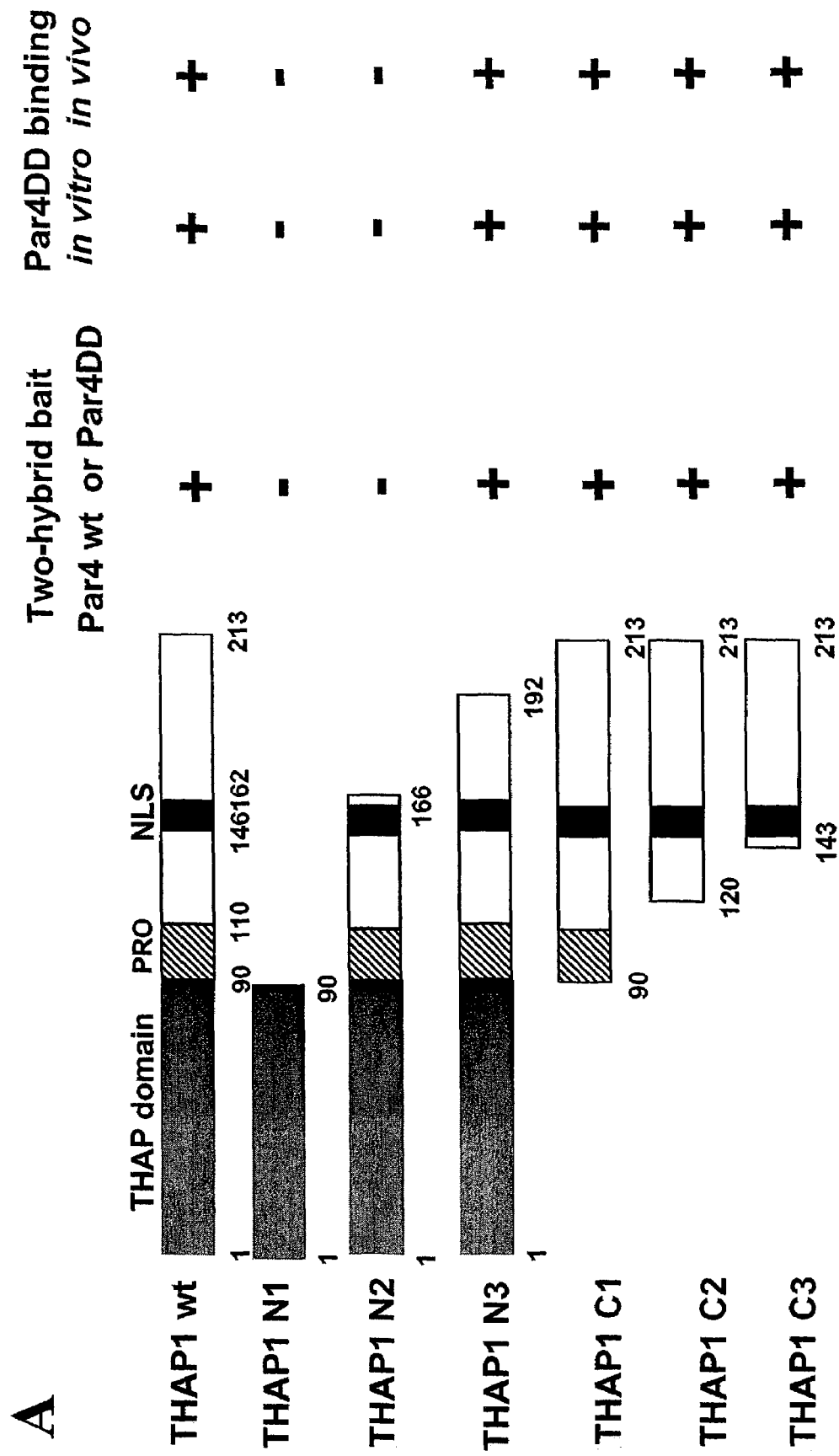
FIG. 4A illustrates the interaction between PAR4 and several THAP1 deletion mutants both in vitro and in vivo. Each THAP1 deletion mutant was tested for binding to either PAR or PAR4DD in a yeast two hybrid system (two hybrid bait), to PAR4DD in GST pull down assays (in vitro) and to myc-Par4DD in primary human endothelial cells (in vivo). A (+) indicates binding whereas a (−) indicated lack of binding.
Figure 4B:
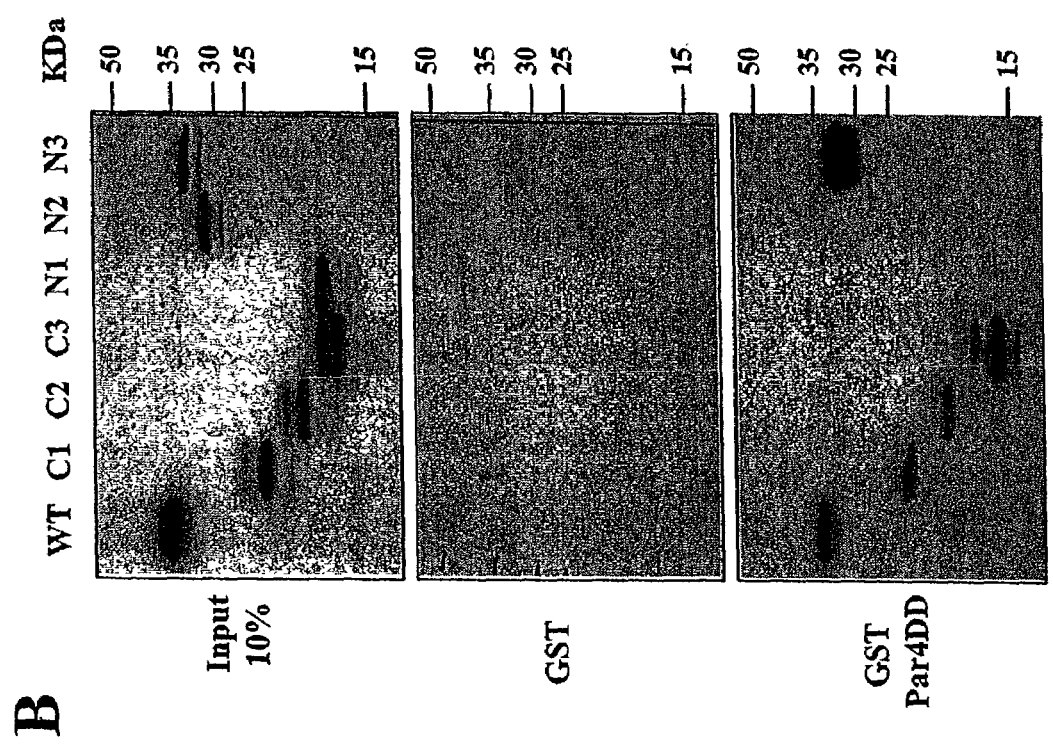
FIG. 4B shows the binding of several in vitro translated, $^{35}$S-methionine-labeled THAP1 deletion mutants to a GST-Par4DD polypeptide fusion. Par4DD was expressed as a GST fusion protein then purified on an affinity matrix of glutathione sepharose. GST served as negative control. The input represents 1/10 of the material used in the binding assay.

Essentially identical results were obtained with the three THAP1/Par4 interactions assays (FIG. 4A). That is, the Par4 binding site was found between residues 143 and 192 of human THAP1. Comparison of this region with the Par4 binding domain of mouse ZIP kinase, another Par4-interacting protein, revealed the existence of a conserved arginine rich-sequence motif (SEQ ID NOs: 205, 263 and 15), that may correspond to the Par4 binding site (FIG. 5A). Mutations in this arginine rich-sequence motif were generated by site directed mutagenesis. These two novel THAP1 mutants, THAP1 RR/AA (replacement of residues R171A and R172A) and THAP1ΔQRCRR (deletion of residues 168-172), were generated by two successive rounds of PCR using pEGFP.C2-THAP1 as template and primers 2HMR10 and 2HMR9 together with primers
RR/AA-1 (5'-CCGCACAGCAGCGATGCGCTGCTCAAGAACGGCAGCTTG-3') (SEQ ID NO: 206) and
RR/AA-2 (5'-CAAGCTGCCGTTCTTGAGCAGCGCATCGCTGCTGTGCGG-3') (SEQ ID NO: 207) for mutant THAP1 RR/AA or
primers ΔRR-1 (5'-GCTCAAGACCGCACAGCAAGAACGGCAGCTTG-3'(SEQ ID NO: 208) and
ΔRR-2 (5'-CAAGCTGCCGTTCTTGCTGTGCGGTCTTGAGC-3') (SEQ ID NO: 209)
for mutant THAP1ΔQRCRR. The resulting PCR fragments were digested with EcoRI and BamHI, and cloned in frame downstream of the Gal4 Binding Domain (Gal4-BD) in pGBKT7 two-hybrid vector (Clontech) to generate pGBKT7-THAP1-RR/AA and -Δ(QRCRR), or downstream of the Enhanced Green Fluorescent Protein (EGFP)ORF in pEGFP.C2 vector (Clontech) to generate pEGFP.C2-THAP1-RR/AA and -Δ(QRCRR). THAP1 RR/AA and THAP1ΔQRCRR THAP1 mutants were then tested in the three THAP1/Par4 interaction assays (two-hybrid assay, in vitro THAP1/Par4 interaction assay, in vivo THAP1/Par4 interaction assay) as described above for the THAP1-C1, -C2, -C3, -N1, -N2 or -N3 mutants. This analysis revealed that the two mutants were deficient for interaction with Par4 in all three assays (FIG. 5B), indicating that the novel arginine-rich sequence motif, we have identified, is a novel Par4 binding motif.

Example 8

PAR4 is a Novel Component of PML-NBs that Colocalizes With THAP1 In Vivo

We then wished to determine if PAR4 colocalizes with THAP1 in vivo in order to provide further evidence for a physiological interaction between THAP1 and PAR4. We first analyzed Par4 subcellular localization in primary human endothelial cells. Confocal immunofluorescence microscopy using affinity-purified anti-PAR4 antibodies (Sells et al., 1997; Guo et al; 1998) was performed on HUVEC endothelial cells fixed with methanol/acetone, which makes PML-NBs components accessible for antibodies (Sternsdorf et al., 1997). Cells were fixed in methanol for 5 min at −20° C., followed by incubation in cold acetone at −20° C. for 30 sec. Permeabilized cells were then blocked with PBS-BSA (PBS with 1% bovine serum albumin) for 10' and then incubated 2 hr at room temperature with rabbit polyclonal antibodies against human Par4 (1/50, R-334, Santa Cruz Biotechnology, Santa Cruz, Calif., USA) and mouse monoclonal antibody anti-PML (mouse IgG1, 1/30, mAb PG-M3 from Dako, Glostrup, Denmark). Cells were then washed three times 5 min at room temperature in PBS-BSA, and incubated for 1 hr with Cy3 (red fluorescence)-conjugated goat anti-rabbit IgG (1/1000, Amersham Pharmacia Biotech) and FITC-labeled goat anti-mouse-IgG (1/40, Zymed Laboratories Inc., San Francisco, Calif., USA) secondary antibodies, diluted in PBS-BSA. After extensive washing in PBS, samples were air dried and mounted in Mowiol. Images were collected on a Leica confocal laser scanning microscope. The FITC (green) and Cy3 (red) fluorescence signals were recorded sequentially for identical image fields to avoid cross-talk between the channels. This analysis showed an association of PAR4 immunoreactivity with nuclear dot-like structures, in addition to diffuse nucleoplasmic and cytoplasmic staining. Double immunostaining with anti-PML antibodies, revealed that the PAR4 foci colocalize perfectly with PML-NBs in cell nuclei. Colocalization of Par4 with GFP-THAP1 in PML-NBs was analyzed in transfected HUVEC cells expressing ectopic GFP-THAP1. HUVEC were grown in complete ECGM medium (PromoCell, Heidelberg, Germany), plated on coverslips and transiently transfected with GFP/THAP1 expression construct (pEGFP.C2-THAP1) in RPMI medium using GeneJammer transfection reagent according to manufacturer instructions (Stratagene, La Jolla, Calif., USA). Analysis of transfected cells by indirect immunofluorescence microscopy 24 h later, with anti-Par4 rabbit antibodies, revealed that all endogenous PAR4 foci colocalize with ectopic GFP-THAP1 in PML-NBs further confirming the association of the THAP1/PAR4 complex with PML-NBs in vivo.

Example 9

PML Recruits the THAP1/PAR4 Complex to PML-NBs

Since it has been shown that PML plays a critical role in the assembly of PML-NBs by recruiting other components, we next wanted to determine whether PML plays a role in the recruitment of the THAP1/PAR4 complex to PML-NBs. For this purpose, we made use of the observation that both endogenous PAR4 and ectopic GFP-THAP1 do not accumulate in PML-NBs in human Hela cells. Expression vectors for GFP-THAP1 and HA-PML (or HA-SP100) were cotransfected into these cells and the localization of endogenous PAR4, GFP-THAP1 and HA-PML (or HA-SP100) was analyzed by triple staining confocal microscopy.

Human Hela cells (ATCC) were grown in Dulbecco's Modified Eagle's Medium supplemented with 10% Fetal Calf Serum and 1% Penicillin-streptomycin (all from Life Technologies, Grand Island, N.Y., USA), plated on coverslips, and transiently transfected with calcium phosphate method using 2 μg pEGFP.C2-THAP1 and pcDNA.3-HA-PML3 or pSG5-HA-Sp100 (a gift from Dr Dejean, Institut Pasteur, Paris, France) plasmid DNA. pcDNA.3-HA-PML3 was constructed by sub-cloning a BglII-BamHI fragment from pGADT7-HA-PML3 into the BamHI site of pcDNA3 expression vector (Invitrogen, San Diego, Calif., USA). To generate pGADT7-HA-PML3, PML3 ORF was amplified by PCR, using pACT2-PML3 (a gift from Dr De Thé, Paris, France) as template, with primers PML-1 (5'-GCGGGATCCCTAAATTA-GAAAGGGGTGGGGGTAGCC-3') (SEQ ID NO: 210) and PML-2 (5'-GCGGAATTCATGGAGCCTGCACCCGC-CCGATC-3') (SEQ ID NO: 211), and cloned into the EcoRI and BamHI sites of pGADT7.

Hela cells transfected with GFP-tagged and HA-tagged expression constructs were allowed to grow for 24 h to 48 h on coverslips. Cells were washed twice with PBS, fixed in methanol for 5 min at –20° C., followed by incubation in cold acetone at –20° C. for 30 sec. Permeabilized cells were then blocked with PBS-BSA (PBS with 1% bovine serum albumin) for 10' and then incubated 2 hr at room temperature with the following primary antibodies diluted in PBS-BSA: rabbit polyclonal antibodies against human Par4 (1/50, R-334, Santa Cruz Biotechnology, Santa Cruz, Calif., USA) and mouse monoclonal antibody anti-HA tag (mouse IgG1, 1/1000, mAb 16B12 from BabCO, Richmond, Calif., USA). Cells were then washed three times 5 min at room temperature in PBS-BSA, and incubated for 1 hr with Cy3 (red fluorescence)-conjugated goat anti-rabbit IgG (1/1000, Amersham Pharmacia Biotech) and Alexa Fluor-633 (blue fluorescence) goat anti-mouse IgG conjugate (1/100, Molecular Probes, Eugene, Oreg., USA) secondary antibodies, diluted in PBS-BSA. After extensive washing in PBS, samples were air dried and mounted in Mowiol. Images were collected on a Leica confocal laser scanning microscope. The GFP (green), Cy3 (red) and Alexa 633 (blue) fluorescence signals were recorded sequentially for identical image fields to avoid cross-talk between the channels.

In Hela cells transfected with HA-PML, endogenous PAR4 and GFP-THAP1 were recruited to PML-NBs, whereas in cells transfected with HA-SP100, both PAR4 and GFP-THAP1 exhibited diffuse staining without accumulation in PML-NBs. These findings indicate that recruitment of the THAP1/PAR4 complex to PML-NBs depends on PML but not SP100.

Example 10

THAP1 is an Apoptosis Inducing Polypeptide

THAP1 is a Novel Proapoptotic Factor

Since PML and PML-NBs have been linked to regulation of cell death and PAR4 is a well established pro-apoptotic factor, we examined whether THAP1 can modulate cell survival. Mouse 3T3 cells, which have previously been used to analyze the pro-apoptotic activity of PAR4 (Diaz-Meco et al, 1996; Berra et al., 1997), were transfected with expression vectors for GFP-THAP1, GFP-PAR4 and as a negative control GFP-APS kinase-1 (APSK-1), a nuclear enzyme unrelated to THAP1 and apoptosis (Girard et al., 1998; Besset et al., 2000). We then determined whether ectopic expression of THAP1 enhances the apoptotic response to serum withdrawal. Transfected cells were deprived of serum for up to twenty four hours and cells with apoptotic nuclei, as revealed by DAPI staining and in situ TUNEL assay, were counted.

Cell death assays: Mouse 3T3-TO fibroblasts were seeded on coverslips in 12-well plates at 40 to 50% conflueney and transiently transfected with GFP or GFP-fusion protein expression vectors using Lipofectamine Plus reagent (Life Technologies) according to supplier's instructions. After 6 h at 37° C., the DNA-lipid mixture was removed and the cells were allowed to recover in complete medium for 24 h. Serum starvation of transiently transfected cells was induced by changing the medium to 0% serum, and the amount of GFP-positive apoptotic cells was assessed 24 h after induction of serum starvation. Cells were fixed in PBS containing 3.7% formaldehyde and permeabilized with 0.1% Triton-X100 as described under immunofluorescence, and apoptosis was scored by in situ TUNEL (terminal deoxynucleotidyl transferase-mediated dUTP nick end labeling) and/or DAPI (4,6-Diamidino-2-phenylindole) staining of apoptotic nuclei exhibiting nuclear condensation. The TUNEL reaction was performed for 1 hr at 37° C. using the in situ cell death detection kit, TMR red (Roche Diagnostics, Meylan, France). DAPI staining with a final concentration of 0.2:g/ml was performed for 10 min at room temperature. At least 100 cells were scored for each experimental point using a fluorescence microscope.

Figure 6:
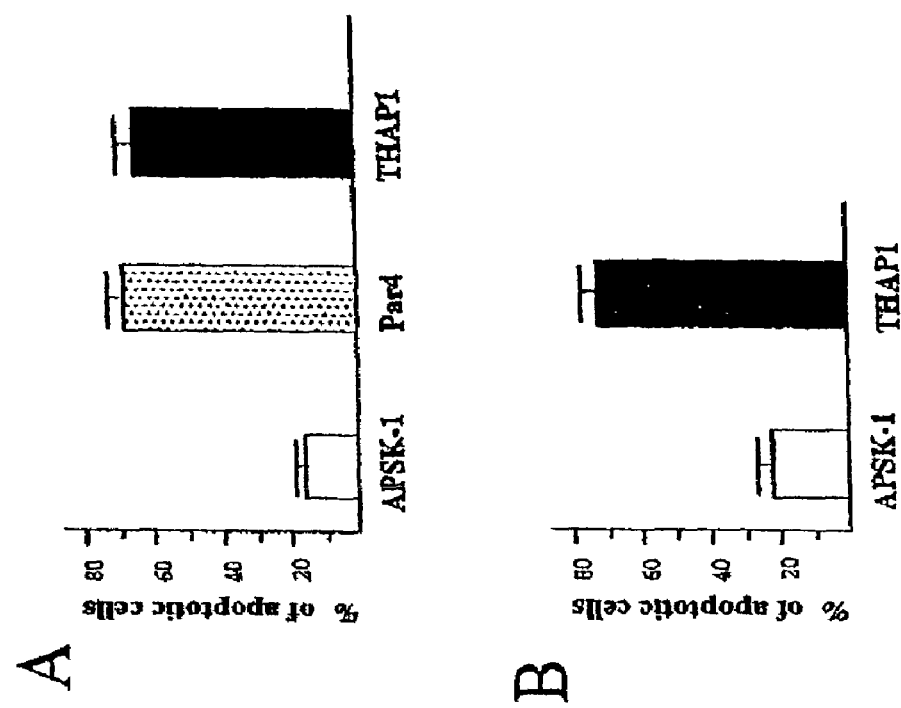
FIG. 6A is a graph which compares apoptosis levels in cells transfected with GFP-APSK1, GFP-Par4 or GFP-THAP1 expression vectors. Apoptosis was quantified by DAPI staining of apoptotic nuclei, 24 h after serum-withdrawal. Values are the means of three independent experiments.
FIG. 6B is a graph which compares apoptosis levels in cells transfected with GFP-APSK1 or GFP-THAP1 expression vectors. Apoptosis was quantified by DAPI staining of apoptotic nuclei, 24 h after addition of TNF α. Values are the means of three independent experiments.

Basal levels of apoptosis in the presence of serum ranged from 1-3%. Twenty four hours after serum withdrawal, apoptosis was found in 18% of untransfected 3T3 cells and in 3T3 cells overexpressing GFP-APSK-1. Levels of serum withdrawal induced apoptosis were significantly increased to about 70% and 65% in cells overexpressing GFP-PAR4 and GFP-THAP1, respectively (FIG. 6A). These results demonstrate that THAP1, similarly to PAR4, is an apoptosis inducing polypeptide.

TNFα-induced apoptosis assays were performed by incubating transiently transfected cells in complete medium containing 30 ng/ml of mTNFα (R & D, Minneapolis, Minn., USA) for 24 h. Apoptosis was scored as described for serum withdrawal-induced apoptosis. The results are shown in FIG. 6B. As shown in FIG. 6B, THAP1 induced apoptosis.

Example 11

The THAP Domain is Essential for THAP1 Pro-Apoptotic Activity

To determine the role of the amino-terminal THAP domain (amino acids 1 to 89) in the functional activity of THAP1, we generated a THAP1 mutant that is deleted of the THAP domain (THAP1αTHAP). THAP1ΔTHAP (amino acids 90-213) was amplified by PCR, using pEGFP.C2-THAP1 as template, with primers 2HMR12 (5'-GCGGAATTCAAA-GAAGATCTTCTGGAGCCACAGGAAC-3') (SEQ ID NO: 212) and 2HMR9 (5'-CGCGGATCCTGCTGGTACT-TCAACTATTTCAAAGTAGTC-3') (SEQ ID NO: 213), digested with EcoRI and BamHI, and cloned in pGBKT7 and pEGFP-C2 vectors, to generate pGBKT7-THAP1ΔTHAP and pEGFP.C2-THAP1ΔTHAP expression vectors. The role of the THAP domain in PML NBs localization, binding to Par4, or pro-apoptotic activity of THAP1 was then analyzed.

To analyze the subcellular localization of THAP1ΔTHAP, the GFP/THAP1ΔTHAP expression construct was transfected into human primary endothelial cells from umbilical vein (HUVEC, PromoCell, Heidelberg, Germany). HUVEC were grown in complete ECGM medium (PromoCell, Heidelberg, Germany), plated on coverslips and transiently transfected in RPMI medium using GeneJammer transfection reagent according to manufacturer instructions (Stratagene, La Jolla, Calif., USA). Transfected cells were allowed to grow for 48 h on coverslips. Cells were then washed twice with PBS, fixed for 15 min at room temperature in PBS containing 3.7% formaldehyde, and washed again with PBS prior to neutralization with 50 mM NH₄Cl in PBS for 5 min at room temperature. Following one more PBS wash, cells were permeabilized 5 min at room temperature in PBS containing 0.1% Triton-X100, and washed again with PBS. Permeabilized cells were then blocked with PBS-BSA (PBS with 1% bovine serum albumin) for 10' and then incubated 2 hr at room temperature with mouse monoclonal antibody anti-PML (mouse IgG1, 1/30, mAb PG-M3 from Dako, Glostrup, Denmark) diluted in PBS-BSA. Cells were then washed three times 5 min at room temperature in PBS-BSA, and incubated for 1 hr with Cy3 (red fluorescence)-conjugated goat anti-mouse IgG (1/1000, Amersham Pharmacia Biotech) secondary antibodies, diluted in PBS-BSA. After extensive washing in PBS, samples were air dried and mounted in Mowiol. Images were collected on a Leica confocal laser scanning microscope. The GFP (green) and Cy3 (red) fluorescence signals were recorded sequentially for identical image fields to avoid cross-talk between the channels.

This analysis revealed that GFP-THAP1ΔTHAP staining exhibits a complete overlap with the staining pattern obtained with antibodies directed against PML, indicating the THAP domain is not required for THAP1 localization to PML NBs.

To examine the role of the THAP domain in binding to Par4, we performed in vitro GST pull down assays. Par4DD, expressed as a GST-tagged fusion protein and immobilized on glutathione sepharose, was incubated with radiolabeled in vitro translated THAP1ΔTHAP. In vitro-translated THAP1ΔTHAP was generated with the TNT-coupled reticulocyte lysate system (Promega, Madison, Wis., USA) using pGBKT7-THAP1ΔTHAP vector as template. 25 μl of $^{35}$S-labelled THAP1)ΔTHAP was incubated with immobilized GST-Par4 or GST proteins overnight at 4° C., in the following binding buffer: 10 mM NaPO4 pH 8.0, 140 mM NaCl, 3 mM MgCl2, 1 mM dithiothreitol (DTT), 0.05% NP40, and 0.2 mM phenylmethyl sulphonyl fluoride (PMSF), 1 mM Na Vanadate, 50 mM β Glycerophosphate, 25 μg/ml chimotrypsine, 5 μg/ml aprotinin, 10 μg/ml Leupeptin. Beads were then washed 5 times in 1 ml binding buffer. Bound proteins were eluted with 2×Laemmli SDS-PAGE sample buffer, fractionated by 10% SDS-PAGE and visualized by fluorography using Amplify (Amersham Pharmacia Biotech).

Figure 7:
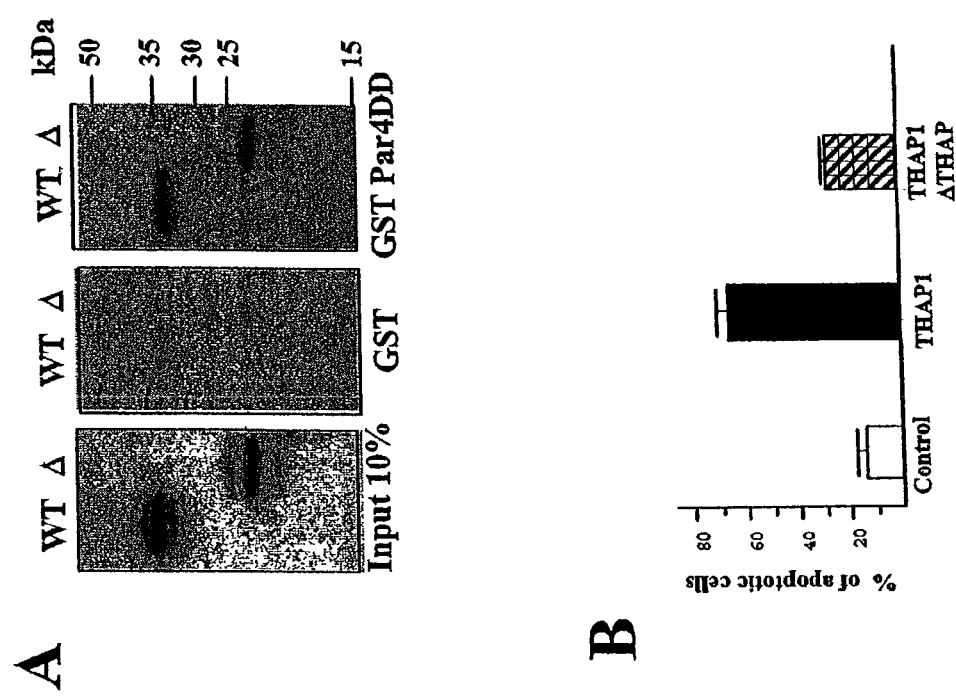
FIG. 7A shows the binding of in vitro translated $^{35}$S-methionine labeled THAP1 (wt) or THAP1ΔTHAP (Δ) to a GST-Par4DD polypeptide fusion. Par4DD was expressed as a GST fusion protein then purified on an affinity matrix of glutathione sepharose. GST served as negative control. The input represents 1/10 of the material used in the binding assay.
FIG. 7B is a graph which compares the proapoptotic activity of THAP1 with a THAP1 mutant having its THAP domain (amino acids 1-90 of SEQ ID NO: 3) deleted. The percentage of apoptotic cells in mouse 3T3 fibroblasts overexpressing GFP-APSK1 (control), GFP-THAP1 (THAP1) or GFP-THAP1ΔTHAP (THAP1ΔTHAP) was determined by counting apoptotic nuclei after DAPI staining. Values are the means of three independent experiments.

This analysis revealed that THAP1ΔTHAP interacts with GST/Par4DD, indicating that the THAP domain is not involved in THAP1/Par4 interaction (FIG. 7A).

To examine the role of the THAP domain in THAP1 pro-apoptotic activity, we performed cell death assays in mouse 3T3 cells. Mouse 3T3-TO fibroblasts were seeded on coverslips in 12-well plates at 40 to 50% confluency and transiently transfected with GFP-APSK1, GFP-THAP1 or GFP-THAP1ΔTHAP fusion proteins expression vectors using Lipofectamine Plus reagent (Life Technologies) according to supplier's instructions. After 6 h at 37° C., the DNA-lipid mixture was removed and the cells were allowed to recover in complete medium for 24 h. Serum starvation of transiently transfected cells was induced by changing the medium to 0% serum, and the amount of GFP-positive apoptotic cells was assessed 24 h after induction of serum starvation. Cells were fixed in PBS containing 3.7% formaldehyde and permeabilized with 0.1% Triton-X100 as described under immunofluorescence, and apoptosis was scored by in situ TUNEL (terminal deoxynucleotidyl transferase-mediated dUTP nick end labeling) and/or DAPI (4,6-Diamidino-2-phenylindole) staining of apoptotic nuclei exhibiting nuclear condensation. The TUNEL reaction was performed for 1 hr at 37° C. using the in situ cell death detection kit, TMR red (Roche Diagnostics, Meylan, France). DAPI staining with a final concentration of 0.2 μg/ml was performed for 10 min at room temperature. At least 100 cells were scored for each experimental point using a fluorescence microscope.

Twenty four hours after serum withdrawal, apoptosis was found in 18% of untransfected 3T3 cells and in 3T3 cells overexpressing GFP-APSK-1. Levels of serum withdrawal induced apoptosis were significantly increased to about 70% in cells overexpressing GFP-THAP1. Deletion of the THAP domain abrogated most of this effect since serum-withdrawal-induced apoptosis was reduced to 28% in cells over-expressing GFP-THAP1ΔTHAP (FIG. 7B). These results indicate that the THAP domain, although not required for THAP1 PML-NBs localization and Par4 binding, is essential for THAP1 pro-apoptotic activity.

Example 12

The THAP Domain Defines a Novel Family of Proteins the THAP Family

Figure 8:
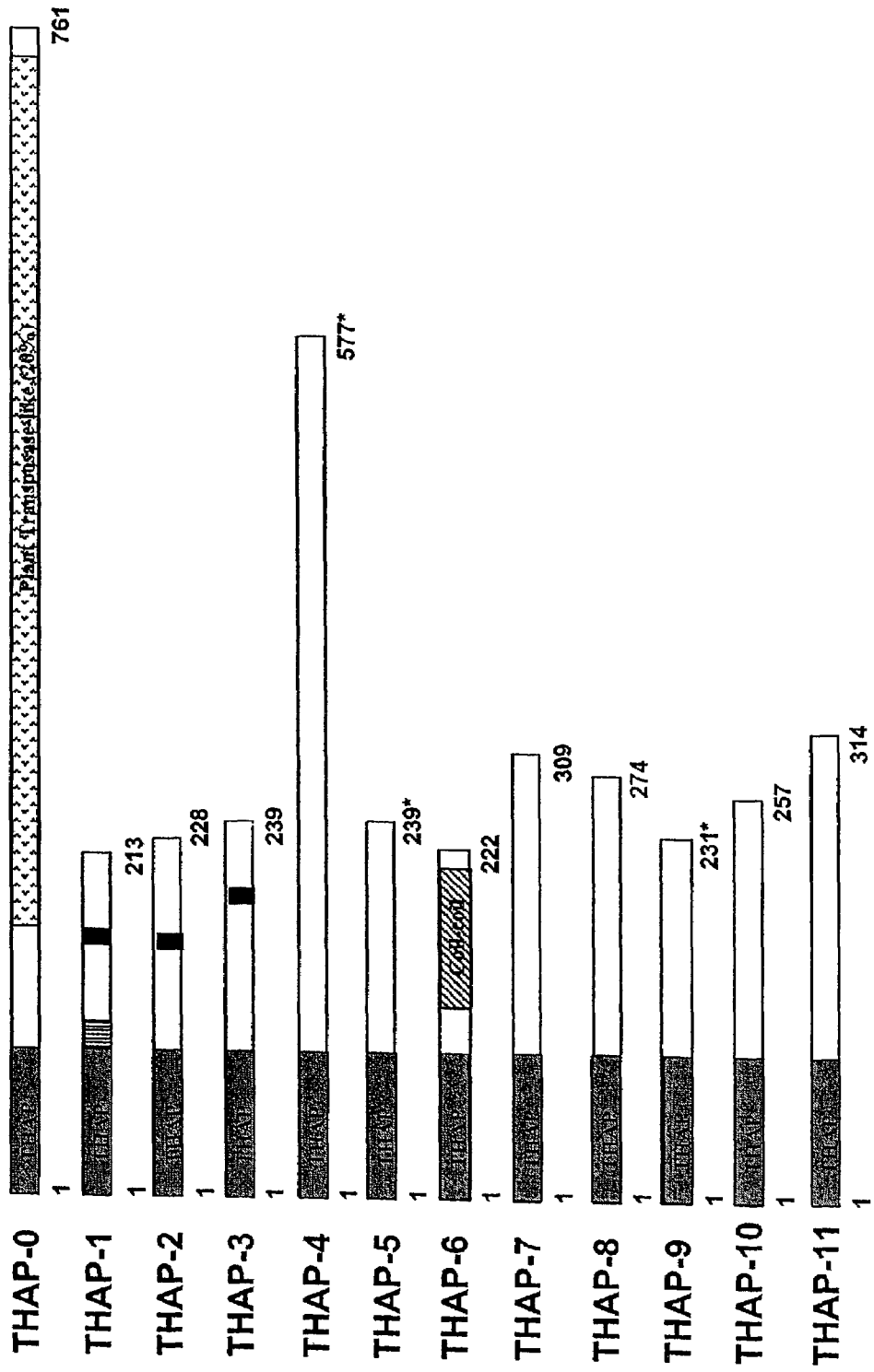
FIG. 8 depicts the primary structure of twelve human THAP proteins. The THAP domain (colored grey) is located at the amino-terminus of each of the twelve human THAP proteins. The black box in THAP1, THAP2 and THAP3 indicates a nuclear localization sequence, rich in basic residues, that is conserved in the three proteins. The number of amino-acids in each THAP protein is indicated; (*) indicates the protein is not full length.
Figure 9C:
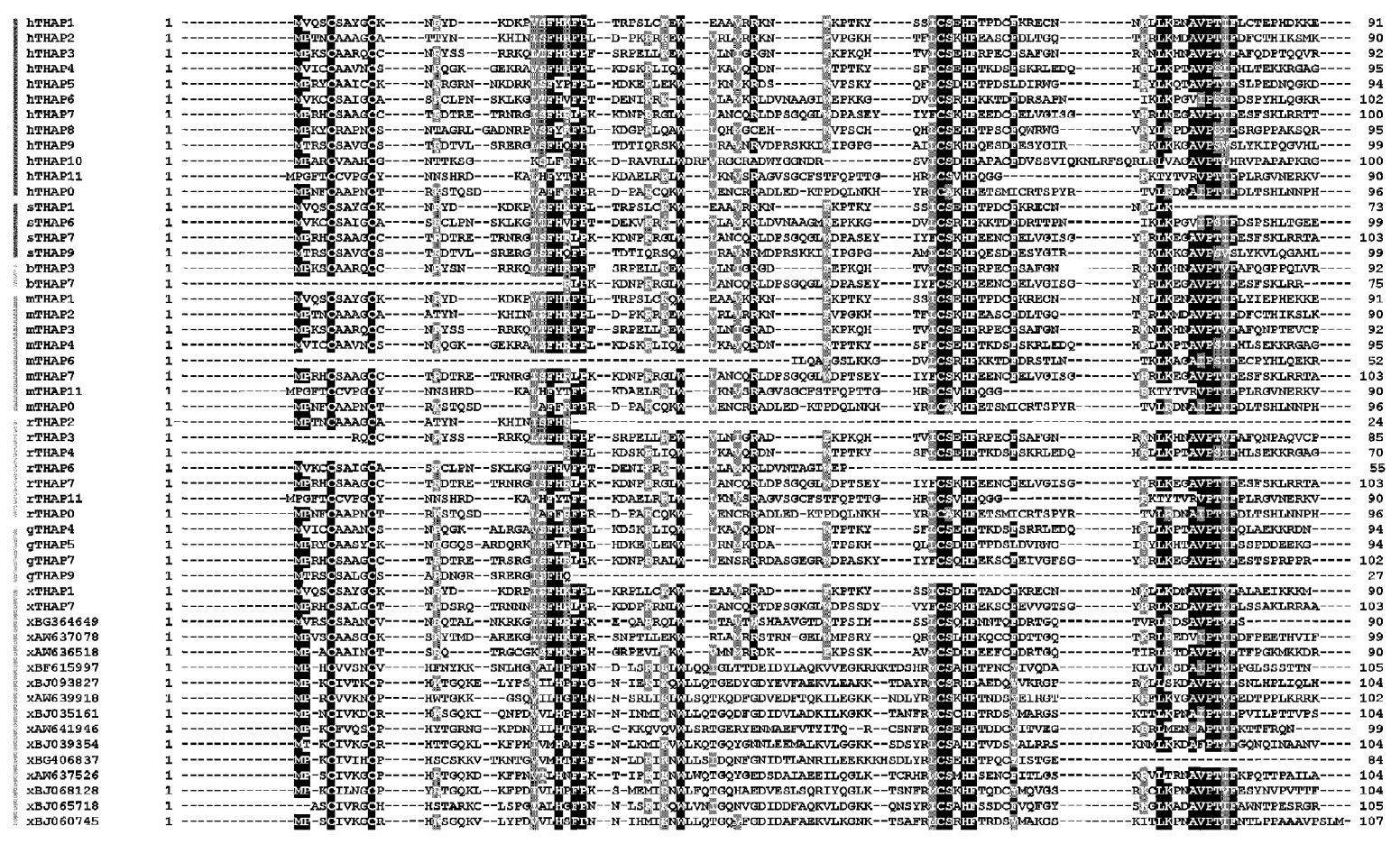
Figure 9C:
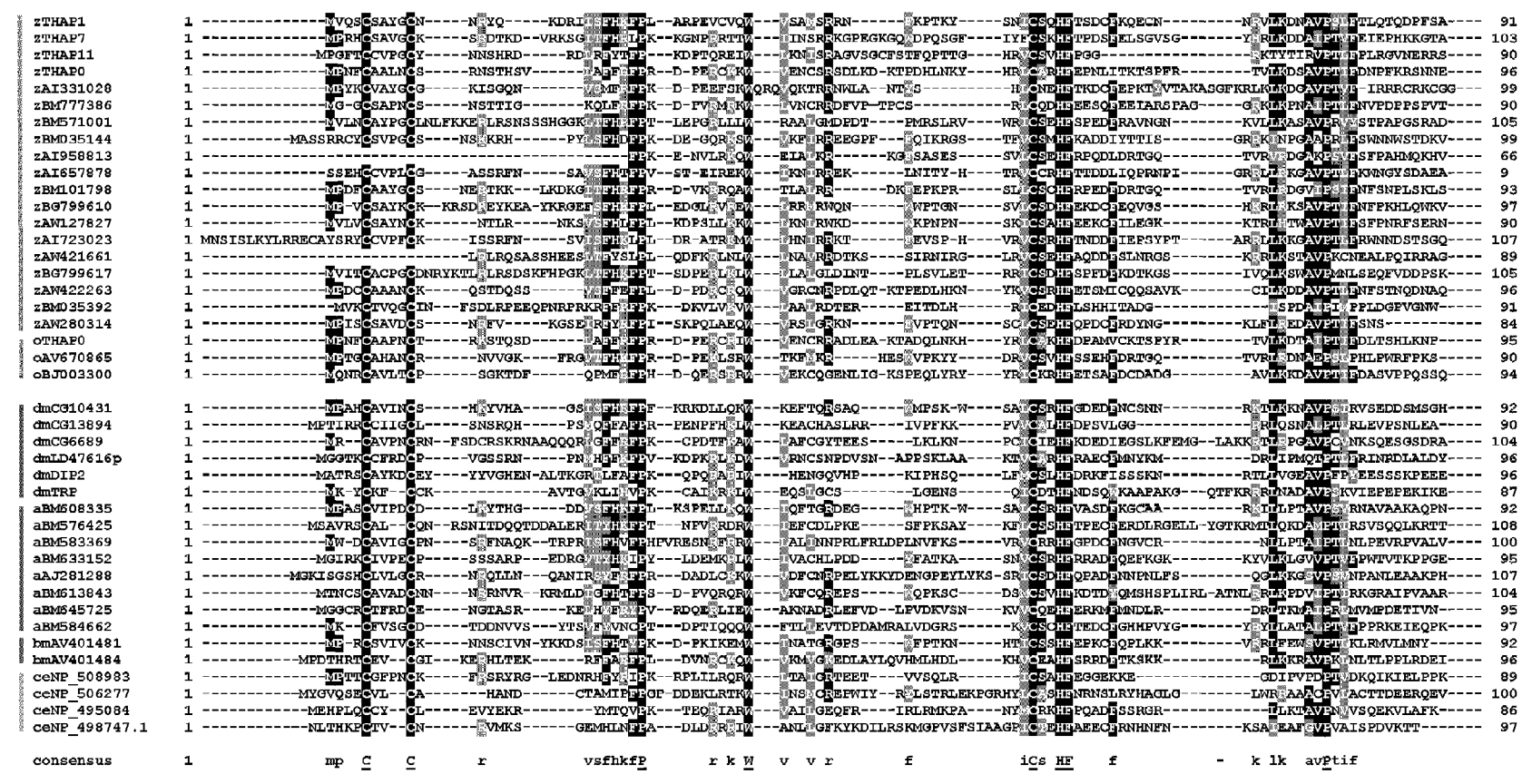
Figure 10:
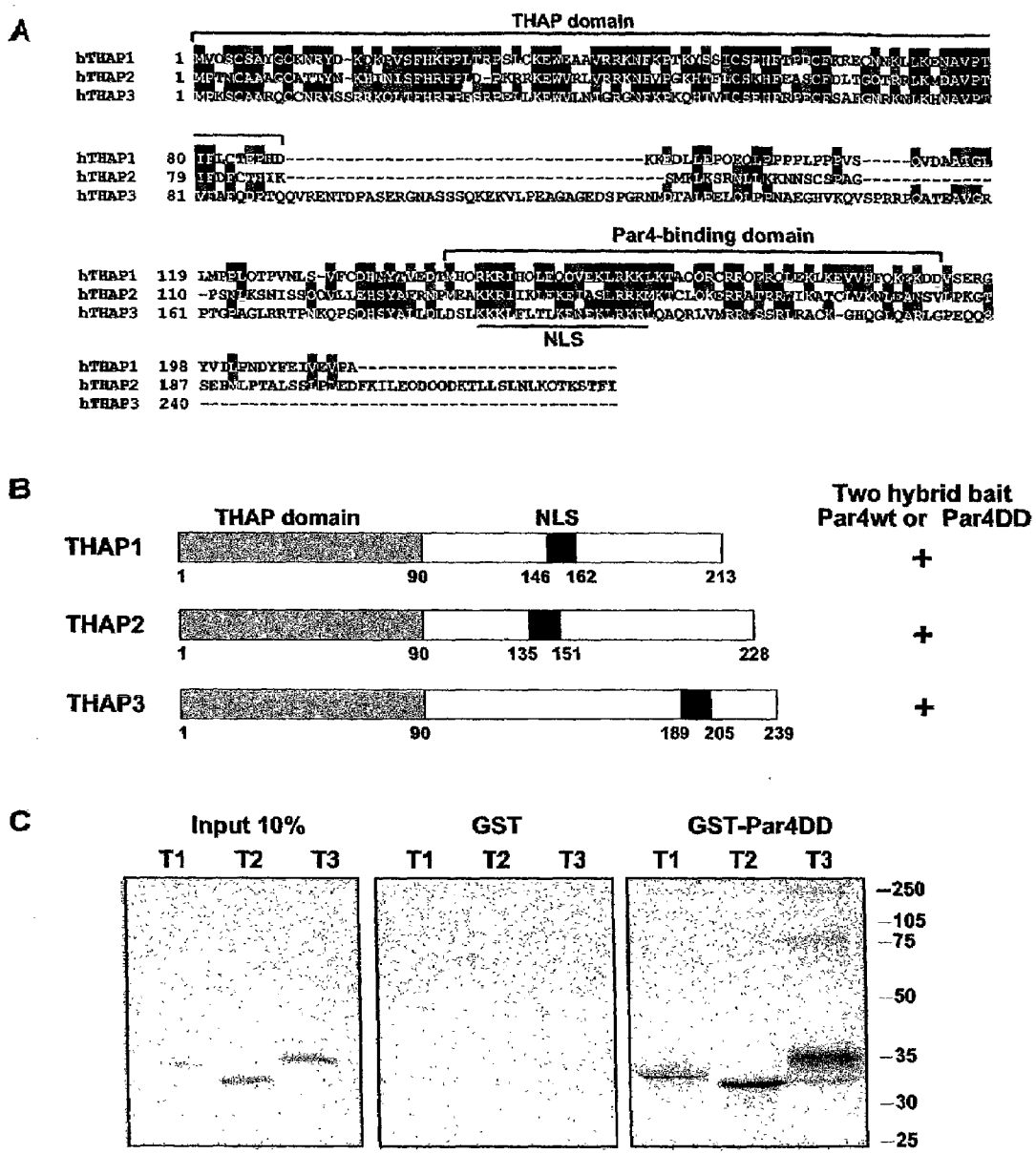
FIG. 10A shows an amino acid sequence alignment of the human THAP1 (SEQ ID NO: 3), THAP2 (SEQ ID NO: 4) and THAP3 (SEQ ID NO: 5) protein sequences. Residues conserved among at least two of the three sequences are boxed. Black boxes indicate identical residues whereas boxes shaded in grey show similar amino acids. Dashed lines represent gaps introduced to align sequences. Regions corresponding to the THAP domain, the PAR4-binding domain, and the nuclear localization signal (NLS) are also indicated.
FIG. 10B shows the primary structure of human THAP1, THAP2 and THAP3 and results of two-hybrid interactions between each THAP protein and Par4 or Par4 death domain (Par4DD) in the yeast two hybrid system.
FIG. 10C shows the binding of in vitro translated, $^{35}$S-methionine-labeled THAP2 and THAP3 to a GST-Par4DD polypeptide fusion. Par4DD was expressed as a GST fusion protein then purified on an affinity matrix of glutathione sepharose. GST served as negative control. The input represents 1/10 of the material used in the binding assay.

To discover novel human proteins homologous to THAP1 and/or containing THAP domains, GenBank non-redundant, human EST and draft human genome databases at the National Center for Biotechnology Information (www.ncbi.nlm.nih.gov) were searched with both the nucleotide and amino acid sequences of THAP1, using the programs BLASTN, TBLASTN and BLASTP (Altschul, S. F., Gish, W., Miller, W., Myers, E. W. and Lipman, D. J. (1990). Basic local alignment search tool. *J Mol Biol* 215: 403-410). This initial step enabled us to identify 12, distinct human THAP-containing, proteins (hTHAP0 to hTHAP11; FIG. 8). In the case of the partial length sequences, assembly of overlapping ESTs together with GENESCAN (Burge, C. and Karlin, S. (1997). Prediction of complete gene structures in human genomic DNA. *J Mol Biol* 268: 78-94) and GENEWISE (Jareborg, N., Birney, E. and Durbin, R. (1999). Comparative analysis of noncoding regions of 77 orthologous mouse and human gene pairs. *Genome Res* 9: 815-824) gene predictions on the corresponding genomic DNA clones, was used to define the full length human THAP proteins as well as their corresponding cDNAs and genes. CLUSTALW (Higgins, D. G., Thompson, J. D. and Gibson, T. J. (1996). Using CLUSTAL for multiple sequence alignments. *Methods Enzymol* 266: 383-402) was used to carry out the alignment of the 12 human THAP domains with the DNA binding domain of Drosophila P-element transposase (Lee, C. C., Beall, E. L., and Rio, D. C. (1998) *Embo J.* 17:4166-74), which was colored using the computer program Boxshade (www.ch.embnet.org/software/BOX_form.html) (see FIGS. 9A and 9B). Equivalent approach to the one described above was used in order to identify the mouse, rat, pig, and various other orthologs of the human THAP proteins (FIG. 9C). Altogether, the in silico and experimental approaches led to the discovery of 12 distinct human members (hTHAP0 to hTHAP11) of the THAP family of pro-apoptotic factors (FIG. 8).

Example 13

THAP2 and THAP3 Interact With Par-4

To assess whether THAP2 and THAP3 are able to interact with Par-4, yeast two hybrid assays using Par-4 wild type bait (FIG. 10B) and in vitro GST pull down assays (FIG. 10C), were performed as described above (Examples 4 and 5). As shown in FIGS. 10B and 10C, THAP2 and THAP3 are able to interact with Par-4. A sequence alignment showing the comparison of the THAP domain and the PAR4-binding domain between THAP1, THAP2 and THAP3 is shown in FIG. 10A.

Example 14

THAP2 and THAP3 are Able to Induce Apoptosis

Figure 11:
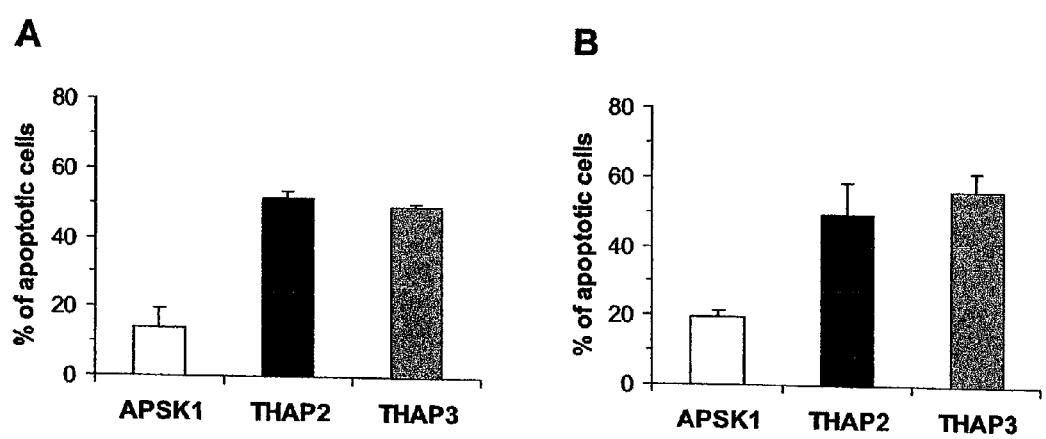
FIG. 11A is a graph which compares apoptosis levels in cells transfected with GFP-APSK1, GFP-THAP2 or GFP-THAP3 expression vectors. Apoptosis was quantified by DAPI staining of apoptotic nuclei, 24 h after serum-withdrawal. Values are the means of two independent representative experiments.
FIG. 11B is a graph which compares apoptosis levels in cells transfected with GFP-APSK1, GFP-THAP2 or GFP-THAP3 expression vectors. Apoptosis was quantified by DAPI staining of apoptotic nuclei, 24 h after additional of TNFα. Values are the means of two independent representative experiments.

Serum-induced or TNFα apoptosis analyses were performed as described above (Example 10) in cells transfected with GFP-APSK1, GFP-THAP2 or GFP-THAP3 expression vectors. Apoptosis was quantified by DAPI staining of apoptotic nuclei 24 hours after serum withdrawal or addition of TNFα. The results are shown in FIG. 11A (serum withdrawal) and FIG. 11B (TNFα). These results indicate that, THAP-2 and THAP3 induce apoptosis.

Example 15

Identification of the SLC/CCL21 Chemokine-Binding Domain of Human THAP1

To identify the SLC/CCL21 chemokine-binding domain of human THAP1, a series of THAP1 deletion constructs was generated as described in Example 7.

Figure 12:
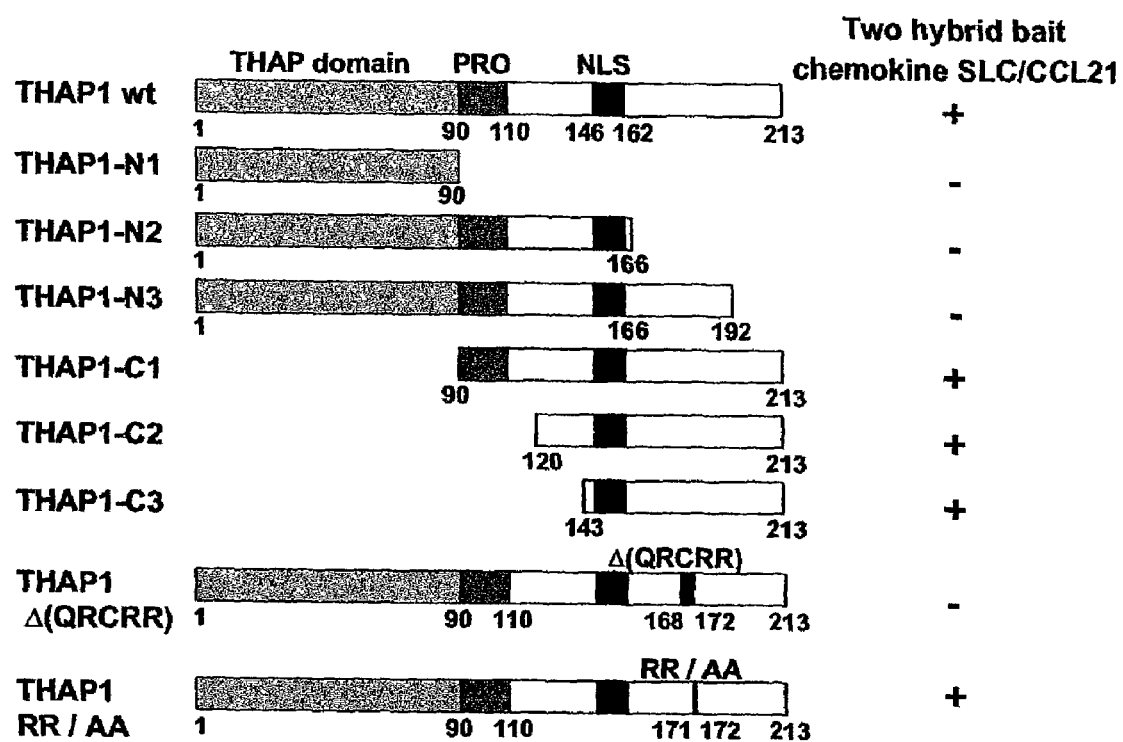
FIG. 12 illustrates the results obtained by screening several different THAP1 mutants in a yeast two-hybrid system with SLC/CCL21 bait. The primary structure of each THAP1 deletion mutant that was tested is shown. The 70 carboxy-terminal residues of THAP1 (amino acids 143-213) are sufficient for binding to chemokine SLC/CCL21.

Two-hybrid interaction between THAP1 mutants and chemokine SLC/CCL21 was tested by cotransformation of AH109 with pGADT7-THAP1-C1, -C2, -C3, -N1, -N2 or -N3 and pGBKT7-SLC/CCL21 and selection of transformants by His and Ade double auxotrophy according to manufacturer's instructions (MATCHMAKER two-hybrid system 3, Clontech). pGBKT7-SLC/CCL21 vector was generated by subcloning the BamHI SLC/CCL21 fragment from pGBT9-SLC (see example 1) into the unique BamHI cloning site of vector pGBKT7 (Clontech). Positive two-hybrid interaction with chemokine SLC/CCL21 was observed with mutants THAP1-C1, -C2, -C3, but not with mutants THAP1-N1, -N2 and -N3, suggesting that the SLC/CCL21 chemokine-binding domain of human THAP1 is found between THAP1 residues 143 and 213 (FIG. 12).

Example 16

In Vitro THAP1/Chemokine SLC-CCL21 Interaction Assay

To confirm the interaction observed in yeast two-hybrid system, we performed in vitro GST pull down assays. THAP1, expressed as a GST-tagged fusion protein and immobilized on glutathione sepharose, was incubated with radiolabeled in vitro translated SLC/CCL21.

To generate the GST-THAP1 expression vector, the full-length coding region of THAP1 (amino acids 1-213) was amplified by PCR from HEVEC cDNA with primers 2HMR8 (5'-CGCGGATCCGTGCAGTCCTGCTCCGCCTACGGC-3') (SEQ ID NO: 214) and 2HMR11 (5'-CCGAATTCTTAT-GCTGGTACTTCAACTATTTCAAAGTAG-3') (SEQ ID NO: 215), digested with BamHI and EcoRI, and cloned in frame downstream of the Glutathion S-Transferase ORF, between the BamHI and EcoRI sites of the pGEX-2T prokaryotic expression vector (Amersham Pharmacia Biotech, Saclay, France). GST-THAP1 fusion protein encoded by plasmid pGEX-2T-THAP1 and control GST protein encoded by plasmid pGEX-2T, were then expressed in *E. Coli* DH5α and purified by affinity chromatography with glutathione sepharose according to supplier's instructions (Amersham Pharmacia Biotech). The yield of proteins used in GST pull-down assays was determined by SDS-Polyarylamide Gel Electrophoresis (PAGE) and Coomassie blue staining analysis.

Figure 13:
FIG. 13 illustrates the interaction of THAP1 with wild type SLC/CCL21 and a SLC/CCL21 mutant deleted of the basic carboxy-terminal extension (SLC/CCL21ΔCOOH). The interaction was analyzed both in yeast two-hybrid system with THAP1 bait and in vitro using GST-pull down assays with GST-THAP1.

In vitro-translated SLC/CCL21 was generated with the TNT-coupled reticulocyte lysate system (Promega, Madison, Wis., USA) using as template pGBKT7-SLC/CCL21 vector (see Example 15). 25 µl of $^{35}$S-labelled wild-type SLC/CCL21 was incubated with immobilized GST-THAP1 or GST proteins overnight at 4° C., in the following binding buffer: 10 mM NaPO4 pH 8.0, 140 mM NaCl, 3 mM MgCl2, 1 mM dithiothreitol (DTT), 0.05% NP40, and 0.2 mM phenylmethyl sulphonyl fluoride (PMSF), 1 mM Na Vanadate, 50 mM β Glycerophosphate, 25 µg/ml chimotrypsine, 5 µg/ml aprotinin, 10 µg/ml Leupeptin. Beads were then washed 5 times in 1 ml binding buffer. Bound proteins were eluted with 2×Laemmli SDS-PAGE sample buffer, fractionated by 10% SDS-PAGE and visualized by fluorography using Amplify (Amersham Pharmacia Biotech). As expected, GST/THAP1 interacted with SLC/CCL21 (FIG. 13). In contrast, SLC/CCL21 failed to interact with GST beads.

Example 17

Identification of the THAP1-Binding Domain of Human Chemokine SLC/CCL21

To determine the THAP1-binding site on human chemokine SLC/CCL21, a SLC/CCL21 deletion mutant (SLC/CCL21ΔCOOH) lacking the SLC-specific basic carboxy-terminal extension (amino acids 102-134; GenBank Accession Number NP_002980) was generated. This SLC/CCL21ΔCOOH mutant, which retains the CCR7 chemokine receptor binding domain of SLC/CCL21 (amino acids 24-101), was used both in yeast two-hybrid assays with THAP1 bait and in in vitro GST-pull down assays with GST-THAP1.

For two-hybrid assays, yeast cells were cotransformed with BD7-THAP1 and AD7-SLC/CCL21 or AD7-SLC/CCL21ΔCOOH expression vectors. AD7-SLC/CCL21 or AD7-SLC/CCL21ΔCOOH expression vectors were generated by subcloning BamHI fragment (encoding SLC amino acids 24-134) or BamHI-PstI fragment (encoding SLC amino acids 24-102) from pGKT7-SLC/CCL21 (see example 15) into pGADT7 expression vector (Clontech). Transformants were selected on media lacking histidine and adenine. FIG. 13 shows that both the SLC/CCL21 wild type and the SLC/CCL21ΔCOOH deletion mutants could bind to THAP1. Identical results were obtained by cotransformation of AD7-THAP1 with BD7-SLC/CCL21 or BD7-SLC/CCL21 ΔCOOH.

GST pull down assays, using in vitro-translated SLC/CCL21ΔCOOH, generated with the TNT-coupled reticulocyte lysate system (Promega, Madison, Wis., USA) using as template pGBKT7-SLC/CCL21ΔCOOH, were performed as described in Example 16. FIG. 13 shows that both the SLC/CCL21 wild type and the SLC/CCL21ΔCOOH deletion mutants could bind to THAP1.

Example 18

Preparation of THAP1/Fc Fusion Proteins

This example describes preparation of a fusion protein comprising THAP1 or the SLC/CCL21 chemokine-binding domain of THAP1 fused to an Fc region polypeptide derived from an antibody. An expression vector encoding the THAP1/Fc fusion protein is constructed as follows.

Briefly, the full length coding region of human THAP1 (SEQ ID NO: 3; amino acids −1 to 213) or the SLC/CCL21 chemokine-binding domain of human THAP1 (SEQ ID NO: 3; amino acids −143 to 213) is amplified by PCR. The oligonucleotides employed as 5' primers in the PCR contain an additional sequence that adds a Not I restriction site upstream. The 3' primer includes an additional sequence that encodes the first two amino acids of an Fc polypeptide, and a sequence that adds a Bgl II restriction site downstream of the THAP1 and Fc sequences.

A recombinant vector containing the human THAP1 cDNA is employed as the template in the PCR, which is conducted according to conventional procedures. The amplified DNA is then digested with Not I and Bgl II, and the desired fragments are purified by electrophoresis on an agarose gel.

A DNA fragment encoding the Fc region of a human IgG1 antibody is isolated by digesting a vector containing cloned Fc-encoding DNA with Bgl II and Not I. Bgl II cleaves at a unique Bgl II site introduced near the 5' end of the Fc-encoding sequence, such that the Bgl II site encompasses the codons for amino acids three and four of the Fc polypeptide. Not I cleaves downstream of the Fc-encoding sequence. The nucleotide sequence of cDNA encoding the Fc polypeptide, along with the encoded amino acid sequence, can be found in International Publication No: WO93/10151, incorporated herein by reference in its entirety.

In a three-way ligation, the above-described THAP1 (or SLC/CCL21 chemokine-binding domain of THAP1)-encoding DNA and Fc-encoding DNA are inserted into an expression vector that has been digested with Not I and treated with a phosphatase to minimize recircularization of any vector DNA without an insert. An example of a vector which can be used is pDC406 (described in McMahan et al., EMBO J. 10:2821, 1991), which is a mammalian expression vector that is also capable of replication in *E. coli*.

*E. coli* cells are then transfected with the ligation mixture, and the desired recombinant vectors are isolated. The vectors encode amino acids-i to 213 of the THAP1 sequence (SEQ ID NO: 3) or amino acids-143 to 213 of the THAP1 sequence of (SEQ ID NO: 3), fused to the N-terminus of the Fc polypeptide. The encoded Fe polypeptide extends from the N-terminal hinge region to the native C-terminus, i.e., is an essentially full-length antibody Fc region.

CV-1/EBNA-1 cells are then transfected with the desired recombinant isolated from *E. coli*. CV-1I/EBNA-1 cells (ATCC CRL 10478) can be transfected with the recombinant vectors by conventional procedures. The CVI-EBNA-1 cell line was derived from the African Green Monkey kidney cell line CV-1 (ATCC CCL 70), as described by McMahan et al. (1991). *EMBO J.* 10:2821. The transfected cells are cultured to allow transient expression of the THAP1/Fc or SLC/CCL21 chemokine-binding domain of THAP1/Fc fusion proteins, which are secreted into the culture medium. The secreted proteins contain the mature form of THAP1 or the SLC/CCL21 chemokine-binding domain of THAP1, fused to the Fc polypeptide. The THAP1/Fc and SLC/CCL21 chemokine-binding domain of THAP1/Fc fusion proteins are believed to form dimers, wherein two such fusion proteins are joined by disulfide bonds that form between the Fc moieties thereof. The THAP1/Fc and SLC/CCL21 chemokine-binding domain of THAP1/Fc fusion proteins can be recovered from the culture medium by affinity chromatography on a Protein A-bearing chromatography column.

Example 19

The THAP Domain Defines a Family of Nuclear Factors

Figure 14:
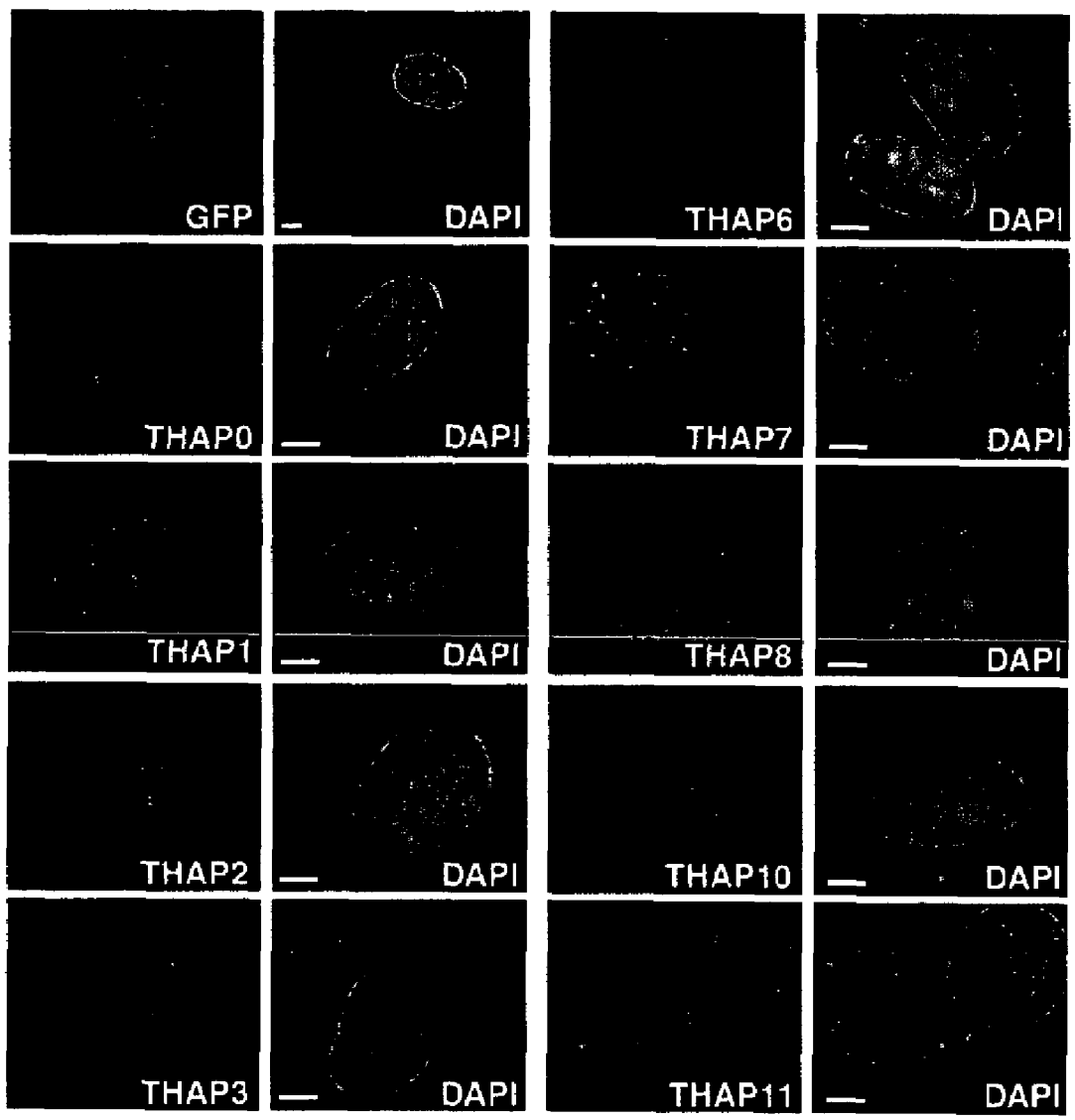
FIG. 14 depicts micrographs of the primary human endothelial cells were transfected with the GFP-THAP0, 1, 2, 3, 6, 7, 8, 10, 11 (green fluorescence) expression constructs. To reveal the nuclear localization of the human THAP proteins, nuclei were counterstained with DAPI (blue). The bar equals 5 μm.

To determine the subcellular localization of the different human THAP proteins, a series of GFP-THAP expression constructs were transfected into primary human endothelial cells. In agreement with the possible functions of THAP proteins as DNA-binding factors, we found that all the human THAP proteins analyzed (THAP0, 1, 2, 3, 6, 7, 8, 10, 11) localize preferentially to the cell nucleus (FIG. 14). In addition to their diffuse nuclear localization, some of the THAP proteins also exhibited association with distinct subnuclear structures: the nucleolus for THAP2 and THAP3, and punctuate nuclear bodies for THAP7, THAP8 and THAP11. Indirect immunofluorescence microscopy with anti-PML antibodies revealed that the THAP8 and THAP11 nuclear bodies colocalize with PML-NBs. Although the THAP7 nuclear bodies often appeared in close association with the PML-NBs, they never colocalized.

Analysis of the subcellular localization of the GFP-THAP fusion proteins was performed as described above (Example 3). The GFP-THAP constructs were generated as follows: the human THAP0 coding region was amplified by PCR from Hevec cDNA with primers THAP0-1 (5'-GCCGAATTCAT-GCCGAACTTCTGCGCTGCCCCC-3') (SEQ ID NO: 216) and THAP0-2 (5'-CGCGGATCCTTAGGTTATTTTCCA-CAGTTTCGGAATTATC-3') (SEQ ID NO: 217), digested with EcoRI and BamHI, and cloned in the same sites of the pEGFP-C2 vector, to generate pEGFPC2-THAP0; the coding region of human THAP2, 3, 7, 6 and 8 were amplified by PCR respectively from Image clone No: 3606376 with primers THAP2-1 (5'-GCGCTGCAGCAAGCTAAATTTAAAT-GAAGGTACTCTTGG-3') (SEQ ID NO: 218) and THAP2-2 (5'-GCGAGATCTGGGAAATGCCGACCAAT-TGCGCTGCG-3') (SEQ ID NO: 219) digested with BglII and PstI, from Image clone No: 4813302 and No: 3633743 with primers THAP3-1 (5'-AGAGGATCCTTAGCTCTGCT-GCTCTGGCCCAAGTC-3') (SEQ ID NO: 220) THAP3-2 (5'-AGAGAATTCATGCCGAAGTCGTGCGCGGCCCG-3') (SEQ ID NO: 221) and primers THAP7-1 (5'-GCGGAAT-TCATGCCGCGTCACTGCTCCGCCGC-3') (SEQ ID NO: 222) THAP7-2 (5'-GCGGGATCCTCAGGCCATGCTGCT-GCTCAGCTGC-3') (SEQ ID NO: 223), digested with EcoRI and BamHI, from Image clone No: 757753 with primers THAP6-1 (5'-GCGAGATCTCGATGGTGAAATGCT-GCTCCGCCATTGGA-3') (SEQ ID NO: 224) and THAP6-2 (5'-GCGGGATCCTCATGAAATATAGTCCTGT-TCTATGCTCTC-3') (SEQ ID NO: 225) digested with BglII and BamHI, and from Image clone No: 4819178 with primers THAP8-1 (5'-GCGAGATCTCGATGCCCAAGTACTG-CAGGGCGCCG-3') (SEQ ID NO: 226) and THAP8-2 (5'-GCGGAATTCTTATGCACTGGGGATC-CGAGTGTCCAGG-3') (SEQ ID NO: 227), digested with BglII and EcoRI and cloned in frame downstream of the Enhanced Green Fluorescent Protein (EGFP)ORF in pEG-FPC2 vector (Clontech) digested with the same enzymes to generate pEGFPC2-THAP2, -THAP3, -THAP7, -THAP6 and -THAP8; the human THAP10 and THAP11 coding region were amplified by PCR from Hela cDNA respectively with primers THAP10-1 (5'-GCGGAATTCATGCCGGC-CCGTTGTGTGGCCGC-3') (SEQ ID NO: 228) THAP10-2 (5'-GCGGGATCCTTAACATGTTTCT-TCTTTCACCTGTACAGC-3') (SEQ ID NO: 229) digested with EcoRI and BamHI, and with primers THAP11-1 (5'-GCGAGATCTCGATGCCTGGCTTTACGTGCTGCGT-GC-3') (SEQ ID NO: 230) and THAP11-2 (5'-GCGGAAT-TCTCACATTCCGTGCTTCTTGCGGATGAC-3') (SEQ ID NO: 231), digested with BglII and EcoRI, cloned in the same sites of the pEGFP-C2 vector, to generate pEGFPC2-THAP10 and -THAP11.

Example 20

Figure 15:
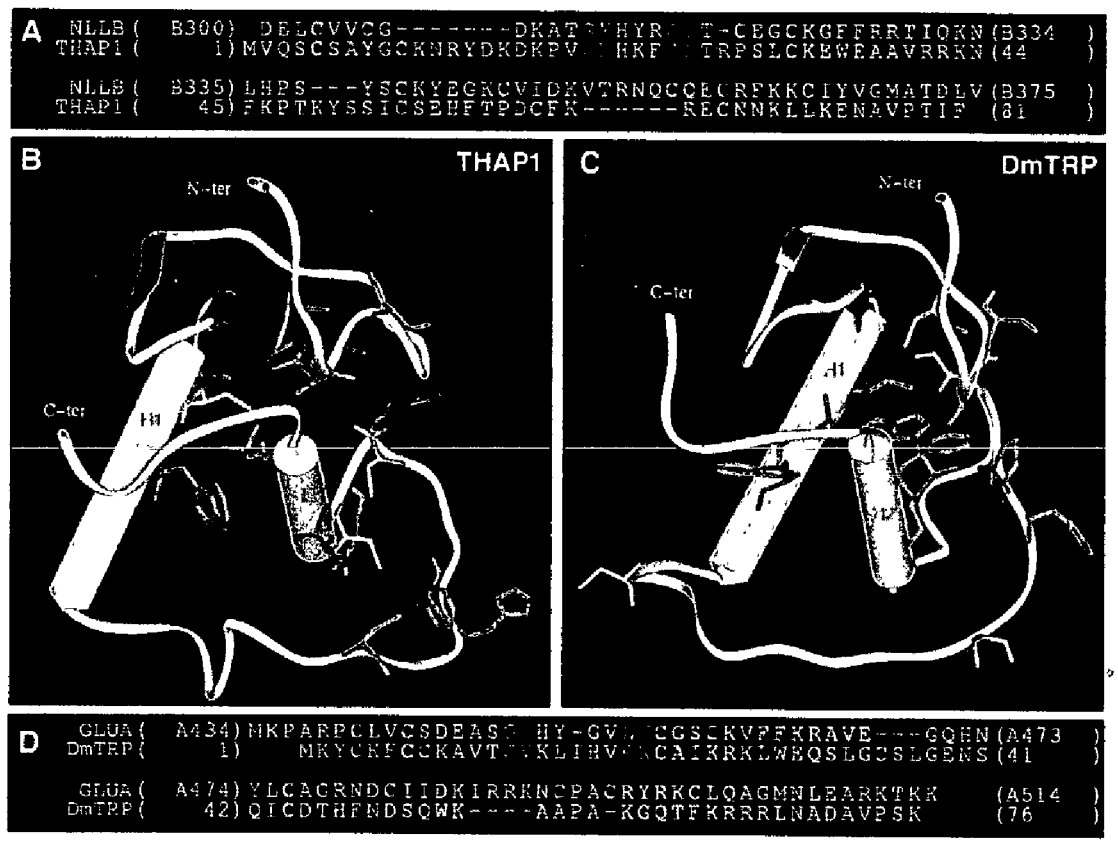
FIG. 15A is a threading-derived structural alignment between the THAP domain of human THAP1 (THAP1) (amino acids 1-81 of SEQ ID NO: 3) and the thyroid receptor βDNA binding domain (NLLB) (SEQ ID NO: 121). The color coding is identical to that described in FIG. 15D.
FIG. 15B shows a model of the three-dimensional structure of the THAP domain of human THAP1 based on its homology with the crystallographic structure of thyroid receptor β. The color coding is identical to that described in FIG. 15D.
FIG. 15C shows a model of the three-dimensional structure of the DNA-binding domain of *Drosophila* transposase (DmTRP) based on its homology with the crystallographic structure of the DNA-binding domain of the glucocorticoid receptor. The color coding is identical to that described in FIG. 15D.
FIG. 15D is a threading-derived structural alignment between the *Drosophila melanogaster* transposase DNA binding domain (DmTRP) (SEQ ID NO: 120) and the glucocorticoid receptor DNA binding domain (GLUA) (SEQ ID NO: 122). In accordance with the sequences and structures in FIGS. 15A-15C, the color-coding is the following: brown indicates residues in α-helices; indigo indicates residues in β-strands; red denotes the eight conserved Cys residues in NLLB and GLUA or for the three Cys residues common to THAP1 and DmTRP; magenta indicates other Cys residues in THAP1 or DmTRP; cyan denotes the residues involved in the hydrophobic interactions networks colored in THAP1 or DmTRP.

The THAP Domain Shares Structural Similarities With the DNA-Binding Domain of Nuclear Hormone Receptors In an effort to model the three-dimensional structure of the THAP domain, we searched the PDB crystallographic database. As sequence homology detection is more sensitive and selective when aided by secondary structure information, structural homologs of the THAP domain of human THAP1 were searched using the SeqFold threading program (Olszewski et al. (1999) Theor. Chem. Acc. 101, 57-61) which combines sequence and secondary structure alignment. The crystallographic structure of the thyroid hormone receptor β DBD (PDB code: 2NLL) gave the best score of the search and we used the resulting structural alignment, displayed in FIG. 15A, to derive a homology-based model of the THAP domain from human THAP1 (FIG. 15B). Note that the distribution of Cys residues in the THAP domain does not fully match that of the thyroid hormone receptor β DBD (FIG. 15A) and hence cannot allow the formation of the two characteristic 'C4-type' Zn-fingers (red color-coding in FIG. 15A). However, a network of stacking interactions between aromatic/hydrophobic residues or aliphatic parts of lysine side-chains ensures the stability of the structure of the THAP domain (cyan color-coding in FIGS. 15A and 15B). Interestingly the same threading method applied independently to the Drosophila P-element transposase DBD identified the crystallographic structure of the glucocorticoid receptor DBD (PDB code: 1GLU) as giving the best score. In the same way, we used the resulting structural alignment, displayed in FIG. 15D, to build a model of the transposase DBD (FIG. 15C). Note the presence of an hydrophobic core equivalent to that of the THAP domain (cyan color-coding in FIGS. 15C and 15D). All the DNA-binding domains of the nuclear receptors fold into a typical pattern which is mainly based on two interacting α-helices, the first one inserting into the target DNA major groove. Our threading and modeling results indicate that the THAP domain and the *D. melanogaster* P-element transposase DBD likely share a common topology which is similar to that of the DBD of nuclear receptors.

Molecular modeling was performed using the InsightII, SeqFold, Homology and Discover modules from the Accelrys (San Diego, Calif.) molecular modeling software (version 98), run on a Silicon Graphics O2 workstation. Optimal secondary structure prediction of the query protein domains was ensured by the DSC method within SeqFold. The threading-derived secondary structure alignments was used as input for homology-modeling, which was performed according to a previously described protocol (Manival et al. (2001) Nucleic Acids Res 29:2223-2233). The validity of the models was checked both by Ramachandran analysis and folding consistency verification as previously reported (Manival et al. (2001) Nucleic Acids Res 29 :2223-2233).

Example 21

Homodimerization Domain of Human THAP1

To identify the sequences mediating homodimerization of THAP1, a series of THAP1 deletion constructs was generated as described in Example 7.

Figure 16:
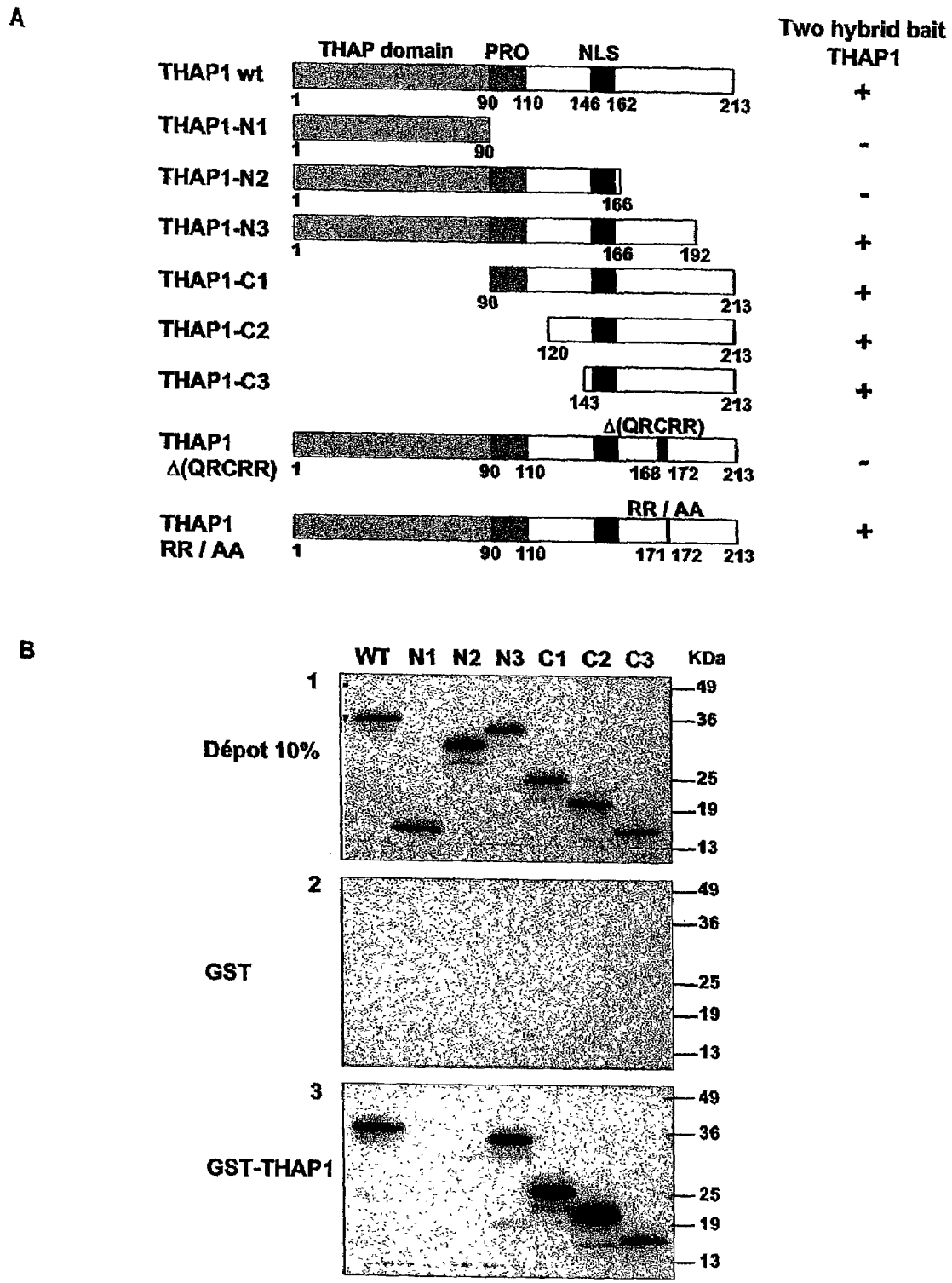
FIG. 16A illustrates the results obtained by screening several different THAP1 mutants in a yeast two-hybrid system with THAP1 bait. The primary structure of each THAP1 deletion mutant that was tested is shown. A (+) indicates binding whereas a (−) indicates no binding.
FIG. 16B shows the binding of several in vitro translated, $^{35}$S-methionine-labeled THAP1 deletion mutants to a GST-THAP1 polypeptide fusion. Wild-type THAP1 was expressed as a GST fusion protein then purified on an affinity matrix of glutathione sepharose. GST served as negative control. The input represents 1/10 of the material used in the binding assay.

Two-hybrid interaction between THAP1 mutants and THAP1 wild type was tested by cotransformation of AH109 with pGADT7-THAP1-C1, -C2, -C3, -N1, -N2 or -N3 and pGBKT7-THAP1 wild-type and selection of transformants by His and Ade double auxotrophy according to manufacturer's instructions (MATCHMAKER two-hybrid system 3, Clontech). Positive two-hybrid interaction with THAP1 wild type was observed with mutants THAP1-C1, -C2, -C3, -and -N3 but not with mutants THAP1-N1 and -N2, suggesting the THAP1 homodimerization domain is found between THAP1 residues 143 and 192 (FIG. 16A).

To confirm the results obtained in yeast, THAP1 mutants were also tested in in vitro GST pull down assays. Wild type THAP1 expressed as a GST-tagged fusion protein and immobilized on glutathione sepharose (as described in example 16), was incubated with radiolabeled in vitro translated THAP1 mutants. In vitro-translated THAP1 mutants were generated with the TNT-coupled reticulocyte lysate system (Promega, Madison, Wis., USA) using pGADT7-THAP1-C1, -C2, -C3, -N1, -N2 or -N3 vector as template. 25 µl of each $^{35}$S-labelled THAP1 mutant was incubated with immobilized GST or GST-THAP1 wild-type protein overnight at 4° C., in the following binding buffer: 10 mM NaPO4 pH 8.0, 140 mM NaCl, 3 mM MgCl2, 1 mM dithiothreitol (DTT), 0.05% NP40, and 0.2 mM phenylmethyl sulphonyl fluoride (PMSF), 1 mM Na Vanadate, 50 mM β Glycerophosphate, 25 µg/ml chimotrypsine, 5 µg/ml aprotinin, 10 µg/ml Leupeptin. Beads were then washed 5 times in 1 ml binding buffer. Bound proteins were eluted with 2×Laemmli SDS-PAGE sample buffer, fractionated by 10% SDS-PAGE and visualized by fluorography using Amplify (Amersham Pharmacia Biotech). As expected, THAP1-C1, -C2, -C3, -and -N3 interacted with GST/THAP1 (FIG. 16B). In contrast, THAP1-N1 and -N2 failed to interact with GST/THAP1 beads. Therefore, essentially identical results were obtained with the two THAP1/THAP1 interactions assays: the THAP1 homodimerization domain of THAP1 is found between residues 143 and 192 of human THAP1.

Example 22

Alternatively Spliced Isoform of Human THAP1

Figure 17:
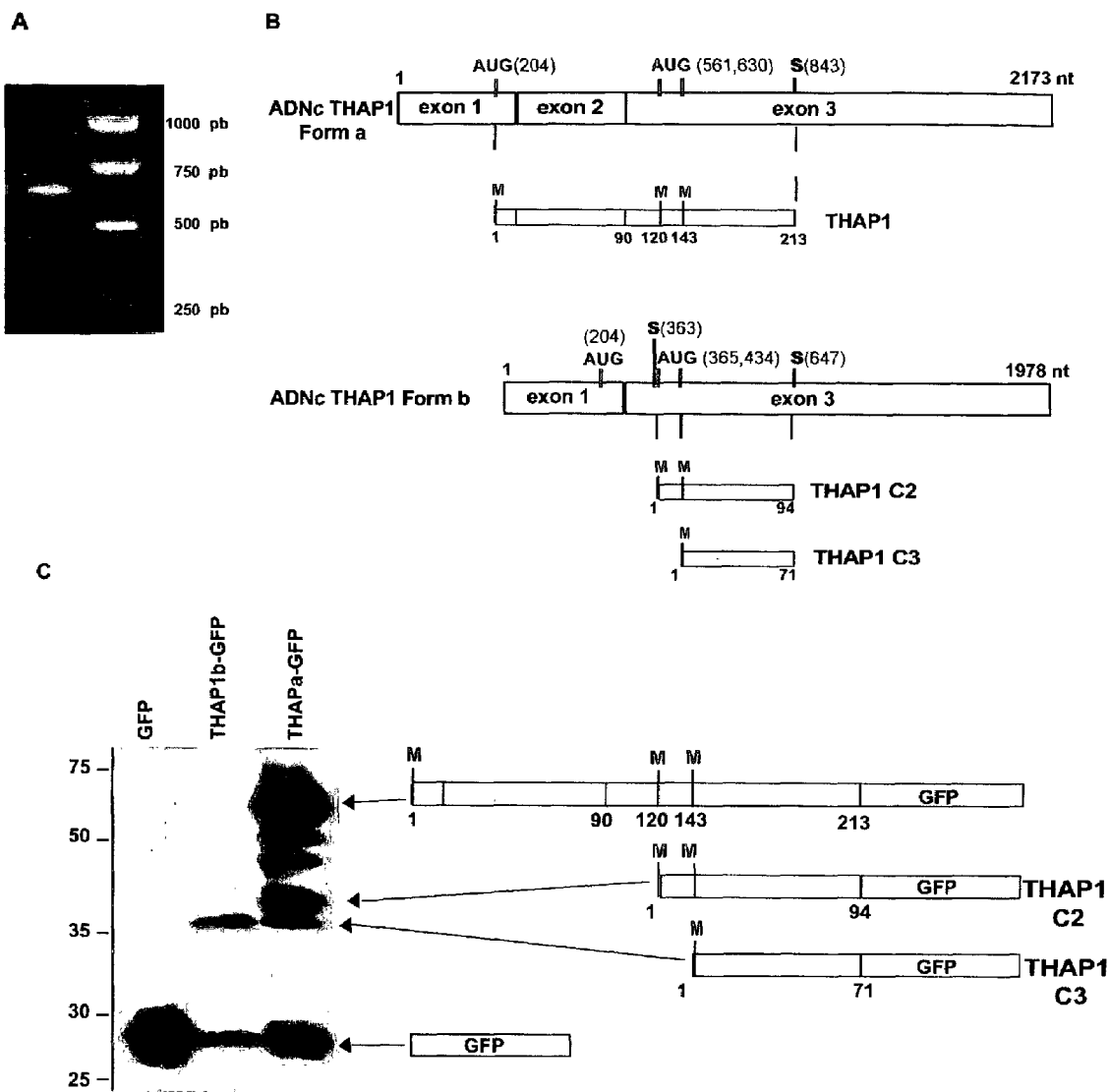
FIG. 17A is an agarose gel showing two distinct THAP1 cDNA fragments were obtained by RT-PCR. Two distinct THAP1 cDNAs were ~400 and 600 nucleotides in length.
FIG. 17B shows that the 400 nucleotide fragment corresponds to an alternatively spliced isoform of human THAP1 cDNA, lacking exon 2 (nucleotides 273-468 of SEQ ID 160).
FIG. 17C is a Western blot which shows that the second isoform of human THAP1 (THAP1b) encodes a truncated THAP1 protein (THAP1 C3) lacking the amino-terminal THAP domain.

The two distinct THAP1 cDNAs, THAP1a and THAP1b have been discovered (FIG. 17A). These splice variants, were amplified by PCR from HEVEC cDNA with primers 2HMR10 (5'-CCGAATTCAGGATGGTGCAGTCCT-GCTCCGCCT-3') (SEQ ID NO: 232) and 2HMR9 (5'-CGCGGATCCTGCTGGTACTTCAAC-TATTTCAAAGTAGTC-3') (SEQ ID NO: 233), digested with EcoRI and BamHI, and cloned in frame upstream of the Enhanced Green Fluorescent Protein (EGFP)ORF in pEG-FP.N3 vector (Clontech) to generate pEGFP.N3-THAP1a and pEGFP-THAP1b. DNA sequencing revealed that THAP1b cDNA isoform lacks exon 2 (nucleotides 273-468) of the human THAP1 gene (FIG. 17B). This alternatively spliced isoform of human THAP1 (~2 kb mRNA) was also observed in many other tissues by Northern blot analysis (see FIG. 2). The THAP1a/GFP and THAP1b/GFP expression constructs were then transfected into COS 7 cells (ATCC) and expression of the fusion proteins was analyzed by western blotting with anti-GFP antibodies. The results are shown in FIG. 17C which demonstrates that the second isoform of human THAP1 (THAP1b) encodes a truncated THAP1 protein (THAP1 C3) lacking a substantial portion of the amino terminus (amino acids 1-142 of SEQ ID NO: 3).

Example 23

High Throughput Screening Assay for Modulators of THAP Family Polypeptide Pro-Apoptotic Activity A high throughput screening assay for molecules that abrogate or stimulate THAP-family polypeptide proapoptotic activity was developed, based on serum-withdrawal induced apoptosis in a 3T3 cell line with tetracycline-regulated expression of a THAP family polypeptide.

In a preferred example, the THAP1 cDNA with an in-frame myc tag sequence, was amplified by PCR using pGBKT7-THAP1 as a template with primers myc.BD7 (5'-GCGCT-CTAGAGCCATCATGGAGGAGCAGAAGCTGATC-3') (SEQ ID NO: 234) and 2HMR15 (5'-GCGCTCTAGATTA-TGCTGGTACTTCAACTATTTCAAAGTAG-3') (SEQ ID NO: 235), and cloned downstream of a tetracycline regulated promoter in plasmid vector pTRE (Clontech, Palo Alto, Calif.), using Xba I restriction site, to generate plasmid pTRE-mycTHAP1. To establish 3T3-TO-mycTHAP1 stable cell lines, mouse 3T3-TO fibroblasts (Clontech) were seeded at 40 to 50% confluency and co-transfected with the pREP4 plasmid (Invitrogen), which contains a hygromycin B resistance gene, and the mycTHAP1 expression vector (pTRE-mycTHAP1) at 1:10 ratio, using Lipofectamine Plus reagent (Life Technologies) according to supplier's instructions. Transfected cells were selected in medium containing hygromycin B (250 U/ml; Calbiochem) and tetracycline (2 ug/ml; Sigma). Several resistant colonies were picked and analyzed for the expression of mycTHAP1 by indirect immunofluorescence using anti-myc epitope monoclonal antibody (mouse IgG1, 1/200, Clontech). A stable 3T3-TO cell line expressing mycTHAP1 (3T3-TO-mycTHAP1) was selected and grown in Dulbecco's Modified Eagle's Medium supplemented with 10% Fetal Calf Serum, 1% Penicillin-streptomycin (all from Life Technologies, Grand Island, N.Y., USA) and tetracycline (2 ug/ml; Sigma). Induction of THAP1 expression into this 3T3-TO-mycTHAP1 cell line was obtained 48 h after removal of tetracycline in the complete medium.

A drug screening assay using the 3T3-TO-mycTHAP1 cell line can be carried out as follows. 3T3-TO-mycTHAP1 cells are plated in 96- or 384-wells microplates and THAP1 expression is induced by removal of tetracycline in the complete medium. 48 h later, the apoptotic response to serum withdrawal is assayed in the presence of a test compound, allowing the identification of test compounds that either enhance or inhibit the ability of THAP1 polypeptide to induce apoptosis. Serum starvation of 3T3-TO-mycTHAP1 cells is induced by changing the medium to 0% serum, and the amount of cells with apoptotic nuclei is assessed 24 h after induction of serum starvation by TUNEL labeling in 96- or 384-wells microplates. Cells are fixed in PBS containing 3.7% formaldehyde and permeabilized with 0.1% Triton-X100, and apoptosis is scored by in situ TUNEL (terminal deoxynucleotidyl transferase-mediated dUTP nick end labeling) staining of apoptotic nuclei for 1 hr at 37° C. using the in situ cell death detection kit, TMR red (Roche Diagnostics, Meylan, France). The intensity of TMR red fluorescence in each well is then quantified to identify test compounds that modify the fluorescence signal and thus either enhance or inhibit THAP1 pro-apoptotic activity.

Example 24

High Throughput Two-Hybrid Screening Assay for Drugs that Modulate THAP-Family Polypeptide/THAP-Family Target Protein Interaction To identify drugs that modulate THAP1/Par4 or THAP1/SLC interactions, a two-hybrid based high throughput screening assay can be used.

As described in Example 17, AH109 yeast cells (Clontech) cotransformed with plasmids pGBKT7-THAP1 and pGADT7-Par4 or pGADT7-SLC can be grown in 384-well plates in selective media lacking histidine and adenine, according to manufacturer's instructions (MATCHMAKER two-hybrid system 3, Clontech).

Growth of the transformants on media lacking histidine and adenine is absolutely dependent on the THAP1/Par4 or THAP1/SLC two-hybrid interaction and drugs that disrupt THAP1/Par4 or THAP1/SLC binding will therefore inhibit yeast cell growth.

Small molecules (5 mg ml$^{-1}$ in DMSO; Chembridge) are added by using plastic 384-pin arrays (Genetix). The plates are incubated for 4 to 5 days at 30° C., and small molecules which inhibit the growth of yeast cells by disrupting THAP1/Par4 or THAP1/SLC two-hybrid interaction are selected for further analysis.

Example 25

High Throughput In Vitro Assay to Identify Inhibitors of THAP-Family Polypeptide/THAP-Family Protein Target Interaction To identify small molecule modulators of THAP function, a high-throughput screen based on fluorescence polarization (FP) is used to monitor the displacement of a fluorescently labelled THAP1 protein from a recombinant glutathione-S-transferase (GST)-THAP binding domain of Par4 (Par4DD) fusion protein or a recombinant GST-SLC/CCL21 fusion protein.

Assays are carried out essentially as in Degterev et al, Nature Cell Biol. 3: 173-182 (2001) and Dandliker et al, Methods Enzymol. 74: 3-28 (1981). The assay can be calibrated by titrating a THAP1 peptide labelled with Oregon Green with increasing amounts of GST-Par4DD or GST-SLC/CCL21 proteins. Binding of the peptide is accompanied by an increase in polarization (mP, millipolarization).

THAP 1 and PAR4 polypeptides and GST-fusions can be produced as previously described. The THAP1 peptide was expressed and purified using a QIAexpressionist kit (Qiagen) according to the manufacturer's instructions. Briefly, the entire THAP1 coding sequence was amplified by PCR using pGBKT7-THAP1 as a template with primers 2HMR8 (5'-CGCGGATCCGTGCAGTCCTGCTCCGCCTACGGC-3') (SEQ ID NO: 236) and 2HMR9 (5'-CGCGGATCCTGCTG-GTACTTCAACTATTTCAAAGTAGTC-3') (SEQ ID NO: 237), and cloned into the BamHI site of pQE30 vector (Qiagen). The resulting pQE30-HisTHAP1 plasmid was transformed in E. coli strain M15 (Qiagen). 6×His-tagged- THAP1 protein was purified from inclusion bodies on a Ni-Agarose column (Qiagen) under denaturing conditions, and the eluate was used for in vitro interaction assays. To produce GST-Par4DD fusion protein, Par4DD (amino acids 250-342) was amplified by PCR with primers Par4.10 (5'-GCCG-GATCCGGGTTCCCTAGATATAACAGGGATGCAA-3') (SEQ ID NO: 238) and Par4.5 (5'-GCGGGATCCCTCTAC-CTGGTCAGCTGACCCACAAC-3') (SEQ ID NO: 239), and cloned in frame downstream of the Glutathione S-Transferase (GST) ORF, into the BamHI site of the pGEX-2T prokaryotic expression vector (Amersham Pharmacia Biotech, Saclay, France). Similarly, to produce GST-SLC/CCL21 fusion protein, the mature form of human SLC/CCL21 (amino acids 24-134) was amplified by PCR with primers hSLCbam.5' (5'-GCGGGATCCAGTGATG-GAGGGGCTCAGGACTGTTG-3') (SEQ ID NO: 240) and hSLCbam.3' (5'-GCGGGATCCCTATGGCCCTT-TAGGGGTCTGTGACC-3') (SEQ ID NO: 241), digested with BamHI and inserted into the BamHI cloning site of the pGEX-2T vector. GST-Par4DD (amino acids 250-342) and GST-SLC/CCL21 (amino acids 24-134) fusion proteins were expressed in E. Coli DH5α (supE44, DELTAlacU169 (801acZdeltaM15), hsdR17, recA1, endA1, gyrA96, thi1, relA 1) and purified by affinity chromatography with glutathione sepharose according to supplier's instructions (Amersham Pharmacia Biotech).

For screening small molecules, THAP1 peptide is labelled with succinimidyl Oregon Green (Molecular Probes, Oregon) and purified by HPLC. 33 nM labelled THAP1 peptide, 2 µM GST-Par4DD or GST-SLC/CCL21 protein, 0.1% bovine gamma-globullin (Sigma) and 1 mM dithiothreitol mixed with PBS, pH 7.2 (Gibco), are added to 384-well black plates (Lab Systems) with Multidrop (Lab Systems). Small molecules (5 mg ml$^{-1}$ in DMSO; Chembridge) are transferred by using plastic 384-pin arrays (Genetix). The plates are incubated for 1-2 hours at 25° C., and FP values are determined with an Analyst plate reader (LJL Biosystems).

Example 26

High Throughput Chip Assay to Identify Inhibitors of THAP-Family Polypeptide/THAP-Family Protein Target Interaction A chip based binding assay Degterev et al, (2001) Nature Cell Biol. 3: 173-182 using unlabelled THAP and THAP-family target protein may be used to identify molecules capable of interfering with THAP-family and THAP-family target interactions, providing high sensitivity and avoiding potential interference from label moieties. In this example, the THAP1 binding domain of Par4 protein (Par4DD) or SLC/CCL21 is covalently attached to a surface-enhanced laser desorption/ionization (SELDI) chip, and binding of unlabelled THAP1 protein to immobilized protein in the presence of a test compound is monitored by mass spectrometry.

Recombinant THAP1 protein, GST-Par4DD and GST-SLC/CCL21 fusion proteins are prepared as described in Example 25. Purified recombinant GST-Par4DD or GST-SLC/CCL21 protein is coupled through its primary amine to SELDI chip surfaces derivatized with cabonyldiimidazole (Ciphergen). THAP1 protein is incubated in a total volume of 1 µl for 12 hours at 4° C. in a humidified chamber to allow binding to each spot of the SELDI chip, then washed with alternating high-pH and low-pH buffers (0.1M sodium acetate containing 0.5M NaCl, followed by 0.01 M HEPES, pH 7.3). The samples are embedded in an alpha-cyano-4-hydroxycinnamic acid matrix and analysed for mass by matrix-assisted laser desorption ionization time-of-flight (MALDI-TOF) mass spectrometry. Averages of 100 laser shots at a constant setting are collected over 20 spots in each sample.

Example 27

High Throughput Cell Assay to Identify Inhibitors of THAP-Family Polypeptide/THAP-Family Protein Target Interaction A fluorescence resonance energy transfer (FRET) assay is carried out between THAP-1 and PAR4 or SLC/CCL21 proteins fused with fluorescent proteins. Assays can be carried out as in Majhan et al, Nature Biotechnology 16: 547-552 (1998) and Degterev et al, Nature Cell Biol. 3: 173-182 (2001).

THAP-1 protein is fused to cyan fluorescent protein (CFP) and PAR4 or SLC/CCL21 protein is fused to yellow fluorescent protein (YFP). Vectors containing THAP-family and THAP-family target proteins can be constructed essentially as in Majhan et al (1998). A THAP-1-CFP expression vector is generated by subcloning a THAP-1 cDNA into the pECFP-N1 vector (Clontech). PAR4-YFP or SLC/CCL21-CYP expression vectors are generated by subcloning a PAR4 or a SLC/CCL21 cDNA into the pEYFP-N1 vector (Clontech).

Vectors are cotransfected to HEK-293 cells and cells are treated with test compounds. HEK-293 cells are transfected with THAP-1-CFP and PAR4-YFP or SLC/CCL21-YFP expression vectors using Lipofect AMINE Plus (Gibco) or TransLT-1 (PanVera). 24 hours later cells are treated with test compounds and incubated for various time periods, preferably up to 48 hours. Cells are harvested in PBS, optionally supplemented with test compound, and fluorescence is determined with a C-60 fluorimeter (PTI) or a Wallac plate reader. Fluorescence in the samples separately expressing THAP-1-CFP and PAR4-YFP or SLC/CCL21-YFP is added together and used to estimate the FRET value in the absence of THAP-1/PAR4 or THAP1/SLC/CCL21 binding.

The extent of FRET between CFP and YFP is determined as the ratio between the fluorescence at 527 nm and that at 475 nm after excitation at 433 nm. The cotransfection of THAP-1 protein and PAR4 or SLC/CCL21 protein results in an increase of FRET ratio over a reference FRET ratio of 1.0 (determined using samples expressing the proteins separately). A change in the FRET ratio upon treatmemt with a test compound (over that observed after cotransfection in the absence of a test compound) indicates a compound capable of modulating the interaction of the THAP-1 protein and the PAR4 or the SLC/CCL21 protein.

Example 28

In Vitro Assay to Identify THAP-Family Polypeptide DNA Targets

DNA binding specificity of THAP1 was determined using a random oligonucleotide selection method allowing unbiased analysis of binding sites selected by the THAP domain of the THAP1 protein from a random pool of possible sites. The method was carried out essentially as described in Bouvet (2001) *Methods Mol. Biol.* 148:603-10. Also, see Pollack and Treisman (1990) *Nuc. Acid Res.* 18:6197-6204; Blackwell and Weintraub, (1990) *Science* 250: 1104-1110; Ko and Engel, (1993) *Mol. Cell. Biol.* 13:4011-4022; Merika and Orkin, (1993) *Mol. Cell. Biol.* 13: 3999-4010; and Krueger and Morimoto, (1994) *Mol. Cell. Biol.* 14:7592-7603), the disclosures of which are incorporated herein by reference in their entireties.

Recombinant THAP Domain Expression and Purification

A cDNA fragment encoding the THAP domain of human THAP-1 (amino acids 1-90, SEQ ID NO: 3) was cloned by PCR using as a template pGADT7-THAP-1 (see Example 4) with the following primers 5'-GCGCATATGGTGCAGTC-CTGCTCCGCCTACGGC-3' (SEQ ID NO: 242) and 5'-GCGCTCGAGTTTCTTGTCATGTGGCT-CAGTACAAAG-3' (SEQ ID NO: 243). The PCR product was cloned as a NdeI-XhoI fragment into pET-21c prokaryotic expression vector (Novagen) in frame with a sequence encoding a carboxy terminal His tag, to generate pET-21c-THAP.

For the expression of THAP-His6, pET-21c-THAP was transformed into *Escherichia coli* strain BL-21 pLysS. Bacteria were grown at 37° C. to an optical density at 600 nm of 0.6 and expression of the protein was induced by adding isopropyl-β-D-thiogalactoside (Sigma) at a final concentration of 1 mM and incubation was continued for 4 hours.

The cells were collected by centrifugation and resuspended in ice cold of buffer A (50 mM sodium-phosphate pH 7.5, 300 mM NaCl, 0.1% β-mercaptoethanol, 10 mM Imidazole). Cells were lysed by sonication and the lysate was cleared by centrifugation at 12000 g for 45 min. The supernatant was loaded onto a Ni-NTA agarose column (Quiagen) equilibrated in buffer A. After washing with buffer A and Buffer A with 40 mM Imidazole, the protein was eluted with buffer B (same as A with 0.05%β-mercaptoethanol and 250 mM Imidazole).

Fractions containing THAP-His6 were pooled and applied to a Superdex 75 gel filtration column equilibrated in Buffer C (Tris-HCl 50 mM pH 7.5, 150 mM NaCl, 1 mM DTT). Fractions containing the THAP-His6 protein were pooled, concentrated by withnYM-3 Amicon filter devices and stored at 4° C. or frozen at −80° C. in buffer C containing 20% glycerol. The purity of the sample was assessed by SDS-Polyarylamide Gel Electrophoresis (PAGE) and Coomassie blue staining analysis. The structural integrity of the protein preparation was checked by ESI mass spectrometry and Peptide mass mapping using a MALDI-TOF Mass spectrometer. The protein concentration was determined with Bradford Protein Assay.

Random Oligonucleotide Selection

According to the SELEX protocol described in Bouvet (2001) *Methods Mol. Biol.* 148:603-10, a 62 bp oligonucleotide having sequences as follows was synthesized: 5'-TGGGCACTATTTATATCAAC-N25-AATGTCGTTG-GTGGCCC-3' (SEQ ID NO: 244) where N is any nucleotide, and primers complementary to each end. Primer P is: 5'-AC-CGCAAGCTTGGGCACTATTTATATCAAC-3' (SEQ ID NO: 245), and primer R is 5'-GGTCTAGAGGGCCAC-CAACGCATT-3' (SEQ ID NO: 246). The 62-mer oligonucleotide is made double stranded by PCR using the P and R primers generating a 80 bp random pool.

About 250 ng of THAP-His6 was incubated with Ni-NTA magnetic beads in NT2 buffer (20 mM Tris-HCl pH 7.5, 100 mM NaCl, 0.05% NP-40) for 30 min at 4° C. on a roller. The beads were washed 2 times with 500 µl of NT2 buffer to remove unbound protein. The immobilized THAP-His6 was incubated with the random pool of double stranded 80 bp DNA (2 to 5%g) in 100 µl of Binding buffer (20 mM Tris-HCl pH 7.5, 100 mM NaCl, 0.05% NP-40, 0.5 mM EDTA, 100 µg/ml BSA, and 20 to 50 µg of poly(dI-dC)) for 10 minutes at room temperature. The beads were then washed 6 times with 500 µl of NT2 buffer. The protein/DNA complex were then subjected to extraction with phenol/chloroform and precipitation with ethanol using 10 µg of glycogen as a carrier. About one fifth of the recovered DNA was then amplified by 15 to 20 cycles of PCR and used for the next round of selection. After 8 rounds of selection, the NaCl concentration was progressively increased to 150 mM.

After 12 rounds of selection by THAP-His6, pools of amplified oligonucleotides were digested with Xba I and Hind III and cloned into pBluescript II KS—(Stratagene) and individual clones were sequenced using Big Dye terminator Kit (Applied Biosystem).

The results of the sequence analysis show that the THAP domain of human THAP1 is a site-specific DNA binding domain. Two consensus sequences were deduced from the alignment of two sets of nucleotide sequences obtained from the above SELEX procedure (each set containing 9 nucleic acid sequences). In particular, it was found that the THAP domain recognizes GGGCAA or TGGCAA DNA target sequences preferentially organized as direct repeats with 5 nucleotide spacing (DR-5 motifs). The consensus sequence being GGGCAAnnnnnTGGCAA (SEQ ID NO: 149). Additionally, THAP recognizes everted repeats with 11 nucleotide spacing (ER-1 motifs) having a consensus sequence of TTGCCAnnnnnnnnnnnGGGCAA (SEQ ID NO: 159). Although GGGCAA and TGGCAA sequences constitute the preferential THAP domain DNA binding sites, GGGCAT, GGGCAG and TGGCAG sequences are also DNA target sequences recognized by the THAP domain.

Example 29

High Throughput In Vitro Assay to Identify Inhibitors of THAP-Family Polypeptide or THAP-Family Interactions With Nonspecific DNA Targets High throughput assays for the detection and quantification of THAP1-nonspecific DNA binding is carried out using a scintillation proximity assay. Materials are available from Amersham (Piscataway, N.J.) and assays can be carried out according to Gal S. et al, 6th Ann. Conf. Soc. Biomol. Screening, 6-9 Sept 2000, Vancouver, B.C.), the disclosure of which is incorporated herein by reference in its entirety.

Random double stranded DNA probes are prepared and labelled using [$^3$H]TTP and terminal transferase to a suitable specific activity (e.g. approx. 420 i/mmol). THAP1 protein or a portion thereof is prepared and the quantity of THAP1 protein or a portion thereof is determined via ELISA. For assay development purposes, electrophoretic mobility shift assays (EMSA) can be carried out to select suitable assay parameters. For the high throughput assay, $^3$H labelled DNA, anti-THAP1 monoclonal antibody and THAP1 in binding buffer (Hepes, pH 7.5; EDTA; DTT; 10 mM ammonium sulfate; KCl and Tween-20) are combined. The assay is configured in a standard 96-well plate and incubated at room temperature for 5 to 30 minutes, followed by the addition of 0.5 to 2 mg of PVT protein A SPA beads in 50-100 µl binding buffer. The radioactivity bound to the SPA beads is measured using a TopCount™ Microplate Counter (Packard Biosciences, Meriden, Conn.).

Example 30

High Throughput In Vitro Assay to Identify Inhibitors of THAP-Family Polypeptide or THAP-Family Interactions With Specific DNA Targets High throughput assays for the detection and quantification of THAP1 specific DNA binding is carried out using a scintillation proximity assay. Materials are available from Amersham (Piscataway, N.J.) and assays can be carried out according to Gal S. et al, 6$^{th}$ Ann. Conf. Soc. Biomol. Screening, Sep. 6-9, 2000, Vancouver, B.C.).

THAP1-specific double stranded DNA probes corresponding to THAP1 DNA binding sequences obtained according to Example 20 are prepared. The probes are labelled using [$^3$H] TTP and terminal transferase to a suitable specific activity (e.g. approx. 420 i/mmol). THAP1 protein or a portion thereof is prepared and the quantity of THAP1 protein or a portion thereof is determined via ELISA. For assay development purposes, electrophoretic mobility shift assays (EMSA) can be carried out to select suitable assay parameters. For the high throughput assay, $^3$H labelled DNA, anti-THAP1 monoclonal antibody, 1 g non-specific DNA (double or single stranded poly-dAdT) and THAP1 protein or a portion thereof in binding buffer (Hepes, pH 7.5; EDTA; DTT; 10 mM ammonium sulfate; KCl and Tween-20) are combined. The assay is configured in a standard 96-well plate and incubated at room temperature for 5 to 30 minutes, followed by the addition of 0.5 to 2 mg of PVT protein A SPA beads in 50-100 µl binding buffer. The radioactivity bound to the SPA beads is measured using a TopCount™ Microplate Counter (Packard Biosciences, Meriden, Conn.).

Example 31

Preparation of Antibody Compositions

Substantially pure THAP1 protein or a portion thereof is obtained. The concentration of protein in the final preparation is adjusted, for example, by concentration on an Amicon filter device, to the level of a few micrograms per ml. Monoclonal or polyclonal antibodies to the protein can then be prepared as follows: Monoclonal Antibody Production by Hybridoma Fusion Monoclonal antibody to epitopes in the THAP1 protein or a portion thereof can be prepared from murine hybridomas according to the classical method of Kohler and Milstein (Nature, 256: 495, 1975) or derivative methods thereof (see Harlow and Lane, Antibodies A Laboratory Manual, Cold Spring Harbor Laboratory, pp. 53-242, 1988), the disclosure of which is incorporated herein by reference in its entirety.

Briefly, a mouse is repetitively inoculated with a few micrograms of the THAP1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70: 419 (1980), the disclosure of which is incorporated herein by reference in its entirety. Selected positive clones can be expanded and their monoclonal antibody product harvested for use. Detailed procedures for monoclonal antibody production are described in Davis, L. et al. Basic Methods in Molecular Biology, Elsevier, New York., Section 21-2, the disclosure of which is incorporated herein by reference in its entirety.

Polyclonal Antibody Production by Immunization

Polyclonal antiserum containing antibodies to heterogeneous epitopes in the THAP1 protein or a portion thereof can be prepared by immunizing suitable non-human animal with the THAP1 protein or a portion thereof, which can be unmodified or modified to enhance immunogenicity. A suitable nonhuman animal, preferably a non-human mammal, is selected. For example, the animal may be a mouse, rat, rabbit, goat, or horse. Alternatively, a crude protein preparation which, has been enriched for THAP1 or a portion thereof can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987), the disclosure of which is incorporated herein by reference in its entirety. An effective immunization protocol for rabbits can be found in Vaitukaitis, J. et al. J. Clin. Endocrinol. Metab. 33: 988-991 (1971), the disclosure of which is incorporated herein by reference in its entirety. Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12: M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either the monoclonal or the polyclonal protocol are useful in quantitative immunoassays which determine concentrations of antigen-bearing substances in biological samples; or they are also used semi-quantitatively or qualitatively to identify the presence of antigen in a biological sample. The antibodies may also be used in therapeutic compositions for killing cells expressing the protein or reducing the levels of the protein in the body.

REFERENCES

Numerous literature and patent references have been cited in the present application. All references cited are incorporated by reference herein in their entireties.

For some references, the complete citation is in the body of the text. For other references the citation in the body of the text is by author and year, the complete citation being as follows:

Alcalay, M., Tomassoni, L., Colombo, E., Stoldt, S., Grignani, F., Fagioli, M., Szekely, L., Helin, K., and Pelicci, P. G. (1998). The promyelocytic leukemia gene product (PML) forms stable complexes with the retinoblastoma protein. Mol Cell Biol 18, 1084-93.

Arcone, et al., Nucl. Acids Res., 16(8): 3195-3207, 1988.

Baichwal and Sugden, In: Gene Transfer, Kucherlapati R, ed., New York, Plenum Press, pp. 117-148, 1986.

Barradas, M., Monjas, A., Diaz-Meco, M. T., Serrano, M., and Moscat, J. (1999). The downregulation of the pro-apoptotic protein Par4 is critical for Ras-induced survival and tumor progression. Embo J 18, 6362-9.

Bartlett et al., Proc. Nat Acad. Sci. USA, 93:8852-8857, 1996.

Benvenisty and Neshif, Proc. Nat Acad. Sci. USA, 83:9551-9555, 1986.

Berra, E., Municio, M. M., Sanz, L., Frutos, S., Diaz-Meco, M. T., and Moscat, J. (1997). Positioning a typical protein kinase C isoforms in the UV-induced apoptotic signaling cascade. Mol Cell Biol 17, 4346-54.

Bloch, D. B., Chiche, J. D., Orth, D., de la Monte, S. M., Rosenzweig, A., and Bloch, K. D. (1999). Structural and functional heterogeneity of nuclear bodies. Mol Cell Biol 19, 4423-30.

Boghaert E. R. et al, Cell Growth Differ. 1997 August;8(8): 881-90

Burge, C., Karlin, S. (1997) Prediction of complete gene structures in human genomic DNA. J. Mol. Biol. 268, 78-94

Carter and Flotte, Ann. N. Y Acad. Sci., 770:79-90, 1995.

Chattedee, et al., Ann. N. Y Acad. Sci., 770:79-90, 1995.

Chen and Okayama, Mol. Cell Biol., 7:2745-2752, 1987.

Coffin, In: Virology, ed., New York: Raven Press, pp. 143 7-15 00, 1990.

Coupar et al., Gene, 68:1-10, 1988.

Dani, et al., J. Biol. Chem., 264:10119-10125, 1989.

Diaz-Meco, M. T., Municio, M. M., Frutos, S., Sanchez, P., Lozano, J., Sanz, L., and Moscat, J. (1996). The product of Par4, a gene induced during apoptosis, interacts selectively with the a typical isoforms of protein kinase C. Cell 86, 777-86.

Dubensky et al., Proc. Nat'l Acad. Sci. USA, 81:7529-7533, 1984.

Fechheimer et al., Proc. Nat Acad. Sci. USA, 84:8463-8467, 1987.

Felsenstein, J. 1989. PHYLIP—Phylogeny Inference Package (Version 3.2). *Cladistics* 5: 164-166.

Ferkol et al., FASEB J., 7:1081-1091, 1993.

Ferrari et al., J. Virol., 70:3227-3234, 1996.

Fisher et al., J. Virol., 70:520-532, 1996.

Flotte et al., Proc. Nat'l Acad. Sci. USA, 90:10613-10617, 1993.

Fogal, V., Gostissa, M., Sandy, P., Zacchi, P., Stemsdorf, T., Jensen, K., Pandolfi, P. P., Will, H., Schneider, C., and Del Sal, G. (2000). Regulation of p53 activity in nuclear bodies by a specific PML isoform. Embo J 19, 6185-95.

Fraley et al., Proc. Nat'l Acad. Sci. USA, 76:3348-3352, 1979.

Friedmann, "Progress toward human gene therapy," Science, 244:1275-1281, 1989.

Ghosh and Bachhawat, In: Liver diseases, targeted diagnosis and therapy using specific receptors and ligands, (Wu G, Wu C ed,), New York: Marcel Dekker, pp. 87 104, 1991.

Girard, J. P., Baekkevold, E. S., Feliu, J., P, B., and Amalric, F. (1999). Molecular cloning and functional analysis of SUT-1, a sulfate transporter from human high endothelial venules. Proc Natl Acad Sci USA 96:12772-12777.

Girard, J. P., Baekkevold, E. S., Yamanaka, T., Haraldsen, G., Brandtzaeg, P., and Amalric, F. (1999). Heterogeneity of endothelial cells: the specialized phenotype of human high endothelial venules characterized by suppression subtractive hybridization. Am J Pathol 155:2043-2055.

Girard, J. P., and Springer, T. A. (1995). Cloning from purified high endothelial venule cells of hevin, a close relative of the antiadhesive extracellular matrix protein SPARC. Immunity 2, 113-123.

Goodman et al., Blood, 84:1492-1500, 1994.

Gopal, Mol. Cell Biol., 5:1188-1190, 1985.

Gossen and Bujard, Proc. Nat Acad. Sci. USA, 89:5547-5551, 1992.

Gossen et al., Science, 268:1766-1769, 1995.

Graham and Van Der Eb, Virology, 52:456-467, 1973.

Guo, Q., Fu, W., Xie, J., Luo, H., Sells, S. F., Geddes, J. W., Bondada, V., Rangnekar, V. M., and Mattson, M. P. (1998). Par4 is a mediator of neuronal degeneration associated with the pathogenesis of Alzheimer disease. Nat Med 4, 957-62.

Hay et al., J. Mol. Biol., 175:493-510, 1984.

Hearing and Shenk, J. Mol. Biol. 167:809-822, 1983.

Hearing et al., J. Virol., 67:2555-2558, 1987.

Higgins, D. G., Thompson, J. D. and Gibson, T. J. (1996) Using CLUSTAL for multiple sequence alignments. Methods Enzymol., 266, 383-402.

Horowitz, Yandell, Park, Canning, Whyte, Buchkovich, Harlow, Weinberg, Dryja, "Point mutational inactivation of the retinoblastoma antioncogene," Science 243, 937 940,1989.

Hunt et al., Proc. Nat Acad. Sci. USA, 83:3786-3790, 1986.

Ishov, A. M., Sotnikov, A. G., Negorev, D., Vladimirova, O. V., Neff, N., Kamitani, T., Yeh, E. T., Strauss, J. F., 3rd, and Maul, G. G. (1999). PML is critical for ND10 formation and recruits the PML-interacting protein daxx to this nuclear structure when modified by SUMO-1. J Cell Biol 147, 221-34.

Jareborg N, Birney E, Durbin R. Genome Res. 1999 September;9(9):815-24.

Jentsch, S., and Pyrowolakis, G. (2000). Ubiquitin and its kin: how close are the family ties? Trends Cell Biol 10, 335-42.

Johnstone, R. W., See, R. H., Sells, S. F., Wang, J., Muthukkumar, S., Englert, C., Haber, D. A., Licht, J. D., Sugrue, S. P., Roberts, T., Rangnekar, V. M., and Shi, Y. (1996). A novel repressor, Par4, modulates transcription and growth suppression functions of the Wilms' tumor suppressor WT1. Mol Cell Biol 16, 6945-56.

Joki et al., Human Gene Ther., 6:1507-1513, 1995.

Kageyama, et al., J. Biol. Chem., 262(5):2345-2351, 1987.

Kaneda et al., Science, 243:375-378, 1989.

Kaplitt et al., Nat Genet., 8:148-153, 1994.

Kato et al, J. Biol. Chem., 266:3361-3364, 1991.

Kessler et al., Proc. Nat Acad. Sci. USA, 93:14082-14087, 1996.

Klein et al., Nature, 327:70-73, 1987.

Koeberl et al., Proc. Nat 7 Acad. Sci. USA, 94:1426-1431, 1997.

Korhonen et al., Blood, 86:1828-1835, 1995.

Lallemand-Breitenbach, V., Zhu, J., Puvion, F., Koken, M., Honore, N., Doubeikovsky, A., Duprez, E., Pandolfi, P. P., Puvion, E., Freemont, P., and de The, H. (2001). Role of Promyelocytic Leukemia (PML) Sumolation in Nuclear Body Formation, 11S Proteasome Recruitment, and As(2) O(3)-induced PML or PML/Retinoic Acid Receptor alpha Degradation. J Exp Med 193, 1361-72.

LaMorte, V. J., Dyck, J. A., Ochs, R. L., and Evans, R. M. (1998). Localization of nascent RNA and CREB binding protein with the PML-containing nuclear body. Proc Natl Acad Sci USA 95, 4991-6.

Levrero et al., Gene, 10 1: 195-202, 199 1.

Li, H., Leo, C., Zhu, J., Wu, X., O'Neil, J., Park, E. J., and Chen, J. D. (2000). Sequestration and inhibition of Daxx-mediated transcriptional repression by PML. Mol Cell Biol 20, 1784-96.

Mann et al., Cell, 33:153-159, 1983.

Mattson, M. P., Duan, W., Chan, S. L., and Camandola, S. (1999). Par4: an emerging pivotal player in neuronal apoptosis and neurodegenerative disorders. J Mol Neurosci 13, 17-30.

Maul, G. G., Negorev, D., Bell, P., and Ishov, A. M. (2000). Review: properties and assembly mechanisms of ND10, PML bodies, or PODs. J Struct Biol 129, 278-87.

Melchlor, F. (2000). SUMO—nonclassical ubiquitin. Annu Rev Cell Dev Biol 16, 591-626.

Mizukami et al., Virology, 217:124-130, 1996.

Muller, S., Matunis, M. J., and Dejean, A. (1998). Conjugation with the ubiquitin-related modifier SUMO-1 regulates the partitioning of PML within the nucleus. Embo J 17,61-70.

McCown et al., Brain Res., 713:99-107, 1996.

Nicolas and Rubenstein, In: Vectors: A survey of molecular cloning vectors and their uses, Rodriguez and Denhardt (eds.), Stoneham: Butterworth, pp. 493-513, 1988.

Nicolau and Sene, Biochim. Biophys. Acta, 721:185-190, 1982.

Nicolau et al., Methods Enzymol., 149:157-176, 1987.

Olivierio, et al., EMBO J, 6(7):1905-1912, 1987.

Page, G., Kogel, D., Rangnekar, V., and Scheidtmann, K. H. (1999). Interaction partners of Dlk/ZIP kinase: co-expression of Dlk/ZIP kinase and Par4 results in cytoplasmic retention and apoptosis. Oncogene 18, 7265-73.

Pape and Kim, Mol. Cell. Biol., 974-982, 1989.

Paskind et al., Virology, 67:242-248, 1975.

Perales et al., Proc. Nat Acad. Sci. 91:4086-4090, 1994.

Ping et al., Microcirculation, 3:225-228, 1996.

Poli and Cortese, Proc. Nat'l Acad. Sci. USA, 86:8202-8206, 1989.

Potter et al., Proc. Nat Acad. Sci. USA, 81:7161-7165, 1984.

Prowse and Baumann, Mol Cell Biol, 8(1):42-51, 1988.

Quignon, F., De Bels, F., Koken, M., Feunteun, J., Ameisen, J. C., and de The, H. (1998). PML induces a novel caspase-independent death process. Nat Genet 20, 259-65.

Radler et al., Science, 275:810-814, 1997. Rb Protein Inhibits p84N5-induced Apoptosis, 10:3261, October 1999.

Ridgeway, In: Vectors: A survey of molecular cloning vectors and their uses, Rodriguez R L, Denhardt D T, ed., Stoneham:Butterworth, pp. 467-492, 1988.

Rippe et al., Mol. Cell Biol., 10:689-695, 1990.

Ron et al., Mol. Cell. Biol., 2887-2895, 199 1.

Roux et al., Proc. Nat Acad. Sci. USA, 86:9079-9083, 1989.

Ruggero, D., Wang, Z. G., and Pandolfi, P. P. (2000). The puzzling multiple lives of PML and its role in the genesis of cancer. Bioessays 22, 827-35.

Sells, S. F., Han, S. S., Muthukkumar, S., Maddiwar, N., Johnstone, R., Boghaert, E., Gillis, D., Liu, G., Nair, P., Monnig, S., Collini, P., Mattson, M. P., Sukhatme, V. P., Zimmer, S. G., Wood, D. P., Jr., McRoberts, J. W., Shi, Y., and Rangnekar, V. M. (1997). Expression and function of the leucine zipper protein Par4 in apoptosis. Mol Cell Biol 17, 3823-32.

Speigelman, et al., J. Biol. Chem., 264(3), 1811-1815, 1989.

Sternsdorf, T., Jensen, K., Reich, B., and Will, H. (1999). The nuclear dot protein sp100, characterization of domains necessary for dimerization, subcellular localization, and modification by small ubiquitin-like modifiers. J Biol Chem 274, 12555-66.

Tartaglia, Ayres, Wong, and Goeddel, "A novel domain within the 55 kd TNF receptor signals cell death," Cell 74, 845-853, 1993.

Temin, In: Gene Transfer, Kucherlapati (ed.), New York: Plenum Press, pp. 149-188, 1986.

Tibbetts Cell, 12:243-249, 1977.

Tur-Kaspa et al., Mol. Cell Biol., 6:716-718, 1986.

Wagner et al., Proc. Nat'l Acad. Sci. 87(9):3410-3414, 1990.

Walther and Stein, J. Mol. Med, 74:3 79-3 92, 1996.

Wang, Z. G., Delva, L., Gaboli, M., Rivi, R., Giorgio, M., Cordon-Cardo, C., Grosveld, F., and Pandolfi, P. P. (1998). Role of PML in cell growth and the retinoic acid pathway. Science 279, 1547-51.

Wang, Z. G., Ruggero, D., Ronchetti, S., Zhong, S., Gaboli, M., Rivi, R., and Pandolfi, P. P. (1998). PML is essential for multiple apoptotic pathways. Nat Genet 20, 266-72.

Watt et al., Proc. Nat'l Acad. Sci., 83(2): 3166-3170, 1986.

Wilson, et al., Mol. Cell. Biol., 6181-6191, 1990.

Wong et al., Gene, 10:87-94, 1980.

Wu and Wu, Adv. Drug Delivery Rev., 12:159-167, 1993.

Wu and Wu, Biochem., 27:887-892,1988.

Wu and Wu, J. Biol. Chem., 262:4429-4432,1987.

Xiao et al., J. Virol., 70:8098-8108, 1996.

Yang et al., Proc. Nat Acad. Sci USA, 87:9568-9572, 1990.

Yeh, E. T., Gong, L., and Kamitani, T. (2000). Ubiquitin-like proteins: new wines in new bottles. Gene 248, 1-14.

Zechner, et al., Mol. Cell. Biol., 23 94-2401, 198 8.

Zhong, S., Hu, P., Ye, T. Z., Stan, R., Ellis, N. A., and Pandolfi, P. P. (1999). A role for PML and the nuclear body in genomic stability. Oncogene 18, 7941-7.

Zhong, S., Muller, S., Ronchetti, S., Freemont, P. S., Dejean, A., and Pandolfi, P. P. (2000). Role of SUMO-1-modified PML in nuclear body formation. Blood 95, 2748-52.

Zhong, S., Salomoni, P., and Pandolfi, P. P. (2000). The transcriptional role of PML and the nuclear body. Nat Cell Biol 2, E85-90.

Zhong, S., Salomoni, P., Ronchetti, S., Guo, A., Ruggero, D., and Pandolfi, P. P. (2000). Promyelocytic leukemia protein (PML) and Daxx participate in a novel nuclear pathway for apoptosis. J Exp Med 191, 631-40.

What is claimed is:

1. An isolated or purified fragment of SEQ ID NO: 3 comprising the amino acid sequence 143-213 of SEQ ID NO: 3.

2. A fusion protein comprising an Fc region of an immunoglobulin fused to a fragment of SEQ ID NO: 3, said fragment comprising the amino acid sequence 143-213 of SEQ ID NO: 3.

3. An oligomeric protein comprising a plurality of fragments of SEQ ID NO: 3, said fragments comprising the amino acid sequence 143-213 of SEQ ID NO: 3.

4. A medicament comprising a fragment of SEQ ID NO: 3 comprising the amino acid sequence 143-213 of SEQ ID NO: 3, together with a pharmaceutically acceptable carrier.

5. The isolated or purified fragment of claim 1, wherein said amino acid sequence consists of the amino acid sequence 143-213 of SEQ ID NO: 3.

6. The fusion protein of claim 2, wherein said fragment of SEQ ID NO: 3 consists of the amino acid sequence 143-213 of SEQ ID NO: 3.

7. The oligomeric protein of claim 3, wherein at least one of said plurality of fragments of SEQ ID NO: 3 consists of the amino acid sequence 143-213 of SEQ ID NO: 3.

8. The medicament of claim 4, wherein said fragment of SEQ ID NO: 3 consists of the amino acid sequence 143-213 of SEQ ID NO: 3.

* * * * *

UNITED STATES PATENT AND TRADEMARK OFFICE
CERTIFICATE OF CORRECTION

PATENT NO. : 7,572,886 B2
APPLICATION NO. : 10/317832
DATED : August 11, 2009
INVENTOR(S) : Girard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1031 days.

Signed and Sealed this

Fourteenth Day of December, 2010

David J. Kappos
*Director of the United States Patent and Trademark Office*